(12) United States Patent
Asai et al.

(10) Patent No.: US 12,209,079 B2
(45) Date of Patent: *Jan. 28, 2025

(54) IDO/TDO INHIBITOR

(71) Applicants: GENERAL INCORPORATED ASSOCIATION PHARMA VALLEY PROJECT SUPPORTING ORGANIZATION, Shizuoka (JP); CanBas Co., Ltd., Shizuoka (JP)

(72) Inventors: Akira Asai, Shizuoka (JP); Naohisa Ogo, Shizuoka (JP); Daisuke Muraoka, Shizuoka (JP); Osamu Takikawa, Shizuoka (JP); Takumi Kawabe, Shizuoka (JP); Takuji Sato, Shizuoka (JP)

(73) Assignees: GENERAL INCORPORATED ASSOCIATION PHARMA VALLEY PROJECT SUPPORTING ORGANIZATION, Shizuoka (JP); CANBAS CO., LTD., Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/755,953

(22) PCT Filed: Oct. 17, 2018

(86) PCT No.: PCT/JP2018/038648
§ 371 (c)(1),
(2) Date: Apr. 14, 2020

(87) PCT Pub. No.: WO2019/078246
PCT Pub. Date: Apr. 25, 2019

(65) Prior Publication Data
US 2020/0239452 A1    Jul. 30, 2020

(30) Foreign Application Priority Data

Oct. 19, 2017 (JP) .................................. 2017-202637

(51) Int. Cl.
*A61P 35/04* (2006.01)
*C07C 335/32* (2006.01)
(Continued)

(52) U.S. Cl.
CPC ............ *C07D 403/12* (2013.01); *A61P 35/04* (2018.01); *C07C 335/32* (2013.01);
(Continued)

(58) Field of Classification Search
CPC .. C07D 403/12; C07D 335/32; C07D 391/00; C07D 209/42; C07D 213/32;
(Continued)

(56) References Cited

U.S. PATENT DOCUMENTS 5,329,012 A    7/1994  Anderson
5,364,875 A *  11/1994 Wilde .................. C07D 473/38
                                           548/312.1
(Continued)

FOREIGN PATENT DOCUMENTS

GB    1585950 A *  3/1981  ............. A01N 43/54
JP    47-49694 B    12/1972
(Continued)

OTHER PUBLICATIONS

Lathe R, Sapronova A, Kotelevtsev Y. Atherosclerosis and Alzheimer—diseases with a common cause? Inflammation, oxysterols, vasculature. BMC Geriatr. Mar. 21, 2014. (Year: 2014).*

(Continued)

*Primary Examiner* — Jared Barsky
(74) *Attorney, Agent, or Firm* — Edwin S. Flores; Daniel J. Chalker; Chalker Flores, LLP

(57) ABSTRACT

A compound of formula (I) given below or a pharmaceutically acceptable salt of the compound is useful as an IDO/TDO inhibitor. Thus, the compound of formula (I) or the pharmaceutically acceptable salt of the compound can be used as, for example, a therapeutic agent for a disease or a disorder selected from tumor, infectious disease, neurodegenerative disorder, cataract, organ transplant rejection, autoimmune disease, postoperative cognitive impairment, and disease related to women's reproductive health [in the following formula (I), ring A represents an aromatic ring, an aliphatic ring, a heterocyclic ring, or a condensed ring of two or more rings selected from an aromatic ring, an aliphatic ring and a heterocyclic ring; X, $R^1$ and $R^2$ represent a substituent on a ring atom constituting ring A; m represents an integer of 0 to 6; X represents, for example, a halogen atom; and $R^1$ and $R^2$ are the same or different and are selected from, for example, the group consisting of groups of formula (a) or formula (b); and in the following formula (a) and formula (b), Y is selected from the group consisting of O, S, and Se, Z is selected from the group consisting of O, S, and Se, n represents an integer of 1 to 8, r represents an integer of 1 to 8, s represents an integer of 1 to 8, $R^4$ represents, for example, —C(=NH)—$HN_2$, and $R^6$ represents, for example, a substituted or unsubstituted aryl group].

(Continued)

-continued

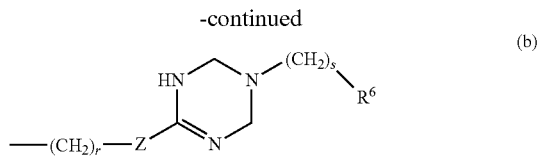
(b)

6 Claims, 4 Drawing Sheets

(51) Int. Cl.

| | |
|---|---|
| C07C 391/00 | (2006.01) |
| C07D 209/42 | (2006.01) |
| C07D 213/32 | (2006.01) |
| C07D 213/81 | (2006.01) |
| C07D 241/42 | (2006.01) |
| C07D 333/18 | (2006.01) |
| C07D 333/54 | (2006.01) |
| C07D 403/12 | (2006.01) |
| C07D 409/14 | (2006.01) |
| A61K 45/06 | (2006.01) |

(52) U.S. Cl.
CPC .......... *C07C 391/00* (2013.01); *C07D 209/42* (2013.01); *C07D 213/32* (2013.01); *C07D 213/81* (2013.01); *C07D 241/42* (2013.01); *C07D 333/18* (2013.01); *C07D 333/54* (2013.01); *C07D 409/14* (2013.01); *A61K 45/06* (2013.01)

(58) Field of Classification Search
CPC .. C07D 213/81; C07D 241/42; C07D 333/18; C07D 333/54; C07D 409/14; A61P 35/04
See application file for complete search history.

(56) References Cited

U.S. PATENT DOCUMENTS

| | | | |
|---|---|---|---|
| 2009/0117125 A1 | 5/2009 | Su et al. | |
| 2010/0240713 A1* | 9/2010 | Cadieux | A61P 43/00 |
| | | | 514/646 |
| 2013/0017862 A1 | 1/2013 | Lee et al. | |
| 2013/0178629 A1 | 7/2013 | Su et al. | |
| 2016/0006026 A1 | 1/2016 | Paulson et al. | |

FOREIGN PATENT DOCUMENTS

| | | | |
|---|---|---|---|
| JP | 11-217365 A | 8/1999 | |
| JP | 2000-302737 A | 4/2000 | |
| JP | 2006-521377 | 9/2006 | |
| JP | 2008-505937 A | 2/2008 | |
| JP | 2008-201756 A | 9/2008 | |
| JP | 5583592 B2 | 7/2014 | |
| JP | 2016-535788 A | 11/2016 | |
| JP | 2017-509667 A | 4/2017 | |
| JP | 2017-149769 A | 8/2017 | |
| JP | 2017-526727 A | 9/2017 | |
| WO | 2008/151288 A1 | 12/2008 | |
| WO | WO-2008151288 A2 * | 12/2008 | ........... A61K 31/155 |
| WO | 2009/033165 A1 | 3/2009 | |
| WO | WO-2009049422 A1 * | 4/2009 | .............. A61P 25/00 |
| WO | WO-2010005851 A1 * | 1/2010 | ......... A61K 31/4412 |
| WO | 2015/091862 A1 | 6/2015 | |
| WO | 2015/150097 A1 | 10/2015 | |
| WO | 2016/026772 A1 | 2/2016 | |
| WO | 2016/071283 A1 | 5/2016 | |
| WO | 2016/071293 A2 | 5/2016 | |
| WO | 2017/007700 A1 | 1/2017 | |
| WO | 2017/048612 A1 | 3/2017 | |

OTHER PUBLICATIONS

Masse et al., "Lipid lowering agents are associated with a slower cognitive decline in Alzheimer's disease," J Neurol Neurosurg Psychiatry 2005;76:1624-1629. (Year: 2005).*
Tian et al., "Effect of statin therapy on the progression of coronary atherosclerosis," National Center for Biotechnology Information, 2012. (Year: 2012).*
Koh et al., "Combination therapy for treatment or prevention of atherosclerosis: Focus on the lipid-RAAS interaction," Atherosclerosis, Apr. 2010, 209(2):307-313. (Year: 2010).*
Okunrobo et al., "Synthesis and pharmacological evaluation of carboxamides," Pakistan Journal of Pharmaceutical Sciences (2006). (Year: 2006).*
Raffa et al., "Pharmacology of oral combination analgesics: rational therapy for pain," Journal of Clinical Pharmacy and Therapeutics (2001) 26, 257-264. (Year: 2001).*
Okunrobo et al., "Ring Opening of Phthalimide Derivatives with Benylamine: Formation of Carboxamides and their Pharmacologic Evaluation," Indian Journal of Pharmaceutical Sciences Jan.-Feb. 2007 (Okunrobo2) . (Year: 2007).*
Bulusu et al., "Modelling of compound combination effects and applications to efficacy and toxicity: state-of-the-art, challenges and perspectives," Drug Discovery Today, vol. 21, Issue 2, Feb. 2016 pp. 225-238. (Year: 2016).*
Crabbe et al., "The Inhibition of Human Placental Diamine Oxidase by Substrate Analogues," Biochem. J. (1974) 139, 183-189. (Year: 1974).*
Alcolea, Veronica et al., "Novel seleno-and thio-urea derivatives with potent in vitro activities against several cancer cell lines" European Journal of Medicinal Chemistry, 2016, 113, p. 134-144.
Anderson, Wayne K. et al.,, "Synthesis and Evaluation of Furan, Thiophene, and Azole Bis[(carbamoyloxy)methyl] Derivatives as Potential Antineoplastic Agents" Journal of Medicinal Chemistry, 1984, 27(12), p. 1559-1565.
Anderson, Wayne K. et al., "Synthesis and Antileukemic Activity of Fluorinated Analogues of 2,3-Dihydro-5-phenyl-6,7-bis(hydroxymethyl)-1H-pyrrolizine Biscarbamate" Journal of Medicinal Chemistry, 1982, 25 (1), p. 84-86.
Anderson, Wayne K. et al., "Antileukemic Activity of Derivatives of 1-Phenyl-2,5-dimethyl-3,4-bis(hydroxymethyl) pyrrole Bis(N-methylcarbamate)" Journal of Medicinal Chemistry, 1977, 20(12), p. 1691-1694.
Lalezari, Iraj et al., "Synthesis and Antineoplastic Activity of 5-Aryl-2,3-dihydropyrrolo[2,1-b]thiazole-6,7-dimethanol 6,7-Bis(isopropylcarbamates)" Journal of Medicinal Chemistry, 1988, 31 (7), p. 1427-1429.
Vana, Jiri et al., "Inverse Neighboring Group Participation : Explanation of an Unusual S->N Alkyl Migration of Isothiuronium Sits Containing a Lactone Group" Journal of Organic Chemistry 2013, 78(9), p. 4456-4462.
Dobrzanska, Liliana, "Structual Heterogeneity of Ah1 Complexes with a Flexible 1,2-Bis[(imidazol-2-yl)thiomethyl] benzene Ligand and Issues Regarding the Phase Purity of the Bulk Material" European Journal of Inorganic Chemistry, 2012(6), p. 945-953.
Fujita, Hiroshi et al., "Synthetic Studies on 2,4-Benzothiazepin-5(1H)-one and 2,4-Benzodiazepin-1-one Derivatives" Chemical & Pharmaceutical Bulletin, 1975, 23(8)p. 1764-1774.
Arya, V. P. et al., "Synthesis of 1H-2,3-Dihydropyrimido-[2,3-b] benzo[e]-1,3-thiazepine" Indian Journal of Chemistry, 1971, 9 (10), p. 1169-1170.
Boyd, R. N. et al., "Characterization of Alkyl Halides by Use of Ethylenethiourea" Anal. Chem., 1960, 32, p. 551-554.
Van Baren, Nicolas et al. "Tumolal Immune Resistance Mediated by Enzymes that Degrade Tryptophan" Cancer Immunology Research;3(9) Sep. 2015, 978-985.
Dounay, Amy et al. "Challenges and Opportunities in the Discovery of New Therapeutics Targeting the Kynurenine Pathway" J. Medicinal Chemistry, 2015, 58, 8762-8782.
Matsuno, Kenji et al. "S-Benzylisothiourea deruvatives as small-molecule inhibitors of indoleamine-2,3dioxygenase" Bioorganic & Medicinal Chemistry Letter 20(2010)5126-5129.

(56) References Cited

OTHER PUBLICATIONS

Nakano, Shintaro et al. "Identification of novel kynumine production-inhibiting benzenesulfonamide derivatives in cancer cells" Biochemical & Biophysical Research Communications 419(2012)556-561.
Matsuno, Kenji et al. "Novel candesartan derivatives as indoleamine 2,3-dioxygenase inhibitors" Med.Chem. Commnun., 2012, 3, 475-479.
N,N'-dimethylphthalamide (https://ppt.cc/fWqxGx) PubChem.
Dimethyl phthalate (https://ppt.cc/fJB0Px) PubChem.

* cited by examiner

IDO/TDO INHIBITOR

CROSS-REFERENCE TO RELATED APPLICATIONS

This application is the National Stage of International Application No. PCT/JP2018/038648, filed on Oct. 17, 2017 claiming the priority of JP 2017-202637, filed on Oct. 19, 2017, the content of each of which is incorporated by reference herein.

TECHNICAL FIELD

The present invention relates to an indoleamine-2,3-dioxygenase (IDO [IDO1 or IDO2]) and/or tryptophan-2,3-dioxygenase (TDO) inhibitor for use in the medical field. The inhibitor of the present invention can be used as a pharmaceutical composition, particularly, a pharmaceutical composition for the treatment of various diseases, conditions and disorders including tumor, infectious disease, inflammatory conditions, and central nervous system disease or disorder.

BACKGROUND ART

Cancer cells are known to suppress the immune response of hosts and proliferate, through the use of their immune tolerance. Proteins responsible for this immune tolerance and their functions have been revealed in recent years. An antibody drug ipilimumab targeting CTLA4 (cytotoxic T-lymphocyte antigen 4), one of the causative molecules, was approved as a therapeutic drug for malignant melanoma by FDA in 2011, demonstrating the effectiveness of an agent conceptually based on the cancelation of cancer immune tolerance. Indoleamine-2,3-dioxygenase (IDO), which was discovered by Hayaishi et al. in 1950s, is an oxygenase that catalyzes the initial reaction of the kynurenine pathway (KP), an in vivo principal pathway of tryptophan metabolism. It was later revealed that this enzyme plays an important role in the establishment of immune tolerance in a tumor microenvironment, such as the control of T cells responsible for immunological action. The mechanism of action thereof is considered as the suppression of antitumor immunocytes due to local decrease in tryptophan concentration and increase in kynurenine concentration caused by the activation of the kynurenine pathway. Human IDO (hIDO) is over-expressed in various human cancers such as cancers of the prostate, the large intestine, the pancreas, the stomach, the ovary, the brain, and the lung.

The kynurenine pathway is responsible for the degradation of more than 95% of the essential amino acid tryptophan. The kynurenine pathway for tryptophan metabolism produces an essential pyridine nucleotide NAD+ and many neuroactive metabolites, for example, kynurenine (KYN), kynurenic acid (KYNA), a neurotoxic free radical generator 3-hydroxykynurenine (3-HK), anthranilic acid, 3-HAA, picolinic acid (PIC), and an excitatory N-methyl-D-aspartic acid (NMDA) receptor agonist, and a neurotoxin, and quinolinic acid (QUIN). The remaining 5% tryptophan is metabolized into 5-hydroxytryptophan by tryptophan hydroxylase and then further into 5-hydroxytryptamine (serotonin) and melatonin.

The first stage of tryptophan catabolism is catalyzed by either TDO or IDO. Both the enzymes catalyze the oxidative cleavage of a 2,3-double bond in an indole ring and convert tryptophan into N-formyl-L-kynurenine. This is a rate-limiting step in the tryptophan catabolism through the kynurenine pathway. TDO is a homotetramer composed of monomers each having a molecular weight of 48 kDa, and IDO has a molecular weight of 45 kDa and a monomeric structure. Although mediating the same reaction, TDO and IDO (IDO1 or IDO2) differ structurally and have homology of only 10%, mainly, within their active sites. By contrast, more relevant IDO1 and IDO2 have homology of 43%. IDO1 and IDO2 are two separate enzymes that catalyze the same reaction. The Michaelis constant of IDO2 for tryptophan is much higher than that of IDO1. Specifically, the affinity of IDO2 for the substrate tryptophan is much lower than that of IDO1. Nicolas van Baren et al. have reported tumor immune resistance mediated by enzymes degrading tryptophan, i.e., IDO1, TDO and IDO2 (non-patent document 1).

TDO is expressed at a high level in the liver and is responsible for regulating systemic tryptophan levels. Although TDO is neither induced nor regulated by signals from the immune system, TDO expression is inducible by tryptophan or corticosteroid. It has been further found recently that TDO is expressed in the brain and regulates the production of neuroactive tryptophan metabolites such as kynurenic acid and quinolinic acid. It has also been found that TDO is highly frequently activated and constitutively expressed in glioma cells. It has been revealed that TDO-derived KYN suppresses antitumor immune response and promotes the survival rate and motility of tumor cells via aryl hydrocarbon receptor (AhR) in an autocrine fashion. It has also been revealed that TDO exhibits elevation in its level in human hepatocellular cancer and is sporadically detected in other cancers. Moreover, it has also been revealed that: in preclinical models, TDO expression prevented the rejection of tumor grafts in mice immunized in advance; the systemic administration of a TDO inhibitor LM10 allowed mice to recover their ability to reject TDO-expressing tumor.

The expression of IDO is found in many cells such as macrophages, microglial cells, neurons and astrocytes. IDO transcription is strictly controlled in response to a specific inflammatory mediator. Mouse and human IDO gene promoters comprise a plurality of sequence elements having responsiveness to type I (IFN-α/β) and stronger type II (IFN-γ) interferons. Cells of certain myeloid lineages (monocyte-derived macrophages and DCs), fibroblasts, endothelial cells and some tumor cell lines express IDO after exposure to IFN-γ. However, the control of IDO transcription is complicated and is specific for a cell type. IDO activity is constantly exerted by human extra-villous trophoblasts at the maternal-fetal boundary. Functional IDO expression has been reported to be highest in the mouse epididymides, intestines (distal ileum and colon), lymph nodes, spleen, thymus gland and lung except for the placenta. It has been revealed that increased IDO expression is an independent prognostic variable for reduction in the survival rates of patients with acute myeloid leukemia (AML), small-cell lung cancer, melanoma, ovary cancer, colorectal cancer, pancreatic cancer and uterine body cancer. In fact, it has been reported that: serum from cancer patients has a higher kynurenine/tryptophan ratio than that of serum from healthy volunteers; and the level of IDO expression also correlates with the number of tumor-infiltrating lymphocytes in colorectal cancer patients.

Tryptophan metabolites such as kynurenine, kynurenic acid, 3-hydroxy-kynurenine, and 3-hydroxy-anthranilic acid can suppress a T cell function and induce T cell apoptosis. Resent research has revealed that aryl hydrocarbon receptor is a direct target of kynurenine. AhR is a transcription factor of the basic helix-loop-helix-Per-Arnt-Sim (PAS) family. As kynurenine accumulates in tumor, KYN binds to Ahr, which is then translocated to the nucleus where the transcription factor activates the transcription of the target gene which is controlled by dioxin response element (DRE). In CD4-positive cells, regulatory T cells (Treg) emerge due to kynurenine.

Thus, an inhibitor of TDO or IDO is considered to have the possibility of having a wide scope of therapeutic efficacy in cancer treatment. Furthermore, a dual inhibitor that blocks both TDO and IDO can exhibit stronger clinical efficacy by targeting both of these important Trp metabolic enzymes, and is thus considered to treat even broader patient groups.

It has been revealed that the inhibitor of IDO and/or TDO has its purpose for a wide range of indications for tumor, infectious disease, many other diseases including neurological conditions, etc.

Against such a situation, various IDO inhibitors and/or TDO inhibitors have been proposed so far. Particularly, many IDO inhibitors and/or TDO inhibitors containing indole derivatives having various structures have been proposed. For example, patent document 1 discloses that certain indole derivatives (680C91 and LM10) are useful as TDO inhibitors while a certain indole derivative (Newlink 1) and a certain oxadiazole derivative (Incyte 1) are useful as IDO inhibitors. Patent document 2 discloses various indole derivatives useful as IDO and/or TDO inhibitors. Patent documents 3 and 4 disclose that various condensed heterocyclic compounds having an indole skeleton can be used as IDO and/or TDO inhibitors. Also, patent document 5 discloses that a certain indole derivative has action as an IDO inhibitor. Further, patent document 6 discloses that a compound having three skeletons, i.e., an indole skeleton, a pyrazole skeleton and a cyclopropane skeleton, can be used as an IDO inhibitor.

For example, use of a heterocyclic compound having a 5-membered ring as a TDO and/or IDO inhibitor (patent documents 7 and 8), use of a heterocyclic compound having a condensed ring of two 6-membered rings as a TDO and/or IDO inhibitor (patent documents 9 and 10), use of a compound having a benzene ring or a tetrahydronaphthyl skeleton as an IDO inhibitor (patent document 11), use of a condensed heterocyclic compound consisting of three rings as an IDO inhibitor (patent documents 12 and 13), and use of a condensed heterocyclic compound consisting of four rings as an IDO inhibitor (patent documents 14 and 15) have been proposed for compounds other than indole derivatives. Amy B. Dounay et al. have introduced a novel therapeutic drug targeting the kynurenine pathway (non-patent document 2). Non-patent document 2 discloses various IDOL inhibitors and TDO inhibitors.

By contrast, the present inventors have found and reported that S-benzylthiourea and its derivatives inhibit IDO (non-patent document 3). The present inventors have also found and reported benzenesulfonamide derivatives and benzyl thioimidocarbamate derivatives that block the production of kynurenine, a product of tryptophan metabolism, in cancer cells (non-patent document 4). The present inventors have further reported that candesartan cilexetil for use as a therapeutic drug for hypertension, renal parenchymal hypertension or the like and its derivatives inhibits IDO (non-patent document 5).

PRIOR ART DOCUMENTS

Patent Documents patent document 1: WO2015/091862
Patent document 2: WO2015/150097 (Japanese unexamined Patent Application Publication (Translation of PCT Application) No. 2017-509682)
Patent document 3: WO2016/071293
Patent document 4: WO2017/007700
Patent document 5: Japanese unexamined Patent Application Publication (Translation of PCT Application) No. 2006-521377
Patent document 6: WO2017/048612
Patent document 7: WO2016/026772
Patent document 8: Japanese unexamined Patent Application Publication (Translation of PCT Application) No. 2017-526727
Patent document 9: WO2016/071283
Patent document 10: Japanese unexamined Patent Application Publication No. 2017-509667
Patent document 11: Japanese Patent No. 5583592
Patent document 12: Japanese unexamined Patent Application Publication No. 2017-149769
Patent document 13: Japanese unexamined Patent Application Publication (Translation of PCT Application) No. 2008-505937
Patent document 14: Japanese unexamined Patent Application Publication No. 2008-201756
Patent document 15: Japanese unexamined Patent Application Publication No. 2016-535788
Non-Patent Documents
Non-patent document 1: Cancer Immunology Research; 3 (9) September 2015, 978-985
Non-patent document 2: J. Medicinal Chemistry, 2015, 58, 8762-8782
Non-patent document 3: Bioorganic & Medicinal Chemistry Letters 20 (2010) 5126-5129
Non-patent document 4: Biochemical & Biophysical Research Communications 419 (2012) 556-561
Non-patent document 5: Med. Chem. Commnun., 2012, 3, 475-479

SUMMARY OF THE INVENTION

Object to be Solved by the Invention

An object of the present invention is to provide a novel IDO inhibitor and/or TDO inhibitor useful for various diseases.

Means to Solve the Object

The present inventors have conducted diligent studies by focusing on a certain compound group structurally different from publicly known IDO inhibitors and/or TDO inhibitors, and consequently found that a compound of formula (I) given below or a pharmaceutically acceptable salt of the compound has excellent inhibitory action on IDO and/or TDO and is applicable as an IDO inhibitor and/or a TDO inhibitor to a wide range of diseases. The present invention has been completed on the basis of these findings.

Specifically, the present invention is as follows.

[1] A compound of formula (I) or a pharmaceutically acceptable salt of the compound:

[wherein
ring A represents an aromatic ring, an aliphatic ring, a heterocyclic ring, or a condensed ring of two or more rings selected from an aromatic ring, an aliphatic ring and a heterocyclic ring;
X, $R^1$ and $R^2$ represent a substituent on a ring atom constituting ring A;
m represents an integer of 0 to 6;
X is selected from the group consisting of a halogen atom, a substituted or unsubstituted linear or branched alkyl group, a substituted or unsubstituted linear or branched alkoxy group, a substituted or unsubstituted linear or branched alkenyl group, a substituted or unsubstituted linear or branched alkenyloxy group, a substituted or unsubstituted linear or branched alkynyl group, a substituted or unsubstituted linear or branched alkynyloxy group, a substituted or unsubstituted cycloalkyl group, a substituted or unsubstituted cycloalkenyl group, an alkyl halide group, an alkyloxy halide group, a cyano group, a hydroxy group, an amino group, a nitro group, a carboxyl group, a substituted or unsubstituted aryl group, and a substituted or unsubstituted aralkyl group, and when m is 2 to 6, each X is the same or different;
$R^1$ and $R^2$ are the same or different;
$R^1$ represents a group represented by formula (II):

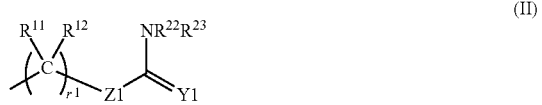

(II)

(wherein $R^{11}$ and $R^{12}$ each independently represent a hydrogen atom, a fluorine atom or a substituted or unsubstituted alkyl group, Y1 represents O or $NR^{21}$, $R^{21}$, $R^{22}$ and $R^{23}$ each independently represent a hydrogen atom, a substituted or unsubstituted linear or branched alkyl group, a substituted or unsubstituted cycloalkyl group, a substituted or unsubstituted aryl group or a substituted or unsubstituted heterocyclic group, $R^{21}$ and $R^{22}$ or $R^{23}$ are optionally bonded to each other to form a ring, Z1 represents S, SO, SO$_2$, O or Se, r1 represents any integer of 1 to 8, and when r1 is 2 or larger, each $R^{11}$ and each $R^{12}$ are the same or different), or formula (III):

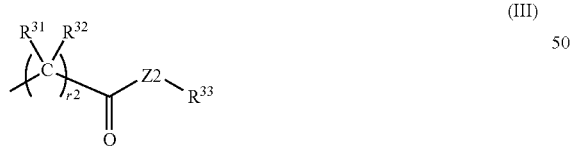

(III)

(wherein $R^{31}$ and $R^{32}$ each independently represent a hydrogen atom, a fluorine atom or a substituted or unsubstituted linear or branched alkyl group, Z2 represents O or $NR^{61}$ (wherein $R^{61}$ represents a hydrogen atom, a substituted or unsubstituted linear or branched alkyl group or a substituted or unsubstituted aryl group), $R^{33}$ represents a substituted or unsubstituted linear or branched alkyl group, a substituted or unsubstituted cycloalkyl group, a substituted or unsubstituted aryl group, a substituted or unsubstituted aralkyl group or a substituted or unsubstituted cycloalkylalkyl group, r2 represents 0 or any integer of 1 to 8, and when r2 is 2 or larger, each $R^{31}$ and each $R^{32}$ are the same or different); and $R^2$ represents, independently from $R^1$, a group represented by formula (II) or formula (III)].

[2] The compound according to [1] or a pharmaceutically acceptable salt of the compound, wherein in formula (II), a functional group containing the ring formed by $R^{21}$ and $R^{22}$ or $R^{23}$ bonded to each other is a functional group represented by the following formula (IV):

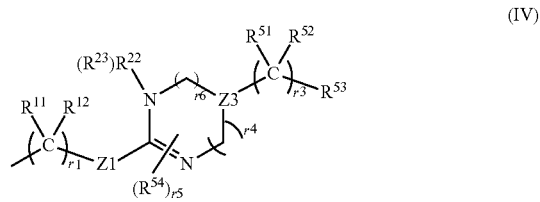

(IV)

[wherein $R^{11}$, $R^{12}$, r1, Z1, $R^{22}$, and $R^{23}$ have the same meaning as described in formula (II), Z3 represents CH, $CR^{54}$ or N, $R^{51}$ and $R^{52}$ each independently represent a hydrogen atom or a substituted or unsubstituted linear or branched alkyl group, $R^{54}$ represents a halogen atom or a substituted or unsubstituted linear or branched alkyl group, $R^{53}$ represents a substituted or unsubstituted aryl group, a substituted or unsubstituted cycloalkyl group or a substituted or unsubstituted heterocyclic group, r3 represents any integer of 1 to 8, when r3 is 2 or larger, each $R^{51}$ and each $R^{52}$ are the same or different, r4 and r6 each independently represent 0 or 1, r4 and r6 are not 0 at the same time, r5 represents 0 or any integer of 1 to 5, when r5 is 2 or larger, each $R^{54}$ is the same or different, and the notation $R^{22}(R^{23})$ represents any one of $R^{22}$ and $R^{23}$).

[3] The compound according to [1] or [2] or a pharmaceutically acceptable salt of the compound, wherein $R^1$ is selected from the group consisting of the following groups:

—COOR$^3$    —(CH$_2$)$_n$—Y—R$^4$

—(CH$_2$)$_p$—CONH—(CH$_2$)$_q$—R$^5$

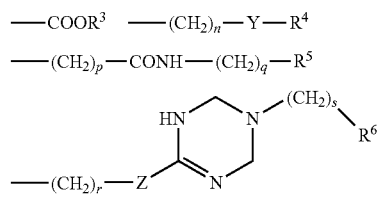

—(CH$_2$)$_r$—Z

[wherein
Y is selected from the group consisting of O, S, SO, SO$_2$, and Se,
Z is selected from the group consisting of O, S, SO, SO$_2$, and Se,
n represents an integer of 1 to 8,
p represents an integer of 0 to 8,
q represents an integer of 1 to 8,
r represents an integer of 1 to 8,
s represents an integer of 1 to 8,
$R^3$ represents a substituted or unsubstituted linear or branched alkyl group,
$R^4$ represents a substituted or unsubstituted heterocyclic group, —CONH$_2$, or

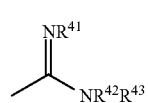

(wherein $R^{41}$, $R^{42}$ and $R^{43}$ are the same or different and are selected from the group consisting of a hydrogen atom, a substituted or unsubstituted linear or branched alkyl group, a substituted or unsubstituted cycloalkyl group, a substituted or unsubstituted aryl group or a substituted or unsubstituted heterocyclic group), $R^5$ is selected from the group consisting of a hydrogen atom, a substituted or unsubstituted cycloalkyl group, and a substituted or unsubstituted aryl group, and $R^6$ is selected from the group consisting of a substituted or unsubstituted aryl group, a substituted or unsubstituted cycloalkyl group, and a substituted or unsubstituted heterocyclic group], and $R^2$ is selected, independently from $R^1$, from the group consisting of the following groups:

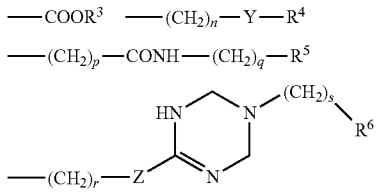

(wherein Y, Z, n, p, q, r, s, $R^3$, $R^4$, $R^5$, and $R^6$ have the same meaning as described above).

[4] The compound according to any one of [1] to [3] or a pharmaceutically acceptable salt of the compound, wherein $R^1$ and $R^2$ are bonded to adjacent ring atoms of ring A.

[5] The compound according to any one of [1] to [4] or a pharmaceutically acceptable salt of the compound, wherein $R^1$ and $R^2$ have the same group.

[6] The compound according to [5] or a pharmaceutically acceptable salt of the compound, wherein in the compound of formula (I), $R^1$ and $R^2$ are a group represented by formula (II), and in formula (II), $R^{11}$ and $R^{12}$ are a hydrogen atom, Y1 represents $NR^{21}$, and r1 is 1.

[7] The compound according to [6] or a pharmaceutically acceptable salt of the compound, wherein the compound is represented by any one of the following formulas:

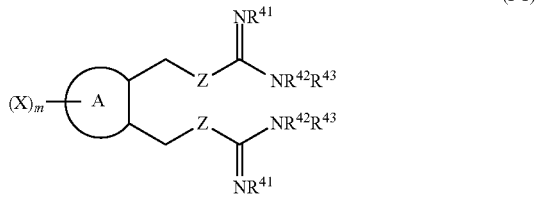

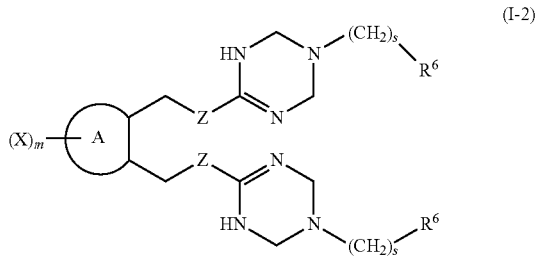

(wherein A, X, and m have the same meaning as defined in [1], and Z, s, $R^{41}$, $R^{42}$, $R^{43}$, and $R^6$ have the same meaning as defined in [3]).

[8] The compound according to any one of [1] to [4] or a pharmaceutically acceptable salt of the compound, wherein $R^1$ and $R^2$ have different groups.

[9] The compound according to [8] or a pharmaceutically acceptable salt of the compound, wherein the compound is represented by the following formula:

(wherein A, X, and m have the same meaning as defined in [1], and $R^7$ and $R^8$ are selected from the group consisting of —$COOR^3$ (wherein $R^3$ represents a substituted or unsubstituted linear or branched alkyl group), —$(CH_2)_n$—Y—$R^4$ (wherein n, Y, and $R^4$ have the same meaning as defined in [3]), —$(CH_2)_p$—CONH—$(CH_2)_q$—$R^5$ (wherein p, q, and $R^5$ have the same meaning as defined in [3]), and the following formula:

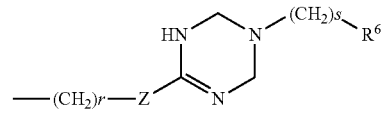

(wherein r, s, $R^6$ and Z have the same meaning as defined in [3]), and $R^7$ and $R^8$ are different from each other).

[10] The compound according to any one of [1] to [9] or a pharmaceutically acceptable salt of the compound, wherein ring A is selected from the group consisting of a benzene ring, a naphthalene ring, a quinoxaline ring, a thiophene ring, an indole ring, a benzothiophene ring, an imidazole ring, a quinoline ring, a quinazoline ring, and a pyridine ring.

[11] The compound according to any one of [1] to [10] or a pharmaceutically acceptable salt of the compound, wherein X is selected from the group consisting of a halogen atom, a substituted or unsubstituted linear or branched $C_1$-$C_8$ alkyl group, a substituted or unsubstituted linear or branched $C_1$-$C_8$ alkoxy group, a substituted or unsubstituted linear or branched $C_2$-$C_8$ alkenyl group, a substituted or unsubstituted linear or branched $C_2$-$C_8$ alkenyloxy group, a substituted or unsubstituted linear or branched $C_2$-$C_8$ alkynyl group, a substituted or unsubstituted linear or branched $C_2$-$C_8$ alkynyloxy group, a substituted or unsubstituted $C_3$-$C_8$ cycloalkyl group, a substituted or unsubstituted $C_3$-$C_8$ cycloalkenyl group, a substituted or unsubstituted $C_3$-$C_8$ cycloalkynyl group, a $C_1$-$C_3$ alkyl halide group, a cyano group, a hydroxy group, an amino group, a carboxyl group, a substituted or unsubstituted $C_6$-$C_{18}$ aryl group, and a substituted or unsubstituted aralkyl group (wherein the number of carbon atoms in the aryl moiety is $C_6$-$C_{10}$, and the number of carbon atoms in the alkylene moiety is $C_1$-$C_4$).

[12] The compound according to any one of [1] to [11] or a pharmaceutically acceptable salt of the compound, wherein X represents a group selected from the following group:
    as a halogen atom, a fluorine atom, a chlorine atom, a bromine atom, and an iodine atom,
    as a substituted or unsubstituted linear or branched alkyl group, a methyl group, an ethyl group, a n-propyl group, an i-propyl group, a n-butyl group, an i-butyl group, a s-butyl group, a t-butyl group, a n-pentyl group, a n-hexyl group, a n-octyl group, a carboxymethyl group, a 2-carboxyethyl group, a 3-hydroxy-1-propyl group, an aminomethyl group, a 2-aminoethyl group, a hydroxymethyl group, and a 2-hydroxyethyl group, as a substituted or unsubstituted linear or branched alkoxy group, a methoxy group, an ethoxy group, a n-propoxy group, and a n-butoxy group, as a substituted or unsubstituted linear or branched alkenyl group, an ethenyl (vinyl) group, a 2-propenyl (allyl) group, and a 3-butenyl group, as a substituted or unsubstituted linear or branched alkenyloxy group, an ethenyloxy (vinyloxy) group, a 2-propenyloxy (allyloxy) group, and a 3-butenyloxy group, as a substituted or unsubstituted linear or branched alkynyl group, an ethynyl group, a 2-propynyl group, and a 3-butynyl group, as a substituted or unsubstituted linear or branched alkynyloxy group, an ethynyloxy group, a 2-propynyloxy group, and a 3-butynyloxy group, as a substituted or unsubstituted cycloalkyl group, a cyclopropyl group, a cyclobutyl group, a cyclopentyl group, a cyclohexyl group, and a cyclooctyl group, as a substituted or unsubstituted cycloalkenyl group, a 1-cyclopropenyl group, a 1-cyclobutenyl group, a 1-cyclopentenyl group, and a 1-cyclohexenyl group, as an alkyl halide group, a fluoromethyl group, a difluoromethyl group, a chloromethyl group, a bromomethyl group, an iodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, and a pentafluoroethyl group, as an alkyloxy halide group, a fluoromethoxy group, a difluoromethoxy group, a chloromethoxy group, a bromomethoxy group, an iodomethoxy group, a trifluoromethoxy group, a trichloromethoxy group, a tribromomethoxy group, a triiodomethoxy group, a 2,2,2-trifluoroethoxy group, a 2,2,2-trichloroethoxy group, a 2,2,2-tribromoethoxy group, a 2,2,2-triiodoethoxy group, and a pentafluoroethoxy group, a cyano group,
a hydroxy group,
an amino group,
a nitro group,
a carboxyl group, as a substituted or unsubstituted aryl group, a phenyl group, a naphthalen-1-yl group, and a naphthalen-2-yl group, and as a substituted or unsubstituted aralkyl group, a benzyl group, a phenethyl group, and a 3-phenyl-1-propyl group.

[13] The compound according to any one of [1] to [12] or a pharmaceutically acceptable salt of the compound, wherein in a compound of the following formula (I-4) containing a benzene ring as ring A, and $R^1$ and $R^2$ are substituted in positions 1 and 2, respectively, of the ring, (I-4)

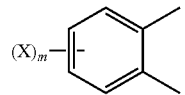

(wherein $R^1$ and $R^2$ have the same meaning as defined in any one of [1] to [3]) the following formula (I-4-a) excluding $R^1$ and $R^2$:

(I-4-a)

is selected from the group consisting of Ph=, 3-F-Ph=, 4-F-Ph=, 5-F-Ph=, 6-F-Ph=, 3-Cl-Ph=, 4-Cl-Ph=, 5-Cl-Ph=, 6-Cl-Ph=, 3-Br-Ph=, 4-Br-Ph=, 5-Br-Ph=, 6-Br-Ph=, 3-I-Ph=, 5-I-Ph=, 6-I-Ph=, 3-Me-Ph=, 4-Me-Ph=, 5-Me-Ph=, 6-Me-Ph=, 3-Et-Ph=, 4-Et-Ph=, 5-Et-Ph=, 6-Et-Ph=, 3-Pr-Ph=, 4-Pr-Ph=, 5-Pr-Ph=, 6-Pr-Ph=, 3-Bu-Ph=, 4-Bu-Ph=, 5-Bu-Ph=, 6-Bu-Ph=, 3-t-Bu-Ph=, 4-t-Bu-Ph=, 5-t-Bu-Ph=, 6-t-Bu-Ph=, 3-MeO-Ph=, 4-MeO-Ph=, 5-MeO-Ph=, 6-MeO-Ph=, 3-EtO-Ph=, 4-EtO-Ph=, 5-EtO-Ph=, 6-EtO-Ph=, 3-$CF_3$-Ph=, 4-$CF_3$-Ph=, 5-$CF_3$-Ph=, 6-$CF_3$-Ph=, 3-$C_2F_5$-Ph=, 4-$C_2F_5$-Ph=, 5-$C_2F_5$-Ph=, 6-$C_2F_5$-Ph=, 3-$CF_3$O-Ph=, 4-$CF_3$O-Ph=, 5-$CF_3$O-Ph=, 6-$CF_3$O-Ph=, 3-$C_2F_5$O-Ph=, 4-$C_2F_5$O-Ph=, 5-$C_2F_5$O-Ph=, 6-$C_2F_5$O-Ph=, 3-CN-Ph=, 4-CN-Ph=, 5-CN-Ph=, 6-CN-Ph=, 3-OH-Ph=, 4-OH-Ph=, 5-OH-Ph=, 6-OH-Ph=, 3-$NH_2$-Ph=, 4-$NH_2$-Ph=, 5-$NH_2$-Ph=, 6-$NH_2$-Ph=, 3-$NO_2$-Ph=, 4-$NO_2$-Ph=, 5-$NO_2$-Ph=, 6-$NO_2$-Ph=, 3-COOH-Ph=, 4-COOH-Ph=, 5-COOH-Ph=, 6-COOH-Ph=, (any two of positions 3, 4, 5 and 6)-$F_2$-Ph=, (any two of positions 3, 4, 5 and 6)-$Cl_2$-Ph=, (any two of positions 3, 4, 5 and 6)-$Br_2$-Ph=, (any two of positions 3, 4, 5 and 6)-$I_2$-Ph=, (any two of positions 3, 4, 5 and 6)-$Me_2$-Ph=, (any two of positions 3, 4, 5 and 6)-$Et_2$-Ph-, (any two of positions 3, 4, 5 and 6)-$Pr_2$-Ph=, (any two of positions 3, 4, 5 and 6)-$Bu_2$-Ph=, (any two of positions 3, 4, 5 and 6)-$(CN)_2$-Ph=, (any two of positions 3, 4, 5 and 6)-$(OH)_2$-Ph=, (any two of positions 3, 4, 5 and 6)-$((NH_2))_2$-Ph=, (any two of positions 3, 4, 5 and 6)-$(NO_2)_2$-Ph=, (any two of positions 3, 4, 5 and 6)-$(MeO)_2$-Ph=, (any two of positions 3, 4, 5 and 6)-$(EtO)_2$-Ph=, (any two of positions 3, 4, 5 and 6)-$(CF_3)_2$-Ph=, (any three of positions 3, 4, 5 and 6)-$F_3$-Ph=, (any three of positions 3, 4, 5 and 6)-$Cl_2$-Ph=, (all four of positions 3, 4, 5 and 6)-$F_4$-Ph=, and (all four of positions 3, 4, 5 and 6)-$Cl_4$-Ph=(wherein "Ph=" represents a moiety of formula (I-4-a) excluding $(X)_m$—).

[14] The compound according to any one of [1] to [13] or a pharmaceutically acceptable salt of the compound, wherein the compound is any of compounds represented by the following formulas:

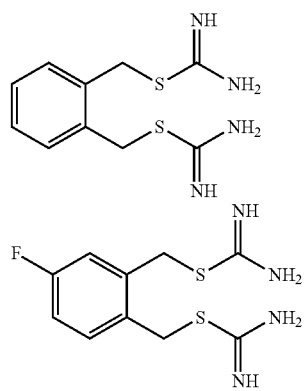

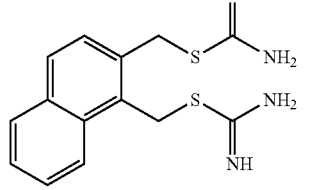
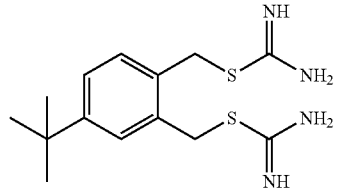
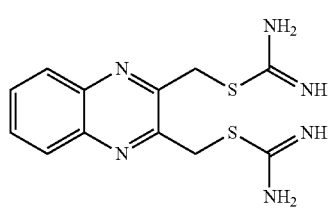
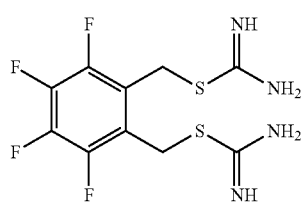
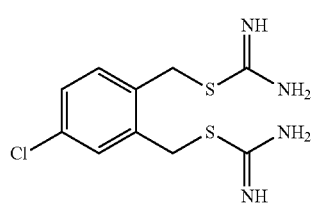
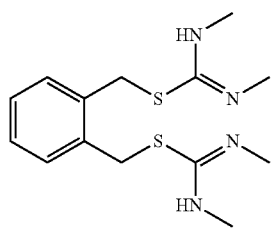
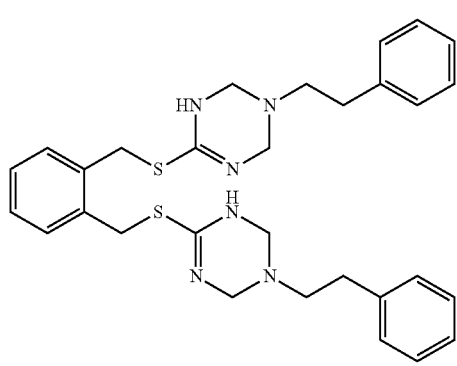
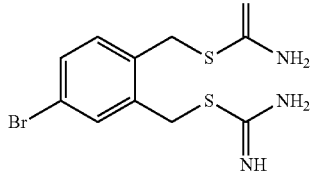
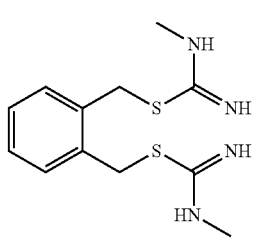
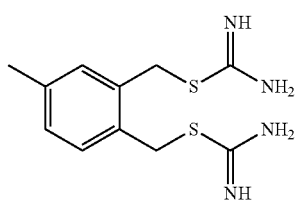
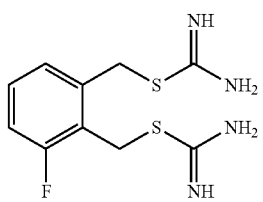
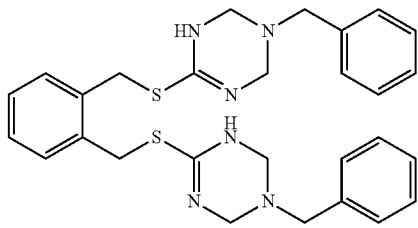
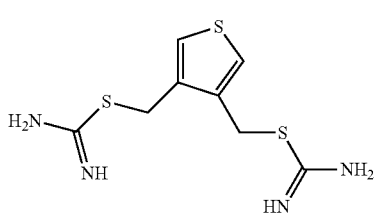
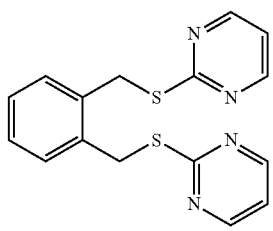

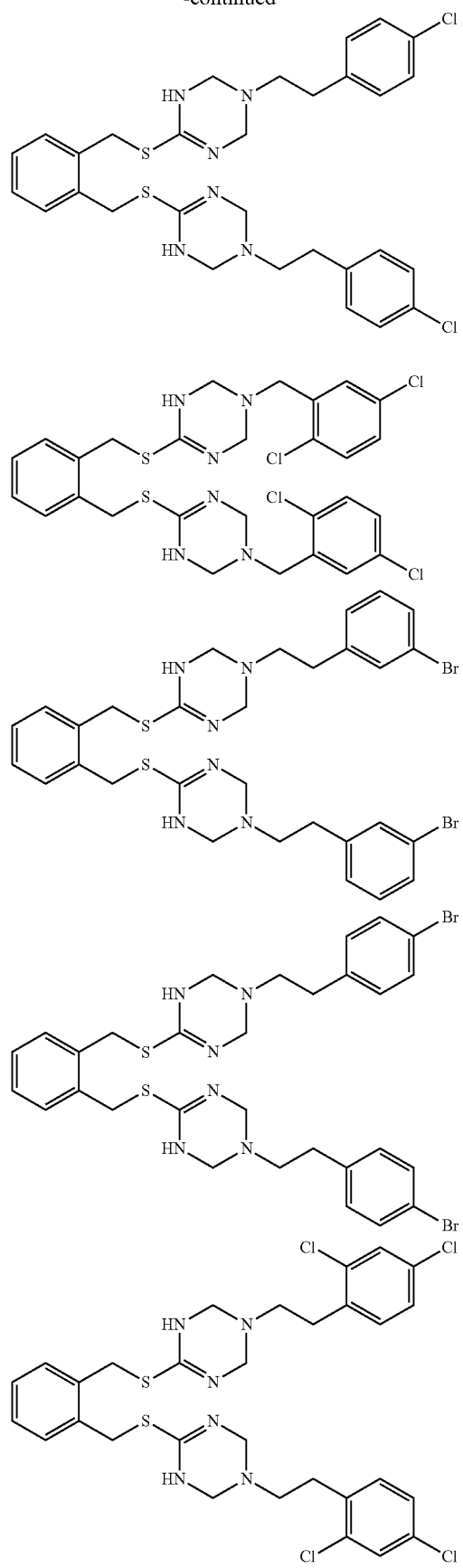

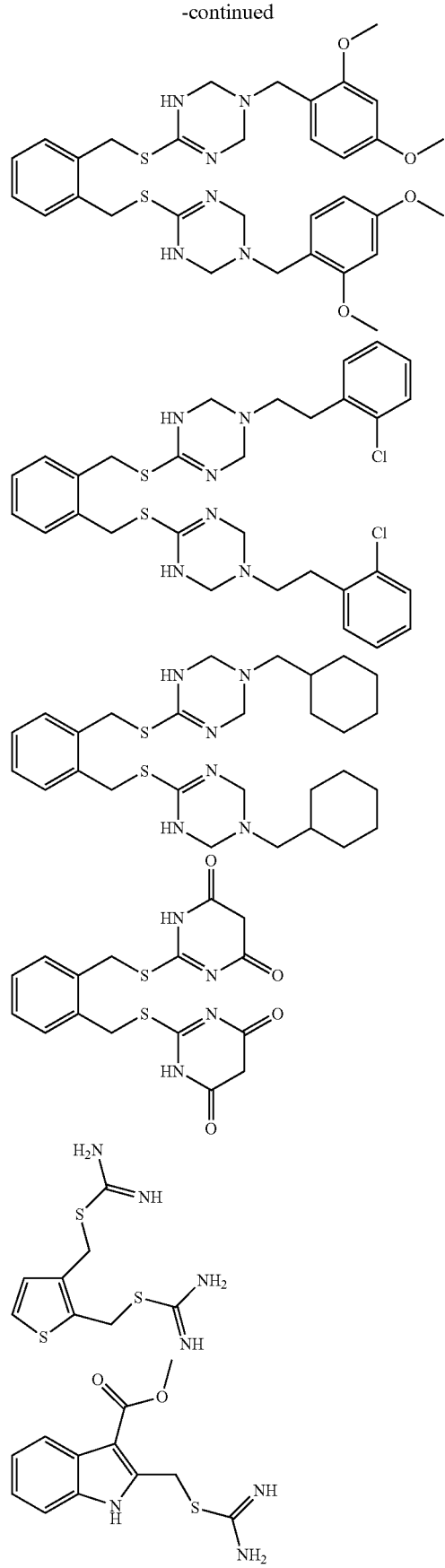
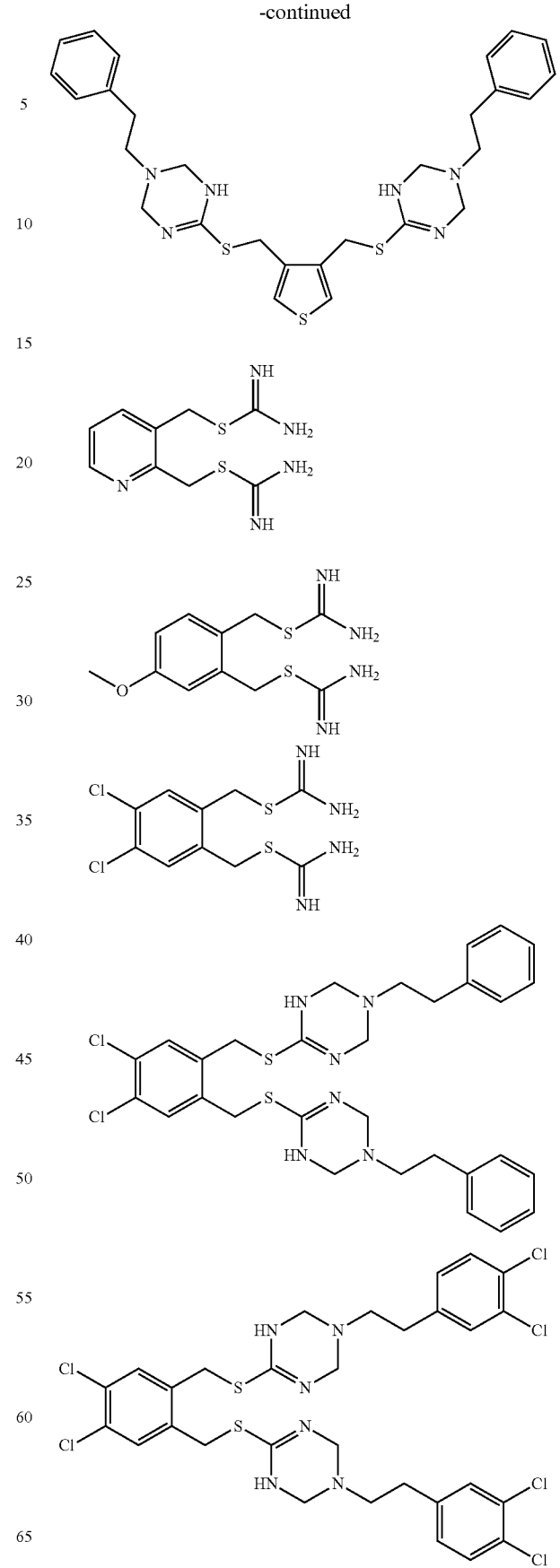

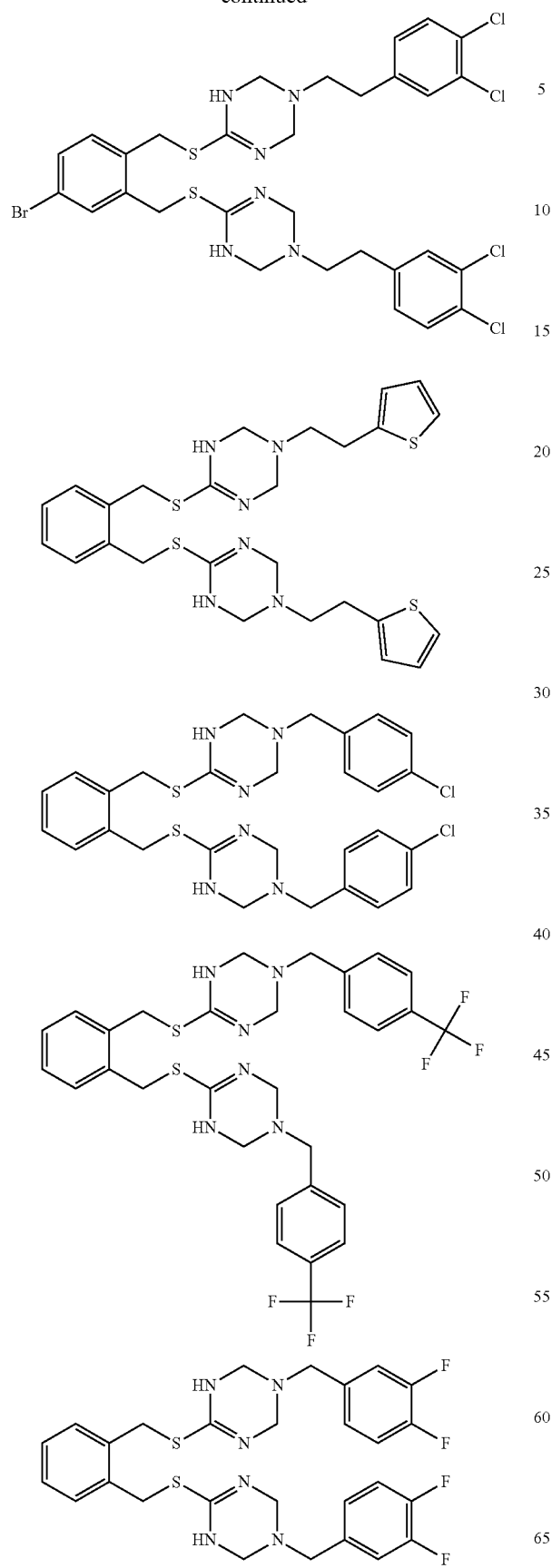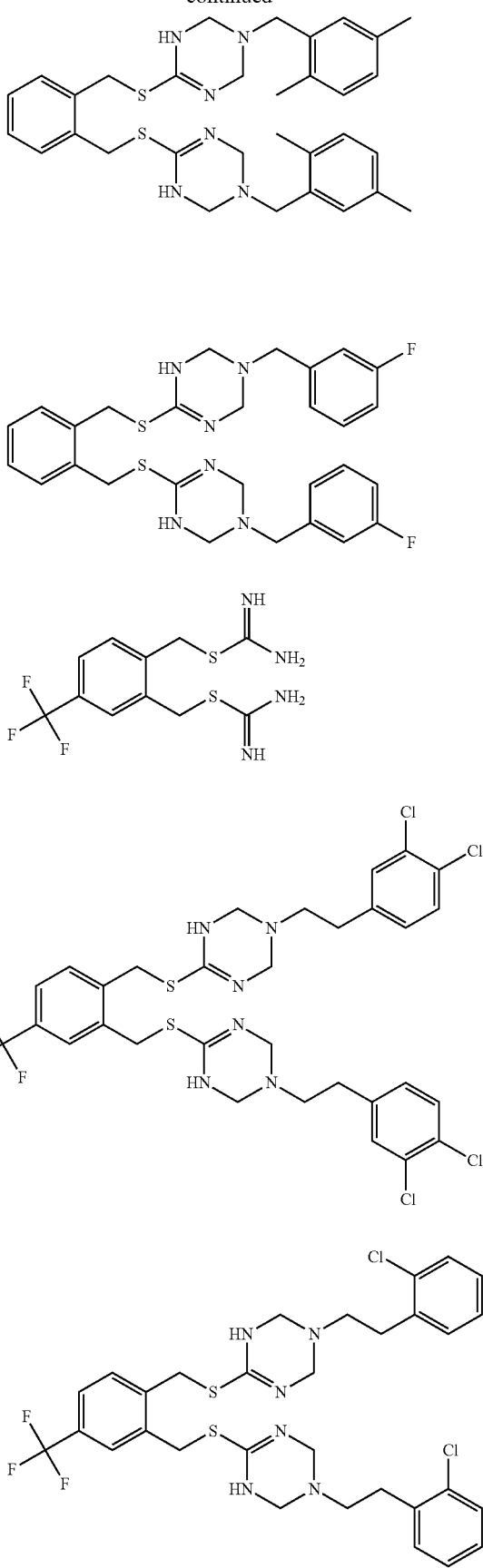

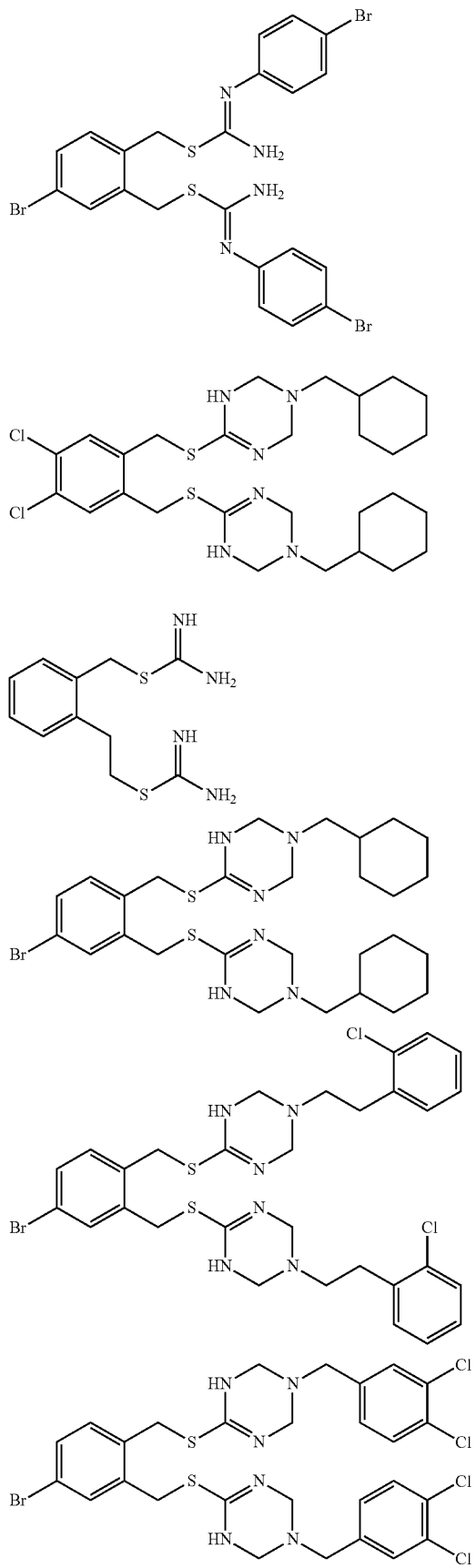

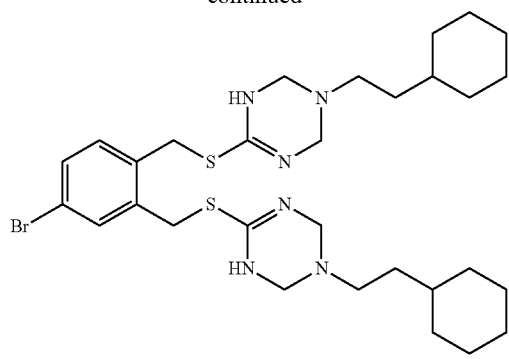
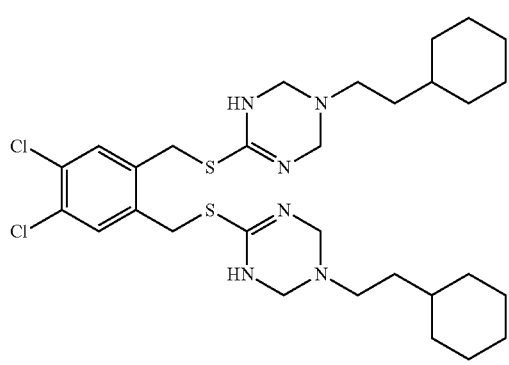
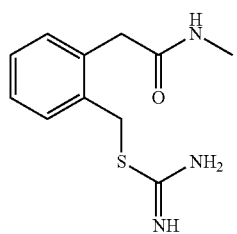
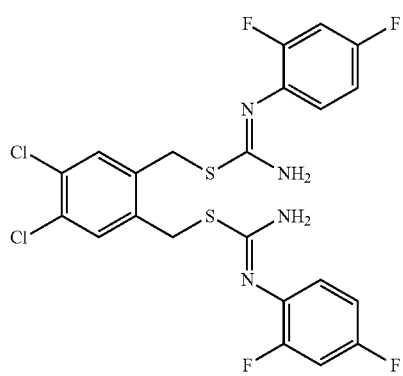
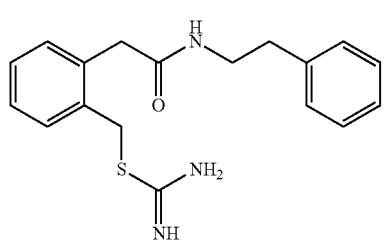
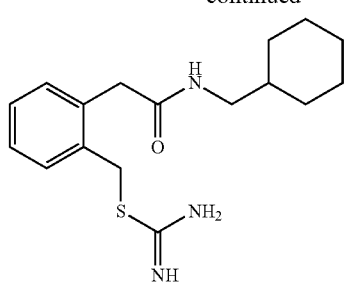
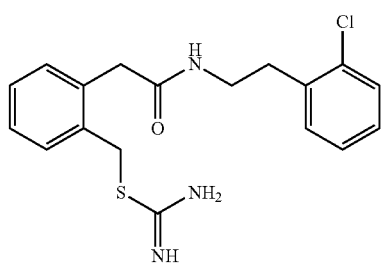
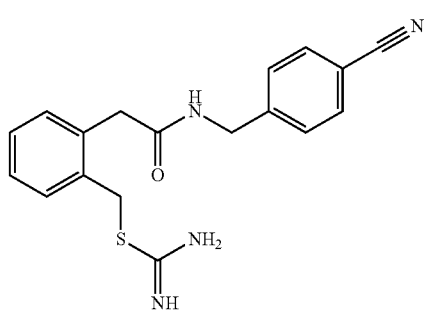
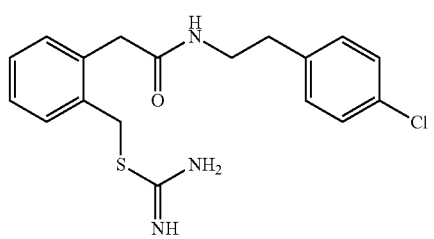
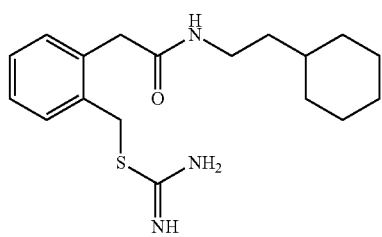
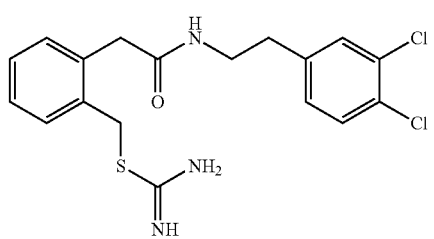

-continued
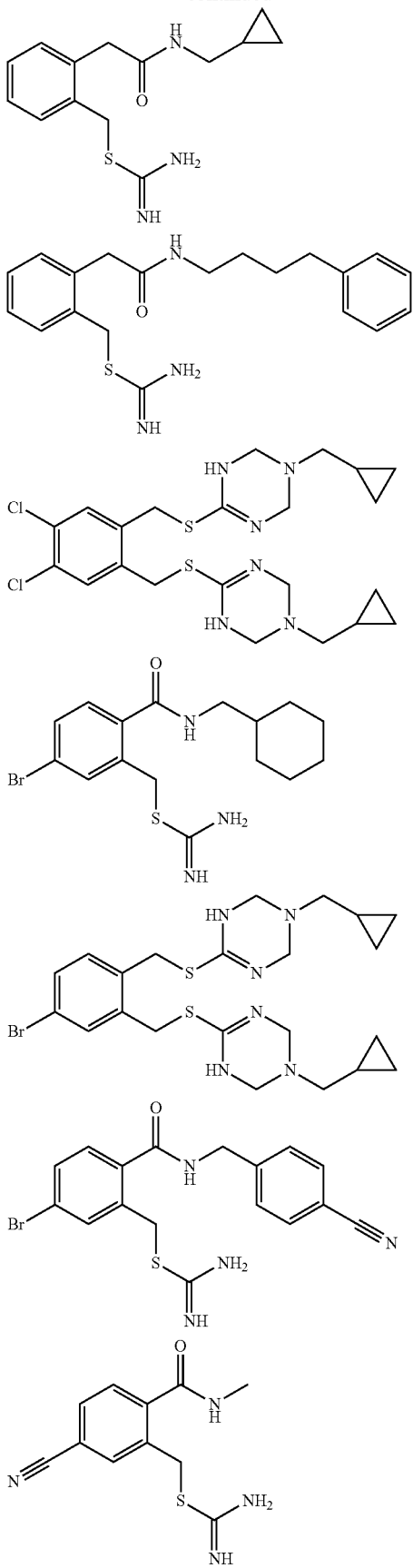
-continued
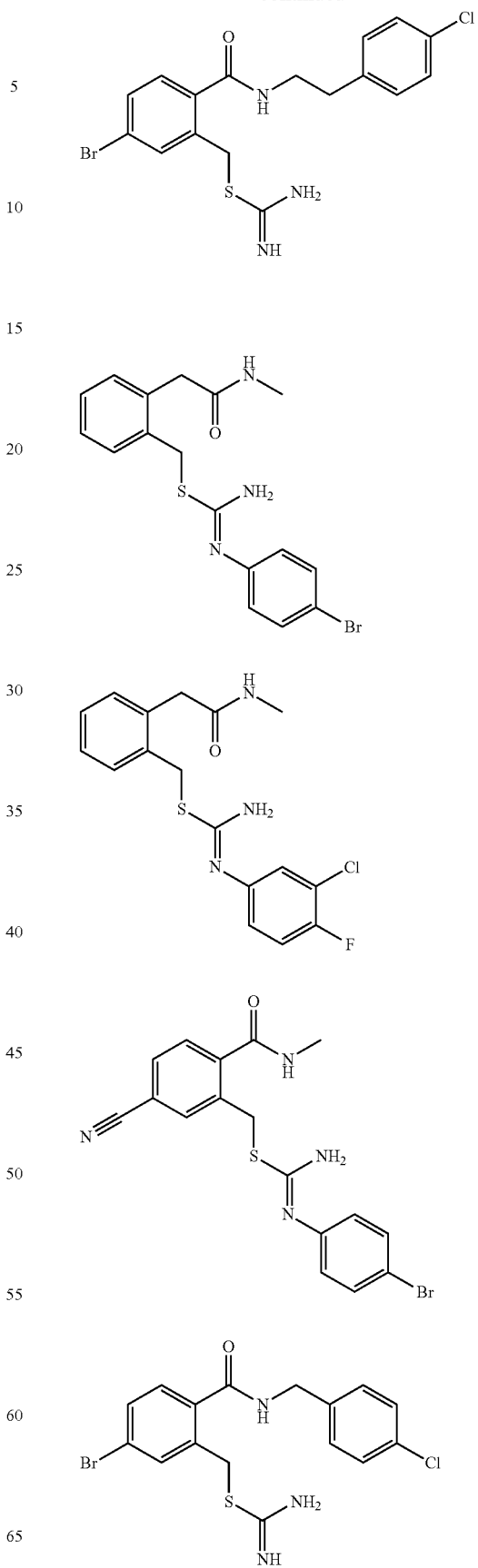

25
-continued
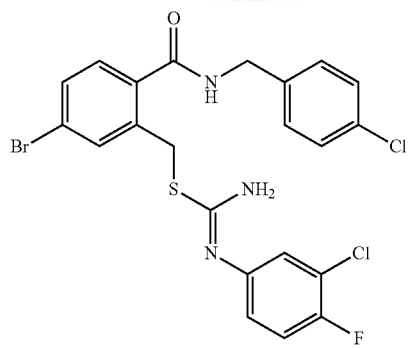
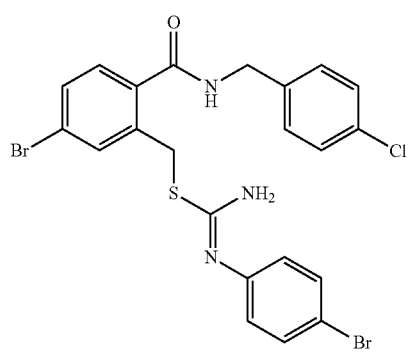
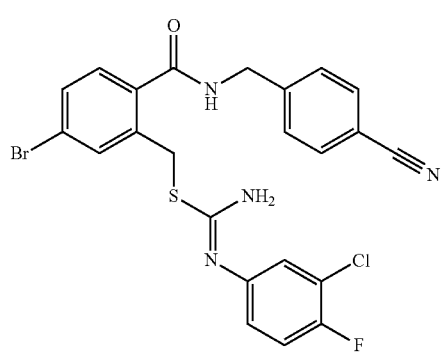
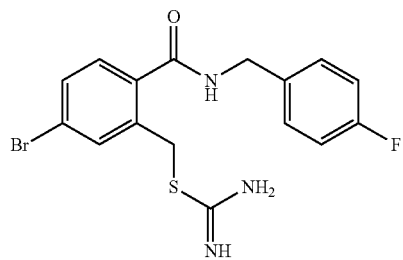
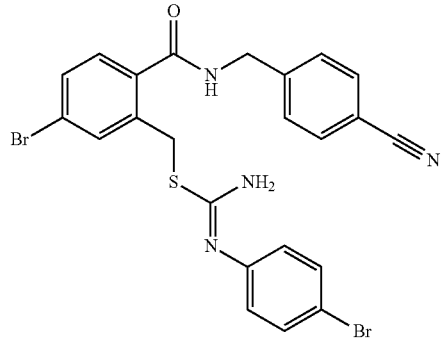
26
-continued
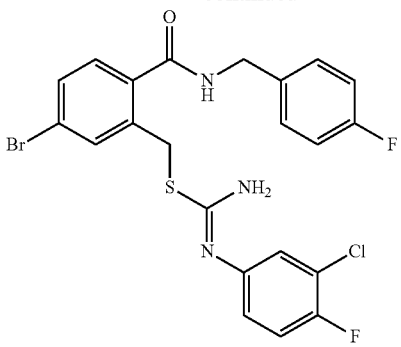
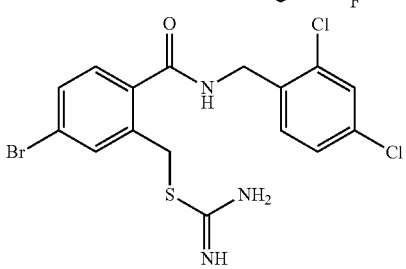
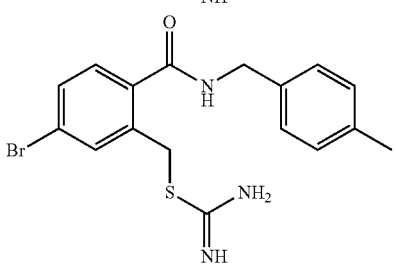
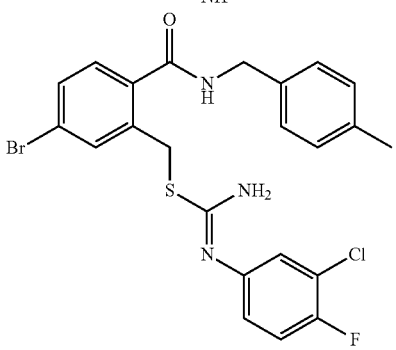
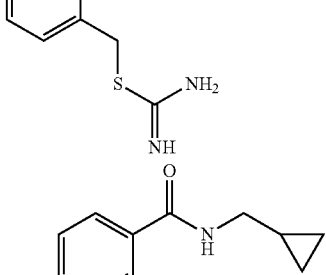
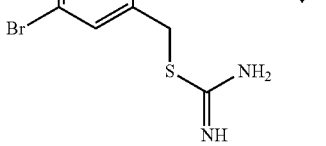

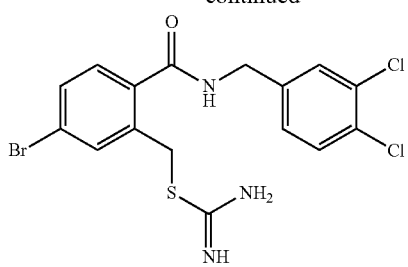
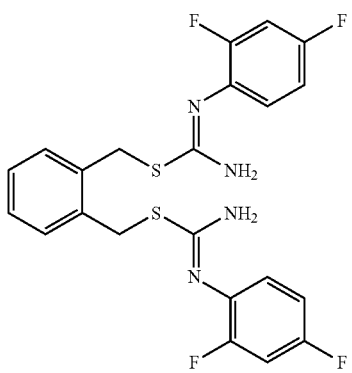
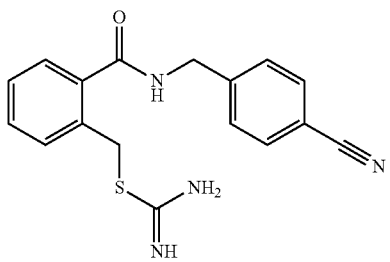
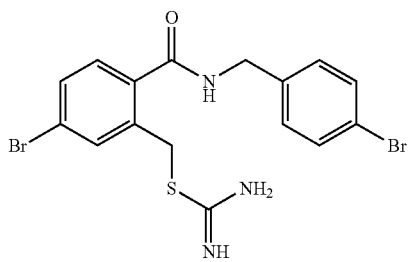
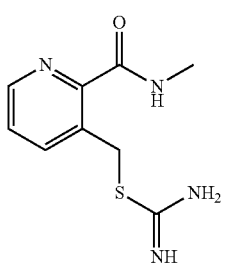
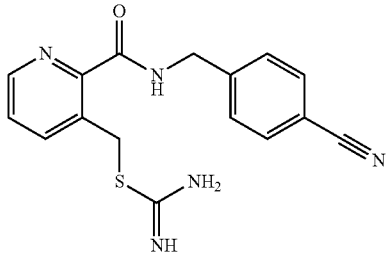
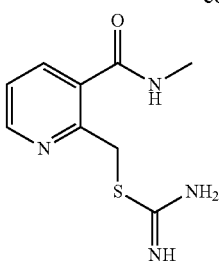
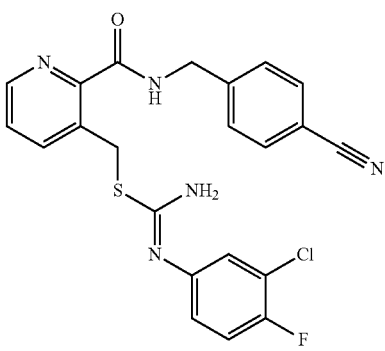
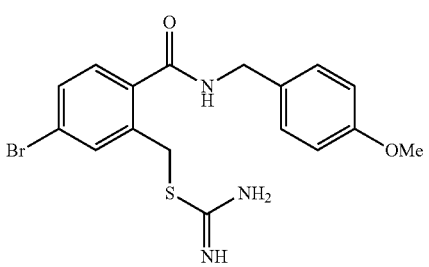
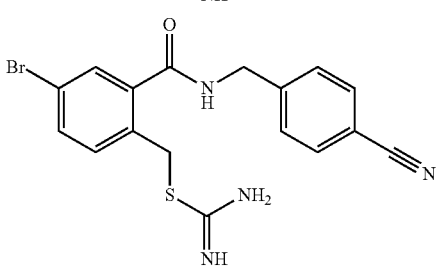
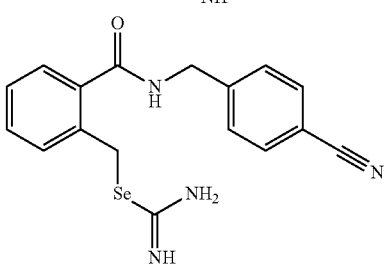
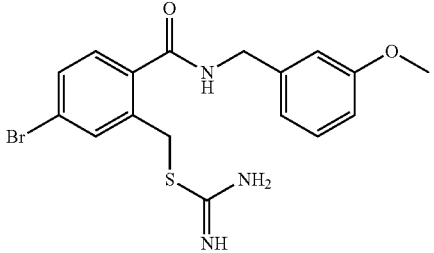

-continued
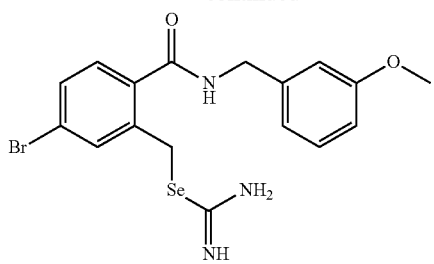
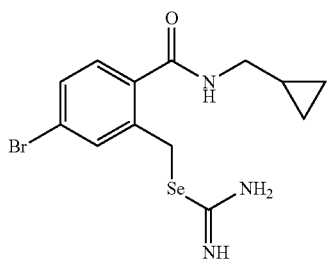
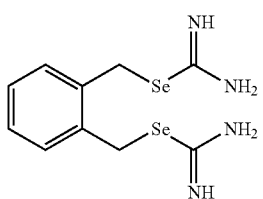
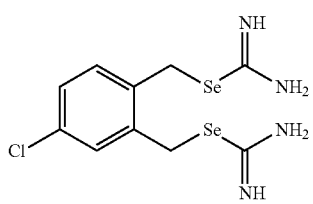
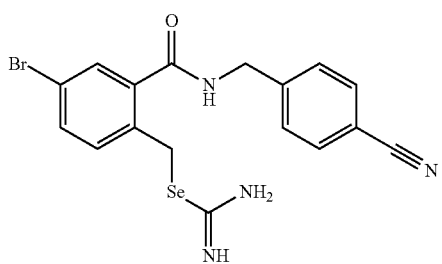
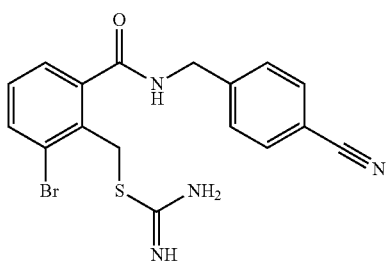
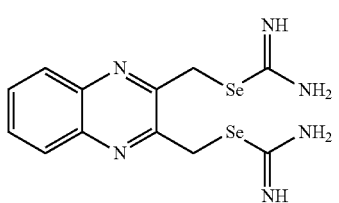
-continued
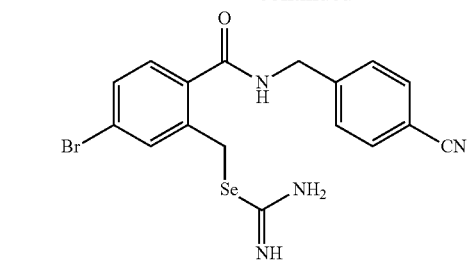
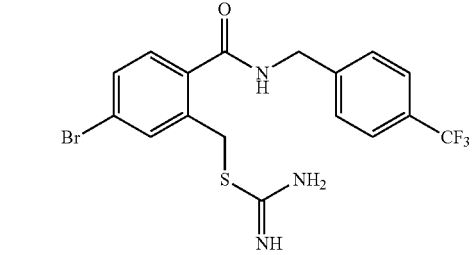
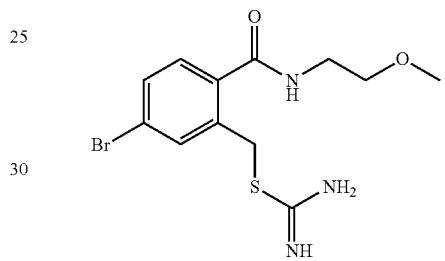
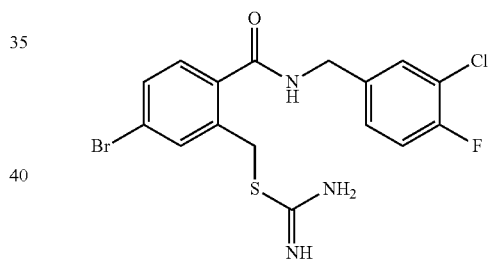
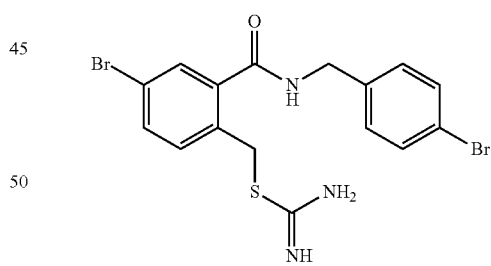
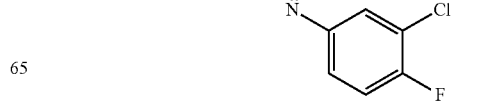

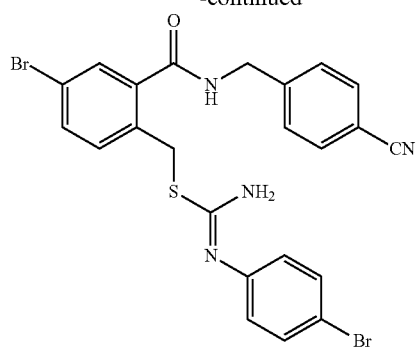
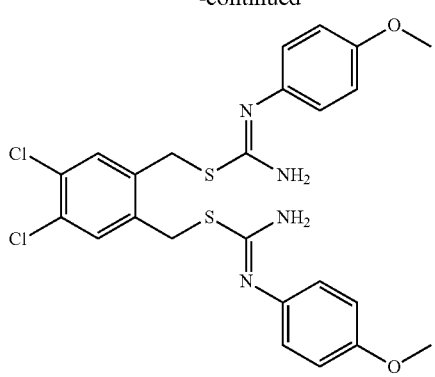
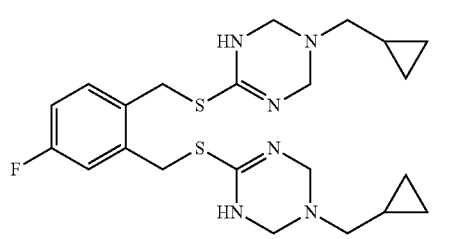
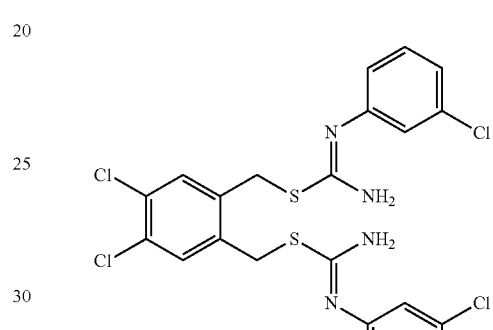
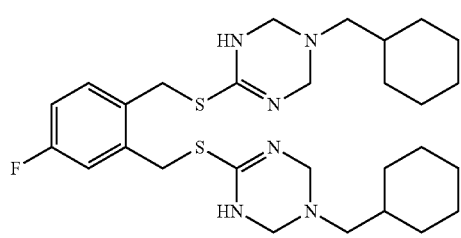
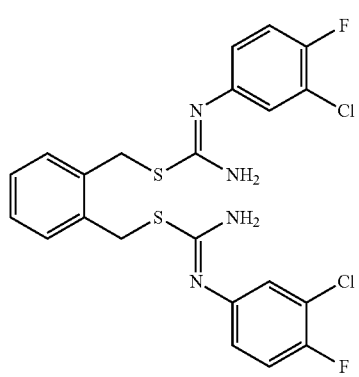
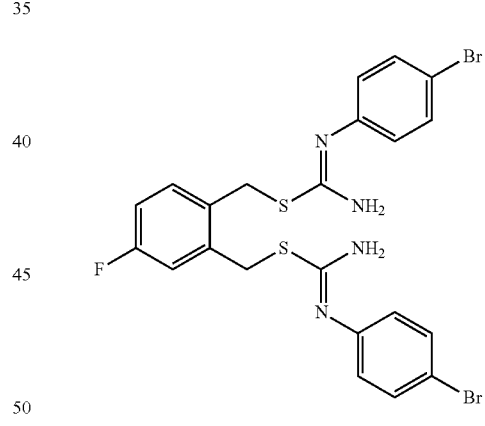
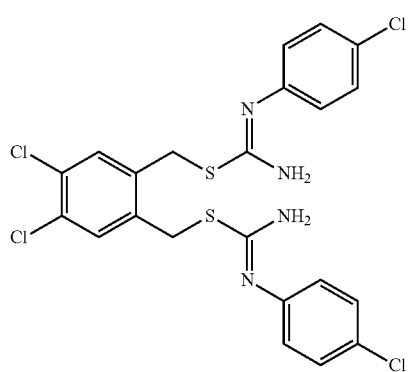
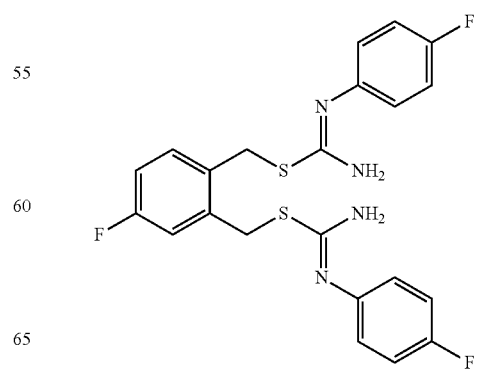

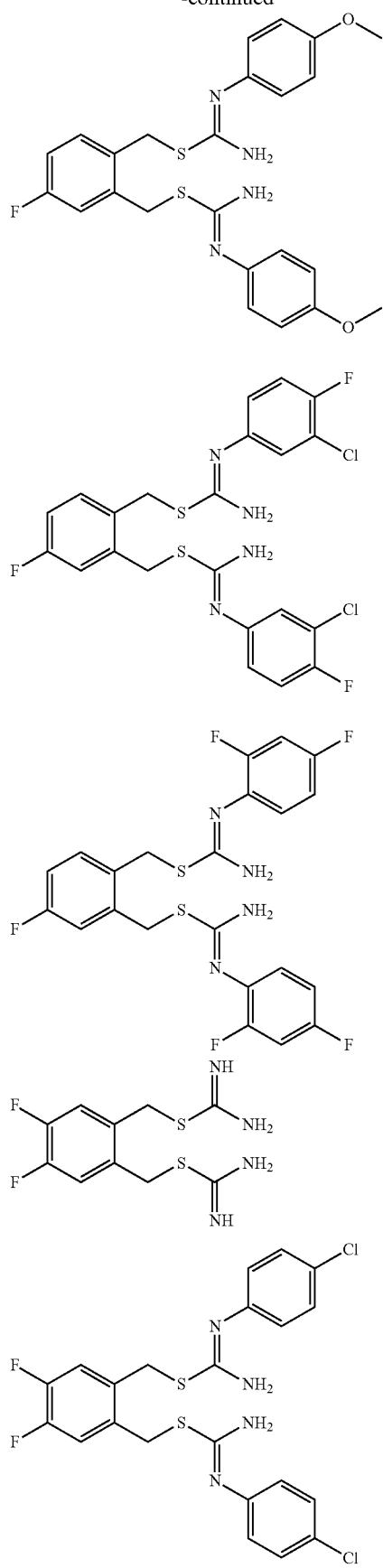
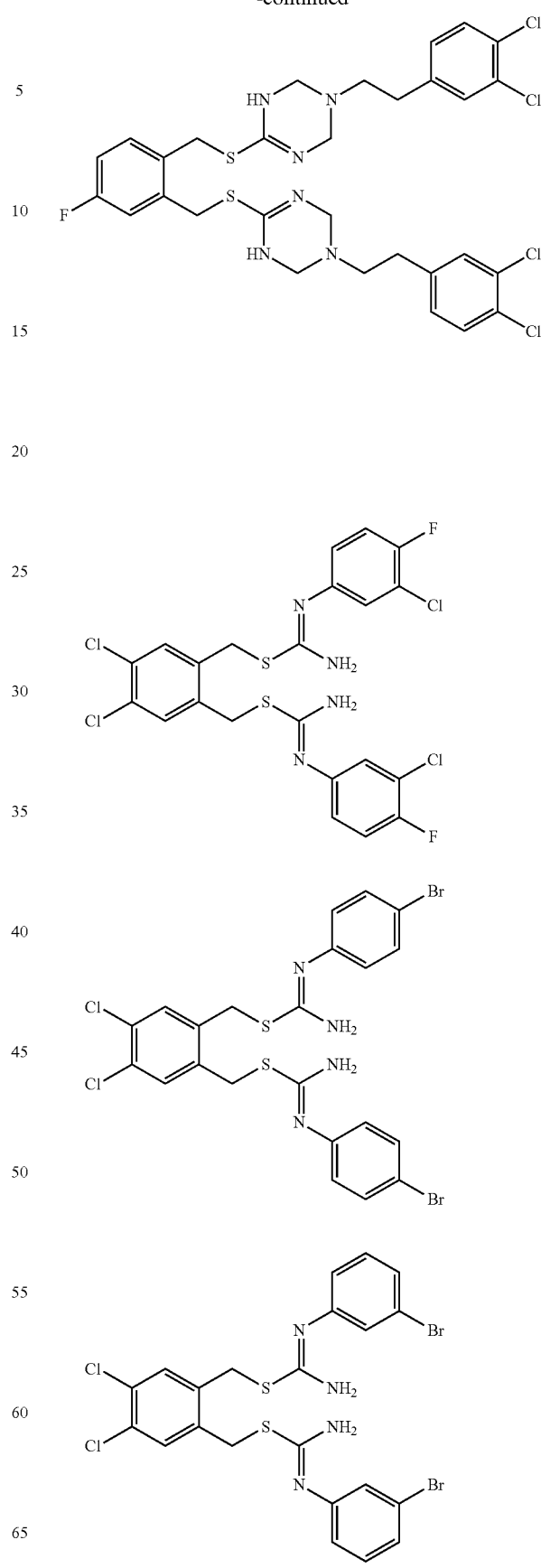

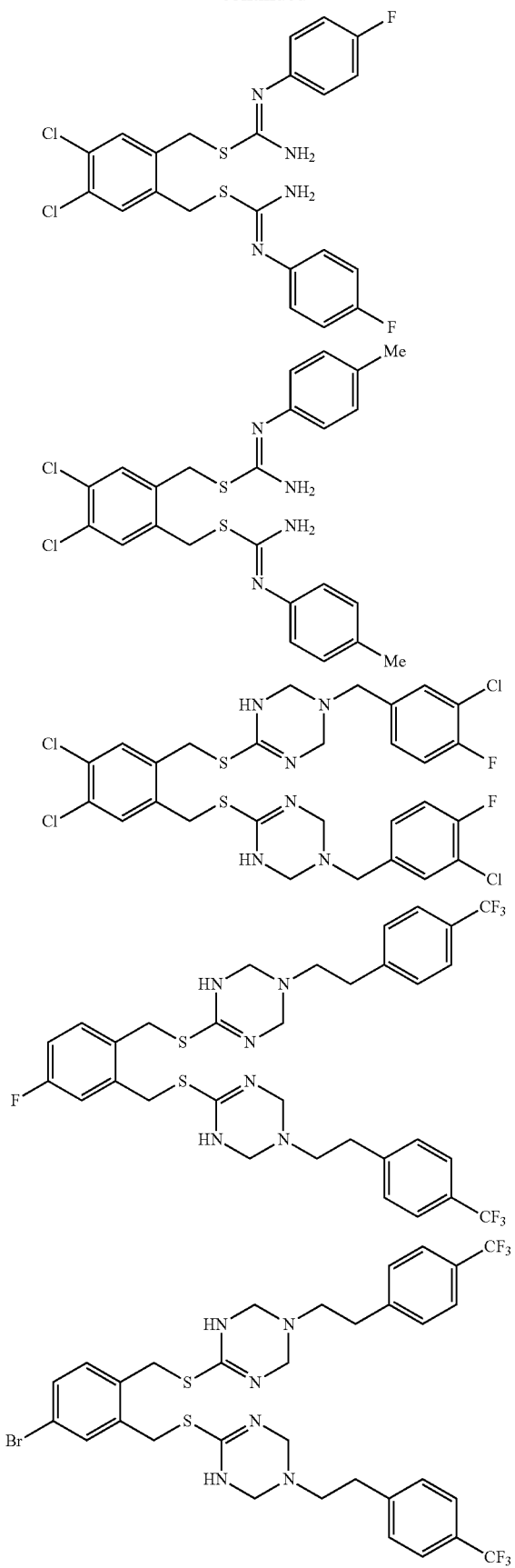
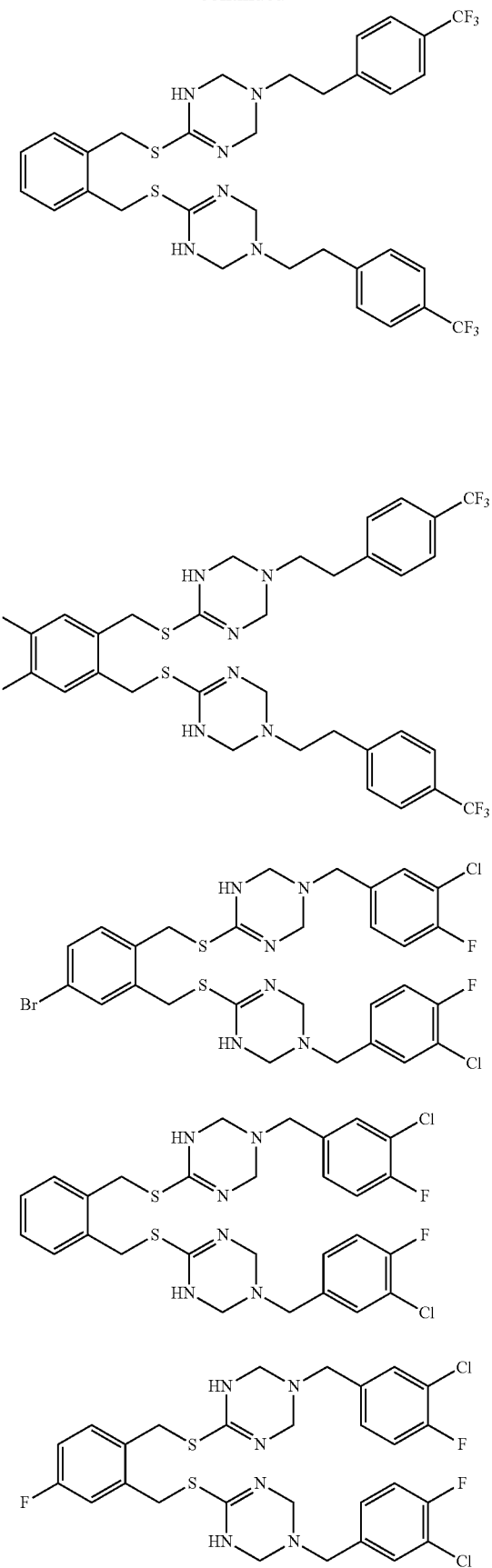

[15] A pharmaceutical composition comprising one or more compounds according to any one of [1] to [14] or pharmaceutically acceptable salts thereof, and a pharmaceutically acceptable carrier.

[16] An inhibitor of IDO and/or TDO, comprising one or more compounds according to any one of [1] to [14] or pharmaceutically acceptable salts thereof as an active ingredient.

[17] A therapeutic agent for a disease or a disorder selected from tumor, infectious disease, neurodegenerative disorder, cataract, organ transplant rejection, autoimmune disease, postoperative cognitive impairment, and disease related to women's reproductive health, comprising one or more compounds according to any one of [1] to [14] or pharmaceutically acceptable salts thereof as an active ingredient.

[18] The therapeutic agent according to [17], wherein the therapeutic agent is an antitumor agent.

[19] The antitumor agent according to [18], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[20] A pharmaceutical kit for treating a disease or a disorder selected from tumor, infectious disease, neurodegenerative disorder, cataract, organ transplant rejection, autoimmune disease, postoperative cognitive impairment, and disease related to women's reproductive health, comprising
(a) one or more compounds according to any one of [1] to [14] or pharmaceutically acceptable salts thereof, and
(b) one or more additional therapeutic agents for treating a disease or disorder selected from tumor, infectious disease, neurodegenerative disorder, cataract, organ transplant rejection, autoimmune disease, postoperative cognitive impairment, and disease related to women's reproductive health, wherein
the compounds or the pharmaceutically acceptable salts thereof and the additional agents are suitable for concurrent, sequential or separate administration.

[21] The pharmaceutical kit according to [20] for treating tumor, comprising
(a) one or more compounds according to any one of [1] to [14] or pharmaceutically acceptable salts thereof, and
(b) one or more additional antitumor agents, wherein
the compounds or the pharmaceutically acceptable salts thereof and the additional agents are suitable for concurrent, sequential or separate administration.

[22] The kit according to [21], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[23] The compound according to any one of [1] to [14] or the pharmaceutically acceptable salt of the compound for use in the treatment of a disease or a disorder selected from tumor, infectious disease, neurodegenerative disorder, cataract, organ transplant rejection, autoimmune disease, postoperative cognitive impairment, and disease related to women's reproductive health.

[24] The compound according to [23] for use in the treatment of tumor.

[25] The compound according to [24], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[26] Use of a compound according to any one of [1] to [14] or a pharmaceutically acceptable salt thereof for producing a medicament treating a disease or a disorder selected from tumor, infectious disease, neurodegenerative disorder, cataract, organ transplant rejection, autoimmune disease, postoperative cognitive impairment, and disease related to women's reproductive health.

[27] The use according to [26] for producing a medicament for treating a tumor.

[28] The use according to [27], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[29] A method for treating a disease or a disorder selected from tumor, infectious disease, neurodegenerative disorder, cataract, organ transplant rejection, autoimmune disease, postoperative cognitive impairment, and disease related to women's reproductive health, comprising administering one or more compounds according to any one of [1] to [14] or pharmaceutically acceptable salts thereof, or a pharmaceutical kit according to any one of [20] to [22] to a patient with the disease or the disorder selected from tumor, infectious disease, neurodegenerative disorder, cataract, organ transplant rejection, autoimmune disease, postoperative cognitive impairment, and disease related to women's reproductive health.

[30] The treatment method according to [29], wherein the disease is a tumor.

[31] The treatment method according to [30], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

Effect of the Invention

The compound of the present invention has excellent inhibitory action on IDO and/or TDO and is applicable as an IDO inhibitor and/or a TDO inhibitor to a wide range of diseases including tumors.

MODE OF CARRYING OUT THE INVENTION

Figure 1:
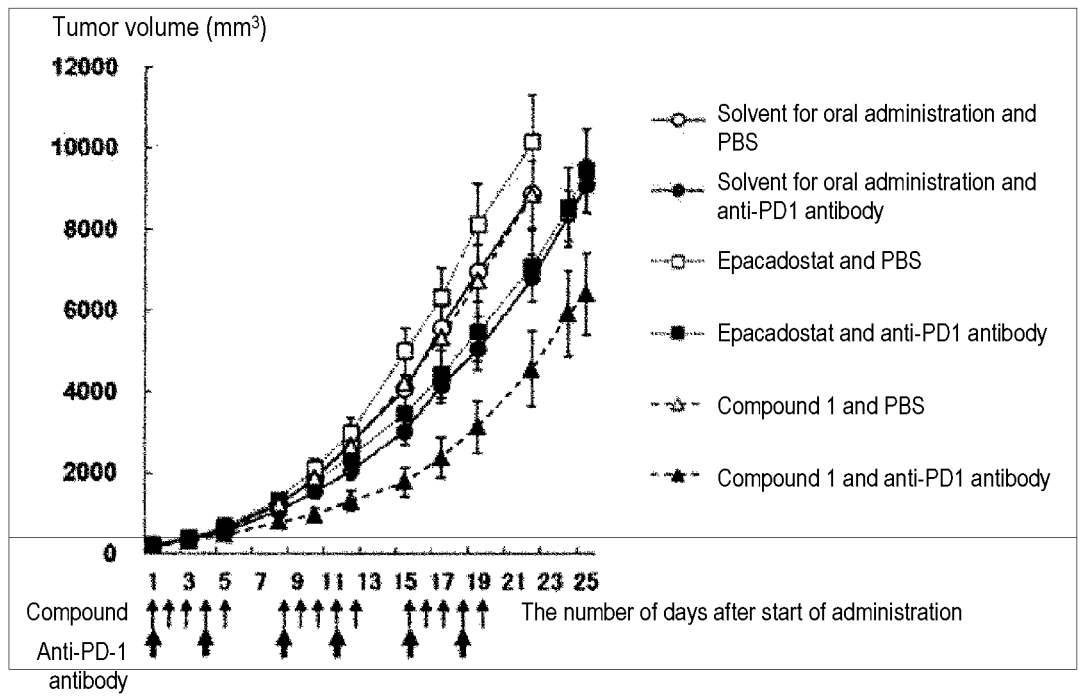
FIG. 1 is a graph showing results of a drug efficacy test on combined use of an IDO/TDO inhibitor and an anti-PD-1 antibody using mice with a subcutaneous CT-26WT syngeneic graft of large intestine cancer.

Hereinafter, the present invention will be described in more detail.

The IDO inhibitor and/or the TDO inhibitor of the present invention comprises a compound of formula (I) or a pharmaceutically acceptable salt of the compound:

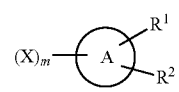

In the formula, ring A represents an aromatic ring, an aliphatic ring, a heterocyclic ring, or a condensed ring of two or more rings selected from an aromatic ring, an aliphatic ring and a heterocyclic ring.

The term "aromatic ring" used in the present application means a cyclic structure that constitutes a single ring or a plurality of rings consisting of hydrocarbon alone and has a delocalized π orbital, or a compound having the cyclic structure. When the aromatic ring is constituted by a plurality of rings, this aromatic ring may be a condensed ring or may be a non-condensed ring (e.g., biphenyl). The phrase "used in the present application" means "described in at least one of the specification, claims, abstract and drawings of the present application".

The term "condensed ring" used in the present application means a cyclic structure where two or more rings are bonded so as to share two or more atoms.

The term "aliphatic ring" used in the present application means a cyclic structure having the properties of both an aliphatic compound (non-aromatic hydrocarbon compound) and a cyclic compound (compound constituted by cyclically bonded atoms), or a compound having the cyclic structure. The aliphatic ring comprises one or more saturated or unsaturated carbon rings having no aromaticity. A spiro compound having a structure where two or more rings are linked through one carbon atom is also included in the "aliphatic ring". When the aliphatic ring is constituted by a plurality of rings, this aliphatic ring may be a condensed ring or may be a non-condensed ring.

The term "heterocyclic ring" used in the present application means a cyclic structure constituted by two or more types of elements, or a compound having the cyclic structure. The heterocyclic ring is constituted by a single ring or a plurality of rings. When the heterocyclic ring is constituted by a plurality of rings, this heterocyclic ring may be a condensed ring or may be a non-condensed ring (e.g., 2,2'-bipyridine and 4,4'-bipyridine).

The term "condensed ring of two or more rings selected from an aromatic ring, an aliphatic ring and a heterocyclic ring" used in the present application means a cyclic structure having a condensed ring of an aromatic ring and an aliphatic ring, a condensed ring of an aliphatic ring and a heterocyclic ring, a condensed ring of an aromatic ring and a heterocyclic ring or a condensed ring of three types of rings, i.e., an aromatic ring, an aliphatic ring and a heterocyclic ring, or a compound having the cyclic structure. The meanings of the aromatic ring, the aliphatic ring and the heterocyclic ring are as defined above.

When ring A represents an aromatic ring, an aliphatic ring, a heterocyclic ring, or a condensed ring of two or more rings selected from an aromatic ring, an aliphatic ring and a heterocyclic ring and when any substituent of the compound of the present application represents a group comprising an aromatic ring, an aliphatic ring, a heterocyclic ring, or a condensed ring of two or more rings selected from an aromatic ring, an aliphatic ring and a heterocyclic ring, these rings can each be completely saturated, partially saturated, or completely unsaturated. Examples of such a ring include benzene, naphthalene, anthracene, phenanthrene, phenalene, biphenylene, pentalene, indene, as-indacene, s-indacene, acenaphthylene, fluorene, fluoranthene, acephenanthrylene, azulene, heptalene, pyrrole, pyrazole, imidazole, 1,2,3-triazole, 1,2,4-triazole, tetrazole, pyrrolidine, furan, tetrahydrofuran, 2-aza-tetrahydrofuran, 3-aza-tetrahydrofuran, oxazole, isoxazole, furazan, 1,2,4-oxadiazole, 1,3,4-oxadiazole, thiophene, isothiazole, thiazole, thiolane, pyridine, pyridazine, pyrimidine, pyrazine, piperidine, 2-azapiperidine, 3-azapiperidine, piperazine, pyran, tetrahydropyran, 2-azapyran, 3-azapyran, 4-azapyran, 2-aza-tetrahydropyran, 3-aza-tetrahydropyran, morpholine, thiopyran, 2-azathiopyran, 3-azathiopyran, 4-azathiopyran, thiane, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, isoquinoline, phthalazine, 6-azaisoquinoline, 7-azaisoquinoline, pteridine, quinoxaline, chromene, isochromene, acridine, phenanthridine, perimidine, phenanthroline, phenoxazine, xanthene, phenoxathiin and thianthrene, and positional isomers of these groups.

In one aspect of the present invention, ring A is selected from the group of rings consisting of benzene, naphthalene, quinoxaline, thiophene, indole, and pyridine.

The "substituent" in the "substituent on a ring atom constituting ring A, represented by each of X, $R^1$ and $R^2$" used in the present application is not particularly limited as long as the function of a TDO or IDO is not impaired. For example, X is selected from the group consisting of a halogen atom, a substituted or unsubstituted linear or branched alkyl group, a substituted or unsubstituted linear or branched alkoxy group, a substituted or unsubstituted linear or branched alkenyl group, a substituted or unsubstituted linear or branched alkenyloxy group, a substituted or unsubstituted linear or branched alkynyl group, a substituted or unsubstituted linear or branched alkynyloxy group, a substituted or unsubstituted cycloalkyl group, a substituted or unsubstituted cycloalkenyl group, an alkyl halide group, an alkyloxy halide group, a cyano group, a hydroxy group, an amino group, a nitro group, a carboxyl group, and a substituted or unsubstituted aryl group, and a substituted or unsubstituted aralkyl group.

X can be bonded to any bondable carbon atom and/or heteroatom of ring A (which represents an aromatic ring, an aliphatic ring, a heterocyclic ring, or a condensed ring of two or more rings selected from an aromatic ring, an aliphatic ring and a heterocyclic ring). Thus, substituent X can also be bonded to any bondable carbon atom and/or heteroatom of an aromatic ring such as a benzene ring as well as a heterocyclic ring or a polycyclic ring such as naphthalene.

For example, X may be selected from the group consisting of a halogen atom, a substituted or unsubstituted linear or branched $C_1$-$C_8$ alkyl group, a substituted or unsubstituted linear or branched $C_1$-$C_8$ alkoxy group, a substituted or unsubstituted linear or branched $C_2$-$C_8$ alkenyl group, a substituted or unsubstituted linear or branched $C_2$-$C_8$ alkenyloxy group, a substituted or unsubstituted linear or branched $C_2$-$C_8$ alkynyl group, a substituted or unsubstituted linear or branched $C_2$-$C_8$ alkynyloxy group, a substituted or unsubstituted $C_3$-$C_8$ cycloalkyl group, a substituted or unsubstituted $C_3$-$C_8$ cycloalkenyl group, a substituted or unsubstituted $C_3$-$C_8$ cycloalkynyl group, a $C_1$-$C_3$ alkyl halide group, a cyano group, a hydroxy group, an amino group, a carboxyl group, a substituted or unsubstituted $C_6$-$C_{18}$ aryl group, and a substituted or unsubstituted aralkyl group (wherein the number of carbon atoms in the aryl moiety is $C_6$-$C_{10}$, and the number of carbon atoms in the alkylene moiety is $C_1$-$C_4$).

For example, X may be selected from the following group:
 as a halogen atom, a fluorine atom, a chlorine atom, a bromine atom, and an iodine atom,
 as a substituted or unsubstituted linear or branched alkyl group, a methyl group, an ethyl group, a n-propyl group, an i-propyl group, a n-butyl group, an i-butyl group, a s-butyl group, a t-butyl group, a n-pentyl group, a n-hexyl group, a n-octyl group, a carboxymethyl group, a 2-carboxyethyl group, a 3-hydroxy-1-propyl group, an aminomethyl group, a 2-aminoethyl group, a hydroxymethyl group, and a 2-hydroxyethyl group,
 as a substituted or unsubstituted linear or branched alkoxy group, a methoxy group, an ethoxy group, a n-propoxy group, and a n-butoxy group,
 as a substituted or unsubstituted linear or branched alkenyl group, an ethenyl (vinyl) group, a 2-propenyl (allyl) group, and a 3-butenyl group,
 as a substituted or unsubstituted linear or branched alkenyloxy group, an ethenyloxy (vinyloxy) group, a 2-propenyloxy (allyloxy) group, and a 3-butenyloxy group,
 as a substituted or unsubstituted linear or branched alkynyl group, an ethynyl group, a 2-propynyl group, and a 3-butynyl group,
 as a substituted or unsubstituted linear or branched alkynyloxy group, an ethynyloxy group, a 2-propynyloxy group, and a 3-butynyloxy group,
 as a substituted or unsubstituted cycloalkyl group, a cyclopropyl group, a cyclobutyl group, a cyclopentyl group, a cyclohexyl group, and a cyclooctyl group,
 as a substituted or unsubstituted cycloalkenyl group, a 1-cyclopropenyl group, a 1-cyclobutenyl group, a 1-cyclopentenyl group, and a 1-cyclohexenyl group,
 as an alkyl halide group, a fluoromethyl group (—$CH_2F$), a difluoromethyl group (—$CHF_2$), a chloromethyl group (—$CH_2Cl$), a bromomethyl group (—$CH_2Br$), an iodomethyl group (—$CH_2I$), a trifluoromethyl group (—$CF_3$), a trichloromethyl group (—$CCl_3$), a tribromomethyl group (—$CBr_3$), a triiodomethyl group (—$CI_3$), a 2,2,2-trifluoroethyl group (—$CH_2CF_3$), a 2,2,2-trichloroethyl group (—$CH_2CCl_3$), a 2,2,2-tribromoethyl group (—$CH_2CBr_3$), a 2,2,2-triiodoethyl group (—$CH_2CI_3$), and a pentafluoroethyl group (—$C_2F_5$),
 as an alkyloxy halide group, a fluoromethoxy group (—$OCH_2F$), a difluoromethoxy group (—$OCHF_2$), a chloromethoxy group (—$OCH_2Cl$), a bromomethoxy group (—$OCH_2Br$), an iodomethoxy group (—$OCH_2I$), a trifluoromethoxy group (—$OCF_3$), a trichloromethoxy group (—$OCCl_3$), a tribromomethoxy group (—$OCBr_3$), a triiodomethoxy group (—$OCI_3$), a 2,2,2-trifluoroethoxy group (—$OCH_2CF_3$), a 2,2,2-trichloroethoxy group (—$OCH_2CCl_3$), a 2,2,2-tribromoethoxy group (—$OCH_2CBr_3$), a 2,2,2-triiodoethoxy group (—$OCH_2CI_3$), and a pentafluoroethoxy group (—$OC_2F_5$),
 a cyano group,
 a hydroxy group, an amino group,
a nitro group,
a carboxyl group,
as a substituted or unsubstituted aryl group, a phenyl group, a naphthalen-1-yl group, and a naphthalen-2-yl group, and
as a substituted or unsubstituted aralkyl group, a benzyl group, a phenethyl group, and a 3-phenyl-1-propyl group.

$R^1$ represents a group represented by formula (II):

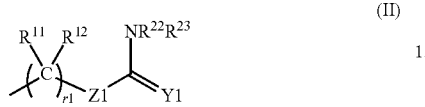

(II)

(wherein $R^{11}$ and $R^{12}$ each independently represent a hydrogen atom, a fluorine atom or a substituted or unsubstituted alkyl group, Y1 represents O or $NR^{21}$, $R^{21}$, $R^{22}$ and $R^{23}$ each independently represent a hydrogen atom, a substituted or unsubstituted linear or branched alkyl group, a substituted or unsubstituted cycloalkyl group, a substituted or unsubstituted aryl group or a substituted or unsubstituted heterocyclic group, $R^{21}$ and $R^{22}$ or $R^{23}$ are optionally bonded to each other to form a ring, Z1 represents S, SO, $SO_2$, O or Se, and r1 represents any integer of 1 to 8), or formula (III):

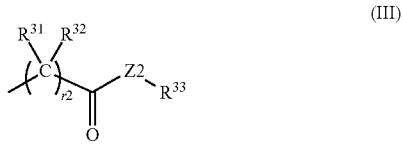

(III)

(wherein $R^{31}$ and $R^{32}$ each independently represent a hydrogen atom, a fluorine atom or a substituted or unsubstituted linear or branched alkyl group, Z2 represents O or $NR^{61}$ (wherein $R^{61}$ represents a hydrogen atom, a substituted or unsubstituted linear or branched alkyl group or a substituted or unsubstituted aryl group), $R^{33}$ represents a substituted or unsubstituted linear or branched alkyl group, a substituted or unsubstituted cycloalkyl group, a substituted or unsubstituted aryl group, a substituted or unsubstituted aralkyl group or a substituted or unsubstituted cycloalkylalkyl group, and r2 represents 0 or any integer of 1 to 8), and $R^2$ represents, independently from R', a group represented by formula (II) or formula (III).

In a preferred aspect of the present invention, $R^1$ represents a group represented by formula (II), and $R^2$ represents a group represented by formula (II) or formula (III). When $R^2$ is a group represented by formula (II), specific groups of $R^1$ and $R^2$ may be any group as long as the groups are included in the scopes defined in formula (II). $R^1$ and $R^2$ are not necessarily required to be the same group.

In a preferred aspect of the present invention, $R^1$ represents a group represented by formula (II), and $R^2$ represents a group represented by formula (II). In this case, specific groups of $R^1$ and $R^2$ may be any group as long as the groups are included in the scopes defined in formula (II). $R^1$ and $R^2$ are not necessarily required to be the same group.

In a preferred aspect of the present invention, $R^1$ represents a group represented by formula (II), and $R^2$ represents a group represented by formula (III).

In a preferred aspect of the present invention, $R^1$ represents a group represented by formula (III), and $R^2$ represents a group represented by formula (II).

In a preferred aspect of the present invention, $R^1$ represents a group represented by formula (III), and $R^2$ represents a group represented by formula (III). In this case, specific groups of $R^1$ and $R^2$ may be any group as long as the groups are included in the scopes defined in formula (III). $R^1$ and $R^2$ are not necessarily required to be the same group.

In formula (II), the functional group containing the ring formed by $R^{21}$ and $R^{22}$ or $R^{23}$ bonded to each other is, for example, a functional group represented by the following formula (IV):

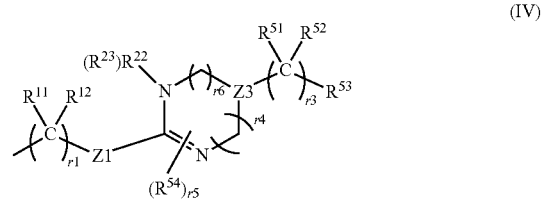

(IV)

[wherein $R^{11}$, $R^{12}$, r1, Z1, $R^{22}$ and $R^{23}$ represent the same meaning as described in formula (II), Z3 represents CH, $CR^{54}$ or N, $R^{51}$ and $R^{52}$ each independently represent a hydrogen atom or a substituted or unsubstituted linear or branched alkyl group, $R^{54}$ represents a halogen atom or a substituted or unsubstituted linear or branched alkyl group, $R^{53}$ represents a substituted or unsubstituted aryl group, a substituted or unsubstituted cycloalkyl group or a substituted or unsubstituted heterocyclic group, r3 represents any integer of 1 to 8, r4 and r6 each independently represent 0 or 1, r4 and r6 are not 0 at the same time, r5 represents 0 or any integer of 1 to 5, and the notation $R^{22}(R^{23})$ represents any one of $R^{22}$ and $R^{23}$).

$R^1$ and $R^2$ are the same or different and are each independently selected from the group consisting of, for example, the following groups:

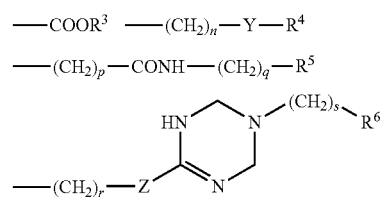

In the formula,
Y is selected from the group consisting of O, S, and Se,
Z is selected from the group consisting of O, S, and Se,
n represents an integer of 1 to 8,
p represents an integer of 0 to 8,
q represents an integer of 1 to 8,
r represents an integer of 1 to 8,
s represents an integer of 1 to 8,
$R^3$ represents a substituted or unsubstituted linear or branched alkyl group,
$R^4$ represents a substituted or unsubstituted heterocyclic group, —$CONH_2$, or

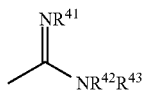

(wherein $R^{41}$, $R^{42}$ and $R^{43}$ are the same or different and are selected from the group consisting of a hydrogen atom, a substituted or unsubstituted linear or branched alkyl group, a substituted or unsubstituted cycloalkyl group, a substituted or unsubstituted aryl group and a substituted or unsubstituted heterocyclic group), $R^5$ is selected from the group consisting of a hydrogen atom, a substituted or unsubstituted cycloalkyl group, and a substituted or unsubstituted aryl group, and $R^6$ is selected from the group consisting of a substituted or unsubstituted aryl group, a substituted or unsubstituted cycloalkyl group, and a substituted or unsubstituted heterocyclic group.

In one aspect of the present invention, r1 represents an integer of 1 to 8. In one aspect of the present invention, r1 represents an integer of 1 to 6. In one aspect of the present invention, r1 represents an integer of 1 to 4. In one aspect of the present invention, r1 represents an integer of 1 or 2. In one aspect of the present invention, r1 represents 1.

In one aspect of the present invention, r2 represents 0 or an integer of 1 to 8. In one aspect of the present invention, r2 represents 0. In one aspect of the present invention, r2 represents an integer of 1 to 6. In one aspect of the present invention, r2 represents an integer of 1 to 4. In one aspect of the present invention, r2 represents an integer of 1 or 2. In one aspect of the present invention, r2 represents 1.

In one aspect of the present invention, r3 represents an integer of 1 to 8. In one aspect of the present invention, r3 represents an integer of 1 to 6. In one aspect of the present invention, r3 represents an integer of 1 to 4. In one aspect of the present invention, r3 represents an integer of 1 or 2. In one aspect of the present invention, r3 represents 1.

In one aspect of the present invention, r4 represents 0 or 1. In one aspect of the present invention, r4 represents 0. In one aspect of the present invention, r4 represents 1.

In one aspect of the present invention, r5 represents 0 or any integer of 1 to 5. In one aspect of the present invention, r5 represents 0. In one aspect of the present invention, r5 represents an integer of 1 to 5. In one aspect of the present invention, r5 represents an integer of 1 to 4. In one aspect of the present invention, r5 represents an integer of 1 or 2. In one aspect of the present invention, r5 represents 1.

In one aspect of the present invention, r6 represents 0 or 1. In one aspect of the present invention, r6 represents 0. In one aspect of the present invention, r6 represents 1.

r4 and r6 are not 0 at the same time.

In one aspect of the present invention, n represents an integer of 1 to 8. In one aspect of the present invention, n represents an integer of 1 to 6. In one aspect of the present invention, n represents an integer of 1 to 4. In one aspect of the present invention, n represents an integer of 1 or 2. In one aspect of the present invention, n represents 1.

In one aspect of the present invention, p represents an integer of 0 to 8. In one aspect of the present invention, p represents an integer of 0 to 6. In one aspect of the present invention, p represents an integer of 0 to 4. In one aspect of the present invention, p represents an integer of 0 to 2. In one aspect of the present invention, p represents 0. In one aspect of the present invention, p represents 1.

In one aspect of the present invention, q represents an integer of 1 to 8. In one aspect of the present invention, q represents an integer of 1 to 6. In one aspect of the present invention, q represents an integer of 1 to 4. In one aspect of the present invention, q represents an integer of 1 or 2. In one aspect of the present invention, q represents 1. In one aspect of the present invention, q represents 2. In one aspect of the present invention, q represents 4.

In one aspect of the present invention, r represents an integer of 1 to 8. In one aspect of the present invention, r represents an integer of 1 to 6. In one aspect of the present invention, r represents an integer of 1 to 4. In one aspect of the present invention, r represents an integer of 1 or 2. In one aspect of the present invention, r represents 1.

In one aspect of the present invention, s represents an integer of 1 to 8. In one aspect of the present invention, s represents an integer of 1 to 6. In one aspect of the present invention, s represents an integer of 1 to 4. In one aspect of the present invention, s represents an integer of 1 or 2. In one aspect of the present invention, s represents 1. In one aspect of the present invention, s represents 2.

The substitution positions of $R^1$ and $R^2$ on the ring atoms of ring A are not particularly limited. For example, $R^1$ and $R^2$ may be bonded to adjacent ring atoms of ring A. For example, $R^1$ and $R^2$ may be bonded to ring atoms sandwiching one ring atom, i.e., two ring atoms away from their respective partners, in ring A.

$R^1$ and $R^2$ may have the same group. $R^1$ and $R^2$ may have groups different from each other.

The term "halogen atom" used in the present application means fluoro (F), chloro (Cl), bromo (Br) or iodo (I). The term "halide" used in the present application means a group in which one or more hydrogen atoms on one or more carbon atoms of the group are replaced with halogen atoms. When two or more hydrogen atoms are replaced with halogen atoms, the two or more halogen atoms are the same or different. A compound having a halogen atom as a substituent or a compound having a substituent comprising a halogen atom is also referred to as a "halogen compound".

The term "substituted" in the term "substituted or unsubstituted" used in the present application means having one or more substituents, and the term "unsubstituted" means having no substituent.

The term "linear" used in the present application means a structure where atoms other than a hydrogen atom are linked in a straight line-like arrangement without being branched.

The term "branched" used in the present application means a structure where any one or more carbon atoms are bonded to two or more other carbon atoms.

The term "alkyl group" used in the present application means a hydrocarbon group formed by the removal of one hydrogen atom from any carbon atom of alkane (aliphatic saturated hydrocarbon) represented by the general formula $C_nH_{2n+2}$ (wherein n represents a positive integer). The number of carbon atoms in the alkyl group is not particularly limited. In one aspect of the present invention, the alkyl group is an alkyl group having 1 to 20 carbon atoms. In one aspect of the present invention, the alkyl group is an alkyl group having 1 to 16 carbon atoms. In one aspect of the present invention, the alkyl group is an alkyl group having 1 to 12 carbon atoms. In one aspect of the present invention, the alkyl group is an alkyl group having 1 to 10 carbon atoms. In one aspect of the present invention, the alkyl group is an alkyl group having 1 to 8 carbon atoms. In one aspect of the present invention, the alkyl group is an alkyl group having 1 to 6 carbon atoms. In one aspect of the present invention, the alkyl group is an alkyl group having 1 to 4 carbon atoms.

Examples of the "alkyl group" can include a methyl group, an ethyl group, a n-propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group, a 1-propylbutyl group, and a n-octyl group.

The term "alkoxy group" used in the present application means a group represented by "—O-alkyl group". The "alkyl group" is as defined above. The term "substituted or unsubstituted linear or branched alkoxy group" used in the present application means "—O-substituted or unsubstituted linear or branched alkyl group". The number of carbon atoms in the alkyl group in the "alkoxy group" is not particularly limited. In one aspect of the present invention, the alkyl group is an alkyl group having 1 to 20 carbon atoms. In one aspect of the present invention, the alkyl group is an alkyl group having 1 to 16 carbon atoms. In one aspect of the present invention, the alkyl group is an alkyl group having 1 to 12 carbon atoms. In one aspect of the present invention, the alkyl group is an alkyl group having 1 to 10 carbon atoms. In one aspect of the present invention, the alkyl group is an alkyl group having 1 to 8 carbon atoms. In one aspect of the present invention, the alkyl group is an alkyl group having 1 to 6 carbon atoms. In one aspect of the present invention, the alkyl group is an alkyl group having 1 to 4 carbon atoms.

Examples of the "alkoxy group" can include a methoxy group, an ethoxy group, a n-propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, a 1-propylbutoxy group, and a n-octyloxy group.

The term "alkenyl group" used in the present application means a hydrocarbon group having only one carbon-carbon double bond in the molecule, formed by the removal of one hydrogen atom from any carbon atom of alkene (olefinic hydrocarbon) represented by the general formula $C_{11}H_{211}$ (wherein n represents a positive integer of 2 or larger). The number of carbon atoms in the alkenyl group is not particularly limited. In one aspect of the present invention, the alkenyl group is an alkenyl group having 2 to 20 carbon atoms. In one aspect of the present invention, the alkenyl group is an alkenyl group having 2 to 16 carbon atoms. In one aspect of the present invention, the alkenyl group is an alkenyl group having 2 to 12 carbon atoms. In one aspect of the present invention, the alkenyl group is an alkenyl group having 2 to 10 carbon atoms. In one aspect of the present invention, the alkenyl group is an alkenyl group having 2 to 8 carbon atoms. In one aspect of the present invention, the alkenyl group is an alkenyl group having 2 to 6 carbon atoms. In one aspect of the present invention, the alkenyl group is an alkenyl group having 2 to 4 carbon atoms.

Examples of the "alkenyl group" can include an ethenyl group (vinyl group), a 1-propenyl group, a 2-propenyl group (allyl group), a 1-butenyl group, a 2-butenyl group, a 3-butenyl group, an isobutenyl group, a 1-pentenyl group, a 2-pentenyl group, a 3-pentenyl group, a 4-pentenyl group, a 1-hexenyl group, a 2-hexenyl group, a 3-hexenyl group, a 1-octenyl group, a 2-octenyl group, a 3-octenyl group, and a 4-octenyl group.

The term "alkenyloxy group" used in the present application means a group represented by "—O-alkenyl group". The "alkenyl group" is as define above. The term "substituted or unsubstituted linear or branched alkenyl group" used in the present application means "—O-substituted or unsubstituted linear or branched alkenyl group". The number of carbon atoms in the alkenyl group in the "alkenyloxy group" is not particularly limited. In one aspect of the present invention, the alkenyl group is an alkenyl group having 2 to 20 carbon atoms. In one aspect of the present invention, the alkenyl group is an alkenyl group having 2 to 16 carbon atoms. In one aspect of the present invention, the alkenyl group is an alkenyl group having 1 to 12 carbon atoms. In one aspect of the present invention, the alkenyl group is an alkenyl group having 2 to 10 carbon atoms. In one aspect of the present invention, the alkenyl group is an alkenyl group having 2 to 8 carbon atoms. In one aspect of the present invention, the alkenyl group is an alkenyl group having 2 to 6 carbon atoms. In one aspect of the present invention, the alkenyl group is an alkenyl group having 2 to 4 carbon atoms.

Examples of the "alkenyloxy group" can include an ethenyloxy group (vinyloxy group), a 1-propenyloxy group, a 2-propenyloxy group (allyloxy group), a 1-butenyloxy group, a 2-butenyloxy group, a 3-butenyloxy group, an isobutenyloxy group, a 1-pentenyloxy group, a 2-pentenyloxy group, a 3-pentenyloxy group, a 4-pentenyloxy group, a 1-hexenyloxy group, a 2-hexenyloxy group, a 3-hexenyloxy group, a 1-octenyloxy group, a 2-octenyloxy group, a 3-octenyloxy group, and a 4-octenyloxy group.

The term "alkynyl group" used in the present application means a hydrocarbon group having only one carbon-carbon triple bond in the molecule, formed by the removal of one hydrogen atom from any carbon atom of alkyne (acetylenic hydrocarbon) represented by the general formula $C_{11}H_{211-2}$ (wherein n represents a positive integer of 2 or larger). In one aspect of the present invention, the alkynyl group is an alkynyl group having 1 to 12 carbon atoms. In one aspect of the present invention, the alkynyl group is an alkynyl group having 2 to 10 carbon atoms. In one aspect of the present invention, the alkynyl group is an alkynyl group having 2 to 8 carbon atoms. In one aspect of the present invention, the alkynyl group is an alkynyl group having 2 to 6 carbon atoms. In one aspect of the present invention, the alkynyl group is an alkynyl group having 2 to 4 carbon atoms.

Examples of the "alkynyl group" can include an ethynyl group, a 1-propynyl group, a 2-propynyl group (propargyl group), a 1-butynyl group, a 2-butynyl group, a 3-butynyl group, a 1-methyl-2-propynyl group, a 2-methyl-3-butynyl group, a 1-pentynyl group, 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group, a 1-octynyl group, a 2-octynyl group, a 3-octynyl group, and a 4-octynyl group.

The term "alkynyloxy group" used in the present application means a group represented by "—O— alkynyl group". The "alkynyl group" is as defined above. The term "substituted or unsubstituted linear or branched alkynyl group" used in the present application means "—O-substituted or unsubstituted linear or branched alkynyl group". The number of carbon atoms in the alkynyl group in the "alkynyloxy group" is not particularly limited. In one aspect of the present invention, the alkynyl group is an alkynyl group having 1 to 12 carbon atoms. In one aspect of the present invention, the alkynyl group is an alkynyl group having 2 to 10 carbon atoms. In one aspect of the present invention, the alkynyl group is an alkynyl group having 2 to 8 carbon atoms. In one aspect of the present invention, the alkynyl group is an alkynyl group having 2 to 6 carbon atoms. In one aspect of the present invention, the alkynyl group is an alkynyl group having 2 to 4 carbon atoms.

Examples of the "alkynyloxy group" can include an ethynyloxy group, a 1-propynyloxy group, a 2-propynyloxy group (propargyloxy group), a 1-butynyloxy group, a 2-butynyloxy group, a 3-butynyloxy group, a 1-methyl-2-propynyloxy group, a 2-methyl-3-butynyloxy group, a 1-pentynyloxy group, 2-pentynyloxy group, a 3-pentynyloxy group, a 4-pentynyloxy group, a 1-methyl-2-butynyloxy group, a 2-methyl-3-pentynyloxy group, a 1-hexynyloxy group, a 1,1-dimethyl-2-butynyloxy group, a 1-octynyloxy group, a 2-octynyloxy group, a 3-octynyloxy group, and a 4-octynyloxy group.

The term "cycloalkyl group" used in the present application means a hydrocarbon group formed by the removal of one hydrogen atom from any carbon atom of cycloalkane (cyclic saturated hydrocarbon) represented by the general formula $C_nH_{2n}$ (wherein n represents a positive integer of 3 or larger). In one aspect of the present invention, the cycloalkyl group is a cycloalkyl group having 3 to 12 carbon atoms. In one aspect of the present invention, the cycloalkyl group is a cycloalkyl group having 3 to 10 carbon atoms. In one aspect of the present invention, the cycloalkyl group is a cycloalkyl group having 3 to 8 carbon atoms. In one aspect of the present invention, the cycloalkyl group is a cycloalkyl group having 3 to 6 carbon atoms. In one aspect of the present invention, the cycloalkyl group is a cycloalkyl group having 3 or 4 carbon atoms.

Examples of the "cycloalkyl group" can include a cyclopropyl group, a cyclobutyl group, a cyclopentyl group, a cyclohexyl group, a cycloheptyl group, a cyclooctyl group, a cyclononyl group, and a cyclodecyl group.

The term "cycloalkenyl group" used in the present application means a hydrocarbon group formed by the removal of one hydrogen atom from any carbon atom of cycloalkene (cyclic alkene) represented by the general formula $C_nH_{2n-2}$ (wherein n represents a positive integer of 3 or larger). In one aspect of the present invention, the cycloalkenyl group is a cycloalkenyl group having 3 to 12 carbon atoms. In one aspect of the present invention, the cycloalkenyl group is a cycloalkenyl group having 3 to 10 carbon atoms. In one aspect of the present invention, the cycloalkenyl group is a cycloalkenyl group having 3 to 8 carbon atoms. In one aspect of the present invention, the cycloalkenyl group is a cycloalkenyl group having 3 to 6 carbon atoms. In one aspect of the present invention, the cycloalkenyl group is a cycloalkenyl group having 3 or 4 carbon atoms.

Examples of the "cycloalkenyl group" can include a cyclopropenyl group, a cyclobutenyl group, a cyclopentenyl group, a cyclohexenyl group, a cycloheptenyl group, a cyclooctenyl group, a cyclononenyl group, and a cyclodecenyl group.

The term "cycloalkynyl group" used in the present application means a hydrocarbon group formed by the removal of one hydrogen atom from any carbon atom of cycloalkyne (cyclic alkyne) represented by the general formula $C_nH_{2n-4}$ (wherein n represents a positive integer of 3 or larger). In one aspect of the present invention, the cycloalkynyl group is a cycloalkynyl group having 8 to 20 carbon atoms. In one aspect of the present invention, the cycloalkynyl group is a cycloalkynyl group having 10 to 16 carbon atoms. In one aspect of the present invention, the cycloalkynyl group is a cycloalkynyl group having 10 to 12 carbon atoms. In one aspect of the present invention, the cycloalkynyl group is a cycloalkynyl group having 8 to 12 carbon atoms. In one aspect of the present invention, the cycloalkynyl group is a cycloalkynyl group having 8 to 10 carbon atoms.

Examples of the "cycloalkynyl group" can include a cyclooctynyl group, a cyclononynyl group, a cyclodecynyl group, a cycloundecynyl group, and a cyclododecynyl group.

The term "aryl group" used in the present application means a hydrocarbon group formed by the removal of one hydrogen atom bonded to a ring atom of the aromatic ring of a compound having an aromatic ring, i.e., aromatic hydrocarbon. The meaning of the aromatic ring is as defined above. In one aspect of the present invention, the aryl group is an aryl group having 6 to 22 ring carbon atoms. In one aspect of the present invention, the aryl group is an aryl group having 6 to 18 ring carbon atoms. In one aspect of the present invention, the aryl group is an aryl group having 6 to 14 ring carbon atoms. In one aspect of the present invention, the aryl group is an aryl group having 6 to 10 ring carbon atoms. In one aspect of the present invention, the aryl group is an aryl group having 6 ring carbon atoms (phenyl group).

Examples of the "aryl group" include a phenyl group, an o-tolyl group, a m-tolyl group, a p-tolyl group, a naphthyl group, an o-xylyl group, a m-xylyl group, and a p-xylyl group.

The term "aralkyl group" used in the present application means an alkyl group in which one hydrogen atom of the alkyl group $(C_nH_{2n+1})$ is replaced with an aryl group. In one aspect of the present invention, the aralkyl group is an aralkyl group having 7 to 26 carbon atoms (among which the number of ring carbon atoms is 6 to 22). In one aspect of the present invention, the aralkyl group is an aralkyl group having 7 to 22 carbon atoms (among which the number of ring carbon atoms is 6 to 18). In one aspect of the present invention, the aralkyl group is an aralkyl group having 7 to 18 carbon atoms (among which the number of ring carbon atoms is 6 to 14). In one aspect of the present invention, the aralkyl group is an aralkyl group having 7 to 14 carbon atoms (among which the number of ring carbon atoms is 6 to 14). In one aspect of the present invention, the aralkyl group is an aralkyl group having 7 to 8 carbon atoms (among which the number of ring carbon atoms is 6).

Examples of the "aralkyl group" include a benzyl group (phenylmethyl group) and a phenethyl group (phenylethyl group).

In one aspect of the present invention, the compound of formula (I) is the following compound (I-0a) wherein $R^1$ and $R^2$ have a group of formula (II) described above and are bonded to adjacent ring atoms of ring A.

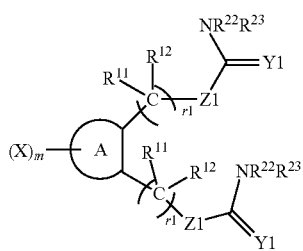

(I-0a)

(wherein A, X, m, Y1, Z1, $R^{11}$, $R^{12}$, $R^{22}$, $R^{23}$, and r1 have the same meaning as described above).

For example, Y1 represents O.

For example, Y1 represents $NR^{21}$ (wherein $R^{21}$ represents a hydrogen atom, a substituted or unsubstituted linear or branched alkyl group, a substituted or unsubstituted cycloalkyl group, a substituted or unsubstituted aryl group or a substituted or unsubstituted heterocyclic group).

For example, Z1 represents S, SO or $SO_2$.

For example, Z1 represents O.

For example, Z1 represents Se.

In one aspect of the present invention, when the functional group containing the ring formed by at least one $R^{21}$ and $R^{22}$ or $R^{23}$ bonded to each other in the compound of formula (I-0a) described above is represented by formula (IV) described above, the compound is any of the following compounds (I-0a-1) to (I-0a-3).

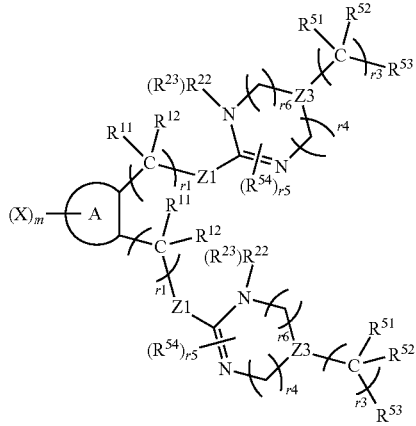

(I-0a-1)

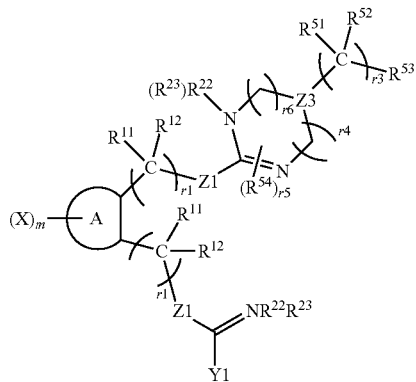

(I-0a-2)

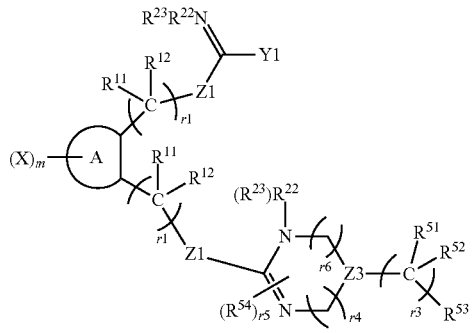

(I-0a-3)

(wherein A, X, m, Z1, Z3, $R^{11}$, $R^{12}$, $R^{22}$, $R^{23}$, $R^{51}$, $R^{52}$, $R^{53}$, $R^{54}$, r1, r3, r4, r5 and r6 have the same, meaning as described above).

For example, Z1 represents S, SO or $SO_2$.
For example, Z1 represents O.
For example, Z1 represents Se.
For example, Z3 represents.
For example, Z3 represents N.
For example, Z3 represents $CR^{54}$ (wherein $R^{54}$ represents a halogen atom or a substituted or unsubstituted linear or branched alkyl group).

In one aspect of the present invention, the compound of formula (I) is the following compound (I-0b) wherein $R^1$ and $R^2$ have the same group and are bonded to adjacent ring atoms of ring A.

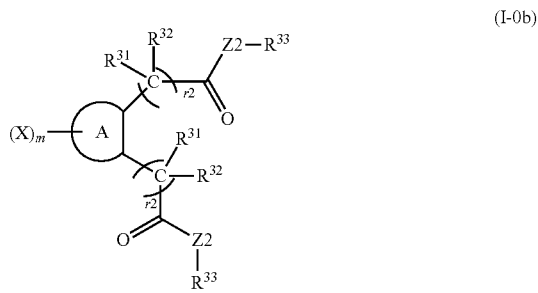

(I-0b)

(wherein A, X, m, Z2, $R^{31}$, $R^{32}$, $R^{33}$, and r2 have the same meaning as described above).

For example, Z2 represents O.

For example, Z2 represents $NR^{61}$ (wherein $R^{61}$ represents a hydrogen atom, a substituted or unsubstituted linear or branched alkyl group or a substituted or unsubstituted aryl group).

In one aspect of the present invention, the compound of formula (I) is the following compound wherein $R^1$ and $R^2$ have the same group and are bonded to adjacent ring atoms of ring A.

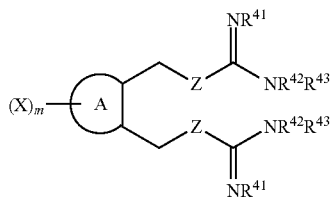
(I-1)

(wherein A, X, Z, m, $R^{41}$, $R^{42}$, and $R^{43}$ have the same meaning as described above).

For example, Z represents S, SO or $SO_2$.

For example, Z represents O.

For example, Z represents Se.

In one aspect of the present invention, the compound of formula (I) is the following compound wherein $R^1$ and $R^2$ have the same group and are bonded to adjacent ring atoms of ring A.

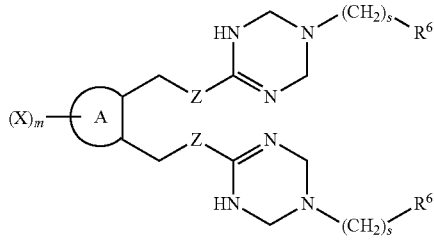
(I-2)

(wherein A, X, Z, m, s, and $R^6$ have the same meaning as described above).

For example, Z represents S, SO or $SO_2$.

For example, Z represents O.

For example, Z represents Se.

In one aspect of the present invention, the compound of formula (I) is any of the following two compounds wherein $R^1$ and $R^2$ have different groups and are bonded to adjacent ring atoms of ring A.

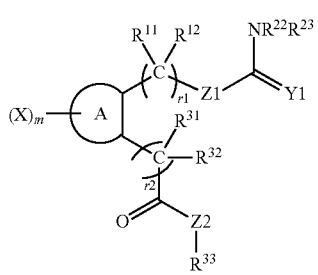
(I-0c)

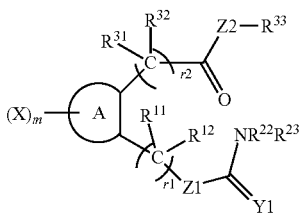
(I-0d)

(wherein A, X, m, Y1, Z1, Z2, $R^{11}$, $R^{12}$, $R^{22}$, $R^{23}$, $R^{31}$, $R^{32}$, $R^{33}$, r1, and r2 have the same meaning as described above).

For example, Y1 represents O.

For example, Y1 represents $NR^{21}$ (wherein $R^{21}$ represents a hydrogen atom, a substituted or unsubstituted linear or branched alkyl group, a substituted or unsubstituted cycloalkyl group, a substituted or unsubstituted aryl group or a substituted or unsubstituted heterocyclic group).

For example, Z1 represents S, SO or $SO_2$.

For example, Z1 represents O.

For example, Z1 represents Se.

For example, Z2 represents O.

For example, Z2 represents $NR^{61}$ (wherein $R^{61}$ represents a hydrogen atom, a substituted or unsubstituted linear or branched alkyl group or a substituted or unsubstituted aryl group).

In one aspect of the present invention, when the functional group containing the ring formed by $R^{21}$ and $R^{22}$ or $R^{23}$ bonded to each other in the compound of formula (I-0c) and the compound of formula (I-0d) described above is represented by formula (IV) described above, the compound is any of the following two compounds.

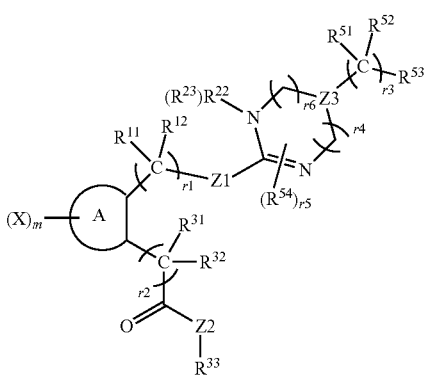
(I-0c-1)

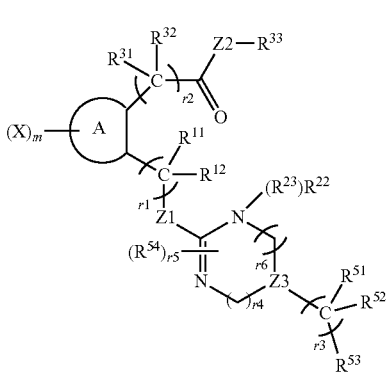
(I-0d-1)

(wherein A, X, m, Z1, Z2, Z3, $R^{11}$, $R^{12}$, $R^{22}$, $R^{23}$, $R^{31}$, $R^{32}$, $R^{33}$, $R^{51}$, $R^{52}$, $R^{53}$, $R^{54}$, r1, r2, r3, r4, r5, and r6 have the same meaning as described above).

For example, Z1 represents S, SO or $SO_2$.
For example, Z1 represents O.
For example, Z1 represents Se.
For example, Z2 represents O.
For example, Z2 represents $NR^{61}$ (wherein $R^{61}$ represents a hydrogen atom, a substituted or unsubstituted linear or branched alkyl group or a substituted or unsubstituted aryl group).
For example, Z3 represents CH.
For example, Z3 represents N.
For example, Z3 represents $CR^{54}$ (wherein $R^{54}$ represents a halogen atom or a substituted or unsubstituted linear or branched alkyl group).

In one aspect of the present invention, the compound of formula (I) is the following compound wherein $R^1$ and $R^2$ have different groups and are bonded to adjacent ring atoms of ring A.

(I-3)

(wherein A, X, and m have the same meaning as described above, and $R^7$ and $R^8$ are different from each other and are selected from the group consisting of the following groups.

—$COOR^3$     —$(CH_2)_n$—Y—$R^4$

—$(CH_2)_p$—CONH—$(CH_2)_q$—$R^5$

—$(CH_2)_r$—Z (wherein $R^3$, $R^4$, $R^5$, $R^6$, Y, Z, n, p, q, r, and s have the same meaning as described above).

For example, Y represents S, SO or $SO_2$.
For example, Y represents O.
For example, Y represents Se.
For example, Z represents S, SO or $SO_2$.
For example, Z represents O.
For example, Z represents Se.

Specific examples of the compound of formula (I-3) wherein $R^7$ and $R^8$ are different from each other can include the following compounds.

(I-3-a)

(I-3-b)

(I-3-c)

(I-3-d)

(I-3-e)

(I-3-f)

(I-3-g)

(I-3-h)

(wherein $R^3$, $R^4$, $R^5$, $R^6$, Y, Z, n, p, q, r, and s have the same meaning as described above).

For example, Y represents S, SO or $SO_2$.
For example, Y represents O.
For example, Y represents Se.
For example, Z represents S, SO or $SO_2$.
For example, Z represents O.
For example, Z represents Se.

In one aspect of the present invention, in the compound of formula (I), the compound of formula (I-0a), the compound of formula (I-0a-1), the compound of formula (I-0b), the compound of formula (I-0c), the compound of formula (I-0d), the compound of formula (I-0c-1), the compound of formula (I-0d-1), the compound of formula (I-1), the compound of formula (I-2), the compound of formula (I-3), and the compounds of formula (I-3-a) to formula (I-3-h), X is selected from the group consisting of a halogen atom, a substituted or unsubstituted linear or branched $C_1$-$C_8$ alkyl group, a substituted or unsubstituted linear or branched $C_1$-$C_8$ alkoxy group, a substituted or unsubstituted linear or branched $C_2$-$C_8$ alkenyl group, a substituted or unsubstituted linear or branched $C_2$-$C_8$ alkenyloxy group, a substituted or unsubstituted linear or branched $C_2$-$C_8$ alkynyl group, a substituted or unsubstituted linear or branched $C_2$-$C_8$ alkynyloxy group, a substituted or unsubstituted $C_3$-$C_8$ cycloalkyl group, a substituted or unsubstituted $C_3$-$C_8$ cycloalkenyl group, a substituted or unsubstituted $C_3$-$C_8$ cycloalkynyl group, a $C_1$-$C_3$ alkyl halide group, a cyano group, a hydroxy group, an amino group, a carboxyl group, a substituted or unsubstituted $C_6$-$C_{18}$ aryl group, and a substituted or unsubstituted aralkyl group (wherein the number of carbon atoms in the aryl moiety is $C_6$-$C_{10}$, and the number of carbon atoms in the alkylene moiety is $C_1$-$C_4$).

In one aspect of the present invention, in the compound of formula (I), the compound of formula (I-0a), the compounds of formula (I-0a-1) to (I-0a-3), the compound of formula (I-0b), the compound of formula (I-0c), the compound of formula (I-0d), the compound of formula (I-0c-1), the compound of formula (I-0d-1), the compound of formula (I-1), the compound of formula (I-2), the compound of formula (I-3), and the compounds of formula (I-3-a) to formula (I-3-h), X represents a group selected from the following group:

- as a halogen atom, a fluorine atom, a chlorine atom, a bromine atom, and an iodine atom,
- as a substituted or unsubstituted linear or branched alkyl group, a methyl group, an ethyl group, a n-propyl group, an i-propyl group, a n-butyl group, an i-butyl group, a s-butyl group, a t-butyl group, a n-pentyl group, a n-hexyl group, a n-octyl group, a carboxymethyl group, a 2-carboxyethyl group, a 3-hydroxy-1-propyl group, an aminomethyl group, a 2-aminoethyl group, a hydroxymethyl group, and a 2-hydroxyethyl group,
- as a substituted or unsubstituted linear or branched alkoxy group, a methoxy group, an ethoxy group, a n-propoxy group, and a n-butoxy group,
- as a substituted or unsubstituted linear or branched alkenyl group, an ethenyl (vinyl) group, a 2-propenyl (allyl) group, and a 3-butenyl group,
- as a substituted or unsubstituted linear or branched alkenyloxy group, an ethenyloxy (vinyloxy) group, a 2-propenyloxy (allyloxy) group, and a 3-butenyloxy group,
- as a substituted or unsubstituted linear or branched alkynyl group, an ethynyl group, a 2-propynyl group, and a 3-butynyl group,
- as a substituted or unsubstituted linear or branched alkynyloxy group, an ethynyloxy group, a 2-propynyloxy group, and a 3-butynyloxy group,
- as a substituted or unsubstituted cycloalkyl group, a cyclopropyl group, a cyclobutyl group, a cyclopentyl group, a cyclohexyl group, and a cyclooctyl group,
- as a substituted or unsubstituted cycloalkenyl group, a 1-cyclopropenyl group, a 1-cyclobutenyl group, a 1-cyclopentenyl group, and a 1-cyclohexenyl group,
- as an alkyl halide group, a fluoromethyl group (—CH$_2$F), a difluoromethyl group (—CHF$_2$), a chloromethyl group (—CH$_2$Cl), a bromomethyl group (—CH$_2$Br), an iodomethyl group (—CH$_2$I), a trifluoromethyl group (—CF$_3$), a trichloromethyl group (—CCl$_3$), a tribromomethyl group (—CBr$_3$), a triiodomethyl group (—CI$_3$), a 2,2,2-trifluoroethyl group (—CH$_2$CF$_3$), a 2,2,2-trichloroethyl group (—CH$_2$CCl$_3$), a 2,2,2-tribromoethyl group (—CH$_2$CBr$_3$), a 2,2,2-triiodoethyl group (—CH$_2$CI$_3$), and a pentafluoroethyl group (—C$_2$F$_5$),
- as an alkyloxy halide group, a fluoromethoxy group (—OCH$_2$F), a difluoromethoxy group (—OCHF$_2$), a chloromethoxy group (—OCH$_2$Cl), a bromomethoxy group (—OCH$_2$Br), an iodomethoxy group (—OCH$_2$I), a trifluoromethoxy group (—OCF$_3$), a trichloromethoxy group (—OCCl$_3$), a tribromomethoxy group (—OCBr$_3$), a triiodomethoxy group (—OCI$_3$), a 2,2,2-trifluoroethoxy group (—OCH$_2$CF$_3$), a 2,2,2-trichloroethoxy group (—OCH$_2$CCl$_3$), a 2,2,2-tribromoethoxy group (—OCH$_2$CBr$_3$), a 2,2,2-triiodoethoxy group (—OCH$_2$CI$_3$), and a pentafluoroethoxy group (—OC$_2$F$_5$),
- a cyano group,
- a hydroxy group,
- an amino group,
- a nitro group,
- a carboxyl group,
- as a substituted or unsubstituted aryl group, a phenyl group, a naphthalen-1-yl group, and a naphthalen-2-yl group, and
- as a substituted or unsubstituted aralkyl group, a benzyl group, a phenethyl group, and a 3-phenyl-1-propyl group.

As described above, in the compound of formula (I), ring A can be selected from the group consisting of a benzene ring, a naphthalene ring, a quinoxaline ring, a thiophene ring, an indole ring, and a pyridine ring. In one aspect of the present invention, in a compound of the following formula (I-4) containing a benzene ring as ring A, and $R^1$ and $R^2$ added to positions 1 and 2, respectively, of the ring, the following formula (I-4-a):

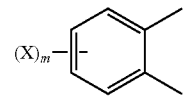

(I-4-a)

excluding $R^1$ and $R^2$ in

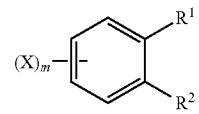

(I-4)

(wherein $R^1$ and $R^2$ have the same meaning as defined in any one of [1] to [3] described above) may be selected from the group consisting of Ph=, 3-F-Ph=, 4-F-Ph=, 5-F-Ph=, 6-F-Ph=, 3-Cl-Ph=, 4-Cl-Ph=, 5-Cl-Ph=, 6-Cl-Ph=, 3-Br-Ph=, 4-Br-Ph=, 5-Br-Ph=, 6-Br-Ph=, 3-I-Ph=, 4-I-Ph=, 5-I-Ph=, 6-I-Ph=, 3-Me-Ph=, 4-Me-Ph=, 5-Me-Ph=, 6-Me-Ph=, 3-Et-Ph=, 4-Et-Ph=, 5-Et-Ph=, 6-Et-Ph=, 3-Pr-Ph=, 4-Pr-Ph=, 5-Pr-Ph=, 6-Pr-Ph=, 3-Bu-Ph=, 4-Bu-Ph=, 5-Bu-Ph=, 6-Bu-Ph=, 3-t-Bu-Ph=, 4-t-Bu-Ph=, 5-t-Bu-Ph=, 6-t-Bu-Ph=, 3-MeO-Ph=, 4-MeO-Ph=, 5-MeO-Ph=, 6-MeO-Ph=, 3-EtO-Ph=, 4-EtO-Ph=, 5-EtO-Ph=, 6-EtO-Ph=, 3-CF$_3$-Ph=, 4-CF$_3$-Ph=, 5-CF$_3$-Ph=, 6-CF$_3$-Ph=, 3-C$_2$F$_5$-Ph=, 4-C$_2$F$_5$-Ph=, 5-C$_2$F$_5$-Ph=, 6-C$_2$F$_5$-Ph=, 3-CF$_3$O-Ph=, 4-CF$_3$O-Ph=, 5-CF$_3$O-Ph=, 6-CF$_3$O-Ph=, 3-C$_2$F$_5$O-Ph=, 4-C$_2$F$_5$O-Ph=, 5-C$_2$F$_5$O-Ph=, 6-C$_2$F$_5$O-Ph=, 3-CN-Ph=, 4-CN-Ph=, 5-CN- Ph=, 6-CN-Ph=, 3-OH-Ph=, 4-OH-Ph=, 5-OH-Ph=, 6-OH-Ph=, 3-NH$_2$-Ph=, 4-NH$_2$-Ph=, 5-NH$_2$-Ph=, 6-NH$_2$-Ph=, 3-NO$_2$-Ph=, 4-NO$_2$-Ph=, 5-NO$_2$-Ph=, 6-NO$_2$-Ph=, 3-COOH-Ph=, 4-COOH-Ph=, 5-COOH-Ph=, 6-COOH-Ph=, (any two of positions 3, 4, 5 and 6)-F$_2$-Ph=, (any two of positions 3, 4, 5 and 6)-Cl$_2$-Ph=, (any two of positions 3, 4, 5 and 6)-Br$_2$-Ph=, (any two of positions 3, 4, 5 and 6)-I$_2$-Ph=, (any two of positions 3, 4, 5 and 6)-Me$_2$-Ph=, (any two of positions 3, 4, 5 and 6)-Et$_2$-Ph-, (any two of positions 3, 4, 5 and 6)-Pr$_2$-Ph=, (any two of positions 3, 4, 5 and 6)-Bu$_2$-Ph=, (any two of positions 3, 4, 5 and 6)-(CN)$_2$-Ph=, (any two of positions 3, 4, 5 and 6)-(OH)$_2$-Ph=, (any two of positions 3, 4, 5 and 6)-((NH$_2$))$_2$-Ph=, (any two of positions 3, 4, 5 and 6)-(NO$_2$)$_2$-Ph=, (any two of positions 3, 4, 5 and 6)-(MeO)$_2$-Ph=, (any two of positions 3, 4, 5 and 6)-(EtO)$_2$-Ph=, (any two of positions 3, 4, 5 and 6)-(CF$_3$)$_2$-Ph=, (any three of positions 3, 4, 5 and 6)-F$_3$-Ph=, (any three of positions 3, 4, 5 and 6)-Cl$_2$-Ph=, (all four of positions 3, 4, 5 and 6)-F$_4$-Ph=, and (all four of positions 3, 4, 5 and 6)-Cl$_4$-Ph=(wherein "Ph=" represents a divalent group which is a moiety of formula (I-4-a) excluding (X)$_m$—).

In the definition of formula (I-4-a) described above, for example, "Ph" in "Ph=" represents a benzene ring, and "=" represents a bond. Thus, "Ph=" represents a phenylene group.

In the definition of formula (I-4-a) described above, for example, "5-F-Ph=" represents a divalent group (phenylene group) in which position 5 of a benzene ring is substituted by fluorine (F).

In the definition of formula (I-4-a) described above, for example, "(any two of positions 3, 4, 5 and 6)-(MeO)$_2$-Ph=" represents a divalent group (phenylene group) in which any two of positions 3, 4, 5 and 6 of a benzene ring are substituted by methoxy groups (—OCH$_3$).

The definitions of formula (I-4) and formula (I-4-a) described above can be translated as follows.

In formula (I), when ring A is a benzene ring and R$^1$ and R$^2$ are adjacently added to ring A with the substitution position of R' as position 1 and the substitution position of R$^2$ as position 2, X is selected from a hydrogen atom, a 3-fluoro group, a 4-fluoro group, a 5-fluoro group, a 6-fluoro group, a 3-chloro group, a 4-chloro group, a 5-chloro group, a 6-chloro group, a 3-bromo group, a 4-bromo group, a 5-bromo group, a 6-bromo group, a 3-iodo group, a 4-iodo group, a 5-iodo group, a 6-iodo group, a 3-methyl group, a 4-methyl group, a 5-methyl group, a 6-methyl group, a 3-ethyl group, a 4-ethyl group, a 5-ethyl group, a 6-ethyl group, a 3-n-propyl group, a 4-n-propyl group, a 5-n-propyl group, a 6-n-propyl group, a 3-n-butyl group, a 4-n-butyl group, a 5-n-butyl group, a 6-n-butyl group, a 3-t-butyl group, a 4-t-butyl group, a 5-t-butyl group, a 6-t-butyl group, a 3-methoxy group, a 4-methoxy group, a 5-methoxy group, a 6-methoxy group, a 3-ethoxy group, a 4-ethoxy group, a 5-ethoxy group, a 6-ethoxy group, a 3-trifluoromethyl group, a 4-trifluoromethyl group, a 5-trifluoromethyl group, a 6-trifluoromethyl group, a 3-pentafluoroethyl group, a 4-pentafluoroethyl group, a 5-pentafluoroethyl group, a 6-pentafluoroethyl group, a 3-trifluoromethoxy group, a 4-trifluoromethoxy group, a 5-trifluoromethoxy group, a 6-trifluoromethoxy group, a 3-pentafluoroethoxy group, a 4-pentafluoroethoxy group, a 5-pentafluoroethoxy group, a 6-pentafluoroethoxy group, a 3-cyano group, a 4-cyano group, a 5-cyano group, a 6-cyano group, a 3-hydroxy group, a 4-hydroxy group, a 5-hydroxy group, a 6-hydroxy group, a 3-amino group, a 4-amino group, a 5-amino group, a 6-amino group, a 3-nitro group, a 4-nitro group, a 5-nitro group, a 6-nitro group, a 3-carboxyl group, a 4-carboxyl group, a 5-carboxyl group, a 6-carboxyl group, a 3,4-difluoro group, a 3,5-difluoro group, a 3,6-difluoro group, a 4,5-difluoro group, a 4,6-difluoro group, a 5,6-difluoro group, a 3,4-dichloro group, a 3,5-dichloro group, a 3,6-dichloro group, a 4,5-dichloro group, a 4,6-dichloro group, a 5,6-dichloro group, a 3,4-dibromo group, a 3,5-dibromo group, a 3,6-dibromo group, a 4,5-dibromo group, a 4,6-dibromo group, a 5,6-dibromo group, a 3,4-dimethyl group, a 3,5-dimethyl group, a 3,6-dimethyl group, a 4,5-dimethyl group, a 4,6-dimethyl group, a 5,6-dimethyl group, a 3,4-diethyl group, a 3,5-diethyl group, a 3,6-diethyl group, a 4,5-diethyl group, a 4,6-diethyl group, a 5,6-diethyl group, a 3,4-di-n-propyl group, a 3,5-di-n-propyl group, a 3,6-di-n-propyl group, a 4,5-di-n-propyl group, a 4,6-di-n-propyl group, a 5,6-di-n-propyl group, a 3,4-di-n-butyl group, a 3,5-di-n-butyl group, a 3,6-di-n-butyl group, a 4,5-di-n-butyl group, a 4,6-di-n-butyl group, a 5,6-di-n-butyl group, a 3,4-dicyano group, a 3,5-dicyano group, a 3,6-dicyano group, a 4,5-dicyano group, a 4,6-dicyano group, a 5,6-dicyano group, a 3,4-dihydroxy group, a 3,5-dihydroxy group, a 3,6-dihydroxy group, a 4,5-dihydroxy group, a 4,6-dihydroxy group, a 5,6-dihydroxy group, a 3,4-diamino group, a 3,5-diamino group, a 3,6-diamino group, a 4,5-diamino group, a 4,6-diamino group, a 5,6-diamino group, a 3,4-dinitro group, a 3,5-dinitro group, a 3,6-dinitro group, a 4,5-dinitro group, a 4,6-dinitro group, a 5,6-dinitro group, a 3,4-dimethoxy group, a 3,5-dimethoxy group, a 3,6-dimethoxy group, a 4,5-dimethoxy group, a 4,6-dimethoxy group, a 5,6-dimethoxy group, a 3,4-diethoxy group, a 3,5-diethoxy group, a 3,6-diethoxy group, a 4,5-diethoxy group, a 4,6-diethoxy group, a 5,6-diethoxy group, a 3,4-ditrifluoromethyl group, a 3,5-ditrifluoromethyl group, a 3,6-ditrifluoromethyl group, a 4,5-ditrifluoromethyl group, a 4,6-ditrifluoromethyl group, a 5,6-ditrifluoromethyl group, a 3,4,5-trifluoro group, a 3,4,6-trifluoro group, a 4,5,6-trifluoro group, a 3,4,5-trichloro group, a 3,4,6-trichloro group, a 4,5,6-trichloro group, a 3,4,5,6-tetrafluoro group, and a 3,4,5,6-tetrachloro group.

The term "pharmaceutically acceptable salt" used in the present application means a compound, a substance, a composition and/or a dosage form that is suitable for a moderate risk/benefit ratio in the absence of excessive toxicity, irritating properties, allergic response or other problems or complications, within the scope of reasonable medical judgment, when used in contact with a human and animal tissue. Such a salt can be formed by reacting a product in a free acid form with 1 equivalent or more of an appropriate base or a product in a free base form with 1 equivalent or more of an appropriate acid in a solvent or a vehicle in which the salt is insoluble, or in a solvent such as water in accordance with a conventional approach, and can be isolated by drying in vacuum or freeze-drying the reaction product, or by exchanging an anion of an existing salt with another anion on a suitable ion-exchange resin.

The pharmaceutically acceptable salt of the compound of the present invention exists as an acid addition salt or basic salt. Examples of the pharmaceutically acceptable acid addition salt of the compound of the present invention include acetate, adipate, ascorbate, benzoate, benzenesulfonate, bicarbonate, bisulfate, butyrate, camphorate, camphorsulfonate, choline, citrate, cyclohexylsulfamate, diethylenediamine, ethanesulfonate, formate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate and undecanoate.

Examples of the pharmaceutically acceptable basic salt of the compound of the present invention include: ammonium salt; an alkali metal salt such as sodium salt, lithium salt and potassium salt; an alkaline earth metal salt such as aluminum salt, calcium salt and magnesium salt; a salt with an organic base such as dicyclohexylamine and N-methyl-D-glucamine; and a salt with an amino acid such as arginine, lysine and ornithine. Furthermore, a basic nitrogen-containing group may be quaternized with a substance including: lower alkyl halide such as methyl halide, ethyl halide, propyl halide and butyl halide; dialkyl sulfate such as dimethyl sulfate, diethyl sulfate and dibutyl sulfate; diamyl sulfate; long-chain halide such as decyl halide, lauryl halide, myristyl halide and stearyl halide; and arylalkyl halide such as benzyl bromide and other substances. Although a nontoxic physiologically acceptable salt is suitable, other salts may be useful, for example, for isolating or purifying products.

Various isomers (e.g., an optical isomer, a positional isomer, and a tautomer), a solvate such as a hydrate, a crystal polymorph, and a prodrug such as an ester form of the compound of the present invention represented by formula (I) are all included in the scope of the present invention.

A compound in which one or more atoms constituting the compound of the present invention represented by formula (I) are isotopes, and a pharmaceutically acceptable salt thereof are also included in the present invention. Examples of the isotope that may be contained in the compound of the present invention include isotopes of hydrogen, carbon, nitrogen, oxygen, phosphorus, fluorine, bromine and chlorine, for example, $^{2}H$, $^{3}H$, $^{11}C$, $^{13}C$, $^{14}C$, $^{13}N$, $^{15}N$, $^{15}O$, $^{17}O$, $^{18}O$, $^{18}F$, $^{75}Br$, $^{76}Br$, $^{77}Br$, $^{82}Br$, and $^{37}Cl$, respectively.

The compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), and formula (I-3-a) to formula (I-3-h) exhibit an excellent inhibitory effect on IDO and/or TDO and can be used as inhibitors of IDO and/or TDO. Thus, the compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), and formula (I-3-a) to formula (I-3-h) can be used as medicaments targeting a wide range of diseases.

Thus, one aspect of the present invention provides an inhibitor of IDO and/or TDO, comprising one or more compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or pharmaceutically acceptable salts thereof as an active ingredient.

Another aspect of the present invention provides a pharmaceutical composition comprising one or more compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or pharmaceutically acceptable salts thereof as an active ingredient.

A further alternative aspect of the present invention provides a therapeutic agent for a disease or a disorder selected from tumor, infectious disease, neurodegenerative disorder, cataract, organ transplant rejection, autoimmune disease, postoperative cognitive impairment, and disease related to women's reproductive health, comprising one or more compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or pharmaceutically acceptable salts thereof as an active ingredient.

A further alternative aspect of the present invention provides an antitumor agent comprising one or more compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or pharmaceutically acceptable salts thereof as an active ingredient.

A further alternative aspect of the present invention provides a pharmaceutical kit comprising one or more compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or pharmaceutically acceptable salts thereof as an active ingredient.

In the case of using the compound of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) as an antitumor agent, examples of the targeted tumor include mesothelioma, tumor of the hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of the uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of the renal pelvis, neoplasm of the central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma. However, the targeted tumor is not limited thereto.

The pharmaceutical composition, the inhibitor of IDO and/or TDO, and the therapeutic agent for a disease such as tumor according to the present invention comprises the compound of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or the pharmaceutically acceptable salt thereof, and at least one pharmaceutically acceptable carrier, diluent or excipient.

The pharmaceutical composition, the inhibitor of IDO and/or TDO, and the therapeutic agent for a disease such as tumor according to the present invention may be in a form suitable for oral use (e.g., as a tablet, a lozenge, a hard or soft capsule, an aqueous or oil suspension agent, an emulsion, a dispersible powder or granules, a syrup or an elixir), local use (e.g., as a cream, an ointment, a gel or an aqueous or oil liquid agent or suspension agent), administration by inhalation (e.g., as a fine powder or a liquid aerosol), administration by insufflation (e.g., as a fine powder) or parenteral administration (e.g., as a sterile aqueous or oil liquid agent for intravenous, intra-arterial, subcutaneous, intraperitoneal, intravesical, intrathoracic, intracranial or intramuscular administration, or as a suppository for rectal administration). In some aspects, the compound and/or the composition of the present invention is administered by intravenous (I.V.) administration.

The pharmaceutical composition, the inhibitor of IDO and/or TDO, and the therapeutic agent for a disease such as tumor according to the present invention can be obtained by conventional procedures using a conventional pharmaceutical excipient well known in the art. Thus, the composition designed for oral use may contain, for example, one or more colorants, sweeteners, flavoring agents and/or preservatives. Since cyclodextrin has a hydrophobic interior and a hydrophilic exterior, the cyclodextrin can form a clathrate compound (inclusion compound) by including a hydrophobic molecule. The clathrate compound can enhance solubility in water and protect a compound that reacts readily with water or oxygen, and can therefore be utilized, if necessary, for producing medicaments in various dosage forms. The cyclodextrin includes substances having various structures. Examples thereof include α-cyclodextrin containing six glucose units bonded (cyclohexaamylose, α-CD), β-cyclodextrin containing seven glucose units bonded (cycloheptaamylose, β-CD), and γ-cyclodextrin containing eight glucose units bonded (cyclooctaamylose, γ-CD). The formation of a clathrate compound with cyclodextrin is applied to, for example, the stabilization of a drug such as prostaglandin or nitroglycerin.

Examples of the pharmaceutically acceptable excipient suitable for a tablet formulation include: an inert diluent such as lactose, sodium carbonate, calcium phosphate and calcium carbonate; a granulating agent and a disintegrant such as starch, carmellose calcium and sodium croscarmellose; a binder such as starch; a lubricant such as magnesium stearate, stearic acid and talc; a preservative such as ethyl p-hydroxybenzoate and propyl p-hydroxybenzoate; and an antioxidant such as ascorbic acid. The tablet formulation may be uncoated, or may be coated so as to change the disintegration of the formulation in the gastrointestinal tract and the subsequent absorption of the active component or so as to improve the stability and/or appearance of the formulation (in both cases, a conventional coating agent and procedures well known in the art may be used in the coating).

The pharmaceutical composition, the inhibitor of IDO and/or TDO, and the therapeutic agent for a disease such as tumor according to the present invention for oral use may be in the form of a hard gelatin capsule containing the active component mixed with an inert solid diluent, for example, calcium carbonate, calcium phosphate or kaolin, or may be used as a soft gelatin capsule containing the active component mixed with water or an oil such as peanut oil, liquid paraffin or olive oil.

The aqueous suspension agent generally contains the active component in a fine powder form or in a nanoparticle or ultrafine particle form together with one or more suspending agents such as sodium carboxymethylcellulose, methylcellulose, hydroxypropylmethylcellulose, sodium alginate, polyvinylpyrrolidone, tragacanth gum and gum arabic; lecithin as a dispersion aid or a wetting agent; or a condensate of fatty acid and alkylene oxide (e.g., polyoxyethylene stearate); or a condensate of long chain aliphatic alcohol and ethylene oxide, for example, heptadecaethyleneoxycetanol; or a condensate of partial ester derived from, fatty acid and hexitol, and ethylene oxide, for example, polyoxyethylene sorbitol monooleate; or a condensate of partial ester derived from fatty acid and hexitol anhydride, and ethylene oxide, for example, polyethylene sorbitan monooleate; etc. The aqueous suspension agent may further contain one or more preservatives such as ethyl p-hydroxybenzoate or propyl p-hydroxybenzoate; an antioxidant such as ascorbic acid; a colorant; a flavoring agent; and/or a sweetener such as sucrose, saccharin or aspartame.

The oil suspension agent can be formulated by suspending the active component in a plant oil such as peanut oil, olive oil, sesame oil or coconut oil or in a mineral oil such as liquid paraffin. Such an oil suspension agent may further contain a thickener such as beeswax, hard paraffin or cetyl alcohol. The sweetener and the flavoring agent such as those listed above may be added in order to provide an oral formulation having good taste or flavor. These compositions can be preserved by the addition of an antioxidant such as ascorbic acid.

The dispersible powder and granules suitable for the production of an aqueous suspension agent by the addition of water generally contain the active component together with a dispersion aid or a wetting agent, a suspending agent and one or more preservatives. The suitable dispersion aid or wetting agent and suspending agent are typified by those already mentioned above. Additional excipients such as a sweetener, a flavoring agent and a colorant may be contained therein.

The pharmaceutical composition, the inhibitor of IDO and/or TDO, and the therapeutic agent for a disease such as tumor according to the present invention may further be in an oil-in-water emulsion. The oil phase may be a plant oil such as olive oil or peanut oil, or a mineral oil, for example, liquid paraffin, or any mixture thereof. The suitable emulsifier may be, for example, naturally occurring gum such as gum arabic or tragacanth gum; naturally occurring phosphatide such as soybean phosphatide or lecithin; ester or partial ester derived from fatty acid and hexitol anhydride (e.g., sorbitan monooleate); and a condensate of ethylene oxide and this partial ester, such as polyoxyethylene sorbitan monooleate. Such an emulsion may further contain a sweetener, a flavoring agent and a preservative.

In the case of using the compound of the present invention as an injection agent, a liposome for injection or a polymeric micelle may be utilized for concentrating the compound onto a particular tissue. The liposome for injection is a closed vesicle consisting of a lipid bilayer membrane based on phospholipid and consists of both a lipid membrane moiety and an aqueous layer moiety. Therefore, the liposome can incorporate both a lipid-soluble drug and a water-soluble drug therein. The liposome generally has a particle size of several μm or smaller and can be utilized for producing the injection agent. On the other hand, the polymeric micelle has a very small particle size (10 to 100 nm) and has a distinct two-layer structure of an inner core and an outer shell. Therefore, the outer shell determines in vivo disposition and distribution through interaction with a living body, while a drug can be physically or chemically enclosed in the inner core. An anticancer agent-incorporating micelle having polyethylene glycol in the outer shell exhibits a sufficient effect by selectively concentrating the agent onto a cancer tissue, and can reduce adverse reactions at the same time therewith. Hence, a polymeric micelle incorporating such a compound is convenient as a DDS (drug delivery system) formulation.

The syrup and the elixir can be formulated together with a sweetener such as glycerol, propylene glycol, sorbitol, aspartame or sucrose. These formulations may further contain a demulcent agent, a preservative, a flavoring agent and/or a colorant.

The pharmaceutical composition, the inhibitor of IDO and/or TDO, and the therapeutic agent for a disease such as tumor according to the present invention may further be in the form of a sterile injectable aqueous or oil suspension. Such a sterile injectable aqueous or oil suspension can be formulated using one or more appropriate dispersion aids or wetting agents and suspending agents listed above according to known procedures. The sterile injectable formulation may further be a sterile injectable solution or suspension in a nontoxic parenterally acceptable diluent or solvent, for example, a solution in 1,3-butanediol.

The pharmaceutical composition, the inhibitor of IDO and/or TDO, and the therapeutic agent for a disease such as tumor according to the present invention for administration by inhalation may be in the form of an aerosol containing a fine solid powder of the active component, or a conventional pressurized aerosol disposed so as to dispense liquid particles of the active component. A conventional aerosol propellant such as volatile fluorinated hydrocarbon or hydrocarbon can be used, and an aerosol apparatus is conveniently disposed so as to dispense a given measured amount of the active component.

The amount of the active component that yields a single dosage form by mixing with one or more excipients inevitably varies depending on a host to be treated and a specific administration route. For example, a formulation designed form oral administration to a human may be blended with an excipient in an appropriate and convenient amount that can be approximately 5 to approximately 98% by weight of the whole composition. The formulation can contain, for example, 0.5 mg to 5 g of the active agent. A unit dosage form can contain, for example, approximately 1 mg to approximately 500 mg of the active component.

The therapeutic dose of the compound of the present invention may differ according to, for example, a particular purpose of treatment, a method for administering the compound, the health and condition of a patient, and prescribing doctor's judgment. The ratio or concentration of the compound of the present invention in the pharmaceutical composition may differ according to many factors including a dose, chemical characteristics (e.g., hydrophobicity), and an administration route. For example, for oral administration or, for example, for parenteral administration, the compound of the present invention can be provided in a physiological buffered aqueous solution containing approximately 0.1 to approximately 10 w/v % of the compound. A typical dose range is approximately 1 µg/kg body weight to approximately 1 g/kg body weight per day. In one aspect of the present invention, the dose range is approximately 0.01 mg/kg body weight to approximately 100 mg/kg body weight per day. The dose is likely to depend on various factors such as the type and degree of progression of the disease or the disorder, the general health condition of a particular patient, the relative biological usefulness of the compound to be selected, the dosage form of an excipient, and the administration route thereof. An effective dose can be predicted from a dose-response curve derived from an in vitro or animal model test system.

A further alternative aspect of the present invention provides a pharmaceutical kit for treating a disease or a disorder selected from tumor, infectious disease, neurodegenerative disorder, cataract, organ transplant rejection, autoimmune disease, postoperative cognitive impairment, and disease related to women's reproductive health, comprising (a) one or more compounds of formula (I), formula (I-0a), formulas (I-0a-1) to (I-0a-3), formula (I-0b), formula (I-0c), formula (I-0d), formula (I-0c-1), formula (I-0d-1), formula (I-1), formula (I-2), formula (I-3), formula (I-3-a), formula (I-3-b), formula (I-3-c), formula (I-3-d), formula (I-3-e), formula (I-3-f), formula (I-3-g), or formula (I-3-h) or pharmaceutically acceptable salts thereof, and (b) one or more additional antitumor agents for treating the disease or the disorder selected from tumor, infectious disease, neurodegenerative disorder, cataract, organ transplant rejection, autoimmune disease, postoperative cognitive impairment, and disease related to women's reproductive health, wherein the compounds or the pharmaceutically acceptable salts thereof and the additional agents are suitable for concurrent, sequential or separate administration. When the component (b) in the pharmaceutical kit is one or more additional antitumor agents, this pharmaceutical kit serves as a pharmaceutical kit for treating tumor.

Examples of the additional antitumor agent include: an alkylating agent (e.g., cisplatin, oxaliplatin, carboplatin, cyclophosphamide, nitrogen mustard, melphalan, chlorambucil, bendamustine, busulfan, temozolamide and nitrosourea); an antimetabolic drug (e.g., gemcitabine, cpecitabine, and an antifolate drug including a fluoropyrimidine such as 5-fluorouracil and tegafur, raltitrexed, methotrexate, cytosine arabinoside and hydroxyurea); an antitumor antibiotic (e.g., an anthracycline-based antibiotic such as adriamycin, bleomycin, doxorubicin, daunomycin, epirubicin, idarubicin, mitomycin C, dactinomycin and mithramycin); an antimitotic drug (e.g., a *vinca* alkaloid-based drug such as vincristine, vinblastine, vindesine and vinorelbine; taxoids such as taxol and Taxotere; and an inhibitor of polo kinase or kinesin motor protein); a topoisomerase inhibitor (e.g., epipodophyllotoxins such as etoposide and teniposide, amsacrine, topotecan, camptothecin, pixantrone and irinotecan); an inhibitor of a DNA repair mechanism including, but not limited to, CHK kinase, an inhibitor of DNA-dependent protein kinase, poly(ADP-ribose)polymerase (PARP inhibitor), and an inhibitor of ATM or ATR; and a Hsp90 inhibitor such as tanespamycin and retaspimycin; a compound inhibiting progression through a cell cycle, such as an antimitotic drug (e.g., but not limited to, a *vinca* alkaloid-based drug such as vincristine, vinblastine, vindesine and vinorelbine; epothilones such as ixabepilone); taxoids such as taxol and Taxotere; a polo-like kinase inhibitor; and an inhibitor of kinesin motor protein, such as Eg5 protein inhibitor); an aurora kinase inhibitor (e.g., but not limited to, AZD1152, PH739358, VX-680, MLN8054, R763, MP235, MP529, VX-528 and AX39459), and a cyclin-dependent kinase inhibitor such as a CDK2 and/or CDK4 inhibitor (e.g., Flavopiridol/alvocidib, roscovitine, and seliciclib); an inhibitor of a centromere protein function, such as a CENP-E inhibitor, and an immune checkpoint blockade (e.g., an anti-PD-1 antibody such as nivolumab and pembrolizumab; an anti-PD-LI antibody such as atezolizumab, durvalumab and avelumab; and an anti-CTLA-4 antibody such as ipilimumab and tremelimumab).

Further, a publicly known cell division suppressive drug, anti-invasive drug, inhibitor of a growth factor function, anti-angiogenic drug, drug for blood vessel injury, endothelin receptor antagonist, or the like may be used in combination therewith.

Hereinafter, specific examples of the compound of the present invention will be listed. However, the present invention is not limited by these compounds.

TABLE 1

| Compound No. | Compound name |
|---|---|
| 1 | 1,2-phenylenebis(methylene) dicarbamimidothioate dihydrochloride |
| 2 | (4-fluoro-1,2-phenylene)bis(methylene) dicarbamimidothioate dihydrobromide |
| 3 | naphthalene-1,2-diylbis(methylene) dicarbamimidothioate dihydrobromide |
| 4 | (4-(tert-butyl)-1,2-phenylene)bis(methylene) dicarbamimidothioate dihydrobromide |
| 5 | quinoxaline-2,3-dilylbis(methylene) dicarbamimidothioate dihydrobromide |
| 6 | (perfluoro-1,2-phenylene)bis(methylene) dicarbamimidothioate dihydrobromide |
| 7 | (4-chloro-1,2-phenylene)bis(methylene) dicarbamimidothioate dihydrobromide |
| 8 | 1,2-phenylenebis(methylene) (E,E)-bis(N,N'-dimethylcarbamimidothioate) dihydrodhloride |
| 9 | 1,2-bis(((5-phenethyl-1,4,5,6-tetrahydro-1,3,5-triazin-2-yl)thio)methyl)benzene |
| 10 | (4-bromo-1,2-phenylene)bis(methylene) dicarbamimidothioate dihydrobromide |
| 11 | 1,2-phenylenebis(methylene) bis(methylcarbamimidothioate) dihydrochloride |
| 12 | (4-methyl-1,2-phenylene)bis(methylene) dicarbamimidothioate dihydrobromide |
| 13 | (3-fluoro-1,2-phenylene)bis(methylene) dicarbamimidothioate dihydrobromide |
| 14 | 1,2-bis(((5-benzyl-1,4,5,6-tetrahydro-1,3,5-triazin-2-yl)thio)methyl)benzene |
| 15 | thiophene-3,4-diylbis(methylene) dicarbamimidothioate dihydrobromide |
| 16 | 1,2-bis((pyrimidin-2-ylthio)methyl)benzene |
| 17 | 1,2-bis(((5-(4-chlorophenethyl)-1,4,5,6-tetrahydro-1,3,5-triazin-2-yl)thio)methyl)benzene |
| 18 | 1,2-bis(((5-(2,5-dichlorobenzyl)-1,4,5,6-tetrahydro-1,3,5-triazin-2-yl)thio)methyl)benzene |
| 19 | 1,2-bis(((5-(3-bromophenethyl)-1,4,5,6-tetrahydro-1,3,5-triazin-2-yl)thio)methyl)benzene |
| 20 | 1,2-bis(((5-(4-bromophenethyl)-1,4,5,6-tetrahydro-1,3,5-triazin-2-yl)thio)methyl)benzene |
| 21 | 1,2-bis(((5-(2,4-dichlorophenethyl)-1,4,5,6-tetrahydro-1,3,5-triazin-2-yl)thio)methyl)benzene |
| 22 | 1,2-bis(((5-(3,4-dichlorophenethyl)-1,4,5,6-tetrahydro-1,3,5-triazin-2-yl)thio)methyl)benzene |
| 23 | 1,2-bis(((5-(3,4-dimethylphenethyl)-1,4,5,6-tetrahydro-1,3,5-triazin-2-yl)thio)methyl)benzene |
| 24 | 1,2-bis(((5-(2,5-dimethylphenethyl)-1,4,5,6-tetrahydro-1,3,5-triazin-2-yl)thio)methyl)benzene |
| 25 | 1,2-bis(((5-(4-ethylphenyl)-1,4,5,6-tetrahydro-1,3,5-triazin-2-yl)thio)methyl)benzene |
| 26 | 1,2-bis(((5-(4-methoxybenzyl)-1,4,5,6-tetrahydro-1,3,5-triazin-2-yl)thio)methyl)benzene |
| 27 | 1,2-bis(((5-(2,4-dimethoxybenzyl)-1,4,5,6-tetrahydro-1,3,5-triazin-2-yl)thio)methyl)benzene |
| 28 | 1,2-bis(((5-(2-chlorophenethyl)-1,4,5,6-tetrahydro-1,3,5-triazin-2-yl)thio)methyl)benzene |
| 29 | 1,2-bis(((5-(cyclohexylmethyl)-1,4,5,6-tetrahydro-1,3,5-triazin-2-yl)thio)methyl)benzene |
| 30 | 2,2'-((1,2-phenylenebis(methylene))bis(sulfanediyl))bis(pyrimidine-4,6(1H,5H)-dione) |
| 31 | thiophene-2,3-diylbis(methylene) dicarbamimidothioate dihydrobromide |
| 32 | methyl 2-((carbamimidoylthio)methyl)-1H-indole-3-carboxylate hydrobromide |
| 33 | 3,4-bis(((5-phenethyl-1,4,5,6-tetrahydro-1,3,5-triazin-2-yl)thio)methyl)thiophene dihydrochloride |
| 34 | pyridine-2,3-diylbis(methylene) dicarbamimidothioate dihydrobromide |
| 35 | (4-methoxy-1,2-phenylene)bis(methylene) dicarbamimidothioate dihydrobromide |
| 36 | (4,5-dichloro-1,2-phenylene)bis(methylene) dicarbamimidothioate dihydrobromide |
| 37 | 6,6'-(((4,5-dichloro-1,2-phenylene)bis(methylene))bis(sulfanediyl))bis(3-phenethyl-1,2,3,4-tetrahydro-1,3,5-triazine) |
| 38 | 6,6'-(((4,5-dichloro-1,2-phenylene)bis(methylene))bis(sulfanediyl))bis(3-(3,4-dichlorophenethyl)-1,2,3,4-tetrahydro-1,3,5-triazine) |
| 39 | 6,6'-(((4-bromo-1,2-phenylene)bis(methylene))bis(sulfanediyl))bis(3-(3,4-dichlorophenethyl)-1,2,3,4-tetrahydro-1,3,5-triazine) |
| 40 | 1,2-bis(((5-(2-thiophen-2-yl)ethyl)-1,4,5,6-tetrahydro-1,3,5-triazin-2-yl)thio)methyl)benzene |
| 41 | 1,2-bis(((5-(4-chlorobenzyl)-1,4,5,6-tetrahydro-1,3,5-triazin-2-yl)thio)methyl)benzene |
| 42 | 1,2-bis(((5-(4-(trifluoromethyl)benzyl)-1,4,5,6-tetrahydro-1,3,5-triazin-2-yl)thio)methyl)benzene |
| 43 | 1,2-bis(((5-(3,4-difluorobenzyl)-1,4,5,6-tetrahydo-1,3,5-traizin-2-yl)thio)methyl)benzene |
| 44 | 1,2-bis(((5-(2,5-dimethylbenzyl)-1,4,5,6-tetrahydro-1,3,5-triazin-2-yl)thio)methyl)benzene |
| 45 | 1,2-bis(((5-(3-fluorobenzyl)-1,4,5,6-tetrahydro-1,3,5-triazin-2-yl)thio)methyl)benzene |
| 46 | (4-(trifluoromethyl)-1,2-phenylene)bis(methylene) dicarbamimidothioate dihydrobromide |
| 47 | 6,6'-(((4-(trifluoromethyl)-1,2-phenylene)bis(methylene))bis(sulfanediyl))bis(3-(3,4-dichlorophenethyl)-1,2,3,4-tetrahydro-1,3,5-triazine) |
| 48 | 6,6'(((4-(trifluoromethyl)-1,2-phenylene)bis(methylene))bis(suflanediyl))bis(3-(2-chlorophenethyl)-1,2,3,4-tetrahydro-1,3,5-triazine) |
| 49 | (4-bromo-1,2-phenylene)bis(methylene) (E,E)-bis(N'-(4-bromophenyl)carbamimidothioate) |
| 50 | 6,6'-(((4,5-dichloro-1,2-phenylene)bis(methylene))bis(sulfanediyl))bis(3-cyclohexylmethyl)-1,2,3,4-tetrahydro-1,3,5-triazine) |
| 51 | 2-(2-(carbamimidoylthio)ethyl)benzyl carbamimidothioate dihydrobromide |
| 52 | 6,6'-(((4-bromo-1,2-phenylene)bis(methylene))bis(sulfanediyl))bis(3-(cyclohexylmethyl)-1,2,3,4-tetrahydro-1,3,5-triazine) |
| 53 | 6,6'-(((4-bromo-1,2-phenylene)bis(methylene))bis(sulfanediyl))bis(3-(2-chlorophenethyl)-1,2,3,4-tetrahydro-1,3,5-triazine) |
| 54 | 6,6'-(((4-bromo-1,2-phenylene)bis(methylene))bis(sulfanediyl))bis(3-(3,4-dichlorobenzyl)-1,2,3,4-tetrahydro-1,3,5-triazine) |
| 55 | methyl 2-((cabamimidoylthio)methyl)benzoate hydrochloride |
| 56 | 6,6'-(((4,5-dichloro-1,2-phenylene)bis(methylene))bis(sulfanediyl))bis(3-(3,4-dichlorobenzyl)-1,2,3,4-tetrahydro-1,3,5-triazine) |
| 57 | (4-bromo-1,2-phenylene)bis(methylene) (E,E)-bis(N,N'-dichlorohexylcarbamimidothioate) dihydrobromide |
| 58 | 1,2-phenylenebis(methylene) (E,E)-bis(N,N'-dicyclohexylcarbamimidothioate) dihydrobromide |
| 59 | 2-(bromomethyl)benzyl (E)-N'-(3-chloro-4-fluorophenyl)carbamimidothioate hydrobromide |
| 60 | 6,6'-(((4-bromo-1,2-pheylene)bis(methylene))bis(sulfanediyl))bis(3-(2-cyclohexylethyl)-1,2,3,4-tetrahydro-1,3,5-triazine) |
| 61 | 6,6'-(((4,5-dichloro-1,2-phenylene)bis(methylene))bis(sulfanediyl))bis(3-(2-cyclohexylethyl)-1,2,3,4-tetrahydro-1,3,5-triazine) |
| 62 | 2-(2-methylamino)-2-oxoethyl)benzyl carbamimidothioate hydrobromide |
| 63 | (4,5-dichloro-1,2-phenylene)bis(methylene) (E,E)-bis(N'-(2,4-difluorophenyl)carbamimidothioate) dihydrobromide |
| 64 | 2-(2-oxo-2-(phenylethylamino)ethyl)benzyl carbamimidothioate hydrobromide |
| 65 | 2-(2-((cyclohexylmethyl)amino)-2-oxoethyl)benzyl carbamimidothioate hydrobromide |

TABLE 1-continued

| Compound No. | Compound name |
|---|---|
| 66 | 2-(2-((2-chlorophenethyl)amino)-2-oxoethyl)benzyl carbamimidothioate hydrobromide |
| 67 | 2-(2-((4-cyanobenzyl)amino)-2-oxoethyl)benzyl carbamimidothioate hydrobromide |
| 68 | 2-(2-((4-chlorophenethyl)amino)-2-oxoethyl)benzyl carbamimidothioate hydrobromide |
| 69 | 2-(2-((2-cyclohexylethyl)amino)-2-oxoethyl)benzyl carbamimidothioate hydrobromide |
| 70 | 2-(2-((3,4-dichlorophenethyl)amino)-2-oxoethyl)benzyl carbamimidothioate hydrobromide |
| 71 | 2-(2-((cyclopropylmethyl)amino)-2-oxoethyl)benzyl carbamimidothioate hydrobromide |
| 72 | 2-(2-oxo-2-((4-phenylbutyl)amino)ethyl)benzyl carbamimidothioate hydrobromide |
| 73 | 6,6'-(((4,5-dichloro-1,2-phenylene)bis(methylene))bis(sulfanediyl))bis(3-(cyclopropylmethyl)-1,2,3,4-tetrahydro-1,3,5-triazine) |
| 74 | 5-bromo-2-(cyclohexylmethyl)carbamoyl)benzyl carbamimidothioate hydrobromide |
| 75 | 6,6'-(((4-bromo-1,2-phenylene)bis(methylene))bis(sulfanediyl))bis(3-(cyclopropylmethyl)-1,2,3,4-tetrahydro-1,3,5-triazine) |
| 76 | 5-bromo-2-((4-cyanobenzyl)carbamoyl)benzyl carbamimidothioate hydrobromide |
| 77 | 5-cyano-2-(methylcarbamoyl)benzyl carbamimidothioate hydrobromide |
| 78 | 5-bromo-2-((4-chlorophenethyl)carbamoyl)benzyl carbamimidothioate hydrobromide |
| 79 | 2-(2-(methylamino)-2-oxoethyl)benzyl (E)-N'-(4-bromophenyl)carbamimidothioate hydrobromide |
| 80 | 2-(2-(methylamino)-2-oxoethyl)benzyl (E)-N'-(3-chloro-4-fluorophenyl)carbamimidothioate hydrobromide |
| 81 | 5-cyano-2-(methylcarbamoyl)benzyl (E)-N'-(4-bromophenyl)carbamimidothioate hydrobromide |
| 82 | 5-bromo-2-((4-chlorobenzyl)carbamoyl)benzyl carbamimidothioate hydrobromide |
| 83 | 5-bromo-2-((4-chlorobenzyl)carbamoyl)benzyl (E)-N'-(3-chloro-4-fluorophenyl)carbamimidothioate hydrobromide |
| 84 | 5-bromo-2-((4-chlorobenzyl)carbamoyl)benzyl (E)-N'-(4-bromophenyl)carbamimidothioate hydrobromide |
| 85 | 5-bromo-2-((4-cyanobenzyl)carbamoyl)benzyl (E)-N'-(3-chloro-4-fluorophenyl)carbamimidothioate hydrobromide |
| 86 | 5-bromo-2-((4-fluorobenzyl)carbamoyl)benzyl carbamimidothioate hydrobromide |
| 87 | 5-bromo-2-((4-cyanobenzyl)carbamoyl)benzyl (E)-N'-(4-bromophenyl)carbamimidothioate hydrobromide |
| 88 | 5-bromo-2-((4-fluorobenzyl)carbamoyl)benzyl (E)-N'-(3-chloro-4-flurophenyl)carbamimidothioate hydrobromide |
| 89 | 5-bromo-2-((2,4-dichlorobenzyl)carbamoyl)benzyl carbamimidothioate hydrobromide |
| 90 | 5-bromo-2-((4-methylbenzyl)carbamoyl)benzyl carbamimidothioate hydrobromide |
| 91 | 5-bromo-2-((4-methylbenzyl)carbamoyl)benzyl (E)-N'-(3-chloro-4-fluorophenyl)carbamimidothioate hydrobromide |
| 92 | 2-(methylcarbamoyl)benzyl carbamimidothioate hydrobromide |
| 93 | 5-bromo-2-((cyclopropylmethyl)carbamoyl)benzyl carbamimidothioate hydrobromide |
| 94 | 5-bromo-2-((3,4-dichlorobenzyl)carbamoyl)benzyl carbamimidothioate hydrobromide |
| 95 | 1,2-phenylenebis(methylene) (E,E)-bis(N'-(2,4-difluorophenyl)carbamimidothioate) dihydrobromide |
| 96 | 2-((4-cyanobenzyl)carbamoyl)benzyl carbamimidothioate hydrobromide |
| 97 | 5-bromo-2-((4-bromobenzyl)carbamoyl)benzyl carbamimidothioate hydrobromide |
| 98 | (2-(methylcarbamoyl)pyridin-3-yl)methyl carbamimidothioate hydrobromide |
| 99 | (2-((4-cyanobenzyl)carbamoyl)pyridin-3-yl)methyl carbamimidothioate hydrobromide |
| 100 | (3-(methylcarbamoyl)pyridin-2-yl)methyl carbamimidothioate hydrobromide |
| 101 | (2-((4-cyanobenzyl)carbamoyl)pyridin-3-yl)methyl (E)-N'-(3-chloro-4-fluorophenyl)carbamimidothioate hydrobromide |
| 102 | 5-bromo-2-((4-methoxybenzyl)carbamoyl)benzyl carbamimidothioate hydrobromide |
| 103 | 4-bromo-2-((4-cyanobenzyl)carbamoyl)benzyl carbamimidothioate hydrobromide |
| 104 | 2-((4-cyanobenzyl)carbamoyl)benzyl carbamimidoselenoate hydrobromide |
| 105 | 5-bromo-2-((3-methoxybenzyl)carbamoyl)benzyl carbamimidothioate hydrobromide |
| 106 | 5-bromo-2-((3-methoxybenzyl)carbamoyl)benzyl carbamimidoselenoate hydrobromide |
| 107 | 5-bromo-2-((cyclopropylmethyl)carbamoyl)benzyl carbamimidoselenoate hydrobromide |
| 108 | 1,2-phenylenbis(methylene) dicarbamimidoselenoate dihydrobromide |
| 109 | (4-chloro-1,2-phenylene)bis(methylene) dicarbamimidoselenoate dihydrobromide |
| 110 | 4-bromo-2-((4-cyanobenzyl)carbamoyl)benzyl carbamimidoselenoate hydrobromide |
| 111 | 2-bromo-6-((4-cyanobenzyl)carbamoyl)benzyl carbamimidothioate hydrobromide |
| 112 | quinoxaline-2,3-diylbis(methylene) dicarbamimidoselenoate dihydrobromide |
| 113 | 5-bromo-2-((4-cyanobenzyl)carbamoyl)benzyl carbamimidoselenoate hydrobromide |
| 114 | 5-bromo-2-((4-(trifluoromethyl)benzyl)carbamoyl)benzyl carbamimidothioate hydrobromide |
| 115 | 5-bromo-2-((2-methoxyethyl)carbamoyl)benzyl carbamimidothioate hydrobromide |
| 116 | 5-bromo-2-((3-chloro-4-fluorobenzyl)carbamoyl)benzyl carbamimidothioate hydrobromide |
| 117 | 4-bromo-2-((4-bromobenzyl)carbamoyl)benzyl carbamimidothioate hydrobromide |
| 118 | 4-bromo-2-((4-cyanobenzyl)carbamoyl)benzyl (E)-N'-(3-chloro-4-fluorphenyl)carbamimidothioate hydrobromide |
| 119 | 4-bromo-2-((4-cyanobenzyl)carbamoyl)benzyl (E)-N'-(4-bromophenyl)carbamimidothioate hydrobromide |
| 120 | 6,6'-(((4-fluoro-1,2-phenylene)bis(methylene))bis(sulfanediyl))bis(3-(cyclopropylene)-1,2,3,4-tetrahydro-1,3,5-triazine) |
| 121 | 6,6'-(((4-fluoro-1,2-phenylene)bis(methylene))bis(sulfanediyl))bis(3-(cyclohexylmethyl)-1,2,3,4-tetrahydro-1,3,5-triazine) |
| 122 | 1,2-phenylenebis(methylene) (E,E)-bis(N'-(3-chloro-4-fluorophenyl)carbamimidothioate) dihydrobromide |
| 123 | (4,5-dichloro-1,2-phenylene)bis(methylene) (E,E)-bis(N'-(4-chlorophenyl)carbamimidothioate) dihydrobromide |
| 124 | (4,5-dichloro-1,2-phenylene)bis(methylene) (E,E)-bis(N'-(4-methoxyphenyl)carbamimidothioate) dihydrobromide |
| 125 | (4,5-dichloro-1,2-phenylene)bis(methylene) (E,E)-bis(N'-(3-chlorophenyl)carbamimidothioate) dihydrobromide |
| 126 | (4-fluoro-1,2-phenylene)bis(methylene) (E,E)-bis(N'-(4-bromophenyl)carbamimidothioate) dihydrobromide |
| 127 | (4-fluoro-1,2-phenylene)bis(methylene) (E,E)-bis(N'-(4-fluorophenyl)carbamimidothioate) dihydrobromide |
| 128 | (4-fluoro-1,2-phenylene)bis(methylene) (E,E)-bis(N'-(4-methoxyphenyl)carbamimidothioate) dihydrobromide |
| 129 | (4-fluoro-1,2-phenylene)bis(methylene) (E,E)-bis(N'-(3-chloro-4-fluorophenyl)carbamimidothioate) dihydrobromide |
| 130 | (4-fluoro-1,2-phenylene)bis(methylene) (E,E)-bis(N'-(2,4-difluorophenyl)carbamimidothioate) dihydrobromide |
| 131 | (4,5-difluoro-1,2-phenylene)bis(methylene) dicarbamimidothioate dihydrobromide |
| 132 | (4,5-difluoro-1,2-phenylene)bis(methylene) (E,E)-bis(N'-(4-chlorophenyl)carbamimidothioate) dihydrobromide |
| 133 | 6,6'(((4-fluoro-1,2-phenylene)bis(methylene))bis(sulfanediyl))bis(3-(3,4-dichlorophenethyl)-1,2,3,4-tetrahydro-1,3,5-triazine) |
| 134 | (4,5-dichloro-1,2-phenylene)bis(methylene) (E,E)-bis(N'-(3-chloro-4-fluorophenyl)carbamimidothioate) dihydrobromide |

TABLE 1-continued

| Compound No. | Compound name |
|---|---|
| 135 | (4,5-dichloro-1,2-phenylene)bis(methylene) (E,E)-bis(N'-(4-bromophenyl)carbamimidothioate) dihydrobromide |
| 136 | (4,5-dichloro-1,2-phenylene)bis(methylene) (E,E)-bis(N'-(3-bromophenyl)carbamimidothioate) dihydrobromide |
| 137 | (4,5-dichloro-1,2-phenylene)bis(methylene) (E,E)-bis(N'-(4-fluorophenyl)carbamimidothioate) dihydrobromide |
| 138 | (4,5-dichloro-1,2-phenylene)bis(methylene) (E,E)-bis(N'-(p-tolyl)carbamimidothioate) dihydrobromide |
| 139 | 6,6'-(((4,5-dichloro-1,2-phenylene)bis(methylene))bis(sulfanediyl))bis(3-(3-chloro-4-fluorobenzyl)-1,2,3,4-tetrahydro-1,3,5-triazine) |
| 140 | 6,6'(((4-fluoro-1,2-phenylene)bis(methylene))bis(sulfanediyl))bis(3-(4-(trifluoromethyl)phenethyl)-1,2,3,4-tetrahydro-1,3,5-triazine) |
| 141 | 6,6'-(((4-bromo-1,2-phenylene)bis(methylene))bis(sulfanediyl))bis(3-(4-(trifluoromethyl)phenethyl)-1,2,3,4-tetrahydro-1,3,5-triazine) |
| 142 | 1,2-bis(((5-(4-trifluoromethyl)phenethyl)-1,4,5,6-tetrahydro-1,3,5-triazin-2-yl)thio)methyl)benzene |
| 143 | 6,6'-(((4,5-dichloro-1,2-phenylene)bis(methylene))bis(sulfanediyl))bis(3-(4-(trifluoromethyl)phenethyl)-1,2,3,4-tetrahydro-1,3,5-triazine) |
| 144 | 6,6'-(((4-bromo-1,2-phenylene)bis(methylene))bis(sulfanediyl))bis(3-(3-chloro-4-fluorobenzyl)-1,2,3,4-tetrahydro-1,3,5-triazine) |
| 145 | 1,2-bis(((5-(3-chloro-4-fluorobenzyl)-1,4,5,6-tetrahydro-1,3,5-triazin-2-yl)thio)methyl)benzene |
| 146 | 6,6'-(((4-fluoro-1,2-phenylene)bis(methylene))bis(sulfanediyl))bis(3-(3-chloro-4-fluorobenzyl)-1,2,3,4-tetrahydro-1,3,5-triazine) |
| 147 | 6,6'-(((4-fluoro-1,2-phenylene)bis(methylene))bis(sulfanediyl))bis(3-(4-methoxyphenethyl)-1,2,3,4-tetrahydro-1,3,5-triazine) |
| 148 | 6,6'-(((4-bromo-1,2-phenylene)bis(methylene))bis(sulfanediyl))bis(3-(4-methoxyphenethyl)-1,2,3,4-tetrahydro-1,3,5-triazine) |
| 149 | 6,6'-(((4-bromo-1,2-phenylene)bis(methylene))bis(sulfanediyl))bis(3-(3-trifluoromethyl)phenethyl)-1,2,3,4-tetrahydro-1,3,5-triazine) |
| 150 | 6,6'-(((4-fluoro-1,2-phenylene)bis(methylene))bis(sulfanediyl))bis(3-(3-(trifluoromethyl)phenethyl)-1,2,3,4-tetrahydro-1,3,5-triazine) |
| 151 | benzo[b]thiophene-2,3-diylbis(methylene) dicarbamimidothioate dihydrobromide |
| 152 | 6,6'-(((4,5-dichloro-1,2-phenylene)bis(methylene))bis(sulfanediyl))bis(3-(3-trifluoromethyl)phenethyl)-1,2,3,4-tetrahydro-1,3,5-triazine) |
| 153 | 6,6'-(((4,5-dichloro-1,2-phenylene)bis(methylene))bis(sulfanediyl))bis(3-(3-methoxyphenethyl)-1,2,3,4-tetrahydro-1,3,5-triazine) |

The structural formulas of compound Nos. 1 to 153 described above will be shown below.

| Compound No. | Structural formula |
|---|---|
| 1 | 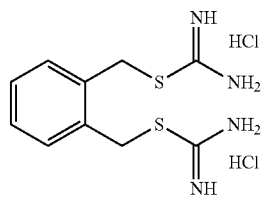 [SMILES: N=C(N)SCc1ccccc1CSC(=N)N ; Cl ; Cl] |
| 2 | 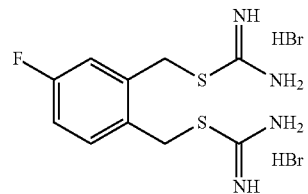 [SMILES: N=C(N)SCc1ccc(F)cc1CSC(=N)N ; Br ; Br] |
| 3 | 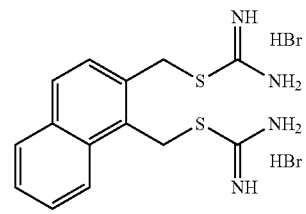 [SMILES: N=C(N)SCc1ccc2ccccc2c1CSC(=N)N ; Br ; Br] |

-continued
| Compound No. | Structural formula |
|---|---|
| 4 | 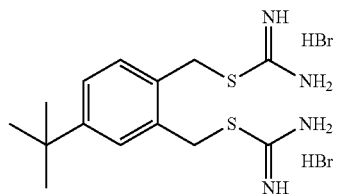 [SMILES: CC(C)(C)c1ccc(CSC(=N)N)c(CSC(=N)N)c1 ; Br ; Br] |
| 5 | 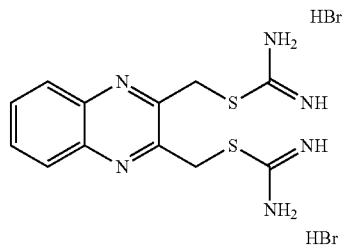 [SMILES: Br ; N=C(N)SCc1nc2ccccc2nc1CSC(=N)N ; Br] |
| 6 | 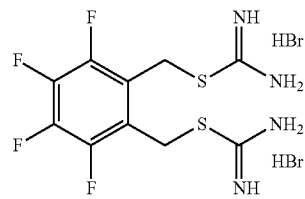 [SMILES: N=C(N)SCc1c(F)c(F)c(F)c(F)c1CSC(=N)N ; Br ; Br] |
| 7 | 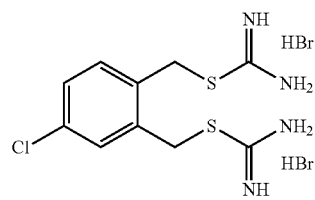 [SMILES: N=C(N)SCc1ccc(Cl)cc1CSC(=N)N ; Br ; Br] |
| 8 | 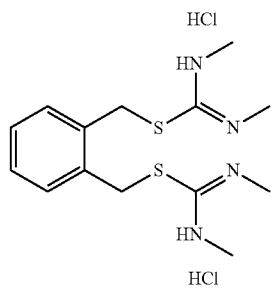 [SMILES: Cl ; C/N=C(\NC)SCc1ccccc1CS/C(=N/C)NC ; Cl] |
| 9 | 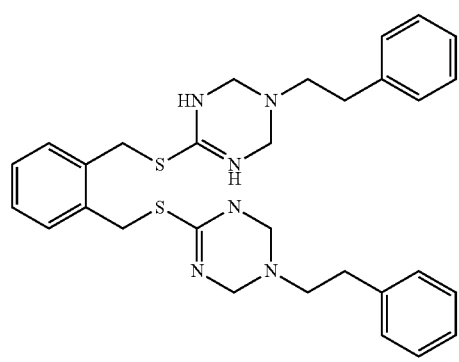 [SMILES: c1ccc(CCN2CN=C(SCc3ccccc3CSC3=NCN(CCc4ccccc4)CN3)NC2)cc1] |

-continued

| Compound No. | Structural formula |
|---|---|
| 10 | (4-bromo-1,2-phenylene)bis(methylene) bis(carbamimidothioate) · 2HBr |
| 11 | 1,2-phenylenebis(methylene) bis(N-methylcarbamimidothioate) · 2HCl |
| 12 | (4-methyl-1,2-phenylene)bis(methylene) bis(carbamimidothioate) · 2HBr |
| 13 | (3-fluoro-1,2-phenylene)bis(methylene) bis(carbamimidothioate) · 2HBr |
| 14 | 1,2-phenylenebis(methylene) bis(5-benzyl-1,4,5,6-tetrahydro-1,3,5-triazin-2-yl sulfide) |
| 15 | thiophene-3,4-diylbis(methylene) bis(carbamimidothioate) · 2HBr |
| 16 | 1,2-bis((pyrimidin-2-ylthio)methyl)benzene |

-continued
| Compound No. | Structural formula |
|---|---|
| 17 | 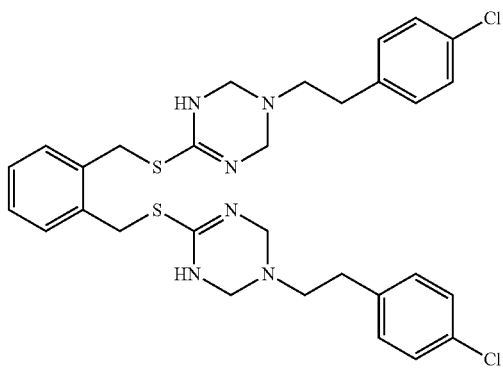 [SMILES: Clc1ccc(CCN2CN=C(SCc3ccccc3CSC3=NCN(CCc4ccc(Cl)cc4)CN3)NC2)cc1] |
| 18 | 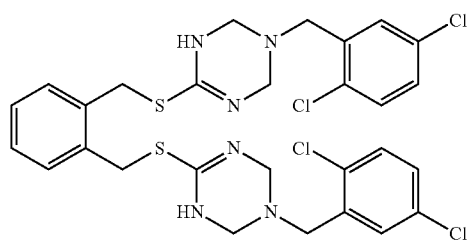 [SMILES: Clc1ccc(Cl)c(CN2CN=C(SCc3ccccc3CSC3=NCN(Cc4cc(Cl)ccc4Cl)CN3)NC2)c1] |
| 19 | 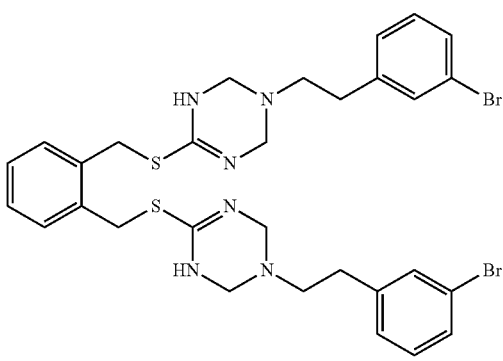 [SMILES: Brc1cccc(CCN2CN=C(SCc3ccccc3CSC3=NCN(CCc4cccc(Br)c4)CN3)NC2)c1] |
| 20 | 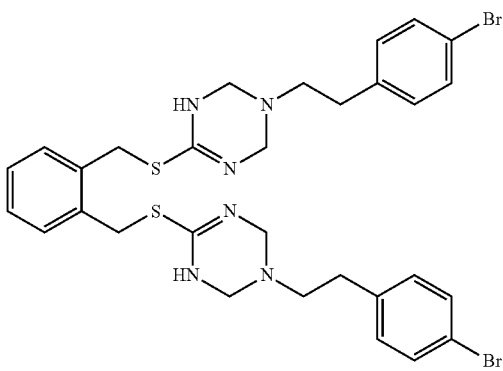 [SMILES: Brc1ccc(CCN2CN=C(SCc3ccccc3CSC3=NCN(CCc4ccc(Br)cc4)CN3)NC2)cc1] |

-continued
| Compound No. | Structural formula |
|---|---|
| 21 | 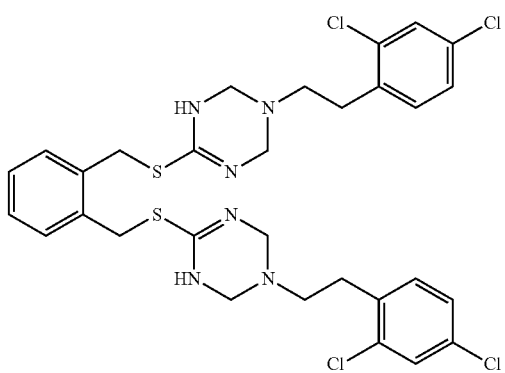 [SMILES: Clc1ccc(CCN2CN=C(SCc3ccccc3CSC3=NCN(CCc4ccc(Cl)cc4Cl)CN3)NC2)c(Cl)c1] |
| 22 | 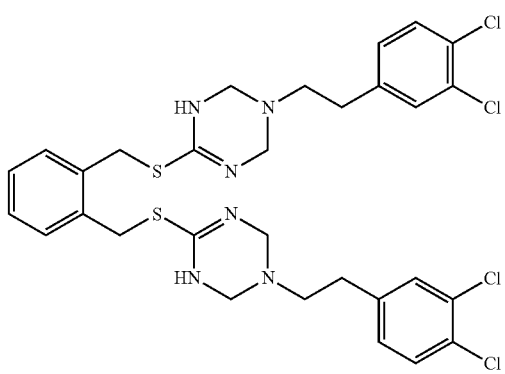 [SMILES: Clc1ccc(CCN2CN=C(SCc3ccccc3CSC3=NCN(CCc4ccc(Cl)c(Cl)c4)CN3)NC2)cc1Cl] |
| 23 | 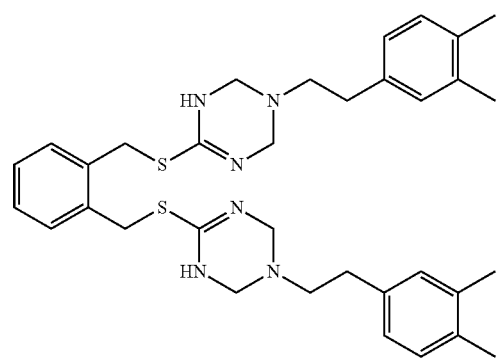 [SMILES: Cc1ccc(CCN2CN=C(SCc3ccccc3CSC3=NCN(CCc4ccc(C)c(C)c4)CN3)NC2)cc1C] |
| 24 | 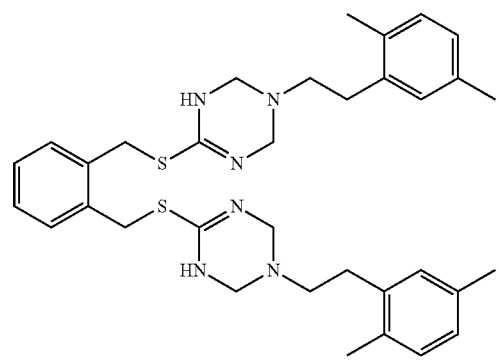 [SMILES: Cc1ccc(C)c(CCN2CN=C(SCc3ccccc3CSC3=NCN(CCc4cc(C)ccc4C)CN3)NC2)c1] |

| Compound No. | Structural formula |
|---|---|
| 25 | 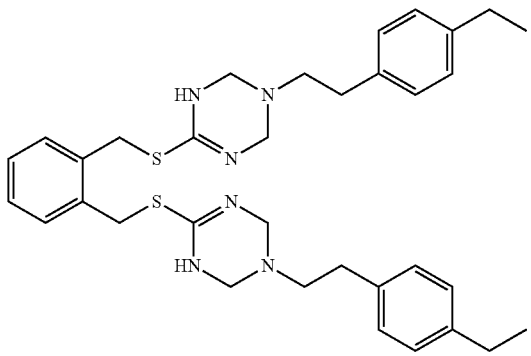 [SMILES: CCc1ccc(CCN2CN=C(SCc3ccccc3CSC3=NCN(CCc4ccc(CC)cc4)CN3)NC2)cc1] |
| 26 | 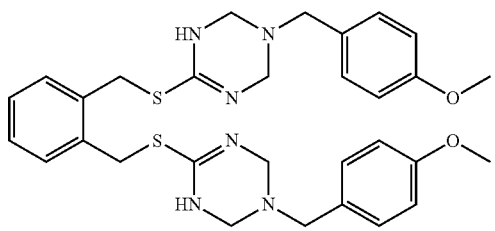 [SMILES: COc1ccc(CN2CN=C(SCc3ccccc3CSC3=NCN(Cc4ccc(OC)cc4)CN3)NC2)cc1] |
| 27 | 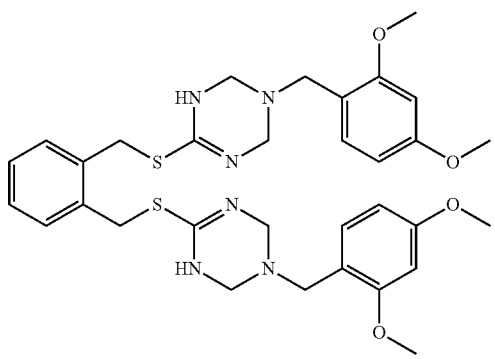 [SMILES: COc1ccc(CN2CN=C(SCc3ccccc3CSC3=NCN(Cc4ccc(OC)cc4OC)CN3)NC2)c(OC)c1] |
| 28 | 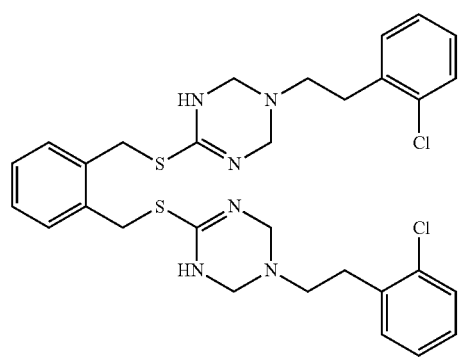 [SMILES: Clc1ccccc1CCN1CN=C(SCc2ccccc2CSC2=NCN(CCc3ccccc3Cl)CN2)NC1] |
| 29 | 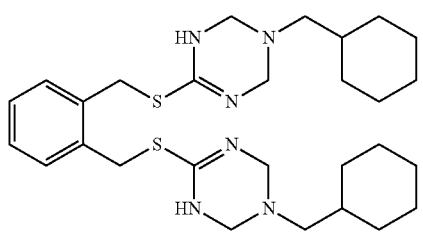 [SMILES: c1ccc(CSC2=NCN(CC3CCCCC3)CN2)c(CSC2=NCN(CC3CCCCC3)CN2)c1] |

-continued
| Compound No. | Structural formula |
|---|---|
| 30 | 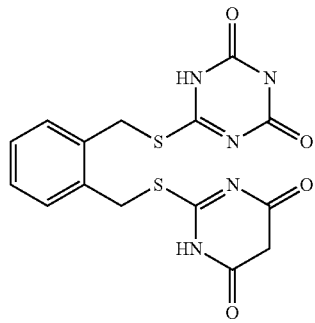 [SMILES: O=C1CC(=O)NC(SCc2ccccc2CSc2nc(=O)[nH]c(=O)[nH]2)=N1] |
| 31 | 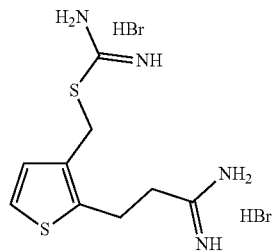 [SMILES: N=C(N)CCc1sccc1CSC(=N)N ; Br ; Br] |
| 32 | 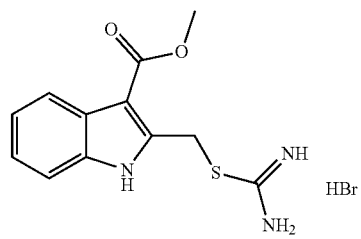 [SMILES: COC(=O)c1c(CSC(=N)N)[nH]c2ccccc12 ; Br] |
| 33 | 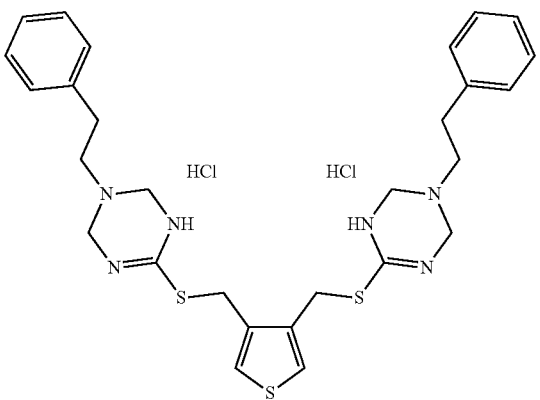 [SMILES: c1ccc(CCN2CN=C(SCc3cscc3CSC3=NCN(CCc4ccccc4)CN3)NC2)cc1 ; Cl ; Cl] |
| 34 | 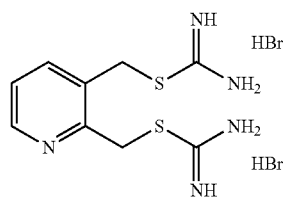 [SMILES: N=C(N)SCc1cccnc1CSC(=N)N ; Br ; Br] |

-continued
| Compound No. | Structural formula |
|---|---|
| 35 | 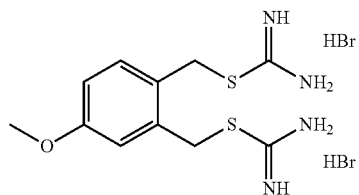 [SMILES: COc1ccc(CSC(=N)N)c(CSC(=N)N)c1 ; Br ; Br] |
| 36 | 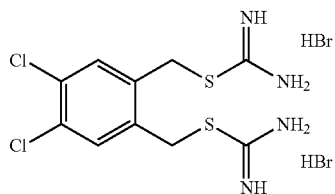 [SMILES: N=C(N)SCc1cc(Cl)c(Cl)cc1CSC(=N)N ; Br ; Br] |
| 37 | 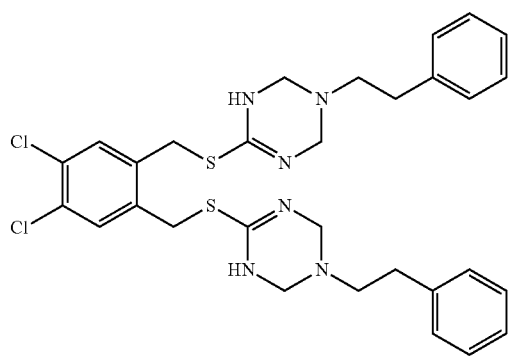 [SMILES: Clc1cc(CSC2=NCN(CCc3ccccc3)CN2)c(CSC2=NCN(CCc3ccccc3)CN2)cc1Cl] |
| 38 | 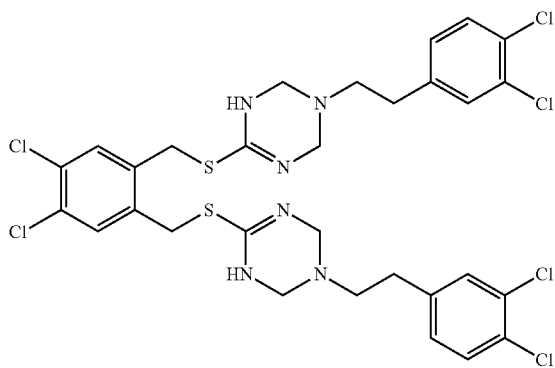 [SMILES: Clc1ccc(CCN2CN=C(SCc3cc(Cl)c(Cl)cc3CSC3=NCN(CCc4ccc(Cl)c(Cl)c4)CN3)NC2)cc1Cl] |
| 39 | 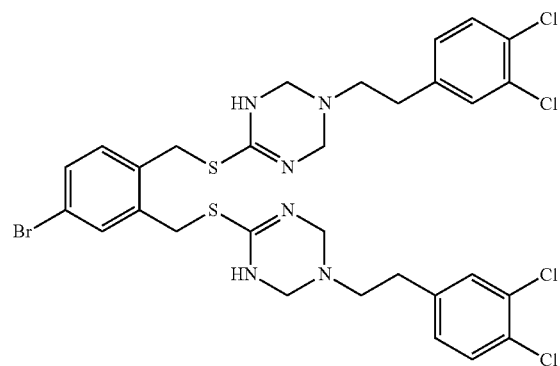 [SMILES: Clc1ccc(CCN2CN=C(SCc3ccc(Br)cc3CSC3=NCN(CCc4ccc(Cl)c(Cl)c4)CN3)NC2)cc1Cl] |

-continued
| Compound No. | Structural formula |
|---|---|
| 40 | 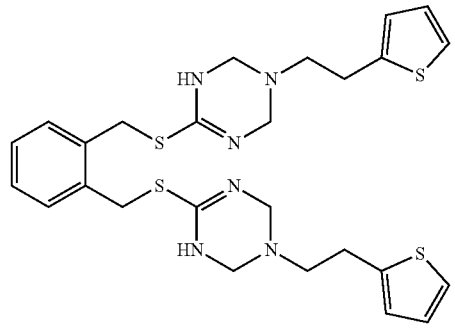 [SMILES: c1csc(CCN2CN=C(SCc3ccccc3CSC3=NCN(CCc4cccs4)CN3)NC2)c1] |
| 41 |  |
| 42 | 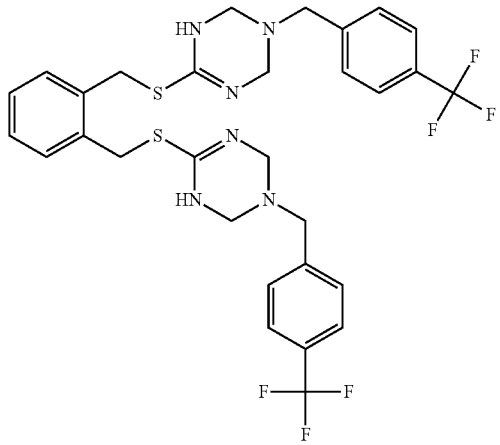 [SMILES: FC(F)(F)c1ccc(CN2CN=C(SCc3ccccc3CSC3=NCN(Cc4ccc(C(F)(F)F)cc4)CN3)NC2)cc1] |
| 43 | 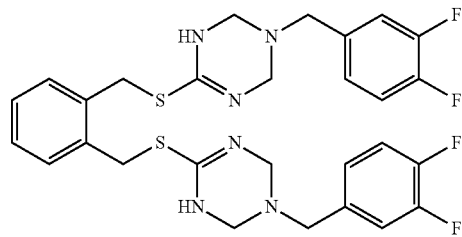 [SMILES: Fc1ccc(CN2CN=C(SCc3ccccc3CSC3=NCN(Cc4ccc(F)c(F)c4)CN3)NC2)cc1F] |
| 44 | 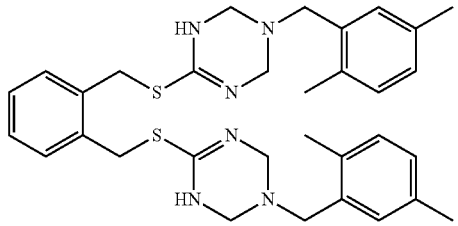 [SMILES: Cc1ccc(C)c(CN2CN=C(SCc3ccccc3CSC3=NCN(Cc4cc(C)ccc4C)CN3)NC2)c1] |

-continued
| Compound No. | Structural formula |
|---|---|
| 45 | 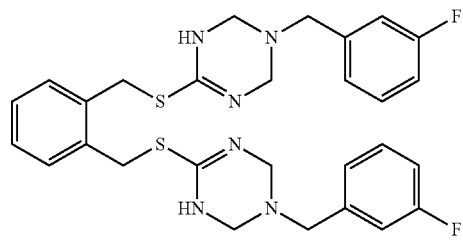 [SMILES: Fc1cccc(CN2CN=C(SCc3ccccc3CSC3=NCN(Cc4cccc(F)c4)CN3)NC2)c1] |
| 46 | 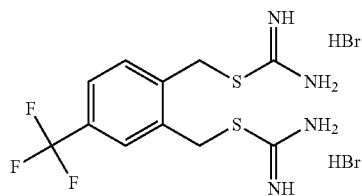 [SMILES: N=C(N)SCc1ccc(C(F)(F)F)cc1CSC(=N)N ; Br ; Br] |
| 47 | 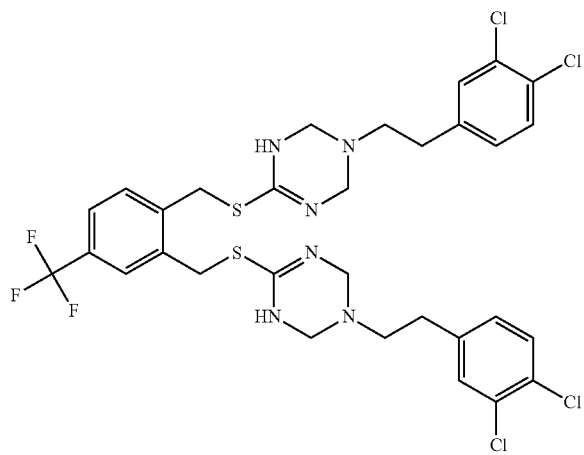 [SMILES: FC(F)(F)c1ccc(CSC2=NCN(CCc3ccc(Cl)c(Cl)c3)CN2)c(CSC2=NCN(CCc3ccc(Cl)c(Cl)c3)CN2)c1] |
| 48 | 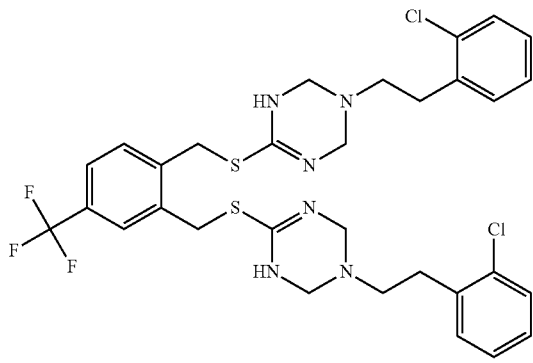 [SMILES: FC(F)(F)c1ccc(CSC2=NCN(CCc3ccccc3Cl)CN2)c(CSC2=NCN(CCc3ccccc3Cl)CN2)c1] |

-continued
| Compound No. | Structural formula |
|---|---|
| 49 | 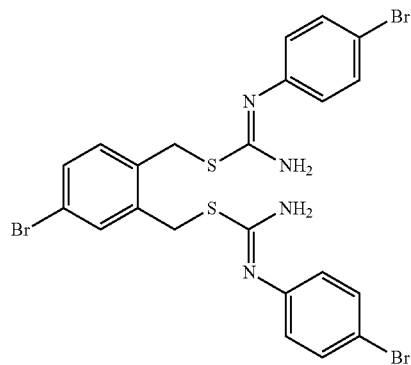 [SMILES: N/C(=N\c1ccc(Br)cc1)SCc1ccc(Br)cc1CS/C(N)=N/c1ccc(Br)cc1] |
| 50 | 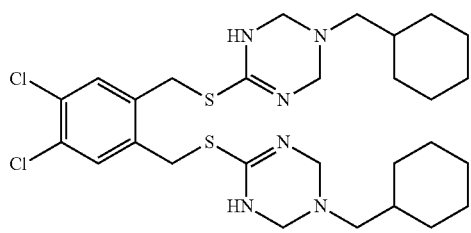 [SMILES: Clc1cc(CSC2=NCN(CC3CCCCC3)CN2)c(CSC2=NCN(CC3CCCCC3)CN2)cc1Cl] |
| 51 | 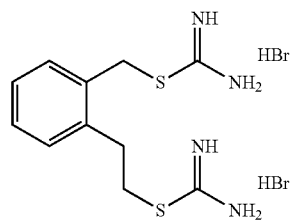 [SMILES: N=C(N)SCCc1ccccc1CSC(=N)N ; Br ; Br] |
| 52 | 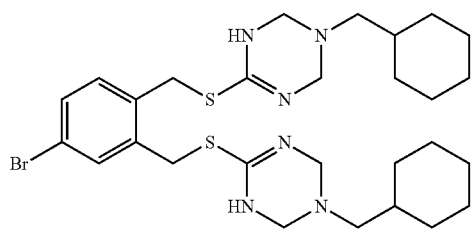 [SMILES: Brc1ccc(CSC2=NCN(CC3CCCCC3)CN2)c(CSC2=NCN(CC3CCCCC3)CN2)c1] |
| 53 | 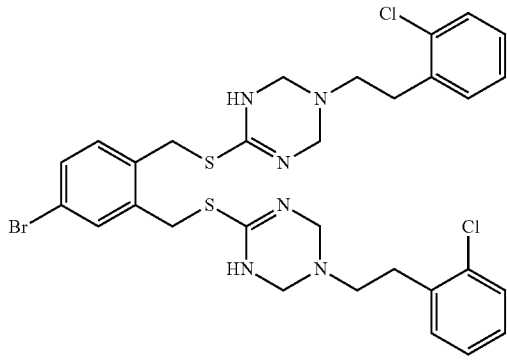 [SMILES: Clc1ccccc1CCN1CN=C(SCc2ccc(Br)cc2CSC2=NCN(CCc3ccccc3Cl)CN2)NC1] |

-continued

| Compound No. | Structural formula |
|---|---|
| 54 | |
| 55 | |
| 56 | |
| 57 | |
| 58 | |

-continued
| Compound No. | Structural formula |
|---|---|
| 59 | 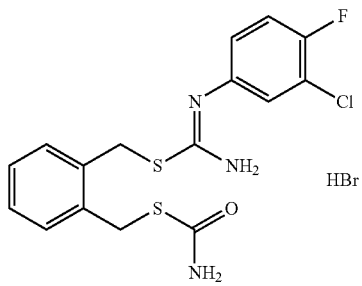 [SMILES: NC(=O)SCc1ccccc1CS/C(N)=N/c1ccc(F)c(Cl)c1 ; Br] |
| 60 | 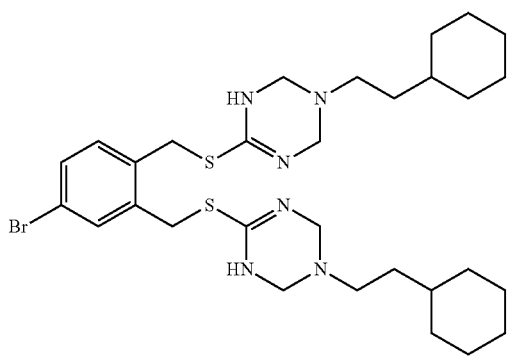 [SMILES: Brc1ccc(CSC2=NCN(CCC3CCCCC3)CN2)c(CSC2=NCN(CCC3CCCCC3)CN2)c1] |
| 61 | 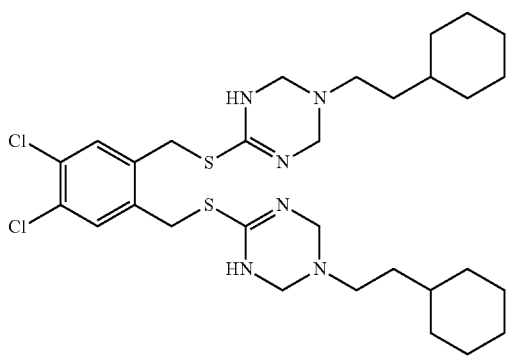 [SMILES: Clc1cc(CSC2=NCN(CCC3CCCCC3)CN2)c(CSC2=NCN(CCC3CCCCC3)CN2)cc1Cl] |
| 62 | 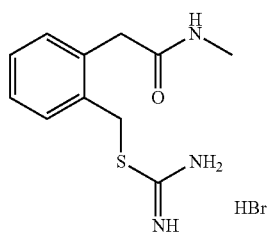 [SMILES: CNC(=O)Cc1ccccc1CSC(=N)N ; Br] |

-continued
| Compound No. | Structural formula |
|---|---|
| 63 | 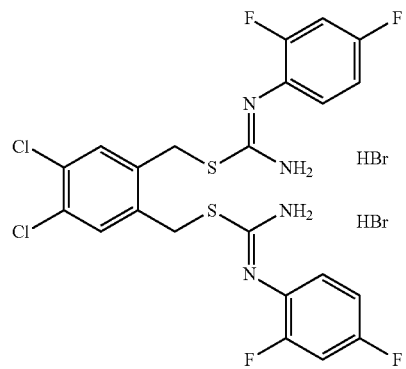 [SMILES: N/C(=N\c1ccc(F)cc1F)SCc1cc(Cl)c(Cl)cc1CS/C(N)=N/c1ccc(F)cc1F ; Br ; Br] |
| 64 | 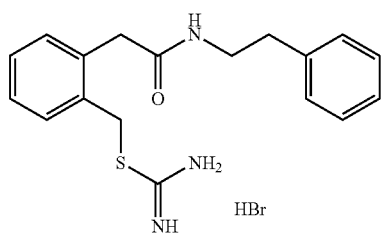 [SMILES: N=C(N)SCc1ccccc1CC(=O)NCCc1ccccc1 ; Br] |
| 65 | 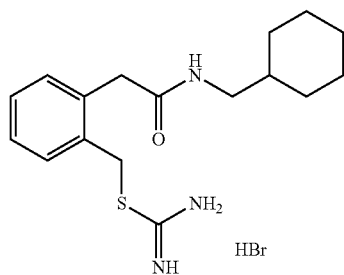 [SMILES: N=C(N)SCc1ccccc1CC(=O)NCC1CCCCC1 ; Br] |
| 66 | 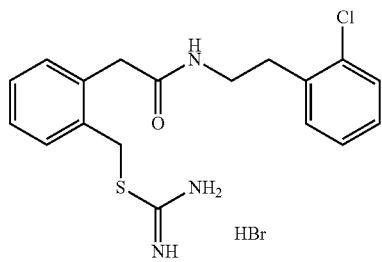 [SMILES: N=C(N)SCc1ccccc1CC(=O)NCCc1ccccc1Cl ; Br] |
| 67 | 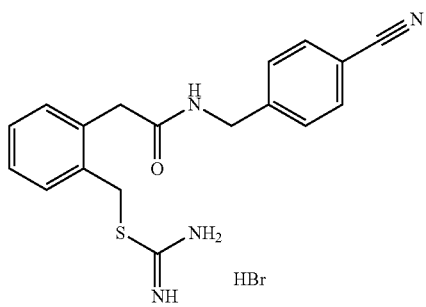 [SMILES: N#Cc1ccc(CNC(=O)Cc2ccccc2CSC(=N)N)cc1 ; Br] |

101
-continued
| Compound No. | Structural formula |
|---|---|
| 68 | 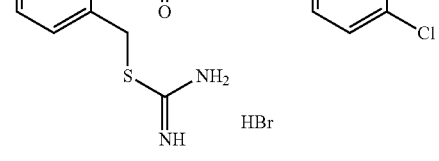 HBr |
| 69 | 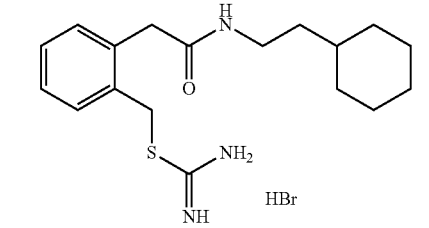 [SMILES: N=C(N)SCc1ccccc1CC(=O)NCCC1CCCCC1 ; Br] HBr |
| 70 | 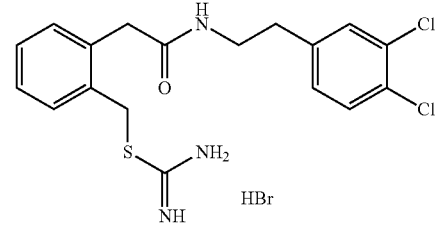 [SMILES: N=C(N)SCc1ccccc1CC(=O)NCCc1ccc(Cl)c(Cl)c1 ; Br] HBr |
| 71 | 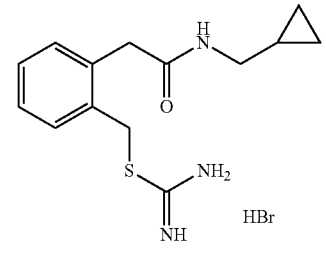 [SMILES: N=C(N)SCc1ccccc1CC(=O)NCC1CC1 ; Br] HBr |
| 72 | 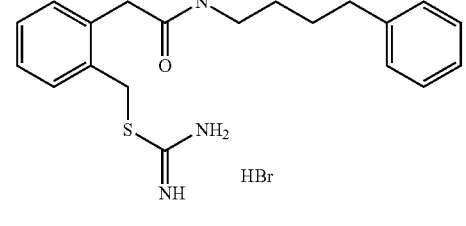 HBr |
| 73 | 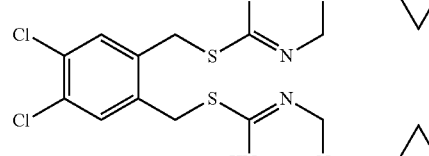 |
102

| Compound No. | Structural formula |
|---|---|
| 74 | 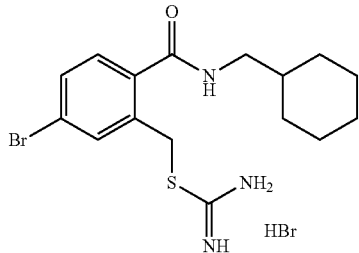 [SMILES: N=C(N)SCc1cc(Br)ccc1C(=O)NCC1CCCCC1 ; Br] |
| 75 | 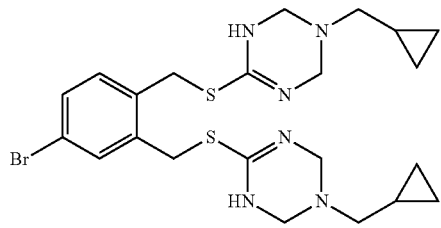 [SMILES: Brc1ccc(CSC2=NCN(CC3CC3)CN2)c(CSC2=NCN(CC3CC3)CN2)c1] |
| 76 | 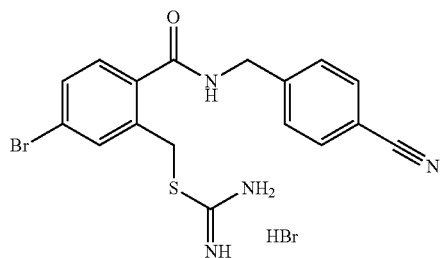 [SMILES: N#Cc1ccc(CNC(=O)c2ccc(Br)cc2CSC(=N)N)cc1 ; Br] |
| 77 | 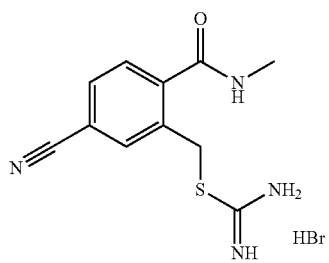 [SMILES: CNC(=O)c1ccc(C#N)cc1CSC(=N)N ; Br] |
| 78 | 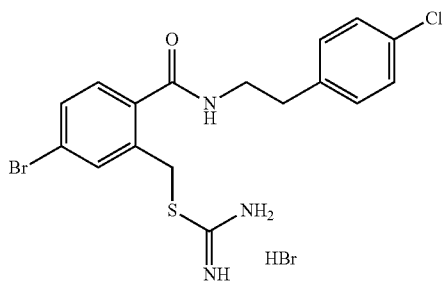 [SMILES: N=C(N)SCc1cc(Br)ccc1C(=O)NCCc1ccc(Cl)cc1 ; Br] |

-continued
| Compound No. | Structural formula |
|---|---|
| 79 | 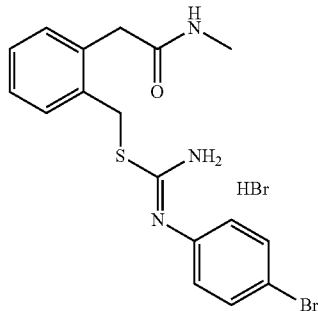 [SMILES: CNC(=O)Cc1ccccc1CS/C(N)=N/c1ccc(Br)cc1 ; Br] |
| 80 | 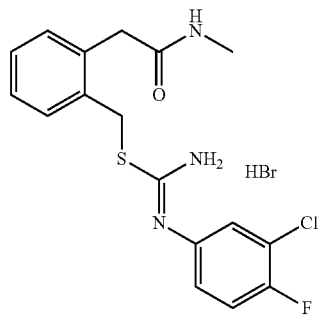 [SMILES: CNC(=O)Cc1ccccc1CS/C(N)=N/c1ccc(F)c(Cl)c1 ; Br] |
| 81 | 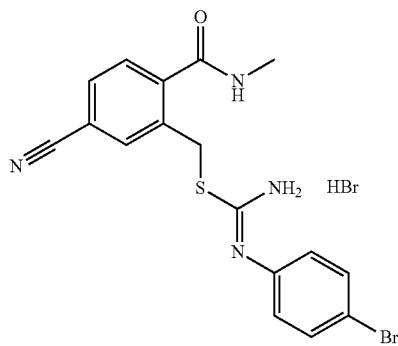 [SMILES: CNC(=O)c1ccc(C#N)cc1CS/C(N)=N/c1ccc(Br)cc1 ; Br] |
| 82 | 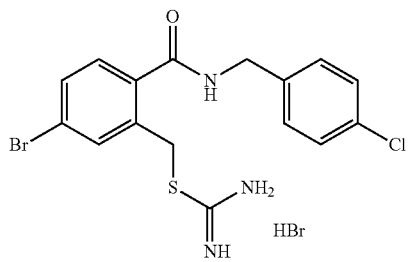 [SMILES: N=C(N)SCc1cc(Br)ccc1C(=O)NCc1ccc(Cl)cc1 ; Br] |

| Compound No. | Structural formula |
|---|---|
| 83 | 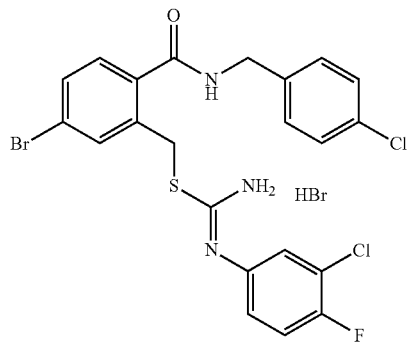 [SMILES: N/C(=N\c1ccc(F)c(Cl)c1)SCc1cc(Br)ccc1C(=O)NCc1ccc(Cl)cc1 ; Br] |
| 84 | 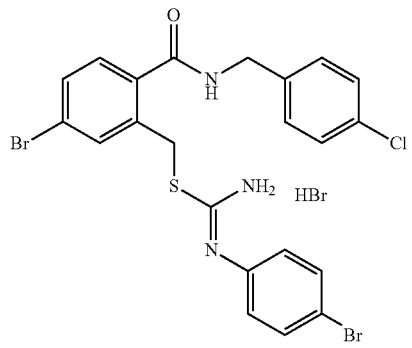 [SMILES: N/C(=N\c1ccc(Br)cc1)SCc1cc(Br)ccc1C(=O)NCc1ccc(Cl)cc1 ; Br] |
| 85 | 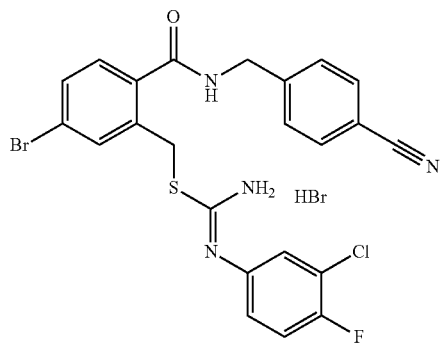 [SMILES: N#Cc1ccc(CNC(=O)c2ccc(Br)cc2CS/C(N)=N/c2ccc(F)c(Cl)c2)cc1 ; Br] |
| 86 | 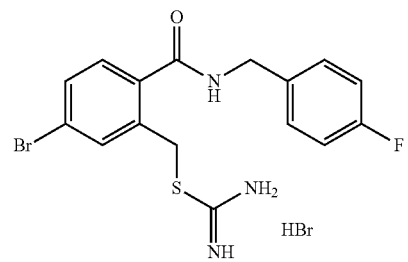 [SMILES: N=C(N)SCc1cc(Br)ccc1C(=O)NCc1ccc(F)cc1 ; Br] |

-continued
| Compound No. | Structural formula |
|---|---|
| 87 | 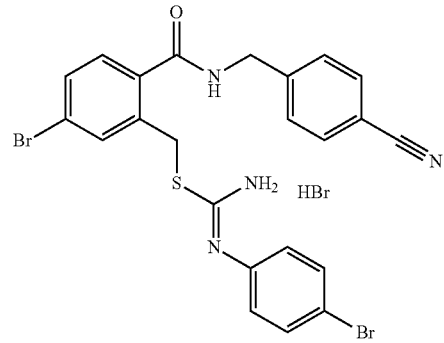 [SMILES: N#Cc1ccc(CNC(=O)c2ccc(Br)cc2CS/C(N)=N/c2ccc(Br)cc2)cc1 ; Br] |
| 88 | 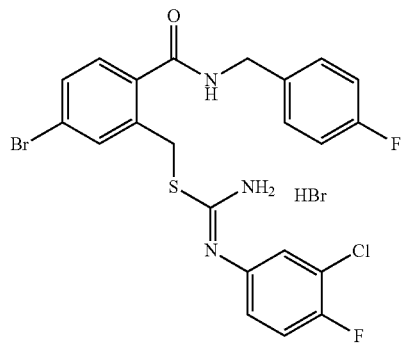 [SMILES: N/C(=N\c1ccc(F)c(Cl)c1)SCc1cc(Br)ccc1C(=O)NCc1ccc(F)cc1 ; Br] |
| 89 | 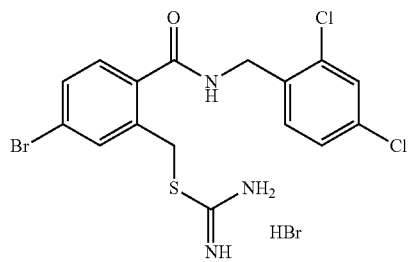 [SMILES: N=C(N)SCc1cc(Br)ccc1C(=O)NCc1ccc(Cl)cc1Cl ; Br] |
| 90 | 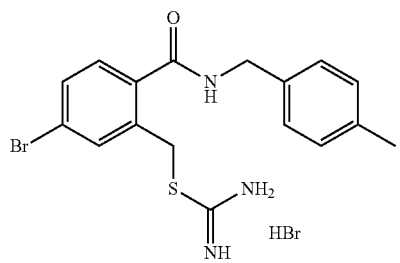 [SMILES: Cc1ccc(CNC(=O)c2ccc(Br)cc2CSC(=N)N)cc1 ; Br] |
| 91 | 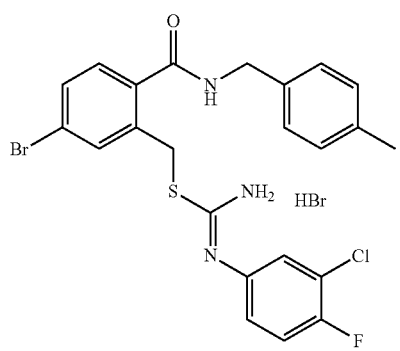 [SMILES: Cc1ccc(CNC(=O)c2ccc(Br)cc2CS/C(N)=N/c2ccc(F)c(Cl)c2)cc1 ; Br] |

-continued

| Compound No. | Structural formula |
|---|---|
| 92 | (structure) |
| 93 | (structure) |
| 94 | (structure) |
| 95 | (structure) |
| 96 | (structure) |

-continued

| Compound No. | Structural formula |
|---|---|
| 97 | |
| 98 | |
| 99 | |
| 100 | |
| 101 | |

-continued
| Compound No. | Structural formula |
|---|---|
| 102 | 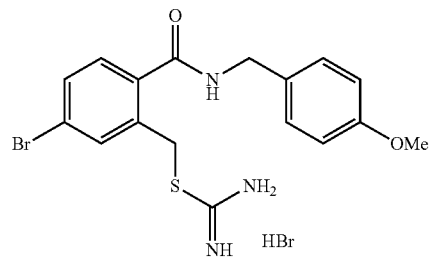 [SMILES: COc1ccc(CNC(=O)c2ccc(Br)cc2CSC(=N)N)cc1 ; Br] |
| 103 | 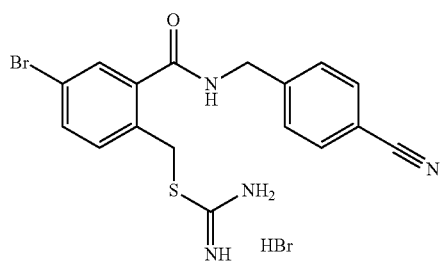 [SMILES: N#Cc1ccc(CNC(=O)c2cc(Br)ccc2CSC(=N)N)cc1 ; Br] |
| 104 | 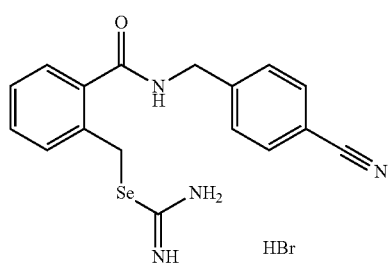 [SMILES: N#Cc1ccc(CNC(=O)c2ccccc2C[Se]C(=N)N)cc1 ; Br] |
| 105 | 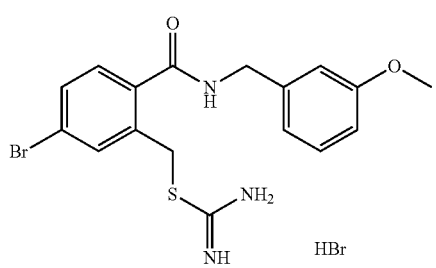 [SMILES: COc1cccc(CNC(=O)c2ccc(Br)cc2CSC(=N)N)c1 ; Br] |
| 106 | 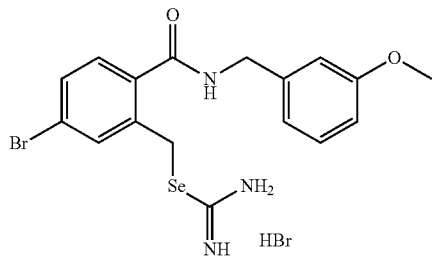 [SMILES: COc1cccc(CNC(=O)c2ccc(Br)cc2C[Se]C(=N)N)c1 ; Br] |

-continued

| Compound No. | Structural formula |
|---|---|
| 107 | 4-bromo-2-(((amino(imino)methyl)selanyl)methyl)-N-(cyclopropylmethyl)benzamide · HBr |
| 108 | 1,2-phenylenebis(methylene) bis(carbamimidoselenoate) · 2HBr |
| 109 | 4-chloro-1,2-phenylenebis(methylene) bis(carbamimidoselenoate) · 2HBr |
| 110 | 5-bromo-2-(((amino(imino)methyl)selanyl)methyl)-N-(4-cyanobenzyl)benzamide · HBr |
| 111 | 3-bromo-2-(((amino(imino)methyl)thio)methyl)-N-(4-cyanobenzyl)benzamide · HBr |
| 112 | quinoxaline-2,3-diylbis(methylene) bis(carbamimidoselenoate) · 2HBr |

-continued
| Compound No. | Structural formula |
|---|---|
| 113 | 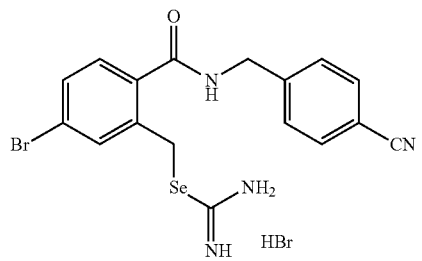 [SMILES: N#Cc1ccc(CNC(=O)c2ccc(Br)cc2C[Se]C(=N)N)cc1 ; Br] |
| 114 | 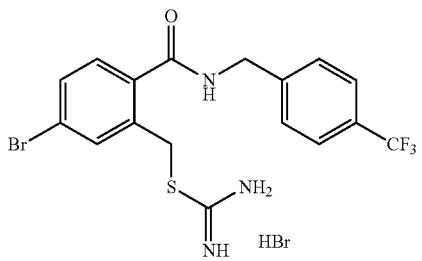 [SMILES: N=C(N)SCc1cc(Br)ccc1C(=O)NCc1ccc(C(F)(F)F)cc1 ; Br] |
| 115 | 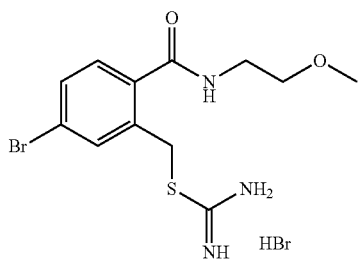 [SMILES: COCCNC(=O)c1ccc(Br)cc1CSC(=N)N ; Br] |
| 116 | 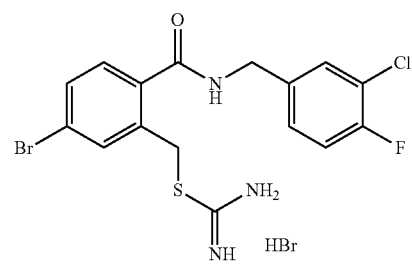 [SMILES: N=C(N)SCc1cc(Br)ccc1C(=O)NCc1ccc(F)c(Cl)c1 ; Br] |
| 117 | 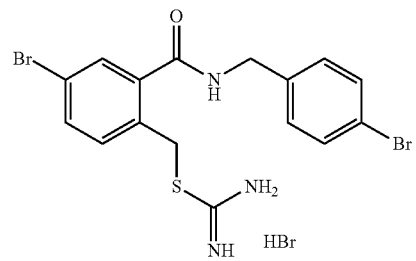 [SMILES: N=C(N)SCc1ccc(Br)cc1C(=O)NCc1ccc(Br)cc1 ; Br] |

-continued
| Compound No. | Structural formula |
|---|---|
| 118 | 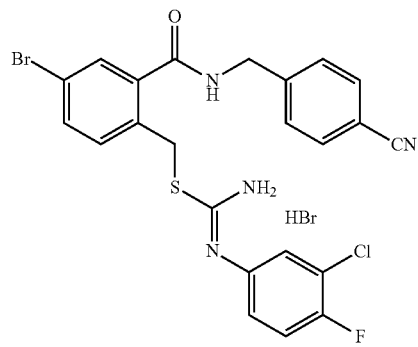 [SMILES: N#Cc1ccc(CNC(=O)c2cc(Br)ccc2CS/C(N)=N/c2ccc(F)c(Cl)c2)cc1 ; Br] |
| 119 | 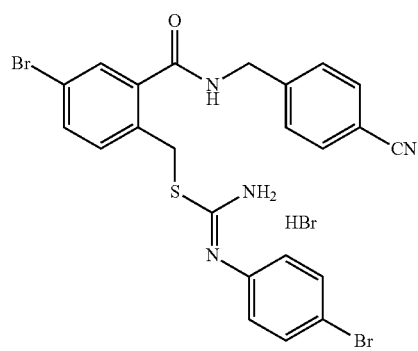 [SMILES: N#Cc1ccc(CNC(=O)c2cc(Br)ccc2CS/C(N)=N/c2ccc(Br)cc2)cc1 ; Br] |
| 120 | 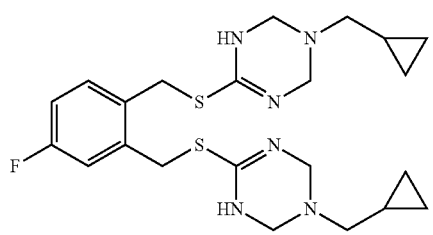 |
| 121 | 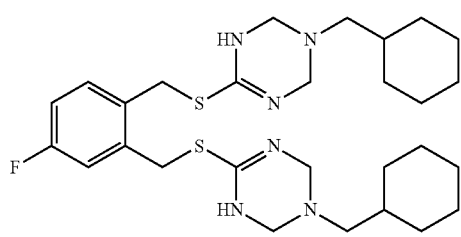 [SMILES: Fc1ccc(CSC2=NCN(CC3CCCCC3)CN2)c(CSC2=NCN(CC3CCCCC3)CN2)c1] |
| 122 | 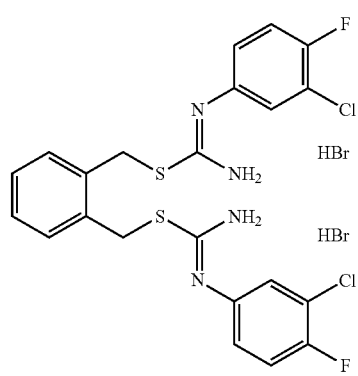 [SMILES: N/C(=N\c1ccc(F)c(Cl)c1)SCc1ccccc1CS/C(N)=N/c1ccc(F)c(Cl)c1 ; Br ; Br] |

-continued
| Compound No. | Structural formula |
|---|---|
| 123 | 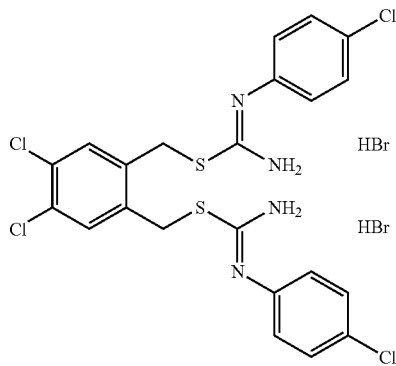 |
| 124 | 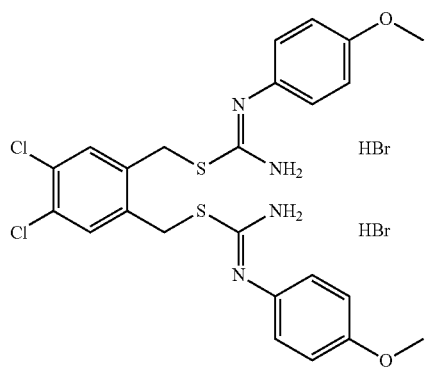 [SMILES: COc1ccc(/N=C(\N)SCc2cc(Cl)c(Cl)cc2CS/C(N)=N/c2ccc(OC)cc2)cc1 ; Br ; Br] |
| 125 | 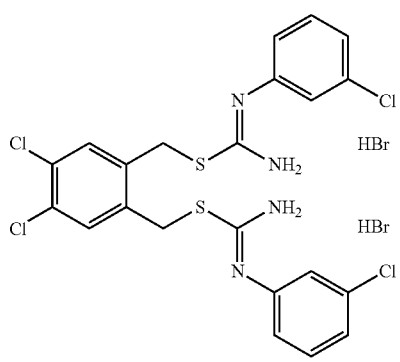 [SMILES: N/C(=N\c1cccc(Cl)c1)SCc1cc(Cl)c(Cl)cc1CS/C(N)=N/c1cccc(Cl)c1 ; Br ; Br] |
| 126 | 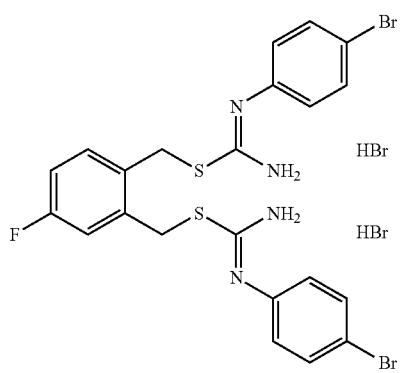 [SMILES: N/C(=N\c1ccc(Br)cc1)SCc1ccc(F)cc1CS/C(N)=N/c1ccc(Br)cc1 ; Br ; Br] |

| Compound No. | Structural formula |
|---|---|
| 127 | 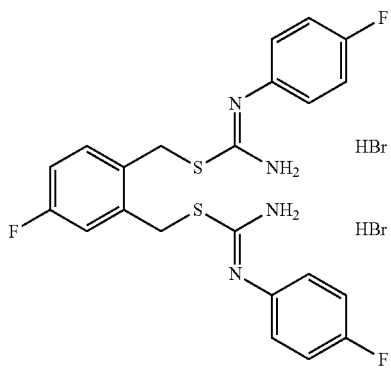 [SMILES: N/C(=N\c1ccc(F)cc1)SCc1ccc(F)cc1CS/C(N)=N/c1ccc(F)cc1 ; Br ; Br] |
| 128 | 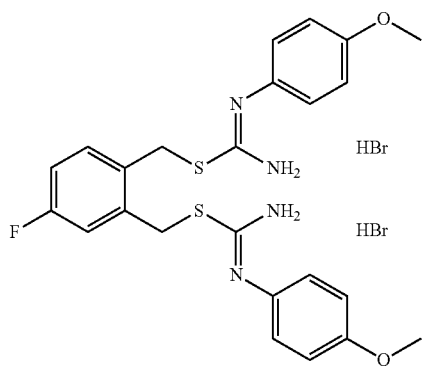 [SMILES: COc1ccc(/N=C(\N)SCc2ccc(F)cc2CS/C(N)=N/c2ccc(OC)cc2)cc1 ; Br ; Br] |
| 129 | 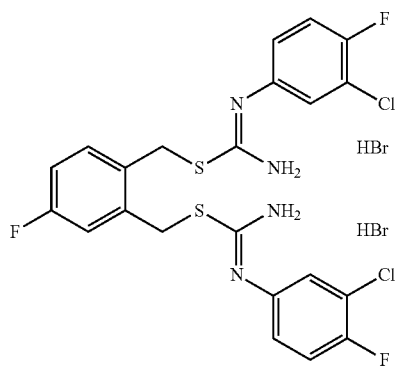 [SMILES: N/C(=N\c1ccc(F)c(Cl)c1)SCc1ccc(F)cc1CS/C(N)=N/c1ccc(F)c(Cl)c1 ; Br ; Br] |
| 130 | 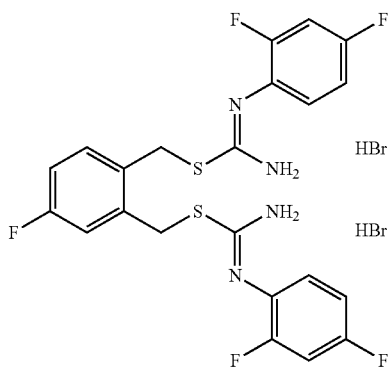 [SMILES: N/C(=N\c1ccc(F)cc1F)SCc1ccc(F)cc1CS/C(N)=N/c1ccc(F)cc1F ; Br ; Br] |

-continued
| Compound No. | Structural formula |
|---|---|
| 131 | 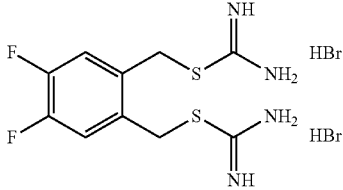 [SMILES: N=C(N)SCc1cc(F)c(F)cc1CSC(=N)N ; Br ; Br] |
| 132 | 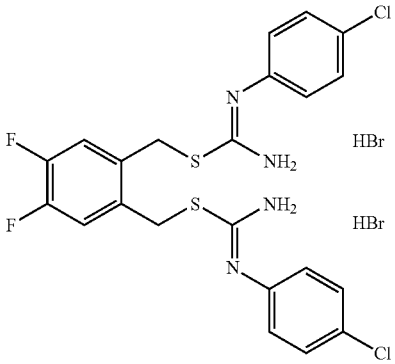 [SMILES: N/C(=N\c1ccc(Cl)cc1)SCc1cc(F)c(F)cc1CS/C(N)=N/c1ccc(Cl)cc1 ; Br ; Br] |
| 133 | 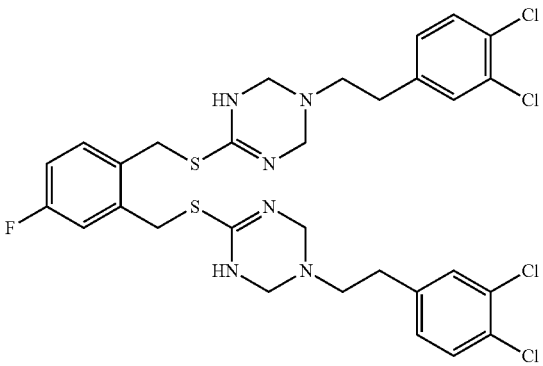 [SMILES: Fc1ccc(CSC2=NCN(CCc3ccc(Cl)c(Cl)c3)CN2)c(CSC2=NCN(CCc3ccc(Cl)c(Cl)c3)CN2)c1] |
| 134 | 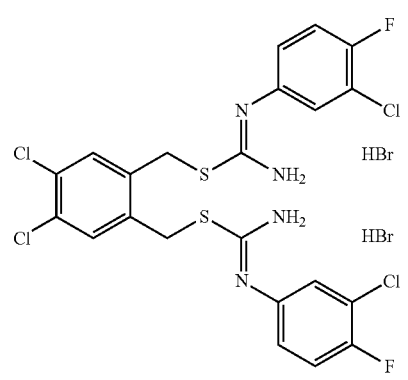 [SMILES: N/C(=N\c1ccc(F)c(Cl)c1)SCc1cc(Cl)c(Cl)cc1CS/C(N)=N/c1ccc(F)c(Cl)c1 ; Br ; Br] |

-continued
| Compound No. | Structural formula | |
|---|---|---|
| 135 | 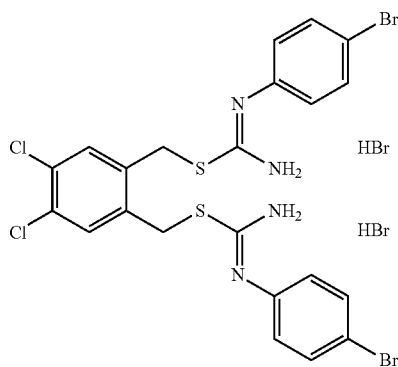 [SMILES: N/C(=N\c1ccc(Br)cc1)SCc1cc(Cl)c(Cl)cc1CS/C(N)=N/c1ccc(Br)cc1 ; Br ; Br] | |
| 136 | 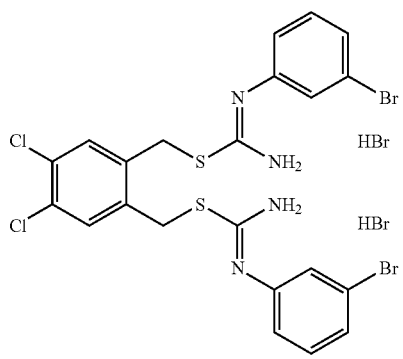 [SMILES: N/C(=N\c1cccc(Br)c1)SCc1cc(Cl)c(Cl)cc1CS/C(N)=N/c1cccc(Br)c1 ; Br ; Br] | |
| 137 | 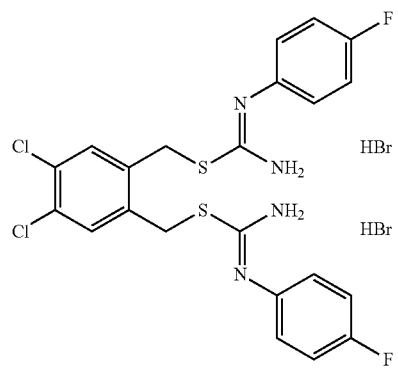 [SMILES: N/C(=N\c1ccc(F)cc1)SCc1cc(Cl)c(Cl)cc1CS/C(N)=N/c1ccc(F)cc1 ; Br ; Br] | |
| 138 | 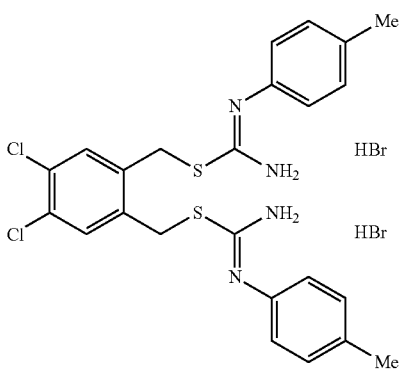 [SMILES: Cc1ccc(/N=C(\N)SCc2cc(Cl)c(Cl)cc2CS/C(N)=N/c2ccc(C)cc2)cc1 ; Br ; Br] | |

-continued
| Compound No. | Structural formula |
|---|---|
| 139 | 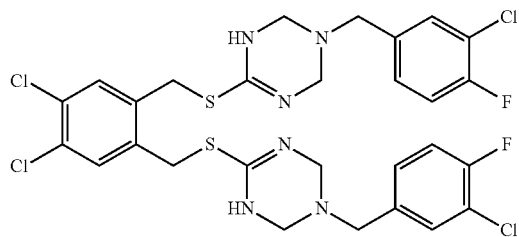 [SMILES: Fc1ccc(CN2CN=C(SCc3cc(Cl)c(Cl)cc3CSC3=NCN(Cc4ccc(F)c(Cl)c4)CN3)NC2)cc1Cl] |
| 140 | 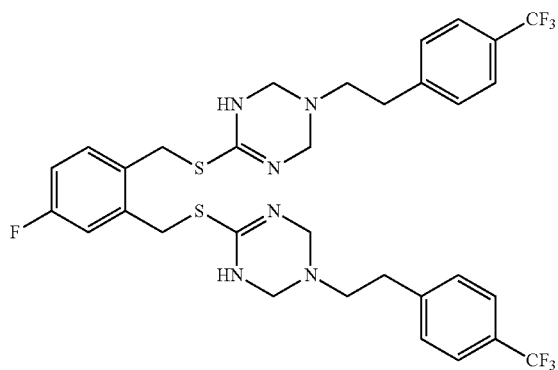 [SMILES: Fc1ccc(CSC2=NCN(CCc3ccc(C(F)(F)F)cc3)CN2)c(CSC2=NCN(CCc3ccc(C(F)(F)F)cc3)CN2)c1] |
| 141 | 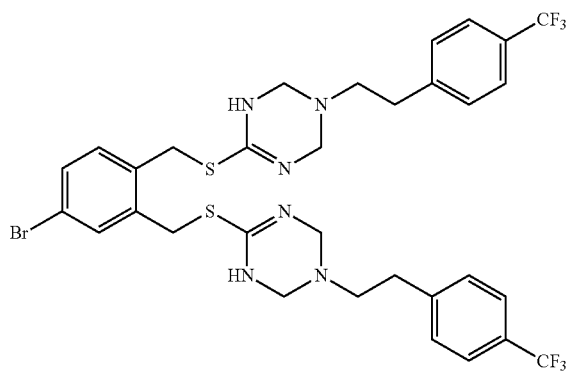 [SMILES: FC(F)(F)c1ccc(CCN2CN=C(SCc3ccc(Br)cc3CSC3=NCN(CCc4ccc(C(F)(F)F)cc4)CN3)NC2)cc1] |
| 142 | 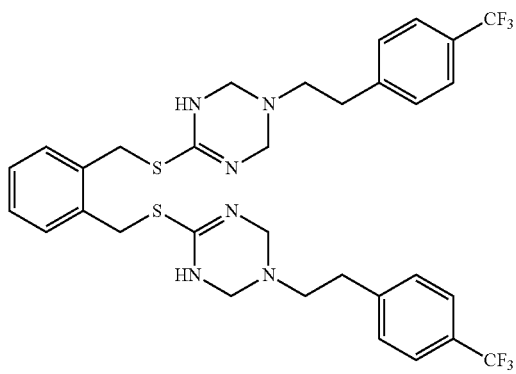 [SMILES: FC(F)(F)c1ccc(CCN2CN=C(SCc3ccccc3CSC3=NCN(CCc4ccc(C(F)(F)F)cc4)CN3)NC2)cc1] |

-continued
| Compound No. | Structural formula |
|---|---|
| 143 | 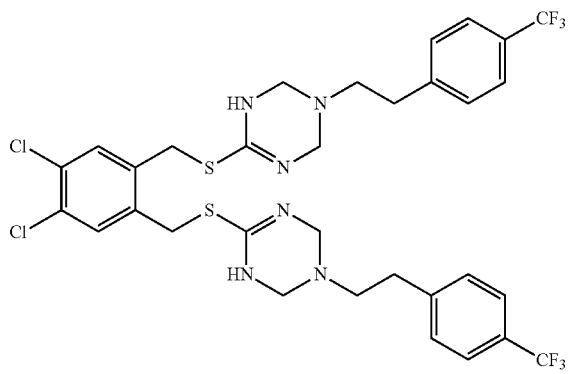 |
| 144 | 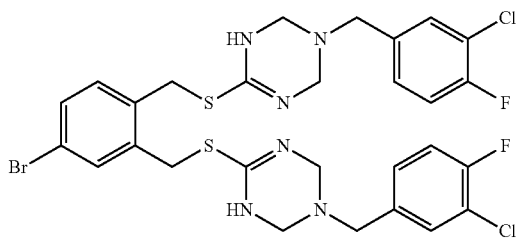 [SMILES: Fc1ccc(CN2CN=C(SCc3ccc(Br)cc3CSC3=NCN(Cc4ccc(F)c(Cl)c4)CN3)NC2)cc1Cl] |
| 145 | 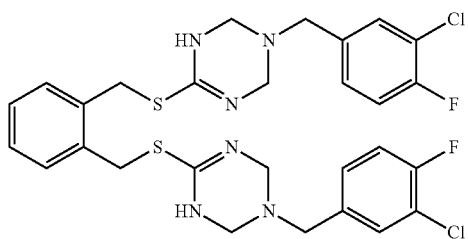 [SMILES: Fc1ccc(CN2CN=C(SCc3ccccc3CSC3=NCN(Cc4ccc(F)c(Cl)c4)CN3)NC2)cc1Cl] |
| 146 | 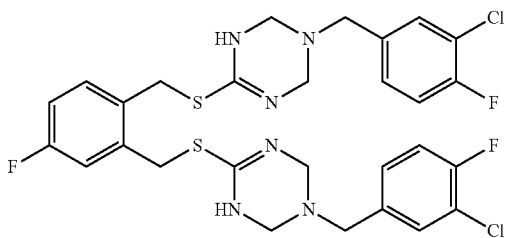 [SMILES: Fc1ccc(CSC2=NCN(Cc3ccc(F)c(Cl)c3)CN2)c(CSC2=NCN(Cc3ccc(F)c(Cl)c3)CN2)c1] |
| 147 | 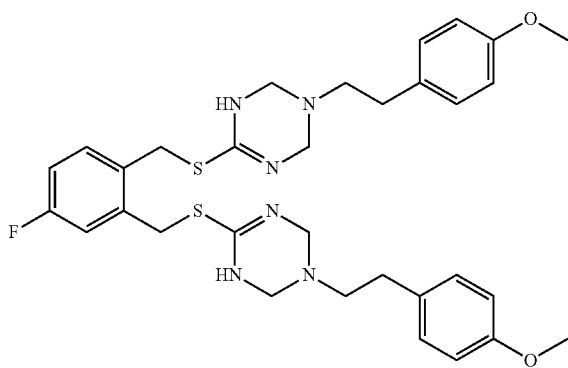 [SMILES: COc1ccc(CCN2CN=C(SCc3ccc(F)cc3CSC3=NCN(CCc4ccc(OC)cc4)CN3)NC2)cc1] |

-continued
| Compound No. | Structural formula |
|---|---|
| 148 | 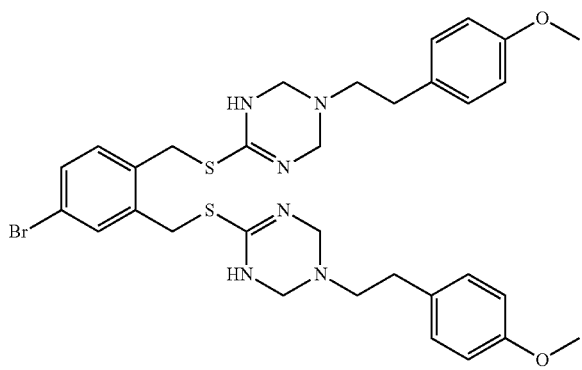 [SMILES: COc1ccc(CCN2CN=C(SCc3ccc(Br)cc3CSC3=NCN(CCc4ccc(OC)cc4)CN3)NC2)cc1] |
| 149 | 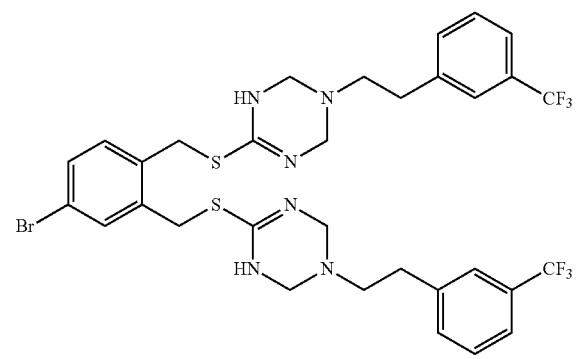 |
| 150 | 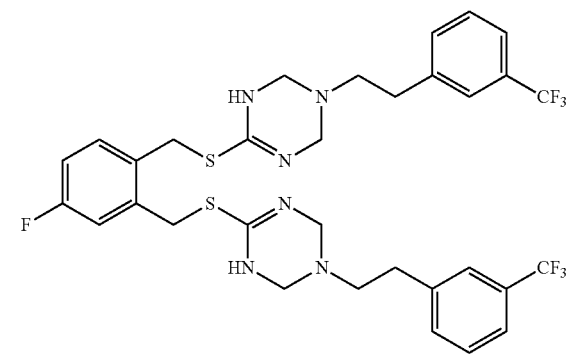 [SMILES: Fc1ccc(CSC2=NCN(CCc3cccc(C(F)(F)F)c3)CN2)c(CSC2=NCN(CCc3cccc(C(F)(F)F)c3)CN2)c1] |
| 151 | 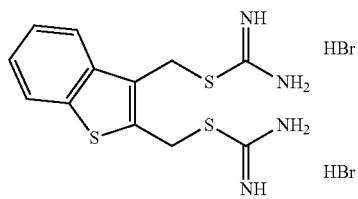 [SMILES: N=C(N)SCc1sc2ccccc2c1CSC(=N)N ; Br ; Br] |

| Compound No. | Structural formula |
|---|---|
| 152 | ![compound 152] |
| 153 | ![compound 153] |

The compound of the present invention of formula (I) can be synthesized by appropriately combining publicly known reactions. A raw material may be purchased as a commercially available product or synthesized by adding a general protective group or the like to a purchased commercially available product (e.g., some compounds (i-a) in scheme 1 were obtained by the methyl-esterification of dicarboxylic acid). The reduction of a carbonyl group or the halogenation of an alcohol group is achieved with a reducing agent, a halogenation reagent, or the like for use in general organic chemistry. Any step is adaptable to, for example, purification by protection and deprotection routinely used in organic chemistry.

Hereinafter, three schemes will be shown as examples of a general synthesis method.

Scheme 1

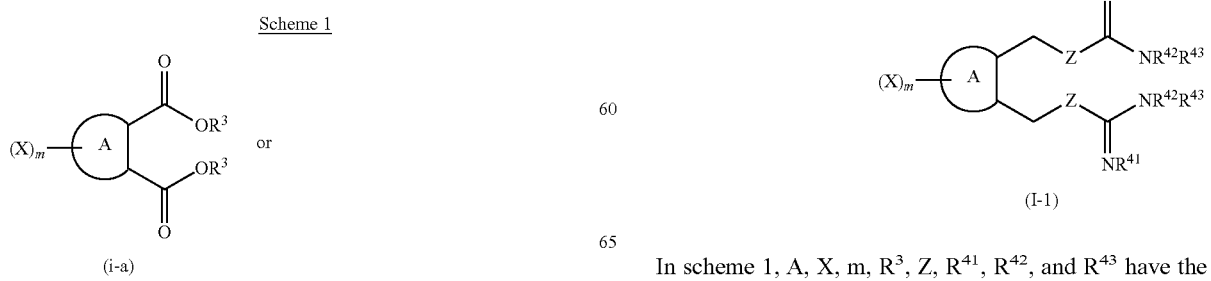

In scheme 1, A, X, m, $R^3$, Z, $R^{41}$, $R^{42}$, and $R^{43}$ have the same meaning as defined above. Substituent X can be

139 bonded to a carbon atom and/or a heteroatom of ring A (which represents an aromatic ring, an aliphatic ring, a heterocyclic ring, or a condensed ring of two or more rings selected from an aromatic ring, an aliphatic ring and a heterocyclic ring).

Synthesis of Compound (ii)

Compound (i-a) or compound (i-b) is dissolved in an organic solvent (e.g., THF, 1,4-dioxane, methanol, ethanol and acetone). The obtained solution is added to a solution containing a reducing agent (e.g., LiAlH$_4$ (lithium aluminum hydride), NaBH$_4$ (1508299713358_13), and DIBAH (1508299713358_14)) (wherein examples of the solvent include THF, 1,4-dioxane, methanol, ethanol and acetone), and the mixture is stirred and then heated to reflux. The reaction mixture is dried over a desiccant (e.g., magnesium sulfate) and then concentrated under reduced pressure. The residue obtained by the concentration under reduced pressure is purified by chromatography (e.g., silica gel chromatography) to obtain compound (ii). This synthesis is preferably performed in an inert gas (nitrogen, argon, etc.) atmosphere.

Synthesis of Compound (iii)

Compound (ii) is dissolved in an organic solvent (e.g., a halogen compound such as methylene chloride, chloroform, and carbon tetrachloride). Phosphorus trihalide (PHal$_3$ wherein Hal represents Cl, Br or I) is added to the obtained solution, and the mixture is stirred. Water and a nonaqueous organic solvent (e.g., ethyl acetate) are added to the obtained reaction solution, and the organic layer is washed with saturated saline, dried over a desiccant (e.g., magnesium sulfate), and then concentrated under reduced pressure. The residue obtained by the concentration under reduced pressure is purified by chromatography (e.g., silica gel chromatography) to obtain compound (iii). This synthesis is also preferably performed in an inert gas (nitrogen, argon, etc.) atmosphere.

Synthesis of Compound (I-1)

Compound (iii) is dissolved in an organic solvent (e.g., THF, 1,4-dioxane, methanol, ethanol and acetone). A compound of formula Z=C(NHR$^{41}$)(NR$^{42}$R$^{43}$) described above is added to the obtained solution, and the reaction mixture is refluxed. The reaction solution is stirred, and the reaction product is concentrated under reduced pressure. Then, the residue is recrystallized using a recrystallization solvent (e.g., a mixed solvent of ethanol and diethyl ether) to obtain compound (I-1).

Scheme 2

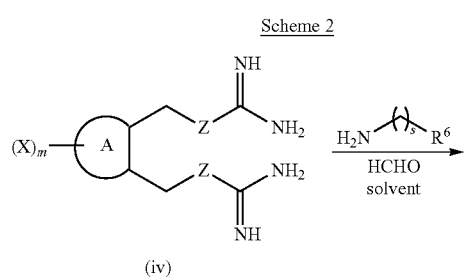

(iv)

140

-continued

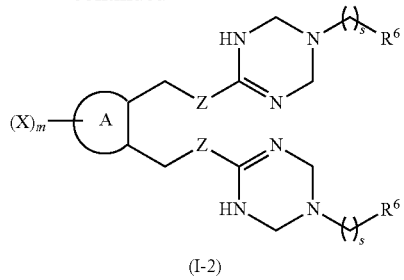

(I-2)

In scheme 2, A, X, m, Z, s, and R$^6$ have the same meaning as defined above.

Synthesis of Compound (I-2)

A compound of formula H$_2$N—(CH$_2$)$_s$—R$^6$ described above is added to a solution of formaldehyde (wherein examples of the solvent include THF, 1,4-dioxane, methanol, ethanol and acetone), and the mixture is stirred. Then, a solution of compound (iv) (wherein examples of the solvent include THF, 1,4-dioxane, methanol, ethanol and acetone) is added thereto, and the mixture is stirred. An organic solvent (e.g., benzene, toluene and hexane) is added to the obtained reaction mixture, and the mixture is concentrated under reduced pressure. The residue obtained by the concentration under reduced pressure is recrystallized using a recrystallization solvent (e.g., a mixed solvent of ethanol and diethyl ether) to obtain compound (I-2).

Scheme 3

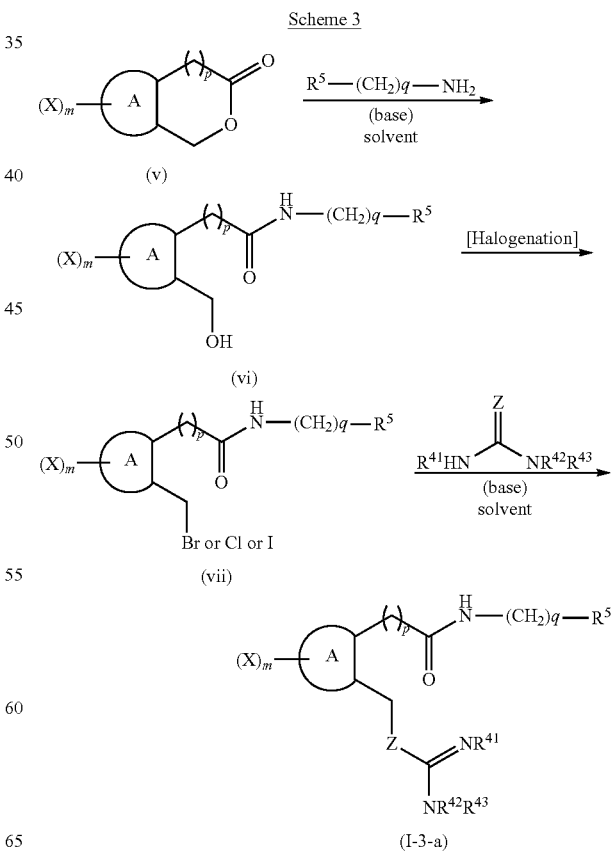

In scheme 3, A, X, m, p, $R^5$, q, Z, $R^{41}$, $R^{42}$, and $R^{43}$ have the same meaning as defined above.

Synthesis of Compound (vi)

A compound of formula (v) described above is dissolved in an organic solvent (e.g., THF, 1,4-dioxane, methanol, ethanol and acetone). A compound of formula $R^5$—$(CH_2)_q$—$NH_2$ described above is added to the obtained solution, and the mixture is refluxed. The obtained reaction solution is concentrated under reduced pressure, and then, water is added to the residue, followed by extraction with an organic solvent (e.g., a halogen compound such as methylene chloride, chloroform, and carbon tetrachloride). The organic layer is washed with saline, dried over a desiccant (e.g., magnesium sulfate), and then concentrated under reduced pressure to obtain compound (vi).

Synthesis of Compound (vii)

Compound (vi) is dissolved in an organic solvent (e.g., a halogen compound such as methylene chloride, chloroform, and carbon tetrachloride). Phosphorus trihalide ($PHal_3$ wherein Hal represents Cl, Br or I) is added to the obtained solution, and the mixture is stirred. Water and a nonaqueous organic solvent (e.g., ethyl acetate) are added to the obtained reaction solution, and the organic layer is washed with saturated saline, dried over a desiccant (e.g., magnesium sulfate), and then concentrated under reduced pressure. The residue obtained by the concentration under reduced pressure is purified by chromatography (e.g., silica gel chromatography) to obtain compound (vii).

Synthesis of Compound (I-3-a)

Compound (vii) is dissolved in an organic solvent (e.g., THF, 1,4-dioxane, methanol, ethanol and acetone). A compound of formula $Z=C(NHR^{41})(NR^{42}R^{43})$ described above is added to the obtained solution, and the reaction mixture is refluxed. The reaction solution is stirred, and the reaction product is concentrated under reduced pressure. Then, the residue is recrystallized using a recrystallization solvent (e.g., a mixed solvent of ethanol and diethyl ether) to obtain compound (I-3-a).

EXAMPLES

Hereinafter, the present invention will be described in more detail with reference to Examples. However, the present invention is in no way limited by these Examples.

Synthesis of Compounds

Nuclear magnetic resonance spectra (NMR) were measured using JEOL JNM-GSX400 or JEOL JNM-ECA500. Chemical shift values were indicated by ppm with tetramethylsilane as an internal standard, and coupling constant J values were indicated by Hz. Abbreviations in NMR were used as follows: s (singlet), d (doublet), t (triplet), q (quartet), m (multiplet), dd (doublet of doublets), br (broad), and brs (broad singlet). Liquid chromatogram-mass spectrometry (LC/MS) employed Waters Quattro micro, Waters 2795 separations module, and 2996 photodiode array detector. The column used was XBridge™ C18-AR-II 5 μM (size 2.1×50 mm, Waters Corp.). Mobile phase A used was 0.1% AcOH, and mobile phase B used was 100% $CH_3CN$. The measurement was performed for 5 minutes at a flow rate of 1.0 mL/min. The analysis was conducted under conditions involving A:B=9:1 in terms of the volume ratio (v/v) of gradient percentage followed by A:B=0:10 4 minutes later. Column chromatography employed Wakogel C-200 (100-200 mesh, Wako Pure Chemical Industries, Ltd.) or Chromatorex NH (100-200 mesh, Fuji Silysia Chemical Ltd.). Flash column chromatography employed SNAP KP-sil (Biotage) or YAMAZEN YFLC-5404-FC (Yamazen Corp.). Gel filtration column chromatography employed Sephadex LH-20 (GE Healthcare). Preparative thin-layer chromatography employed Kiesel gel 60 F254 (1.0 mm, Merck). Thin-layer chromatography employed Kiesel gel 60 F254 (0.25 mm, Merck) or NHTLC-PLZTE (0.25 mm, Fuji Silysia Chemical Ltd). Commercially available reagents and solvents were used in reaction without being purified.

Synthesis of Compound 1

1,2-Phenylenebis(methylene) dicarbamimidothioate dihydrochloride

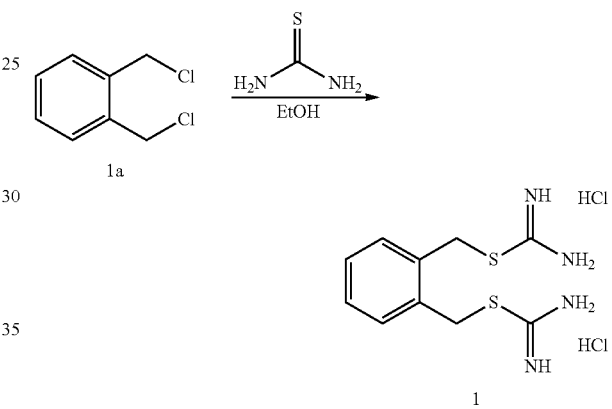

Thiourea (457 mg, 6.00 mmol) was added to a solution of 1,2-bis(chloromethyl)benzene (compound 1a, 525 mg, 3.00 mmol) in EtOH (8 mL) at room temperature, and the reaction mixture was refluxed for 7 hours. Then, the reaction solution was brought back to room temperature and stirred for 2 days. The obtained precipitate was collected by suction filtration and dried to obtain the title compound 1 (white solid, 837 mg, 85% yield).
$^1$H NMR (400 MHz, DMSO-d6): δ=9.29 (6H, brs), 7.48-7.50 (2H, m), 7.37-7.39 (2H, m), 4.67 (4H, s). LC-MS: >99% purity, RT 0.36 min, MS (m/z): 255 (M+H)$^+$.

Synthesis of Compound 2

(4-Fluoro-1,2-phenylene)bis(methylene) dicarbamimidothioate dihydrobromide

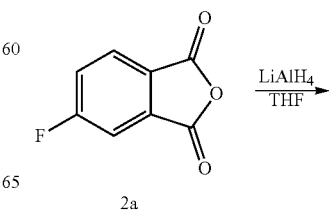

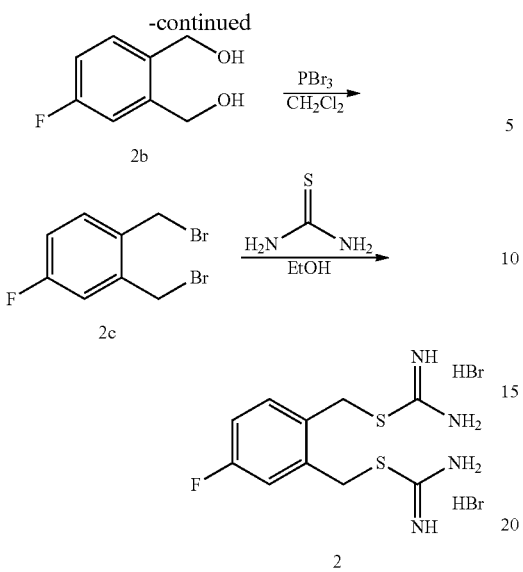

In an argon atmosphere, a solution of 4-fluorophthalic anhydride (compound 2a, 664 mg, 4.00 mmol) in THF (8 mL) was gently added to a solution of LiAlH$_4$ (304 mg, 8.00 mmol) in THF (10 mL) at 0° C., and the mixture was stirred at room temperature for 5 hours and then heated to reflux for 12 hours. The reaction mixture was cooled to room temperature. Then, the reaction was terminated by the addition of 10% NaOH (1.0 mL) and H$_2$O (1.0 mL) and stirring, and the reaction solution was dried over magnesium sulfate and then concentrated under reduced pressure. The residue was purified by silica gel chromatography (n-hexane/EtOAc=4:1 to 1:1) to obtain compound 2b (421 mg, 67% yield) as a colorless oil substance.

$^1$H NMR (400 MHz, CDCl$_3$): δ=7.31-7.26 (1H, m), 7.08-7.05 (1H, m), 7.00-6.95 (1H, m), 4.66 (4H, s), 3.31 (1H, brs), 3.11 (1H, brs).

In an argon atmosphere, phosphorous tribromide (0.265 mL, 2.79 mmol) was added to a solution of compound 2b (363 mg, 2.32 mmol) in CH$_2$Cl$_2$ (5 mL) at 0° C., and the mixture was stirred at the same temperature as above for 45 minutes. Water and ethyl acetate were added to the reaction solution, and the organic layer was washed with saturated saline, dried over magnesium sulfate, and then concentrated under reduced pressure. The residue was purified by silica gel chromatography (n-hexane) to obtain compound 2c (155 mg, 24% yield) as white crystals.

$^1$H NMR (400 MHz, CDCl$_3$): δ=7.36-7.31 (1H, m), 7.11-7.08 (1H, m), 7.02-6.97 (1H, m), 4.67 (2H, s), 4.60 (2H, s).

Thiourea (83.6 mg, 1.10 mmol) was added to a solution of compound 2c (155 mg, 0.550 mmol) in EtOH (3 mL) at room temperature, and the reaction mixture was refluxed for 7 hours. Then, the reaction solution was brought back to room temperature and stirred for 3 days. The reaction product was concentrated under reduced pressure. Then, the residue was recrystallized from EtOH and Et$_2$O (1:1) to obtain the title compound 2 (143 mg, 95% yield) as white crystals.

$^1$HNMR (400 MHz, DMSO-d6): δ=9.08 (6H, brs), 7.52-7.55 (1H, m), 7.34-7.37 (1H, m), 7.25-7.29 (1H, m), 4.56 (4H, s). LC-MS: >99% purity, RT 0.41 min, MS (m/z): 273 (M+H)$^+$.

Synthesis of Compound 3

Naphthalene-1,2-diylbis(methylene) dicarbamimidothioate dihydrobromide

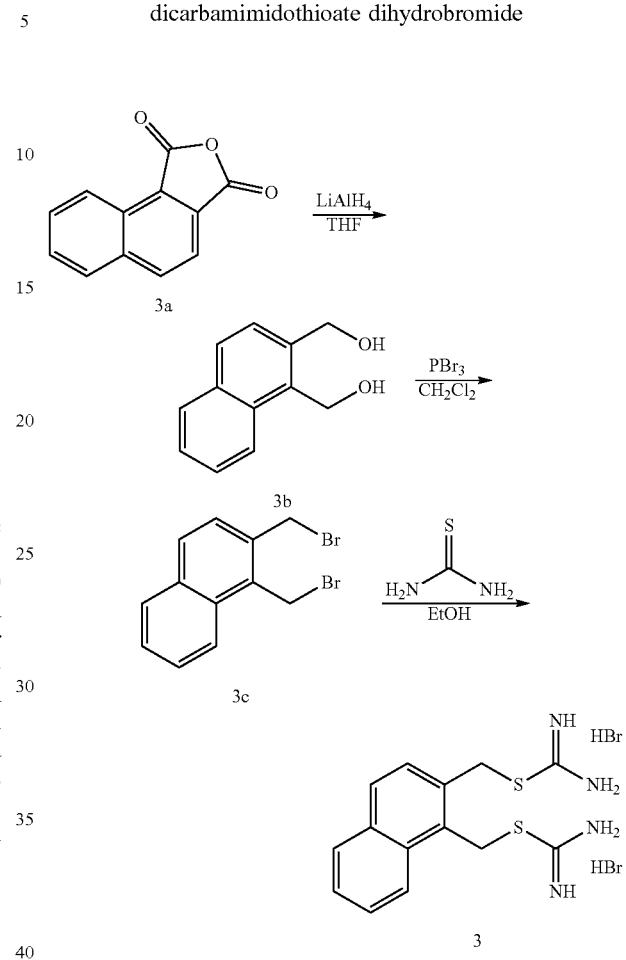

Reaction was performed by the same operation as in the synthesis of compound 2b from 1,2-naphthalic anhydride (compound 3a, 793 mg, 4.00 mmol) and LiAlH$_4$ (304 mg, 8.00 mmol), and the reaction residue was purified by silica gel chromatography (n-hexane/EtOAc=4:1 to 1:2) to obtain compound 3b (195 mg, 26% yield) as white crystals.

$^1$H NMR (400 MHz, CDCl$_3$): δ=8.28 (1H, d, J=8.0 Hz), 7.88-7.83 (2H, m), 7.60-7.57 (1H, m), 7.54-7.47 (2H, m), 5.26 (2H, s), 4.98 (2H, s).

Reaction was performed by the same operation as in the synthesis of compound 2c from compound 3b (145 mg, 0.77 mmol) and phosphorous tribromide (0.088 mL, 0.92 mmol), and the residue was purified by silica gel chromatography (n-hexane) to obtain compound 3c (68.3 mg, 28% yield) as white crystals.

$^1$H NMR (400 MHz, CDCl$_3$): δ=8.15 (1H, d, J=8.0 Hz), 7.85 (2H, dd, J=8.0, 8.0 Hz), 7.65 (1H, dd, J=8.0, 8.0 Hz), 7.54 (1H, dd, J=8.0, 8.0 Hz), 7.44 (1H, d, J=8.0 Hz), 5.11 (2H, s), 4.77 (2H, s).

The same operation as in the synthesis of compound 2 was performed from compound 3c (68.3 mg, 0.22 mmol) and thiourea (33.1 mg, 0.44 mmol), and the residue was recrystallized from EtOH and Et$_2$O (1:1) to obtain compound 3 (35.3 mg, 53% yield) as white crystals.

¹HNMR (400 MHz, DMSO-d6): δ=9.14 (6H, brs), 8.26-8.23 (1H, m), 8.03-8.00 (2H, m), 7.60-7.72 (3H, m), 5.06 (2H, s), 4.77 (2H, s). LC-MS: >99% purity, RT 0.59 min, MS (m/z): 305 (M+H)⁺.

Synthesis of Compound 4

(4-t-Bu-1,2-phenylene)bis(methylene) dicarbamimidothioate dihydrobromide

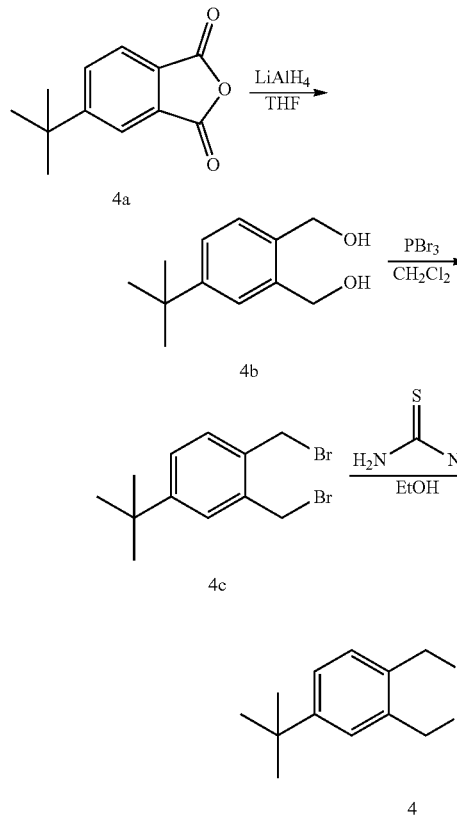

The same operation as in the synthesis of compound 2b was performed from 4-t-Bu-phthalic anhydride (compound 4a, 817 mg, 4.00 mmol) and LiAlH₄ (304 mg, 8.00 mmol), and the reaction residue was purified by silica gel chromatography (n-hexane/EtOAc=3:1 to 2:1) to obtain compound 4b (389 mg, 50% yield) as colorless oil substance.

¹H NMR (400 MHz, CDCl₃): δ=7.39-7.28 (3H, m), 4.76 (2H, s), 4.74 (2H, s), 1.33 (9H, s).

A residue obtained by the same operation as in the synthesis of compound 2c from compound 4b (308 mg, 1.59 mmol) and phosphorous tribromide (0.181 mL, 1.90 mmol) was purified by silica gel chromatography (EtOAc) to obtain compound 4c (148 mg, 29% yield) as a yellow oil substance.

¹H NMR (400 MHz, CDCl₃): δ=7.36-7.31 (3H, m), 4.68 (2H, s), 4.67 (2H, s), 1.31 (9H, s).

The same operation as in the synthesis of compound 2 was performed from compound 4c (148 mg, 0.46 mmol) and thiourea (70.4 mg, 0.93 mmol), and the residue was recrystallized from EtOH and Et₂O (1:1) to obtain compound 4 (159 mg, 73% yield) as white crystals.

¹HNMR (400 MHz, DMSO-d6): δ=9.11 (6H, brs), 7.54-7.51 (1H, m), 7.43-7.39 (2H, m), 4.58 (2H, s), 4.55 (2H, s), 1.27 (9H, s).

LC-MS: >99% purity, RT 0.55 min, MS (m/z): 311 (M+H)⁺.

Synthesis of Compound 5

Quinoxaline-2,3-diylbis(methylene) dicarbamimidothioate dihydrobromide

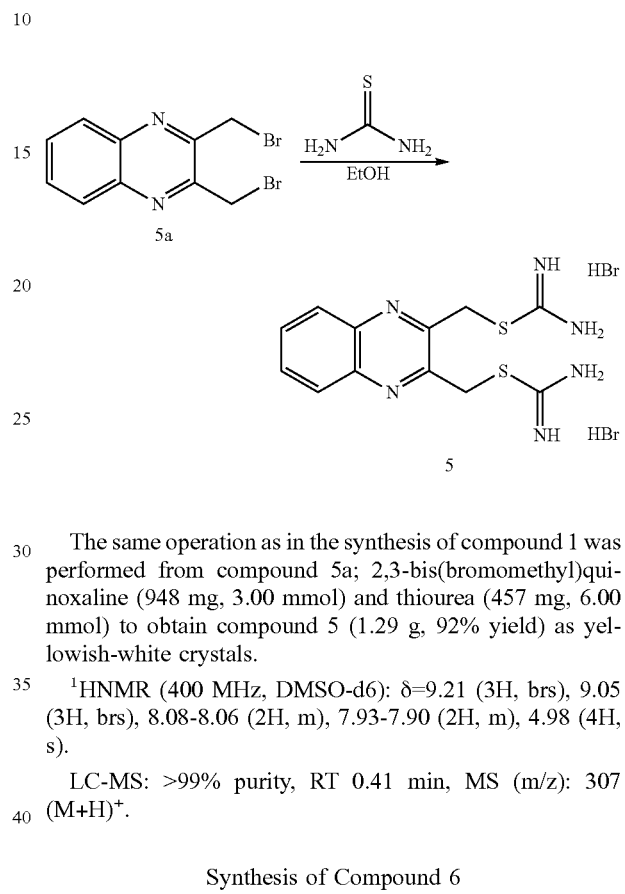

The same operation as in the synthesis of compound 1 was performed from compound 5a; 2,3-bis(bromomethyl)quinoxaline (948 mg, 3.00 mmol) and thiourea (457 mg, 6.00 mmol) to obtain compound 5 (1.29 g, 92% yield) as yellowish-white crystals.

¹HNMR (400 MHz, DMSO-d6): δ=9.21 (3H, brs), 9.05 (3H, brs), 8.08-8.06 (2H, m), 7.93-7.90 (2H, m), 4.98 (4H, s).

LC-MS: >99% purity, RT 0.41 min, MS (m/z): 307 (M+H)⁺.

Synthesis of Compound 6

(3,4,5,6-Fluoro-1,2-phenylene)bis(methylene) dicarbamimidothioate dihydrobromide

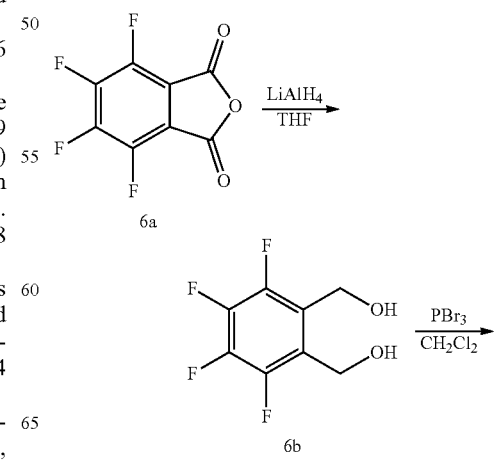

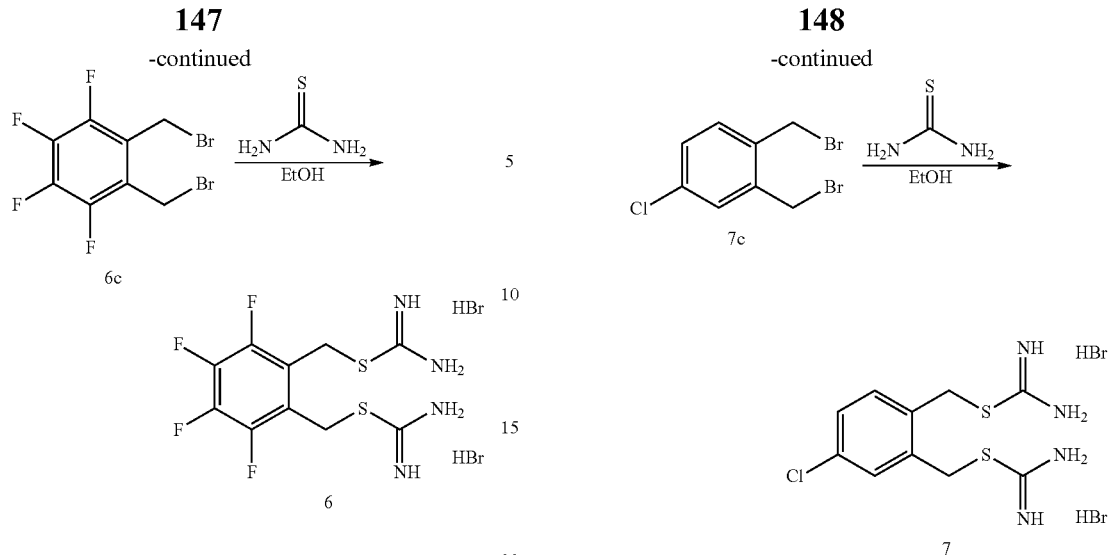

Reaction was performed by the same operation as in the synthesis of compound 2b from compound 6a; 3,4,5,6-fluorophthalic anhydride (880 mg, 4.00 mmol) and LiAlH$_4$ (304 mg, 8.00 mmol), and the reaction residue was purified by silica gel chromatography (n-hexane/EtOAc=5:1 to 3:1) to obtain compound 6b (219 mg, 26% yield) as white crystals.

$^1$H NMR (400 MHz, CDCl$_3$): δ=4.84 (4H, s), 2.78 (2H, brs).

A residue obtained by the same operation as in the synthesis of compound 2c from compound 6b (209 mg, 0.99 mmol) and phosphorous tribromide (0.113 mL, 1.19 mmol) was purified by silica gel chromatography (EtOAc) to obtain compound 6c (48.9 mg, 15% yield) as a yellow oil substance.

$^1$H NMR (400 MHz, CDCl$_3$): δ=4.63-4.60 (4H, m).

The same operation as in the synthesis of compound 2 was performed from compound 6c (48.9 mg, 0.15 mmol) and thiourea (22.2 mg, 0.29 mmol), and the residue was recrystallized from EtOH and Et$_2$O (1:1) to obtain compound 6 (17.2 mg, 24% yield) as white crystals. $^1$HNMR (400 MHz, DMSO-d6): δ=9.25 (6H, brs), 4.67 (4H, s).

LC-MS: >99% purity, RT 0.49 min, MS (m/z): 327 (M+H)$^+$.

Synthesis of Compound 7

(4-Chloro-1,2-phenylene)bis(methylene) dicarbamimidothioate dihydrobromide

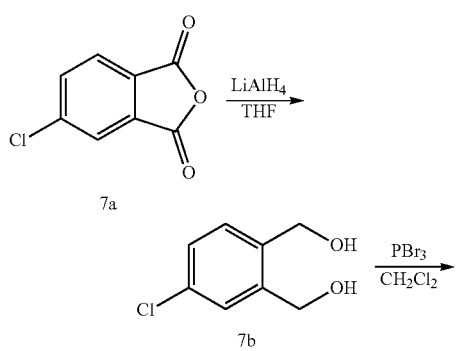

The same operation as in the synthesis of compound 2b was performed from compound 7a; 4-chlorophthalic anhydride (913 mg, 5.00 mmol) and LiAlH$_4$ (380 mg, 10.0 mmol), and the reaction residue was purified by silica gel chromatography (n-hexane/EtOAc=6:1 to 1:1) to obtain compound 7b (567 mg, 66% yield) as white crystals.

$^1$H NMR (400 MHz, CDCl$_3$): δ=7.37-7.35 (1H, m), 7.30-7.27 (2H, m), 4.70-4.68 (4H, m).

A residue obtained by the same operation as in the synthesis of compound 2c from compound 7b (567 mg, 3.29 mmol) and phosphorous tribromide (0.374 mL, 3.94 mmol) was purified by silica gel chromatography (EtOAc) to obtain compound 7c (253 mg, 26% yield) as yellow crystals.

$^1$H NMR (400 MHz, CDCl$_3$): δ=7.39-7.36 (1H, m), 7.32-7.29 (2H, m), 4.61 (2H, s), 4.59 (2H, s).

The same operation as in the synthesis of compound 2 was performed from compound 7c (225 mg, 0.75 mmol) and thiourea (115 mg, 1.51 mmol), and the residue was recrystallized from EtOH and Et$_2$O (1:1) to obtain compound 7 (104 mg, 48% yield) as white crystals.

$^1$HNMR (400 MHz, DMSO-d6): δ=9.17 (6H, brs), 7.60-7.59 (1H, m), 7.51-7.48 (2H, m), 4.61 (4H, s).

LC-MS: >99% purity, RT 0.47 min, MS (m/z): 289 (M+H)$^+$.

Synthesis of Compound 8

1,2-Phenylenebis(methylene) bis(N,N'-dimethylcarbamimidothioate) dihydrochloride

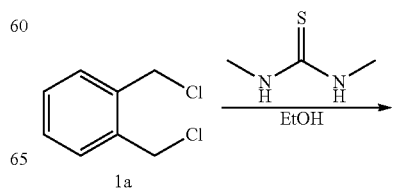

-continued

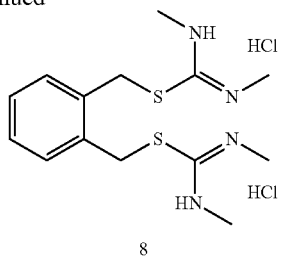

8

Reaction was performed by the same operation as in the synthesis of compound 1 from compound 1a; 1,2-bis(chloromethyl)benzene (700 mg, 4.00 mmol) and 1,3-dimethylthiourea (833 mg, 8.00 mmol), and the residue was recrystallized from EtOH and Et$_2$O (1:3) to obtain compound 8 (1.27 g, 83% yield) as white crystals.

$^1$HNMR (400 MHz, DMSO-d6): δ=9.91 (1H, brs), 9.52 (1H, brs), 7.52-7.48 (2H, m), 7.41-7.37 (2H, m), 4.83 (4H, s), 2.95 (12H, s).

LC-MS: >99% purity, RT 0.57 min, MS (m/z): 311 (M+H)$^+$.

Synthesis of Compound 9

1,2-Bis{[(5-phenethyl-1,4,5,6-tetrahydro-1,3,5-triazin-2-yl)thio]methyl}benzene

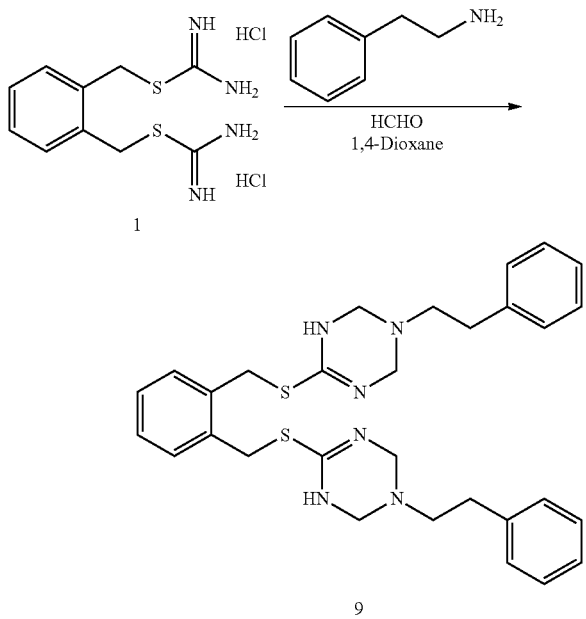

Phenethylamine (60.6 mg, 0.50 mmol) was gently added to a solution of formaldehyde (81 μL, 37% wt. solution in water, 1.0 mmol) in 1,4-dioxane (5.0 mL), and the mixture was stirred at room temperature for 10 minutes. Then, a solution of 1,2-phenylenebis(methylene) dicarbamimidothioate dihydrochloride (compound 1, 57.6 mg, 0.25 mmol) in 1,4-dioxane (2.0 mL) was added thereto, and the mixture was stirred at 80° C. for 12 hours. The reaction mixture was brought back to room temperature. Toluene (3.0 mL) was added thereto, and the mixture was concentrated under reduced pressure. The residue was recrystallized from EtOH and Et$_2$O (2:3) to obtain the title compound 9 (26.3 mg, 19% yield) as yellow crystals.

$^1$H NMR (400 MHz, CDCl$_3$): δ=7.33-7.18 (12H, m), 7.12-7.09 (2H, m), 4.47-4.07 (12H, m), 2.88-2.79 (8H, m).

LC-MS: >99% purity, RT 2.25 min, MS (m/z): 545 (M+H)$^+$.

Synthesis of Compound 10

(4-Bromo-1,2-phenylene)bis(methylene) dicarbamimidothioate dihydrobromide

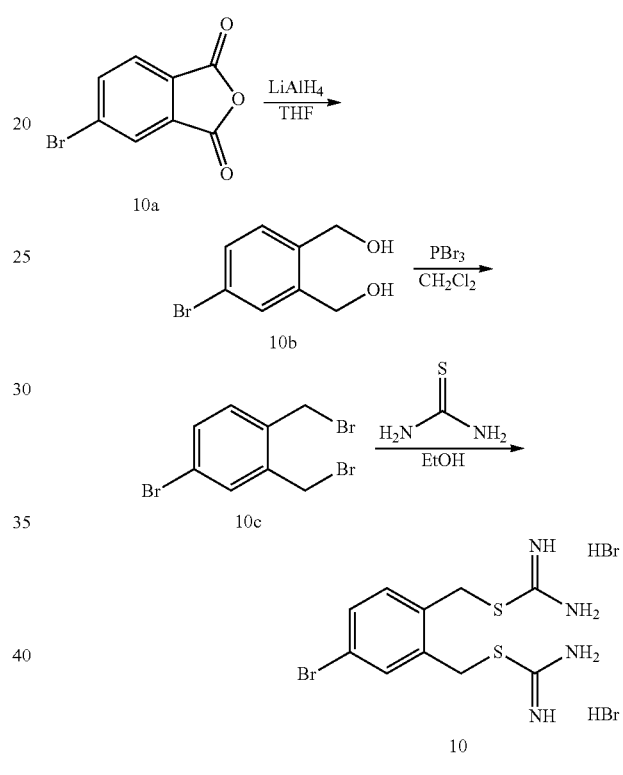

The same operation as in the synthesis of compound 2b was performed from compound 10a; 4-bromophthalic anhydride (1135 mg, 5.00 mmol) and LiAlH$_4$ (380 mg, 10.0 mmol), and the reaction residue was purified by silica gel chromatography (n-hexane/EtOAc=5:1 to 1:1) to obtain compound 10b (539 mg, 50% yield) as white crystals.

$^1$H NMR (400 MHz, CDCl$_3$): δ=7.52-7.51 (1H, m), 7.45 (1H, dd, J=8.0, 4.0 Hz), 7.23 (1H, d, J=8.0 Hz), 4.69-4.68 (4H, m), 2.82 (2H, brs).

A residue obtained by the same operation as in the synthesis of compound 2c from compound 10b (509 mg, 2.35 mmol) and phosphorous tribromide (0.267 mL, 2.82 mmol) was purified by silica gel chromatography with n-hexane/EtOAc (3:1) to obtain compound 10c (198 mg, 25% yield) as yellow crystals.

$^1$H NMR (400 MHz, CDCl$_3$): δ=7.53 (1H, d, J=4.0 Hz), 7.44 (1H, dd, J=8.0, 4.0 Hz), 7.24 (1H, d, J=8.0 Hz), 4.59 (2H, s), 4.58 (2H, s).

The same operation as in the synthesis of compound 2 was performed from compound 10c (174 mg, 0.51 mmol) and thiourea (77.2 mg, 1.01 mmol), and the residue was recrystallized from EtOH and Et₂O (2:3) to obtain compound 10 (108 mg, 43% yield) as white crystals.

¹HNMR (400 MHz, DMSO-d6): δ=9.09 (6H, brs), 7.71 (1H, s), 7.61 (1H, d, J=8.4 Hz), 7.43 (1H, d, J=8.4 Hz), 4.55 (4H, s).

LC-MS: >99% purity, RT 0.45 min, MS (m/z): 335 ($^{79}$BrM+H)⁺, 333 ($^{77}$BrM+H)⁺.

Synthesis of Compound 11

1,2-Phenylenebis(methylene) bis(metylcarbamimidothioate) dihydrochloride

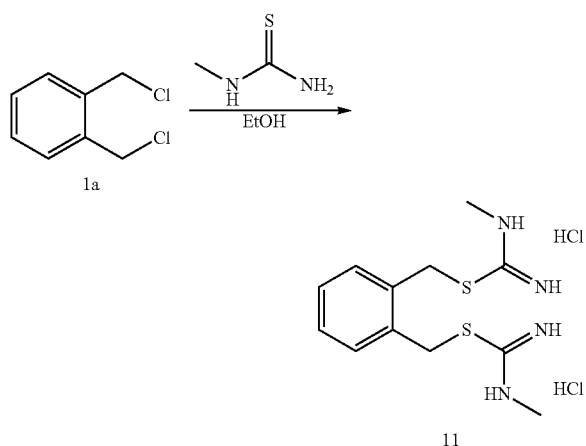

Reaction was performed by the same operation as in the synthesis of compound 1 from 1,2-bis(chloromethyl)benzene (compound 1a, 525 mg, 3.00 mmol) and N-methylthiourea (541 mg, 6.00 mmol), and the residue was recrystallized from EtOH and Et₂O (2:3) to obtain compound 11 (1.09 g, 102% yield) as white crystals.

¹HNMR (400 MHz, DMSO-d6): δ=9.62 (4H, brs), 7.46-7.43 (2H, m), 7.38-7.35 (2H, m), 4.74 (4H, s), 2.89 (6H, s).

LC-MS: >99% purity, RT 0.39 min, MS (m/z): 283 (M+H)⁺.

Synthesis of Compound 12

(4-Methyl-1,2-phenylene)bis(methylene) dicarbamimidothioate dihydrobromide

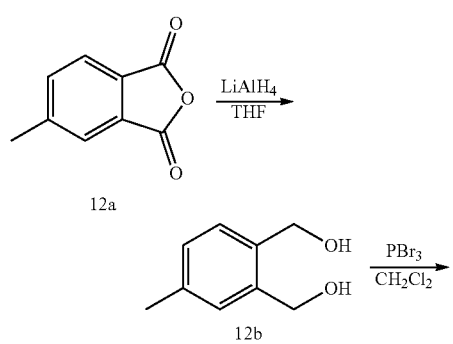

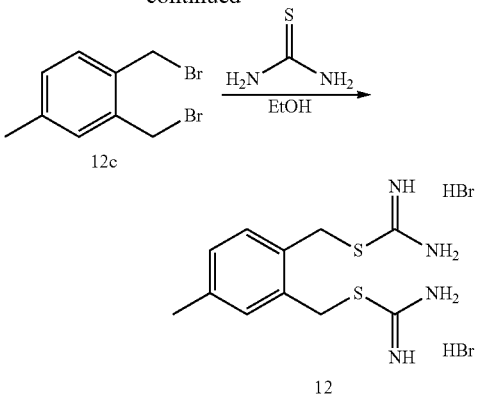

The same operation as in the synthesis of compound 2b was performed from 4-methylphthalic anhydride (compound 12a, 649 mg, 4.00 mmol) and LiAlH₄ (304 mg, 8.00 mmol), and the reaction residue was purified by silica gel chromatography (n-hexane/EtOAc=5:1 to 2:1) to obtain compound 12b (296 mg, 49% yield) as a colorless oil substance.

¹H NMR (400 MHz, CDCl₃): δ=7.24 (1H, d, J=8.0 Hz), 7.18 (1H, s), 7.13 (1H, d, J=8.0 Hz), 4.71 (4H, s), 2.82 (2H, brs), 2.35 (3H, s).

A residue obtained by the same operation as in the synthesis of compound 2c from compound 12b (296 mg, 1.95 mmol) and phosphorous tribromide (0.222 mL, 2.34 mmol) was purified by silica gel chromatography with n-hexane/EtOAc (3:1) to obtain compound 12c (177 mg, 33% yield) as white crystals.

¹H NMR (400 MHz, CDCl₃): δ=7.26 (1H, d, J=8.0 Hz), 7.19 (1H, s), 7.12 (1H, d, J=8.0 Hz), 4.65 (2H, s), 4.64 (2H, s), 2.34 (3H, s).

The same operation as in the synthesis of compound 2 was performed from compound 12c (150 mg, 0.54 mmol) and thiourea (82.3 mg, 1.08 mmol), and the residue was recrystallized from EtOH and Et₂O (2:3) to obtain compound 12 (85.5 mg, 37% yield) as white crystals.

¹HNMR (400 MHz, DMSO-d6): δ=9.13 (6H, brs), 7.37 (1H, d, J=8.0 Hz), 7.29 (1H, s), 7.21 (1H, d, J=8.0 Hz), 4.57 (2H, s), 4.56 (2H, s), 2.30 (3H, s).

LC-MS: >99% purity, RT 0.41 min, MS (m/z): 269 (M+H)⁺.

Synthesis of Compound 13

(3-Fluoro-1,2-phenylene)bis(methylene) dicarbamimidothioate dihydrobromide

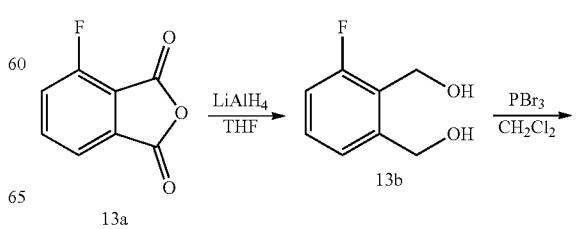

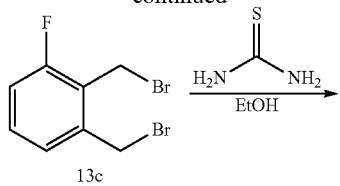

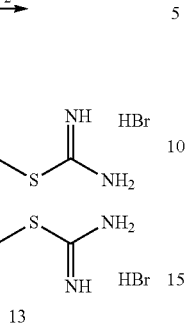

The same operation as in the synthesis of compound 2b was performed from 3-fluorophthalic anhydride (compound 13a, 664 mg, 4.00 mmol) and LiAlH$_4$ (304 mg, 8.00 mmol), and the reaction residue was purified by silica gel chromatography (n-hexane/EtOAc=5:1 to 2:1) to obtain compound 13b (282 mg, 45% yield) as white crystals.

$^1$H NMR (400 MHz, CDCl$_3$): δ=7.32-7.28 (1H, m), 7.16 (1H, d, J=8.0 Hz), 7.09-7.04 (1H, m), 4.85-4.84 (2H, m), 4.77 (2H, s), 2.87 (2H, brs).

A residue obtained by the same operation as in the synthesis of compound 2c from compound 13b (260 mg, 1.67 mmol) and phosphorous tribromide (0.190 mL, 2.00 mmol) was purified by silica gel chromatography with n-hexane/EtOAc (3:1) to obtain compound 13c (106 mg, 23% yield) as white crystals.

$^1$H NMR (400 MHz, CDCl$_3$): δ=7.32-7.28 (1H, m), 7.18 (1H, d, J=8.0 Hz), 7.08-7.04 (1H, m), 4.70-4.68 (2H, m), 4.63 (2H, s).

The same operation as in the synthesis of compound 2 was performed from compound 13c (95.1 mg, 0.34 mmol) and thiourea (51.5 mg, 0.68 mmol), and the residue was recrystallized from EtOH and Et$_2$O (2:3) to obtain compound 13 (122 mg, 83% yield) as white crystals.

$^1$HNMR (400 MHz, DMSO-d6): δ=9.14 (6H, brs), 7.51-7.45 (1H, m), 7.36-7.30 (2H, m), 4.62-4.60 (4H, m).

LC-MS: >99% purity, RT 0.38 min, MS (m/z): 273 (M+H)$^+$.

Synthesis of Compound 14

1,2-Bis{[(5-benzyl-1,4,5,6-tetrahydoro-1,3,5-triazin-2-yl)thio]methyl}benzene

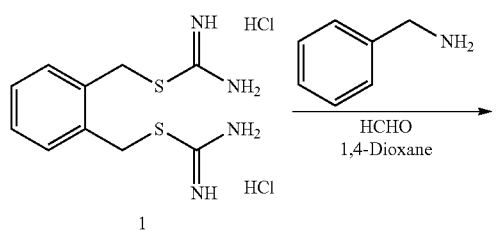

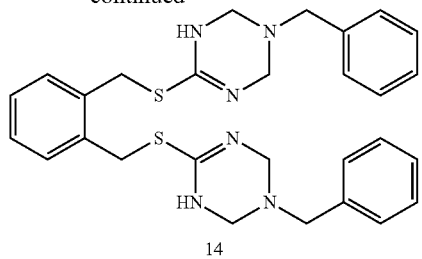

Reaction was performed by the same operation as in the synthesis of compound 9 from benzylamine (107 mg, 1.00 mmol), formaldehyde (162 μL, 37% wt. solution in water, 2.00 mmol) and 1,2-phenylenebis(methylene) dicarbamimidothioate dihydrochloride (compound 1,127 mg, 0.50 mmol), and the reaction residue was purified by silica gel chromatography (n-hexane:EtOAc=1:2) to obtain the title compound 14 (78.9 mg, 31% yield) as white crystals.

$^1$HNMR (400 MHz, CD$_3$OD): δ=7.42-7.24 (14H, m), 4.34 (4H, s), 4.16 (8H, s), 3.67 (4H, s). LC-MS: >99% purity, RT 2.15 min, MS (m/z): 517 (M+H)$^+$.

Synthesis of Compound 15

Thiophene-3,4-diylbis(methylene) dicarbamimidothioate dihydrobromide

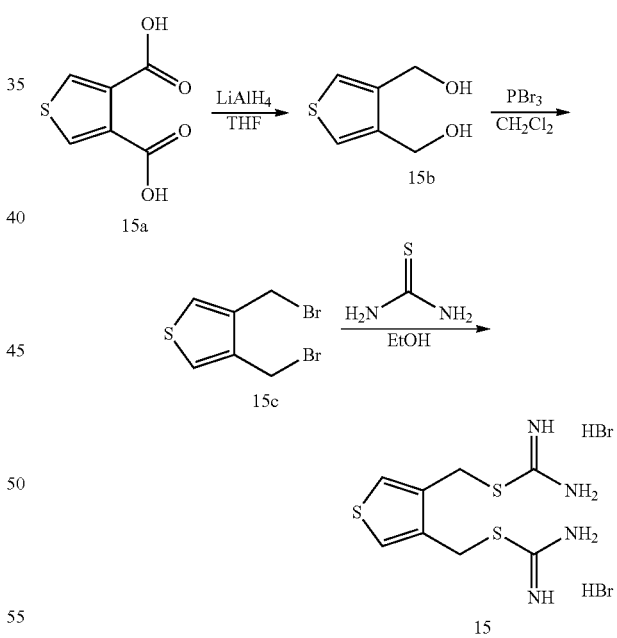

The same operation as in the synthesis of compound 2b was performed from 3,4-thiophenedicarboxylic acid (compound 15a, 689 mg, 4.00 mmol) and LiAlH$_4$ (304 mg, 8.00 mmol), and the reaction residue was purified by silica gel chromatography (n-hexane/EtOAc=5:1 to 1:1) to obtain compound 15b (64.7 mg, 11% yield) as white crystals.

$^1$H NMR (400 MHz, CDCl$_3$): δ=7.25 (2H, s), 4.67 (4H, s).

A residue obtained by the same operation as in the synthesis of compound 2c from compound 15b (47.7 mg, 0.33 mmol) and phosphorous tribromide (0.038 mL, 0.40 mmol) was purified by silica gel chromatography with n-hexane/EtOAc (3:1) to obtain compound 15c (43.7 mg, 49% yield) as white crystals.

$^1$H NMR (400 MHz, CDCl$_3$): δ=7.35 (2H, s), 4.63 (4H, s).

The same operation as in the synthesis of compound 2 was performed from compound 15c (38.0 mg, 0.14 mmol) and thiourea (21.4 mg, 0.28 mmol), and the residue was recrystallized from EtOH and Et$_2$O (3:1) to obtain compound 15 (38.1 mg, 64% yield) as white crystals. $^1$HNMR (400 MHz, DMSO-d6): δ=9.07 (6H, brs), 7.62 (2H, s), 4.51 (4H, s).

LC-MS: >99% purity, RT 0.38 min, MS (m/z): 261 (M+H)$^+$.

Synthesis of Compound 16

1,2-Bis[(pyrimidin-2-ylthio)methyl]benzene

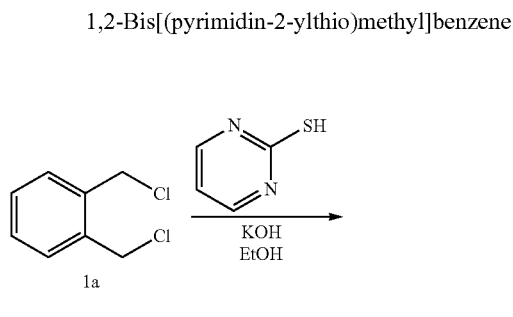

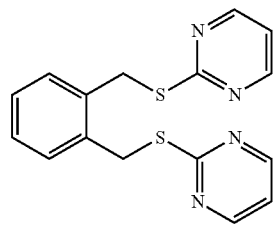

16

2-Mercaptopyrimidine (112 mg, 1.00 mmol) was added to a solution of KOH (66.0 mg, 1.00 mmol) in EtOH (3.5 mL), and the mixture was stirred at room temperature for 30 minutes. Then, 1,2-bis(chloromethyl)benzene (compound 1a, 87.5 mg, 0.50 mmol) was added to the reaction solution, and the mixture was heated and stirred at 70° C. for 6 hours. The reaction mixture was cooled to room temperature. Then, water and chloroform were added thereto, and the organic layer was washed with saturated saline, dried over magnesium sulfate, and then concentrated under reduced pressure. The residue was purified by silica gel chromatography (n-hexane:EtOAc=2:1) to obtain the title compound 16 (122 mg, 75% yield) as a colorless oil substance.

$^1$H NMR (400 MHz, CDCl$_3$): δ=8.52-8.51 (4H, m), 7.51-7.47 (2H, m), 7.24-7.21 (2H, m), 6.97-6.95 (2H, m), 4.61 (4H, s).

LC-MS: >99% purity, RT 3.45 min, MS (m/z): 327 (M+H)$^+$.

Synthesis of Compound 17

1,2-Bis{{[5-(4-chlorophenethyl)-1,4,5,6-tetrahydro-1,3,5-triazin-2-yl]thio}methyl}benzene

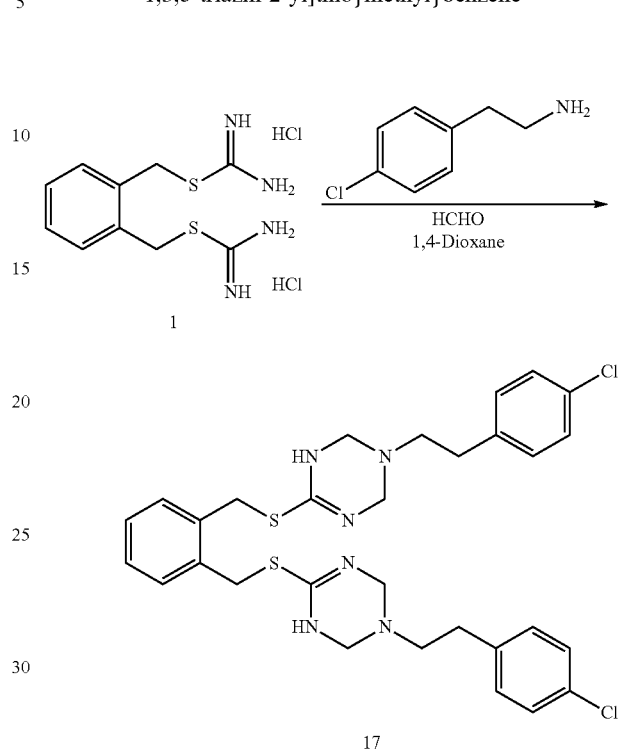

17

Reaction was performed by the same operation as in the synthesis of compound 9 from 2-(4-chlorophenyl)ethylamine (158 mg, 1.02 mmol), formaldehyde (166 μL, 37% wt. solution in water, 2.04 mmol) and 1,2-phenylenebis(methylene) dicarbamimidothioate dihydrochloride (compound 1, 127 mg, 0.50 mmol), and the reaction residue was purified by silica gel chromatography (n-hexane:EtOAc=3:1 to 1:1) to obtain the title compound 17 (46.5 mg, 15% yield) as a colorless oil substance.

$^1$H NMR (400 MHz, CDCl$_3$): δ=7.33-7.08 (14H, m), 4.29-4.22 (12H, m), 2.86-2.70 (8H, m). LC-MS: >99% purity, RT 2.74 min, MS (m/z): δ14 (M+H)$^+$.

Synthesis of Compound 18

1,2-Bis {[5-(2,5-dichlorobenzyl)-1,4,5,6-tetrahydro-1,3,5-triazin-2-yl]thio}methyl benzene

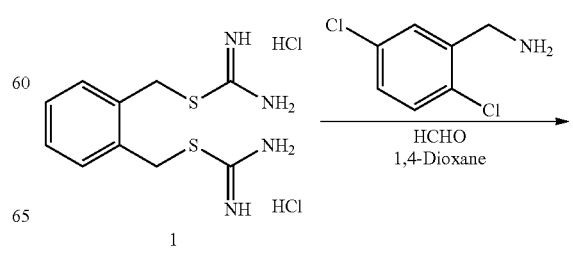

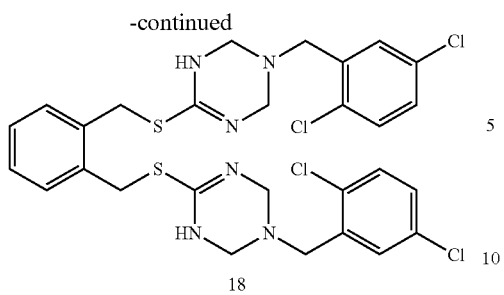

18

Reaction was performed by the same operation as in the synthesis of compound 9 from 2,5-dichlorobenzylamine (181 mg, 1.03 mmol), formaldehyde (168 μL, 37% wt. solution in water, 2.06 mmol) and 1,2-phenylenebis(methylene) dicarbamimidothioate dihydrochloride (compound 1, 131 mg, 0.52 mmol), and the reaction residue was recrystallized from 2-propanol to obtain the title compound 18 (230 mg, 68% yield) as white crystals.

$^1$HNMR (400 MHz, DMSO-d6): δ=7.55-7.37 (10H, m), 4.82 (4H, s), 4.39 (4H, s), 3.73 (4H, s). LC-MS: >99% purity, RT 2.70 min, MS (m/z): δ55 (M+H)$^+$.

Synthesis of Compound 19

1,2-Bis {[5-(3-bromophenethyl)-1,4,5,6-tetrahydro-1,3,5-triazin-2-yl]thio}methyl benzene

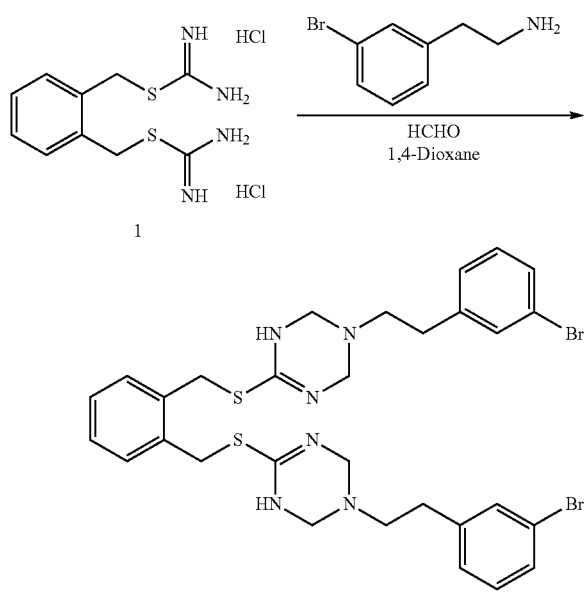

19

Reaction was performed by the same operation as in the synthesis of compound 9 from 2-(3-bromophenyl)ethylamine (208 mg, 1.04 mmol), formaldehyde (168 μL, 37% wt. solution in water, 2.08 mmol) and 1,2-phenylenebis(methylene) dicarbamimidothioate dihydrochloride (compound 1, 132 mg, 0.52 mmol), and the reaction residue was purified by silica gel chromatography (EtOAc) and recrystallized from 2-propanol to obtain the title compound 19 (97.5 mg, 27% yield) as white crystals.

$^1$H NMR (400 MHz, CDCl$_3$): δ=7.35-7.11 (12H, m), 4.29 (12H, brs), 2.84-2.74 (8H, m). LC-MS: >99% purity, RT 2.76 min, MS (m/z): 703 (M+H)$^+$.

Synthesis of Compound 20

1,2-Bis {[5-(4-bromophenethyl)-1,4,5,6-tetrahydro-1,3,5-triazin-2-yl]thio}methyl benzene

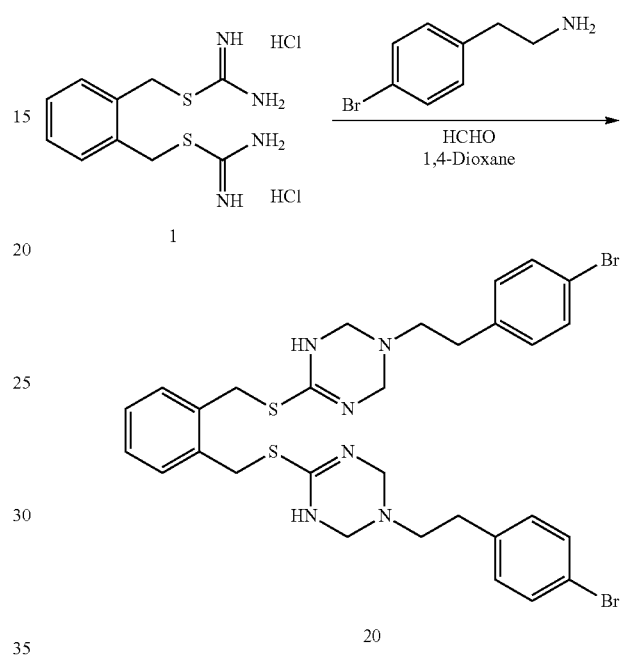

20

Reaction was performed by the same operation as in the synthesis of compound 9 from 2-(3-bromophenyl)ethylamine (208 mg, 1.04 mmol), formaldehyde (168 μL, 37% wt. solution in water, 2.08 mmol) and 1,2-phenylenebis(methylene) dicarbamimidothioate dihydrochloride (compound 1, 132 mg, 0.52 mmol), and the reaction residue was purified by silica gel chromatography (EtOAc) and recrystallized from 2-propanol to obtain the title compound 20 (75.7 mg, 21% yield) as white crystals.

$^1$H NMR (400 MHz, CDCl$_3$): δ=7.40 (4H, d, J=8.0 Hz), 7.32 (2H, dd, J=8.0, 4.0 Hz), 7.12 (2H, dd, J=8.0, 4.0 Hz), 7.06 (4H, d, J=8.0 Hz), 4.28 (12H, brs), 2.84-2.73 (8H, m). LC-MS: >99% purity, RT 2.87 min, MS (m/z): 703 (M+H)$^+$.

Synthesis of Compound 21

1,2-Bis{{[5-(2,4-dichlorophenethyl)-1,4,5,6-tetrahydro-1,3,5-triazin-2-yl]thio}methyl}benzene

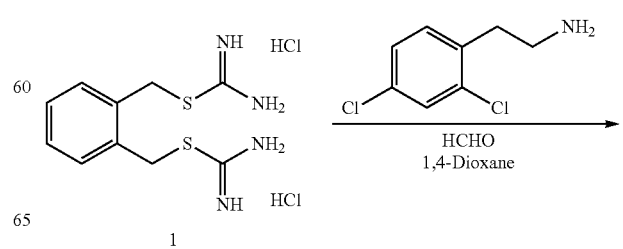

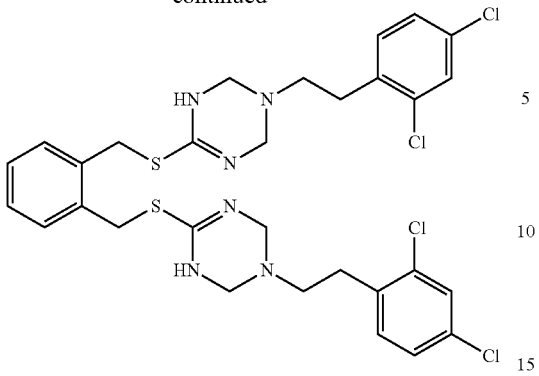

21

Reaction was performed by the same operation as in the synthesis of compound 9 from 2-(2,4-dichlorophenyl)ethylamine (198 mg, 1.04 mmol), formaldehyde (169 μL, 37% wt. solution in water, 2.08 mmol) and 1,2-phenylenebis(methylene) dicarbamimidothioate dihydrochloride (compound 1, 132 mg, 0.52 mmol), and the reaction residue was purified by silica gel chromatography with n-hexane/EtOAc (1:3 to 1:6) and recrystallized from 2-propanol to obtain the title compound 21 (51.3 mg, 14% yield) as white crystals.

$^1$H NMR (400 MHz, CDCl$_3$): δ=7.37 (2H, d, J=8.0 Hz), 7.30 (2H, dd, J=8.0, 4.0 Hz), 7.17-7.16 (4H, m), 7.08 (2H, dd, J=8.0, 4.0 Hz), 4.31-4.26 (12H, m), 2.91-2.86 (4H, m), 2.82-2.77 (4H, m). LC-MS: >99% purity, RT 2.74 min, MS (m/z): δ83 (M+H)$^+$.

Synthesis of Compound 22

1,2-Bis{{[5-(3,4-dichlorophenethyl)-1,4,5,6-tetrahydro-1,3,5-triazin-2-yl]thio}methyl}benzene

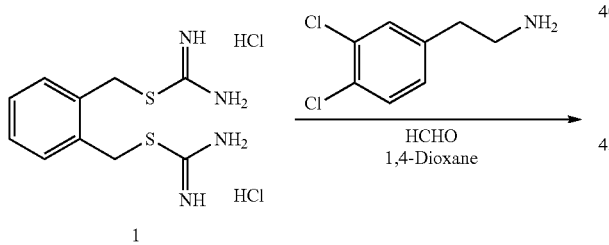

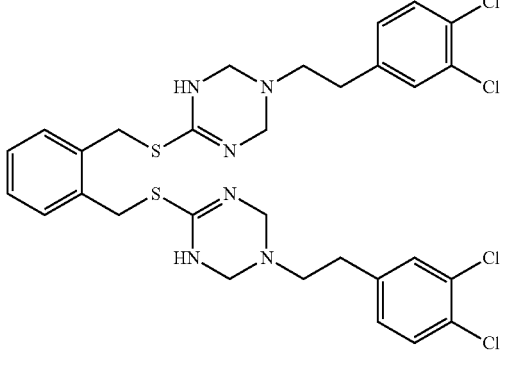

22

Reaction was performed by the same operation as in the synthesis of compound 9 from 3,4-dichlorophenethylamine (191 mg, 1.01 mmol), formaldehyde (163 μL, 37% wt. solution in water, 2.02 mmol) and 1,2-phenylenebis(methylene) dicarbamimidothioate dihydrochloride (compound 1, 128 mg, 0.50 mmol), and the reaction residue was purified by silica gel chromatography with n-hexane/EtOAc (1:3 to 1:6) and recrystallized from 2-propanol to obtain the title compound 22 (61.0 mg, 18% yield) as white crystals.

$^1$H NMR (400 MHz, CDCl$_3$): δ=7.35 (2H, d, J=8.0 Hz), 7.33-7.28 (4H, m), 7.13 (2H, dd, J=8.0, 4.0 Hz), 7.03 (2H, dd, J=8.0, 4.0 Hz), 4.34-4.21 (12H, m), 2.83-2.72 (8H, m). LC-MS: >99% purity, RT 2.88 min, MS (m/z): δ83 (M+H)$^+$.

Synthesis of Compound 23

1,2-Bis{{[5-(3,4-dimethylphenethyl)-1,4,5,6-tetrahydro-1,3,5-triazin-2-yl]thio}methyl}benzene

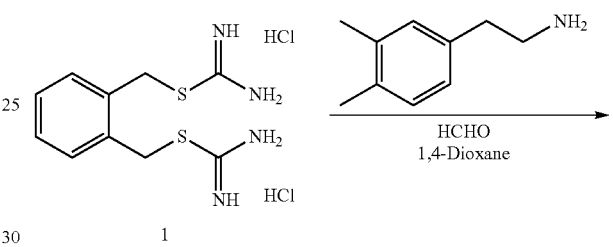

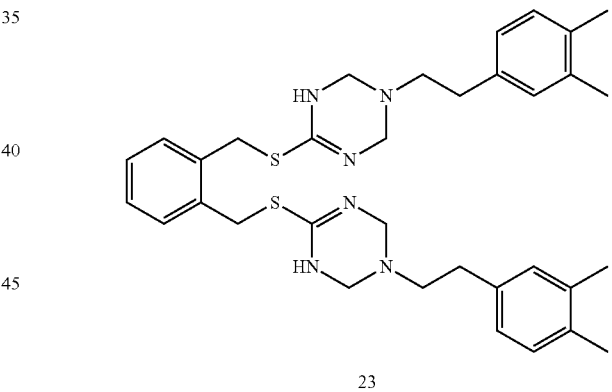

23

Reaction was performed by the same operation as in the synthesis of compound 9 from 3,4-dimethylphenethylamine (155 mg, 1.04 mmol), formaldehyde (169 μL, 37% wt. solution in water, 2.08 mmol) and 1,2-phenylenebis(methylene) dicarbamimidothioate dihydrochloride (compound 1, 132 mg, 0.52 mmol), and the reaction residue was purified by silica gel chromatography with n-hexane/EtOAc (1:3 to 1:6) to obtain the title compound 23 (54.2 mg, 17% yield) as a colorless oil substance.

$^1$H NMR (400 MHz, CDCl$_3$): δ=7.32 (2H, dd, J=8.0, 4.0 Hz), 7.12 (2H, dd, J=8.0, 4.0 Hz), 7.05 (2H, d, J=8.0 Hz), 6.96-6.91 (4H, m), 4.28-4.24 (12H, m), 2.83-2.72 (8H, m), 2.24 (6H, s), 2.22 (6H, s).

LC-MS: >99% purity, RT 2.88 min, MS (m/z): δ01 (M+H)$^+$.

Synthesis of Compound 24

1,2-Bis{{[5-(2,5-dimethylphenethyl)-1,4,5,6-tetra-hydro-1,3,5-triazin-2-yl]thio}methyl}benzene

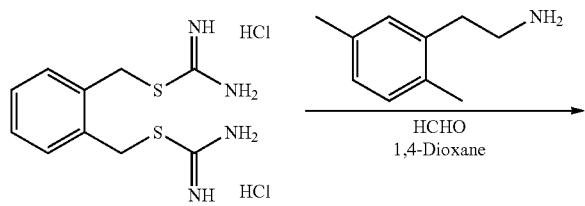

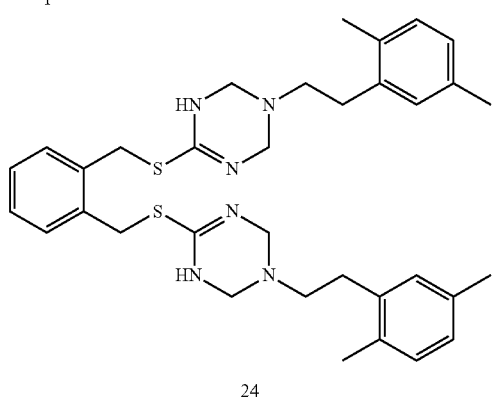

Reaction was performed by the same operation as in the synthesis of compound 9 from 2,5-dimethylphenethylamine (157 mg, 1.05 mmol), formaldehyde (170 µL, 37% wt. solution in water, 2.10 mmol) and 1,2-phenylenebis(methylene) dicarbamimidothioate dihydrochloride (compound 1, 134 mg, 0.53 mmol), and the reaction residue was purified by silica gel chromatography with n-hexane/EtOAc (1:3 to 1:6) to obtain the title compound 24 (70.0 mg, 22% yield) as a colorless oil substance.

$^1$H NMR (400 MHz, CDCl$_3$): δ=7.30 (2H, dd, J=8.0, 4.0 Hz), 7.08 (2H, dd, J=8.0, 4.0 Hz), 7.02 (2H, d, J=8.0 Hz), 6.94-6.92 (4H, m), 4.30-4.27 (12H, m), 2.79-2.77 (8H, m), 2.29 (6H, s), 2.25 (6H, s). LC-MS: >99% purity, RT 3.10 min, MS (m/z): δ01 (M+H)$^+$.

Synthesis of Compound 25

1,2-Bis{{[5-(4-ethylphenethyl)-1,4,5,6-tetrahydro-1,3,5-triazin-2-yl]thio}methyl}benzene

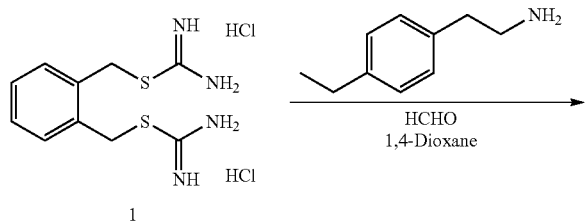

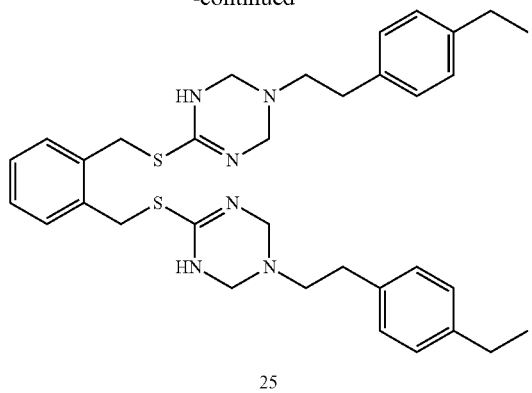

Reaction was performed by the same operation as in the synthesis of compound 9 from 4-ethylphenethylamine (155 mg, 1.04 mmol), formaldehyde (169 µL, 37% wt. solution in water, 2.10 mmol) and 1,2-phenylenebis(methylene) dicarbamimidothioate dihydrochloride (compound 1, 132 mg, 0.52 mmol), and the reaction residue was purified by silica gel chromatography with n-hexane/EtOAc (1:2 to 1:6) to obtain the title compound 25 (53.9 mg, 17% yield) as a colorless oil substance.

$^1$H NMR (400 MHz, CDCl$_3$): δ=7.33-7.29 (2H, m), 7.14-7.09 (10H, m), 4.29-4.23 (12H, m), 2.86-2.75 (8H, m), 2.62 (4H, q, J=8.0 Hz), 1.22 (6H, t, J=8.0 Hz).

LC-MS: >99% purity, RT 2.88 min, MS (m/z): δ01 (M+H)$^+$.

Synthesis of Compound 26

1,2-Bis{{[5-(4-methoxybenzyl)-1,4,5,6-tetrahydro-1,3,5-triazin-2-yl]thio}methyl}benzene

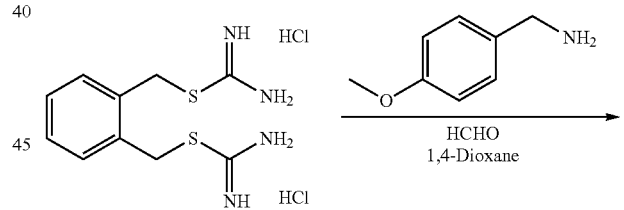

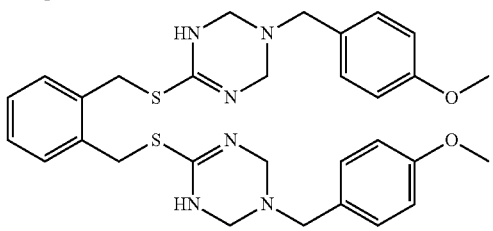

Reaction was performed by the same operation as in the synthesis of compound 9 from 4-methoxybenzylamine (144 mg, 1.05 mmol), formaldehyde (170 µL, 37% wt. solution in water, 2.10 mmol) and 1,2-phenylenebis(methylene) dicarbamimidothioate dihydrochloride (compound 1, 134 mg, 0.53 mmol), and the residue was purified by silica gel chromatography with n-hexane/EtOAc (1:2 to 1:6) and recrystallized from 2-propanol to obtain the title compound 26 (23.0 mg, 7.5% yield) as white crystals.

¹H NMR (400 MHz, CDCl₃): δ=7.42-7.40 (2H, m), 7.25-7.21 (6H, m), 6.87-6.83 (4H, m), 4.39-4.12 (8H, m), 4.36 (4H, s), 3.80 (6H, s), 3.68 (4H, s).

LC-MS: >99% purity, RT 2.17 min, MS (m/z): 577 (M+H)⁺.

Synthesis of Compound 27

1,2-Bis{{[5-(2,4-dimethoxybenzyl)-1,4,5,6-tetra-hydro-1,3,5-triazin-2-yl]thio}methyl}benzene

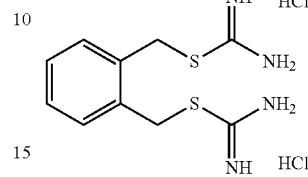
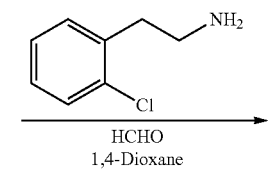

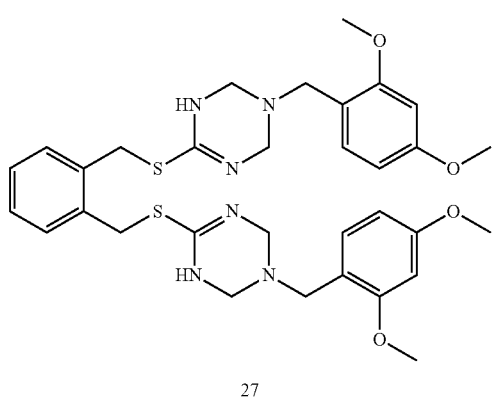

Reaction was performed by the same operation as in the synthesis of compound 9 from 2,4-dimethoxybenzylamine (173 mg, 1.03 mmol), formaldehyde (167 μL, 37% wt. solution in water, 2.06 mmol) and 1,2-phenylenebis(methylene) dicarbamimidothioate dihydrochloride (compound 1, 132 mg, 0.52 mmol), and the reaction residue was purified by silica gel chromatography with n-hexane/EtOAc (1:3 to 1:7) and recrystallized from 2-propanol to obtain the title compound 27 (12.9 mg, 4.0% yield) as white crystals.

¹H NMR (400 MHz, CDCl₃): δ=7.42-7.40 (2H, m), 7.21-7.19 (2H, m), 7.14 (4H, d, J=8.0 Hz), 6.45-6.42 (4H, m), 4.39-4.18 (8H, m), 4.37 (4H, s), 3.80 (12H, s), 3.71 (4H, s).

LC-MS: >99% purity, RT 2.27 min, MS (m/z): δ37 (M+H)⁺.

Synthesis of Compound 28

1,2-Bis (((5-(2-chlorophenethyl)-1,4,5,6-tetrahydro-1,3,5-triazin-2-yl)thio)methyl)benzene

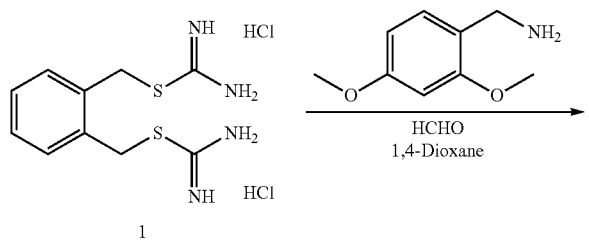

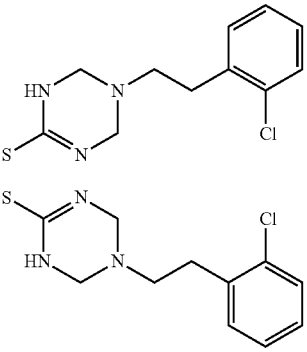

Reaction was performed by the same operation as in the synthesis of compound 9 from 2-chlorophenethylamine (164 mg, 1.05 mmol), formaldehyde (171 μL, 37% wt. solution in water, 2.11 mmol) and 1,2-phenylenebis(methylene) dicarbamimidothioate dihydrochloride (compound 1, 134 mg, 0.53 mmol), and the reaction residue was purified by silica gel chromatography with n-hexane/EtOAc (1:3 to 1:6) and recrystallized from 2-propanol to obtain the title compound 28 (57.1 mg, 17.7% yield) as white crystals.

¹H NMR (400 MHz, CDCl₃): δ=7.35-7.14 (10H, m), 7.07-7.05 (2H, m), 4.36-4.25 (8H, m), 4.28 (4H, s), 2.95-2.80 (8H, m).

LC-MS: >99% purity, RT 2.96 min, MS (m/z): δ14 (M+H)⁺.

Synthesis of Compound 29

1,2-Bis{[(5-methylcyclohexyl-1,4,5,6-tetrahydro-1,3,5-triazin-2-yl)thio]methyl}benzene

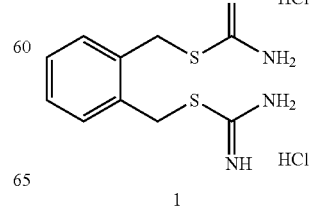
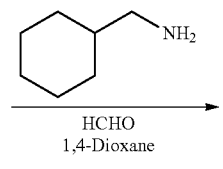

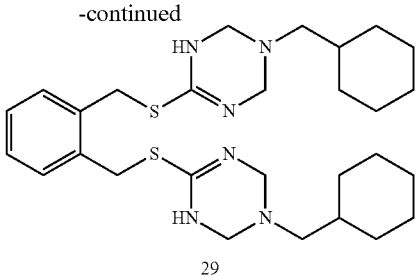

Reaction was performed by the same operation as in the synthesis of compound 9 from aminomethylcyclohexane (115 mg, 1.01 mmol), formaldehyde (164 μL, 37% wt. solution in water, 2.03 mmol) and 1,2-phenylenebis(methylene) dicarbamimidothioate dihydrochloride (compound 1, 130 mg, 0.51 mmol), and the reaction residue was recrystallized from 2-propanol to obtain the title compound 29 (161 mg, 60% yield) as pale yellow crystals.

$^1$H NMR (400 MHz, CDCl$_3$): δ=10.64 (2H, brs), 7.42 (2H, dd, J=8.0, 4.0 Hz), 7.19 (2H, dd, J=8.0, 4.0 Hz), 4.69 (4H, s), 4.34 (8H, s), 2.29-2.27 (4H, m), 1.71-0.81 (22H, m).

LC-MS: >99% purity, RT 2.62 min, MS (m/z): 529 (M+H)$^+$.

Synthesis of Compound 30

2,2'-(((1,2-Phenylenebis(methylene))bis(sulfanediyl))bis(pyrimidine-4,6(1H,5H)-dione)

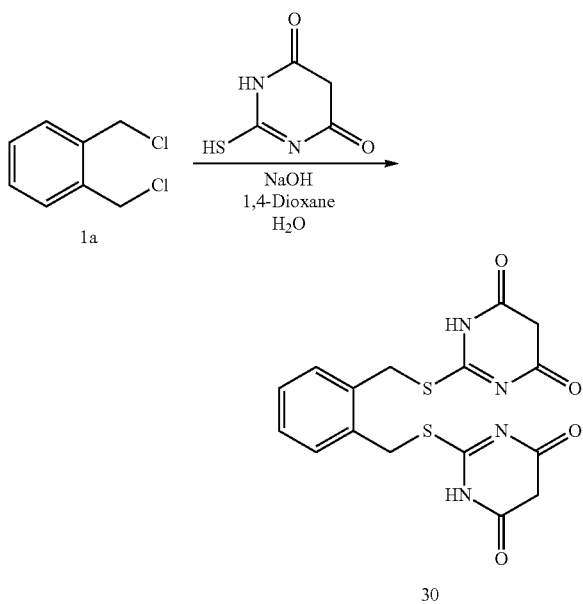

1.1 mmol/L NaOH (2.0 mL, 2.20 mmol) was added to a solution of 2-mercaptopyrimidine (112 mg, 1.00 mmol) in a 1,4-dioxane/H$_2$O mixed solvent (3:1, 4.0 mL), and the mixture was stirred at room temperature for 1 hour. Then, a solution of 1,2-bis(chloromethyl)benzene (compound 1a; 175 mg, 1.00 mmol) in 1,4-dioxane (4.0 mL) was added to the reaction solution, and the mixture was stirred at room temperature for 12 hours. The reaction mixture was concentrated under reduced pressure. Then, the residue was recrystallized from EtOH to obtain the title compound 30 (355 mg, 91% yield) as yellow crystals.

$^1$H NMR (400 MHz, DMSO-d6): δ=10.44 (2H, brs), 7.51 (2H, dd, J=8.0, 4.0 Hz), 7.26 (2H, dd, J=8.0, 4.0 Hz), 5.24 (2H, brs), 4.49 (4H, s), 4.09 (2H, brs).

LC-MS: >99% purity, RT 1.96 min, MS (m/z): 391 (M+H)$^+$.

Synthesis of Compound 31

Thiophene-2,3-diylbis(methylene) dicarbamimidothioate dihydrobromide

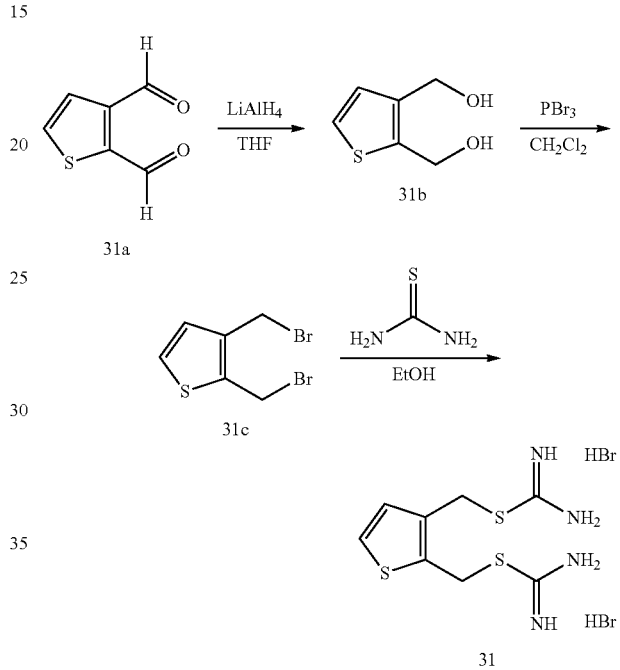

The same operation as in the synthesis of compound 2b was performed from 2,3-thiophenedicarboxaldehyde (compound 31a, 561 mg, 4.00 mmol) and LiAlH$_4$ (304 mg, 8.00 mmol), and the reaction residue was purified by silica gel chromatography (n-hexane/EtOAc=5:1 to 1:4) to obtain compound 31b (428 mg, 74% yield) as a colorless oil substance.

$^1$H NMR (400 MHz, CDCl$_3$): δ=7.19-7.18 (1H, m), 7.00-6.98 (1H, m), 4.74 (2H, s), 4.64 (2H, s), 3.25 (1H, brs), 2.95 (1H, brs).

A residue obtained by the same operation as in the synthesis of compound 2c from compound 31b (386 mg, 2.68 mmol) and phosphorous tribromide (0.305 mL, 3.21 mmol) was purified by silica gel chromatography with n-hexane/EtOAc (3:1) to obtain compound 31c (611 mg, 85% yield) as a yellow oil substance.

$^1$H NMR (400 MHz, CDCl$_3$): δ=7.27-7.26 (1H, m), 7.02-7.01 (1H, m), 4.75 (2H, s), 4.53 (2H, s).

The same operation as in the synthesis of compound 2 was performed from compound 31c (537 mg, 1.99 mmol) and thiourea (303 mg, 3.98 mmol), and the residue was recrystallized from EtOH and Et$_2$O (1:1) to obtain the title compound 31 (597 mg, 71% yield) as white crystals.

$^1$H NMR (400 MHz, DMSO-d6): δ=4.53 (2H, s), 4.80 (2H, s), 7.08 (1H, d, J=4.0 Hz), 7.59 (1H, d, J=4.0 Hz), 9.12 (6H, brs).

LC-MS: >99% purity, RT 0.35 min, MS (m/z): 261 (M+H)⁺.

Synthesis of Compound 32

Methyl 2-((carbamimidoylthio)methyl)-1H-indole-3-carboxylate hydrobromide

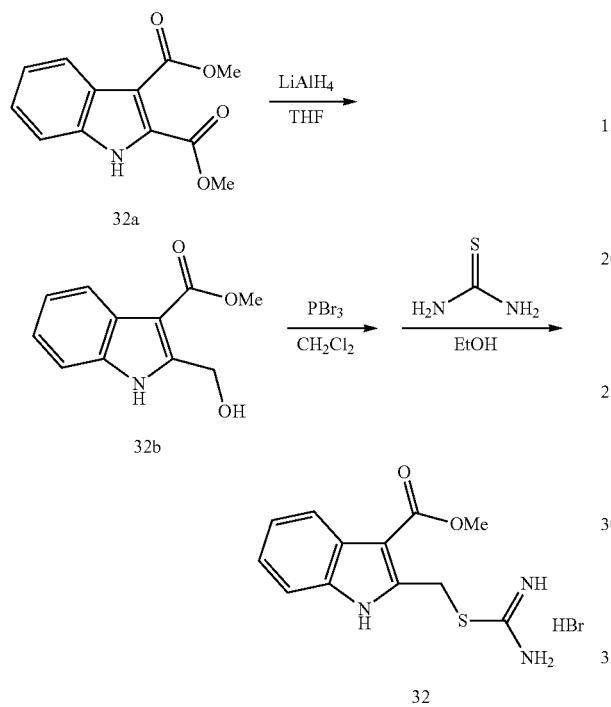

In an argon atmosphere, a solution of dimethyl 1H-indole-2,3-dicarboxylate (compound 32a, 670 mg, 3.00 mmol) in THF (12 mL) was gently added to a solution of LiAlH₄ (228 mg, 6.00 mmol) in THF (10 mL) at 0° C., and the mixture was stirred at room temperature for 5 hours and then heated to reflux for 12 hours. The reaction mixture was cooled to room temperature. Then, the reaction was terminated by the addition of 10% NaOH (1.0 mL) and H₂O (1.0 mL) and stirring, and the reaction solution was dried over magnesium sulfate and then concentrated under reduced pressure. The residue was purified by silica gel chromatography (n-hexane/EtOAc=9:1 to 3:7) to obtain compound 32b (213 mg, 42% yield) as pale yellow crystals.

¹H NMR (400 MHz, CD₃OD): δ=3.89 (3H, s), 5.08 (2H, s), 7.13-7.16 (2H, m), 7.41-7.44 (1H, m), 7.97-8.00 (1H, m).

LC-MS: >99% purity, RT 2.39 min, MS (m/z): 188 (M−OH)⁺.

A reaction residue obtained by the same operation as in the synthesis of compound 2c from compound 32b (350 mg, 1.97 mmol) and phosphorous tribromide (0.225 mL, 2.37 mmol) was purified by silica gel chromatography (n-hexane/EtOAc=9:1 to 3:7) and concentrated under reduced pressure. Then, the obtained purified product (123 mg, 0.46 mmol) was added to a solution of thiourea (77.5 mg, 1.02 mmol) in EtOH (5 mL) at room temperature and the reaction mixture was refluxed for 12 hours. Then, the reaction solution was concentrated under reduced pressure and then recrystallized from EtOH and Et₂O (1:1) to obtain the title compound 32 (25.6 mg, 3.8% yield from compound 32b (yield 3.8% was a yield with compound 32b as a starting material)) as white crystals.

¹H NMR (400 MHz, DMSO-d6): δ=9.08 (3H, brs), 7.96 (1H, d, J=8.0 Hz), 7.49 (1H, d, J=8.0 Hz), 7.27-7.19 (2H, m), 4.87 (2H, s), 3.87 (3H, s).

LC-MS: >99% purity, RT 1.13 min, MS (m/z): 264 (M+H)⁺.

Synthesis of Compound 33

3,4-Bis{[(5-phenethyl-1,4,5,6-tetrahydro-1,3,5-triazin-2-yl)thio]methyl}thiophene dihydrochloride

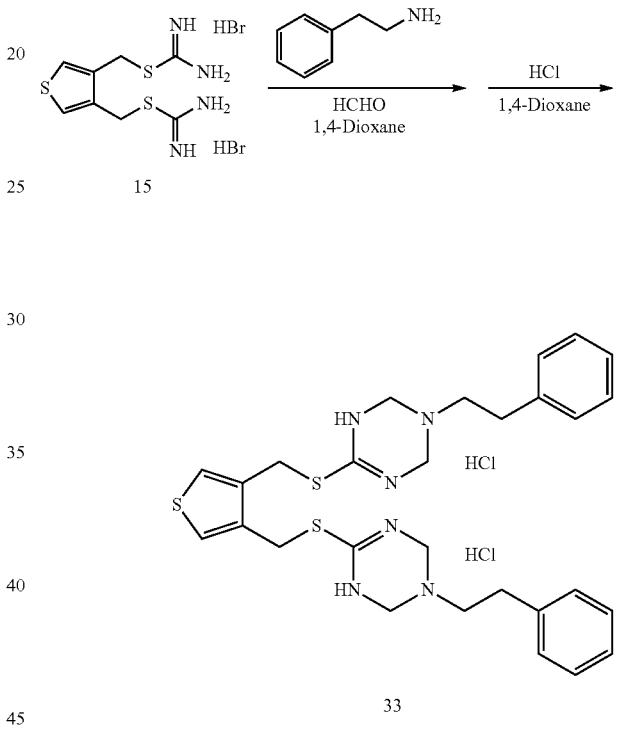

Reaction was performed by the same operation as in the synthesis of compound 9 from phenethylamine (121 mg, 1.00 mmol), formaldehyde (162 μL, 37% wt. solution in water, 2.00 mmol) and thiophene-3,4-diylbis(methylene) dicarbamimidothioate dihydrobromide (compound 15, 130 mg, 0.50 mmol), and the reaction residue was purified by silica gel chromatography with EtOAc/EtOH (4:1 to 7:3) to obtain a free form of compound 33 as a colorless oil substance (23.3 mg, 8.5% yield). 4.0 mol/L HCl (19.5 μL, 0.078 mmol) was added to a solution of the free form of compound 33 in 1,4-dioxane (3.0 mL), and the mixture was stirred at room temperature for 1 hour. The reaction residue was concentrated under reduced pressure and recrystallized from n-hexane to obtain the title compound 33 (23.8 mg, 98% yield) as white crystals.

¹H NMR (400 MHz, CDCl₃): δ=10.56 (2H, brs), 7.50-7.17 (12H, m), 4.61 (4H, s), 4.36-4.20 (8H, m), 2.98-2.58 (8H, m).

LC-MS: >99% purity, RT 2.29 min, MS (m/z): 551 (M+H)⁺.

Synthesis of Compound 34

Pyridine-2,3-diylbis(methylene) dicarbamimidothioate dihydrobromide

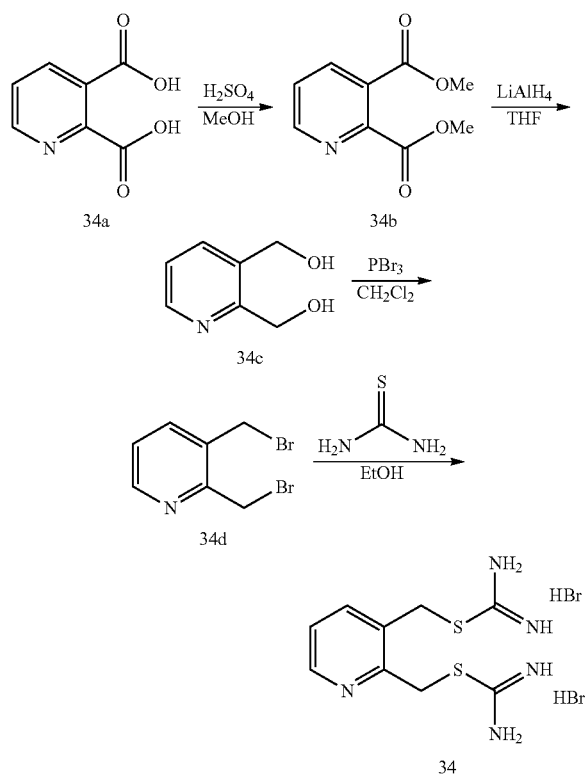

Concentrated sulfuric acid (1.0 ml) was added to a solution of pyridine-2,3-dicarboxylic acid (compound 34a, 2.5 g, 15.0 mmol) in MeOH (10 ml), and the mixture was refluxed for 6 hours and then stirred at room temperature for 2 days. The reaction solution was concentrated, and then, an aqueous sodium bicarbonate solution was added to the residue, followed by extraction with ethyl acetate. The organic layer was washed with brine, dried over magnesium sulfate, and then concentrated under reduced pressure to obtain compound 34b (2.18 g, 74% yield) as pale yellow crystals.

$^1$H NMR (400 MHz, CDCl$_3$): δ=8.78 (1H, dd, J=4.9, 1.5 Hz), 8.18 (1H, dd, J=7.8, 1.5 Hz), 7.51 (1H, dd, J=7.8, 4.9 Hz), 4.01 (3H, s), 3.95 (3H, s).

LC-MS: >99% purity, RT 1.23 min, MS (m/z): 196 (M+H)$^+$.

The same operation as in the synthesis of compound 2b was performed from compound 34b (976 mg, 5.00 mmol) and LiAlH$_4$ (380 mg, 10.0 mmol), and the reaction residue was purified by silica gel chromatography (CHCl$_3$/MeOH=1:0 to 9:1) to obtain compound 34c (221 mg, 32% yield) as a colorless oil substance.

$^1$H NMR (400 MHz, CDCl$_3$): δ=8.50 (1H, d, J=4.4 Hz), 7.76 (1H, d, J=7.8 Hz), 7.29-7.25 (1H, m), 4.80 (2H, s), 4.71 (2H, s), 4.51 (1H, brs), 2.09 (1H, brs). LC-MS: >99% purity, RT 0.35 min, MS (m/z): 140 (M+H)$^+$.

A reaction residue obtained by the same operation as in the synthesis of compound 2c from compound 34c (196 mg, 1.41 mmol) and phosphorous tribromide (0.161 mL, 1.69 mmol) was purified by silica gel chromatography (CHCl$_3$) to obtain compound 34d (42.1 mg, 11% yield) as a yellow oil substance.

$^1$H NMR (400 MHz, CDCl$_3$): δ=8.55-8.53 (1H, m), 7.71-7.69 (1H, m), 7.28-7.25 (1H, m), 4.73 (2H, s), 4.62 (2H, s).

LC-MS: >99% purity, RT 2.58 min, MS (m/z): 266 (M+H)$^+$.

The same operation as in the synthesis of compound 2 was performed from compound 34d (38.1 mg, 0.14 mmol) and thiourea (21.9 mg, 0.28 mmol), and the residue was recrystallized from EtOH and Et$_2$O (1:1) to obtain the title compound 34 (36.4 mg, 61% yield) as white crystals.

$^1$H NMR (400 MHz, DMSO-d6): δ=9.21 (6H, brs), 8.55 (1H, dd, J=4.8, 1.6 Hz), 7.93 (1H, dd, J=7.8, 1.6 Hz), 7.48 (1H, dd, J=7.8, 4.8 Hz), 4.74 (2H, s), 4.64 (2H, s).

LC-MS: >99% purity, RT 0.35 min, MS (m/z): 256 (M+H)$^+$.

Synthesis of Compound 35

(4-Methoxy-1,2-phenylene)bis(methylene) dicarbamimidothioate dihydrobromide

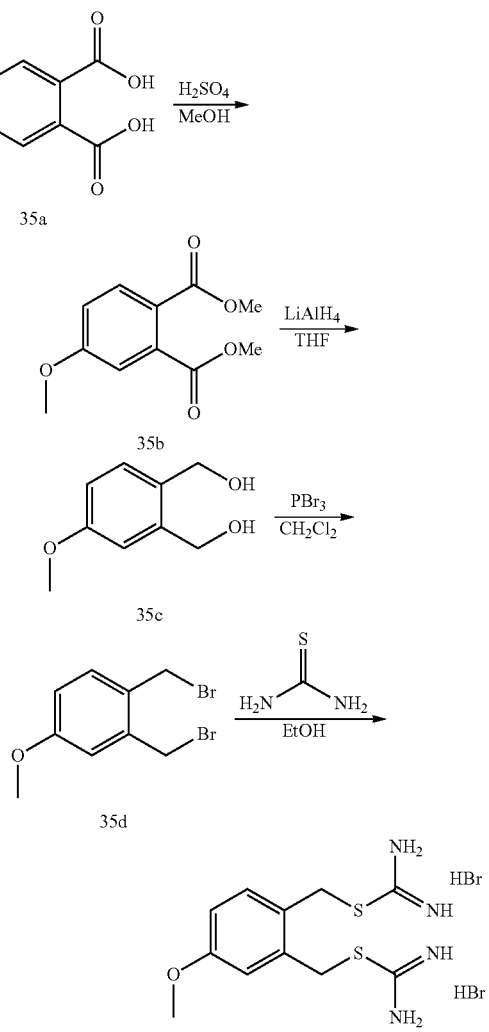

The same operation as in the synthesis of compound 34b was performed from a solution of 4-methoxyphthalic acid (compound 35a, 588 mg, 3.0 mmol) in MeOH (7 ml) and concentrated sulfuric acid (0.5 ml), and the residue was purified by silica gel chromatography with EtOAc/EtOH (1:1) to obtain compound 35b (574 mg, 85% yield) as a pale yellow oil substance.

$^1$H NMR (400 MHz, CDCl$_3$): δ=7.82 (1H, d, J=8.4 Hz), 7.07 (1H, d, J=2.8 Hz), 6.99 (1H, dd, J=8.4, 2.8 Hz), 3.92 (3H, s), 3.87 (3H, s), 3.87 (3H, s).

The same operation as in the synthesis of compound 2b was performed from compound 35b (497 mg, 2.22 mmol) and LiAlH$_4$ (168 mg, 4.43 mmol), and the reaction residue was purified by silica gel chromatography (n-hexane/EtOAc=4:1 to 1:2) to obtain compound 35c (222 mg, 59% yield) as a colorless oil substance.

$^1$H NMR (400 MHz, CDCl$_3$): δ=7.27-7.25 (1H, m), 6.92 (1H, d, J=2.9 Hz), 6.82 (1H, dd, J=8.3, 2.9 Hz), 4.69 (2H, s), 4.67 (2H, s), 3.82 (3H, s).

A reaction residue obtained by the same operation as in the synthesis of compound 2c from compound 35c (183 mg, 1.09 mmol) and phosphorous tribromide (0.124 mL, 1.31 mmol) was purified by silica gel chromatography (n-hexane/EtOAc=3:1) to obtain compound 35d (72.7 mg, 23% yield) as a yellow oil substance.

$^1$H NMR (400 MHz, CDCl$_3$): δ=7.29 (1H, d, J=8.3 Hz), 6.90 (1H, d, J=2.4 Hz), 6.83 (1H, dd, J=8.3, 2.9 Hz), 4.66 (2H, s), 4.62 (2H, s), 3.82 (3H, s).

The same operation as in the synthesis of compound 2 was performed from compound 35d (73.0 mg, 0.247 mmol) and thiourea (38.0 mg, 0.495 mmol), and the residue was recrystallized from EtOH and Et$_2$O (1:1) to obtain the title compound 35 (62.8 mg, 57% yield) as white crystals.

$^1$H NMR (400 MHz, DMSO-d6): δ=9.13 (6H, brs), 7.41 (1H, d, J=8.0 Hz), 7.07 (1H, d, J=2.8 Hz), 6.97 (1H, dd, J=8.0, 2.8 Hz), 4.55-4.54 (4H, m), 3.77 (3H,$).

LC-MS: >99% purity, RT 0.34 min, MS (m/z): 285 (M+H)$^+$.

Synthesis of Compound 36

(4,5-Dichloro-1,2-phenylene)bis(methylene) dicarbamimidothioate dihydrobromide

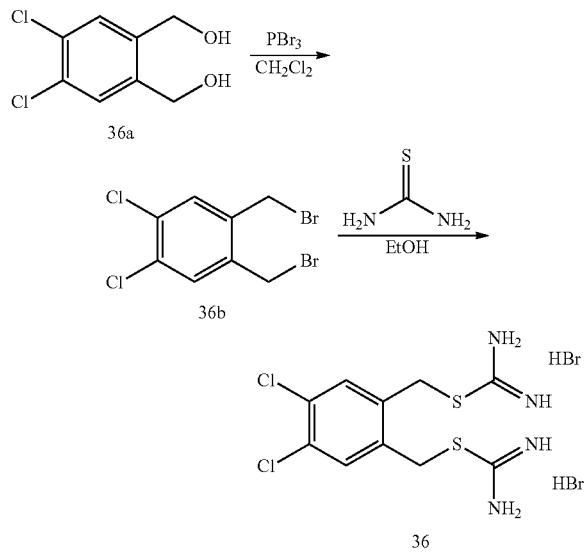

A reaction residue obtained by the same operation as in the synthesis of compound 2c from (4,5-dichloro-1,2-phenylene)dimethanol (compound 36a, 2.18 g, 10.5 mmol) and phosphorous tribromide (1.103 mL, 12.6 mmol) was purified by silica gel chromatography (n-hexane/EtOAc=4:1) to obtain compound 36b (823 mg, 24% yield) as white crystals.

$^1$H NMR (400 MHz, CDCl$_3$): δ=7.47 (2H, s), 4.55 (4H, s).

The same operation as in the synthesis of compound 2 was performed from compound 36b (723 mg, 2.17 mmol) and thiourea (331 mg, 4.34 mmol), and the residue was recrystallized from EtOH and Et$_2$O (1:2) to obtain the title compound 36 (856 mg, 82% yield) as white crystals.

$^1$H NMR (400 MHz, DMSO-d6): δ=9.21 (6H, brs), 7.80 (2H, s), 4.62 (4H, s).

LC-MS: >99% purity, RT 0.45 min, MS (m/z): 324 (M+H)$^+$.

Synthesis of Compound 37

6,6'-(((4,5-Dichloro-1,2-phenylene)bis(methylene))bis(sulfanediyl))bis(3-phenethyl-1,2,3,4-tetrahydro-1,3,5-triazine)

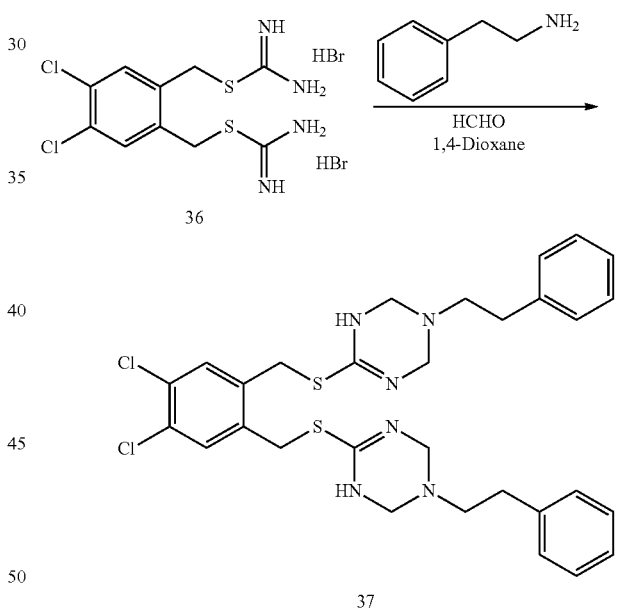

Reaction was performed by the same operation as in the synthesis of compound 9 from 2-phenylethan-1-amine (121 mg, 1.00 mmol), formaldehyde (162 μL, 37% wt. solution in water, 2.00 mmol) and (4,5-dichloro-1,2-phenylene)bis(methylene) dicarbamimidothioate dihydrobromide (compound 36, 162 mg, 0.50 mmol), and the reaction residue was recrystallized from 2-propanol to obtain the title compound 37 (200 mg, 65% yield) as white crystals.

$^1$H NMR (400 MHz, DMSO-d6): δ=10.25 (2H, brs), 7.72 (2H, s), 7.32-7.20 (10H, m), 4.60 (4H, brs), 4.41 (8H, brs), 2.78-2.63 (8H, m).

LC-MS: >99% purity, RT 3.87 min, MS (m/z): δ14 (M+H)$^+$.

Synthesis of Compound 38

6,6'-(((4,5-Dichloro-1,2-phenylene)bis(methylene))bis(sulfanediyl))bis(3-(3,4-dichlorophenethyl)-1,2,3,4-tetrahydro-1,3,5-triazine)

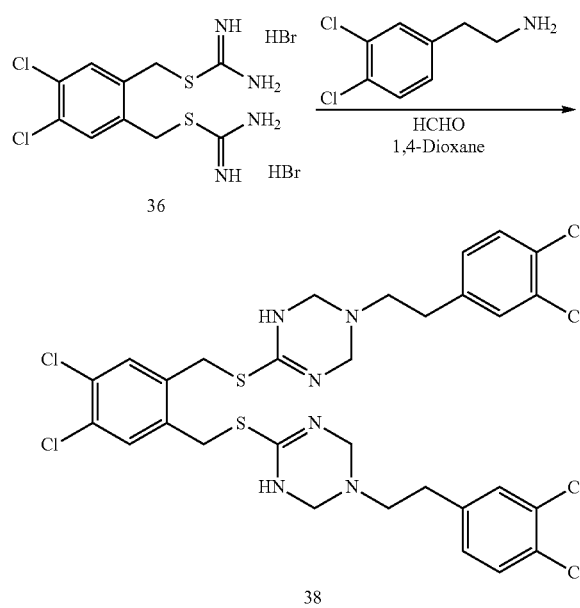

Reaction was performed by the same operation as in the synthesis of compound 9 from 2-(3,4-dichlorophenyl)ethan-1-amine (190 mg, 1.00 mmol), formaldehyde (162 μL, 37% wt. solution in water, 2.00 mmol) and (4,5-dichloro-1,2-phenylene)bis(methylene) dicarbamimidothioate dihydrobromide (compound 36, 162 mg, 0.50 mmol), and the reaction residue was purified by NH-silica gel chromatography with n-hexane/EtOAc (3:2 to 0:1) to obtain the title compound 38 (38.2 mg, 10% yield) as an amorphous substance.

$^1$H NMR (400 MHz, DMSO-d6): δ=7.51-7.48 (6H, m), 7.21-7.18 (2H, m), 4.24 (4H, brs), 4.17 (4H, brs), 3.99 (4H, brs), 2.73-2.65 (8H, m).

LC-MS: >99% purity, RT 2.54 min, MS (m/z): 752 (M+H)$^+$.

Synthesis of Compound 39

6,6'-(((4-Bromo-1,2-phenylene)bis(methylene))bis(sulfanediyl))bis(3-(3,4-dichlorophenethyl)-1,2,3,4-tetrahydro-1,3,5-triazine)

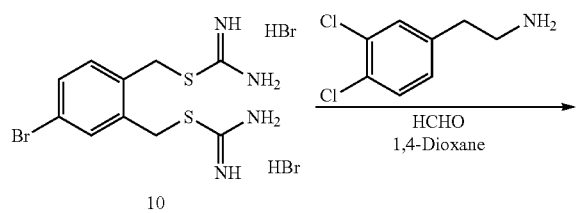

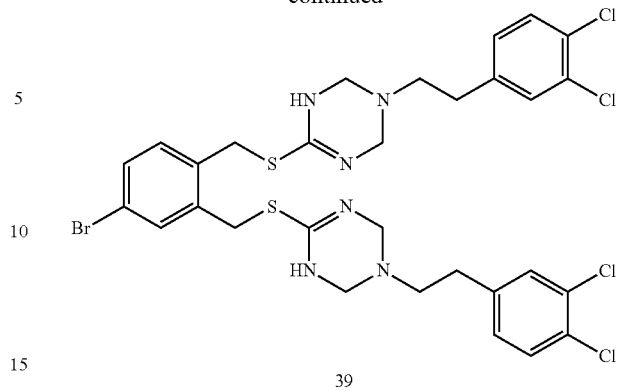

Reaction was performed by the same operation as in the synthesis of compound 9 from 2-(3,4-dichlorophenyl)ethan-1-amine (190 mg, 1.00 mmol), formaldehyde (162 μL, 37% wt. solution in water, 2.00 mmol) and (4-bromo-1,2-phenylene)bis(methylene) dicarbamimidothioate dihydrobromide (compound 10, 167 mg, 0.50 mmol), and the reaction residue was purified by NH-silica gel chromatography with n-hexane/EtOAc (3:2 to 0:1) and recrystallized from 2-propanol to obtain the title compound 39 (16.7 mg, 4.4% yield) as white crystals.

$^1$H NMR (400 MHz, DMSO-d6): δ=7.53-7.47 (6H, m), 7.23-7.20 (2H, m), 6.88-6.85 (1H, m), 4.24 (4H, brs), 4.17-4.15 (4H, m), 4.17-4.15 (4H, m), 2.74-2.67 (8H, m).

LC-MS: >99% purity, RT 2.74 min, MS (m/z): 763 (M+H)$^+$.

Synthesis of Compound 40

1,2-Bis (((5-(2-(thiophen-2-yl)ethyl)-1,4,5,6-tetrahydro-1,3,5-triazin-2-yl)thio)methyl)benzene

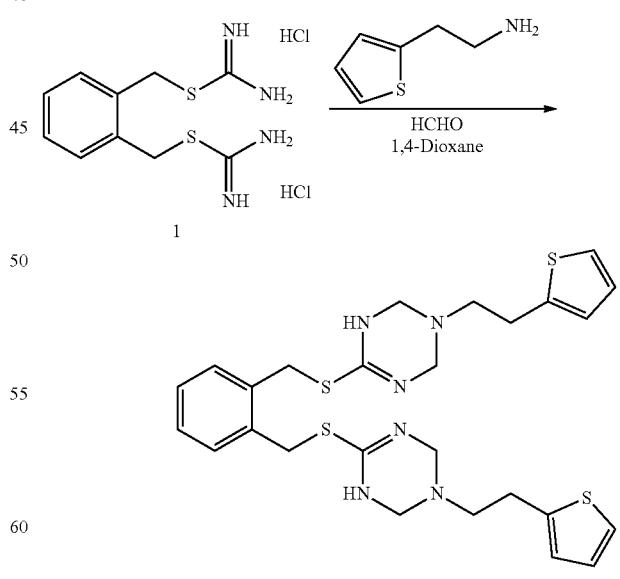

Reaction was performed by the same operation as in the synthesis of compound 9 from 2-(thiophen-2-yl)ethan-1-amine (763 mg, 6.00 mmol), formaldehyde (973 μL, 37% wt. solution in water, 4.00 mmol) and 1,2-phenylenebis (methylene) dicarbamimidothioate dihydrochloride (compound 1, 763 mg, 3.00 mmol), and the reaction residue was purified by NH-silica gel chromatography with n-hexane/EtOAc (3:2 to 0:1) to obtain the title compound 40 (9.5 mg, 5.7% yield) as a pale yellow oil substance.

$^1$H NMR (400 MHz, CDCl$_3$): δ=7.33-7.30 (2H, m), 7.15-7.11 (4H, m), 6.93-6.91 (2H, m), 6.82-6.81 (2H, m), 4.48-4.06 (12H, m), 3.03-2.87 (8H, m). LC-MS: >99% purity, RT 1.66 min, MS (m/z): 557 (M+H)$^+$.

Synthesis of Compound 41

1,2-Bis(((5-(4-chlorobenzyl)-1,4,5,6-tetrahydro-1,3,5-triazin-2-yl)thio)methyl)benzene

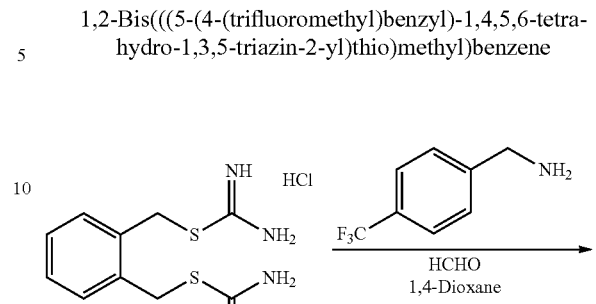

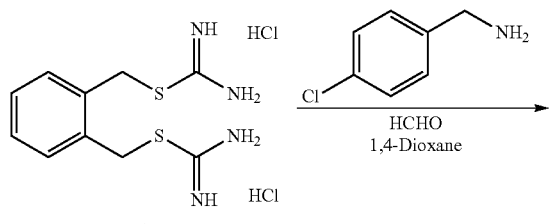

Reaction was performed by the same operation as in the synthesis of compound 9 from (4-chlorophenyl)methanamine (566 mg, 4.00 mmol), formaldehyde (649 μL, 37% wt. solution in water, 800 mmol) and 1,2-phenylenebis (methylene) dicarbamimidothioate dihydrochloride (compound 1, 509 mg, 2.00 mmol), and the reaction residue was purified by NH-silica gel chromatography with n-hexane/EtOAc (45:55 to 0:1) to obtain the title compound 41 (27.4 mg, 2.3% yield) as a colorless oil substance.

$^1$H NMR (400 MHz, CDCl$_3$): δ=7.42-7.39 (2H, m), 7.30-7.21 (10H, m), 4.34 (4H, s), 4.23 (8H, brs), 3.70 (4H, brs).

LC-MS: >99% purity, RT 2.13 min, MS (m/z): 586 (M+H)$^+$.

Synthesis of Compound 42

1,2-Bis(((5-(4-(trifluoromethyl)benzyl)-1,4,5,6-tetrahydro-1,3,5-triazin-2-yl)thio)methyl)benzene

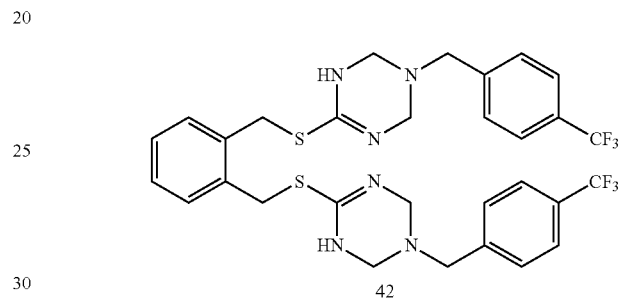

Reaction was performed by the same operation as in the synthesis of compound 9 from (4-(trifluoromethyl)phenyl) methanamine (701 mg, 4.00 mmol), formaldehyde (649 μL, 37% wt. solution in water, 800 mmol) and 1,2-phenylenebis (methylene) dicarbamimidothioate dihydrochloride (compound 1, 509 mg, 2.00 mmol), and the reaction residue was purified by NH-silica gel chromatography with n-hexane/EtOAc (45:55 to 0:1) to obtain the title compound 42 (303 mg, 23.2% yield) as a colorless oil substance.

$^1$H NMR (400 MHz, CDCl$_3$): δ=7.59-7.57 (4H, m), 7.45-7.40 (6H, m), 7.25-7.22 (2H, m), 4.36 (4H, brs), 4.31-4.21 (8H, m), 3.79 (4H, brs).

LC-MS: >99% purity, RT 1.91 min, MS (m/z): δ53 (M+H)$^+$.

Synthesis of Compound 43

1,2-Bis(((5-(3,4-difluorobenzyl)-1,4,5,6-tetrahydro-1,3,5-triazin-2-yl)thio)methyl)benzene

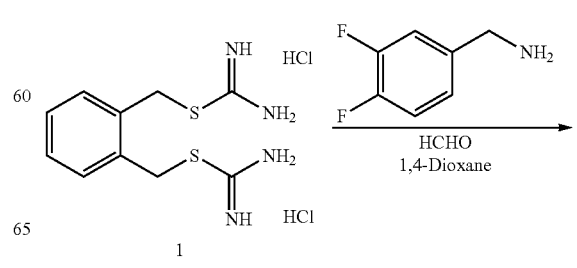

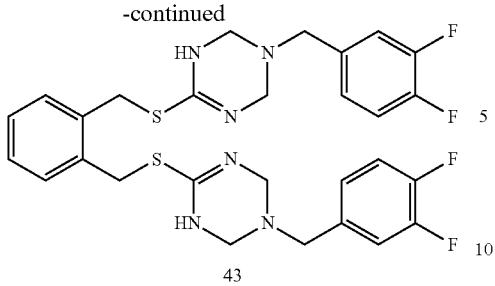

43

Reaction was performed by the same operation as in the synthesis of compound 9 from (3,4-difluorophenyl)methanamine (573 mg, 4.00 mmol), formaldehyde (649 μL, 37% wt. solution in water, 800 mmol) and 1,2-phenylenebis (methylene) dicarbamimidothioate dihydrochloride (compound 1, 509 mg, 2.00 mmol), and the reaction residue was purified by NH-silica gel chromatography with n-hexane/EtOAc (3:2 to 0:1) to obtain the title compound 43 (300 mg, 25.4% yield) as a colorless oil substance.

$^1$H NMR (400 MHz, CDCl$_3$): δ=7.42-7.39 (2H, m), 7.24-7.02 (8H, m), 4.35 (4H, brs), 4.31-4.20 (8H, m), 3.69 (4H, brs).

LC-MS: >99% purity, RT 2.42 min, MS (m/z): 589 (M+H)$^+$.

Synthesis of Compound 44

1,2-Bis(((5-(2,5-dimethylbenzyl)-1,4,5,6-tetrahydro-1,3,5-triazin-2-yl)thio)methyl)benzene

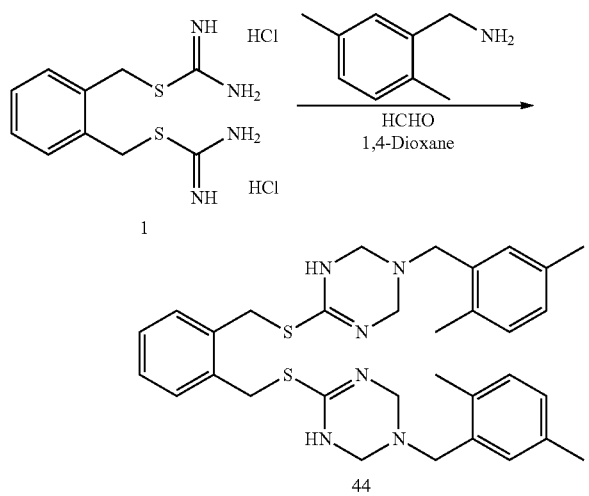

44

Reaction was performed by the same operation as in the synthesis of compound 9 from (2,5-dimethylphenyl)methanamine (541 mg, 4.00 mmol), formaldehyde (649 μL, 37% wt. solution in water, 800 mmol) and 1,2-phenylenebis (methylene) dicarbamimidothioate dihydrochloride (compound 1, 509 mg, 2.00 mmol), and the reaction residue was purified by NH-silica gel chromatography with n-hexane/EtOAc (3:2 to 0:1) to obtain the title compound 44 (157 mg, 13.7% yield) as a colorless amorphous substance.

$^1$H NMR (400 MHz, CDCl$_3$): δ=7.44-7.41 (2H, m), 7.22-7.20 (2H, m), 7.05-6.98 (6H, m), 4.40 (4H, brs), 4.37-4.13 (8H, m), 3.71 (4H, brs), 2.30 (6H, s), 2.28 (6H, s).

LC-MS: >99% purity, RT 2.50 min, MS (m/z): 573 (M+H)$^+$.

Synthesis of Compound 45

1,2-Bis(((5-(2,5-dimethylbenzyl)-1,4,5,6-tetrahydro-1,3,5-triazin-2-yl)thio)methyl)benzene

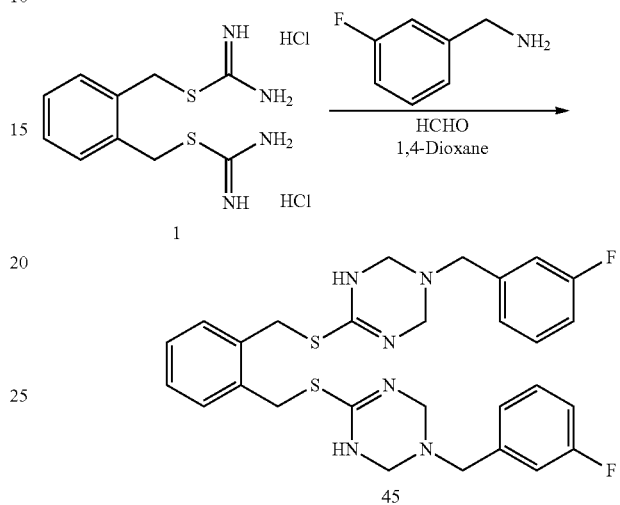

45

Reaction was performed by the same operation as in the synthesis of compound 9 from (3-fluorophenyl)methanamine (501 mg, 4.00 mmol), formaldehyde (649 μL, 37% wt. solution in water, 800 mmol) and 1,2-phenylenebis (methylene) dicarbamimidothioate dihydrochloride (compound 1, 509 mg, 2.00 mmol), and the reaction residue was purified by NH-silica gel chromatography with n-hexane/EtOAc (55:45 to 0:1) to obtain the title compound 45 (121 mg, 10.9% yield) as a colorless oil substance.

$^1$H NMR (400 MHz, CDCl$_3$): δ=7.42-7.40 (2H, m), 7.28-7.23 (4H, m), 7.09-7.05 (4H, m), 6.98-6.93 (2H, m), 4.36 (4H, brs), 4.32-4.20 (8H, m), 3.73 (4H, brs).

LC-MS: >99% purity, RT 2.33 min, MS (m/z): 553 (M+H)$^+$.

Synthesis of Compound 46

(4-(Trifluoromethyl)-1,2-phenylene)bis(methylene) dicarbamimidothioate dihydrobromide

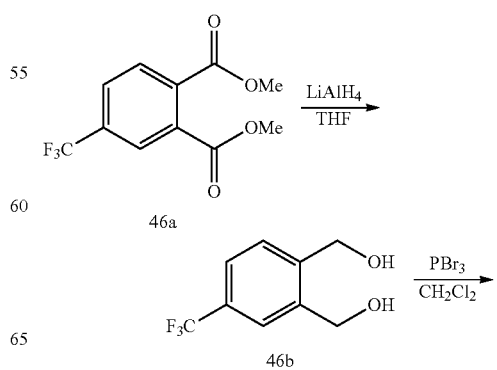

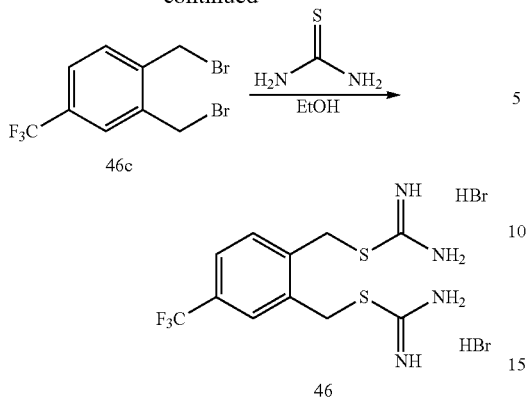

46c

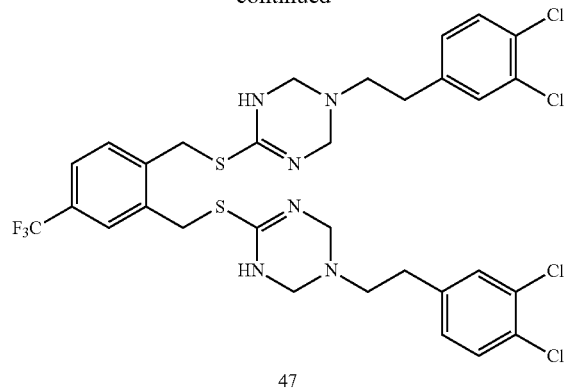

47

The same operation as in the synthesis of compound 2b was performed from dimethyl 4-(trifluoromethyl)phthalate (compound 46a, 2621 mg, 10.00 mmol) and LiAlH$_4$ (759 mg, 20.00 mmol), and the reaction residue was purified by silica gel chromatography (n-hexane/EtOAc=5:1 to 1:2) to obtain compound 46b (1116 mg, 54.1% yield) as a pale yellow oil substance.

$^1$HNMR (400 MHz, CDCl$_3$): δ=7.63 (1H, s), 7.59 (1H, d, J=7.8 Hz), 7.49 (1H, d, J=7.8 Hz), 4.79 (4H, d, J=5.9 Hz), 2.88 (2H, dt, J=15.1, 5.9 Hz).

LC-MS: >99% purity, RT 1.97 min, MS (m/z): 189 (M+H)$^+$

A residue obtained by the same operation as in the synthesis of compound 2c from compound 46b (1025 mg, 4.97 mmol) and phosphorous tribromide (0.566 mL, 5.96 mmol) was purified by silica gel chromatography with n-hexane/EtOAc (3:1) to obtain compound 46c (600 mg, 36.4% yield) as a pale yellow oil substance.

$^1$HNMR (400 MHz, CDCl$_3$): δ=7.63 (1H, s), 7.57 (1H, d, J=7.8 Hz), 7.50 (1H, d, J=7.8 Hz), 4.66 (4H, d, J=2.9 Hz).

The same operation as in the synthesis of compound 2 was performed from compound 46c (585 mg, 1.76 mmol) and thiourea (268 mg, 3.52 mmol), and the residue was recrystallized from EtOH and Et$_2$O (1:2) to obtain compound 46 (659 mg, 77.3% yield) as white crystals.

$^1$HNMR (400 MHz, DMSO-d6): δ=9.17 (6H, brs), 7.89 (1H, s), 7.80 (1H, d, J=8.29 Hz), 7.72 (1H, d, J=8.29 Hz), 4.36 (4H, brs).

LC-MS: >99% purity, RT 0.47 min, MS (m/z): 323 (M+H)$^+$

Synthesis of Compound 47

6,6'-(((4-(Trifluoromethyl)-1,2-phenylene)bis(methylene))bis(sulfanediyl))bis(3-(3,4-dichlorophenethyl)-1,2,3,4-tetrahydro-1,3,5-triazine)

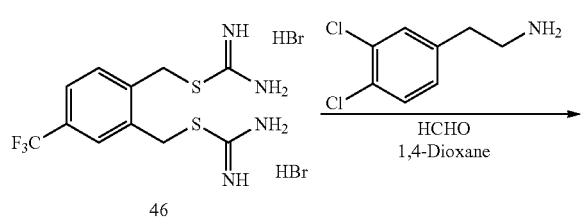

46

Reaction was performed by the same operation as in the synthesis of compound 9 from 2-(3,4-dichlorophenyl)ethan-1-amine (0.239 mL, 1.60 mmol), formaldehyde (241 µL, 37% wt. solution in water, 3.20 mmol) and (4-(trifluoromethyl)-1,2-phenylene)bis(methylene)dicarbamimidothioate dihydrobromide (compound 46, 258 mg, 0.80 mmol), and the reaction residue was purified by NH-silica gel chromatography twice with n-hexane/EtOAc (1:2 to 1:10) and with n-hexane/EtOAc (1:10) to obtain the title compound 47 (6.90 mg, 1.2% yield) as white crystals.

$^1$H NMR (400 MHz, CDCl$_3$): δ=7.64-7.25 (7H, m), 7.04-6.99 (2H, m), 4.37-4.20 (12H, m), 2.89-2.69 (8H, m).

LC-MS: >99% purity, RT 2.47 min, MS (m/z): 751 (M+H)$^+$

Synthesis of Compound 48

6,6'-(((4-(Trifluoromethyl)-1,2-phenylene)bis(methylene))bis(sulfanediyl))bis(3-(2-chlorophenethyl)-1,2,3,4-tetrahydro-1,3,5-triazine)

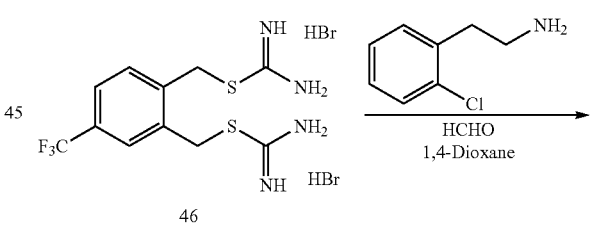

46

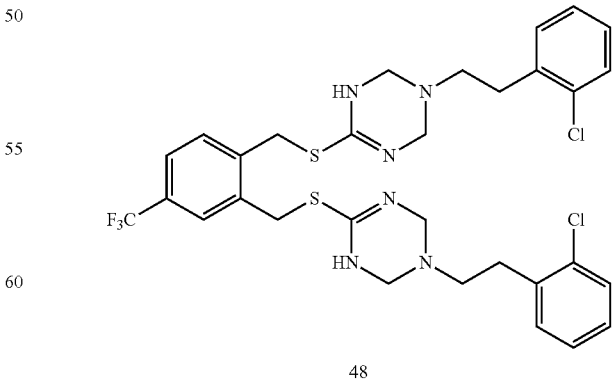

48

Reaction was performed by the same operation as in the synthesis of compound 9 from 2-(2-chlorophenyl)ethan-1- amine (0.220 mL, 1.60 mmol), formaldehyde (241 µL, 37% wt. solution in water, 3.20 mmol) and (4-(trifluoromethyl)-1,2-phenylene)bis(methylene)dicarbamimidothioate dihydrobromide (compound 46, 258 mg, 0.8 mmol), and the reaction residue was purified by NH-silica gel chromatography with n-hexane/EtOAc (1:2 to 1:5) to obtain the title compound 48 (13.7 mg, 2.5% yield) as a white oil substance.

¹H NMR (400 MHz, CDCl₃): δ=7.37-7.00 (11H, m), 4.28-4.21 (12H, m), 3.00-2.89 (8H, m).

LC-MS: >99% purity, RT 3.32 min, MS (m/z): δ82 (M+H)⁺

Synthesis of Compound 49

(4-Bromo-1,2-phenylene)bis(methylene) (E,E)-bis(N'-(4-bromophenyl)carbamimidothioate)

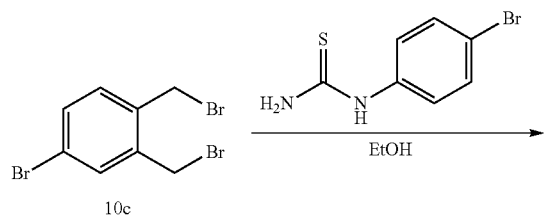

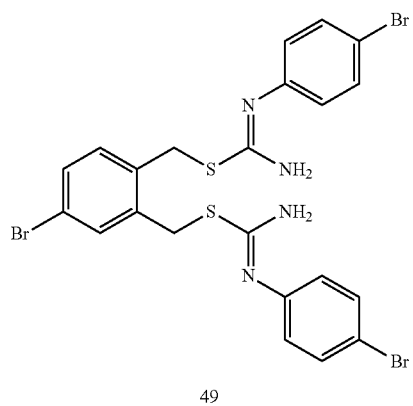

The same operation as in the synthesis of compound 10 was performed from 4-bromo-1,2-bis(bromomethyl)benzene (compound 10c, 151 mg, 0.44 mmol) and 1-(4-bromophenyl)thiourea (203 mg, 0.88 mmol), and the reaction residue was purified by NH-silica gel chromatography with n-hexane/EtOAc (1:1 to 1:4) and silica gel chromatography with n-hexane/EtOAc (4:1 to 2:1) to obtain the title compound 49 (17.3 mg, 6.1% yield) as white crystals.

¹HNMR (400 MHz, CD₃OD): δ=7.60 (1H, brs), 7.40-7.37 (5H, m), 7.32-7.30 (1H, m), 6.78 (4H, d, J=7.8 Hz), 4.40-4.36 (4H, m).

LC-MS: >99% purity, RT 3.42 min, MS (m/z): δ44 (M+H)⁺

Synthesis of Compound 50

6,6'-(((4,5-Dichloro-1,2-phenylene)bis(methylene))bis(sulfanediyl))bis(3-(cyclohexylmethyl)-1,2,3,4-tetrahydro-1,3,5-triazine)

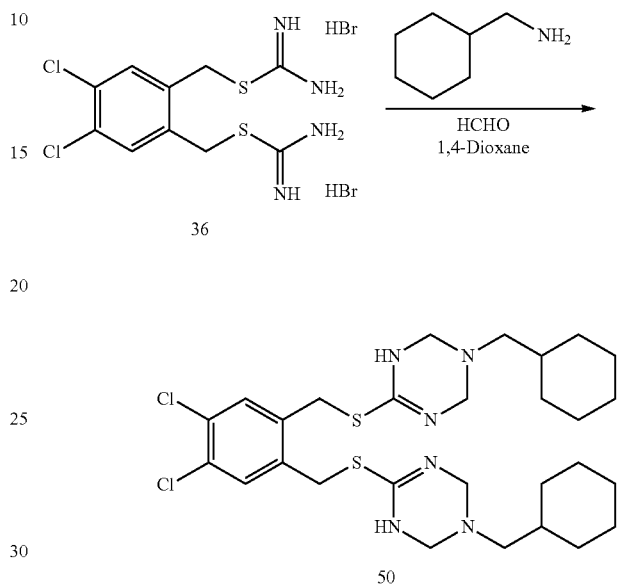

Reaction was performed by the same operation as in the synthesis of compound 9 from cyclohexylmethanamine (130 mL, 1.00 mmol), formaldehyde (150 µL, 37% wt. solution in water, 2.00 mmol) and (4,5-dichloro-1,2-phenylene)bis(methylene) dicarbamimidothioate dihydrobromide (compound 36, 162 mg, 0.50 mmol), and the reaction residue was recrystallized from 2-propanol to obtain the title compound 50 (130 mg, 43.5% yield) as white crystals.

¹HNMR (400 MHz, DMSO-d6): δ=10.17 (2H, brs), 7.71 (2H, s), 4.52 (4H, brs), 4.31 (8H, brs), 2.04 (4H, d, J=6.8 Hz), 1.64-1.61 (10H, m), 1.36 (2H, brs), 1.21-1.16 (6H, m), 0.82-0.79 (4H, m).

LC-MS: 86% purity, RT 3.02 min, MS (m/z): 597 (M+H)⁺

Synthesis of Compound 51

2-(2-(Carbamimidoylthio)ethyl)benzyl carbamimidothioate dihydrobromide

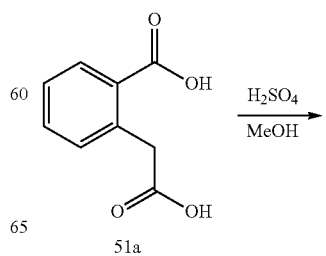

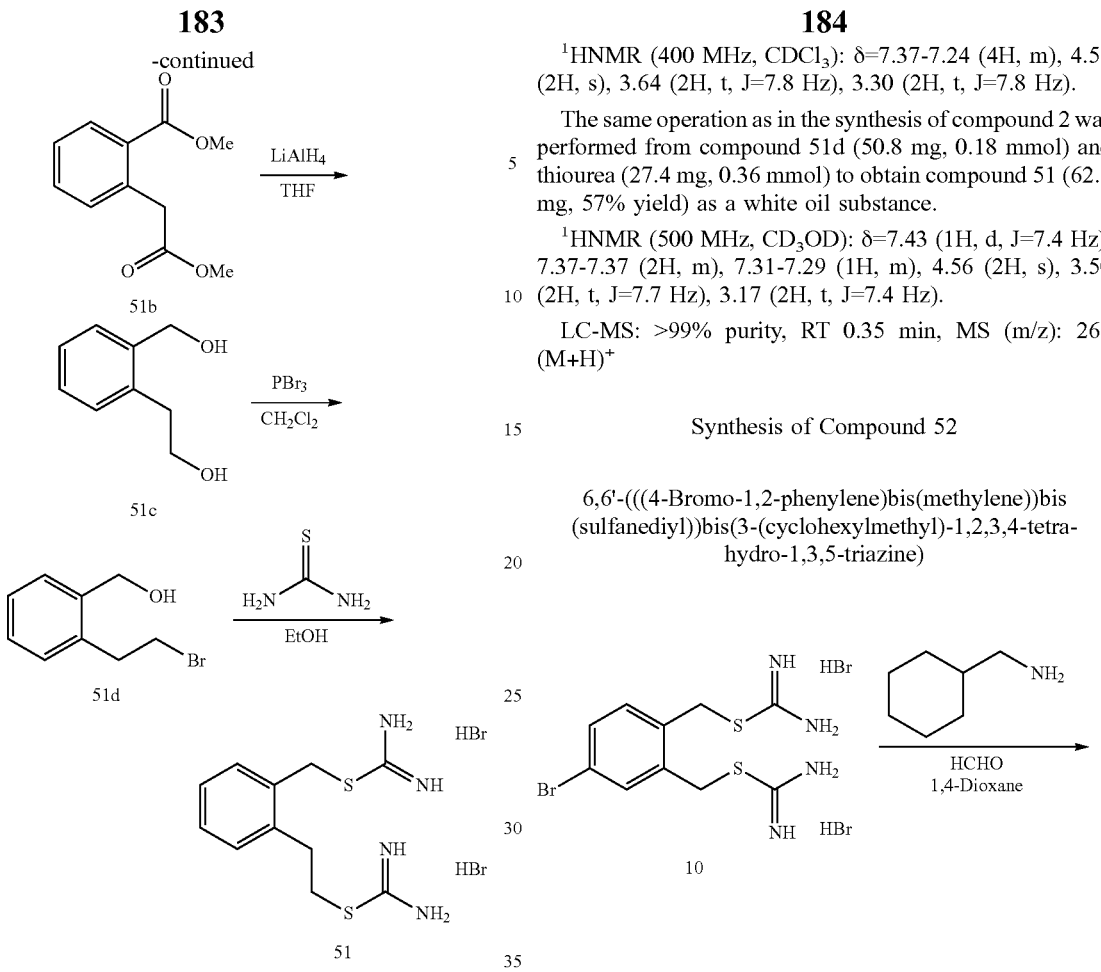

The same operation as in the synthesis of compound 34b was performed from a solution of 2-(carboxymethyl)benzoic acid (compound 51a, 9.008 g, 50 mmol) in MeOH (180 ml) and concentrated sulfuric acid (5.0 ml), and the residue was purified by silica gel chromatography with EtOAc/n-hexane (1:1) to obtain compound 51b (10.56 g, 100% yield) as a colorless oil substance.

$^1$HNMR (400 MHz, CDCl$_3$): δ=8.02 (1H, dd, J=7.8, 1.5 Hz), 7.49 (1H, td, J=7.6, 1.5 Hz), 7.37 (1H, td, J=7.6, 1.5 Hz), 7.26 (1H, d, J=7.3 Hz), 4.01 (2H, s), 3.87 (3H, s), 3.70 (3H, s).

LC-MS: >99% purity, RT 2.59 min, MS (m/z): 231 (M+Na)$^+$

The same operation as in the synthesis of compound 2b was performed from compound 51b (2.08 mg, 10.0 mmol) and LiAlH$_4$ (759 mg, 20.0 mmol), and the residue was purified by silica gel chromatography with EtOAc/n-hexane (35:65 to 3:2) to obtain compound 51c (971 mg, 63.8% yield) as a colorless oil substance.

$^1$HNMR (400 MHz, CDCl$_3$): δ=7.33-7.30 (2H, m), 7.24-7.22 (2H, m), 4.65 (2H, s), 3.89 (2H, t, J=5.9 Hz), 2.96 (2H, t, J=6.1 Hz).

LC-MS: >99% purity, RT 0.88 min, MS (m/z): 135 (M-OH)$^+$

The same operation as in the synthesis of compound 2c was performed from compound 51c (307 mg, 2.02 mmol) and phosphorous tribromide (0.230 mL, 2.42 mmol), and the residue was purified by silica gel chromatography with n-hexane/EtOAc (3:1) to obtain compound 51d (51.3 mg, 9.1% yield) as a yellow oil substance.

$^1$HNMR (400 MHz, CDCl$_3$): δ=7.37-7.24 (4H, m), 4.56 (2H, s), 3.64 (2H, t, J=7.8 Hz), 3.30 (2H, t, J=7.8 Hz).

The same operation as in the synthesis of compound 2 was performed from compound 51d (50.8 mg, 0.18 mmol) and thiourea (27.4 mg, 0.36 mmol) to obtain compound 51 (62.8 mg, 57% yield) as a white oil substance.

$^1$HNMR (500 MHz, CD$_3$OD): δ=7.43 (1H, d, J=7.4 Hz), 7.37-7.37 (2H, m), 7.31-7.29 (1H, m), 4.56 (2H, s), 3.50 (2H, t, J=7.7 Hz), 3.17 (2H, t, J=7.4 Hz).

LC-MS: >99% purity, RT 0.35 min, MS (m/z): 269 (M+H)$^+$

Synthesis of Compound 52

6,6'-(((4-Bromo-1,2-phenylene)bis(methylene))bis(sulfanediyl))bis(3-(cyclohexylmethyl)-1,2,3,4-tetrahydro-1,3,5-triazine)

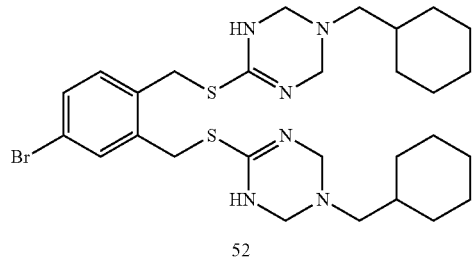

Reaction was performed by the same operation as in the synthesis of compound 9 from cyclohexylmethanamine (0.130 mL, 1.00 mmol), formaldehyde (150 μL, 37% wt. solution in water, 2.00 mmol) and (4-bromo-1,2-phenylene)bis(methylene) dicarbamimidothioate dihydrobromide (compound 10, 167 mg, 0.50 mmol), and the reaction residue was recrystallized from 2-propanol to obtain the title compound 52 (197 mg, 65% yield) as white crystals.

$^1$HNMR (400 MHz, DMSO-d6): δ=7.68-7.34 (3H, m), 4.59-4.57 (4H, m), 4.32 (8H, brs), 2.15-2.03 (4H, m), 1.66-1.64 (10H, m), 1.38 (2H, s), 1.22-1.12 (6H, m), 0.84-0.79 (4H, m).

LC-MS: 75% purity, RT 2.65 min, MS (m/z): 609 (M+H)$^+$

Synthesis of Compound 53

6,6'-(((4-Bromo-1,2-phenylene)bis(methylene))bis(sulfanediyl))bis(3-(2-chlorophenethyl)-1,2,3,4-tetrahydro-1,3,5-triazine)

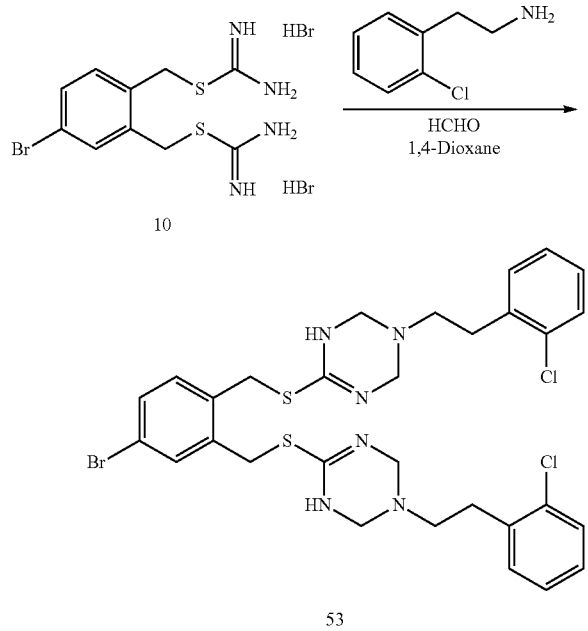

53

Reaction was performed by the same operation as in the synthesis of compound 9 from 2-(2-chlorophenyl)ethan-1-amine (0.138 mL, 1.00 mmol), formaldehyde (150 µL, 37% wt. solution in water, 2.00 mmol) and (4-bromo-1,2-phenylene)bis(methylene) dicarbamimidothioate dihydrobromide (compound 10, 167 mg, 0.50 mmol), and the reaction residue was recrystallized from 2-propanol to obtain the title compound 53 (410 mg, 100% yield) as yellow crystals.

$^1$HNMR (400 MHz, DMSO-d6): δ=7.43-7.29 (11H, m), 4.67 (4H, brs), 4.42 (8H, brs), 2.88-2.84 (8H, m).

LC-MS: RT 2.42 min, MS (m/z): δ93 (M+H)$^+$

Synthesis of Compound 54

6,6'-(((4-Bromo-1,2-phenylene)bis(methylene))bis(sulfanediyl))bis(3-(3,4-dichlorobenzyl)-1,2,3,4-tetrahydro-1,3,5-triazine)

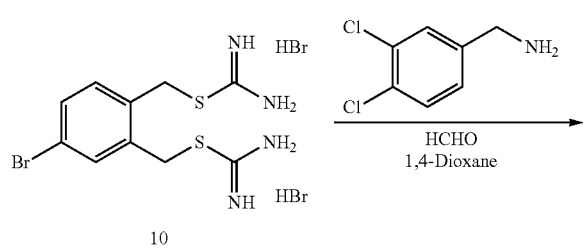

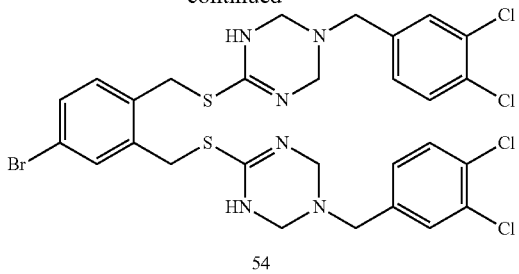

54

Reaction was performed by the same operation as in the synthesis of compound 9 from (3,4-dichlorophenyl)methanamine (0.132 mL, 1.00 mmol), formaldehyde (150 µL, 37% wt. solution in water, 2.00 mmol) and (4-bromo-1,2-phenylene)bis(methylene) dicarbamimidothioate dihydrobromide (compound 10, 167 mg, 0.50 mmol), and the reaction residue was purified by gel filtration chromatography (MeOH) to obtain the title compound 54 (15.0 mg, 4% yield) as white crystals.

$^1$HNMR (400 MHz, CD$_3$OD): δ=7.61-7.50 (9H, m), 4.77-4.74 (4H, m), 4.46 (8H, brs), 3.77 (4H, d, J=6.3 Hz).

LC-MS: >99% purity, RT 3.66 min, MS (m/z): 733 (M+H)$^+$

Synthesis of Compound 55

Methyl 2-((carbamimidoylthio)methyl)benzoate hydrochloride

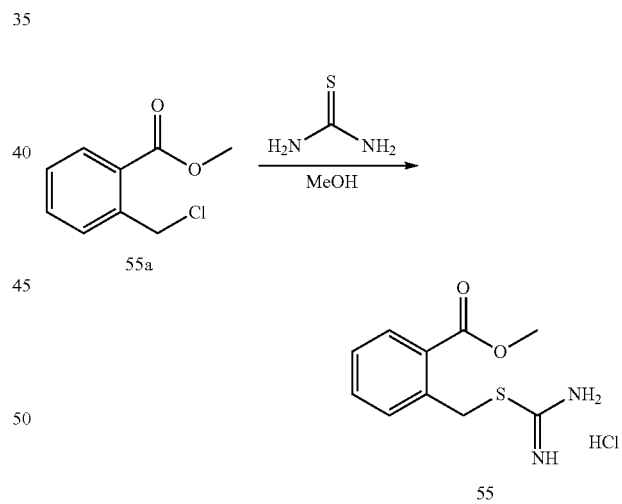

55

Thiourea (76.1 mg, 1.00 mmol) was added to a solution of methyl 2-(chloromethyl)benzoate (compound 55a, 185 mg, 1.00 mmol) in MeOH (3 mL) at room temperature, and the reaction mixture was refluxed for 12 hours. Then, the reaction solution was brought back to room temperature, concentrated under reduced pressure, and then recrystallized from ethyl acetate to obtain the title compound 55 (246 mg, 94% yield) as white crystals.

$^1$HNMR (400 MHz, CD$_3$OD): δ=8.04 (1H, dd, J=7.8, 1.5 Hz), 7.60 (1H, td, J=7.6, 1.5 Hz), 7.52 (1H, dd, J=6.1, 4.6 Hz), 7.49 (1H, td, J=7.6, 1.3 Hz), 4.77 (2H, s), 3.93 (3H, s).

LC-MS: >99% purity, RT 0.59 min, MS (m/z): 225 (M+H)$^+$

Synthesis of Compound 56

6,6'-(((4,5-Dichloro-1,2-phenylene)bis(methylene))bis(sulfanediyl))bis(3-(3,4-dichlorobenzyl)-1,2,3,4-tetrahydro-1,3,5-triazine)

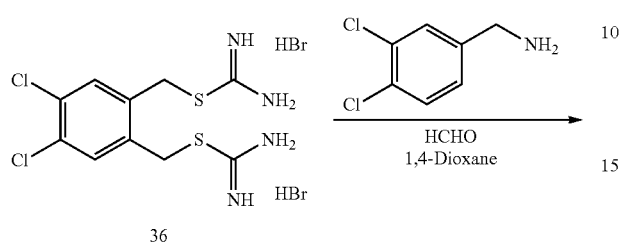

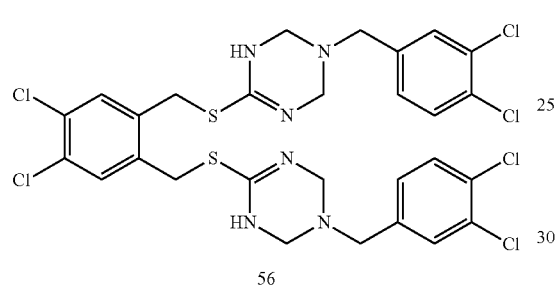

Reaction was performed by the same operation as in the synthesis of compound 9 from (3,4-dichlorophenyl)methanamine (0.132 mg, 1.00 mmol), formaldehyde (150 μL, 37% wt. solution in water, 2.00 mmol) and (4,5-dichloro-1,2-phenylene)bis(methylene) dicarbamimidothioate dihydrobromide (compound 36, 162 mg, 0.50 mmol), and the reaction residue was recrystallized from 2-propanol to obtain the title compound 56 (21.4 mg, 6% yield) as white crystals.

$^1$HNMR (400 MHz, CD$_3$OD): δ=7.78 (2H, s), 7.51 (4H, d, J=8.4 Hz), 7.29 (2H, d, J=8.4 Hz), 4.64 (4H, brs), 4.43 (8H, brs), 3.76 (4H, brs).

LC-MS: 95% purity, RT 3.02 min, MS (m/z): 723 (M+H)$^+$

Synthesis of Compound 57

(4-Bromo-1,2-phenylene)bis(methylene) (E,E)-bis(N,N'-dicyclohexylcarbamimidothioate) dihydrobromide

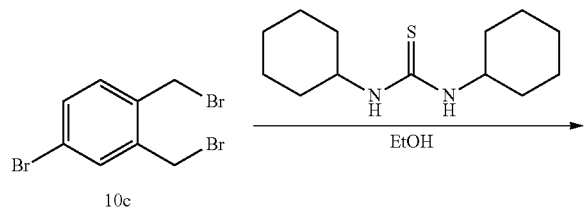

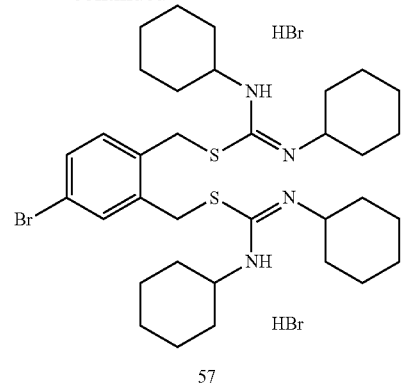

The same operation as in the synthesis of compound 10 was performed from 4-bromo-1,2-bis(bromomethyl)benzene (compound 10c, 343 mg, 1.00 mmol) and 1,3-dicyclohexylthiourea (481 mg, 2.00 mmol) to obtain compound 57 (615 mg, 83% yield) as white crystals.

$^1$HNMR (400 MHz, DMSO-d6) δ: =7.44-7.36 (3H, m), 4.72-4.70 (4H, m), 3.73-3.67 (4H, m), 1.90-1.76 (22H, m), 1.37-1.24 (22H, m).

LC-MS: RT 3.82 min, MS (m/z): δ63 (M+H)$^+$

Synthesis of Compound 58

1,2-Phenylenebis(methylene) (E,E)-bis(N,N'-dicyclohexylcarbamimidothioate) dihydrobromide

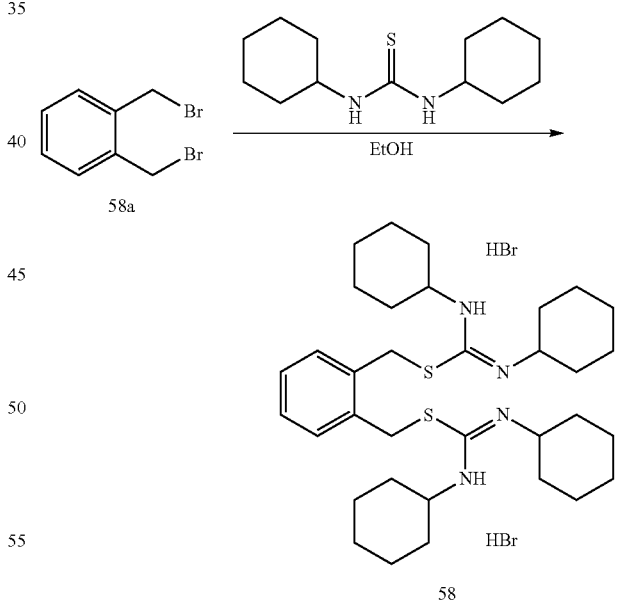

The same operation as in the synthesis of compound 10 was performed from 1,2-bis(bromomethyl)benzene (compound 58a, 263 mg, 1.00 mmol) and 1,3-dicyclohexylthiourea (481 mg, 2.00 mmol) to obtain compound 58 (701 mg, 94% yield) as white crystals.

$^1$HNMR (400 MHz, CD$_3$OD): δ=7.48-7.40 (4H, m), 4.70 (4H, brs), 3.73 (4H, brs), 1.95-1.69 (22H, m), 1.42-1.17 (22H, m).

LC-MS: >99% purity, RT 2.69 min, MS (m/z): 583 (M+H)+

Synthesis of Compound 59

(E)-S-(2-(((N'-(3-Chloro-4-fluorophenyl)carbamimidoyl)thio)methyl)benzyl) carbamothioate hydrobromide

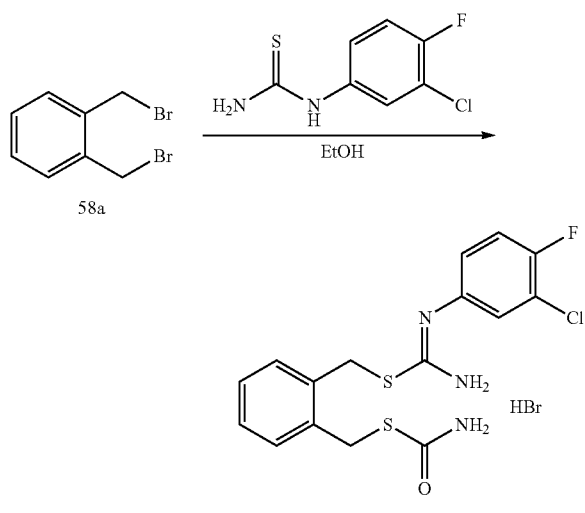

1-(3-Chloro-4-fluorophenyl)thiourea (205 mg, 1.00 mmol) was added to a solution of 1,2-bis(bromomethyl)benzene (compound 58a, 132 mg, 0.50 mmol) in EtOH (8 mL) at room temperature, and the reaction mixture was refluxed for 12 hours. The reaction solution was brought back to room temperature and concentrated under reduced pressure. Then, the residue was recrystallized from 2-propanol to obtain the title compound 59 (32.5 mg, 14% yield) as white crystals. $^1$HNMR (500 MHz, DMSO-d6): δ=7.66-7.28 (7H, m), 4.68 (2H, s), 4.19 (2H, s).

LC-MS: >99% purity, RT 2.45 min, MS (m/z): 384 (M+H)+

Synthesis of Compound 60

6,6'-(((4-Bromo-1,2-phenylene)bis(methylene))bis(sulfanediyl))bis(3-(2-cyclohexylethyl)-1,2,3,4-tetrahydro-1,3,5-triazine)

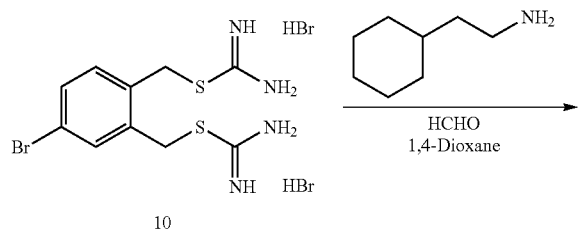

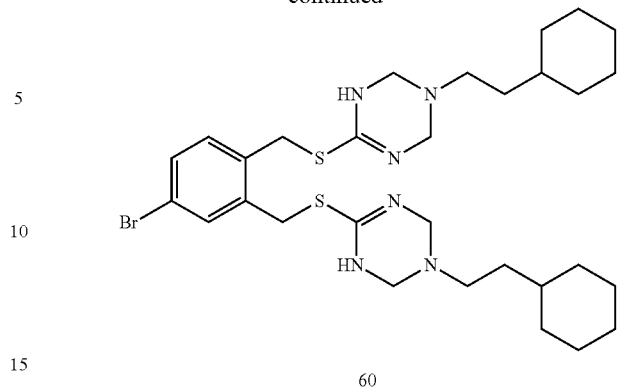

Reaction was performed by the same operation as in the synthesis of compound 9 from 2-cyclohexylethan-1-amine (0.146 mg, 1.00 mmol), formaldehyde (150 μL, 37% wt. solution in water, 2.00 mmol) and (4-bromo-1,2-phenylene)bis(methylene) dicarbamimidothioate dihydrobromide (compound 10, 167 mg, 0.50 mmol), and the reaction residue was purified by gel filtration chromatography (CDCl$_3$) to obtain the title compound 60 (14.7 mg, 5% yield) as white crystals.

$^1$H-NMR (CDCl$_3$) δ: =7.63 (1H, s), 7.33 (2H, brs), 4.73 (4H, d, J=4.4 Hz), 4.40 (8H, s), 2.47 (4H, q, J=6.3 Hz), 1.71-1.64 (10H, m), 1.40-1.12 (12H, m), 0.93-0.85 (4H, m).

LC-MS: 95% purity, RT 2.19 min, MS (m/z): δ37 (M+H)+

Synthesis of Compound 61

6,6'-(((4,5-Dichloro-1,2-phenylene)bis(methylene))bis(sulfanediyl))bis(3-(2-cyclohexylethyl)-1,2,3,4-tetrahydro-1,3,5-triazine)

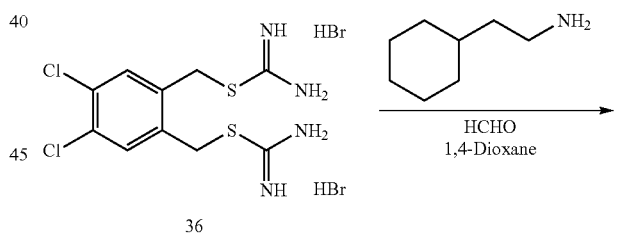

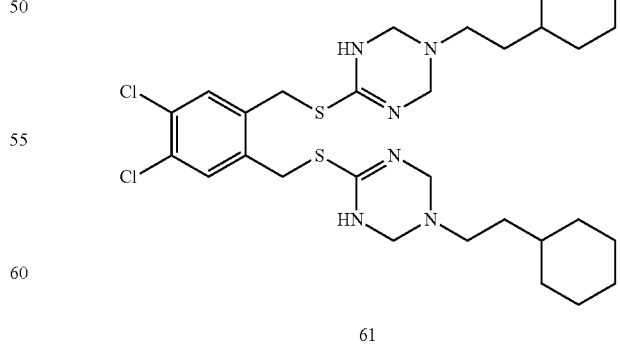

Reaction was performed by the same operation as in the synthesis of compound 9 from 2-cyclohexylethan-1-amine (0.146 mg, 1.00 mmol), formaldehyde (150 μL, 37% wt.

solution in water, 2.00 mmol) and (4,5-dichloro-1,2-phenylene)bis(methylene) dicarbamimidothioate dihydrobromide (compound 36, 162 mg, 0.50 mmol), and the reaction residue was recrystallized from 2-propanol to obtain the title compound 61 (171 mg, 55% yield) as white crystals.

¹HNMR (400 MHz, CD₃OD): δ=7.69 (2H, s), 4.59 (4H, s), 4.43 (8H, s), 2.50 (4H, t, J=7.6 Hz), 1.70-1.68 (10H, m), 1.39-1.24 (12H, m), 0.94-0.91 (4H, m).

LC-MS: 72% purity, RT 3.00 min, MS (m/z): δ27 (M+H)⁺

Synthesis of Compound 62

2-(2-(Methylamino)-2-oxoethyl)benzyl carbamimidothioate hydrobromide

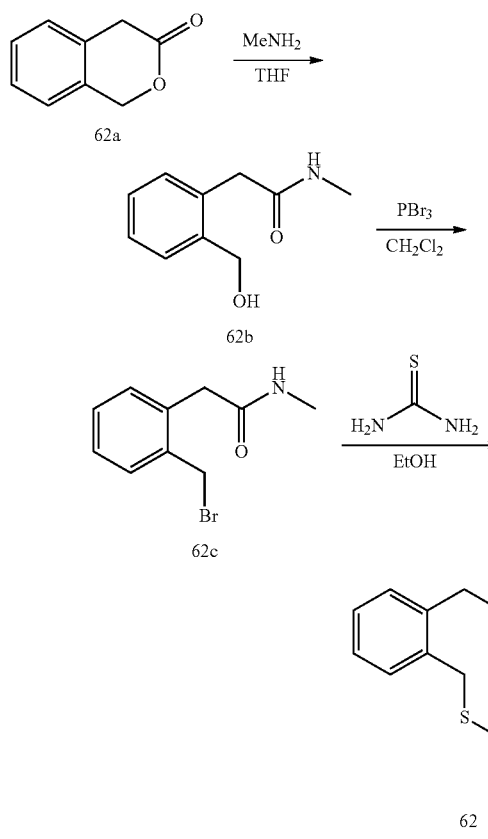

40% MeNH₂ (1553 mg, 50.0 mmol) was added to a solution of isochroman-3-one (compound 62a, 741 mg, 5.00 mmol) in THF (15 ml), and the mixture was stirred at room temperature for 8 hours. The reaction solution was concentrated under reduced pressure, and then, water was added to the residue, followed by extraction with dichloromethane. The organic layer was washed with brine, dried over magnesium sulfate, and then concentrated under reduced pressure to obtain compound 62b (832 mg, 93% yield) as pale yellow crystals.

¹HNMR (400 MHz, CDCl₃): =δ 7.41-7.38 (1H, m), 7.31-7.28 (2H, m), 7.25-7.24 (1H, m), 5.97 (1H, brs), 4.68 (2H, d, J=5.9 Hz), 3.77 (1H, t, J=5.6 Hz), 3.63 (2H, s), 2.77 (3H, d, J=4.9 Hz). LC-MS: >99% purity, RT 0.68 min, MS (m/z): 162 (M-OH)⁺

The same operation as in the synthesis of compound 2c was performed from compound 62b (358 mg, 2.00 mmol) and phosphorous tribromide (0.228 mL, 2.40 mmol) to obtain compound 62c (428 mg, 88% yield) as an orange oil substance.

¹HNMR (400 MHz, CDCl₃): δ=7.49-7.31 (4H, m), 4.55-4.52 (2H, m), 3.72 (2H, s), 2.78 (3H, d, J=4.9 Hz).

LC-MS: >99% purity, RT 2.09 min, MS (m/z): 243 (M+H)⁺

The same operation as in the synthesis of compound 2 was performed from compound 62c (428 mg, 1.77 mmol) and thiourea (135 mg, 1.77 mmol) to obtain the title compound 62 (434 mg, 77% yield) as white crystals.

¹HNMR (400 MHz, CD₃OD): δ=7.50-7.49 (1H, m), 7.32-7.26 (3H, m), 4.57 (2H, s), 3.68 (2H, s), 2.73 (3H, s).

LC-MS: >99% purity, RT 0.47 min, MS (m/z): 238 (M+H)⁺

Synthesis of Compound 63

(4,5-Dichloro-1,2-phenylene)bis(methylene) (E,E)-bis(N'-(2,4-difluorophenyl)carbamimidothioate) dihydrobromide

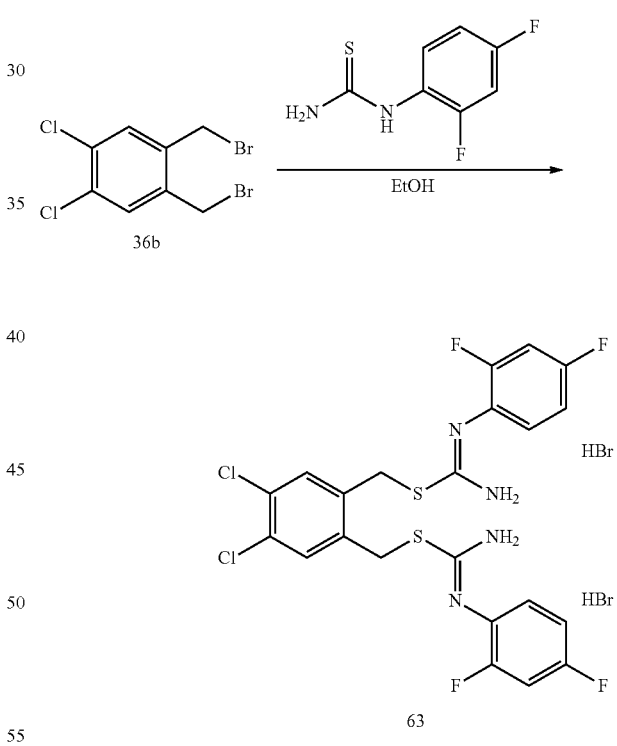

The same operation as in the synthesis of compound 2 was performed from compound 36b (166 mg, 0.50 mmol) and 1-(2,4-difluorophenyl)thiourea (188 mg, 1.00 mmol), and the reaction residue was purified by silica gel chromatography with n-hexane/EtOAc (3:1 to 45:55) to obtain the title compound 63 (3.0 mg, 1% yield) as white crystals.

¹HNMR (400 MHz, CDCl₃): δ=6.91-6.88 (8H, m), 4.55 (4H, s), 4.44 (4H, s).

LC-MS: >99% purity, RT 4.11 min, MS (m/z): 548 (M+H)⁺

Synthesis of Compound 64

2-(2-Oxo-2-(phenethylamino)ethyl)benzyl carbamimidothioate hydrobromide

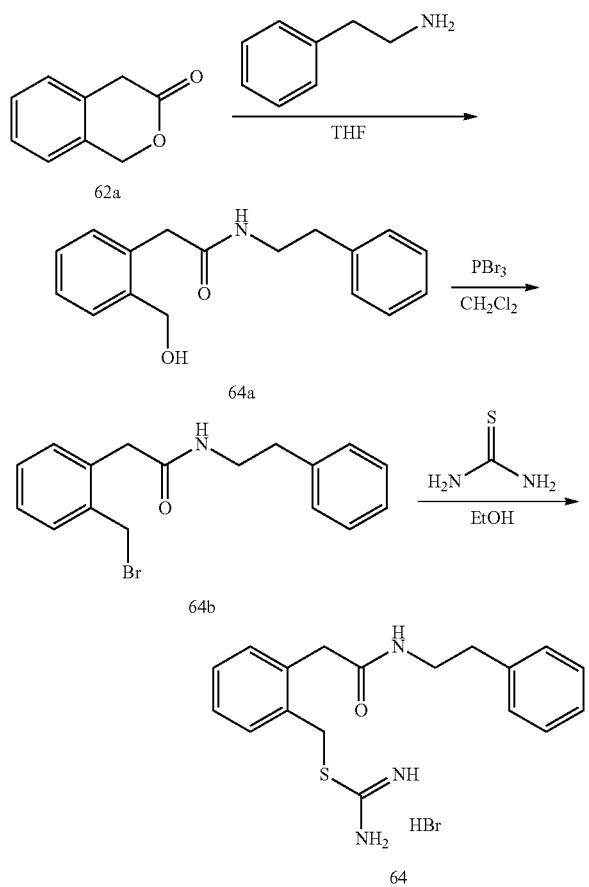

The same operation as in the synthesis of compound 62b was performed from isochroman-3-one (compound 62a, 445 mg, 3.00 mmol) and 2-phenylethan-1-amine (3.780 mL, 30.0 mmol), and the reaction residue was purified by silica gel chromatography with n-hexane/EtOAc (3:2 to 3:7) to obtain compound 64a (734 mg, 91% yield) as pale yellow crystals.

$^1$HNMR (400 MHz, CDCl$_3$): δ=7.37-7.21 (7H, m), 7.03-7.01 (2H, m), 6.05 (1H, brs), 4.60 (2H, d, J=4.9 Hz), 3.56 (2H, s), 3.47 (2H, q, J=6.5 Hz), 3.32 (1H, t, J=5.4 Hz), 2.73 (2H, t, J=6.6 Hz).

LC-MS: >99% purity, RT 2.65 min, MS (m/z): 270 (M+H)$^+$

The same operation as in the synthesis of compound 2c was performed from compound 64a (734 mg, 2.72 mmol) and phosphorous tribromide (0.310 mL, 3.27 mmol) to obtain compound 64b (565 mg, 63% yield) as a pale yellow oil substance.

$^1$HNMR (400 MHz, CDCl$_3$): δ=7.48-7.12 (7H, m), 7.05-7.03 (2H, m), 4.45-4.41 (2H, m), 3.67 (2H, s), 3.51-3.46 (2H, m), 2.76-2.73 (2H, m).

LC-MS: >99% purity, RT 3.44 min, MS (m/z): 333 (M+H)$^+$

The same operation as in the synthesis of compound 2 was performed from compound 64b (523 mg, 1.57 mmol) and thiourea (120 mg, 1.57 mmol), and the residue was recrystallized from EtOH to obtain the title compound 64 (92.8 mg, 14% yield) as white crystals.

$^1$HNMR (400 MHz, DMSO-d6): δ=8.98 (3H, brs), 8.30 (1H, brs), 7.43-7.17 (9H, m), 4.52 (2H, s), 3.56 (2H, s), 3.28 (2H, t, J=6.6 Hz), 2.72 (2H, t, J=7.3 Hz). LC-MS: >99% purity, RT 1.72 min, MS (m/z): 328 (M+H)$^+$

Synthesis of Compound 65

2-(2-((Cyclohexylmethyl)amino)-2-oxoethyl)benzyl carbamimidothioate hydrobromide

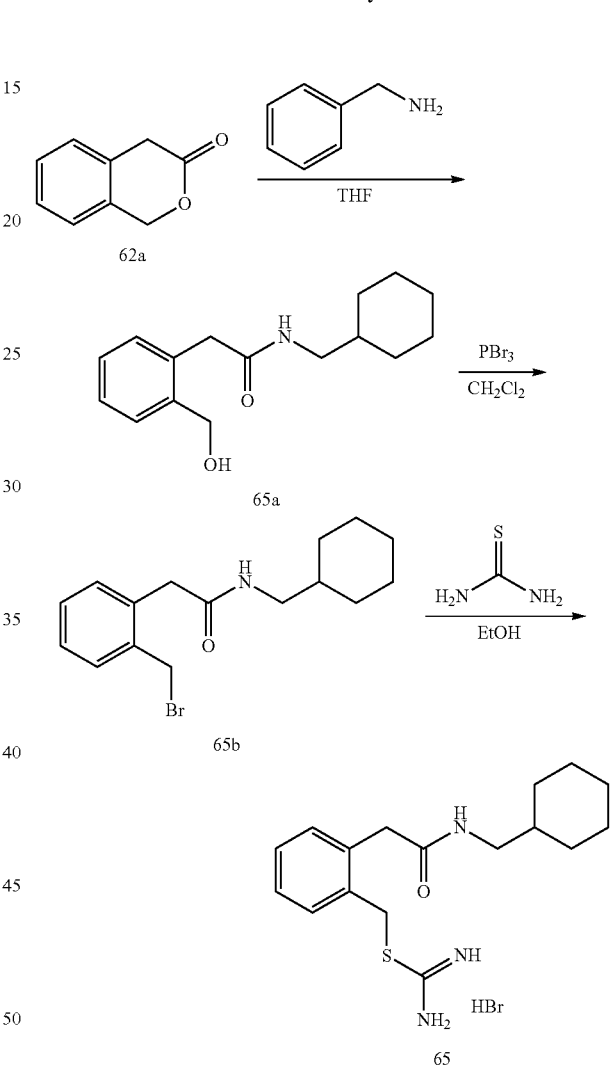

The same operation as in the synthesis of compound 62b was performed from isochroman-3-one (compound 62a, 445 mg, 3.00 mmol) and cyclohexylmethanamine (1.952 mL, 15.0 mmol), and the reaction residue was purified by silica gel chromatography with n-hexane/EtOAc (55:45 to 3:7) to obtain compound 65a (542 mg, 69% yield) as white crystals.

$^1$HNMR (400 MHz, CDCl$_3$): δ=7.41 (1H, brs), 7.31-7.23 (3H, m), 5.92 (1H, brs), 4.68 (2H, d, J=5.9 Hz), 3.81 (1H, brs), 3.63 (2H, s), 3.05 (2H, t, J=6.3 Hz), 1.70-1.61 (5H, m), 1.41 (1H, brs), 1.23-1.10 (3H, m), 0.90-0.81 (2H, m).

LC-MS: >99% purity, RT 2.96 min, MS (m/z): 262 (M+H)$^+$

The same operation as in the synthesis of compound 2c was performed from compound 65a (534 mg, 2.04 mmol)

and phosphorous tribromide (0.233 mL, 2.45 mmol) to obtain compound 65b (367 mg, 55% yield) as yellow crystals.

$^1$HNMR (400 MHz, CDCl$_3$): δ=7.40-7.26 (4H, m), 5.48 (1H, brs), 4.66-4.56 (2H, m), 3.72 (2H, s), 3.07-3.03 (2H, m), 1.69-1.58 (5H, m), 1.39 (1H, brs), 1.19-1.11 (3H, m), 0.87-0.82 (2H, m).

LC-MS: >99% purity, RT 3.66 min, MS (m/z): 326 (M+H)$^+$

The same operation as in the synthesis of compound 2 was performed from compound 65b (367 mg, 1.13 mmol) and thiourea (86.0 mg, 1.13 mmol) to obtain the title compound 65 (224 mg, 49% yield) as white crystals.

$^1$HNMR (400 MHz, DMSO-d6): δ=9.09 (4H, brs), 8.25 (1H, brs), 7.42 (1H, d, J=5.9 Hz), 7.28 (3H, s), 4.56 (2H, s), 3.59 (2H, s), 2.90 (2H, t, J=6.1 Hz), 1.66 (5H, d, J=11.2 Hz), 1.38 (1H, s), 1.16-1.11 (3H, m), 0.88-0.82 (2H, m).

LC-MS: >99% purity, RT 1.87 min, MS (m/z): 320 (M+H)$^+$

Synthesis of Compound 66

2-(2-((2-chlorophenethyl)amino)-2-oxoethyl)benzyl carbamimidothioate hydrobromide by silica gel chromatography with n-hexane/EtOAc (65:35 to 3:7) to obtain compound 66a (615 mg, 67% yield) as white crystals.

$^1$HNMR (400 MHz, CDCl$_3$): δ=7.40-7.29 (4H, m), 7.23-7.09 (3H, m), 6.99 (1H, dd, J=7.6, 1.7 Hz), 6.03 (1H, brs), 4.63 (2H, d, J=6.3 Hz), 3.59 (2H, s), 3.53-3.48 (3H, m), 2.90 (2H, t, J=6.8 Hz). LC-MS: >99% purity, RT 2.83 min, MS (m/z): 304 (M+H)$^+$ The same operation as in the synthesis of compound 2c was performed from compound 66a (613 mg, 2.02 mmol) and phosphorous tribromide (0.230 mL, 2.42 mmol) to obtain compound 66b (470 mg, 63% yield) as a white oil substance.

$^1$HNMR (400 MHz, CDCl$_3$): δ=7.48-6.97 (8H, m), 5.50 (1H, brs), 4.48 (2H, s), 3.68 (2H, s), 3.54-3.49 (2H, m), 2.92-2.89 (2H, m).

LC-MS: >99% purity, RT 3.64 min, MS (m/z): 367 (M+H)$^+$

The same operation as in the synthesis of compound 2 was performed from compound 66b (470 mg, 1.28 mmol) and thiourea (97.6 mg, 1.28 mmol), and the residue was recrystallized from EtOH to obtain the title compound 66 (170 mg, 30% yield) as white crystals.

$^1$HNMR (400 MHz, DMSO-d6): δ=9.02 (3H, brs), 8.38 (1H, t, J=5.6 Hz), 7.44-7.41 (2H, m), 7.31-7.26 (6H, m), 4.52 (2H, s), 3.56 (2H, s), 3.32-3.29 (2H, m), 2.85 (2H, t, J=7.3 Hz).

LC-MS: >99% purity, RT 1.95 min, MS (m/z): 362 (M+H)$^+$

Synthesis of Compound 67

2-(2-((4-Cyanobenzyl)amino)-2-oxoethyl)benzyl carbamimidothioate hydrobromide

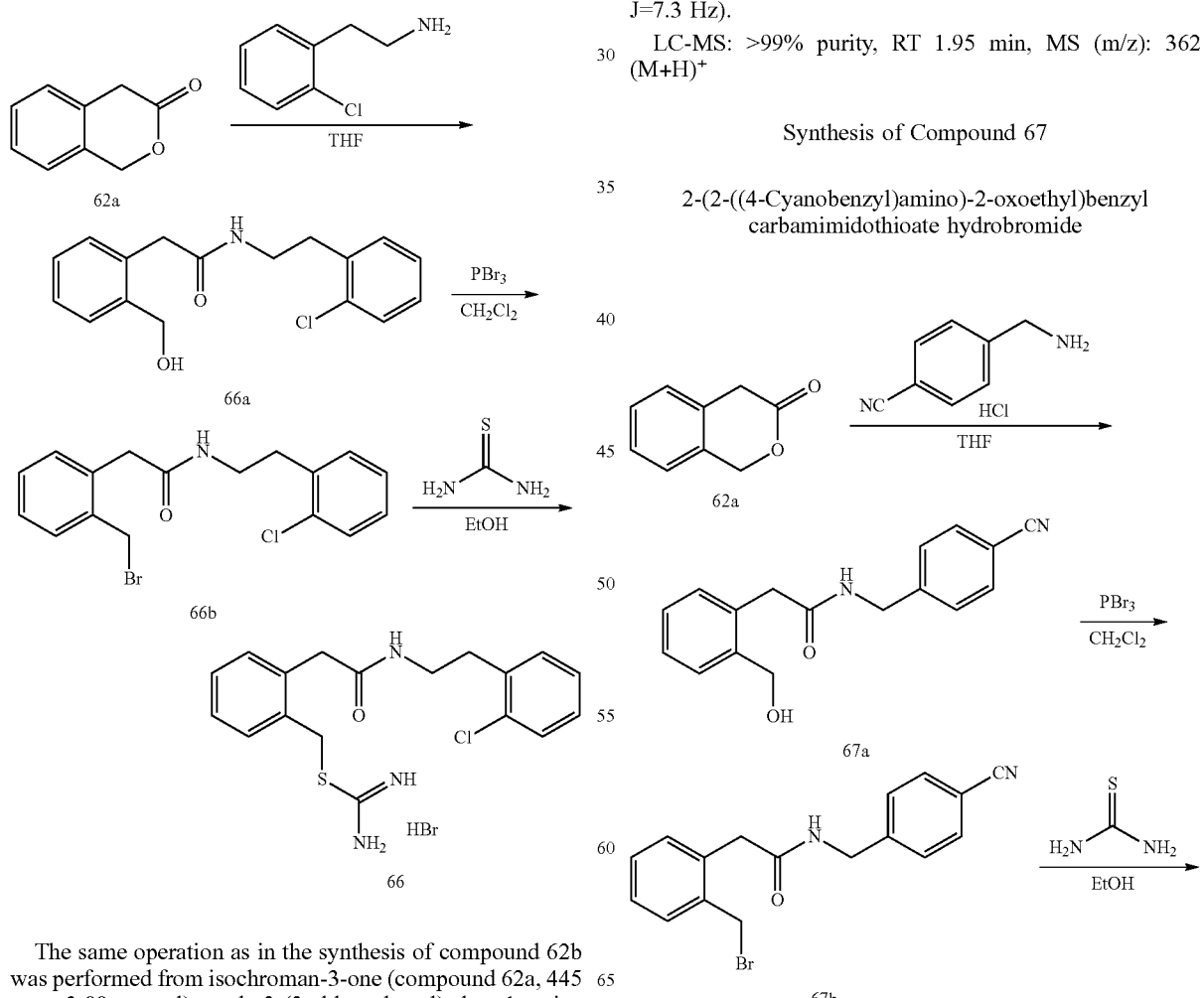

The same operation as in the synthesis of compound 62b was performed from isochroman-3-one (compound 62a, 445 mg, 3.00 mmol) and 2-(2-chlorophenyl)ethan-1-amine (0.826 mL, 6.0 mmol), and the reaction residue was purified

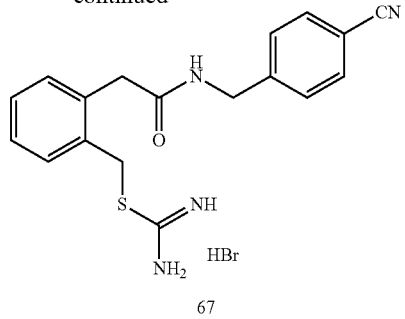

4-(Aminomethyl)benzonitrile hydrochloride (405 mg, 2.40 mmol) and triethylamine (418 μL, 3.00 mmol) were added to a solution of isochroman-3-one (compound 62a, 296 mg, 2.00 mmol) in THF (8 ml), and the mixture was stirred at 50° C. for 24 hours. The reaction solution was concentrated under reduced pressure, and then, water was added to the residue, followed by extraction with dichloromethane. The organic layer was washed with brine, dried over magnesium sulfate, and then concentrated under reduced pressure. The reaction residue was purified by silica gel chromatography with n-hexane/EtOAc (3:2 to 0:1) to obtain compound 67a (438 mg, 78% yield) as white crystals.

$^1$HNMR (400 MHz, CDCl$_3$): δ=7.56 (2H, d, J=8.3 Hz), 7.39-7.23 (6H, m), 6.61 (1H, brs), 4.72 (2H, d, J=5.4 Hz), 4.44 (2H, d, J=5.9 Hz), 3.73 (2H, s), 3.07 (1H, t, J=5.4 Hz).

LC-MS: >99% purity, RT 2.03 min, MS (m/z): 281 (M+H)$^+$

The same operation as in the synthesis of compound 2c was performed from compound 67a (438 mg, 1.56 mmol) and phosphorous tribromide (0.178 mL, 1.88 mmol) to obtain compound 67b (189 mg, 35% yield) as pale yellow crystals.

$^1$HNMR (400 MHz, CDCl$_3$): δ=7.59 (2H, d, J=8.3 Hz), 7.41 (1H, d, J=6.8 Hz), 7.31-7.29 (5H, m), 5.90 (1H, brs), 4.56 (2H, d, J=1.5 Hz), 4.47 (2H, d, J=6.3 Hz), 3.79 (2H, s).

LC-MS: >99% purity, RT 3.06 min, MS (m/z): 344 (M+H)$^+$

The same operation as in the synthesis of compound 2 was performed from compound 67b (189 mg, 0.55 mmol) and thiourea (41.9 mg, 0.55 mmol) to obtain the title compound 67 (88 mg, 38% yield) as white crystals.

$^1$HNMR (500 MHz, DMSO-d6): δ=9.03 (3H, brs), 8.81 (1H, s), 7.80 (2H, d, J=8.5 Hz), 7.44-7.28 (6H, m), 4.55 (2H, s), 4.37 (2H, d, J=5.7 Hz), 3.69 (2H, s).

LC-MS: >99% purity, RT 0.74 min, MS (m/z): 339 (M+H)$^+$

Synthesis of Compound 68

2-(2-((4-Chlorophenethyl)amino)-2-oxoethyl)benzyl carbamimidothioate hydrobromide

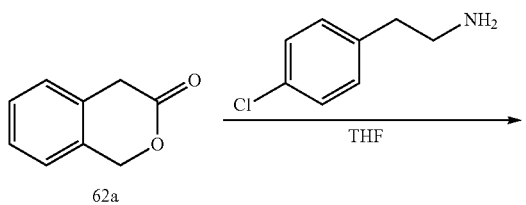

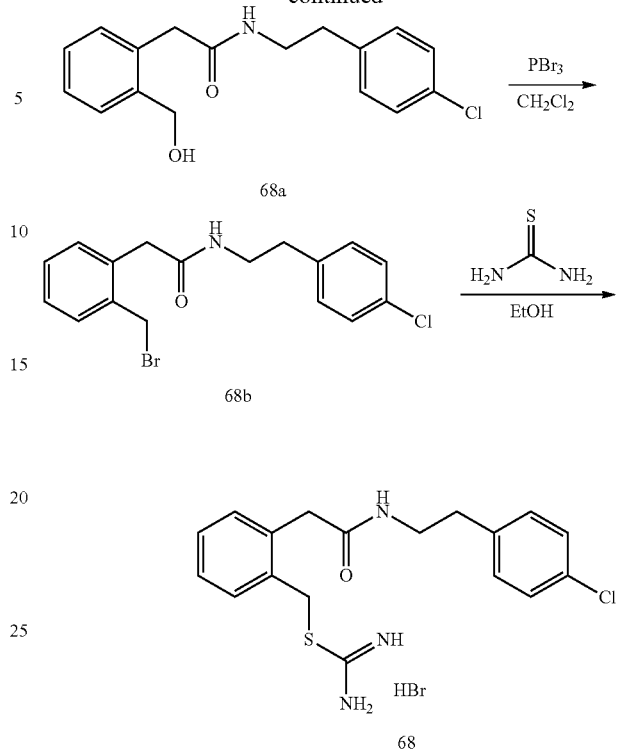

The same operation as in the synthesis of compound 62b was performed from isochroman-3-one (compound 62a, 445 mg, 3.00 mmol) and 2-(4-chlorophenyl)ethan-1-amine (0.504 mL, 3.60 mmol), and the reaction residue was purified by silica gel chromatography with n-hexane/EtOAc (2:3 to 1:9) to obtain compound 68a (751 mg, 82% yield) as white crystals.

$^1$HNMR (400 MHz, CDCl$_3$): δ=7.39-7.19 (6H, m), 6.95 (2H, d, J=7.8 Hz), 5.98 (1H, brs), 4.63 (2H, d, J=5.9 Hz), 3.58 (2H, s), 3.44 (2H, q, J=6.3 Hz), 3.26 (1H, t, J=5.9 Hz), 2.71 (2H, t, J=6.8 Hz).

LC-MS: >99% purity, RT 2.92 min, MS (m/z): 304 (M+H)$^+$

The same operation as in the synthesis of compound 2 was performed from compound 68a (751 mg, 2.47 mmol) and phosphorous tribromide (0.282 mL, 2.97 mmol) to obtain compound 68b (445 mg, 49% yield) as a white oil substance.

$^1$HNMR (400 MHz, CDCl$_3$): δ=7.48-7.09 (6H, m), 6.97 (2H, d, J=8.8 Hz), 5.40 (2H, brs), 4.47 (2H, s), 3.66 (2H, s), 3.46 (2H, q, J=6.5 Hz), 2.72 (2H, t, J=6.8 Hz).

LC-MS: >99% purity, RT 3.68 min, MS (m/z): 367 (M+H)$^+$

The same operation as in the synthesis of compound 2 was performed from compound 68b (445 mg, 1.21 mmol) and thiourea (92.3 mg, 1.21 mmol) to obtain the title compound 68 (279 mg, 52% yield) as white crystals.

$^1$HNMR (500 MHz, CD$_3$OD): δ=7.49 (1H, t, J=4.5 Hz), 7.30 (2H, t, J=4.0 Hz), 7.23-7.20 (3H, m), 7.13 (2H, d, J=8.5 Hz), 4.53 (2H, s), 3.63 (2H, s), 3.43 (2H, t, J=6.8 Hz), 2.78 (2H, t, J=7.1 Hz).

LC-MS: >99% purity, RT 2.11 min, MS (m/z): 362 (M+H)$^+$

Synthesis of Compound 69

2-(2-((2-Cyclohexylethyl)amino)-2-oxoethyl)benzyl carbamimidothioate hydrobromide

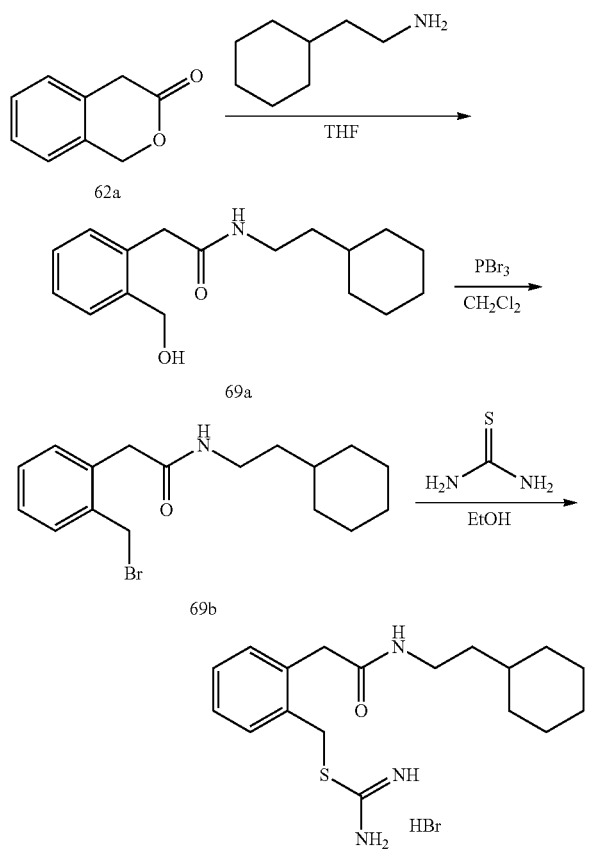

The same operation as in the synthesis of compound 62b was performed from isochroman-3-one (compound 62a, 296 mg, 2.00 mmol) and 2-cyclohexylethan-1-amine (0.322 mL, 2.20 mmol), and the reaction residue was purified by silica gel chromatography with n-hexane/EtOAc (3:2 to 35:65) to obtain compound 69a (520 mg, 94% yield) as white crystals.

$^1$HNMR (400 MHz, CDCl$_3$): =δ 7.41-7.39 (1H, m), 7.29 (2H, dd, J=5.6, 3.7 Hz), 7.23 (1H, dd, J=5.1, 3.7 Hz), 5.85 (1H, brs), 4.68 (2H, d, J=5.9 Hz), 3.87 (1H, t, J=5.9 Hz), 3.62 (2H, s), 3.25-3.20 (2H, m), 1.66-1.64 (5H, m), 1.34 (2H, q, J=7.3 Hz), 1.21-1.09 (4H, m), 0.89-0.83 (2H, m).

LC-MS: >99% purity, RT 3.26 min, MS (m/z): 276 (M+H)$^+$

The same operation as in the synthesis of compound 2c was performed from compound 69a (520 mg, 1.89 mmol) and phosphorous tribromide (0.215 mL, 2.57 mmol) to obtain compound 69b (320 mg, 50% yield) as white crystals.

$^1$HNMR (400 MHz, CDCl$_3$): δ=7.41-7.24 (4H, m), 5.36 (1H, brs), 4.65-4.56 (2H, m), 3.70 (2H, s), 3.26-3.20 (2H, m), 1.69-1.50 (5H, m), 1.32-1.29 (2H, m), 1.21-1.09 (4H, m), 0.89-0.81 (2H, m).

LC-MS: >99% purity, RT 4.05 min, MS (m/z): 340 (M+H)$^+$

The same operation as in the synthesis of compound 2 was performed from compound 69b (320 mg, 0.94 mmol) and thiourea (71.9 mg, 0.94 mmol) to obtain the title compound 69 (110 mg, 28% yield) as white crystals.

$^1$HNMR (500 MHz, DMSO-d6): δ=8.97 (3H, brs), 8.13 (1H, t, J=5.7 Hz), 7.39 (1H, d, J=7.4 Hz), 7.25-7.21 (3H, m), 4.51 (2H, s), 3.52 (2H, s), 3.05-3.02 (2H, m), 1.62-1.55 (5H, m), 1.32-1.11 (6H, m), 0.84-0.80 (2H, m).

LC-MS: >99% purity, RT 2.49 min, MS (m/z): 334 (M+H)$^+$

Synthesis of Compound 70

2-(2-((3,4-Dichlorophenethyl)amino)-2-oxoethyl)benzyl carbamimidothioate hydrobromide

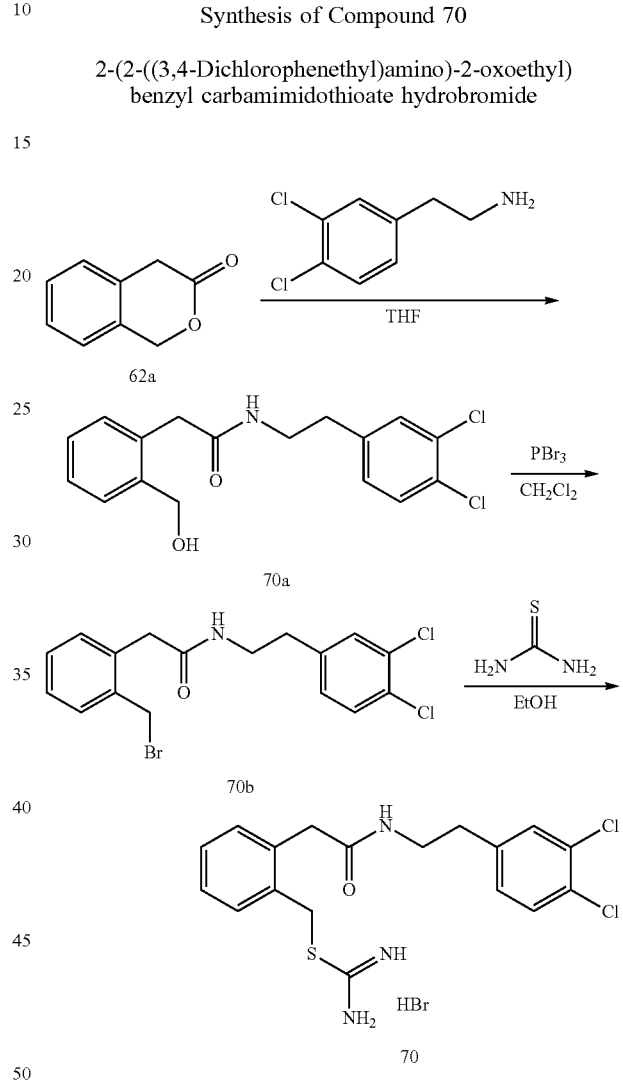

The same operation as in the synthesis of compound 62b was performed from isochroman-3-one (compound 62a, 296 mg, 2.00 mmol) and 2-(3,4-dichlorophenyl)ethan-1-amine (0.329 mL, 2.20 mmol), and the reaction residue was purified by silica gel chromatography with n-hexane/EtOAc (1:1 to 1:4) to obtain compound 70a (392 mg, 58% yield) as white crystals.

$^1$HNMR (400 MHz, CDCl$_3$): δ=7.39-7.38 (1H, m), 7.32-7.28 (3H, m), 7.21-7.16 (2H, m), 6.86 (1H, dd, J=8.3, 2.0 Hz), 6.00 (1H, brs), 4.65 (2H, d, J=5.9 Hz), 3.59 (2H, s), 3.44 (2H, q, J=6.5 Hz), 3.28 (1H, t, J=5.6 Hz), 2.70 (2H, t, J=6.6 Hz).

LC-MS: >99% purity, RT 3.26 min, MS (m/z): 339 (M+H)$^+$

The same operation as in the synthesis of compound 2c was performed from compound 70a (392 mg, 1.16 mmol)

and phosphorous tribromide (0.132 mL, 1.39 mmol) to obtain compound 70b (386 mg, 83% yield) as white crystals.

¹HNMR (400 MHz, CDCl₃): δ=7.49-7.12 (6H, m), 6.89 (1H, dd, J=8.0, 2.2 Hz), 5.42 (1H, brs), 5.32 (2H, s), 3.67 (2H, s), 3.48-3.43 (2H, m), 2.73-2.70 (2H, m).

LC-MS: >99% purity, RT 4.01 min, MS (m/z): 402 (M+H)⁺

The same operation as in the synthesis of compound 2 was performed from compound 70b (386 mg, 0.96 mmol) and thiourea (73.2 mg, 0.96 mmol) to obtain the title compound 70 (248 mg, 54% yield) as white crystals.

¹HNMR (500 MHz, CD₃OD): δ=7.49 (1H, t, J=4.5 Hz), 7.37-7.35 (2H, m), 7.30-7.29 (2H, m), 7.18 (1H, t, J=4.5 Hz), 7.08 (1H, dd, J=8.2, 2.0 Hz), 4.52 (2H, s), 3.62 (2H, s), 3.44 (2H, t, J=6.8 Hz), 2.78 (2H, t, J=6.8 Hz).

LC-MS: >99% purity, RT 2.55 min, MS (m/z): 398 (M+H)⁺

Synthesis of Compound 71

2-(2-(((Cyclopropylmethyl)amino)-2-oxoethyl)benzyl carbamimidothioate hydrobromide

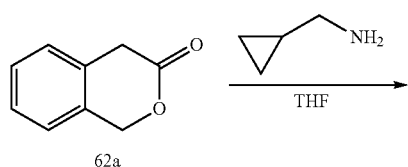

62a

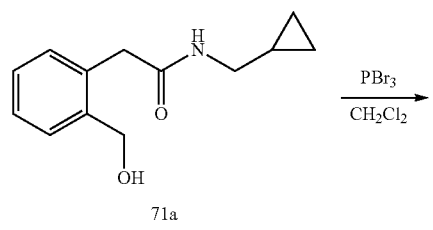

71a

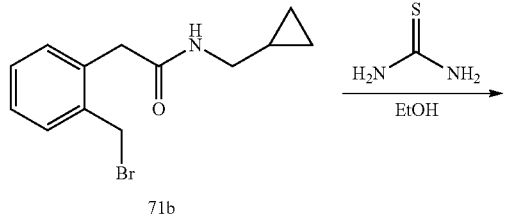

71b

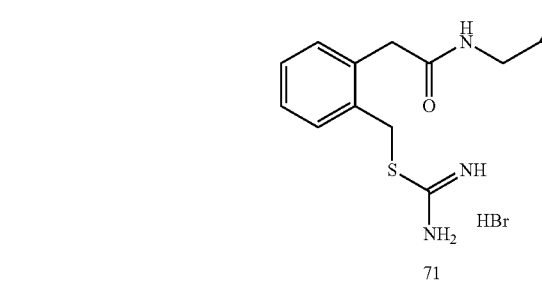

71

The same operation as in the synthesis of compound 62b was performed from Isochroman-3-one (compound 62a, 296 mg, 2.00 mmol) and cyclopropylmethanamine (0.189 mL, 2.20 mmol), and the reaction residue was purified by silica gel chromatography with n-hexane/EtOAc (1:1 to 1:3) to obtain compound 71a (356 mg, 81% yield) as white crystals.

¹HNMR (400 MHz, CDCl₃): δ=7.41 (1H, t, J=4.4 Hz), 7.31-7.27 (3H, m), 4.68 (2H, d, J=6.3 Hz), 3.98 (1H, t, J=5.9 Hz), 3.65 (2H, s), 3.08 (2H, dd, J=7.3, 5.4 Hz), 0.92 (1H, s), 0.50-0.48 (2H, m), 0.17 (2H, q, J=5.2 Hz).

LC-MS: >99% purity, RT 1.77 min, MS (m/z): 220 (M+H)⁺

The same operation as in the synthesis of compound 2c was performed from compound 71a (356 mg, 1.62 mmol) and phosphorous tribromide (0.185 mL, 1.95 mmol) to obtain compound 71b (111 mg, 24% yield) as a white oil substance.

¹HNMR (400 MHz, CDCl₃): δ=7.49-7.30 (4H, m), 4.59-4.58 (2H, m), 3.72 (2H, s), 3.11-3.08 (2H, m), 0.88 (1H, brs), 0.69-0.13 (4H, m).

LC-MS: >99% purity, RT 2.90 min, MS (m/z): 284 (M+H)⁺

The same operation as in the synthesis of compound 2 was performed from compound 71b (111 mg, 0.39 mmol) and thiourea (30.0 mg, 0.39 mmol) to obtain the title compound 71 (57 mg, 41% yield) as white crystals.

¹HNMR (500 MHz, DMSO-d6): δ=8.94 (3H, brs), 8.30 (1H, t, J=5.4 Hz), 7.42 (1H, d, J=5.7 Hz), 7.29-7.25 (3H, m), 4.53 (2H, s), 3.59 (2H, s), 2.95 (2H, t, J=6.0 Hz), 0.91-0.88 (1H, m), 0.43-0.40 (2H, m), 0.16-0.13 (2H, m).

LC-MS: >99% purity, RT 0.68 min, MS (m/z): 278 (M+H)⁺

Synthesis of Compound 72

2-(2-Oxo-2-((4-phenylbutyl)amino)ethyl)benzyl carbamimidothioate hydrobromide

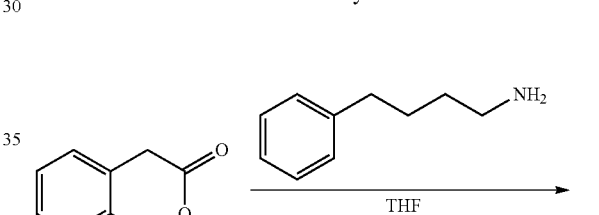

62a

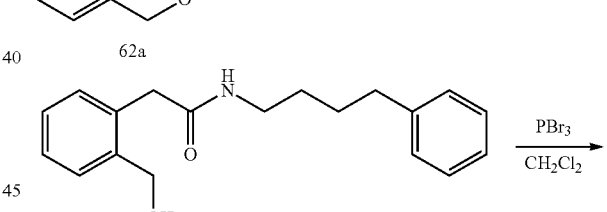

72a

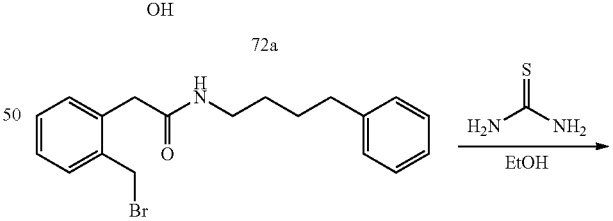

72b

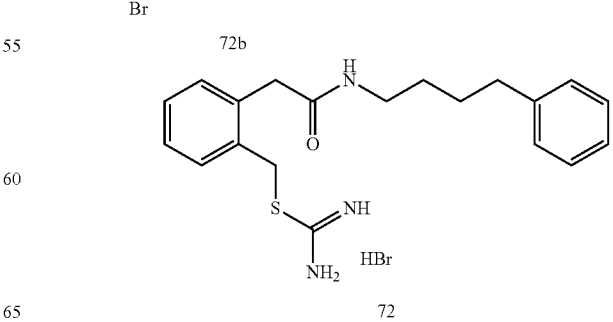

72

The same operation as in the synthesis of compound 62b was performed from isochroman-3-one (compound 62a, 246 mg, 2.00 mmol) and 4-phenylbutan-1-amine (349 mL, 2.20 mmol), and the reaction residue was purified by silica gel chromatography with n-hexane/EtOAc (55:45 to 3:7) to obtain compound 72a (509 mg, 85% yield) as white crystals.

$^1$HNMR (400 MHz, CDCl$_3$): δ=7.40 (1H, dd, J=5.6, 3.7 Hz), 7.30-7.19 (6H, m), 7.12 (2H, d, J=6.8 Hz), 5.88 (1H, brs), 4.67 (2H, d, J=5.9 Hz), 3.71 (1H, t, J=5.9 Hz), 3.61 (2H, s), 3.23 (2H, q, J=6.5 Hz), 2.58 (2H, t, J=7.6 Hz), 1.60-1.47 (4H, m).

LC-MS: >99% purity, RT 3.18 min, MS (m/z): 298 (M+H)$^+$

The same operation as in the synthesis of compound 2c was performed from compound 72a (509 mg, 1.71 mmol) and phosphorous tribromide (0.195 mL, 2.05 mmol) to obtain compound 72b (251 mg, 41% yield) as a white oil substance.

$^1$HNMR (400 MHz, CDCl$_3$): δ=7.49-7.11 (9H, m), 4.54-4.52 (2H, m), 3.69 (2H, s), 3.26-3.21 (2H, m), 2.67-2.63 (2H, m), 1.85-1.28 (4H, m).

LC-MS: >99% purity, RT 3.84 min, MS (m/z): 362 (M+H)$^+$

The same operation as in the synthesis of compound 2 was performed from compound 72b (251 mg, 0.70 mmol) and thiourea (53.0 mg, 0.70 mmol), and the residue was recrystallized from EtOH to obtain the title compound 72 (198 mg, 65% yield) as white crystals.

$^1$HNMR (500 MHz, DMSO-d6): δ=9.04 (4H, brs), 8.21 (1H, t, J=5.4 Hz), 7.42 (1H, t, J=3.7 Hz), 7.28-7.25 (5H, m), 7.17-7.15 (3H, m), 4.56 (2H, s), 3.56 (2H, s), 3.08 (2H, q, J=6.4 Hz), 2.57 (2H, d, J=7.9 Hz), 1.58-1.52 (2H, m), 1.45-1.39 (2H, m).

LC-MS: >99% purity, RT 2.27 min, MS (m/z): 356 (M+H)$^+$

Synthesis of Compound 73

6,6'-(((4,5-Dichloro-1,2-phenylene)bis(methylene))bis(sulfanediyl))bis(3-(cyclopropylmethyl)-1,2,3,4-tetrahydro-1,3,5-triazine)

Reaction was performed by the same operation as in the synthesis of compound 9 from cyclopropylmethanamine (0.086 mL, 1.00 mmol), formaldehyde (150 μL, 37% wt.

solution in water, 2.00 mmol) and (4,5-dichloro-1,2-phenylene)bis(methylene) dicarbamimidothioate dihydrobromide (compound 36, 162 mg, 0.50 mmol), and the reaction residue was recrystallized from EtOH to obtain the title compound 73 (115 mg, 45% yield) as white crystals.

$^1$HNMR (400 MHz, CDCl$_3$): δ=7.60 (2H, s), 4.76 (4H, s), 4.52 (8H, s), 2.35 (4H, d, J=5.9 Hz), 0.90 (2H, s), 0.58 (4H, q, J=5.2 Hz), 0.18 (4H, q, J=5.2 Hz). LC-MS: >99% purity, RT 1.64 min, MS (m/z): 514 (M+H)$^+$ Synthesis of Compound 74

5-Bromo-2-((cyclohexylmethyl)carbamoyl)benzyl carbamimidothioate hydrobromide

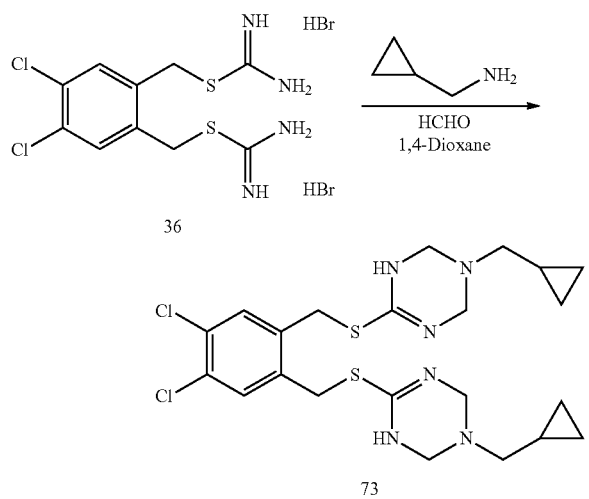

Cyclohexylmethanamine (623 mg, 5.50 mmol) was added to a solution of 5-bromoisobenzofuran-1(3H)-one (compound 74a, 1.07 g, 5.00 mmol) in THF (15 ml), and the mixture was stirred at room temperature for 8 hours. The reaction solution was concentrated under reduced pressure, and then, water was added to the residue, followed by extraction with dichloromethane. The organic layer was washed with brine, dried over magnesium sulfate, and then concentrated under reduced pressure, and the residue was purified by silica gel chromatography with n-hexane/EtOAc (4:1 to 1:1) to obtain compound 74b (210 mg, 13% yield) as white crystals.

$^1$HNMR (400 MHz, CDCl$_3$): δ=7.57 (1H, d, J=2.0 Hz), 7.50 (1H, dd, J=8.3, 2.0 Hz), 7.39 (1H, d, J=7.8 Hz), 6.28 (1H, brs), 4.57 (2H, d, J=6.8 Hz), 4.29 (1H, t, J=6.8 Hz), 3.30 (2H, t, J=6.6 Hz), 1.75-1.70 (5H, m), 1.59-1.58 (1H, m), 1.28-1.16 (3H, m), 1.04-1.01 (2H, m).

LC-MS: >99% purity, RT 3.28 min, MS (m/z): 327 (M+H)$^+$

CBr$_4$ (79.6 mg, 0.24 mmol) was added to a solution of compound 74b (65.2 mg, 0.20 mmol) in CH$_2$Cl$_2$ (4 ml) at 0°

C., and further, a solution of PPh$_3$ (78.7 mg, 0.30 mmol) in CH$_2$Cl$_2$ (5 ml) was added. The reaction solution was stirred at room temperature for 1 hour. Then, thiourea (15.2 mg, 0.20 mmol) was added thereto, and the mixture was stirred at 40° C. for 12 hours. Crystals deposited during the reaction were collected by filtration to obtain the title compound 74 (61 mg, 66% yield) as white crystals.

$^1$HNMR (500 MHz, DMSO-d6): δ=9.38 (1H, brs), 8.90 (2H, brs), 8.79 (1H, t, J=5.7 Hz), 7.81 (1H, d, J=1.7 Hz), 7.66 (1H, dd, J=8.2, 2.0 Hz), 7.45 (1H, d, J=8.5 Hz), 4.51 (2H, s), 3.09 (2H, t, J=6.2 Hz), 1.71 (4H, t, J=14.5 Hz), 1.63 (1H, d, J=8.5 Hz), 1.55-1.53 (1H, m), 1.21-1.15 (3H, m), 0.93 (2H, q, J=10.8 Hz).

LC-MS: >99% purity, RT 2.33 min, MS (m/z): 386 (M+H)$^+$

Synthesis of Compound 75

6,6'-(((4-Bromo-1,2-phenylene)bis(methylene))bis(sulfanediyl))bis(3-(cyclopropylmethyl)-1,2,3,4-tetrahydro-1,3,5-triazine)

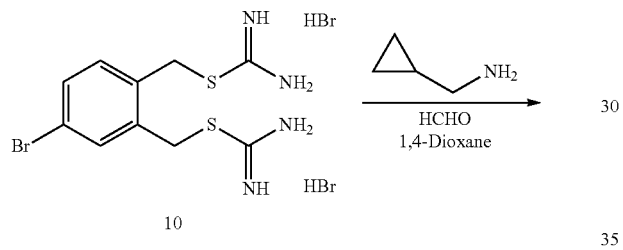

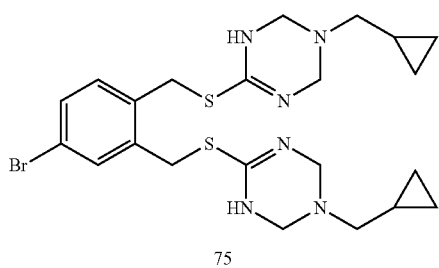

Reaction was performed by the same operation as in the synthesis of compound 9 from cyclopropylmethanamine (0.086 mL, 1.00 mmol), formaldehyde (150 μL, 37% wt. solution in water, 2.00 mmol) and (4-bromo-1,2-phenylene)bis(methylene) dicarbamimidothioate dihydrobromide (compound 10, 167 mg, 0.50 mmol), and the reaction residue was recrystallized from EtOH and Et$_2$O (1:2) to obtain the title compound 75 (115 mg, 44% yield) as white crystals.

$^1$HNMR (500 MHz, CDCl$_3$): δ=7.48-7.22 (3H, m), 4.64 (4H, brs), 4.54 (8H, brs), 2.36-2.34 (4H, brs), 0.91 (2H, brs), 0.58-0.55 (4H, m), 0.19-0.16 (4H, m).

LC-MS: RT 1.70 min, MS (m/z): 525 (M+H)$^+$

Synthesis of Compound 76

5-Bromo-2-((4-cyanobenzyl)carbamoyl)benzyl carbamimidothioate hydrobromide

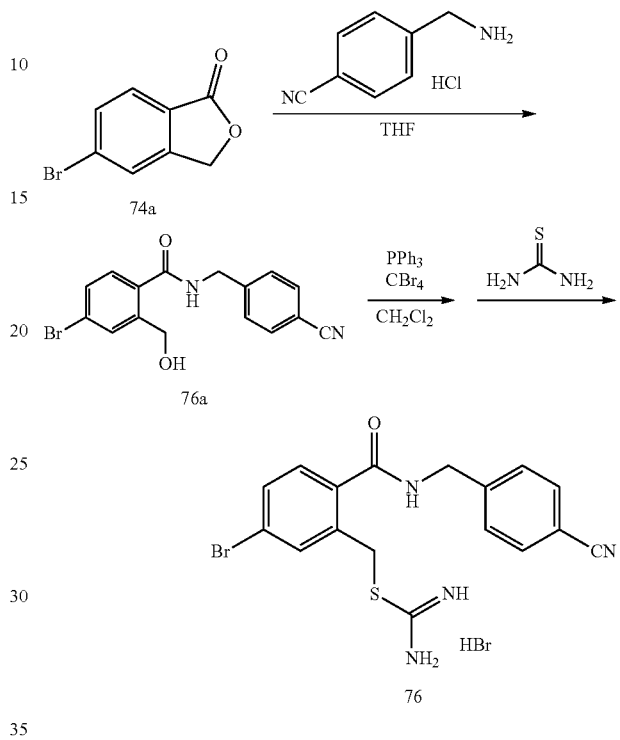

4-(Aminomethyl)benzonitrile hydrochloride (556 mg, 3.30 mmol) and triethylamine (418 μL, 3.00 mmol) were added to a solution of 5-bromoisobenzofuran-1(3H)-one (compound 74a, 639 mg, 3.00 mmol) in THF (15 ml), and the mixture was stirred at 50° C. for 24 hours. The reaction solution was concentrated under reduced pressure, and then, water was added to the residue, followed by extraction with dichloromethane. The organic layer was washed with brine, dried over magnesium sulfate, and then concentrated under reduced pressure, and the residue was purified by silica gel chromatography with n-hexane/EtOAc (65:35 to 3:7) to obtain compound 76a (142 mg, 14% yield) as yellow crystals.

$^1$HNMR (500 MHz, CDCl$_3$): δ=7.67-7.65 (2H), 7.58 (1H, d, J=1.7 Hz), 7.52 (1H, dd, J=8.2, 2.0 Hz), 7.49-7.46 (3H, m), 6.99 (1H, brs), 4.69 (2H, d, J=5.7 Hz), 4.60 (2H, d, J=6.8 Hz), 3.83 (1H, t, J=6.8 Hz).

LC-MS: >99% purity, RT 2.61 min, MS (m/z): 347 (M+H)$^+$

The same operation as in the synthesis of compound 74 was performed from compound 76a (123 mg, 0.36 mmol), CBr$_4$ (142 mg, 0.43 mmol), PPh$_3$ (140 mg, 0.54 mmol), and thiourea (27.2 mg, 0.36 mmol), and the residue was recrystallized from EtOH to obtain the title compound 76 (26.5 mg, 15% yield) as gray crystals.

$^1$HNMR (500 MHz, DMSO-d6): δ=9.43 (1H, t, J=6.0 Hz), 9.32 (1H, brs), 8.95 (2H, brs), 7.78-7.76 (3H, m), 7.65 (1H, dd, J=8.5, 2.3 Hz), 7.53-7.48 (3H, m), 4.55 (4H, brs).

LC-MS: >99% purity, RT 1.79 min, MS (m/z): 405 (M+H)$^+$

Synthesis of Compound 77

5-Cyano-2-(methylcarbamoyl)benzyl carbamimidothioate hydrobromide

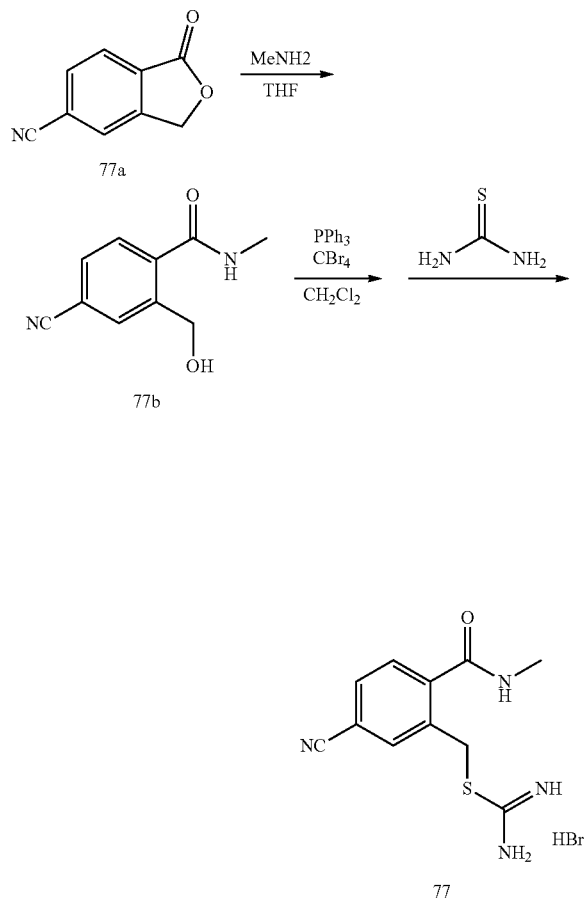

The same operation as in the synthesis of compound 74b was performed from 5-cyano-isobenzofuran-1(3H)-one (compound 77a, 796 mg, 5.00 mmol) and 40% MeNH$_2$ (4.309 mL, 50.0 mmol) to obtain compound 77b (562 mg, 59% yield) as white crystals.

$^1$HNMR (400 MHz, CDCl$_3$): δ=7.73 (1H, d, J=1.5 Hz), 7.68-7.62 (2H, m), 6.40 (1H, brs), 4.66 (2H, d, J=6.8 Hz), 3.91 (1H, t, J=6.8 Hz), 3.05 (3H, d, J=4.9 Hz).

LC-MS: >99% purity, RT 0.51 min, MS (m/z): 191 (M+H)$^+$

The same operation as in the synthesis of compound 74 was performed from compound 77b (190 mg, 1.00 mmol), CBr$_4$ (398 mg, 1.20 mmol), PPh$_3$ (393 mg, 1.50 mmol), and thiourea (76.1 mg, 1.00 mmol), and the residue was recrystallized from EtOH to obtain the title compound 77 (29.5 mg, 9% yield) as light green crystals.

$^1$HNMR (500 MHz, DMSO-d6): δ=9.04 (3H, s), 8.83 (1H, d, J=5.1 Hz), 8.04 (1H,$), 7.94 (1H, d, J=7.9 Hz), 7.67 (1H, d, J=7.9 Hz), 4.55 (2H, s), 2.80 (3H, d, J=4.5 Hz).

LC-MS: >99% purity, RT 0.41 min, MS (m/z): 249 (M+H)$^+$

Synthesis of Compound 78

5-Bromo-2-((4-chlorophenethyl)carbamoyl)benzyl carbamimidothioate hydrobromide

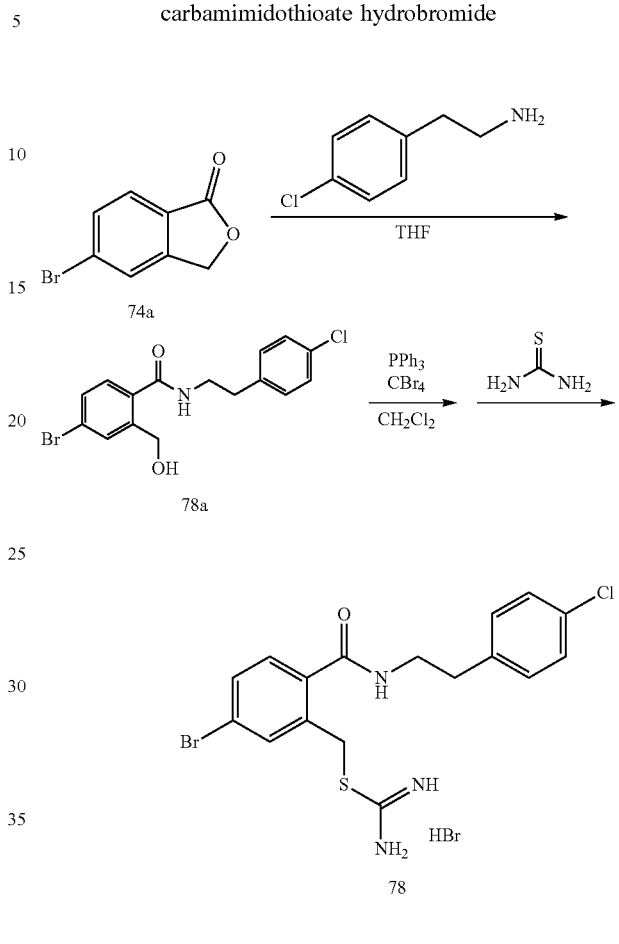

The same operation as in the synthesis of compound 74b was performed from 5-bromoisobenzofuran-1(3H)-one (compound 74a, 1065 mg, 5.00 mmol) and 2-(4-chlorophenyl)ethan-1-amine (0.840 mL, 6.00 mmol), and the reaction residue was purified by silica gel chromatography with n-hexane/EtOAc (7:3 to 3:7) to obtain compound 78a (919 mg, 50% yield) as white crystals.

$^1$HNMR (400 MHz, CDCl$_3$): δ=7.56 (1H, d, J=2.0 Hz), 7.48-7.47 (1H, m), 7.31-7.18 (5H, m), 6.28 (1H, brs), 4.52 (2H, d, J=6.8 Hz), 4.03 (1H, t, J=7.1 Hz), 3.71 (2H, q, J=6.5 Hz), 2.93 (2H, t, J=6.8 Hz).

LC-MS: >99% purity, RT 3.30 min, MS (m/z): 370 (M+H)$^+$

The same operation as in the synthesis of compound 74 was performed from compound 78a (369 mg, 1.00 mmol), CBr$_4$ (398 mg, 1.20 mmol), PPh$_3$ (393 mg, 1.50 mmol), and thiourea (76.1 mg, 1.00 mmol), and the residue was recrystallized from EtOH to obtain the title compound 78 (244 mg, 48% yield) as white crystals.

$^1$HNMR (500 MHz, DMSO-d6): δ=9.10 (3H, brs), 8.85 (1H, t, J=5.7 Hz), 7.80 (1H, d, J=2.3 Hz), 7.65 (1H, dd, J=8.2, 2.0 Hz), 7.37-7.35 (3H, m), 7.28 (2H, d, J=8.5 Hz), 4.45 (2H, s), 3.48 (2H, q, J=6.6 Hz), 2.85 (2H, t, J=7.1 Hz).

LC-MS: >99% purity, RT 2.29 min, MS (m/z): 428 (M+H)$^+$

Synthesis of Compound 79

2-(2-(Methylamino)-2-oxoethyl)benzyl (E)-N'-(4-bromophenyl)carbamimidothioate hydrobromide

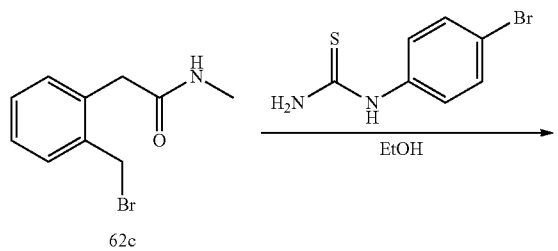

The same operation as in the synthesis of compound 2 was performed from compound 62c (102 mg, 0.42 mmol) and 1-(4-bromophenyl)thiourea (97.5 mg, 0.42 mmol) to obtain the title compound 79 (74.2 mg, 37% yield) as white crystals.

$^1$HNMR (500 MHz, DMSO-d6): δ=8.07 (1H. brs), 7.66 (2H, d, J=7.9 Hz), 7.39 (1H, d, J=7.4 Hz), 7.28-7.18 (5H, m), 4.62 (2H, s), 3.56 (2H, s), 2.56 (3H, d, J=4.5 Hz).

LC-MS: >99% purity, RT 1.83 min, MS (m/z): 394 (M+H)$^+$

Synthesis of Compound 80

2-(2-(Methylamino)-2-oxoethyl)benzyl (E)-N'-(3-chloro-4-fluorophenyl)carbamimidothioate hydrobromide The same operation as in the synthesis of compound 2 was performed from compound 62c (88.3 mg, 0.36 mmol) and 1-(3-chloro-4-fluorophenyl)thiourea (74.6 mg, 0.36 mmol), and the residue was recrystallized from 2-propanol and hexane (1:1) to obtain the title compound 80 (64.7 mg, 40% yield) as white crystals.

$^1$HNMR (500 MHz, DMSO-d6): δ=8.09 (1H, brs), 7.54 (2H, brs), 7.43 (1H, d, J=6.2 Hz), 7.38-7.18 (4H, m), 4.64 (2H, s), 3.59 (2H, s), 2.59 (3H, d, J=4.5 Hz).

LC-MS: >99% purity, RT 2.21 min, MS (m/z): 366 (M+H)$^+$

Synthesis of Compound 81

5-Cyano-2-(methylcarbamoyl)benzyl (E)-N'-(4-bromophenyl)carbamimidothioate hydrobromide The same operation as in the synthesis of compound 74 was performed from compound 77b (190 mg, 1.00 mmol), CBr$_4$ (398 mg, 1.20 mmol), PPh$_3$ (393 mg, 1.50 mmol), and 1-(4-bromophenyl)thiourea (231 mg, 1.00 mmol), and the residue was recrystallized from EtOH to obtain the title compound 81 (249 mg, 51% yield) as white crystals.

$^1$HNMR (500 MHz, DMSO-d6): δ=8.79 (1H, brs), 8.06 (1H, s), 7.94 (1H, d, J=7.9 Hz), 7.68-7.65 (3H, m), 7.22 (2H, brs), 4.63 (2H, s), 2.78 (3H, d, J=4.5 Hz).

LC-MS: >99% purity, RT 1.77 min, MS (m/z): 405 (M+H)$^+$

Synthesis of Compound 82

5-Bromo-2-((4-chlorobenzyl)carbamoyl)benzyl carbamimidothioate hydrobromide

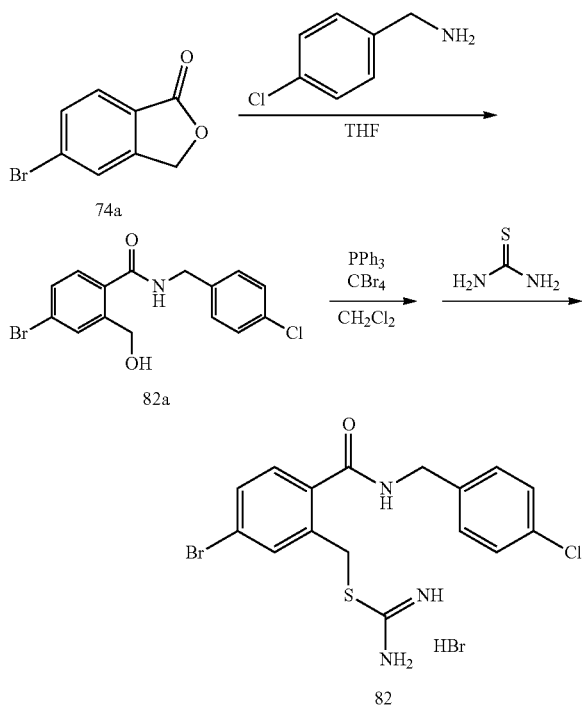

The same operation as in the synthesis of compound 74b was performed from 5-bromoisobenzofuran-1(3H)-one (compound 74a, 1065 mg, 5.00 mmol) and (4-Chlorophenyl)methanamine (0.732 mg, 6.00 mmol), and the reaction residue was purified by silica gel chromatography with n-hexane/EtOAc (3:1 to 1:1) to obtain compound 82a (438 mg, 25% yield) as white crystals.

$^1$HNMR (400 MHz, CDCl$_3$): δ=7.58 (1H, d, J=2.0 Hz), 7.50 (1H, dd, J=8.3, 2.0 Hz), 7.43 (1H, d, J=8.3 Hz), 7.34 (2H, d, J=8.3 Hz), 7.29 (2H, d, J=8.3 Hz), 4.61 (2H, d, J=3.4 Hz), 4.59 (2H, d, J=4.9 Hz), 4.06-4.04 (1H, m).

LC-MS: >99% purity, RT 3.13 min, MS (m/z): 355 (M+H)$^+$

The same operation as in the synthesis of compound 74 was performed from compound 82a (142 mg, 0.40 mmol), CBr$_4$ (159 mg, 0.48 mmol), PPh$_3$ (157 mg, 0.60 mmol), and thiourea (30.4 mg, 0.40 mmol), and the residue was recrystallized from EtOH to obtain the title compound 82 (112 mg, 57% yield) as white crystals.

$^1$HNMR (500 MHz, DMSO-d6): δ=9.32 (3H, brs), 8.93 (1H, brs), 7.83 (1H, d, J=2.3 Hz), 7.68 (1H, dd, J=8.2, 2.0 Hz), 7.54 (1H, d, J=8.5 Hz), 7.41 (2H, d, J=8.5 Hz), 7.37 (2H, d, J=8.5 Hz), 4.56 (2H, s), 4.45 (2H, d, J=6.2 Hz).

LC-MS: >99% purity, RT 2.01 min, MS (m/z): 414 (M+H)$^+$

Synthesis of Compound 83

5-Bromo-2-((4-chlorobenzyl)carbamoyl)benzyl (E)-N'-(3-chloro-4-fluorophenyl)carbamimidothioate hydrobromide

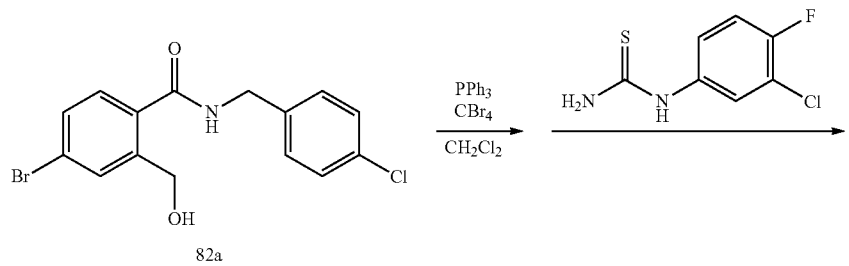

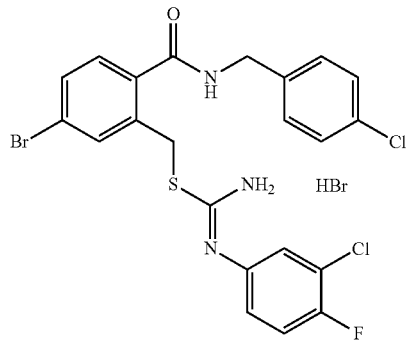

The same operation as in the synthesis of compound 74 was performed from compound 82a (106 mg, 0.30 mmol), CBr$_4$ (119 mg, 0.36 mmol), PPh$_3$ (118 mg, 0.45 mmol), and 1-(3-chloro-4-fluorophenyl)thiourea (61.4 mg, 0.30 mmol), and the residue was purified by silica gel chromatography with n-hexane/EtOAc (1:1) to obtain the title compound 83 (90.4 mg, 48% yield) as pale pink crystals.

$^1$HNMR (500 MHz, DMSO-d6): δ=9.09 (1H, t, J=6.0 Hz), 7.75 (1H, d, J=1.7 Hz), 7.56 (1H, dd, J=7.9, 2.3 Hz), 7.42-7.24 (7H, m), 6.84 (1H, dd, J=6.8, 2.3 Hz), 6.70-6.67 (1H, m), 6.60 (1H, brs), 4.41 (2H, d, J=5.7 Hz), 4.37 (2H, s).

LC-MS: >99% purity, RT 3.44 min, MS (m/z): 542 (M+H)$^+$

Synthesis of Compound 84

5-Bromo-2-((4-chlorobenzyl)carbamoyl)benzyl (E)-N'-(4-bromophenyl)carbamimidothioate hydrobromide

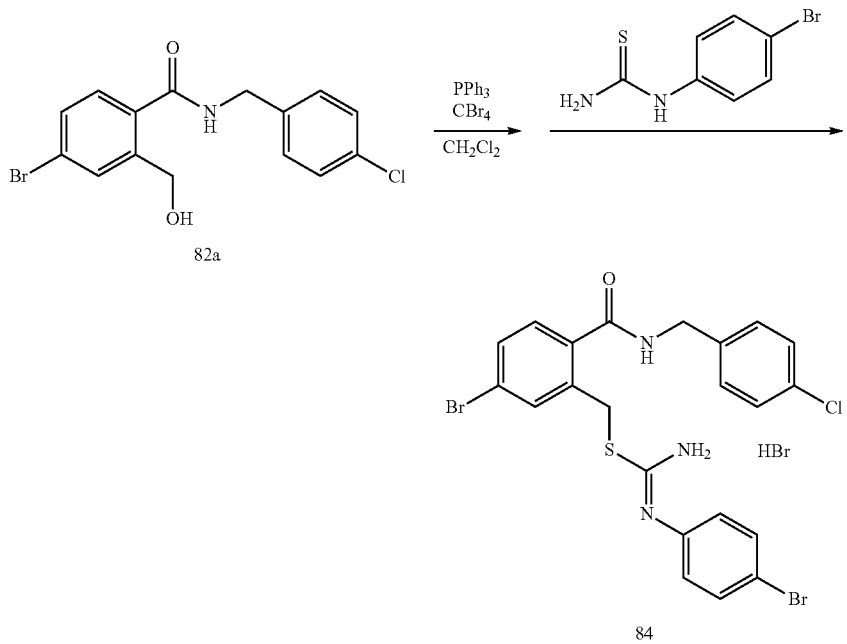

The same operation as in the synthesis of compound 74 was performed from compound 82a (130 mg, 0.37 mmol), CBr$_4$ (146 mg, 0.44 mmol), PPh$_3$ (144 mg, 0.50 mmol), and 1-(4-bromophenyl)thiourea (84.7 mg, 0.37 mmol), and the residue was purified by silica gel chromatography with n-hexane/EtOAc (1:1) to obtain the title compound 84 (63.4 mg, 26% yield) as white crystals.

$^1$HNMR (500 MHz, DMSO-d6): δ=9.09 (1H, t, J=6.0 Hz), 7.75 (1H, d, J=1.7 Hz), 7.55 (1H, dd, J=8.2, 2.0 Hz), 7.40-7.36 (7H, m), 6.69 (2H, d, J=8.5 Hz), 6.51 (2H, brs), 4.41 (2H, d, J=5.7 Hz), 4.37 (2H, s).

LC-MS: >99% purity, RT 3.24 min, MS (m/z): 568 (M+H)$^+$

Synthesis of Compound 85

5-Bromo-2-((4-cyanobenzyl)carbamoyl)benzyl (E)-N'-(3-chloro-4-fluorophenyl)carbamimidothioate hydrobromide

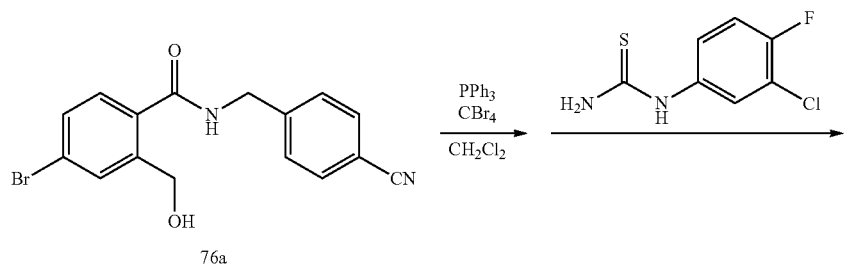

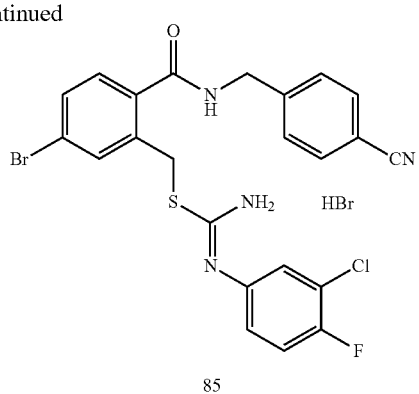

85

The same operation as in the synthesis of compound 74 was performed from compound 76a (104 mg, 0.30 mmol), CBr$_4$ (119 mg, 0.36 mmol), PPh$_3$ (118 mg, 0.45 mmol), and 1-(3-chloro-4-fluorophenyl)thiourea (61.4 mg, 0.30 mmol), and the residue was recrystallized from EtOH to obtain the title compound 85 (128 mg, 70% yield) as white crystals.

$^1$HNMR (500 MHz, DMSO-d6): δ=9.41 (1H, t, J=6.0 Hz), 7.88 (1H, d, J=1.7 Hz), 7.82 (2H, d, J=8.5 Hz), 7.71 (1H, dd, J=8.2, 2.0 Hz), 7.61-7.54 (5H, m), 7.31 (1H, brs), 4.65 (2H, s), 4.54 (2H, d, J=6.2 Hz), 1.06 (2H, t, J=6.8 Hz).

LC-MS: >99% purity, RT 3.00 min, MS (m/z): 533 (M+H)$^+$

Synthesis of Compound 86

5-Bromo-2-((4-fluorobenzyl)carbamoyl)benzyl carbamimidothioate hydrobromide

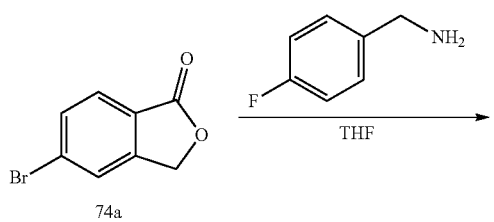

74a

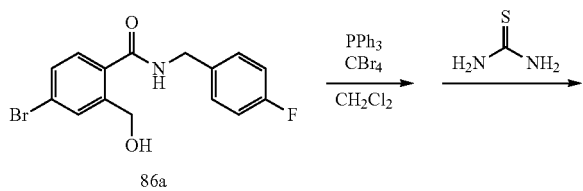

86a

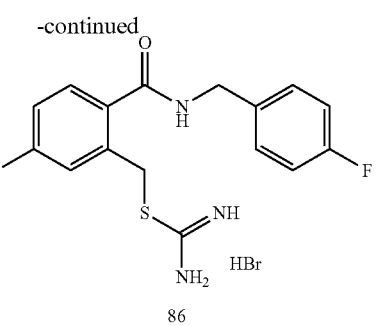

86

The same operation as in the synthesis of compound 74b was performed from 5-bromoisobenzofuran-1(3H)-one (compound 74a, 1065 mg, 5.00 mmol) and (4-fluorophenyl)methanamine (0.683 mL, 6.00 mmol), and the reaction residue was purified by silica gel chromatography with n-hexane/EtOAc (3:1 to 1:1) to obtain compound 86a (229 mg, 14% yield) as pale yellow crystals.

$^1$HNMR (500 MHz, CDCl$_3$): δ=7.58 (1H, d, J=2.3 Hz), 7.49 (1H, dd, J=8.2, 2.0 Hz), 7.42 (1H, d, J=7.9 Hz), 7.33 (2H, dd, J=8.8, 5.4 Hz), 7.06 (2H, dd, J=8.8, 2.0 Hz), 6.67 (1H, brs), 4.61-4.58 (4H, m), 4.08 (1H, t, J=6.8 Hz).

LC-MS: >99% purity, RT 2.88 min, MS (m/z): 340 (M-OH)$^+$

The same operation as in the synthesis of compound 74 was performed from compound 86a (102 mg, 0.30 mmol), CBr$_4$ (119 mg, 0.36 mmol), PPh$_3$ (118 mg, 0.45 mmol), and thiourea (22.8 mg, 0.30 mmol) to obtain the title compound 86 (20.3 mg, 14% yield) as white crystals.

$^1$HNMR (500 MHz, DMSO-d6): δ=9.31 (1H, t, J=6.0 Hz), 9.04 (3H, brs), 7.82 (1H, d, J=2.3 Hz), 7.67 (1H, dd, J=8.2, 2.0 Hz), 7.52 (1H, d, J=8.5 Hz), 7.39 (2H, dd, J=8.5, 5.7 Hz), 7.17 (2H, t, J=9.1 Hz), 4.54 (2H, s), 4.45 (2H, d, J=5.7 Hz).

LC-MS: >99% purity, RT 1.81 min, MS (m/z): 398 (M+H)$^+$

Synthesis of Compound 87

5-Bromo-2-((4-cyanobenzyl)carbamoyl)benzyl (E)-N'-(4-bromophenyl)carbamimidothioate hydrobromide

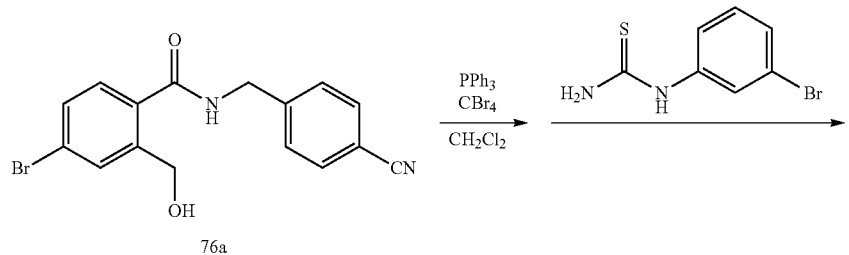

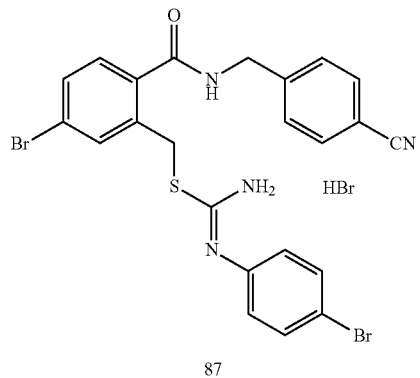

The same operation as in the synthesis of compound 74 was performed from compound 76a (69 mg, 0.20 mmol), CBr$_4$ (79.6 mg, 0.24 mmol), PPh$_3$ (78.7 mg, 0.30 mmol), and 1-(4-bromophenyl)thiourea (46.2 mg, 0.20 mmol) to obtain the title compound 87 (66.1 mg, 52% yield) as white crystals.

$^1$HNMR (500 MHz, DMSO-d6): δ=9.38 (1H, t, J=6.0 Hz), 7.87 (1H, d, J=1.7 Hz), 7.82 (2H, d, J=8.5 Hz), 7.72-7.68 (3H, m), 7.59 (1H, d, J=8.5 Hz), 7.54 (2H, d, J=8.5 Hz), 7.23 (2H, d, J=8.5 Hz), 4.65 (2H, s), 4.53 (2H, d, J=5.7 Hz).

LC-MS: >99% purity, RT 2.83 min, MS (m/z): 559 (M+H)$^+$

Synthesis of Compound 88

5-Bromo-2-((4-fluorobenzyl)carbamoyl)benzyl (E)-N'-(3-chloro-4-fluorophenyl)carbamimidothioate hydrobromide

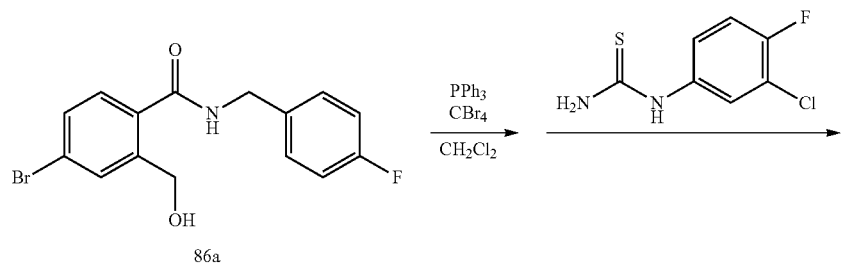

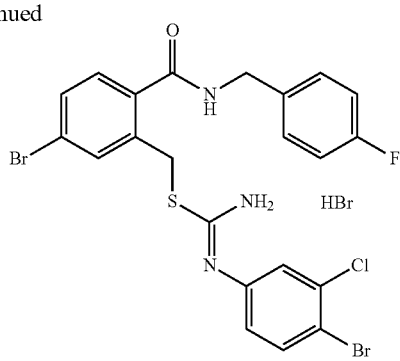

The same operation as in the synthesis of compound 74 was performed from compound 86a (121 mg, 0.36 mmol), CBr$_4$ (143 mg, 0.43 mmol), PPh$_3$ (141 mg, 0.54 mmol), and 1-(3-chloro-4-fluorophenyl)thiourea (73.3 mg, 0.36 mmol), and the residue was purified by silica gel chromatography with n-hexane/EtOAc (1:1) to obtain the title compound 88 (91.4 mg, 42% yield) as pale yellow crystals.

$^1$HNMR (500 MHz, DMSO-d6): δ=9.07 (1H, t, J=6.0 Hz), 7.75 (1H, d, J=1.1 Hz), 7.55 (1H, dd, J=8.2, 2.0 Hz), 7.41 (1H, d, J=8.5 Hz), 7.36 (2H, t, J=7.1 Hz), 7.26 (1H, t, J=9.1 Hz), 7.14 (2H, t, J=8.8 Hz), 6.84 (1H, dd, J=6.5, 2.0 Hz), 6.69 (1H, t, J=4.5 Hz), 6.60 (2H, brs), 4.40 (2H, d, J=5.7 Hz), 4.37 (2H, s).

LC-MS: >99% purity, RT 3.20 min, MS (m/z): 526 (M+H)$^+$

Synthesis of Compound 89

5-Bromo-2-((2,4-dichlorobenzyl)carbamoyl)benzyl carbamimidothioate hydrobromide

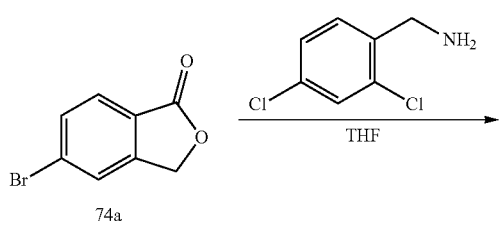

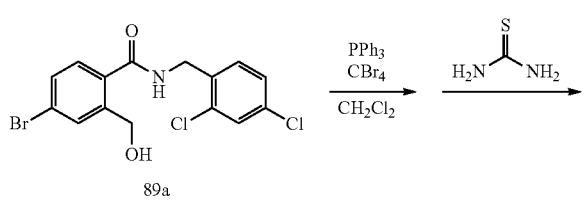

The same operation as in the synthesis of compound 74b was performed from 5-bromoisobenzofuran-1(3H)-one (compound 74a, 1065 mg, 5.00 mmol) and (2,4-dichlorophenyl)methanamine (0.808 mL, 6.00 mmol), and the reaction residue was purified by silica gel chromatography twice with n-hexane/EtOAc (4:1 to 3:2) and with n-hexane/EtOAc (4:1 to 3:2) to obtain compound 89a (105 mg, 5% yield) as white crystals.

$^1$HNMR (500 MHz, CDCl$_3$): δ=7.57 (1H, d, J=1.7 Hz), 7.50 (1H, dd, J=8.2, 2.0 Hz), 7.43-7.41 (3H, m), 7.27-7.25 (1H, m), 6.85 (1H, brs), 4.67 (2H, d, J=6.2 Hz), 4.57 (2H, d, J=6.8 Hz), 3.96 (1H, t, J=6.5 Hz).

LC-MS: 81% purity, RT 3.42 min, MS (m/z): 390 (M+H)$^+$

The same operation as in the synthesis of compound 74 was performed from compound 89a (105 mg, 0.27 mmol), CBr$_4$ (108 mg, 0.32 mmol), PPh$_3$ (106 mg, 0.41 mmol), and thiourea (20.6 mg, 0.27 mmol), and the residue was recrystallized from EtOH and Et$_2$O (1:1) to obtain the title compound 89 (76 mg, 54% yield) as white crystals.

$^1$HNMR (500 MHz, DMSO-d6): δ=9.32 (1H, t, J=6.0 Hz), 9.28 (2H, brs), 8.94 (2H, brs), 7.84 (1H, d, J=2.3 Hz), 7.70 (1H, dd, J=8.2, 2.0 Hz), 7.65 (1H, d, J=1.7 Hz), 7.58 (1H, d, J=8.5 Hz), 7.45 (2H, t, J=2.0 Hz), 4.56 (2H, s), 4.50 (2H, d, J=5.7 Hz).

LC-MS: >99% purity, RT 2.53 min, MS (m/z): 448 (M+H)$^+$

Synthesis of Compound 90

5-Bromo-2-((4-methylbenzyl)carbamoyl)benzyl carbamimidothioate hydrobromide

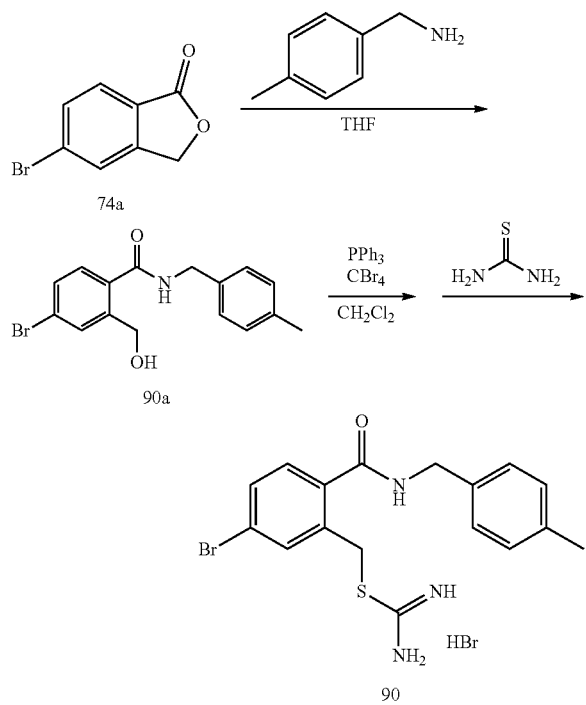

The same operation as in the synthesis of compound 74b was performed from 5-bromoisobenzofuran-1(3H)-one (compound 74a, 1065 mg, 5.00 mmol) and p-tolylmethanamine (0.757 mL, 6.00 mmol), and the reaction residue was purified by silica gel chromatography with n-hexane/EtOAc (3:1 to 55:45) to obtain compound 90a (200 mg, 12% yield) as white crystals.

$^1$HNMR (500 MHz, CDCl$_3$): δ=7.57 (1H, d, J=1.7 Hz), 7.48 (1H, dd, J=8.2, 2.0 Hz), 7.40 (1H, d, J=7.9 Hz), 7.24 (2H, d, J=7.9 Hz), 7.18 (2H, d, J=7.9 Hz), 6.53 (1H, brs), 4.60 (2H, d, J=2.8 Hz), 4.58 (2H, s), 4.20 (1H, t, J=6.8 Hz), 2.35 (3H, s).

LC-MS: >99% purity, RT 3.06 min, MS (m/z): 336 (M+H)$^+$

The same operation as in the synthesis of compound 74 was performed from compound 90a (94 mg, 0.28 mmol), CBr$_4$ (112 mg, 0.34 mmol), PPh$_3$ (111 mg, 0.42 mmol), and thiourea (21 mg, 0.28 mmol), and the residue was recrystallized from EtOH to obtain the title compound 90 (60 mg, 46% yield) as white crystals.

$^1$HNMR (500 MHz, DMSO-d6): δ=9.27 (1H, t, J=5.7 Hz), 9.12 (3H, brs), 7.82 (1H, d, J=1.7 Hz), 7.67 (1H, dd, J=8.5, 2.3 Hz), 7.50 (1H, d, J=8.5 Hz), 7.23 (2H, d, J=7.9 Hz), 7.15 (2H, d, J=7.9 Hz), 4.55 (2H, s), 4.42 (2H, d, J=6.2 Hz), 2.29 (3H, s).

LC-MS: >99% purity, RT 1.95 min, MS (m/z): 394 (M+H)$^+$

Synthesis of Compound 91

5-Bromo-2-((4-methylbenzyl)carbamoyl)benzyl (E)-N'-(3-chloro-4-fluorophenyl)carbamimidothioate hydrobromide

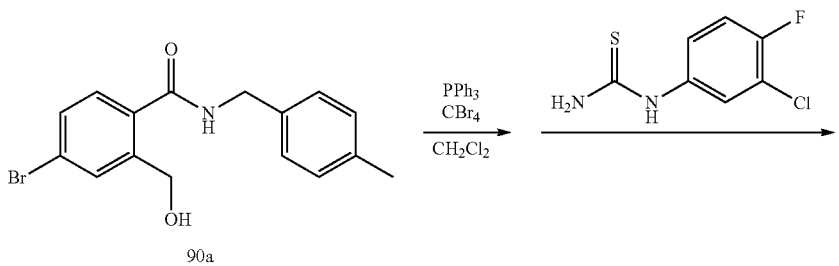

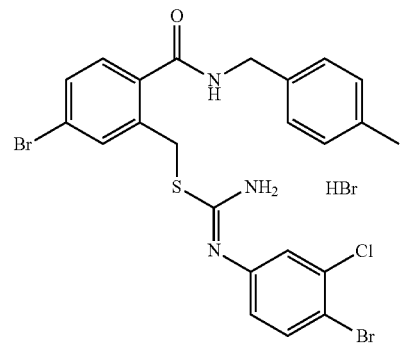

The same operation as in the synthesis of compound 74 was performed from compound 90a (100 mg, 0.30 mmol), CBr$_4$ (119 mg, 0.36 mmol), PPh$_3$ (118 mg, 0.45 mmol), and 1-(3-chloro-4-fluorophenyl)thiourea (61 mg, 0.30 mmol), and the residue was purified by silica gel chromatography with n-hexane/EtOAc (1:1) to obtain the title compound 91 (90 mg, 50% yield) as pale yellow crystals.

$^1$HNMR (500 MHz, DMSO-d6): δ=9.01 (1H, t, J=6.0 Hz), 7.75 (1H, s), 7.54 (1H, dd, J=8.2, 2.0 Hz), 7.39 (1H, d, J=7.9 Hz), 7.26 (1H, t, J=9.1 Hz), 7.21 (2H, d, J=7.9 Hz), 7.13 (2H, d, J=7.9 Hz), 6.84 (1H, dd, J=6.8, 2.3 Hz), 6.70-6.67 (1H, m), 6.60 (2H, brs), 4.38-4.36 (4H, m), 2.28 (3H, s).

LC-MS: >99% purity, RT 3.30 min, MS (m/z): 522 (M+H)$^+$

Synthesis of Compound 92

2-(Methylcarbamoyl)benzyl carbamimidothioate hydrobromide

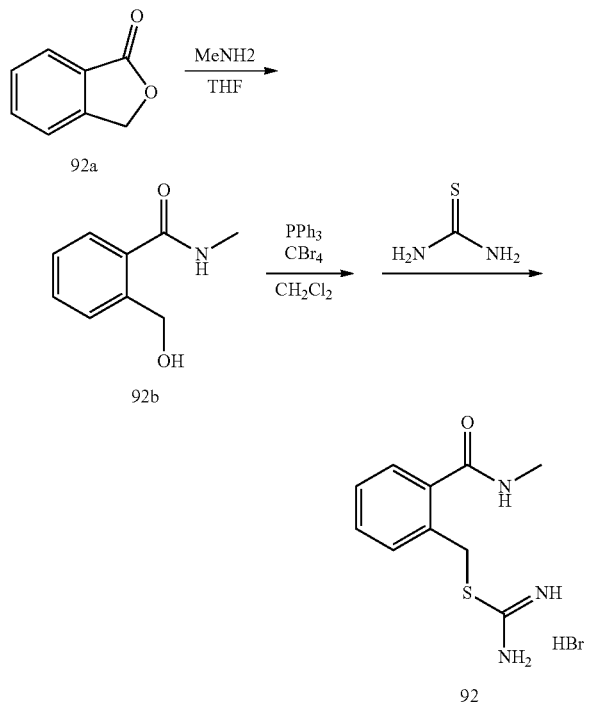

The same operation as in the synthesis of compound 74b was performed from isobenzofuran-1(3H)-one (compound 92a, 671 mg, 5.00 mmol) and 40% MeNH$_2$ (4.309 mL, 50.0 mmol) to obtain compound 92b (577 mg, 70% yield) as white crystals.

$^1$H-NMR (DMSO-d$_6$) δ: =8.27 (1H, brs), 7.53 (1H, d, J=7.9 Hz), 7.45-7.39 (2H, m), 7.30 (1H, t, J=7.4 Hz), 5.23 (1H, t, J=5.4 Hz), 4.58 (2H, d, J=5.1 Hz), 2.75 (3H, d, J=4.5 Hz).

LC-MS: >99% purity, RT 1.49 min, MS (m/z): 166 (M+H)+

The same operation as in the synthesis of compound 74 was performed from compound 92b (66 mg, 0.40 mmol), CBr$_4$ (159 mg, 0.48 mmol), PPh$_3$ (157 mg, 0.60 mmol), and thiourea (30 mg, 0.40 mmol) to obtain the title compound 92 (69.5 mg, 57% yield) as white crystals.

$^1$HNMR (500 MHz, DMSO-d6): δ=9.05 (3H, brs), 8.67 (1H, d, J=4.5 Hz), 7.57 (1H, d, J=7.4 Hz), 7.51 (2H, t, J=8.5 Hz), 7.42 (1H, t, J=7.4 Hz), 4.54 (2H, s), 2.79 (3H, d, J=4.5 Hz). LC-MS: >99% purity, RT 0.49 min, MS (m/z): 224 (M+H)$^+$ Synthesis of Compound 93

5-Bromo-2-((cyclopropylmethyl)carbamoyl)benzyl carbamimidothioate hydrobromide

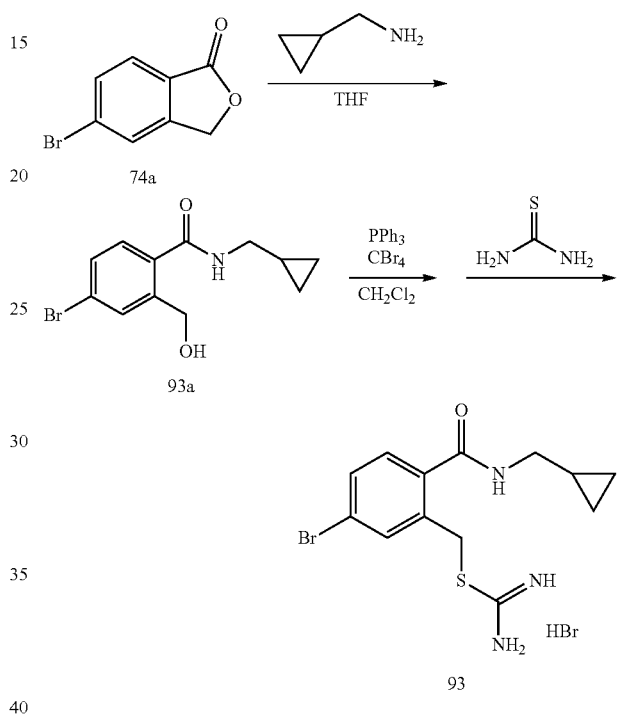

The same operation as in the synthesis of compound 74b was performed from 5-bromoisobenzofuran-1(3H)-one (compound 74a, 1065 mg, 5.00 mmol) and cyclopropylmethanamine (0.514 mL, 6.00 mmol), and the reaction residue was purified by silica gel chromatography with n-hexane/EtOAc (7:3 to 1:1) to obtain compound 93a (607 mg, 43% yield) as white crystals.

$^1$HNMR (500 MHz, CDCl$_3$): δ=7.57 (1H, s), 7.50 (1H, d, J=7.9 Hz), 7.42 (1H, d, J=8.5 Hz), 6.41 (1H, s), 4.57 (2H, d, J=6.8 Hz), 4.29 (1H, t, J=6.5 Hz), 3.31 (2H, t, J=6.2 Hz), 1.09-1.04 (1H, m), 0.58 (2H, q, J=4.8 Hz), 0.29 (2H, q, J=4.9 Hz).

LC-MS: >99% purity, RT 2.27 min, MS (m/z): 285 (M+H)$^+$

The same operation as in the synthesis of compound 74 was performed from compound 93a (142 mg, 0.50 mmol), CBr$_4$ (199 mg, 0.60 mmol), PPh$_3$ (197 mg, 0.75 mmol), and thiourea (38 mg, 0.50 mmol) to obtain the title compound 93 (124 mg, 59% yield) as white crystals.

$^1$HNMR (500 MHz, DMSO-d6): δ=9.09 (3H, brs), 8.89 (1H, t, J=5.4 Hz), 7.81 (1H, s), 7.66 (1H, d, J=7.9 Hz), 7.45 (1H, d, J=7.9 Hz), 4.53 (2H, s), 3.14 (2H, t, J=6.2 Hz), 1.05-1.00 (1H, m), 0.46 (2H, q, J=4.8 Hz), 0.24 (2H, q, J=4.7 Hz).

LC-MS: >99% purity, RT 1.06 min, MS (m/z): 344 (M+H)$^+$

225

Synthesis of Compound 94

5-Bromo-2-((3,4-dichlorobenzyl)carbamoyl)benzyl carbamimidothioate hydrobromide

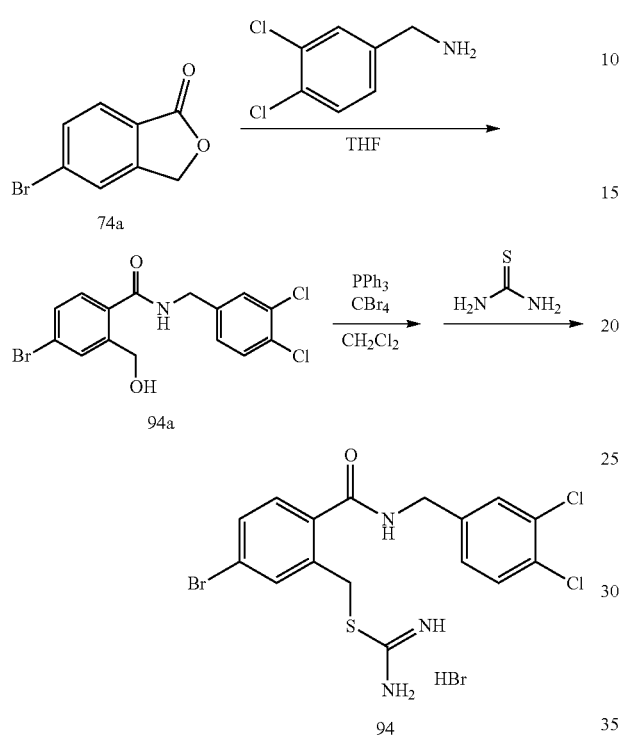

The same operation as in the synthesis of compound 74b was performed from 5-bromoisobenzofuran-1(3H)-one (compound 74a, 1065 mg, 5.00 mmol) and (3,4-dichlorophenyl)methanamine (0.794 mg, 6.00 mmol), and the reaction residue was purified by silica gel chromatography twice with n-hexane/EtOAc (7:3 to 45:55) and with n-hexane/EtOAc (7:3 to 1:1) to obtain compound 94a (133 mg, 7% yield) as white crystals.

$^1$HNMR (500 MHz, CDCl$_3$): δ=7.59 (1H, d, J=1.7 Hz), 7.52 (1H, dd, J=7.9, 1.7 Hz), 7.46-7.43 (3H, m), 7.21 (1H, dd, J=8.2, 2.0 Hz), 6.79 (1H, brs), 4.61-4.58 (4H, m), 3.85 (1H, t, J=6.8 Hz).

LC-MS: >99% purity, RT 3.46 min, MS (m/z): 390 (M+H)$^+$

The same operation as in the synthesis of compound 74 was performed from compound 94a (117 mg, 0.30 mmol), CBr$_4$ (119 mg, 0.36 mmol), PPh$_3$ (118 mg, 0.45 mmol), and thiourea (22.8 mg, 0.30 mmol), and the residue was recrystallized from EtOH to obtain the title compound 94 (14.6 mg, 9% yield) as white crystals.

$^1$HNMR (500 MHz, DMSO-d6): δ=9.33 (1H, t, J=6.0 Hz), 9.02 (3H, s), 7.82 (1H, d, J=1.7 Hz), 7.69 (1H, dd, J=8.2, 1.4 Hz), 7.62-7.61 (2H, m), 7.54 (1H, d, J=7.9 Hz), 7.35 (1H, dd, J=7.9, 1.7 Hz), 4.54 (2H, s), 4.46 (2H, d, J=5.7 Hz).

LC-MS: >99% purity, RT 6.76 min, MS (m/z): 448 (M+H)$^+$

226

Synthesis of Compound 95

1,2-Phenylenebis(methylene) (E,E)-bis(N-(2,4-difluorophenyl)carbamimidothioate)dihydrobromide

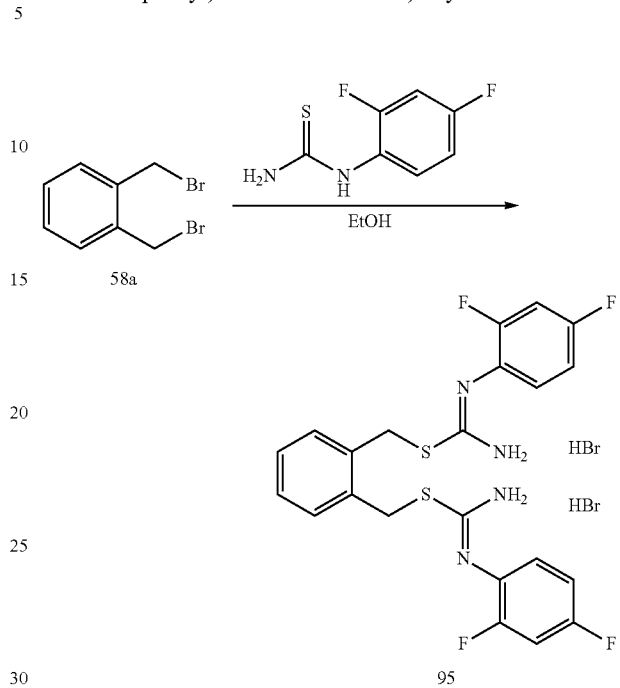

The same operation as in the synthesis of compound 2 was performed from 1,2-bis(bromomethyl)benzene (compound 58a, 132 mg, 0.50 mmol) and 1-(2,4-difluorophenyl)thiourea (188 mg, 1.00 mmol), and the residue was recrystallized from 2-propanol and hexane (1:1) to obtain the title compound 95 (256 mg, 80% yield) as white crystals.

$^1$HNMR (500 MHz, DMSO-d6): δ=9.51 (4H, s), 7.52-7.41 (8H, m), 7.26-7.23 (2H, m), 4.78 (4H, brs).

LC-MS: >99% purity, RT 1.51 min, MS (m/z): 479 (M+H)$^+$

Synthesis of Compound 96

2-((4-Cyanobenzyl)carbamoyl)benzyl carbamimidothioate hydrobromide

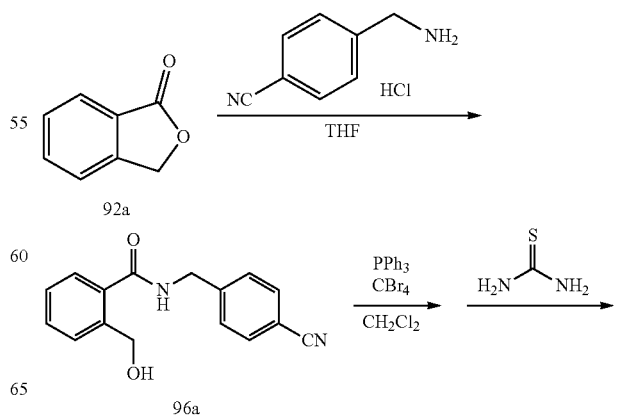

-continued

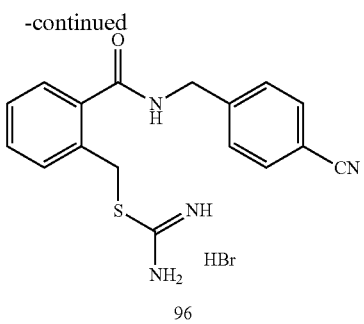

96

-continued

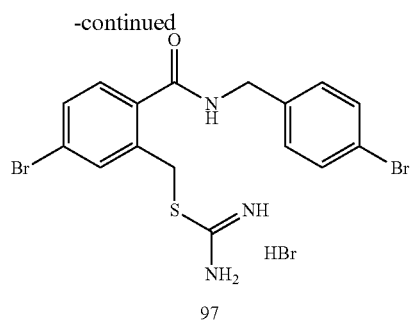

97

The same operation as in the synthesis of compound 76a was performed from isobenzofuran-1(3H)-one (compound 92a, 805 mg, 6.00 mmol), 4-(aminomethyl)benzonitrile hydrochloride (1113 mg, 50.0 mmol) and triethylamine (2.509 mL, 18.00 mmol), and the reaction residue was purified by silica gel chromatography with n-hexane/EtOAc (7:3 to 35:65) to obtain compound 96a (731 mg, 46% yield) as pale yellow crystals.

$^1$HNMR (500 MHz, CDCl$_3$): δ=7.66 (2H, d, J=7.9 Hz), 7.61 (1H, d, J=7.4 Hz), 7.50-7.47 (3H, m), 7.43-7.38 (2H, m), 6.95 (1H, brs), 4.72 (2H, d, J=6.2 Hz), 4.64 (2H, d, J=6.8 Hz), 3.92 (1H, t, J=6.8 Hz).

LC-MS: >99% purity, RT 2.42 min, MS (m/z): 249 (M-OH)$^+$

The same operation as in the synthesis of compound 74 was performed from compound 96a (133 mg, 0.50 mmol), CBr$_4$ (199 mg, 0.60 mmol), PPh$_3$ (197 mg, 0.75 mmol), and thiourea (38.1 mg, 0.50 mmol), and the residue was recrystallized from EtOH to obtain the title compound 96 (9.3 mg, 5% yield) as white crystals.

$^1$HNMR (500 MHz, DMSO-d6): δ=9.34 (1H, t, J=6.0 Hz), 9.26 (2H, brs), 8.87 (1H, brs), 7.82 (2H, d, J=7.9 Hz), 7.62 (1H, d, J=7.4 Hz), 7.59-7.53 (4H, m), 7.47 (1H, t, J=7.4 Hz), 4.57 (2H, s), 4.56 (2H, d, J=5.7 Hz).

LC-MS: >99% purity, RT 0.92 min, MS (m/z): 325 (M+H)$^+$

Synthesis of Compound 97

5-Bromo-2-((4-bromobenzyl)carbamoyl)benzyl carbamimidothioate hydrobromide

The same operation as in the synthesis of compound 74b was performed from 5-bromoisobenzofuran-1(3H)-one (compound 74a, 639 mg, 3.00 mmol) and (4-bromophenyl) methanamine (670 mg, 3.60 mmol), and the reaction residue was purified by silica gel chromatography with n-hexane/ EtOAc (7:3 to 1:1) to obtain compound 97a (114 mg, 10% yield) as white crystals.

$^1$HNMR (500 MHz, CDCl$_3$): δ=7.58 (1H, d, J=2.3 Hz), 7.51-7.47 (3H, m), 7.43 (1H, d, J=8.5 Hz), 7.24 (2H, d, J=8.5 Hz), 6.68 (1H, brs), 4.60-4.58 (4H, m), 3.97 (1H, t, J=6.8 Hz).

LC-MS: >99% purity, RT 8.23 min, MS (m/z): 382 (M-OH)$^+$

The same operation as in the synthesis of compound 74 was performed from compound 97a (111 mg, 0.28 mmol), CBr$_4$ (111 mg, 0.33 mmol), PPh$_3$ (110 mg, 0.42 mmol), and thiourea (21.2 mg, 0.28 mmol), and the residue was recrystallized from EtOH to obtain the title compound 97 (70.0 mg, 46% yield) as white crystals.

$^1$HNMR (500 MHz, DMSO-d6): δ=9.34-9.31 (2H, m), 8.93 (2H, brs), 7.83 (1H, d, J=1.7 Hz), 7.69 (1H, dd, J=8.2, 2.0 Hz), 7.55-7.53 (3H, m), 7.31 (2H, d, J=8.5 Hz), 4.56 (2H, s), 4.43 (2H, d, J=5.7 Hz).

LC-MS: >99% purity, RT 5.99 min, MS (m/z): 458 (M+H)$^+$

Synthesis of Compound 98

(2-(Methylcarbamoyl)pyridin-3-yl)methyl carbamimidothioate hydrobromide

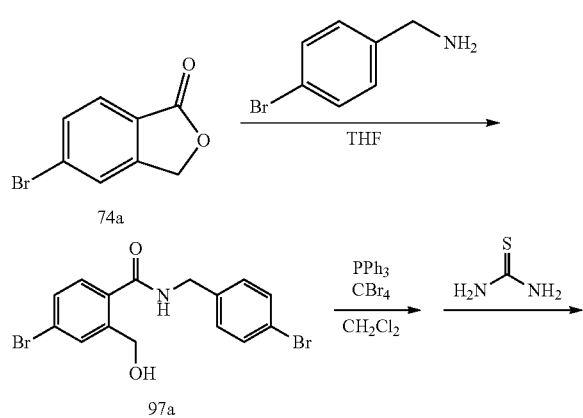

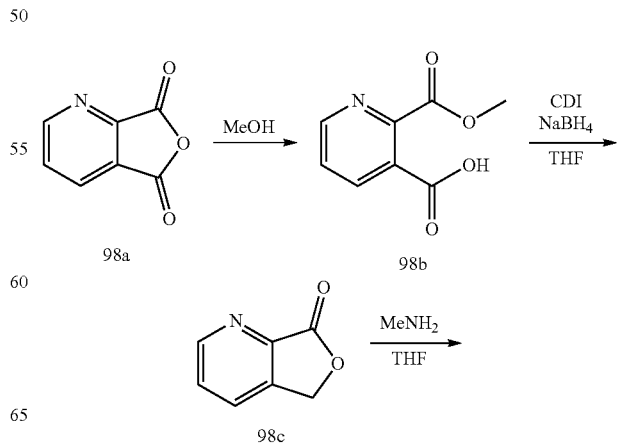

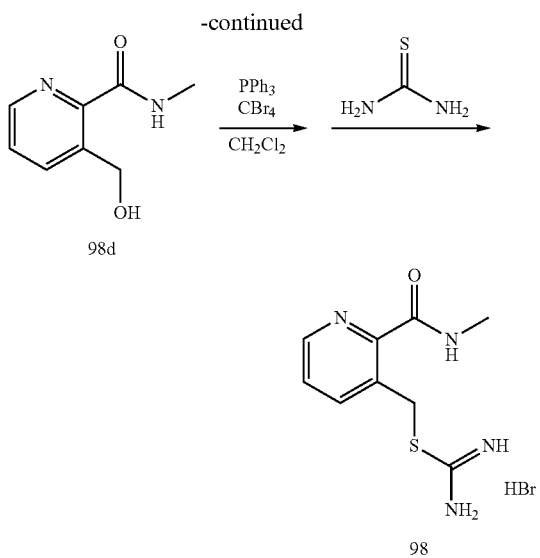

A solution of furo[3,4-b]pyridine-5,7-dione (compound 98a, 5.0 g, 34.0 mmol) in MeOH (25 ml) was stirred at 70° C. for 2 hours. The reaction solution was concentrated under reduced pressure and then recrystallized from ethyl acetate to obtain compound 98b (3.94 g, 64% yield) as white crystals.

$^1$HNMR (500 MHz, CDCl$_3$): δ=8.84 (1H, d, J=5.1 Hz), 8.34 (1H, d, J=7.9 Hz), 7.56 (1H, dd, J=7.9, 4.5 Hz), 4.02 (3H, s).

LC-MS: >99% purity, RT 0.58 min, MS (m/z): 182 (M+H)$^+$

A solution of 1,1'-carbonyldiimidazole; CDI (535 mg, 3.31 mmol) in THF (4 ml) was added to a solution of compound 98b (450 mg, 2.50 mmol) in THF (7 ml) at 0° C., and the mixture was stirred at room temperature for 1 hour. Then, NaBH$_4$ was added to the reaction solution, and the mixture was stirred at room temperature for 2 hours. After the completion of reaction, the reaction solution was cooled to 0° C., and MeOH (3 ml) and water were added thereto, followed by extraction with ethyl acetate. The organic layer was washed with brine, dried over magnesium sulfate, and then concentrated under reduced pressure, and the residue was purified by silica gel chromatography with n-hexane/EtOAc (1:3 to 0:1) to obtain compound 98c (116 mg, 34% yield) as white crystals.

$^1$HNMR (500 MHz, CDCl$_3$): δ=8.92 (1H, d, J=4.5 Hz), 7.92 (1H, d, J=7.4 Hz), 7.59 (1H, dd, J=7.7, 4.8 Hz), 5.40 (2H, s).

40% MeNH$_2$ (260 mg, 8.38 mmol) was added to a solution of compound 98c (113 mg, 0.84 mmol) in THF (12 ml), and the mixture was stirred at room temperature for 8 hours. The reaction solution was concentrated under reduced pressure, and then, water was added to the residue, followed by extraction with dichloromethane. The organic layer was washed with brine, dried over magnesium sulfate, and then concentrated under reduced pressure to obtain compound 98d (104 mg, 75% yield) as white crystals.

$^1$HNMR (500 MHz, CDCl$_3$): δ=8.50 (1H, d, J=4.0 Hz), 8.36 (1H, brs), 7.74 (1H, d, J=6.8 Hz), 7.41 (1H, dd, J=7.7, 4.8 Hz), 5.31 (1H, t, J=7.4 Hz), 4.82 (2H, d, J=7.4 Hz), 3.05 (3H, d, J=5.1 Hz).

CBr$_4$ (146 mg, 0.74 mmol) was added to a solution of compound 98d (103 mg, 0.62 mmol) in CH$_2$Cl$_2$ (5 ml) at 0° C., and further, a solution of PPh$_3$ (243 mg, 0.93 mmol) in CH$_2$Cl$_2$ (4 ml) was added. The reaction solution was stirred at room temperature for 1 hour. Then, thiourea (47.0 mg, 0.62 mmol) was added thereto, and the mixture was stirred at 40° C. for 12 hours. Crystals deposited during the reaction were collected by filtration to obtain the title compound 98 (11.7 mg, 6% yield) as white crystals.

$^1$HNMR (500 MHz, DMSO-d6): δ=9.06-8.94 (4H, m), 8.61 (1H, d, J=4.5 Hz), 8.01 (1H, d, J=7.4 Hz), 7.62 (1H, dd, J=7.9, 4.5 Hz), 4.80 (2H, s), 2.81 (3H, d, J=4.5 Hz).

LC-MS: >99% purity, RT 0.38 min, MS (m/z): 225 (M+H)$^+$

Synthesis of Compound 99

(2-((4-Cyanobenzyl)carbamoyl)pyridin-3-yl)methyl carbamimidothioate hydrobromide

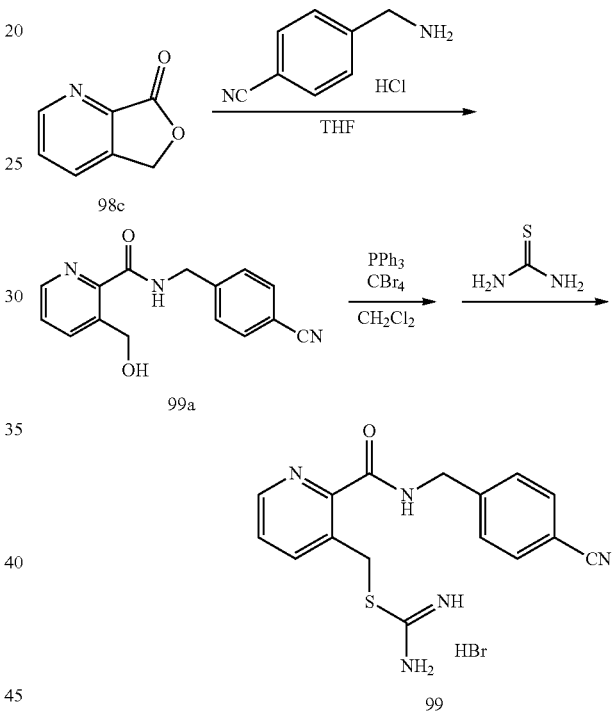

The same operation as in the synthesis of compound 76a was performed from compound 98c (511 mg, 3.78 mmol), 4-(aminomethyl)benzonitrile hydrochloride (702 mg, 4.16 mmol), and triethylamine (1.581 mL, 11.35 mmol), and the reaction residue was purified by silica gel chromatography with n-hexane/EtOAc (2:3 to 1:4) to obtain compound 99a (519 mg, 51% yield) as pale yellow crystals.

$^1$HNMR (500 MHz, CDCl$_3$): δ=8.84 (1H, br s), 8.51 (1H, d, J=4.5 Hz), 7.79 (1H, d, J=7.9 Hz), 7.65 (2H, d, J=7.9 Hz), 7.48-7.44 (3H, m), 4.98 (1H, t, J=7.4 Hz), 4.86 (2H, d, J=7.9 Hz), 4.73 (2H, d, J=6.2 Hz).

LC-MS: >99% purity, RT 2.15 min, MS (m/z): 250 (M-OH)$^+$

The same operation as in the synthesis of compound 98 was performed from compound 99a (245 mg, 0.92 mmol), CBr$_4$ (365 mg, 1.10 mmol), PPh$_3$ (361 mg, 1.38 mmol), and thiourea (69.8 mg, 0.92 mmol) to obtain the title compound 99 (105 mg, 28% yield) as white crystals.

$^1$HNMR (500 MHz, DMSO-d6): δ=9.68 (1H, t, J=6.2 Hz), 9.06 (3H, brs), 8.66 (1H, d, J=4.5 Hz), 8.03 (1H, d, J=7.9 Hz), 7.81 (2H, d, J=7.9 Hz), 7.67 (1H, dd, J=7.7, 4.8 Hz), 7.52 (2H, d, J=7.9 Hz), 4.80 (2H, s), 4.56 (2H, d, J=6.2 Hz).

LC-MS: >99% purity, RT 0.81 min, MS (m/z): 326 (M+H)⁺

Synthesis of Compound 100

(3-(Methylcarbamoyl)pyridin-2-yl)methyl carbamimidothioate hydrobromide

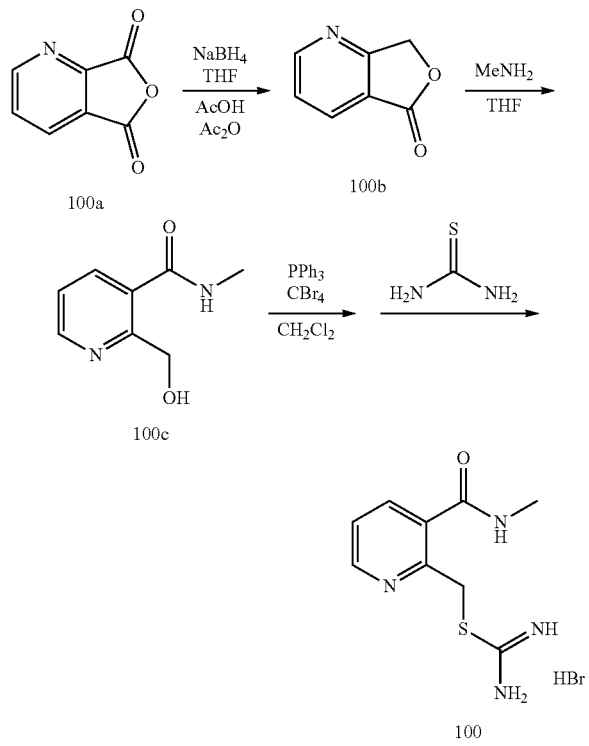

A solution of furo[3,4-b]pyridine-5,7-dione (compound 100a, 5.0 g, 33.5 mmol) in THF (30 ml) and acetic acid (4.0 g, 67.0 mmol) were added to a solution of NaBH₄ (1.14 mg, 33.5 mmol) in THF (5 ml) at 15° C., and the mixture was stirred for 4 hours. The reaction solution was concentrated under reduced pressure. Then, acetic acid (13.5 ml) and acetic anhydride (13.5 ml) were added thereto, and the mixture was refluxed for 3 hours. The reaction solution was concentrated under reduced pressure, followed by extraction with dichloromethane. The organic layer was washed with brine, dried over magnesium sulfate, and then concentrated under reduced pressure, and the residue was recrystallized from 2-propanol to obtain compound 100b (1.29 g, 29% yield) as pale yellow crystals.

¹HNMR (500 MHz, CDCl₃): δ=8.89 (1H, d, J=4.0 Hz), 8.23 (1H, d, J=6.8 Hz), 7.50 (1H, dd, J=7.4, 5.1 Hz), 5.36 (2H, s).

40% MeNH₂ (621 mg, 20.0 mmol) was added to a solution of compound 100b (270 mg, 2.0 mmol) in THF (10 ml), and the mixture was stirred at room temperature for 5 hours. The reaction solution was concentrated under reduced pressure, and then, water was added to the residue, followed by extraction with dichloromethane. The organic layer was washed with brine and dried over magnesium sulfate. Then, toluene was added to the residue, and the mixture was concentrated under reduced pressure to obtain compound 100c (222 mg, 67% yield) as yellow crystals.

¹HNMR (500 MHz, CDCl₃): δ=8.62 (1H, d, J=4.5 Hz), 7.89 (1H, d, J=7.9 Hz), 7.31 (1H, t, J=6.2 Hz), 6.38 (1H, brs), 4.89 (2H, s), 4.24 (1H, brs), 3.03 (3H, d, J=4.5 Hz).

CBr₄ (519 mg, 1.6 mmol) was added to a solution of compound 100c (217 mg, 1.3 mmol) in CH₂Cl₂ (6 ml) at 0° C., and further, a solution of PPh₃ (514 mg, 2.0 mmol) in CH₂Cl₂ (4 ml) was added. The reaction solution was stirred at room temperature for 1 hour. Then, thiourea (99.4 mg, 1.3 mmol) was added thereto, and the mixture was stirred at 40° C. for 12 hours. Crystals deposited during the reaction were collected by filtration to obtain the title compound 100 (98.4 mg, 25% yield) as light orange crystals.

¹HNMR (500 MHz, DMSO-d6): δ=9.20 (3H, brs), 8.77 (1H, d, J=4.0 Hz), 8.66 (1H, d, J=4.5 Hz), 7.99 (1H, d, J=7.4 Hz), 7.52 (1H, dd, J=7.7, 4.8 Hz), 4.64 (2H, s), 2.80 (3H, d, J=4.5 Hz).

LC-MS: >99% purity, RT 0.38 min, MS (m/z): 225 (M+H)⁺

Synthesis of Compound 101

(2-((4-Cyanobenzyl)carbamoyl)pyridin-3-yl)methyl (E)-N'-(3-chloro-4-fluorophenyl)carbamimidothioate hydrobromide

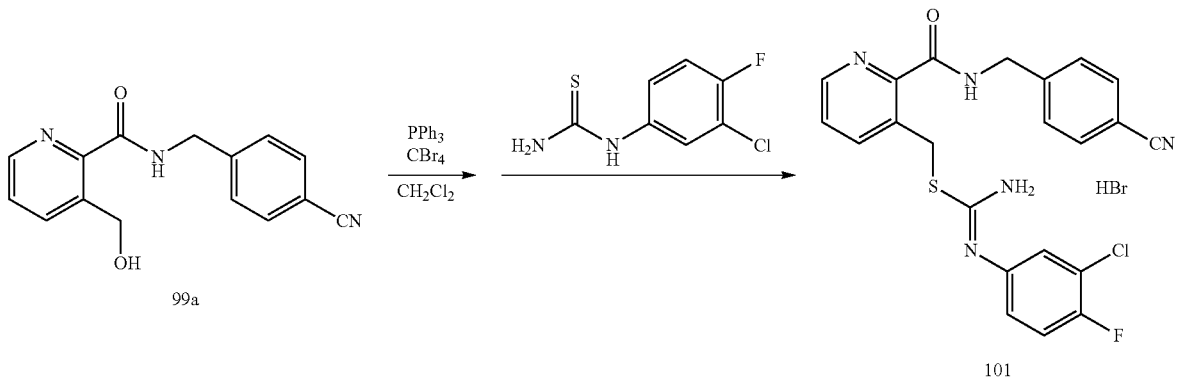 [SMILES: N#Cc1ccc(CNC(=O)c2ncccc2CO)cc1 ; "CH2Cl2" ; NC(=S)Nc1ccc(F)c(Cl)c1 ; N#Cc1ccc(CNC(=O)c2ncccc2CS/C(N)=N/c2ccc(F)c(Cl)c2)cc1 ; Br]

The same operation as in the synthesis of compound 98 was performed from compound 99a (134 mg, 0.50 mmol), CBr₄ (199 mg, 0.60 mmol), PPh₃ (197 mg, 0.75 mmol), and (3-chloro-4-fluorophenyl)thiourea (102 mg, 0.50 mmol), and the residue was purified by silica gel chromatography with n-hexane/EtOAc (1:1) to obtain the title compound 101 (37.3 mg, 14% yield) as white crystals.

$^1$HNMR (500 MHz, DMSO-d6): δ=9.44 (1H, d, J=6.2 Hz), 8.54 (1H, d, J=4.0 Hz), 7.98 (1H, d, J=7.9 Hz), 7.78 (2H, d, J=8.5 Hz), 7.57-7.50 (3H, m), 7.24 (1H, t, J=9.1 Hz), 6.85 (1H, brs), 6.69 (1H, brs), 6.53 (2H, brs), 4.61 (2H, s), 4.54 (2H, d, J=6.2 Hz).

LC-MS: >99% purity, RT 6.72 min, MS (m/z): 454 (M+H)$^+$

Synthesis of Compound 102

5-Bromo-2-((4-methoxybenzyl)carbamoyl)benzyl carbamimidothioate hydrobromide

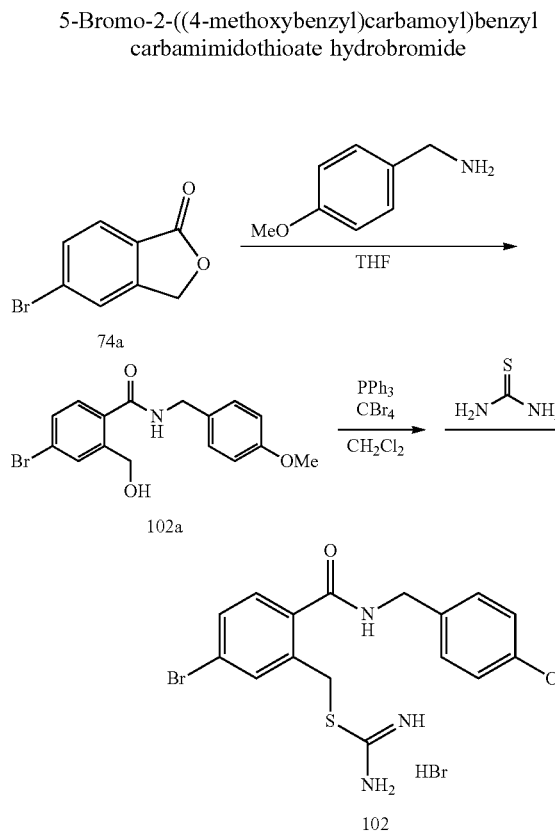

The same operation as in the synthesis of compound 74b was performed from 5-bromoisobenzofuran-1(3H)-one (compound 74a, 852 g, 4.00 mmol) and (4-methoxyphenyl)methanamine (0.627 mL, 4.80 mmol), and the reaction residue was purified by silica gel chromatography with n-hexane/EtOAc (7:3 to 45:55) to obtain compound 102a (372 mg, 27% yield) as white crystals.

$^1$HNMR (500 MHz, CDCl$_3$): δ=7.57 (1H, d, J=1.7 Hz), 7.48 (1H, dd, J=8.5, 1.7 Hz), 7.39 (1H, d, J=7.9 Hz), 7.28 (2H, d, J=9.1 Hz), 6.90 (2H, d, J=8.5 Hz), 6.50 (1H, brs), 4.59-4.56 (4H, m), 4.23 (1H, t, J=6.8 Hz), 3.81 (3H, s).

LC-MS: >99% purity, RT 2.77 min, MS (m/z): 351 (M+H)+

The same operation as in the synthesis of compound 74 was performed from compound 102a (175 mg, 0.50 mmol), CBr$_4$ (199 mg, 0.60 mmol), PPh$_3$ (197 mg, 0.75 mmol), and thiourea (38.1 mg, 0.50 mmol), and the residue was recrystallized from EtOH to obtain the title compound 102 (22.4 mg, 9% yield) as white crystals.

$^1$HNMR (500 MHz, DMSO-d6): δ=9.27 (1H, t, J=6.0 Hz), 7.82 (1H, d, J=1.7 Hz), 7.67 (1H, dd, J=8.2, 2.0 Hz), 7.49 (1H, d, J=8.5 Hz), 7.27 (2H, d, J=8.5 Hz), 6.91 (2H, d, J=8.5 Hz), 4.54 (2H, s), 4.39 (2H, d, J=6.2 Hz), 3.74 (3H, s).

LC-MS: >99% purity, RT 1.81 min, MS (m/z): 409 (M+H)$^+$

Synthesis of Compound 103

4-Bromo-2-((4-cyanobenzyl)carbamoyl)benzyl carbamimidothioate hydrobromide

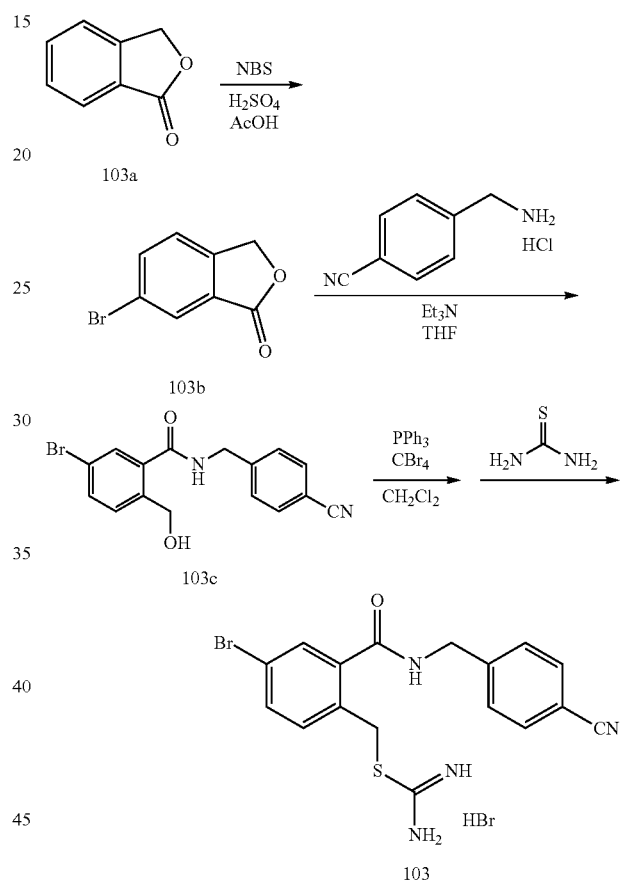

Sulfuric acid (1.5 ml) was added to a solution of isobenzofuran-1(3H)-one (compound 103a, 500 mg, 3.73 mmol) in acetic acid (3 ml), and then, NBS (995 mg, 5.59 mmol) was added in small portions over 9 hours with stirring at room temperature. Water (50 ml) was added to the reaction solution, followed by extraction with dichloromethane. The organic layer was washed with brine, dried over magnesium sulfate, and then concentrated under reduced pressure, and the residue was purified by silica gel chromatography with n-hexane/EtOAc (1:0 to 7:3) to obtain compound 103b (445 mg, 56% yield) as white crystals.

$^1$HNMR (500 MHz, CDCl$_3$): δ=8.07 (1H, d, J=1.1 Hz), 7.81 (1H, dd, J=7.9, 1.7 Hz), 7.39 (1H, d, J=7.9 Hz), 5.29 (2H, s).

LC-MS: >99% purity, RT 2.17 min, MS (m/z): 214 (M+H)+

4-(Aminomethyl)benzonitrile hydrochloride (371 mg, 2.2 mmol) and Et$_3$N (607 mg, 6.0 mmol) were added to a solution of compound 103b (426 mg, 2.0 mmol) in THF (10 ml), and the mixture was stirred at 50° C. for 12 hours. After reaction, water was added to the reaction solution, followed by extraction with dichloromethane. The organic layer was washed with brine and dried over magnesium sulfate. Then, the residue was purified by silica gel chromatography with n-hexane/EtOAc (3:2 to 2:3) to obtain compound 103c (208 mg, 30% yield) as white crystals.

$^1$HNMR (500 MHz, CDCl$_3$): δ=7.74 (1H, d, J=1.7 Hz), 7.67 (2H, d, J=7.9 Hz), 7.60 (1H, dd, J=8.2, 2.0 Hz), 7.48 (2H, d, J=7.9 Hz), 7.29 (1H, d, J=7.9 Hz), 7.03 (1H, brs), 4.70 (2H, d, J=5.7 Hz), 4.60 (2H, d, J=6.8 Hz), 3.71 (1H, t, J=6.8 Hz).

LC-MS: >99% purity, RT 2.62 min, MS (m/z): 346 (M+H)$^+$

CBr$_4$ (79.6 mg, 0.24 mmol) was added to a solution of compound 103c (69.0 mg, 0.20 mmol) in CH$_2$Cl$_2$ (8 ml) at 0° C., and further, a solution of PPh$_3$ (78.7 mg, 0.30 mmol) in CH$_2$Cl$_2$ (4 ml) was added. The reaction solution was stirred at room temperature for 1 hour. Then, thiourea (15.2 mg, 0.20 mmol) was added thereto, and the mixture was stirred at 40° C. for 12 hours. The reaction solution was concentrated under reduced pressure. Then, the residue was purified by silica gel chromatography with CHCl$_3$/MeOH (19:1 to 7:3) and recrystallized from EtOH and Et$_2$O to obtain the title compound 103 (11.4 mg, 12% yield) as white crystals.

$^1$HNMR (500 MHz, DMSO-d6): δ=9.44 (1H, t, J=6.0 Hz), 9.04 (3H, brs), 7.83-7.81 (3H, m), 7.77 (1H, dd, J=8.2, 2.0 Hz), 7.56-7.52 (3H, m), 4.55-4.53 (4H, m).

LC-MS: >99% purity, RT 1.95 min, MS (m/z): 404 (M+H)$^+$

Synthesis of Compound 104

2-((4-Cyanobenzyl)carbamoyl)benzyl carbamimidoselenoate hydrobromide

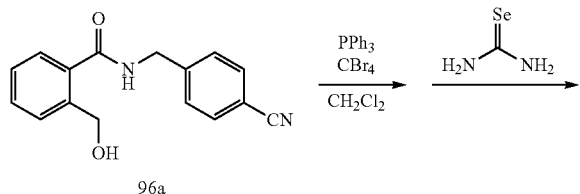

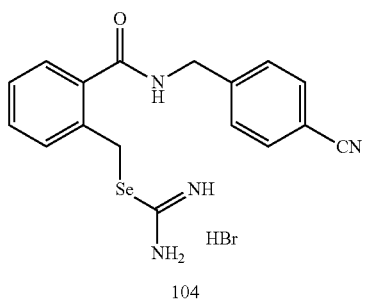

The same operation as in the synthesis of compound 74 was performed from compound 96a (133 mg, 0.50 mmol), CBr$_4$ (199 mg, 0.60 mmol), PPh$_3$ (197 mg, 0.75 mmol), and selenourea (61.5 mg, 0.50 mmol), and the residue was recrystallized from EtOH and Et$_2$O to obtain the title compound 104 (138 mg, 61% yield) as grayish-white crystals.

$^1$HNMR (500 MHz, DMSO-d6): δ=9.35-9.32 (2H, m), 9.05 (2H, brs), 7.83 (2H, d, J=8.5 Hz), 7.64 (1H, d, J=6.8 Hz), 7.55-7.51 (4H, m), 7.43 (1H, td, J=7.4, 1.7 Hz), 4.55 (2H, d, J=5.7 Hz), 4.50 (2H, s).

LC-MS: >99% purity, RT 0.65 min, MS (m/z): 372 (M+H)$^+$

Synthesis of Compound 105

5-Bromo-2-((3-methoxybenzyl)carbamoyl)benzyl carbamimidothioate hydrobromide

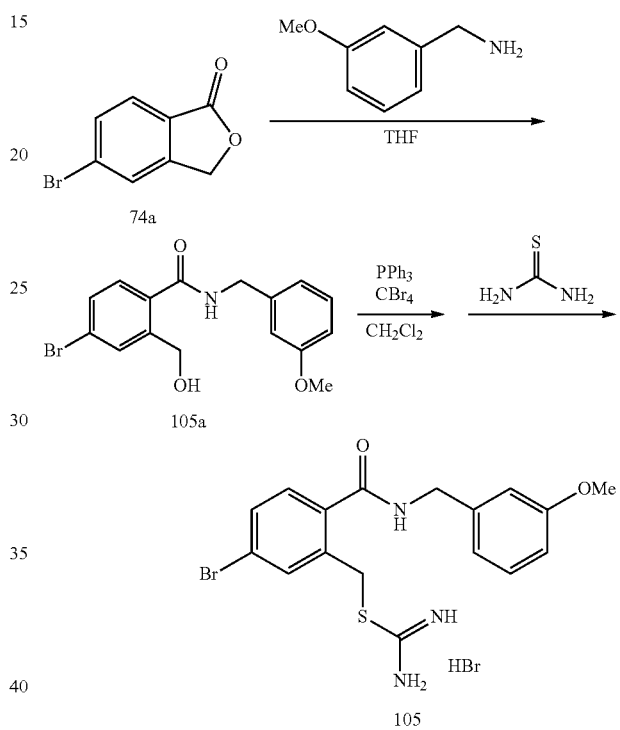

The same operation as in the synthesis of compound 74b was performed from 5-bromoisobenzofuran-1(3H)-one (compound 74a, 1065 mg, 5.00 mmol) and (3-methoxyphenyl)methanamine (0.776 mL, 6.00 mmol), and the reaction residue was purified by silica gel chromatography twice with n-hexane/EtOAc (7:3 to 2:3) and with n-hexane/EtOAc (7:3 to 1:1) to obtain compound 105a (364 mg, 21% yield) as white crystals.

$^1$HNMR (500 MHz, CD$_3$OD): δ=7.73 (1H, d, J=1.7 Hz), 7.51 (1H, dd, J=7.9, 1.7 Hz), 7.41 (1H, d, J=7.9 Hz), 7.25 (1H, t, J=7.9 Hz), 6.93 (2H, dd, J=4.3, 2.0 Hz), 6.82 (1H, dd, J=8.5, 2.3 Hz), 4.69 (2H, s), 4.51 (2H, s), 3.79 (3H, s).

LC-MS: >99% purity, RT 2.81 min, MS (m/z): 351 (M+H)$^+$

The same operation as in the synthesis of compound 74 was performed from compound 105a (105 mg, 0.30 mmol), CBr$_4$ (119 mg, 0.36 mmol), PPh$_3$ (118 mg, 0.45 mmol), and thiourea (22.8 mg, 0.30 mmol), and the residue was recrystallized from EtOH and Et$_2$O to obtain the title compound 105 (22.7 mg, 15% yield) as white crystals.

$^1$HNMR (500 MHz, DMSO-d6): δ=9.32 (1H, t, J=6.0 Hz), 9.04 (3H, brs), 7.82 (1H, d, J=1.7 Hz), 7.68 (1H, dd, J=8.2, 2.0 Hz), 7.52 (1H, d, J=8.5 Hz), 7.27 (1H, t, J=7.9

Hz), 6.92-6.91 (2H, m), 6.84 (1H, dd, J=8.2, 2.0 Hz), 5.76 (1H, s), 4.54 (2H, s), 4.44 (2H, d, J=5.7 Hz), 3.75 (3H, s).

LC-MS: >99% purity, RT 2.08 min, MS (m/z): 409 (M+H)+

Synthesis of Compound 106

5-Bromo-2-((3-methoxybenzyl)carbamoyl)benzyl carbamimidoselenoate hydrobromide

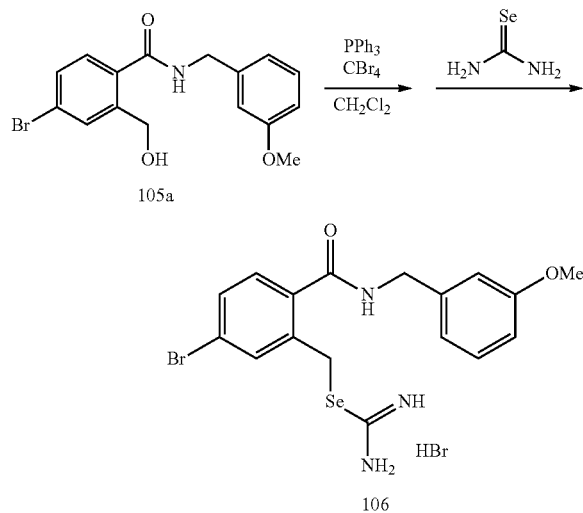

The same operation as in the synthesis of compound 74 was performed from compound 105a (105 mg, 0.30 mmol), CBr4 (119 mg, 0.36 mmol), PPh3 (118 mg, 0.45 mmol), and selenourea (22.8 mg, 0.19 mmol) to obtain the title compound 106 (74.6 mg, 46% yield) as white crystals.

$^1$HNMR (500 MHz, DMSO-d6): δ=9.33-9.28 (2H, m), 9.07 (2H, brs), 7.81 (1H, d, J=2.3 Hz), 7.65 (1H, dd, J=8.2, 2.0 Hz), 7.53 (1H, d, J=7.9 Hz), 7.27 (1H, t, J=7.9 Hz), 6.92-6.90 (2H, m), 6.84 (1H, d, J=8.5 Hz), 4.45-4.43 (4H, m), 3.75 (3H, s).

LC-MS: >99% purity, RT 1.95 min, MS (m/z): 456 (M+H)+

Synthesis of Compound 107

5-Bromo-2-((cyclopropylmethyl)carbamoyl)benzyl carbamimidoselenoate hydrobromide

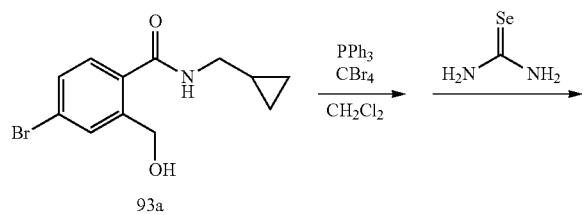

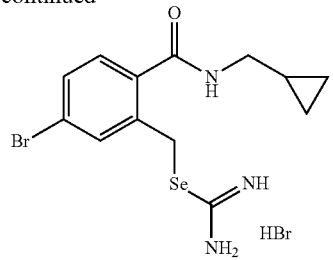

The same operation as in the synthesis of compound 74 was performed from compound 93a (85.2 mg, 0.30 mmol), CBr4 (119 mg, 0.336 mmol), PPh3 (118 mg, 0.45 mmol), and selenourea (22.8 mg, 0.19 mmol) to obtain the title compound 107 (64.6 mg, 46% yield) as white crystals.

$^1$HNMR (500 MHz, DMSO-d6): δ=9.36 (2H, brs), 9.06 (2H, brs), 8.87 (1.0H, t, J=5.7 Hz), 7.80 (1H, d, J=2.3 Hz), 7.63 (1H, dd, J=8.5, 2.3 Hz), 7.47 (1H, d, J=8.5 Hz), 4.45 (2H, s), 3.13 (2H, t, J=6.2 Hz), 1.02-1.01 (1H, m), 0.47-0.44 (2H, m), 0.23 (2H, q, J=4.9 Hz).

LC-MS: >99% purity, RT 1.40 min, MS (m/z): 391 (M+H)+

Synthesis of Compound 108

1,2-Phenylenebis(methylene) dicarbamimidoselenoate dihydrobromide

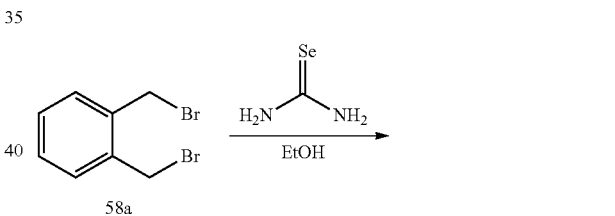

The same operation as in the synthesis of compound 2 was performed from 1,2-bis(bromomethyl)benzene (compound 58a, 264 mg, 1.00 mmol) and selenourea (246 mg, 2.00 mmol), and the residue was recrystallized from EtOH:Et2O (5:3) to obtain the title compound 108 (393 mg, 77% yield) as light orange crystals.

$^1$HNMR (500 MHz, CD3OD): δ=7.42 (2H, dd, J=8.0, 4.0 Hz), 7.33 (2H, dd, J=8.0, 4.0 Hz), 4.65 (4H, s).

LC-MS: >99% purity, RT 0.34 min, MS (m/z): 349 (M+H)+.

Synthesis of Compound 109

(4-Chloro-1,2-phenylene)bis(methylene) dicarbamimidoselenoate dihydrobromide

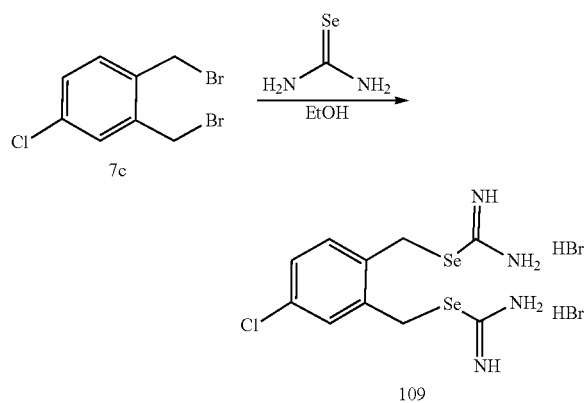

The same operation as in the synthesis of compound 2 was performed from 1,2-bis(bromomethyl)benzene (compound 7c, 308 mg, 1.00 mmol) and selenourea (246 mg, 2.00 mmol), and the residue was recrystallized from EtOH:Et$_2$O (5:3) to obtain the title compound 109 (263 mg, 48.4% yield) as pale yellow crystals.
$^1$HNMR (500 MHz, CD$_3$OD): δ=7.47-7.34 (3H, m), 4.67-4.60 (4H, m).
LC-MS: >99% purity, RT 0.37 min, MS (m/z): 385 (M+H)$^+$.

Synthesis of Compound 110

4-Bromo-2-((4-cyanobenzyl)carbamoyl)benzyl carbamimidoselenoate hydrobromide

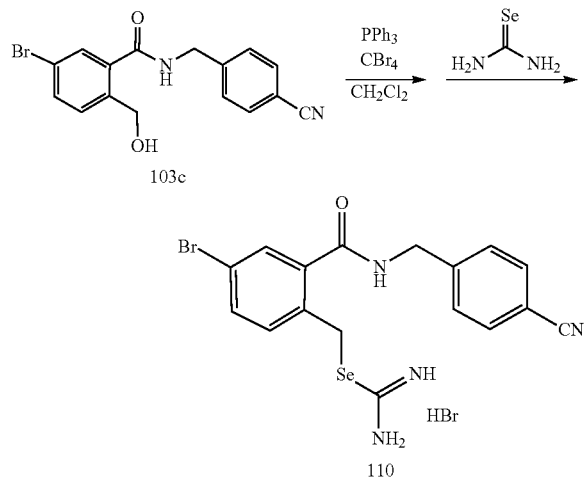

CBr$_4$ (79.6 mg, 0.24 mmol) was added to a solution of compound 103c (69.0 mg, 0.20 mmol) in CH$_2$Cl$_2$ (8 ml) at 0° C., and further, a solution of PPh$_3$ (78.7 mg, 0.30 mmol) in CH$_2$Cl$_2$ (4 ml) was added. The reaction solution was stirred at room temperature for 1 hour. Then, selenourea (24.6 mg, 0.20 mmol) was added thereto, and the mixture was stirred at 40° C. for 12 hours. The reaction solution was concentrated under reduced pressure. Then, the residue was recrystallized from EtOH and Et$_2$O to obtain the title compound 110 (6.7 mg, 6% yield) as white crystals.
$^1$HNMR (500 MHz, DMSO-d6): δ=9.39 (1H, t, J=5.7 Hz), 7.81-7.78 (3H, m), 7.72-7.70 (1H, m), 7.52 (2H, d, J=8.5 Hz), 7.46 (1H, d, J=8.5 Hz), 4.50 (2H, d, J=5.7 Hz), 4.42 (2H, s).
LC-MS: RT 2.06 min, MS (m/z): 451 (M+H)$^+$ Synthesis of Compound 111

2-Bromo-6-((4-cyanobenzyl)carbamoyl)benzyl carbamimidothioate hydrobromide

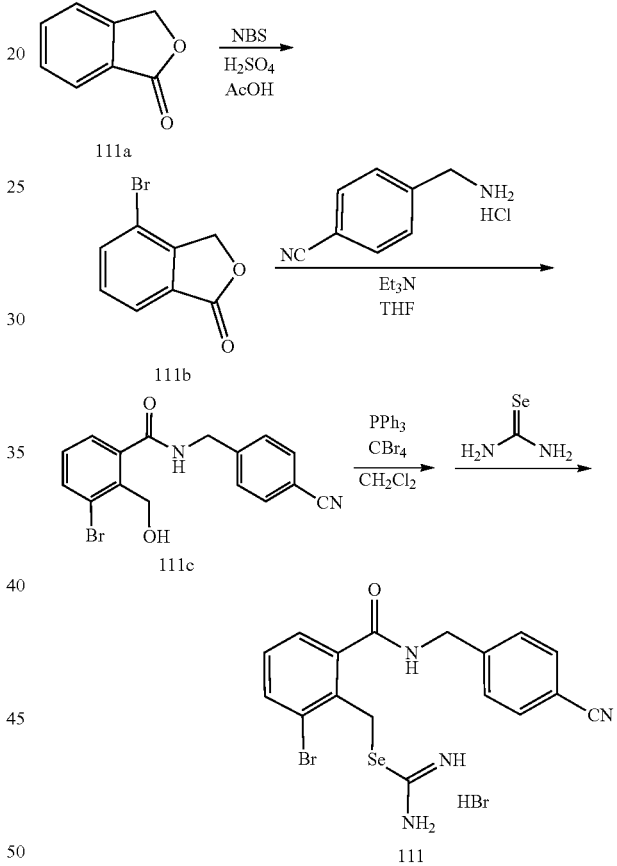

Sulfuric acid (4.5 ml) was added to a solution of isobenzofuran-1(3H)-one (compound 111a, 5.0 g, 37.3 mmol) in acetic acid (10 ml), and then, NBS (N-bromosuccinimide, 9.95 g, 55.9 mmol) was added in small portions over 9 hours with stirring at room temperature. Water (100 ml) was added to the reaction solution, followed by extraction with dichloromethane. The organic layer was washed with brine, dried over magnesium sulfate, and then concentrated under reduced pressure, and the residue was purified by silica gel chromatography with n-hexane/EtOAc (4:1 to 3:2) to obtain compound 111b (1.09 g, 14% yield) as white crystals.
$^1$HNMR (500 MHz, CDCl$_3$): δ=7.89 (1H, d, J=7.4 Hz), 7.81 (1H, d, J=7.4 Hz), 7.46 (1H, t, J=7.9 Hz), 5.24 (2H, s).
LC-MS: >99% purity, RT 5.95 min, MS (m/z): 215 (M+H)+

4-(Aminomethyl)benzonitrile hydrochloride (371 mg, 2.2 mmol) and Et₃N (607 mg, 6.0 mmol) were added to a solution of compound 111b (426 mg, 2.0 mmol) in THF (10 ml), and the mixture was stirred at 50° C. for 12 hours. After reaction, water was added to the reaction solution, followed by extraction with dichloromethane. The organic layer was washed with brine and dried over magnesium sulfate. Then, the residue was purified by silica gel chromatography with n-hexane/EtOAc (3:2 to 2:3) to obtain compound 111c (99.6 mg, 14% yield) as white crystals.

¹HNMR (500 MHz, CDCl₃): δ=7.72 (1H, dd, J=7.9, 1.1 Hz), 7.67 (2H, d, J=8.5 Hz), 7.53 (1H, dd, J=7.9, 1.1 Hz), 7.49 (2H, d, J=8.5 Hz), 7.24-7.23 (1H, m), 6.97 (1H, brs), 4.83 (2H, d, J=6.8 Hz), 4.71 (2H, d, J=6.2 Hz), 3.34 (1H, t, J=7.1 Hz).

LC-MS: >99% purity, RT 2.45 min, MS (m/z): 346 (M+H)⁺

CBr₄ (115 mg, 0.35 mmol) was added to a solution of compound 111c (99.6 mg, 0.29 mmol) in CH₂Cl₂ (10 ml) at 0° C., and further, a solution of PPh₃ (114 mg, 0.43 mmol) in CH₂Cl₂ (4 ml) was added. The reaction solution was stirred at room temperature for 1 hour. Then, thiourea (22.0 mg, 0.29 mmol) was added thereto, and the mixture was stirred at 40° C. for 12 hours. The reaction solution was concentrated under reduced pressure. Then, the residue was recrystallized from 2-propanol and n-hexane to obtain the title compound 111 (44.0 mg, 31% yield) as white crystals.

¹HNMR (500 MHz, DMSO-d6): δ=9.37 (1H, t, J=5.7 Hz), 9.08 (3H, brs), 7.86 (1H, d, J=6.8 Hz), 7.82 (2H, d, J=8.5 Hz), 7.60 (1H, d, J=7.4 Hz), 7.54 (2H, d, J=8.5 Hz), 7.44 (1H, t, J=7.9 Hz), 4.57 (2H, s), 4.55 (2H, d, J=6.2 Hz).

LC-MS: >99% purity, RT 0.80 min, MS (m/z): 404 (M+H)⁺

Synthesis of Compound 112

Quinoxaline-2,3-diylbis(methylene) dicarbamimidoselenoate dihydrobromide

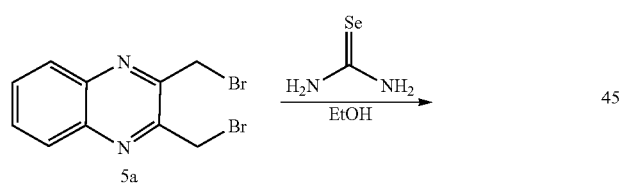

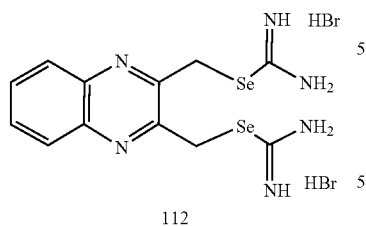

The same operation as in the synthesis of compound 1 was performed from compound 5a; 2,3-bis(bromomethyl)quinoxaline (316 mg, 1.00 mmol) and selenourea (246 mg, 2.00 mmol), and the residue was recrystallized from EtOH:Et₂O (1:1) to obtain the title compound 112 (432 mg, 77% yield) as grayish-white crystals.

¹HNMR (500 MHz, DMSO-d6): δ=9.38 (3H, brs), 9.25 (3H, brs), 8.08-8.06 (2H, m), 7.93-7.90 (2H, m), 5.05 (4H, s).

LC-MS: 96% purity, RT 0.35 min, MS (m/z): 403 (M+H)⁺.

Synthesis of Compound 113

5-Bromo-2-((4-cyanobenzyl)carbamoyl)benzyl carbamimidoselenoate hydrobromide

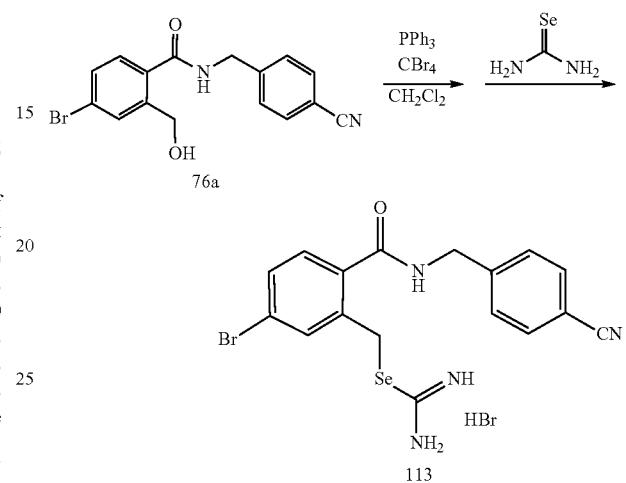

The same operation as in the synthesis of compound 74 was performed from compound 76a (103 mg, 0.30 mmol), CBr₄ (119 mg, 0.36 mmol), PPh₃ (118 mg, 0.45 mmol), and selenourea (22.8 mg, 0.30 mmol), and the residue was recrystallized from 2-propanol to obtain the title compound 113 (62.8 mg, 40% yield) as white crystals.

¹HNMR (500 MHz, DMSO-d6): δ=9.35-9.33 (1H, m), 9.10 (3H, brs), 7.80-7.78 (3H, m), 7.63-7.61 (1H, m), 7.55-7.49 (3H, m), 4.50 (2H, d, J=5.67 Hz), 4.42 (2H, s).

LC-MS: >99% purity, RT 1.64 min, MS (m/z): 451 (M+H)⁺

Synthesis of Compound 114

5-Bromo-2-((4-(trifluoromethyl)benzyl)carbamoyl) benzyl carbamimidothioate hydrobromide

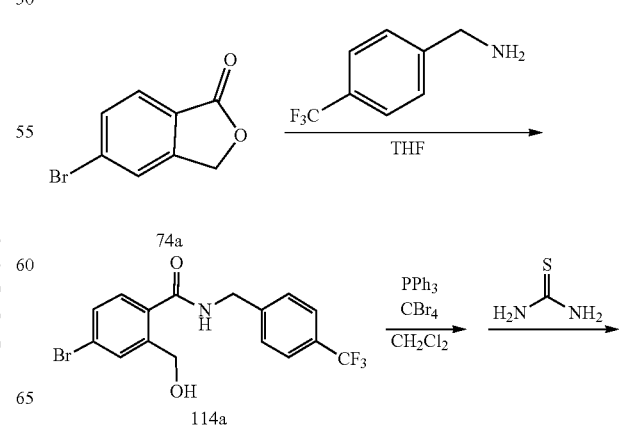

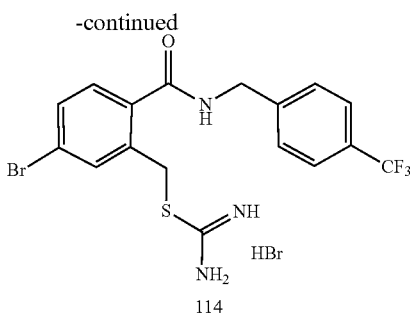

114

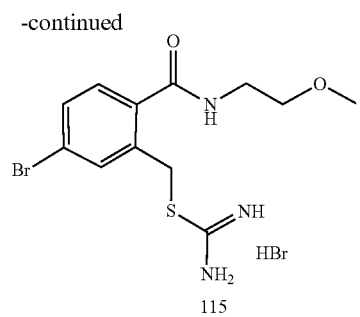

115

(4-(Trifluoromethyl)phenyl)methanamine (0.848 mL, 6.00 mmol) was added to a solution of compound 74a; 5-bromoisobenzofuran-1(3H)-one (1065 mg, 5.00 mmol) in THF (15 ml), and the mixture was stirred at 50° C. for 24 hours. The reaction solution was concentrated under reduced pressure, and then, water was added to the residue, followed by extraction with dichloromethane. The organic layer was washed with brine, dried over magnesium sulfate, and then concentrated under reduced pressure, and the residue was purified by silica gel chromatography with n-hexane/EtOAc (7:3 to 1:1) to obtain compound 114a (137 mg, 7.0% yield) as white crystals.

$^1$HNMR (500 MHz, CDCl$_3$): δ=7.63 (2H, d, J=8.5 Hz), 7.58 (1H, d, J=1.7 Hz), 7.51 (1H, dd, J=8.5, 1.7 Hz), 7.49 (1H, s), 7.46 (2H, d, J=8.5 Hz), 6.86 (1H, brs), 4.70 (2H, d, J=6.2 Hz), 4.60 (2H, d, J=6.8 Hz), 3.97 (1H, t, J=7.1 Hz).

LC-MS: >99% purity, RT 3.35 min, MS (m/z): 389 (M+H)$^+$

The same operation as in the synthesis of compound 74 was performed from compound 114a (137 mg, 0.35 mmol), CBr$_4$ (140 mg, 0.42 mmol), PPh$_3$ (138 mg, 0.53 mmol), and thiourea (26.8 mg, 0.35 mmol), and the residue was recrystallized from EtOH and Et$_2$O to obtain the title compound 114 (11.3 mg, 6.1% yield) as white crystals.

$^1$HNMR (400 MHz, DMSO-d6): δ=9.41 (1H, t, J=6.3 Hz), 8.96 (3H, brs), 7.83 (1H, d, J=2.0 Hz), 7.73-7.68 (3H, m), 7.58-7.55 (3H, m), 4.56-4.53 (4H, m).

LC-MS: >99% purity, RT 2.72 min, MS (m/z): 447 (M+H)$^+$

Synthesis of Compound 115

5-Bromo-2-((2-methoxyethyl)carbamoyl)benzyl carbamimidothioate hydrobromide

2-Methoxyethan-1-amine (0.491 mL, 5.71 mmol) was added to a solution of compound 74a; 5-bromoisobenzofuran-1(3H)-one (1013 mg, 4.76 mmol) in THF (15 ml), and the mixture was stirred at 50° C. for 24 hours. The reaction solution was concentrated under reduced pressure, and then, water was added to the residue, followed by extraction with dichloromethane. The organic layer was washed with brine, dried over magnesium sulfate, and then concentrated under reduced pressure, and the residue was purified by silica gel chromatography with n-hexane/EtOAc (1:1 to 3:7) to obtain compound 115a (246 mg, 18% yield) as a colorless oil substance.

$^1$HNMR (400 MHz, CDCl$_3$): δ=7.57 (1H, d, J=2.0 Hz), 7.50 (1H, dd, J=8.3, 2.0 Hz), 7.41 (1H, d, J=8.3 Hz), 6.64 (1H, brs), 4.57 (2H, d, J=6.3 Hz), 4.37 (1H, t, J=7.1 Hz), 3.67-3.63 (2H, m), 3.60-3.56 (2H, m), 3.40 (3H, s).

LC-MS: >99% purity, RT 1.65 min, MS (m/z): 289 (M+H)$^+$

The same operation as in the synthesis of compound 74 was performed from compound 115a (86.4 mg, 0.30 mmol), CBr$_4$ (119 mg, 0.36 mmol), PPh$_3$ (118 mg, 0.45 mmol), and thiourea (22.8 mg, 0.30 mmol), and the residue was recrystallized from EtOH and Et$_2$O to obtain the title compound 115 (24.2 mg, 19% yield) as white crystals.

$^1$HNMR (500 MHz, DMSO-d6): δ=8.82 (1H, brs), 7.76 (H, d, J=2.3 Hz), 7.61 (1H, dd, J=7.9, 2.3 Hz), 7.39 (1H, d, J=7.9 Hz), 4.46 (2H, s), 3.44-3.35 (4H, m), 3.24 (3H, s).

LC-MS: >99% purity, RT 0.72 min, MS (m/z): 347 (M+H)$^+$

Synthesis of Compound 116

5-Bromo-2-((3-chloro-4-fluorobenzyl)carbamoyl) benzyl carbamimidothioate hydrobromide

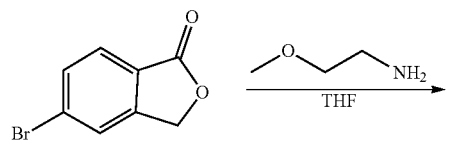

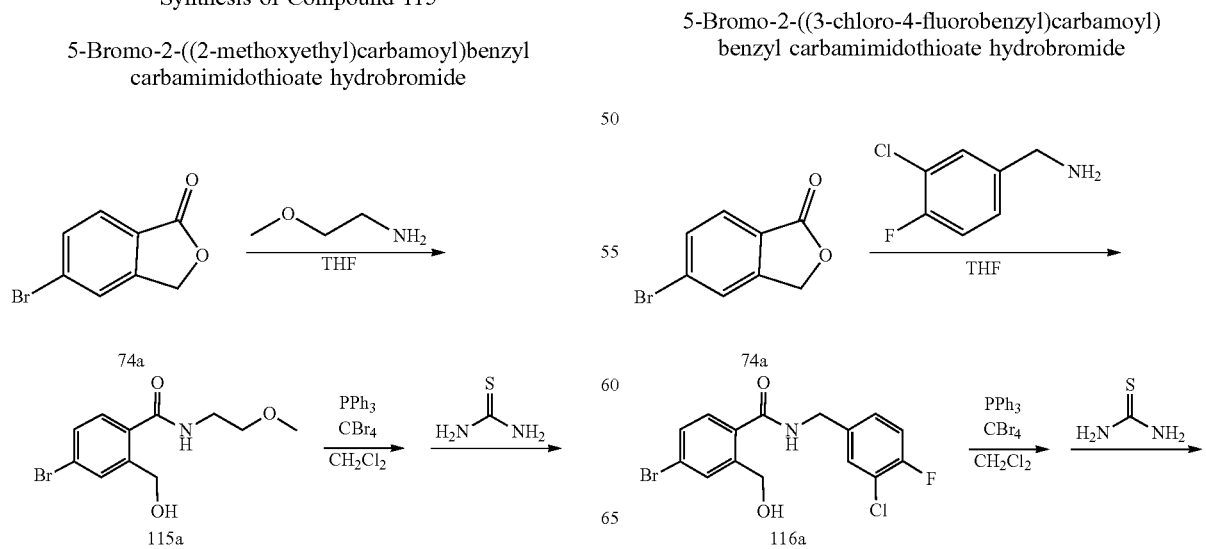

-continued

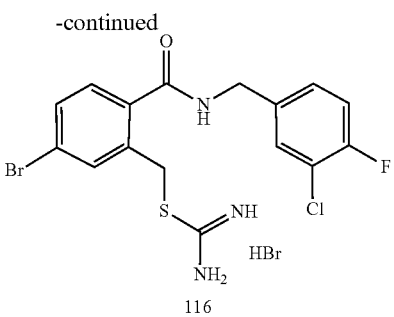

116

(3-Chloro-4-fluorophenyl)methanamine (0.491 mL, 5.71 mmol) was added to a solution of compound 74a; 5-bromoisobenzofuran-1(3H)-one (1013 mg, 4.76 mmol) in THF (15 ml), and the mixture was stirred at 50° C. for 24 hours. The reaction solution was concentrated under reduced pressure, and then, water was added to the residue, followed by extraction with dichloromethane. The organic layer was washed with brine, dried over magnesium sulfate, and then concentrated under reduced pressure, and the residue was purified by silica gel chromatography with n-hexane/EtOAc (7:3 to 1:1) to obtain compound 116a (260 mg, 23% yield) as yellow crystals.

$^1$HNMR (500 MHz, CDCl$_3$): δ=7.57 (1H, d, J=1.7 Hz), 7.51 (1H, dd, J=8.2, 2.0 Hz), 7.45 (1H, d, J=8.5 Hz), 7.40 (1H, dd, J=6.8, 2.3 Hz), 7.24-7.22 (1H, m), 7.14 (1H, t, J=8.5 Hz), 6.80 (1H, brs), 4.59-4.57 (4H, m), 3.96 (1H, t, J=6.8 Hz).

LC-MS: >99% purity, RT 3.21 min, MS (m/z): 373 (M+H)$^+$

The same operation as in the synthesis of compound 74 was performed from compound 116a (112 mg, 0.30 mmol), CBr$_4$ (119 mg, 0.36 mmol), PPh$_3$ (118 mg, 0.45 mmol), and thiourea (22.8 mg, 0.30 mmol), and the residue was recrystallized from EtOH and Et$_2$O to obtain the title compound 116 (54.3 mg, 35% yield) as white crystals.

$^1$HNMR (500 MHz, DMSO-d6): δ=9.33 (1H, t, J=6.0 Hz), 9.03 (3H, brs), 7.82 (1H, d, J=1.7 Hz), 7.68 (1H, dd, J=8.2, 2.0 Hz), 7.57-7.53 (2H, m), 7.41-7.36 (2H, m), 4.53 (2H, s), 4.45 (2H, d, J=5.7 Hz).

LC-MS: >99% purity, RT 2.24 min, MS (m/z): 431 (M+H)$^+$

Synthesis of Compound 117

4-Bromo-2-((4-bromobenzyl)carbamoyl)benzyl carbamimidothioate hydrobromide

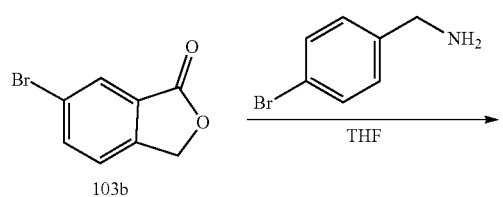

103b

-continued

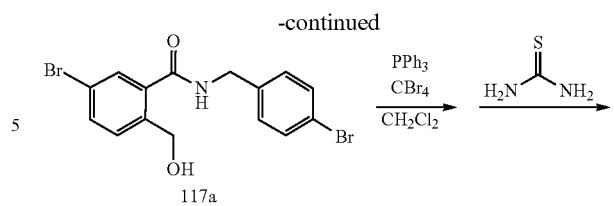

117a

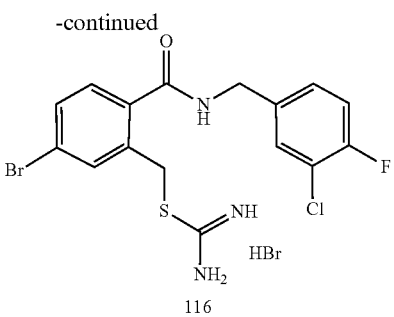

117

(4-Bromophenyl)methanamine (335 mg, 1.80 mmol) was added to a solution of compound 103b; 6-bromoisobenzofuran-1(3H)-one (320 mg, 1.50 mmol) in THF (15 ml), and the mixture was stirred at 50° C. for 24 hours. The reaction solution was concentrated under reduced pressure, and then, water was added to the residue, followed by extraction with dichloromethane. The organic layer was washed with brine, dried over magnesium sulfate, and then concentrated under reduced pressure, and the residue was purified by silica gel chromatography with n-hexane/EtOAc (7:3 to 1:1) to obtain compound 117a (242 mg, 40% yield) as yellow crystals.

$^1$HNMR (500 MHz, CDCl$_3$): δ=7.69 (1H, d, J=2.3 Hz), 7.58 (1H, dd, J=8.2, 2.0 Hz), 7.50 (2H, d, J=8.5 Hz), 7.29 (1H, d, J=7.9 Hz), 7.24 (2H, d, J=8.5 Hz), 6.75 (1H, brs), 4.60-4.58 (4H, m), 3.89 (1H, t, J=6.8 Hz).

LC-MS: >99% purity, RT 3.28 min, MS (m/z): 400 (M+H)$^+$

The same operation as in the synthesis of compound 74 was performed from compound 117a (112 mg, 0.30 mmol), CBr$_4$ (119 mg, 0.36 mmol), PPh$_3$ (118 mg, 0.45 mmol), and thiourea (22.8 mg, 0.30 mmol), and the residue was recrystallized from EtOH to obtain the title compound 117 (14.8 mg, 9.2% yield) as white crystals.

$^1$HNMR (500 MHz, DMSO-d6): δ=9.38 (1H, t, J=6.0 Hz), 8.97 (3H, brs), 7.76-7.75 (2H, m), 7.55 (2H, d, J=8.5 Hz), 7.52 (1H, d, J=9.1 Hz), 7.32 (2H, d, J=7.9 Hz), 4.51 (2H, s), 4.43 (2H, d, J=5.7 Hz).

LC-MS: >99% purity, RT 2.51 min, MS (m/z): 458 (M+H)$^+$

Synthesis of Compound 118

4-Bromo-2-((4-cyanobenzyl)carbamoyl)benzyl (E)-N'-(3-chloro-4-fluorophenyl)carbamimidothioate hydrobromide

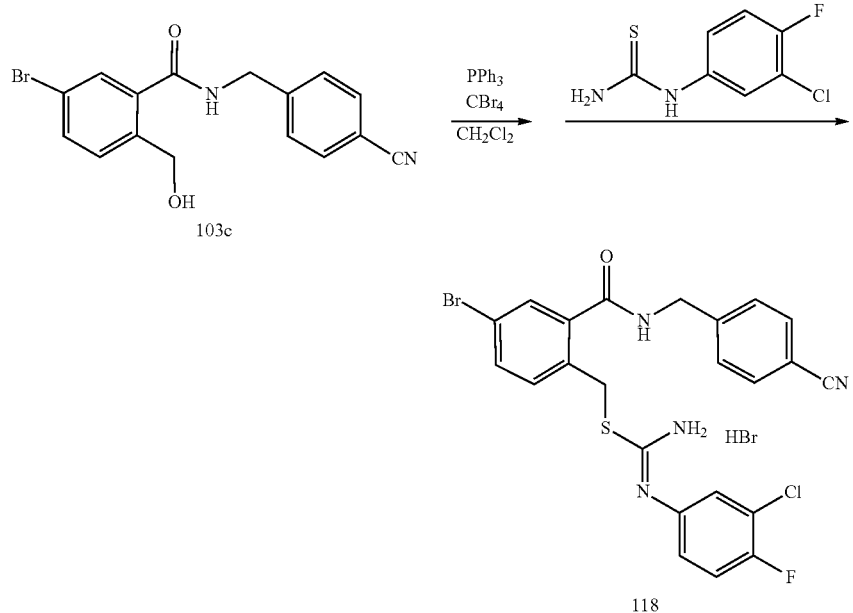

The same operation as in the synthesis of compound 74 was performed from compound 103c; 5-bromo-N-(4-cyanobenzyl)-2-(hydroxymethyl)benzamide (173 mg, 0.50 mmol), CBr$_4$ (199 mg, 0.60 mmol), PPh$_3$ (197 mg, 0.75 mmol), and 1-(3-chloro-4-fluorophenyl)thiourea (102 mg, 0.50 mmol), and the residue was recrystallized from EtOH to obtain the title compound 118 (232 mg, 76% yield) as white crystals.

$^1$HNMR (500 MHz, DMSO-d6): δ=9.41-9.38 (1H, m), 7.79-7.74 (5H, m), 7.53-7.48 (5H, m), 7.25 (1H, brs), 4.58 (2H, s), 4.50-4.49 (2H, m).

LC-MS: >99% purity, RT 3.14 min, MS (m/z): 533 (M+H)$^+$

Synthesis of Compound 119

4-Bromo-2-((4-cyanobenzyl)carbamoyl)benzyl (E)-N'-(4-bromophenyl)carbamimidothioate hydrobromide

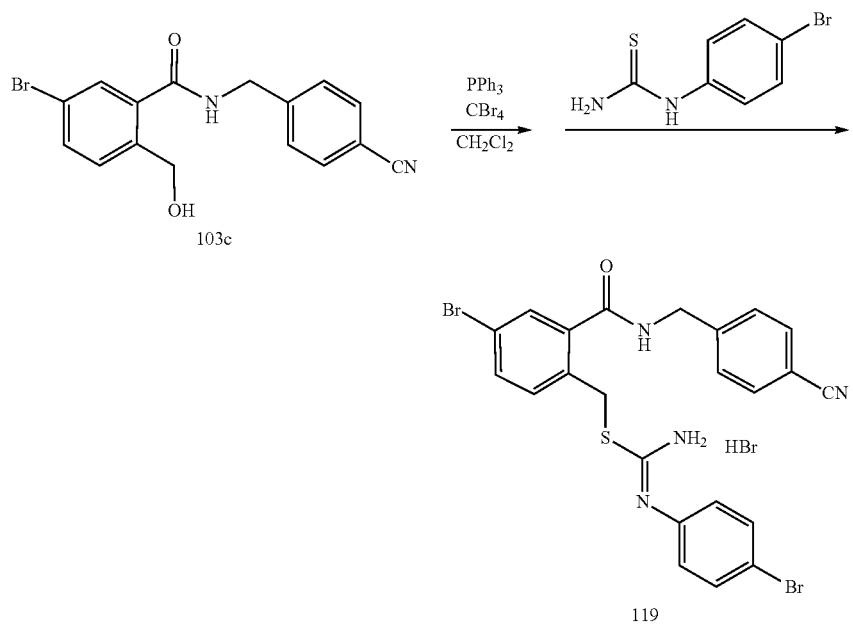

The same operation as in the synthesis of compound 74 was performed from compound 103c; 5-bromo-N-(4-cyanobenzyl)-2-(hydroxymethyl)benzamide (173 mg, 0.50 mmol), CBr$_4$ (199 mg, 0.60 mmol), PPh$_3$ (197 mg, 0.75 mmol), and 1-(4-bromophenyl)thiourea (102 mg, 0.50 mmol), and the residue was recrystallized from EtOH to obtain the title compound 118 (143 mg, 45% yield) as white crystals.

$^1$HNMR (500 MHz, DMSO-d6): δ=9.40 (1H, brs), 7.83-7.81 (4H, m), 7.78-7.77 (1H, m), 7.67-7.65 (2H, m), 7.55-7.53 (4H, m), 7.19 (1H, brs), 4.60 (2H, brs), 4.53 (2H, d, J=5.7 Hz).

LC-MS: >99% purity, RT 2.84 min, MS (m/z): 559 (M+H)$^+$

Synthesis of Compound 120

6,6'-(((4-Fluoro-1,2-phenylene)bis(methylene))bis(sulfanediyl))bis(3-(cyclopropylmethyl)-1,2,3,4-tetrahydro-1,3,5-triazine)

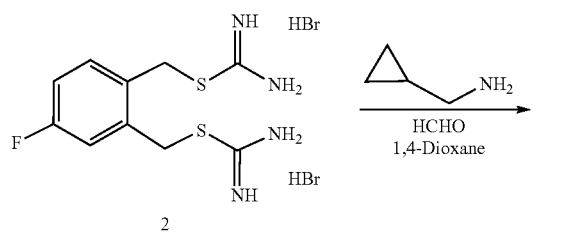

120

Reaction was performed by the same operation as in the synthesis of compound 9 from cyclopropylmethanamine (88.9 mg, 1.25 mmol), formaldehyde (187.5 μL, 37% wt. solution in water, 2.51 mmol) and (4-fluoro-1,2-phenylene)bis(methylene) dicarbamimidothioate dihydrobromide (compound 2, 272.2 mg, 0.63 mmol), and the reaction residue was recrystallized from EtOH and Et$_2$O (1:2) and subsequently from 2-propanol to obtain the title compound 120 (337.7 mg, 58.4% yield) as white crystals.

$^1$HNMR (500 MHz, DMSO-d6): δ=7.50-7.48 (1H, m), 7.33-7.31 (1H, m), 7.26-7.22 (1H, m), 4.60 (4H, brs), 4.43 (8H, brs), 2.23-2.20 (4H, m), 0.84-0.82 (2H, m), 0.49-0.46 (4H, m), 0.03-0.01 (4H, m).

LC-MS: 92% purity, RT 0.45 min, MS (m/z): 464 (M+H)$^+$

Synthesis of Compound 121

6,6'-(((4-Fluoro-1,2-phenylene)bis(methylene))bis(sulfanediyl))bis(3-(cyclohexylmethyl)-1,2,3,4-tetrahydro-1,3,5-triazine)

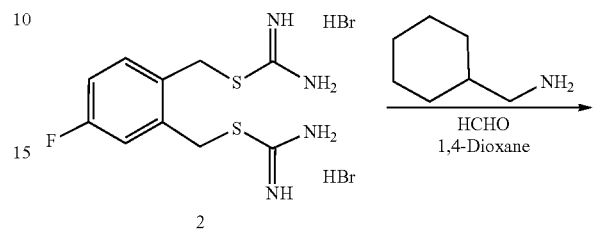

121

Reaction was performed by the same operation as in the synthesis of compound 9 from cyclohexylmethanamine (56.6 mg, 0.50 mmol), formaldehyde (75.0 μL, 37% wt. solution in water, 1.00 mmol) and (4-fluoro-1,2-phenylene) bis(methylene) dicarbamimidothioate dihydrobromide (compound 2, 108.5 mg, 0.25 mmol), and the reaction residue was recrystallized from 2-propanol and Et$_2$O (1:1) to obtain the title compound 121 (147.1 mg, 53.8% yield) as white crystals.

$^1$HNMR (500 MHz, DMSO-d6): δ=7.51-7.49 (1H, m), 7.34-7.33 (1H, m), 7.22-7.20 (1H, m), 4.62-4.60 (4H, m), 4.34-4.31 (8H, m), 2.13-2.07 (4H, m), 1.65-1.62 (10H, m), 1.44-1.42 (2H, m), 1.21-1.11 (6H, m), 0.89-0.80 (4H, m).

LC-MS: 91% purity, RT 2.00 min, MS (m/z): 547 (M+H)$^+$

Synthesis of Compound 122

1,2-Phenylenebis(methylene) (E,E)-bis(N-(3-chloro-4-fluorophenyl)carbamimidothioate) dihydrobromide

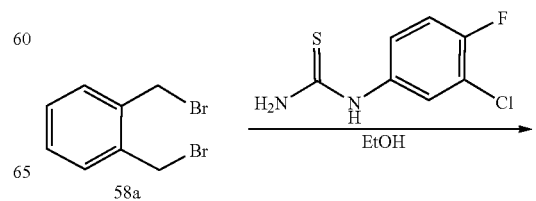

58a

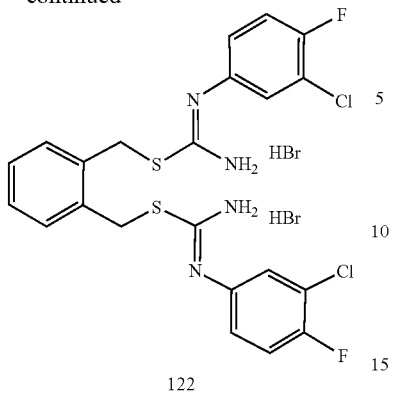

122

In an argon atmosphere, 1-(3-chloro-4-fluorophenyl)thiourea (205 mg, 1.00 mmol) was added to a solution of compound 58a; 1,2-bis(bromomethyl)benzene (132 mg, 0.50 mmol) in EtOH (8 mL) at room temperature, and the reaction mixture was stirred at 80° C. for 3 hours. The reaction solution was brought back to room temperature and concentrated under reduced pressure. Then, the residue was recrystallized from EtOH and Et$_2$O (1:2) to obtain the title compound 122 (236.7 mg, 70% yield) as white crystals.

$^1$HNMR (500 MHz, DMSO-d6): δ=7.62-7.43 (8H, m), 7.30-7.14 (2H, m), 4.72 (4H, brs).

LC-MS: >99% purity, RT 3.03 min, MS (m/z): 512 (M+H)$^+$

Synthesis of Compound 123

(4,5-Dichloro-1,2-phenylene)bis(methylene) (E,E)-bis(N'-(4-chlorophenyl)carbamimidothioate) dihydrobromide

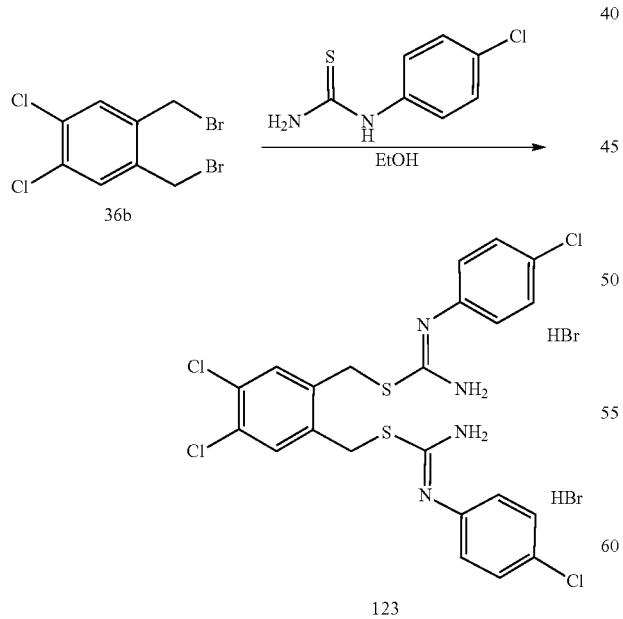

123

The same operation as in the synthesis of compound 2 was performed from compound 36b; 1,2-bis(bromomethyl)-4,5-dichlorobenzene (180 mg, 0.54 mmol) and 1-(4-chlorophenyl)thiourea (202 mg, 1.08 mmol), and the reaction product was concentrated under reduced pressure. Then, the residue was recrystallized from EtOH and Et$_2$O (1:1) to obtain the title compound 123 (263 mg, 68.8% yield) as white crystals.

$^1$HNMR (500 MHz, DMSO-d6): δ=7.81 (2H, s), 7.59 (4H, d, J=8.5 Hz), 7.32 (4H, d, J=8.5 Hz), 4.81 (4H, brs).

LC-MS: >99% purity, RT 4.19 min, MS (m/z): 545 (M+H)$^+$

Synthesis of Compound 124

(4,5-Dichloro-1,2-phenylene)bis(methylene) (E,E)-bis(N'-(4-methoxyphenyl)carbamimidothioate) dihydrobromide

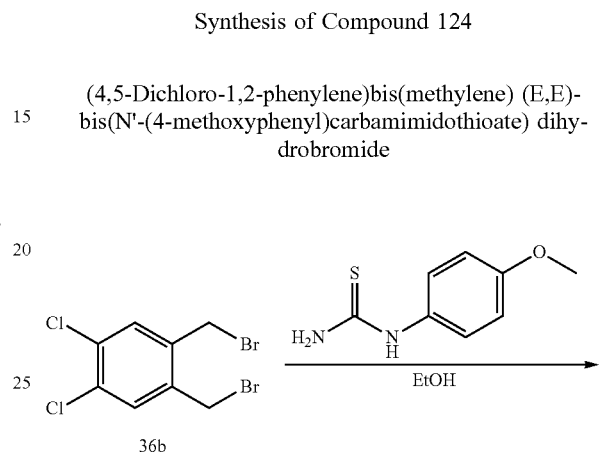

36b

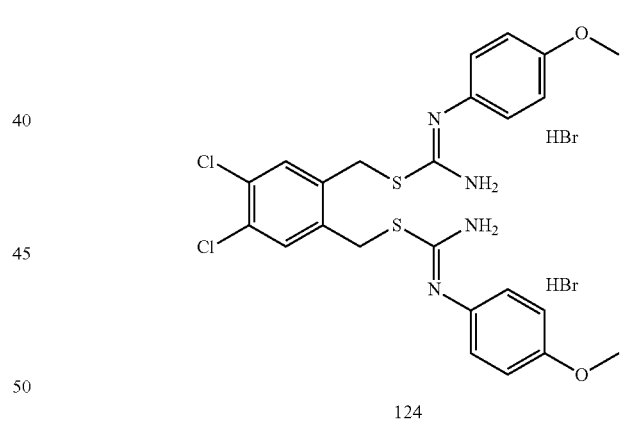

124

The same operation as in the synthesis of compound 2 was performed from compound 36b; 1,2-bis(bromomethyl)-4,5-dichlorobenzene (370 mg, 1.11 mmol) and 1-(4-methoxyphenyl)thiourea (405 mg, 2.22 mmol), and the reaction product was concentrated under reduced pressure. Then, the residue was recrystallized from EtOH and Et$_2$O (1:1) to obtain the title compound 124 (770 mg, 99% yield) as white crystals.

$^1$HNMR (500 MHz, DMSO-d6): δ=7.77 (2H, s), 7.21-7.11 (4H, m), 7.03 (4H, d, J=8.5 Hz), 4.75 (4H, brs), 3.75 (6H, s).

LC-MS: >99% purity, RT 2.02 min, MS (m/z): 536 (M+H)$^+$

Synthesis of Compound 125

(4,5-Dichloro-1,2-phenylene)bis(methylene) (E,E)-bis(N'-(3-chlorophenyl)carbamimidothioate) dihydrobromide

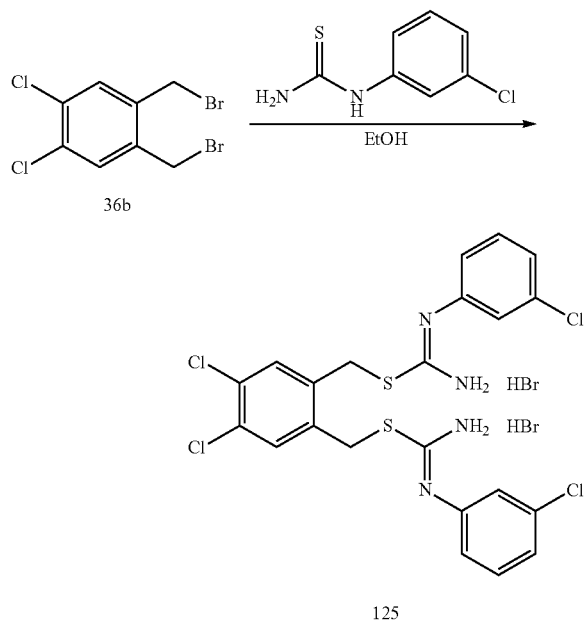

The same operation as in the synthesis of compound 2 was performed from compound 36b; 1,2-bis(bromomethyl)-4,5-dichlorobenzene (151 mg, 0.454 mmol) and 1-(3-chlorophenyl)thiourea (169 mg, 0.907 mmol), and the reaction product was concentrated under reduced pressure. Then, the residue was recrystallized from EtOH and Et$_2$O (1:1) to obtain the title compound 125 (269 mg, 84% yield) as white crystals.

$^1$HNMR (500 MHz, DMSO-d6): δ=7.82 (2H, s), 7.56-7.47 (4H, m), 7.40 (2H, s), 7.27 (2H, d, J=7.9 Hz), 4.87 (4H, s).

LC-MS: >99% purity, RT 4.72 min, MS (m/z): 545 (M+H)$^+$

Synthesis of Compound 126

(4-Fluoro-1,2-phenylene)bis(methylene) (E,E)-bis(N'-(4-bromophenyl)carbamimidothioate) dihydrobromide

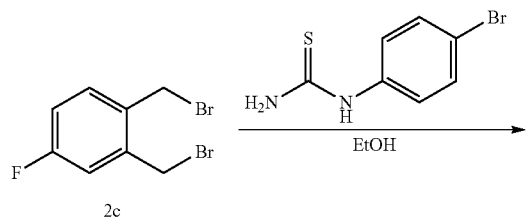

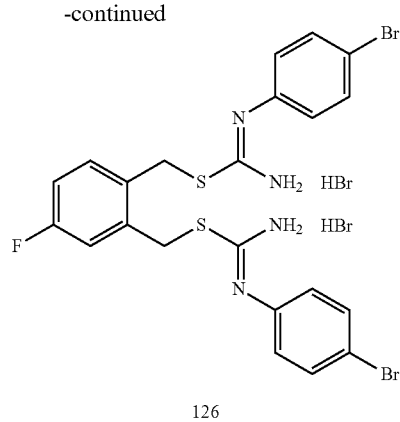

The same operation as in the synthesis of compound 2 was performed from compound 2c; 1,2-bis(bromomethyl)-4-fluorobenzene (211 mg, 0.75 mmol) and 1-(4-bromophenyl)thiourea (347 mg, 1.50 mmol), and the reaction product was concentrated under reduced pressure. Then, the residue was recrystallized from EtOH and Et$_2$O (1:1) to obtain the title compound 126 (468 mg, 84% yield) as white crystals.

$^1$HNMR (500 MHz, DMSO-d6): δ=9.67 (4H, brs), 7.73-7.71 (4H, m), 7.58-7.57 (1H, m), 7.42-7.40 (1H, m), 7.32-7.26 (5H, m), 4.86-4.85 (4H, m).

LC-MS: 90% purity, RT 3.39 min, MS (m/z): 583 (M+H)$^+$

Synthesis of Compound 127

(4-Fluoro-1,2-phenylene)bis(methylene) (E,E)-bis(N'-(4-fluorophenyl)carbamimidothioate) dihydrobromide

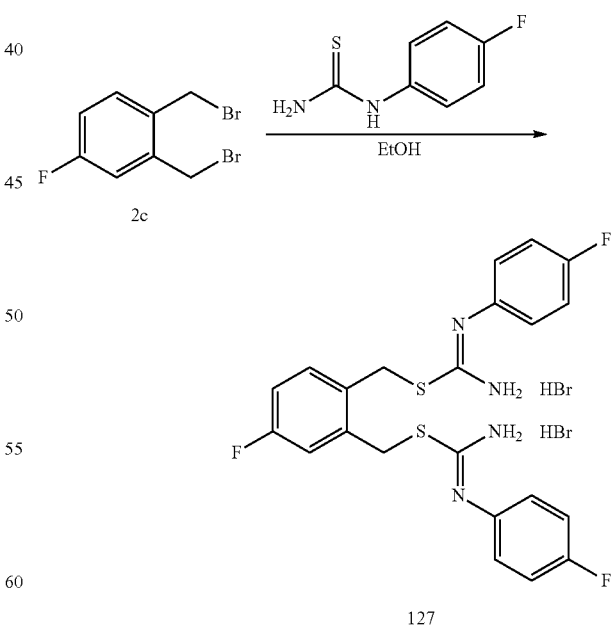

The same operation as in the synthesis of compound 2 was performed from compound 2c; 1,2-bis(bromomethyl)-4-fluorobenzene (211 mg, 0.75 mmol) and 1-(4-fluorophenyl)thiourea (256 mg, 1.50 mmol), and the reaction product was concentrated under reduced pressure. Then, the residue was recrystallized from EtOH and Et₂O (1:1) to obtain the title compound 127 (409 mg, 88% yield) as white crystals.

¹HNMR (500 MHz, DMSO-d6): δ=9.75 (4H, brs), 7.58-7.28 (11H, m), 4.85 (4H, brs).

LC-MS: 93% purity, RT 1.70 min, MS (m/z): 461 (M+H)⁺

Synthesis of Compound 128

(4-Fluoro-1,2-phenylene)bis(methylene) (E,E)-bis (N'-(4-methoxyphenyl)carbamimidothioate) dihydrobromide

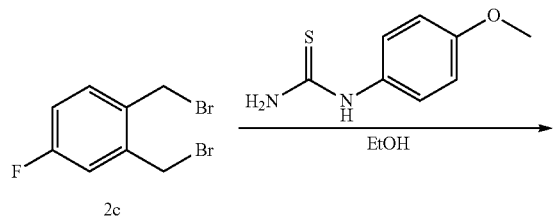

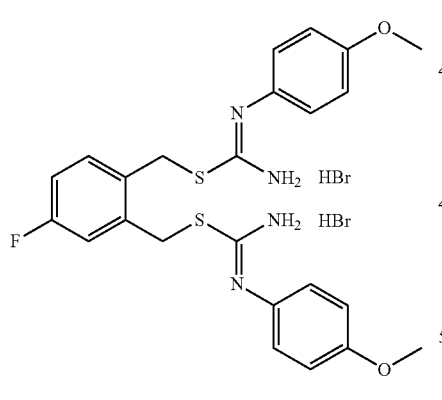

The same operation as in the synthesis of compound 2 was performed from compound 2c; 1,2-bis(bromomethyl)-4-fluorobenzene (211 mg, 0.75 mmol) and 1-(4-methoxyphenyl)thiourea (274 mg, 1.50 mmol), and the reaction product was concentrated under reduced pressure. Then, the residue was recrystallized from EtOH and Et₂O (1:1) to obtain the title compound 128 (400 mg, 83% yield) as white crystals.

¹HNMR (500 MHz, DMSO-d6): δ=7.59-7.56 (1H, m), 7.41-7.39 (1H, m), 7.32-7.31 (1H, m), 7.23-7.20 (4H, m), 7.07-7.06 (4H, m), 4.80 (4H, brs), 3.79 (6H, s).

LC-MS: >99% purity, RT 1.60 min, MS (m/z): 485 (M+H)⁺

Synthesis of Compound 129

(4-Fluoro-1,2-phenylene)bis(methylene) (E,E)-bis (N'-(3-chloro-4-fluorophenyl)carbamimidothioate) dihydrobromide

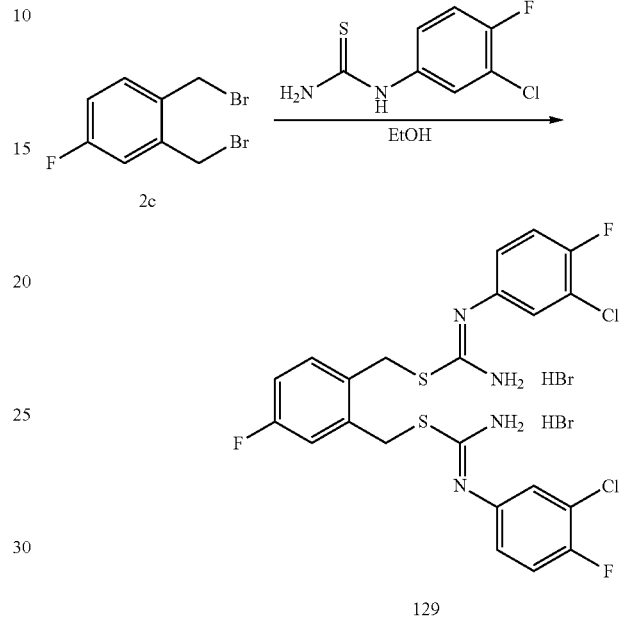

The same operation as in the synthesis of compound 2 was performed from compound 2c; 1,2-bis(bromomethyl)-4-fluorobenzene (211 mg, 0.75 mmol) and 1-(3-chloro-4-fluorophenyl)thiourea (307 mg, 1.50 mmol), and the reaction product was concentrated under reduced pressure. Then, the residue was recrystallized from EtOH and Et₂O (1:1), and the crystals were washed with Et₂O:n-hexane (1:2) to obtain the title compound 129 (506 mg, 98% yield) as white crystals.

¹HNMR (500 MHz, DMSO-d6): δ=9.65 (4H, brs), 7.66-7.57 (5H, m), 7.43-7.30 (4H, m), 4.87-4.86 (4H, m).

LC-MS: 92% purity, RT 3.74 min, MS (m/z): 530 (M+H)⁺

Synthesis of Compound 130

(4-Fluoro-1,2-phenylene)bis(methylene) (E,E)-bis (N'-(2,4-difluorophenyl)carbamimidothioate) dihydrobromide

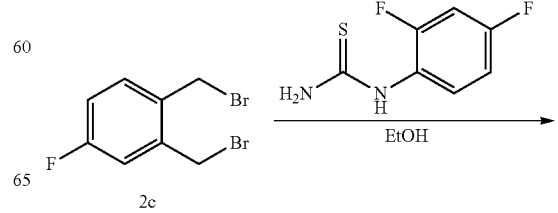

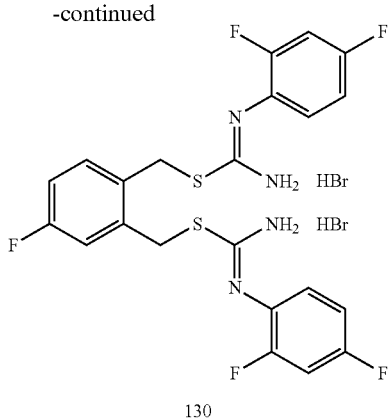

130

The same operation as in the synthesis of compound 2 was performed from compound 2c; 1,2-bis(bromomethyl)-4-fluorobenzene (211 mg, 0.75 mmol) and 1-(2,4-difluorophenyl)thiourea (283 mg, 1.50 mmol), and the reaction product was concentrated under reduced pressure. Then, the residue was recrystallized from EtOH and Et$_2$O (1:1), and the crystals were washed with Et$_2$O:n-hexane (1:2) to obtain the title compound 130 (420 mg, 85% yield) as white crystals.

$^1$HNMR (500 MHz, DMSO-d6): δ=9.67 (4H, brs), 7.61-7.43 (6H, m), 7.31-7.24 (3H, m), 4.86 (4H, brs).

LC-MS: 95% purity, RT 3.22 min, MS (m/z): 497 (M+H)$^+$

Synthesis of Compound 131

(4,5-Difluoro-1,2-phenylene)bis(methylene) dicarbamimidothioate dihydrobromide

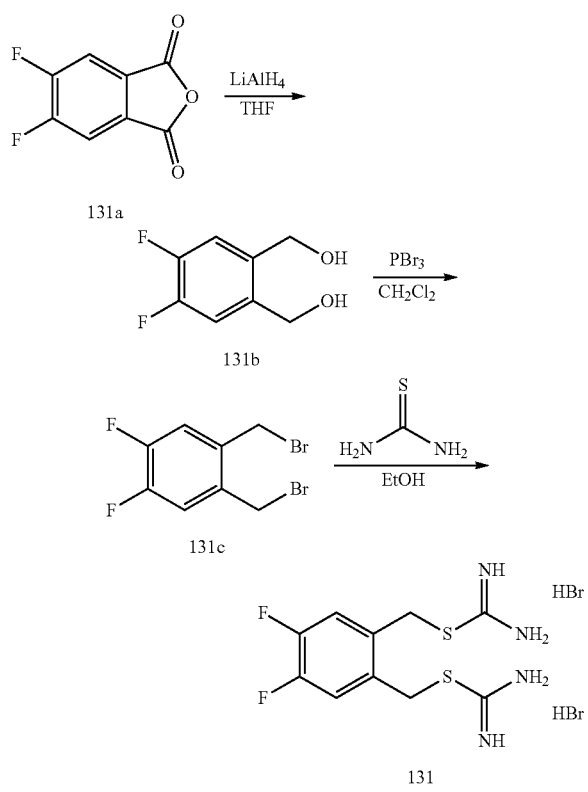

131

The same operation as in the synthesis of compound 2b was performed from compound 131a; 5,6-difluoroisobenzofuran-1,3-dione (1000 mg, 5.43 mmol) and LiAlH$_4$ (618 mg, 16.3 mmol), and the reaction residue was purified by silica gel chromatography (n-hexane/EtOAc=5:1 to 1:1) to obtain compound 131b (620 mg, 66% yield) as white crystals.

LC-MS: 95% purity, RT 1.13 min, MS (m/z): 197 (M+Na)$^+$.

A residue obtained by the same operation as in the synthesis of compound 2c from compound 131b (548 mg, 3.15 mmol) and phosphorous tribromide (0.359 mL, 3.78 mmol) was purified by silica gel chromatography with n-hexane/EtOAc (3:1) to obtain compound 131c (293 mg, 31% yield) as white crystals.

The same operation as in the synthesis of compound 2 was performed from compound 131c (168 mg, 0.56 mmol) and thiourea (85 mg, 1.12 mmol), and the residue was recrystallized from EtOH and Et$_2$O (2:3) to obtain compound 131 (229 mg, 91% yield) as white crystals. $^1$HNMR (500 MHz, DMSO-d6): δ=9.22 (6H, brs), 7.67-7.63 (2H, m), 4.64 (4H, brs).

LC-MS: >99% purity, RT 0.37 min, MS (m/z): 291 (M+H)$^+$.

Synthesis of Compound 132

(4,5-Difluoro-1,2-phenylene)bis(methylene) (E,E)-bis(N'-(4-chlorophenyl)carbamimidothioate) dihydrobromide

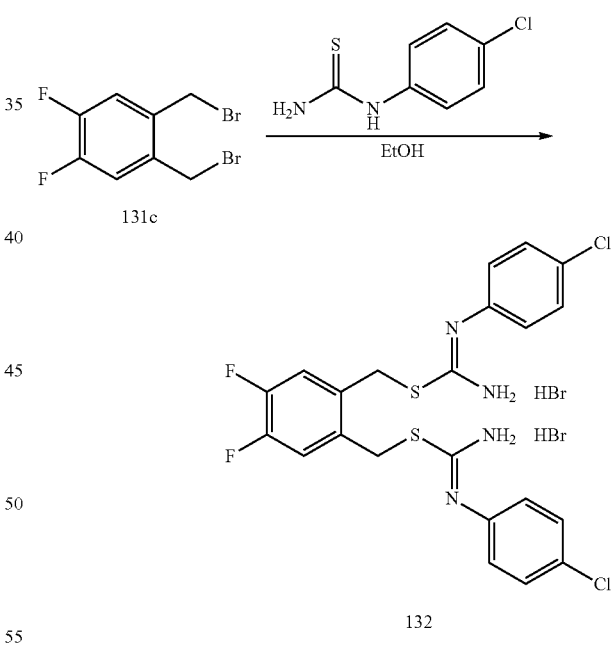

132

The same operation as in the synthesis of compound 2 was performed from compound 131c; 1,2-bis(bromomethyl)-4,5-difluorobenzene (117 mg, 0.39 mmol) and 1-(4-chlorophenyl)thiourea (146 mg, 0.78 mmol), and the reaction product was concentrated under reduced pressure. Then, the residue was recrystallized from EtOH and Et$_2$O (1:1) to obtain the title compound 132 (119 mg, 45% yield) as white crystals.

$^1$HNMR (500 MHz, DMSO-d6): δ=7.67-7.58 (6H, m), 7.36-7.32 (4H, m), 4.82 (4H, brs).

LC-MS: 91% purity, RT 3.41 min, MS (m/z): 512 (M+H)$^+$

Synthesis of Compound 133

6,6'-(((4-Fluoro-1,2-phenylene)bis(methylene))bis(sulfanediyl))bis(3-(3,4-dichlorophenethyl)-1,2,3,4-tetrahydro-1,3,5-triazine)

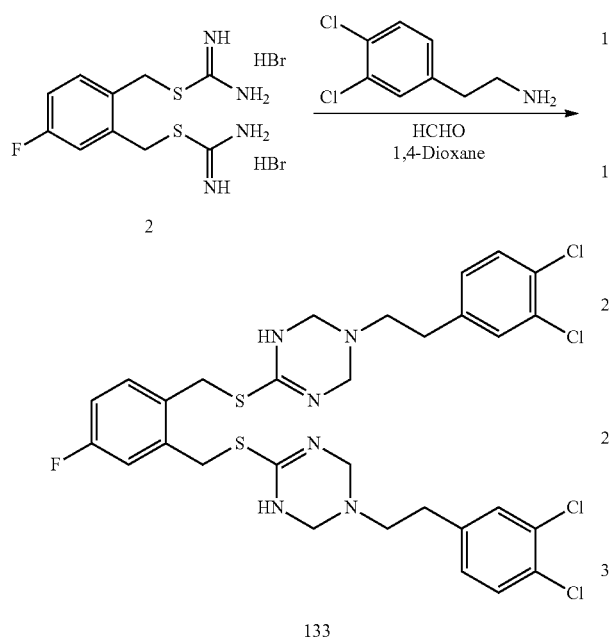

Reaction was performed by the same operation as in the synthesis of compound 9 from 2-(3,4-dichlorophenyl)ethan-1-amine (190 mg, 1.00 mmol), formaldehyde (150 μL, 37% wt. solution in water, 2.00 mmol) and (4-fluoro-1,2-phenylene)bis(methylene) dicarbamimidothioate dihydrobromide (compound 2, 217 mg, 0.50 mmol), and the reaction residue was purified by amino silica gel chromatography (n-hexane/EtOAc=1:1 to 1:3) to obtain the title compound 133 (82 mg, 23.4% yield) as white crystals.

$^1$HNMR (500 MHz, DMSO-d6): δ=7.52-7.48 (4H, m), 7.33-7.30 (1H, m), 7.23-7.20 (2H, m), 7.13-7.11 (1H, m), 6.92-6.88 (1H, m), 4.24-3.99 (12H, m), 2.77-2.68 (8H, m).

LC-MS: 85% purity, RT 2.36 min, MS (m/z): 701 (M+H)$^+$

Synthesis of Compound 134

(4,5-Dichloro-1,2-phenylene)bis(methylene) (E,E)-bis(N'-(3-chloro-4-fluorophenyl)carbamimidothioate) dihydrobromide

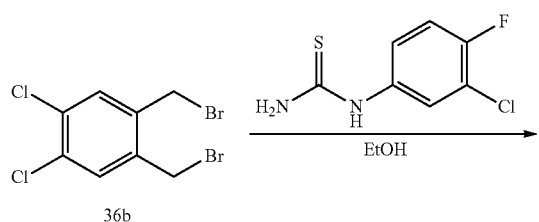

The same operation as in the synthesis of compound 2 was performed from compound 36b; 1,2-bis(bromomethyl)-4,5-dichlorobenzene (200 mg, 0.60 mmol) and 1-(3-chloro-4-fluorophenyl)thiourea (246 mg, 1.20 mmol), and the reaction product was concentrated under reduced pressure. Then, the residue was recrystallized from n-hexane and Et$_2$O (1:1) to obtain the title compound 134 (363 mg, 81% yield) as white crystals.

$^1$HNMR (500 MHz, DMSO-d6): δ=7.79 (2H, s), 7.57-7.52 (4H, m), 7.31-7.29 (2H, m), 4.82 (4H, s).

LC-MS: 97% purity, RT 4.47 min, MS (m/z): 581 (M+H)$^+$

Synthesis of Compound 135

(4,5-Dichloro-1,2-phenylene)bis(methylene) (E,E)-bis(N'-(4-bromophenyl)carbamimidothioate) dihydrobromide

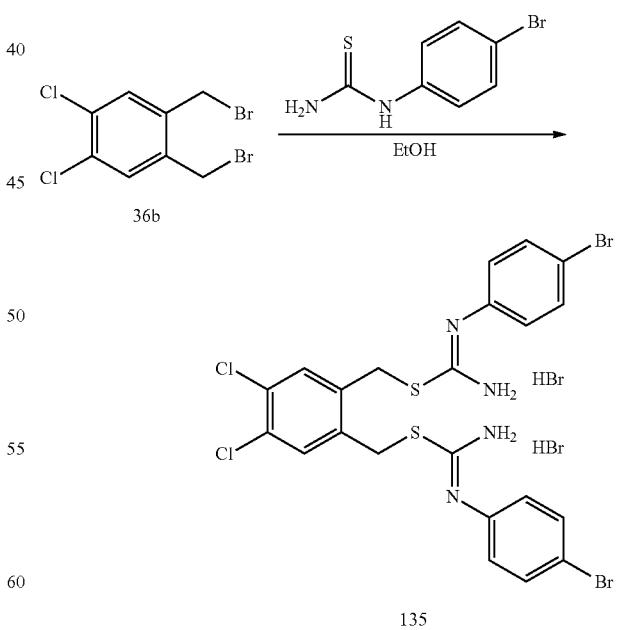

The same operation as in the synthesis of compound 2 was performed from compound 36b; 1,2-bis(bromomethyl)-4,5-dichlorobenzene (200 mg, 0.60 mmol) and 1-(4-bromophenyl)thiourea (278 mg, 1.20 mmol), and the reaction product was concentrated under reduced pressure. Then, the residue was recrystallized from n-hexane and Et₂O (1:3) to obtain the title compound 135 (460 mg, 96% yield) as white crystals.

¹HNMR (500 MHz, DMSO-d6): δ=7.82 (2H, s), 7.72 (4H, d, J=8.5 Hz), 7.27 (4H, d, J=8.5 Hz), 4.84 (4H, s).

LC-MS: 95% purity, RT 4.48 min, MS (m/z): δ34 (M+H)⁺

Synthesis of Compound 136

(4,5-Dichloro-1,2-phenylene)bis(methylene) (E,E)-bis(N'-(3-bromophenyl)carbamimidothioate) dihydrobromide

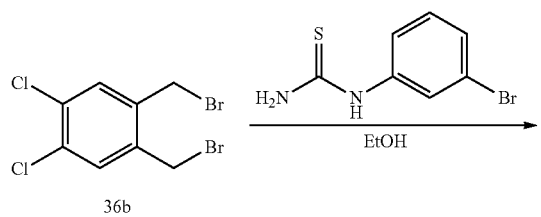

36b

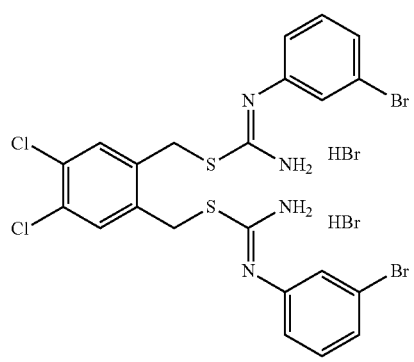

136

The same operation as in the synthesis of compound 2 was performed from compound 36b; 1,2-bis(bromomethyl)-4,5-dichlorobenzene (200 mg, 0.60 mmol) and 1-(3-bromophenyl)thiourea (278 mg, 1.20 mmol), and the reaction product was concentrated under reduced pressure. Then, the residue was recrystallized from n-hexane and Et₂O (1:3) to obtain the title compound 136 (419 mg, 88% yield) as white crystals.

¹HNMR (500 MHz, DMSO-d6): δ=7.82 (2H, s), 7.61 (2H, d, J=7.9 Hz), 7.51 (2H, s), 7.48 (2H, t, J=7.9 Hz), 7.31 (2H, d, J=7.9 Hz), 4.85 (4H, s).

LC-MS: 93% purity, RT 4.79 min, MS (m/z): δ34 (M+H)⁺

Synthesis of Compound 137

(4,5-Dichloro-1,2-phenylene)bis(methylene) (E,E)-bis(N'-(4-fluorophenyl)carbamimidothioate) dihydrobromide

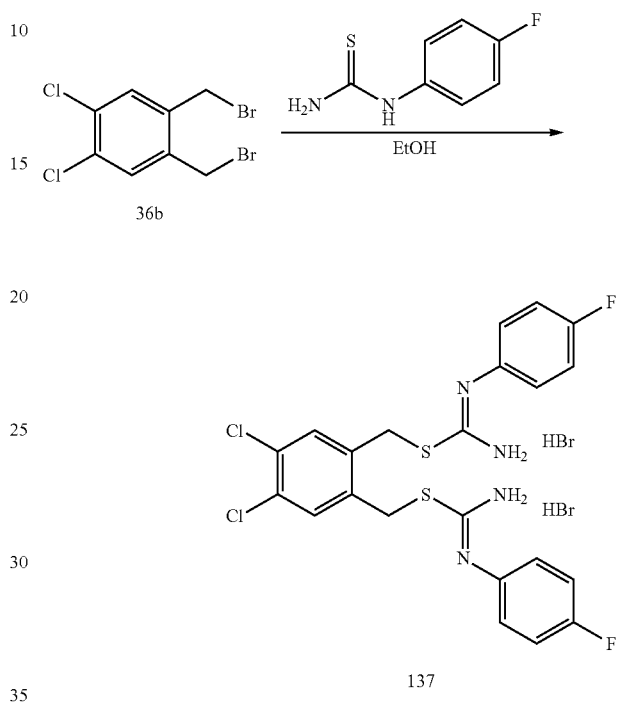

137

The same operation as in the synthesis of compound 2 was performed from compound 36b; 1,2-bis(bromomethyl)-4,5-dichlorobenzene (200 mg, 0.60 mmol) and 1-(4-fluorophenyl)thiourea (204 mg, 1.20 mmol), and the reaction product was concentrated under reduced pressure. Then, the residue was recrystallized from n-hexane and Et₂O (1:3) to obtain the title compound 137 (364 mg, 90% yield) as white crystals.

¹HNMR (500 MHz, DMSO-d6): δ=7.83 (2H, s), 7.40-7.34 (8H, m), 4.86 (4H, brs).

LC-MS: 98% purity, RT 2.78 min, MS (m/z): 512 (M+H)⁺

Synthesis of Compound 138

(4,5-Dichloro-1,2-phenylene)bis(methylene) (E,E)-bis(N'-(p-tolyl)carbamimidothioate) dihydrobromide

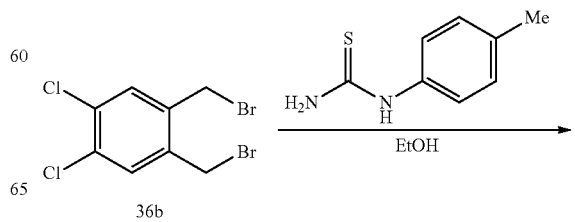

36b

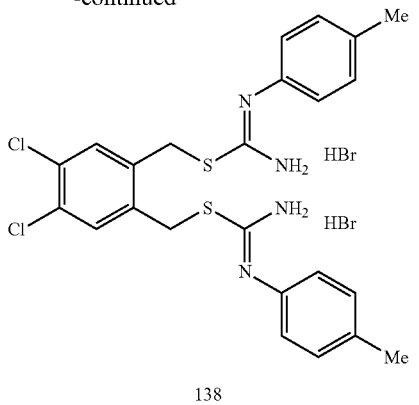

138

The same operation as in the synthesis of compound 2 was performed from compound 36b; 1,2-bis(bromomethyl)-4,5-dichlorobenzene (290 mg, 0.87 mmol) and 1-(p-tolyl)thiourea (290 mg, 1.74 mmol), and the reaction product was concentrated under reduced pressure. Then, the residue was recrystallized from n-hexane and Et$_2$O (1:3) to obtain the title compound 138 (499 mg, 86% yield) as white crystals.

$^1$HNMR (500 MHz, DMSO-d6): δ=7.77 (2H, s), 7.29 (4H, d, J=7.9 Hz), 7.12 (4H, d, J=8.5 Hz), 4.78 (4H, brs), 2.30 (6H, s).

LC-MS: 99% purity, RT 2.54 min, MS (m/z): 504 (M+H)$^+$

Synthesis of Compound 139

6,6'-(((4,5-Dichloro-1,2-phenylene)bis(methylene))bis(sulfanediyl))bis(3-(3-chloro-4-fluorobenzyl)-1,2,3,4-tetrahydro-1,3,5-triazine)

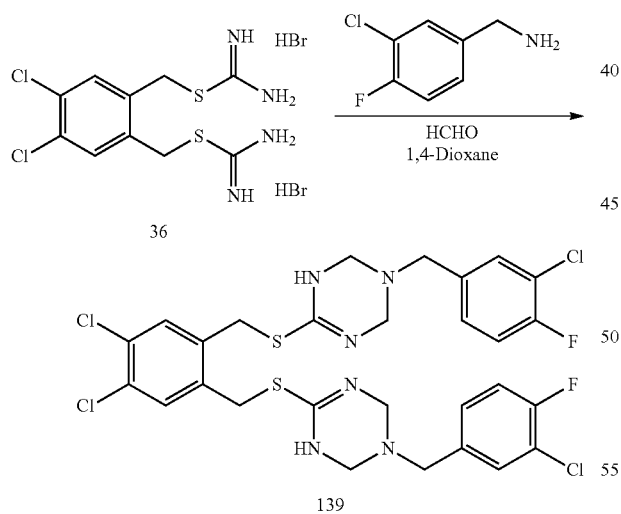

Reaction was performed by the same operation as in the synthesis of compound 9 from (3-chloro-4-fluorophenyl)methanamine (160 mg, 1.00 mmol), formaldehyde (150 μL, 37% wt. solution in water, 2.00 mmol) and (4,5-dichloro-1,2-phenylene)bis(methylene) dicarbamimidothioate dihydrobromide (compound 36, 242 mg, 0.50 mmol), and the reaction residue was recrystallized from n-hexane and AcOEt (5:1) to obtain the title compound 139 (196 mg, 57% yield) as white crystals.

$^1$H NMR (500 MHz, DMSO-d6): δ=10.39 (2H, brs), 7.89 (2H, s), 7.50-7.48 (2H, m), 7.45-7.41 (2H, m), 7.33-7.30 (2H, m), 4.79 (4H, s), 4.38 (8H, s), 3.62 (4H, s).

LC-MS: 89% purity, RT 2.31 min, MS (m/z): δ91 (M+H)$^+$.

Synthesis of Compound 140

6,6'-(((4-Fluoro-1,2-phenylene)bis(methylene))bis(sulfanediyl))bis(3-(4-(trifluoromethyl)phenethyl)-1,2,3,4-tetrahydro-1,3,5-triazine)

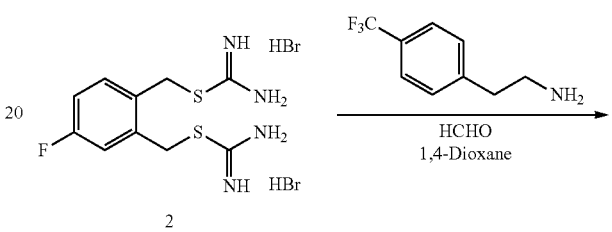

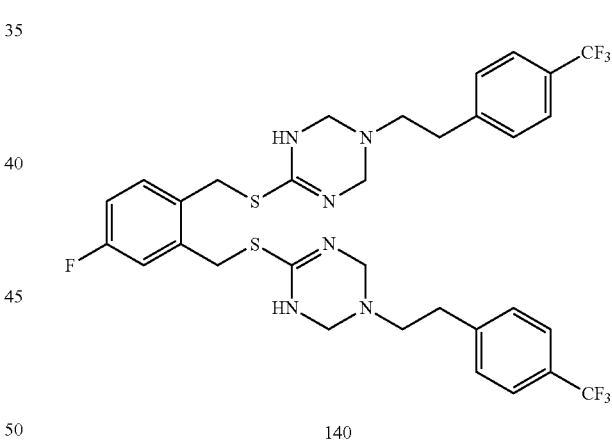

140

Reaction was performed by the same operation as in the synthesis of compound 9 from 2-(4-(trifluoromethyl)phenyl)ethan-1-amine (189 mg, 1.00 mmol), formaldehyde (150 μL, 37% wt. solution in water, 2.00 mmol) and (4-fluoro-1,2-phenylene)bis(methylene) dicarbamimidothioate dihydrobromide (compound 2, 217 mg, 0.50 mmol), and the reaction residue was recrystallized from n-hexane and AcOEt (5:1) to obtain the title compound 140 (187 mg, 54% yield) as pale yellow crystals.

$^1$HNMR (500 MHz, DMSO-d6): δ=10.29 (2H, brs), 7.66-7.65 (4H, m), 7.49-7.45 (5H, m), 7.31-7.28 (1H, m), 6.96-6.94 (1H, m), 4.70-4.68 (4H, m), 4.42 (8H, s), 2.88-2.85 (4H, m), 2.64-2.59 (4H, m).

LC-MS: 91% purity, RT 2.27 min, MS (m/z): δ99 (M+H)$^+$

Synthesis of Compound 141

6,6'-(((4-Bromo-1,2-phenylene)bis(methylene))bis(sulfanediyl))bis(3-(4-(trifluoromethyl)phenethyl)-1,2,3,4-tetrahydro-1,3,5-triazine)

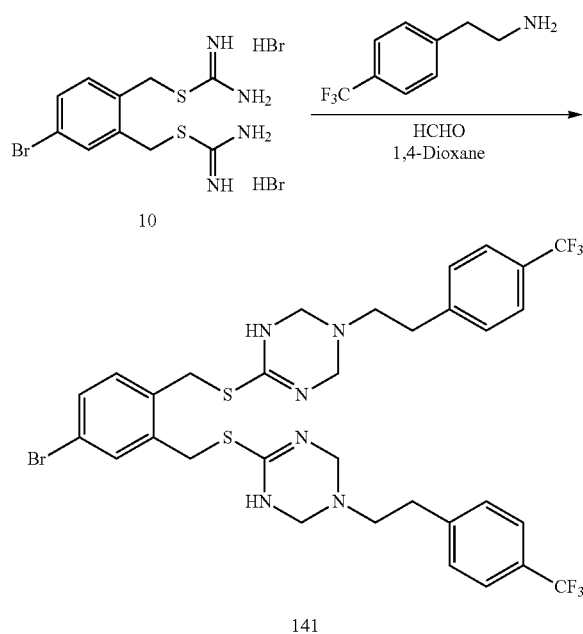

Reaction was performed by the same operation as in the synthesis of compound 9 from 2-(4-(trifluoromethyl)phenyl)ethan-1-amine (189 mg, 1.00 mmol), formaldehyde (150 μL, 37% wt. solution in water, 2.00 mmol) and (4-bromo-1,2-phenylene)bis(methylene) dicarbamimidothioate dihydrobromide (compound 10, 247 mg, 0.50 mmol), and the reaction residue was recrystallized from n-hexane and AcOEt (5:1) to obtain the title compound 141 (249 mg, 65% yield) as pale yellow crystals.

$^1$H NMR (500 MHz, DMSO-d6): δ=10.32 (2H, brs), 7.67-7.33 (11H, m), 4.70-4.69 (4H, m), 4.42 (8H, s), 2.87 (4H, t, J=6.5 Hz), 2.65-2.62 (4H, m).

LC-MS: 87% purity, RT 2.74 min, MS (m/z): 761 (M+H)$^+$.

Synthesis of Compound 142

1,2-Bis (((5-(4-(Trifluoromethyl)phenethyl)-1,4,5,6-tetrahydro-1,3,5-triazin-2-yl)thio)methyl)benzene

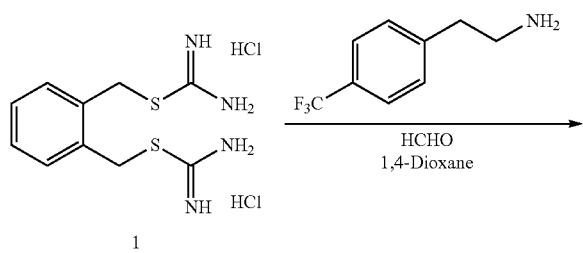

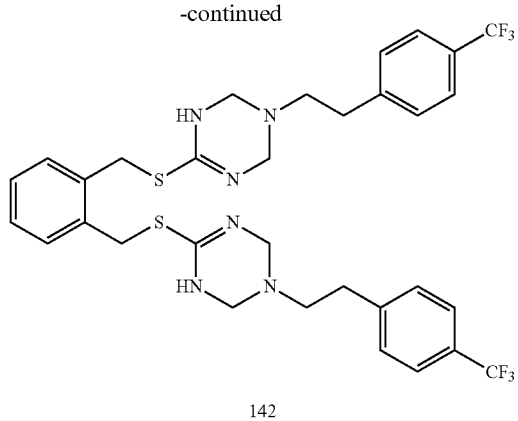

142

2-(4-(Trifluoromethyl)phenyl)ethan-1-amine (189 mg, 1.00 mmol) was gently added to a solution of formaldehyde (150 μL, 37% wt. solution in water, 2.00 mmol) in 1,4-dioxane (5.0 mL), and the mixture was stirred at room temperature for 20 minutes. Then, 1,2-phenylenebis(methylene) dicarbamimidothioate dihydrochloride (compound 1, 164 mg, 0.500 mmol) was added thereto, and the mixture was stirred at 80° C. for 12 hours. The reaction mixture was brought back to room temperature. Toluene (3.0 mL) was added thereto, and the mixture was concentrated under reduced pressure. The residue was recrystallized from EtOH and Et$_2$O (2:3) to obtain the title compound 142 (199 mg, 58% yield) as white crystals.

$^1$H NMR (500 MHz, DMSO-d6): δ=10.73 (2H, brs), 7.65 (4H, d, J=7.9 Hz), 7.47-7.44 (6H, m), 7.10-7.08 (2H, m), 4.82 (4H, brs), 4.38 (8H, s), 2.83 (4H, t, J=7.4 Hz), 2.56 (4H, t, J=7.4 Hz).

LC-MS: 90% purity, RT 2.18 min, MS (m/z): δ81 (M+H)$^+$.

Synthesis of Compound 143

6,6'-(((4,5-Dichloro-1,2-phenylene)bis(methylene))bis(sulfanediyl))bis(3-(4-(trifluoromethyl)phenethyl)-1,2,3,4-tetrahydro-1,3,5-triazine)

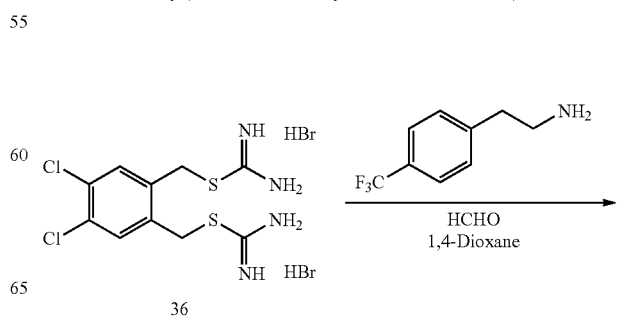

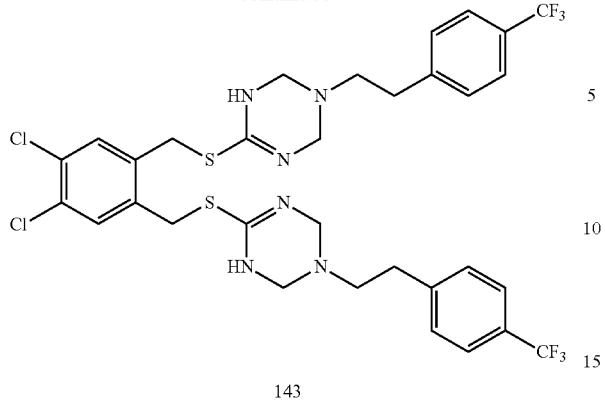

143

Reaction was performed by the same operation as in the synthesis of compound 9 from 2-(4-(trifluoromethyl)phenyl) ethan-1-amine (189 mg, 1.00 mmol), formaldehyde (150 μL, 37% wt. solution in water, 2.00 mmol) and (4,5-dichloro-1,2-phenylene)bis(methylene) dicarbamimidothioate dihydrobromide (compound 36, 243 mg, 0.50 mmol), and the reaction residue was recrystallized from 2-propanol to obtain the title compound 143 (268 mg, 71% yield) as white crystals.

$^1$H NMR (500 MHz, DMSO-d6): δ=10.33 (2H, brs), 7.72 (2H, s), 7.65 (4H, d, J=7.9 Hz), 7.46 (4H, d, J=7.9 Hz), 4.70 (4H, s), 4.43 (8H, s), 2.86 (4H, t, J=7.4 Hz), 2.64-2.61 (4H, m).

LC-MS: 92% purity, RT 2.51 min, MS (m/z): 751 (M+H)$^+$.

Synthesis of Compound 144

6,6'-(((4-Bromo-1,2-phenylene)bis(methylene))bis(sulfanediyl))bis(3-(3-chloro-4-fluorobenzyl)-1,2,3,4-tetrahydro-1,3,5-triazine)

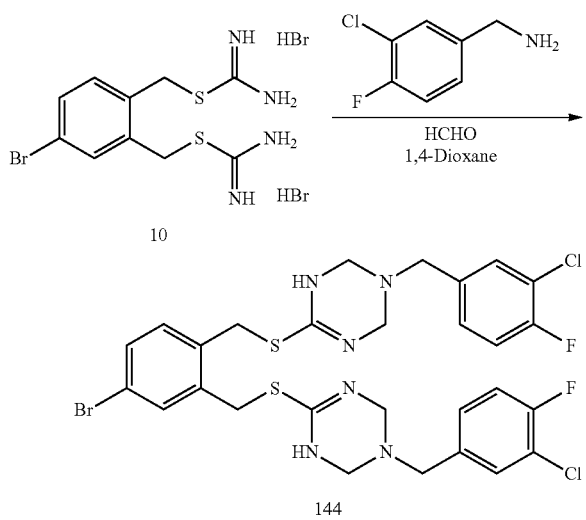

Reaction was performed by the same operation as in the synthesis of compound 9 from (3-chloro-4-fluorophenyl) methanamine (159 mg, 1.00 mmol), formaldehyde (150 μL, 37% wt. solution in water, 2.00 mmol) and (4-bromo-1,2-phenylene)bis(methylene) dicarbamimidothioate dihydrobromide (compound 10, 247 mg, 0.50 mmol), and the reaction residue was purified by NH-silica gel chromatography with n-hexane/EtOAc (2:1 to 1:3) to obtain the title compound 144 (109 mg, 31% yield) as a pale yellow oil substance.

$^1$H NMR (500 MHz, DMSO-d6): δ=7.59-7.29 (9H, m), 4.25-4.00 (8H, m), 3.63 (8H, s).

LC-MS: 87% purity, RT 2.26 min, MS (m/z): 701 (M+H)$^+$.

Synthesis of Compound 145

1,2-Bis(((5-(3-Chloro-4-fluorobenzyl)-1,4,5,6-tetrahydro-1,3,5-triazin-2-yl)thio)methyl)benzene

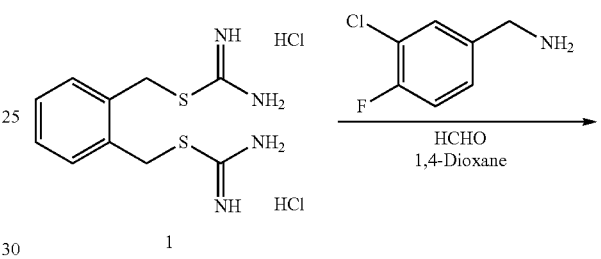

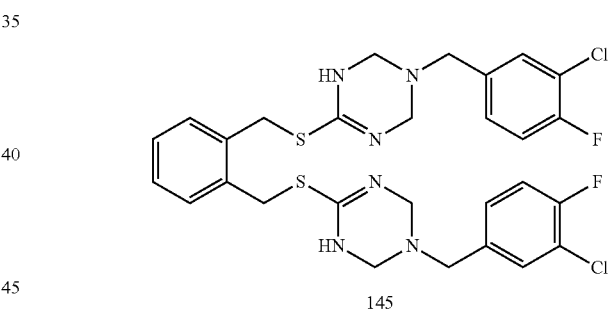

145

(3-Chloro-4-fluorophenyl)methanamine (319 mg, 2.00 mmol) was gently added to a solution of formaldehyde (301 μL, 37% wt. solution in water, 4.0 mmol) in 1,4-dioxane (5.0 mL), and the mixture was stirred at room temperature for 10 minutes. Then, a solution of 1,2-phenylenebis(methylene) dicarbamimidothioate dihydrochloride (compound 1, 327 mg, 1.00 mmol) in 1,4-dioxane (2.0 mL) was added thereto, and the mixture was stirred at 80° C. for 12 hours. The reaction mixture was brought back to room temperature. Toluene (3.0 mL) was added thereto, and the mixture was concentrated under reduced pressure. The residue was recrystallized from EtOH and Et$_2$O (2:3) to obtain the title compound 145 (200 mg, 32% yield) as a pale yellow oil substance.

$^1$HNMR (500 MHz, DMSO-d6): δ=10.83 (2H, brs), 7.62-7.60 (2H, m), 7.51-7.49 (2H, m), 7.42-7.38 (4H, m), 7.32-7.29 (2H, m), 4.93 (4H, s), 4.34 (8H, s), 3.56 (4H, s).

LC-MS: 96% purity, RT 1.88 min, MS (m/z): δ22 (M+H)$^+$

Synthesis of Compound 146

6,6'-(((4-Fluoro-1,2-phenylene)bis(methylene))bis(sulfanediyl))bis(3-(3-chloro-4-fluorobenzyl)-1,2,3,4-tetrahydro-1,3,5-triazine)

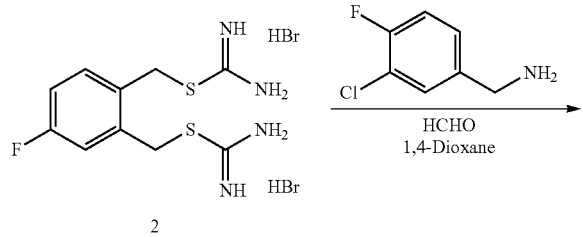

2

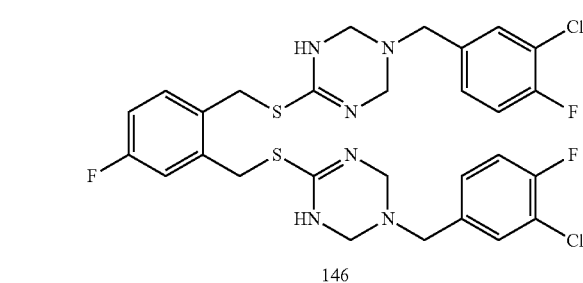

146

Reaction was performed by the same operation as in the synthesis of compound 9 from (3-chloro-4-fluorophenyl)methanamine (319 mg, 2.00 mmol), formaldehyde (301 µL, 37% wt. solution in water, 4.00 mmol) and (4-fluoro-1,2-phenylene)bis(methylene) dicarbamimidothioate dihydrobromide (compound 2, 434 mg, 1.00 mmol), and the reaction residue was recrystallized from 2-propanol and Et$_2$O (1:1) to obtain the title compound 146 (209 mg, 32.7% yield) as white crystals.

$^1$HNMR (500 MHz, DMSO-d6): δ=10.39-10.35 (2H, m), 7.65-7.31 (9H, m), 4.82-4.80 (4H, m), 4.39 (8H, s), 3.66-3.65 (4H, m).

LC-MS: 75% purity, RT 2.17 min, MS (m/z): δ41 (M+H)$^+$

Synthesis of Compound 147

6,6'-(((4-Fluoro-1,2-phenylene)bis(methylene))bis(sulfanediyl))bis(3-(4-methoxyphenethyl)-1,2,3,4-tetrahydro-1,3,5-triazine)

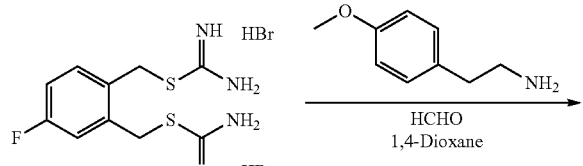

2

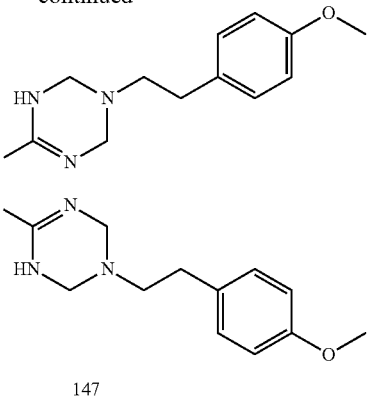

147

Reaction was performed by the same operation as in the synthesis of compound 9 from 2-(4-methoxyphenyl)ethan-1-amine (151 mg, 1.00 mmol), formaldehyde (150 µL, 37% wt. solution in water, 2.00 mmol) and (4-fluoro-1,2-phenylene)bis(methylene) dicarbamimidothioate dihydrobromide (compound 2, 217 mg, 0.50 mmol), and the reaction residue was recrystallized from 2-propanol and Et$_2$O (1:1) to obtain the title compound 147 (225 mg, 72% yield) as pale yellow crystals.

$^1$HNMR (500 MHz, DMSO-d6): δ=10.28-10.25 (2H, m), 7.49-7.46 (1H, m), 7.33-7.31 (1H, m), 7.13-7.10 (4H, m), 7.00-6.98 (1H, m), 6.86-6.84 (4H, m), 4.69-4.68 (4H, m), 4.40 (8H, s), 3.72 (6H, s), 2.70-2.67 (4H, m), 2.57-2.53 (4H, m).

LC-MS: 96% purity, RT 1.70 min, MS (m/z): δ23 (M+H)$^+$

Synthesis of Compound 148

6,6'-(((4-Bromo-1,2-phenylene)bis(methylene))bis(sulfanediyl))bis(3-(4-methoxyphenethyl)-1,2,3,4-tetrahydro-1,3,5-triazine)

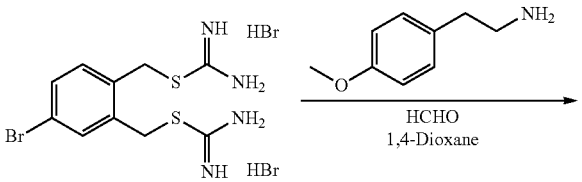

10

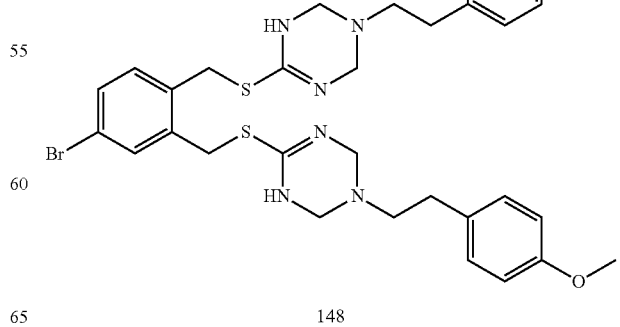

148

Reaction was performed by the same operation as in the synthesis of compound 9 from 2-(4-methoxyphenyl)ethan-1-amine (151 mg, 1.00 mmol), formaldehyde (150 µL, 37% wt. solution in water, 2.00 mmol) and (4-bromo-1,2-phenylene)bis(methylene) dicarbamimidothioate dihydrobromide (compound 10, 248 mg, 0.50 mmol), and the reaction residue was recrystallized from 2-propanol and Et$_2$O (1:1) to obtain the title compound 148 (246 mg, 72% yield) as pale yellow crystals.

$^1$H NMR (500 MHz, DMSO-d6): δ=10.27-10.25 (2H, m), 7.65 (1H, brs), 7.37-7.35 (1H, m), 7.31-7.29 (1H, m), 7.11-7.07 (4H, m), 6.83-6.81 (4H, m), 4.68 (4H, brs), 4.36 (8H, brs), 3.69 (6H, s), 2.67-2.62 (4H, m), 2.54-2.48 (4H, m).

LC-MS: 80% purity, RT 1.86 min, MS (m/z): δ85 (M+H)$^+$

Synthesis of Compound 149

6,6'-(((4-Bromo-1,2-phenylene)bis(methylene))bis(sulfanediyl))bis(3-(3-(trifluoromethyl)phenethyl)-1,2,3,4-tetrahydro-1,3,5-triazine)

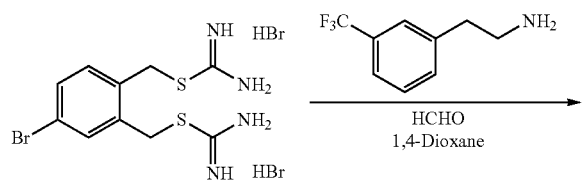

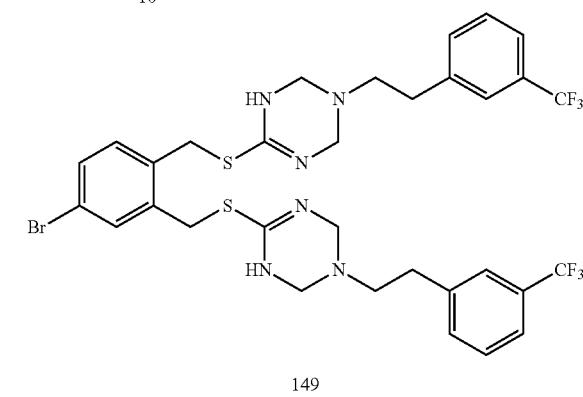

Reaction was performed by the same operation as in the synthesis of compound 9 from 2-(3-(trifluoromethyl)phenyl)ethan-1-amine (189 mg, 1.00 mmol), formaldehyde (150 µL, 37% wt. solution in water, 2.00 mmol) and (4-bromo-1,2-phenylene)bis(methylene) dicarbamimidothioate dihydrobromide (compound 10, 248 mg, 0.50 mmol), and the reaction residue was purified by NH-silica gel chromatography with n-hexane/EtOAc (3:2 to 0:1) and recrystallized from 2-propanol to obtain the title compound 149 (268 mg, 71% yield) as pale yellow crystals.

$^1$HNMR (500 MHz, DMSO-d6): δ=10.29-10.26 (2H, m), 7.63-7.54 (9H, m), 7.35-7.26 (2H, m), 4.66 (4H, s), 4.42 (8H, s), 2.86 (4H, brs), 2.65-2.60 (4H, m).

LC-MS: 81% purity, RT 2.35 min, MS (m/z): 761 (M+H)$^+$.

Synthesis of Compound 150

6,6'-(((4-Fluoro-1,2-phenylene)bis(methylene))bis(sulfanediyl))bis(3-(3-(trifluoromethyl)phenethyl)-1,2,3,4-tetrahydro-1,3,5-triazine)

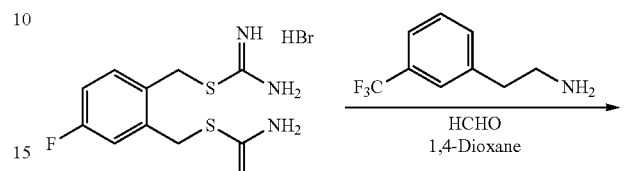

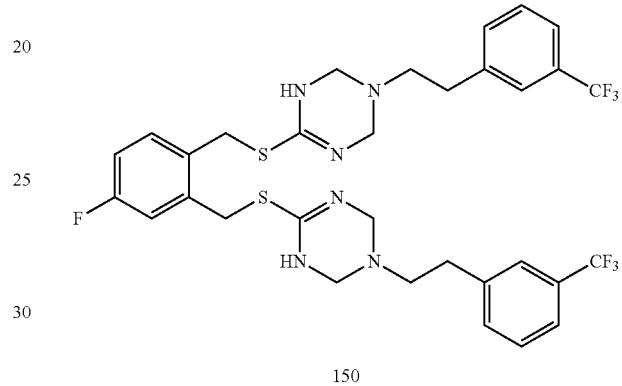

Reaction was performed by the same operation as in the synthesis of compound 9 from 2-(3-(trifluoromethyl)phenyl)ethan-1-amine (189 mg, 1.00 mmol), formaldehyde (150 µL, 37% wt. solution in water, 2.00 mmol) and (4-fluoro-1,2-phenylene)bis(methylene) dicarbamimidothioate dihydrobromide (compound 2, 217 mg, 0.50 mmol), and the reaction residue was recrystallized from 2-propanol and Et$_2$O (1:1) to obtain the title compound 150 (316 mg, 90% yield) as pale yellow crystals.

$^1$HNMR (500 MHz, DMSO-d6): δ=10.31-10.28 (2H, m), 7.66-7.27 (10H, m), 6.89-6.87 (1H, m), 4.70 (4H, s), 4.43 (8H, s), 2.89-2.85 (4H, m), 2.65-2.61 (4H, m).

LC-MS: 84% purity, RT 2.25 min, MS (m/z): 700 (M+H)$^+$

Synthesis of Compound 151

Benzo[b]thiophene-2,3-diylbis(methylene) dicarbamimidothioate dihydrobromide

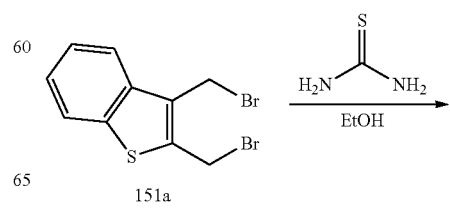

-continued

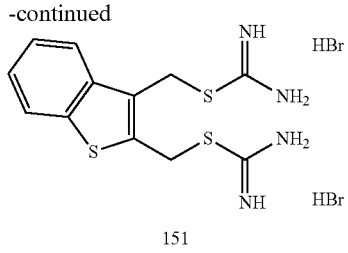

151

The same operation as in the synthesis of compound 1 was performed from compound 151a; 2,3-bis(bromomethyl)benzo[b]thiophene (1000 mg, 3.13 mmol) and thiourea (476 mg, 6.25 mmol), and the residue was recrystallized from EtOH and Et$_2$O (2:3) to obtain compound 151 (807 mg, 55% yield) as white crystals.

$^1$HNMR (500 MHz, DMSO-d6): δ=9.34-9.16 (6H, m), 8.04-7.94 (2H, m), 7.51-7.46 (2H, m), 4.98 (2H, s), 4.89 (2H, s).

LC-MS: 95% purity, RT 0.45 min, MS (m/z): 311 (M+H)$^+$.

Synthesis of Compound 152

6,6'-(((4,5-Dichloro-1,2-phenylene)bis(methylene))bis(sulfanediyl))bis(3-(3-(trifluoromethyl)phenethyl)-1,2,3,4-tetrahydro-1,3,5-triazine)

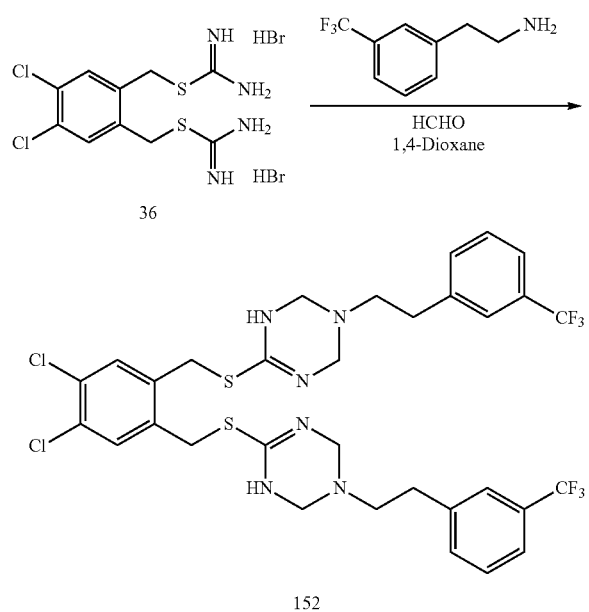

152

Reaction was performed by the same operation as in the synthesis of compound 9 from 2-(3-(trifluoromethyl)phenyl)ethan-1-amine (189 mg, 1.00 mmol), formaldehyde (150 μL, 37% wt. solution in water, 2.00 mmol) and (4,5-dichloro-1,2-phenylene)bis(methylene) dicarbamimidothioate dihydrobromide (compound 36, 243 mg, 0.50 mmol), and the reaction residue was recrystallized from 2-propanol to obtain the title compound 152 (269 mg, 72% yield) as white crystals.

$^1$HNMR (500 MHz, DMSO-d6): δ=10.33 (2H, brs), 7.71 (2H, s), 7.62 (2H, s), 7.57-7.54 (6H, m), 4.71 (4H, s), 4.44 (8H, s), 2.89-2.86 (4H, m), 2.68-2.65 (4H, m).

LC-MS: 78% purity, RT 2.52 min, MS (m/z): 751 (M+H)$^+$.

Synthesis of Compound 153

6,6'-(((4,5-Dichloro-1,2-phenylene)bis(methylene))bis(sulfanediyl))bis(3-(3-methoxyphenethyl)-1,2,3,4-tetrahydro-1,3,5-triazine)

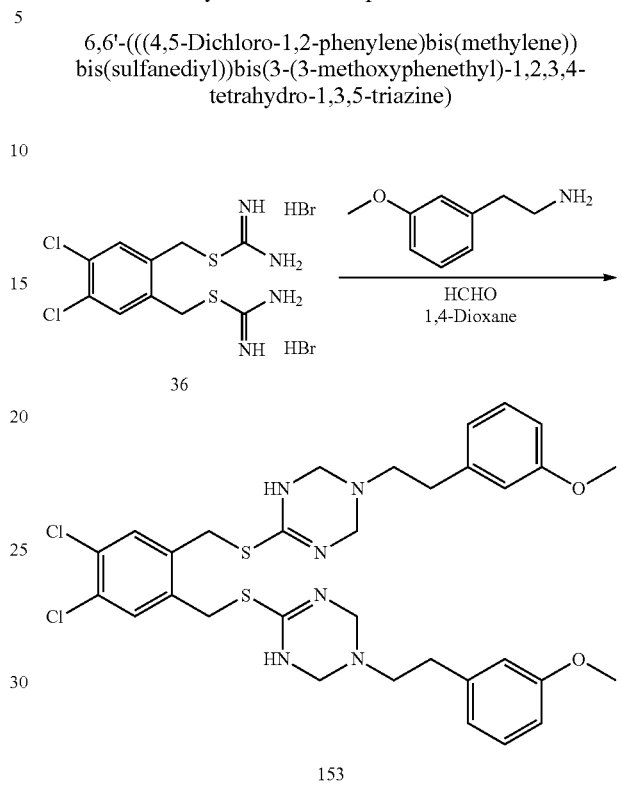

153

Reaction was performed by the same operation as in the synthesis of compound 9 from 2-(3-methoxyphenyl)ethan-1-amine (189 mg, 1.00 mmol), formaldehyde (150 μL, 37% wt. solution in water, 2.00 mmol) and (4,5-dichloro-1,2-phenylene)bis(methylene) dicarbamimidothioate dihydrobromide (compound 36, 243 mg, 0.50 mmol), and the reaction residue was recrystallized from 2-propanol to obtain the title compound 153 (222 mg, 66% yield) as white crystals.

$^1$HNMR (500 MHz, DMSO-d6): δ=7.74 (2H, s), 7.22-7.19 (2H, m), 6.84-6.76 (6H, m), 4.69 (4H, s), 4.41 (8H, s), 3.74 (6H, s), 2.75-2.72 (4H, m), 2.66-2.63 (4H, m).

LC-MS: 86% purity, RT 2.00 min, MS (m/z): δ75 (M+H)$^+$.

Test Example 1

Experimental Method for Evaluating Compound In Vitro

Each compound was evaluated in vitro in accordance with the following protocol.

Enzyme Assay Protocol Using rhIDO (Recombinant Human IDO)

4 μL of a compound solution was added to 176 μL of a rhIDO reaction solution (0.5 M potassium phosphate buffer (20 μL), 0.2 M ascorbic acid (20 μL), 0.5 mM methylene blue (4 μL), 10 mg/mL catalase (2 μL), H$_2$O (128 μL), and rhIDO (2 μL)). The mixture was pipetted and preincubated at 37° C. for 10 minutes. Then, the whole amount was brought to 200 μL by the addition of 20 μL of a 2 mM aqueous tryptophan solution, and the mixture was pipetted again and reacted at 37° C. for 120 minutes. After the reaction, the enzymatic reaction was terminated by the addition of 40 µL of a 30% [v/v] aqueous trichloroacetic acid solution to the reaction solution. The mixture was well stirred by pipetting and heated at 50° C. for 15 minutes so that N-formylkynurenine was converted to kynurenine. The reaction solution thus heated was centrifuged (15,000 rpm, 5 min, 24° C.), and 150 µL of the supernatant was transferred to a transparent 96-well flat-bottomed plate, followed by the measurement of absorbance at 490 nm using SpectraMax MSSK (background measurement). After the measurement, a solution of 2% [w/v] p-dimethylbenzaldehyde in acetic acid was added at 150 µL/well and reacted for 5 minutes, followed by the measurement of absorbance at 490 nm again. The rate of kynurenine production was calculated according to the following expression.

> Rate of kynurenine production (%) for each compound in the case of using rhIDO={(Absorbance at 490 nm in the tryptophan-containing aqueous solution comprising rhIDO and the compound of the present invention−Absorbance of the background)/(Absorbance at 490 nm in the tryptophan-containing aqueous solution without the addition of the compound solution−Absorbance of the background)}×100

Enzyme Assay Protocol Using rhTDO (Recombinant Human TDO)

4 µL of a compound solution was added to 176 µL of a rhTDO reaction solution (0.5 M potassium phosphate buffer (20 µL), 0.2 M ascorbic acid (20 µL), 0.5 mM methylene blue (4 µL), 10 mg/mL catalase (2 µL), $H_2O$ (128 µL), and rhTDO (2 µL)). The mixture was pipetted and preincubated at 37° C. for 10 minutes. Then, the whole amount was brought to 200 µL by the addition of 20 µL of a 20 mM aqueous tryptophan solution, and the mixture was pipetted again and reacted at 37° C. for 120 minutes. After the reaction, the enzymatic reaction was terminated by the addition of 40 µL of a 30% [v/v] aqueous trichloroacetic acid solution to the reaction solution. The mixture was well stirred by pipetting and heated at 50° C. for 15 minutes so that N-formylkynurenine was converted to kynurenine. The reaction solution thus heated was centrifuged (15,000 rpm, 5 min, 24° C.), and 150 µL of the supernatant was transferred to a transparent 96-well flat-bottomed plate, followed by the measurement of absorbance at 490 nm using SpectraMax M5 SK (background measurement). After the measurement, a solution of 2% [w/v] p-dimethylbenzaldehyde in acetic acid was added at 150 µL/well and reacted for 5 minutes, followed by the measurement of absorbance at 490 nm again. The rate of kynurenine production was calculated according to the following expression.

> Rate of kynurenine production (%) for each compound in the case of using rhTDO={(Absorbance at 490 nm in the tryptophan-containing aqueous solution comprising rhTDO and the compound of the present invention−Absorbance of the background)/(Absorbance at 490 nm in the tryptophan-containing aqueous solution without the addition of the compound solution−Absorbance of the background)}×100

IDO Cell-Based Assay Protocol

A431 cells ($3.0 \times 10^5$ cells/mL) suspended in a culture medium for assay (D-MEM; Wako 040-30095, 5% FBS, 50 units/mL penicillin, 50 µg/mL streptomycin, and 2 mM L-glutamine) were inoculated at 100 µL/well to a transparent 96-well flat-bottomed plate and cultured at 37° C. for 24 hours in 5% $CO_2$. The culture medium was removed from the cells thus cultured. A tryptophan-containing culture medium (culture medium for assay supplemented with 178 µM L-tryptophan) was added at 80 µL/well, and further, a compound solution was added at 10 µL/well. The cells were preincubated for 1 hour. Then, the whole amount was brought to 100 µL/well by the addition of 10 µL/well of IFN-γ diluted into 100 ng/mL with a tryptophan-containing culture medium, and the cells were cultured for 24 hours. After the culture, absorbance was measured at 460 nm using SpectraMax MSSK (Molecular Devices, LLC) (background measurement). After the measurement, a kynurenine quantification reagent (prepared with 7% [v/v] aqueous trichloroacetic acid solution and a solution of 2% [w/v] p-dimethylbenzaldehyde in acetic acid at 2:5 [v/v]) was added at 200 µL/well and reacted for 5 minutes, followed by the measurement of absorbance at 460 nm again. The rate of kynurenine production was calculated according to the following expression.

> Rate of kynurenine production (%) for each compound in the case of using A431 cells={(Absorbance at 460 nm in the tryptophan-containing culture medium comprising the A431 cells and the solution of the compound of the present invention−Absorbance of the background)/(Absorbance at 460 nm in the tryptophan-containing culture medium without the addition of the compound solution−Absorbance of the background)}×100

TDO Cell-Based Assay Protocol

A172 cells ($3.0 \times 10^5$ cells/mL) suspended in a culture medium for assay (PRMI-1640; Wako 186-02155, 5% FBS, 50 units/mL penicillin, and 50 µg/mL streptomycin) were inoculated at 100 µL/well to a transparent 96-well flat-bottomed plate and cultured at 37° C. for 24 hours in 5% $CO_2$. The culture medium was removed from the cells thus cultured. A culture medium for assay was added at 80 µL/well, and further, a compound solution was added at 10 µL/well. The cells were preincubated for 1 hour. Then, the whole amount was brought to 100 µL/well by the addition of 10 µL/well of a 5 mM aqueous tryptophan solution (final concentration of L-tryptophan: 524 µM), and the cells were cultured for 24 hours. After the culture, absorbance was measured at 460 nm using SpectraMax MSSK (Molecular Devices, LLC) (background measurement). After the measurement, a kynurenine quantification reagent (prepared with 7% [v/v] aqueous trichloroacetic acid solution and a solution of 2% [w/v] p-dimethylbenzaldehyde in acetic acid at 2:5 [v/v]) was added at 200 µL/well and reacted for 5 minutes, followed by the measurement of absorbance at 460 nm again. The rate of kynurenine production was calculated according to the following expression.

> Rate of kynurenine production (%) for each compound in the case of using A172 cells={(Absorbance at 460 nm in the tryptophan-containing culture medium comprising the A172 cells and the solution of the compound of the present invention−Absorbance of the background)/(Absorbance at 460 nm in the tryptophan-containing culture medium without the addition of the compound solution−Absorbance of the background)}×100

The experimental results based on these four protocols will be shown in the following table.

TABLE 2

| | Enzyme assay | | IDO cell-based assay | TDO cell-based assay |
|---|---|---|---|---|
| Compound No. | rhIDO-mediated kynurenine production <10 μM> | rhTDO-mediated kynurenine production <10 μM> | Kynurenine production in A431 cells <10 μM> | Kynurenine production in A172 cells <10 μM> |
| 1 | 26% | 13% | 11% | −3% |
| 2 | 11% | 6% | 7% | 7% |
| 3 | 6% | 30% | 7% | 78% |
| 4 | 64% | 56% | 68% | 102% |
| 5 | 69% | 84% | 85% | 113% |
| 6 | 15% | 9% | 75% | 74% |
| 7 | 10% | 3% | 0% | −1% |
| 8 | 77% | 52% | 10% | 20% |
| 9 | 30% | 36% | 10% | 0% |
| 10 | 1% | 3% | −1% | 2% |
| 11 | 51% | 58% | 6% | 19% |
| 12 | 20% | 10% | 13% | 0% |
| 13 | 15% | 9% | 32% | 42% |
| 14 | 52% | 31% | 7% | 4% |
| 15 | 22% | 12% | 12% | 7% |
| 16 | 66% | 68% | 76% | 74% |
| 17 | 30% | 25% | 8% | 0% |
| 18 | 23% | 27% | 7% | −1% |
| 19 | 43% | 46% | 5% | 1% |
| 20 | 27% | 44% | 6% | 0% |
| 21 | 30% | 54% | 6% | −1% |
| 22 | 20% | 21% | 6% | −1% |
| 23 | 18% | 24% | 6% | −4% |
| 24 | 27% | 25% | 4% | −2% |
| 25 | 14% | 26% | 7% | −3% |
| 26 | 36% | 44% | 5% | −5% |
| 27 | 33% | 56% | 7% | −3% |
| 28 | 40% | 53% | 7% | 3% |
| 29 | 23% | 15% | 10% | 0% |
| 30 | 141% | 126% | 82% | 94% |
| 31 | 11% | 17% | 13% | 20% |
| 32 | 59% | 51% | 54% | 52% |
| 33 | 37% | 21% | 3% | 4% |
| 34 | 25% | 27% | 29% | 47% |
| 35 | 24% | 7% | 4% | 0% |
| 36 | <1% | <3% | 1% | −15% |
| 37 | <9% | <7% | 1% | −9% |
| 38 | 16% | 37% | 2% | −1% |
| 39 | 7% | 38% | 0% | 7% |
| 40 | 34% | 29% | 9% | 1% |
| 41 | 41% | 45% | 6% | 4% |
| 42 | 68% | 41% | 6% | 2% |
| 43 | 71% | 41% | 11% | −2% |
| 44 | 50% | 26% | 11% | 1% |
| 45 | 65% | 33% | 13% | 0% |
| 46 | 3% | 14% | 10% | 24% |
| 47 | 16% | 53% | 15% | 45% |
| 48 | 80% | 73% | 63% | 71% |
| 49 | 1% | 15% | 4% | 8% |
| 50 | 9% | 4% | 4% | 4% |
| 51 | 19% | 13% | 23% | 25% |
| 52 | 14% | 5% | 1% | 5% |
| 53 | 16% | 19% | 5% | 17% |
| 54 | 13% | 14% | 4% | 6% |
| 55 | 91% | 111% | 73% | 121% |
| 56 | 41% | 35% | 4% | 2% |
| 57 | 83% | 80% | 3% | 12% |
| 58 | 73% | 83% | 1% | 9% |
| 59 | −3% | 1% | 1% | 4% |
| 60 | 6% | 6% | 1% | 4% |
| 61 | 7% | 4% | 1% | −11% |
| 62 | 58% | 21% | 86% | 56% |
| 63 | 0% | 16% * | 2% | 5% |
| 64 | 81% | 42% | 102% | 76% |
| 65 | 89% | 76% | 104% | 94% |
| 66 | 80% | 49% | 101% | 74% |
| 67 | 39% | 46% | 36% | 64% |
| 68 | 82% | 31% | 101% | 81% |
| 69 | 76% | 60% | 101% | 73% |
| 70 | 72% | 35% | 98% | 96% |
| 71 | 87% | 67% | 96% | 77% |
| 72 | 70% | 47% | 69% | 68% |
| 73 | 29% * | 4% | 4% | −3% |

TABLE 2-continued

| | Enzyme assay | | IDO cell-based assay | TDO cell-based assay |
|---|---|---|---|---|
| | rhIDO-mediated kynurenine production | rhTDO-mediated kynurenine production | Kynurenine production in A431 cells | Kynurenine production in A172 cells |
| Compound No. | <10 μM> | <10 μM> | <10 μM> | <10 μM> |
| 74 | 70% | 29% | 75% | 47% |
| 75 | 35% | 15% | 9% | 3% |
| 76 | 78% | 15% | 82% | 24% |
| 77 | 74% | 101% | 103% | 89% |
| 78 | 74% | 25% | 112% | 56% |
| 79 | 90% | 34% | 60% | 38% |
| 80 | 97% | 38% | 66% | 45% |
| 81 | 81% | 121% | 78% | 89% |
| 82 | 89% | 27% | 99% | 37% |
| 83 | 80% | 59% | 75% | 21% |
| 84 | 84% | 65% | 56% | 18% |
| 85 | 71% | 50% | 56% | 16% |
| 86 | 92% | 46% | 109% | 36% |
| 87 | 75% | 51% | 67% | 13% |
| 88 | 82% | 92% | 64% | 28% |
| 89 | 81% | 12% | 122% | 51% |
| 90 | 90% | 45% | 96% | 51% |
| 91 | 78% | 103% | 51% | 26% |
| 92 | 90% | 68% | 112% | 81% |
| 93 | 103% | 53% | 124% | 49% |
| 94 | 80% | 15% | 158% | 59% |
| 95 | 3% | 6% | 2% | −7% |
| 96 | 71% | 26% | 93% | 38% |
| 97 | 85% | 16% | 83% | 37% |
| 98 | 95% | 91% | 107% | 133% |
| 99 | 96% | 75% | 102% | 106% |
| 100 | 88% | 84% | 93% | 123% |
| 101 | 78% | 84% | 61% | 70% |
| 102 | 97% | 58% | 112% | 38% |
| 103 | 0% | 22% | 3% | 18% |
| 104 | 78% | 81% | −4% | −1% |
| 105 | 98% | 68% | 107% | 42% |
| 106 | 90% | 98% | 64% | 48% |
| 107 | 97% | 103% | 44% | 12% |
| 108 | 51% | 55% | 5% | 41% |
| 109 | 61% | 57% | 19% | 63% |
| 110 | 61% | 59% | 13% | 38% |
| 111 | 17% | 122% | 53% | 87% |
| 112 | 94% | 90% | −2% | 5% |
| 113 | 92% | 58% | 73% | 44% |
| 114 | 98% | 36% | 17% | 37% |
| 115 | 91% | 63% | 121% | 71% |
| 116 | 85% | 21% | 92% | 55% |
| 117 | 2% | 9% | 7% | 31% |
| 118 | 15% | 35% | 3% | 20% |
| 119 | 25% | 50% | 4% | 12% |
| 120 | 41% | 8% | 14% | 7% |
| 121 | 29% | 7% | 14% | 11% |
| 122 | −3% | 8% | 2% | 7% |
| 123 | −2% | 10% | 12% | 4% |
| 124 | −1% | 20% | 10% | 0% |
| 125 | −2% | 7% | 11% | 3% |
| 126 | −1% | 6% | 13% | 10% |
| 127 | 0% | 12% | 8% | 10% |
| 128 | 3% | 14% | 11% | 8% |
| 129 | −2% | 8% | 7% | 14% |
| 130 | 1% | 8% | 1% | 9% |
| 131 | 7% | 3% | 5% | 6% |
| 132 | −2% | 5% | 11% | 5% |
| 133 | 1% | 10% | 13% | 6% |
| 134 | −2% | 5% | 10% | 5% |
| 135 | −2% | 8% | 12% | 0% |
| 136 | −2% | 10% | 13% | 3% |
| 137 | −3% | 9% | 8% | 2% |
| 138 | −1% | 14% | 8% | 0% |
| 139 | 24% | 14% | 8% | 11% |
| 140 | 34% | 16% | 15% | 9% |
| 141 | 21% | 14% | 5% | 11% |
| 142 | 43% | 18% | 16% | 6% |
| 143 | 17% | 6% | 9% | 7% |
| 144 | 15% | 19% | 6% | 18% |
| 145 | 69% | 40% | 18% | 12% |
| 146 | 54% | 26% | 16% | 17% |

TABLE 2-continued

|  | Enzyme assay | | IDO cell-based assay | TDO cell-based assay |
|---|---|---|---|---|
| Compound No. | rhIDO-mediated kynurenine production <10 μM> | rhTDO-mediated kynurenine production <10 μM> | Kynurenine production in A431 cells <10 μM> | Kynurenine production in A172 cells <10 μM> |
| 147 | 32% | 10% | 16% | 16% |
| 148 | 13% | 8% | 7% | 18% |
| 149 | 8% | 11% | 7% | 17% |
| 150 | 23% | 11% | 15% | 13% |
| 151 | 13% | 11% | 33% | 76% |
| 152 | 7% | 7% | 9% | 6% |
| 153 | 8% | 6% | 12% | 9% |

In Table 2, "<10 μM>" means a final concentration of the compound of the present invention. However, data with "*", i.e., means that the final concentration of the compound was 3 μM in the rate of rhTDO-mediated kynurenine production for compound 63 and the rate of the rhIDO-mediated kynurenine production for compound 73.

As is evident from Table 2, the compound of the present invention has excellent inhibitory activity against IDO and/or TDO.

Test Example 2

Drug Efficacy Test on Combined Use of IDO/TDO Inhibitor and Anti-PD-1 Antibody Using Mice with Subcutaneous CT-26WT Syngeneic Graft of Large Intestine Cancer
<Legend, Material, and Method>

$5 \times 10^5$ cells of syngeneic large intestine cancer cell line CT26WT were subcutaneously transplanted to each of 6-week-old female Balb/c mice. The mice were divided into 6 groups each involving 6 to 8 individuals 11 days later when the average tumor size was 212 mm$^3$. The oral administration (solvent for oral administration and 40 mg/kg each of epacadostat and compound 1 were administered twice a day at a 5-hour interval from days 1 to 5, days 8 to 12, and days 15 to 19) and intraperitoneal administration (PBS and 200 μg/individual of an anti-PD1 antibody were administered once a day on days 1, 4, 8, 11, 15, and 18) of each agent were started. Then, the major axis and minor axis of subcutaneous tumor were measured three times a week using calipers, and a mean and standard error of the mean of the calculated volumes in each group were plotted. The calculation expression was Volume (mm$^3$)=[Width$^2$ (mm$^2$)×Length (mm)]/2. The oral administration agent was dissolved in a solvent for oral administration of DMSO:PEG400:PBS=5:20:75. The results are shown in FIG. 1.

The meaning of each symbol is as described below.
○: the solvent for oral administration and PBS, •: the solvent for oral administration and the anti-PD-1 antibody, □: epacadostat and PBS, ■: epacadostat and the anti-PD-1 antibody, Δ: compound 1 and PBS, and ▲: compound 1 and the anti-PD1 antibody.

As is evident from FIG. 1, combined use of compound 1 of the present invention and the anti-PD-1 antibody can suppress tumor growth.

Test Example 3

Drug Efficacy Test on Combined Use of Compound 1 and Oxaliplatin Using Mice with Subcutaneous CT-26CL25 Syngeneic Graft of Large Intestine Cancer
<Legend, Material, and Method>

$5 \times 10^5$ cells of syngeneic large intestine cancer cell line CT26CL25 were subcutaneously transplanted to each of 8-week-old female Balb/c mice. The mice were divided into 4 groups each involving 8 individuals 10 days later when the average tumor size was 185 mm$^3$. The oral administration (solvent for oral administration and 40 mg/kg compound 1 were administered twice a day at a 5-hour interval from days 1 to 5 and days 8 to 12) and intravenous administration (5% glucose solution and 10 mg/kg oxaliplatin were administered once a day on days 1 and 8) of each agent were started. Then, the major axis and minor axis of subcutaneous tumor were measured three times a week using calipers, and a mean and standard error of the mean of the ratios of the calculated volumes to the volumes at the administration start day in each group were plotted. The calculation expression was Volume (mm$^3$)=[Width$^2$ (mm$^2$)×Length (mm)]/2. Compound 1 was dissolved in a solvent for oral administration of DMSO:PEG400:PBS=5:20:75. The results are shown in FIG. 2.

The meaning of each symbol is as described below.
○: the solvent for oral administration and the 5% glucose solution, •: the solvent for oral administration and oxaliplatin, Δ: compound 1 and the 5% glucose solution, and ▲: compound 1 and oxaliplatin.

Figure 2:
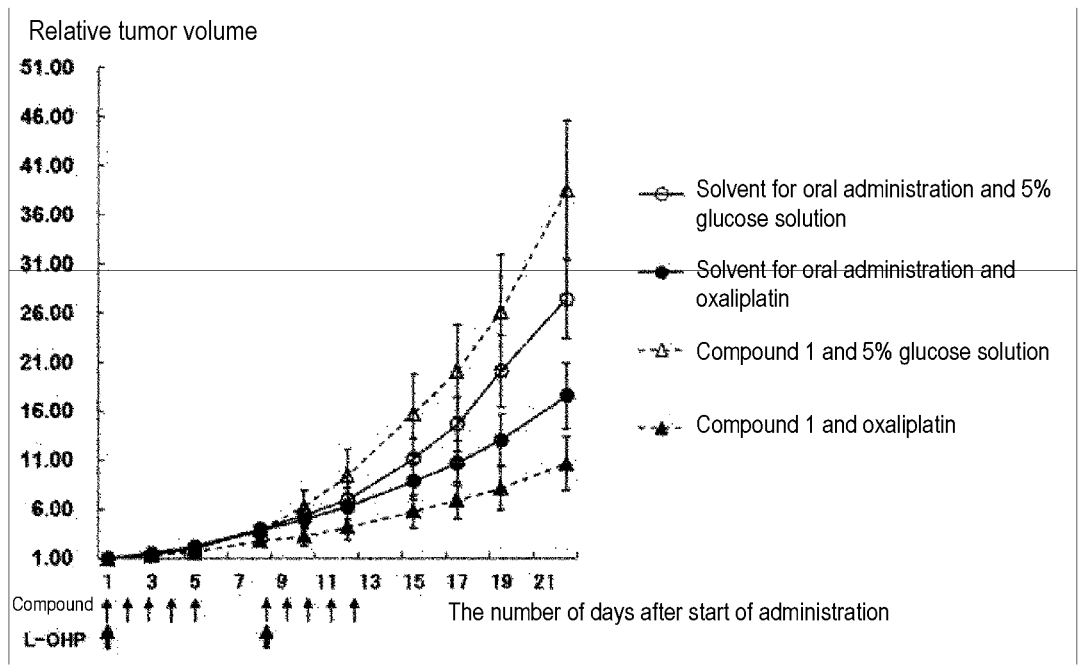
FIG. 2 is a graph showing results of a drug efficacy test on combined use of compound 1 and oxaliplatin using mice with a subcutaneous CT-26CL25 syngeneic graft of large intestine cancer.

As is evident from FIG. 2, combined use of compound 1 of the present invention and oxaliplatin can suppress tumor growth.

Test Example 4

Drug Efficacy Test on Combined Use of Compound 1, Compound 15 or Compound 29 and Oxaliplatin Using Mice with Subcutaneous CT-26WT Syngeneic Graft of Large Intestine Cancer
<Legend, Material, and Method>

$5 \times 10^5$ cells of syngeneic large intestine cancer cell line CT26WT were subcutaneously transplanted to each of 6-week-old female Balb/c mice. The mice were divided into 5 groups each involving 6 individuals 10 days later when the average tumor size was 139 mm$^3$. The oral administration (solvent for oral administration and 40 mg/kg each of compound 1, compound 15 and compound 29 were administered twice a day at a 5-hour interval from days 1 to 5 and days 8 to 12) and intravenous injection (5% glucose solution and 10 mg/kg oxaliplatin were administered once a day on days 1 and 8) of each agent were started. Then, the major axis and minor axis of subcutaneous tumor were measured three times a week using calipers, and a mean and standard error of the mean of the ratios of the calculated volumes to the volumes at the administration start day in each group were plotted. The calculation expression was Volume (mm$^3$) =[Width$^2$ (mm$^2$)×Length (mm)]/2. The solvent group, compound 1 and compound 15 were each dissolved in a solvent for oral administration of DMSO:PEG400:PBS=10:40:150, and compound 29 was dissolved in a solvent for oral administration of DMSO:PEG400:PBS=20:80:50. The results are shown in FIG. 3.

The meaning of each symbol is as described below.
o: the solvent for oral administration and the 5% glucose solution, •: the solvent for oral administration and oxaliplatin, ▲: compound 1 and oxaliplatin, ■: compound 15 and oxaliplatin, and x: compound 29 and oxaliplatin.

Figure 3:
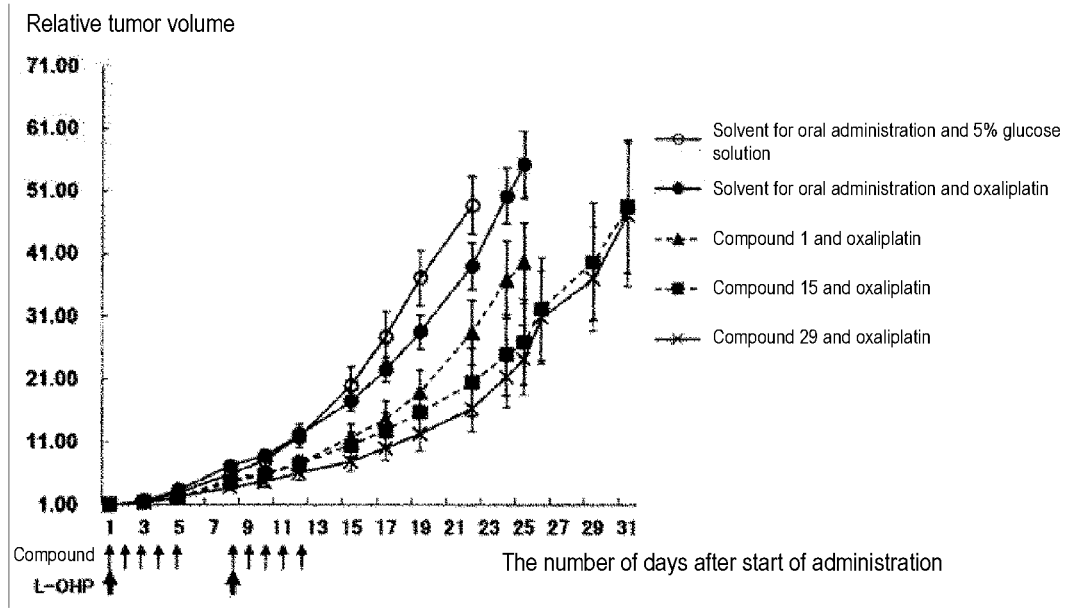
FIG. 3 is a graph showing results of a drug efficacy test on combined use of compound 1, compound 15 or compound 29 and oxaliplatin using mice with a subcutaneous CT-26WT syngeneic graft of large intestine cancer.

As is evident from FIG. 3, combined use of compound 1, compound 15 or compound 29 and oxaliplatin can suppress tumor growth.

Test Example 5

Drug Efficacy Test on Combined Use of IDO/TDO Inhibitor and Oxaliplatin Using Mice with a Subcutaneous CT-26WT Syngeneic Graft of Large Intestine Cancer
<Legend, Material, and Method>

$5 \times 10^5$ cells of syngeneic large intestine cancer cell line CT26WT were subcutaneously transplanted to each of 6-week-old female Balb/c mice. The mice were divided into groups each involving 6 individuals 10 days later within a tumor size range of 41-427 mm$^3$. The oral administration (solvent for oral administration and 40 mg/kg each of epacadostat and compounds 37, 31, 7, 15, 1, 50, 52, 76, 95, 33, 49, 2, 10, 36, 103, 38 and 29 were administered twice a day at a 5-hour interval from days 1 to 5 and days 8 to 12) and intravenous injection (5% glucose solution and 10 mg/kg oxaliplatin were administered once a day on days 1 and 8) of each agent were started. Then, the major axis and minor axis of subcutaneous tumor were measured three times a week using calipers, and a mean and standard error of the mean of the ratios of the calculated volumes to the volumes at the administration start day in each group were plotted. The calculation expression was Volume (mm$^3$)= [Width (mm$^2$)×Length (mm)]/2. The agent for oral administration was suspended in 0.5% methyl cellulose as a solvent for oral administration. The results are shown in FIG. 4 (if a plurality of experiments were conducted for the same agent, the results were combined).

The meaning of each symbol is as described below.
• with the solid line: the solvent for oral administration and the 5% glucose solution, ■ with the solid line: compound 37 and oxaliplatin, ▲ with the solid line: epacadostat and oxaliplatin, X with the solid line: compound 31 and oxaliplatin, o with the solid line: the solvent for oral administration and oxaliplatin, □ with the solid line: compound 7 and oxaliplatin, Δ with the solid line: compound 15 and oxaliplatin, X with the solid line: compound 1 and oxaliplatin, • with the broken line: compound 50 and oxaliplatin, ■ with the broken line: compound 52 and oxaliplatin, ▲ with the broken line: compound 76 and oxaliplatin, X with the broken line: compound 95 and oxaliplatin, o with the broken line: compound 33 and oxaliplatin, □ with the broken line: compound 49 and oxaliplatin, Δ with the broken line: compound 2 and oxaliplatin, + with the solid line: compound 10 and oxaliplatin, rectangle with the solid line: compound 36 and oxaliplatin, • with the dotted line: compound 103 and oxaliplatin, ■ with the dotted line: compound 38 and oxaliplatin, and ▲ with the dotted line: compound 29 and oxaliplatin.

Figure 4:
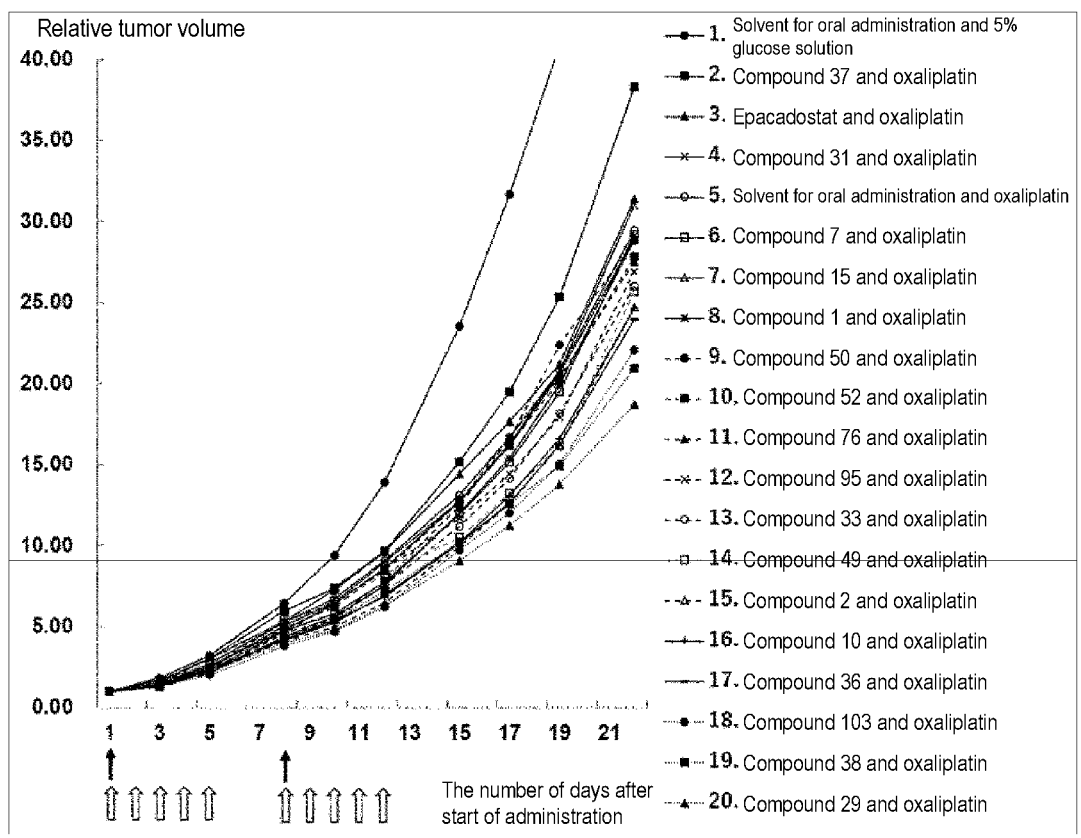
FIG. 4 is a graph showing results of a drug efficacy test on combined use of an IDO/TDO inhibitor and oxaliplatin using mice with a subcutaneous CT-26WT syngeneic graft of large intestine cancer.

As is evident from FIG. 4, combined use of compound 37, 31, 7, 15, 1, 50, 52, 76, 95, 33, 49, 2, 10, 36, 103, 38 or 29 of the present invention and oxaliplatin can suppress tumor growth.

Test Example 6

Drug Efficacy Test on Combined Use of Compound 29 or 38 and Anti-PD1 Antibody Using Mice with Subcutaneous CT-26WT Syngeneic Graft of Large Intestine Cancer
<Legend, Material, and Method>

Figure 5:
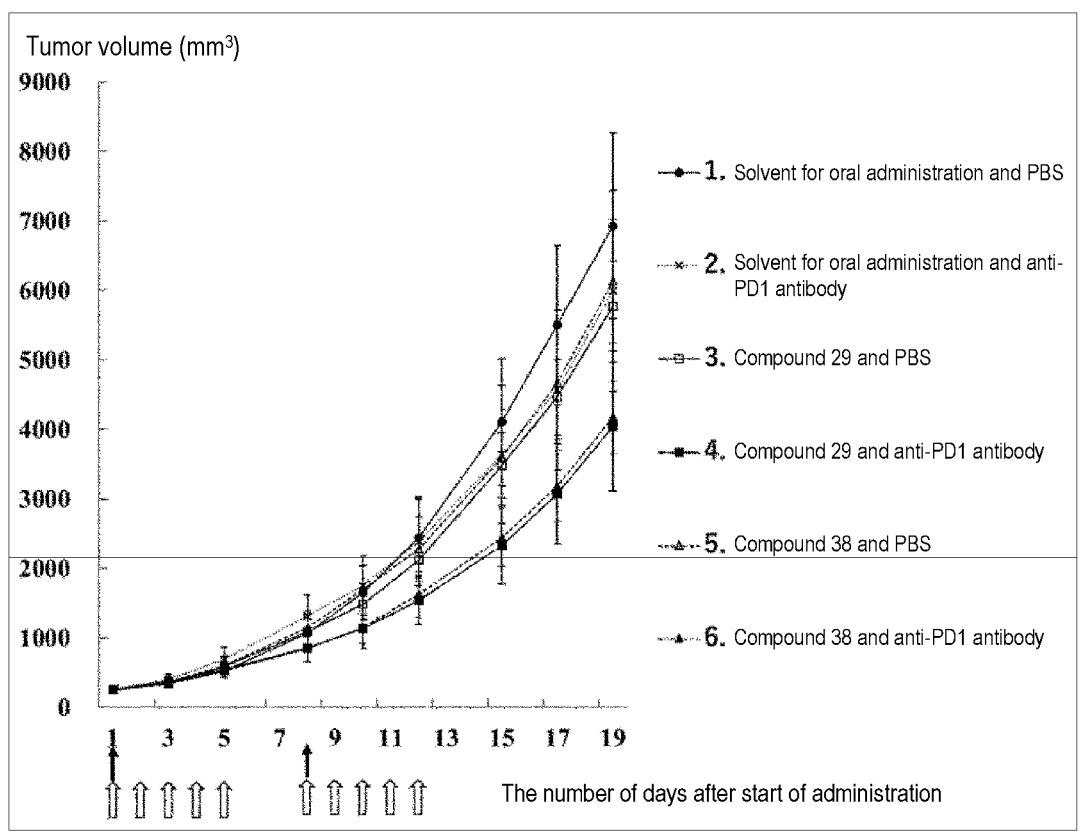
FIG. 5 is a graph showing results of a drug efficacy test on combined use of compound 29 or 38 and an anti-PD-1 antibody using mice with a subcutaneous CT-26WT syngeneic graft of large intestine cancer.

$5 \times 10^5$ cells of syngeneic large intestine cancer cell line CT26WT were subcutaneously transplanted to each of 6-week-old female Balb/c mice. The mice were divided into 6 groups each involving 6 individuals 10 days later when the average tumor size was 250 mm$^3$. The oral administration (solvent for oral administration and 40 mg/kg each of compounds 29 and 38 were administered twice a day at a 5-hour interval from days 1 to 5 and days 8 to 12) and intraperitoneal administration (PBS and 200 μg/individual of an anti-PD1 antibody were administered once a day on days 1 and 8) of each agent were started. Then, the major axis and minor axis of subcutaneous tumor were measured three times a week using calipers, and a mean and standard error of the mean of the calculated volumes in each group were plotted. The calculation expression was Volume (mm$^3$)= [Width (mm$^2$)×Length (mm)]/2. Compound 29 or 38 was suspended in 0.5% methyl cellulose as a solvent for oral administration. The results are shown in FIG. 5.

The meaning of each symbol is as described below.
• with the solid line: the solvent for oral administration and PBS, X with the dotted line: the solvent for oral administration and the anti-PD-1 antibody, □ with the solid line: compound 29 and PBS, ■ with the solid line: compound 29 and the anti-PD1 antibody, Δ with the broken line: compound 38 and PBS, and ▲ with the broken line: compound 38 and the anti-PD1 antibody As is evident from FIG. 5, combined use of compound 29 or 38 of the present invention and the anti-PD1 antibody can suppress tumor growth.

Test Example 7

Drug Efficacy Test on Combined Use of Compound 103 and Anti-PD1 Antibody Using Mice with Subcutaneous CT-26WT Syngeneic Graft of Large Intestine Cancer
<Legend, Material, and Method>

$5 \times 10^5$ cells of syngeneic large intestine cancer cell line CT26WT were subcutaneously transplanted to each of 6-week-old female Balb/c mice. The mice were divided into 3 groups each involving 8 individuals 10 days later when the average tumor size was 176 mm$^3$. The oral administration (40 mg/kg of compound 103 was administered twice a day at a 5-hour interval from days 1 to 5 and days 8 to 12), intravenous administration (5% glucose solution was administered once a day on days 1 and 8) and intraperitoneal administration (PBS and 200 μg/individual of an anti-PD1 antibody were administered once a day on days 1 and 8) of each agent were started. Then, the major axis and minor axis of subcutaneous tumor were measured three times a week using calipers, and a mean and standard error of the mean of the calculated volumes in each group were plotted. The calculation expression was Volume (mm$^3$)=[Width$^2$ (mm$^2$)× Length (mm)]/2. Compound 103 was suspended in 0.5% methyl cellulose. The results are shown in FIG. 6.

The meaning of each symbol is as described below.
• with the solid line: the 5% glucose solution and PBS, X with the dotted line: the 5% glucose solution and the anti-PD1 antibody, and o with the solid line: compound 103 and the anti-PD1 antibody.

Figure 6:
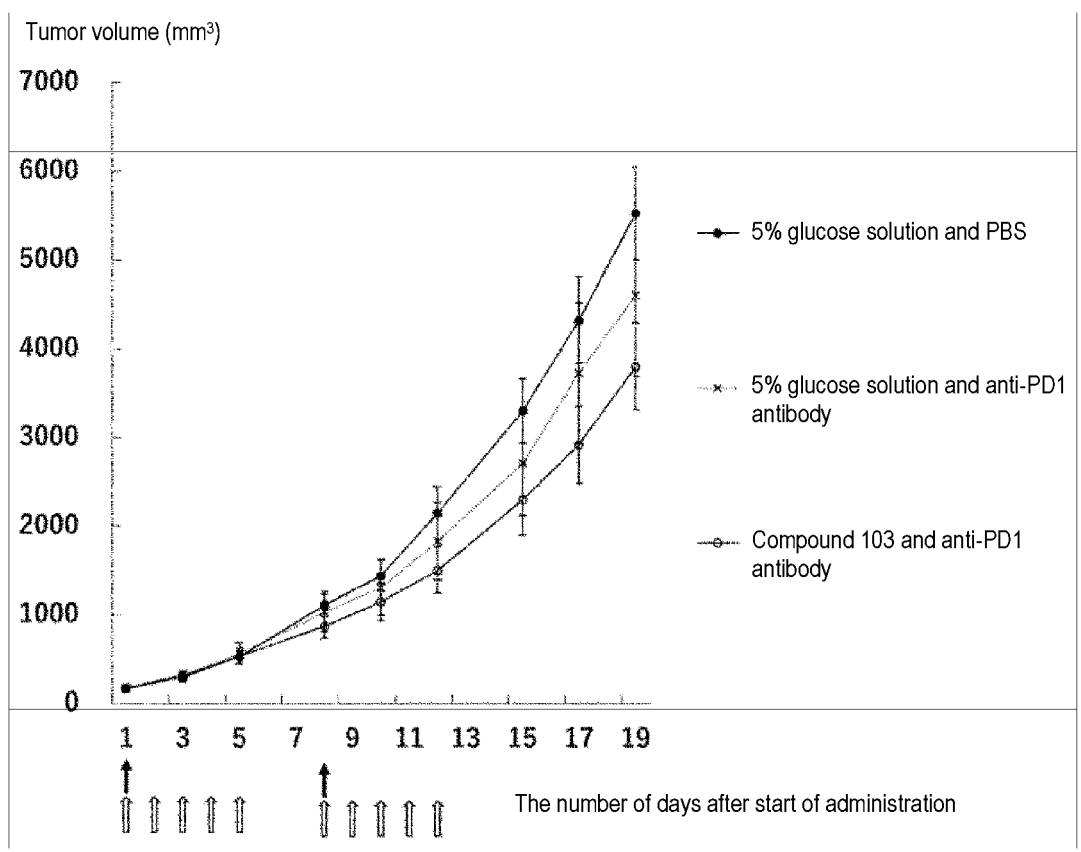
FIG. 6 is a graph showing results of a drug efficacy test on combined use of compound 103 and an anti-PD-1 antibody using mice with a subcutaneous CT-26WT syngeneic graft of large intestine cancer.

As is evident from FIG. 6, combined use of compound 103 and the anti-PD1 antibody can suppress tumor growth.

The following items numbered [1] to [31] provide various modes of the present invention.

[1] A compound of formula (I) or a pharmaceutically acceptable salt of the compound:

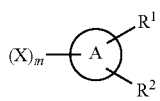

(I)

[wherein
ring A represents an aromatic ring, an aliphatic ring, a heterocyclic ring, or a condensed ring of two or more rings selected from an aromatic ring, an aliphatic ring and a heterocyclic ring;
X, $R^1$ and $R^2$ represent a substituent on a ring atom constituting ring A;
m represents an integer of 0 to 6;
X is selected from the group consisting of a halogen atom, a substituted or unsubstituted linear or branched alkyl group, a substituted or unsubstituted linear or branched alkoxy group, a substituted or unsubstituted linear or branched alkenyl group, a substituted or unsubstituted linear or branched alkenyloxy group, a substituted or unsubstituted linear or branched alkynyl group, a substituted or unsubstituted linear or branched alkynyloxy group, a substituted or unsubstituted cycloalkyl group, a substituted or unsubstituted cycloalkenyl group, an alkyl halide group, an alkyloxy halide group, a cyano group, a hydroxy group, an amino group, a nitro group, a carboxyl group, a substituted or unsubstituted aryl group, and a substituted or unsubstituted aralkyl group, and when m is 2 to 6, each X is the same or different;
$R^1$ and $R^2$ are the same or different;
$R^1$ represents a group represented by formula (II):

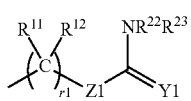

(II)

(wherein $R^{11}$ and $R^{12}$ each independently represent a hydrogen atom, a fluorine atom or a substituted or unsubstituted alkyl group, Y1 represents O or $NR^{21}$, $R^{21}$, $R^{22}$ and $R^{23}$ each independently represent a hydrogen atom, a substituted or unsubstituted linear or branched alkyl group, a substituted or unsubstituted cycloalkyl group, a substituted or unsubstituted aryl group or a substituted or unsubstituted heterocyclic group, $R^{21}$ and $R^{22}$ or $R^{23}$ are optionally bonded to each other to form a ring, Z1 represents S, SO, $SO_2$, O or Se, r1 represents any integer of 1 to 8, and when r1 is 2 or larger, each $R^{11}$ and each $R^{12}$ are the same or different),
or formula (III):

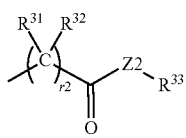

(III)

(wherein $R^{31}$ and $R^{32}$ each independently represent a hydrogen atom, a fluorine atom or a substituted or unsubstituted linear or branched alkyl group, Z2 represents O or $NR^{61}$ (wherein $R^{61}$ represents a hydrogen atom, a substituted or unsubstituted linear or branched alkyl group or a substituted or unsubstituted aryl group), $R^{33}$ represents a substituted or unsubstituted linear or branched alkyl group, a substituted or unsubstituted cycloalkyl group, a substituted or unsubstituted aryl group, a substituted or unsubstituted aralkyl group or a substituted or unsubstituted cycloalkylalkyl group, r2 represents 0 or any integer of 1 to 8, and when r2 is 2 or larger, each $R^{31}$ and each $R^{32}$ are the same or different); and
$R^2$ represents, independently from $R^1$, a group represented by formula (II) or formula (III)].

[2] The compound according to [1] or a pharmaceutically acceptable salt of the compound, wherein in formula (II), a functional group containing the ring formed by $R^{21}$ and $R^{22}$ or $R^{23}$ bonded to each other is a functional group represented by the following formula (IV):

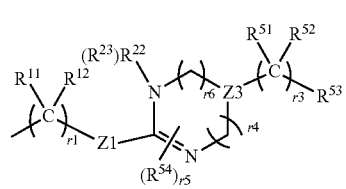

(IV)

[wherein $R^{11}$, $R^{12}$, r1, Z1, $R^{22}$, and $R^{23}$ have the same meaning as described in formula (II), Z3 represents CH, $CR^{54}$ or N, $R^{51}$ and $R^{52}$ each independently represent a hydrogen atom or a substituted or unsubstituted linear or branched alkyl group, $R^{54}$ represents a halogen atom or a substituted or unsubstituted linear or branched alkyl group, $R^{53}$ represents a substituted or unsubstituted aryl group, a substituted or unsubstituted cycloalkyl group or a substituted or unsubstituted heterocyclic group, r3 represents any integer of 1 to 8, when r3 is 2 or larger, each $R^{51}$ and each $R^{52}$ are the same or different, r4 and r6 each independently represent 0 or 1, r4 and r6 are not 0 at the same time, r5 represents 0 or any integer of 1 to 5, when r5 is 2 or larger, each $R^{54}$ is the same or different, and the notation $R^{22}(R^{23})$ represents any one of $R^{22}$ and $R^{23}$).

[3] The compound according to [1] or [2] or a pharmaceutically acceptable salt of the compound, wherein
$R^1$ is selected from the group consisting of the following groups:

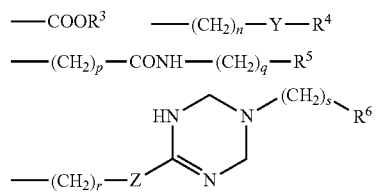

[wherein
Y is selected from the group consisting of O, S, SO, $SO_2$, and Se,
Z is selected from the group consisting of O, S, SO, $SO_2$, and Se,
n represents an integer of 1 to 8,
p represents an integer of 0 to 8, q represents an integer of 1 to 8,
r represents an integer of 1 to 8,
s represents an integer of 1 to 8,
$R^3$ represents a substituted or unsubstituted linear or branched alkyl group,
$R^4$ represents a substituted or unsubstituted heterocyclic group, —$CONH_2$, or

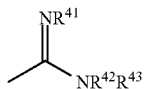

(wherein $R^{41}$, $R^{42}$ and $R^{43}$ are the same or different and are selected from the group consisting of a hydrogen atom, a substituted or unsubstituted linear or branched alkyl group, a substituted or unsubstituted cycloalkyl group, a substituted or unsubstituted aryl group or a substituted or unsubstituted heterocyclic group),
$R^5$ is selected from the group consisting of a hydrogen atom, a substituted or unsubstituted cycloalkyl group, and a substituted or unsubstituted aryl group, and
$R^6$ is selected from the group consisting of a substituted or unsubstituted aryl group, a substituted or unsubstituted cycloalkyl group, and a substituted or unsubstituted heterocyclic group], and $R^2$ is selected, independently from $R^1$, from the group consisting of the following groups:

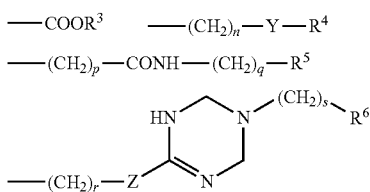

(wherein Y, Z, n, p, q, r, s, $R^3$, $R^4$, $R^5$, and $R^6$ have the same meaning as described above).

[4] The compound according to any one of [1] to [3] or a pharmaceutically acceptable salt of the compound, wherein $R^1$ and $R^2$ are bonded to adjacent ring atoms of ring A.

[5] The compound according to any one of [1] to [4] or a pharmaceutically acceptable salt of the compound, wherein $R^1$ and $R^2$ have the same group.

[6] The compound according to [5] or a pharmaceutically acceptable salt of the compound, wherein in the compound of formula (I), $R^1$ and $R^2$ are a group represented by formula (II), and in formula (II), $R^{11}$ and $R^{12}$ are a hydrogen atom, Y1 represents $NR^{21}$, and r1 is 1.

[7] The compound according to [6] or a pharmaceutically acceptable salt of the compound, wherein the compound is represented by any one of the following formulae:

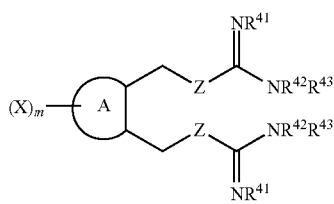

(I-1)

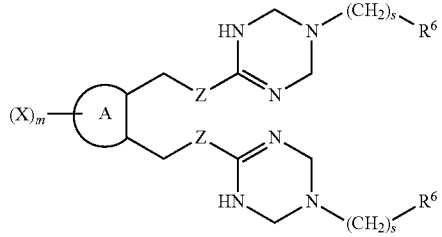

(I-2)

(wherein A, X, and m have the same meaning as defined in [1], and Z, s, $R^{41}$, $R^{42}$, $R^{43}$, and $R^6$ have the same meaning as defined in [3]).

[8] The compound according to any one of [1] to [4] or a pharmaceutically acceptable salt of the compound, wherein $R^1$ and $R^2$ have different groups.

[9] The compound according to [8] or a pharmaceutically acceptable salt of the compound, wherein the compound is represented by the following formula:

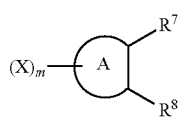

(I-3)

(wherein A, X, and m have the same meaning as defined in [1], $R^7$ and $R^8$ are selected from the group consisting of —$COOR^3$ (wherein $R^3$ represents a substituted or unsubstituted linear or branched alkyl group), —$(CH_2)_n$—Y—$R^4$ (wherein n, Y, and $R^4$ have the same meaning as defined in [3]), —$(CH_2)_p$—CONH—$(CH_2)_q$—$R^5$ (wherein p, q, and $R^5$ have the same meaning as defined in [3]), and the following formula:

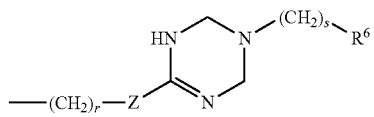

(wherein r, s, $R^6$ and Z have the same meaning as defined in [3]), and $R^7$ and $R^8$ are different from each other).

[10] The compound according to any one of [1] to [9] or a pharmaceutically acceptable salt of the compound, wherein ring A is selected from the group consisting of a benzene ring, a naphthalene ring, a quinoxaline ring, a thiophene ring, an indole ring, a benzothiophene ring, an imidazole ring, a quinoline ring, a quinazoline ring, and a pyridine ring.

[11] The compound according to any one of [1] to [10] or a pharmaceutically acceptable salt of the compound, wherein X is selected from the group consisting of a halogen atom, a substituted or unsubstituted linear or branched $C_1$-$C_8$ alkyl group, a substituted or unsubstituted linear or branched $C_1$-$C_8$ alkoxy group, a substituted or unsubstituted linear or branched $C_2$-$C_8$ alkenyl group, a substituted or unsubstituted linear or branched $C_2$-$C_8$ alkenyloxy group, a substituted or unsubstituted linear or branched $C_2$-$C_8$ alkynyl group, a substituted or unsubstituted linear or branched $C_2$-$C_8$ alkynyloxy group, a substituted or unsubstituted $C_3$-$C_8$ cycloalkyl group, a substituted or unsubstituted $C_3$-$C_8$ cycloalkenyl group, a substituted or unsubstituted $C_3$-$C_8$ cycloalkynyl group, a $C_1$-$C_3$ alkyl halide group, a cyano group, a hydroxy group, an amino group, a carboxyl group, a substituted or unsubstituted $C_6$-$C_{18}$ aryl group, and a substituted or unsubstituted aralkyl group (wherein the number of carbon atoms in the aryl moiety is $C_6$-$C_{10}$, and the number of carbon atoms in the alkylene moiety is $C_1$-$C_4$).

[12] The compound according to any one of [1] to [11] or a pharmaceutically acceptable salt of the compound, wherein X represents a group selected from the following group:
- as a halogen atom, a fluorine atom, a chlorine atom, a bromine atom, and an iodine atom,
- as a substituted or unsubstituted linear or branched alkyl group, a methyl group, an ethyl group, a n-propyl group, an i-propyl group, a n-butyl group, an i-butyl group, a s-butyl group, a t-butyl group, a n-pentyl group, a n-hexyl group, a n-octyl group, a carboxymethyl group, a 2-carboxyethyl group, a 3-hydroxy-1-propyl group, an aminomethyl group, a 2-aminoethyl group, a hydroxymethyl group, and a 2-hydroxyethyl group,
- as a substituted or unsubstituted linear or branched alkoxy group, a methoxy group, an ethoxy group, a n-propoxy group, and a n-butoxy group,
- as a substituted or unsubstituted linear or branched alkenyl group, an ethenyl (vinyl) group, a 2-propenyl (allyl) group, and a 3-butenyl group,
- as a substituted or unsubstituted linear or branched alkenyloxy group, an ethenyloxy (vinyloxy) group, a 2-propenyloxy (allyloxy) group, and a 3-butenyloxy group,
- as a substituted or unsubstituted linear or branched alkynyl group, an ethynyl group, a 2-propynyl group, and a 3-butynyl group,
- as a substituted or unsubstituted linear or branched alkynyloxy group, an ethynyloxy group, a 2-propynyloxy group, and a 3-butynyloxy group,
- as a substituted or unsubstituted cycloalkyl group, a cyclopropyl group, a cyclobutyl group, a cyclopentyl group, a cyclohexyl group, and a cyclooctyl group,
- as a substituted or unsubstituted cycloalkenyl group, a 1-cyclopropenyl group, a 1-cyclobutenyl group, a 1-cyclopentenyl group, and a 1-cyclohexenyl group,
- as an alkyl halide group, a fluoromethyl group, a difluoromethyl group, a chloromethyl group, a bromomethyl group, an iodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, and a pentafluoroethyl group,
- as an alkyloxy halide group, a fluoromethoxy group, a difluoromethoxy group, a chloromethoxy group, a bromomethoxy group, an iodomethoxy group, a trifluoromethoxy group, a trichloromethoxy group, a tribromomethoxy group, a triiodomethoxy group, a 2,2,2-trifluoroethoxy group, a 2,2,2-trichloroethoxy group, a 2,2,2-tribromoethoxy group, a 2,2,2-triiodoethoxy group, and a pentafluoroethoxy group,
- a cyano group,
- a hydroxy group,
- an amino group,
- a nitro group,
- a carboxyl group,
- as a substituted or unsubstituted aryl group, a phenyl group, a naphthalen-1-yl group, and a naphthalen-2-yl group, and
- as a substituted or unsubstituted aralkyl group, a benzyl group, a phenethyl group, and a 3-phenyl-1-propyl group.

[13] The compound according to any one of [1] to [12] or a pharmaceutically acceptable salt of the compound, wherein in a compound of the following formula (I-4) containing a benzene ring as ring A, and $R^1$ and $R^2$ are substituted in positions 1 and 2, respectively, of the ring,

(I-4)

(wherein $R^1$ and $R^2$ have the same meaning as defined in any one of [1] to [3])
the following formula (I-4-a) excluding $R^1$ and $R^2$:

(I-4-a)

is selected from the group consisting of Ph=, 3-F-Ph=, 4-F-Ph=, 5-F-Ph=, 6-F-Ph=, 3-Cl-Ph=, 4-Cl-Ph=, 5-Cl-Ph=, 6-Cl-Ph=, 3-Br-Ph=, 4-Br-Ph=, 5-Br-Ph=, 6-Br-Ph=, 3-I-Ph=, 5-I-Ph=, 6-I-Ph=, 3-Me-Ph=, 4-Me-Ph=, 5-Me-Ph=, 6-Me-Ph=, 3-Et-Ph=, 4-Et-Ph=, 5-Et-Ph=, 6-Et-Ph=, 3-Pr-Ph=, 4-Pr-Ph=, 5-Pr-Ph=, 6-Pr-Ph=, 3-Bu-Ph=, 4-Bu-Ph=, 5-Bu-Ph=, 6-Bu-Ph=, 3-t-Bu-Ph=, 4-t-Bu-Ph=, 5-t-Bu-Ph=, 6-t-Bu-Ph=, 3-MeO-Ph=, 4-MeO-Ph=, 5-MeO-Ph=, 6-MeO-Ph=, 3-EtO-Ph=, 4-EtO-Ph=, 5-EtO-Ph=, 6-EtO-Ph=, 3-$CF_3$-Ph=, 4-$CF_3$-Ph=, 5-$CF_3$-Ph=, 6-$CF_3$-Ph=, 3-$C_2F_5$-Ph=, 4-$C_2F_5$-Ph=, 5-$C_2F_5$-Ph=, 6-$C_2F_5$-Ph=, 3-$CF_3$O-Ph=, 4-$CF_3$O-Ph=, 5-$CF_3$O-Ph=, 6-$CF_3$O-Ph=, 3-$C_2F_5$O-Ph=, 4-$C_2F_5$O-Ph=, 5-$C_2F_5$O-Ph=, 6-$C_2F_5$O-Ph=, 3-CN-Ph=, 4-CN-Ph=, 5-CN-Ph=, 6-CN-Ph=, 3-OH-Ph=, 4-OH-Ph=, 5-OH-Ph=, 6-OH-Ph=, 3-$NH_2$-Ph=, 4-$NH_2$-Ph=, 5-$NH_2$-Ph=, 6-$NH_2$-Ph=, 3-$NO_2$-Ph=, 4-$NO_2$-Ph=, 5-$NO_2$-Ph=, 6-$NO_2$-Ph=, 3-COOH-Ph=, 4-COOH-Ph=, 5-COOH-Ph=, 6-COOH-Ph=, (any two of positions 3, 4, 5 and 6)-$F_2$-Ph=, (any two of positions 3, 4, 5 and 6)-$Cl_2$-Ph=, (any two of positions 3, 4, 5 and 6)-$Br_2$-Ph=, (any two of positions 3, 4, 5 and 6)-$I_2$-Ph=, (any two of positions 3, 4, 5 and 6)-$Me_2$-Ph=, (any two of positions 3, 4, 5 and 6)-$Et_2$-Ph-, (any two of positions 3, 4, 5 and 6)-$Pr_2$-Ph=, (any two of positions 3, 4, 5 and 6)-$Bu_t$-Ph=, (any two of positions 3, 4, 5 and 6)-$(CN)_2$-Ph=, (any two of positions 3, 4, 5 and 6)-$(OH)_2$-Ph=, (any two of positions 3, 4, 5 and 6)-$((NH_2))_2$-Ph=, (any two of positions 3, 4, 5 and 6)-$(NO_2)_2$-Ph=, (any two of positions 3, 4, 5 and 6)-$(MeO)_2$-Ph=, (any two of positions 3, 4, 5 and 6)-$(EtO)_2$-Ph=, (any two of positions 3, 4, 5 and 6)-$(CF_3)_2$-Ph=, (any three of positions 3, 4, 5 and 6)-$F_3$-Ph=, (any three of positions 3, 4, 5 and 6)-$Cl_3$-Ph=, (all four of positions 3, 4, 5 and 6)-$F_4$-Ph=, and (all four of positions 3, 4, 5 and 6)-$Cl_4$-Ph= (wherein "Ph=" represents a moiety of formula (I-4-a) excluding $(X)_m$—).

The definitions of formula (I-4) and formula (I-4-a) described above can be translated as follows.

In formula (I), when ring A is a benzene ring and R¹ and R² are adjacently added to ring A with the substitution position of R¹ as position 1 and the substitution position of R² as position 2, X is selected from a hydrogen atom, a 3-fluoro group, a 4-fluoro group, a 5-fluoro group, a 6-fluoro group, a 3-chloro group, a 4-chloro group, a 5-chloro group, a 6-chloro group, a 3-bromo group, a 4-bromo group, a 5-bromo group, a 6-bromo group, a 3-iodo group, a 4-iodo group, a 5-iodo group, a 6-iodo group, a 3-methyl group, a 4-methyl group, a 5-methyl group, a 6-methyl group, a 3-ethyl group, a 4-ethyl group, a 5-ethyl group, a 6-ethyl group, a 3-n-propyl group, a 4-n-propyl group, a 5-n-propyl group, a 6-n-propyl group, a 3-n-butyl group, a 4-n-butyl group, a 5-n-butyl group, a 6-n-butyl group, a 3-t-butyl group, a 4-t-butyl group, a 5-t-butyl group, a 6-t-butyl group, a 3-methoxy group, a 4-methoxy group, a 5-methoxy group, a 6-methoxy group, a 3-ethoxy group, a 4-ethoxy group, a 5-ethoxy group, a 6-ethoxy group, a 3-trifluoromethyl group, a 4-trifluoromethyl group, a 5-trifluoromethyl group, a 6-trifluoromethyl group, a 3-pentafluoroethyl group, a 4-pentafluoroethyl group, a 5-pentafluoroethyl group, a 6-pentafluoroethyl group, a 3-trifluoromethoxy group, a 4-trifluoromethoxy group, a 5-trifluoromethoxy group, a 6-trifluoromethoxy group, a 3-pentafluoroethoxy group, a 4-pentafluoroethoxy group, a 5-pentafluoroethoxy group, a 6-pentafluoroethoxy group, a 3-cyano group, a 4-cyano group, a 5-cyano group, a 6-cyano group, a 3-hydroxy group, a 4-hydroxy group, a 5-hydroxy group, a 6-hydroxy group, a 3-amino group, a 4-amino group, a 5-amino group, a 6-amino group, a 3-nitro group, a 4-nitro group, a 5-nitro group, a 6-nitro group, a 3-carboxyl group, a 4-carboxyl group, a 5-carboxyl group, a 6-carboxyl group, a 3,4-difluoro group, a 3,5-difluoro group, a 3,6-difluoro group, a 4,5-difluoro group, a 4,6-difluoro group, a 5,6-difluoro group, a 3,4-dichloro group, a 3,5-dichloro group, a 3,6-dichloro group, a 4,5-dichloro group, a 4,6-dichloro group, a 5,6-dichloro group, a 3,4-dibromo group, a 3,5-dibromo group, a 3,6-dibromo group, a 4,5-dibromo group, a 4,6-dibromo group, a 5,6-dibromo group, a 3,4-dimethyl group, a 3,5-dimethyl group, a 3,6-dimethyl group, a 4,5-dimethyl group, a 4,6-dimethyl group, a 5,6-dimethyl group, a 3,4-diethyl group, a 3,5-diethyl group, a 3,6-diethyl group, a 4,5-diethyl group, a 4,6-diethyl group, a 5,6-diethyl group, a 3,4-di-n-propyl group, a 3,5-di-n-propyl group, a 3,6-di-n-propyl group, a 4,5-di-n-propyl group, a 4,6-di-n-propyl group, a 5,6-di-n-propyl group, a 3,4-di-n-butyl group, a 3,5-di-n-butyl group, a 3,6-di-n-butyl group, a 4,5-di-n-butyl group, a 4,6-di-n-butyl group, a 5,6-di-n-butyl group, a 3,4-dicyano group, a 3,5-dicyano group, a 3,6-dicyano group, a 4,5-dicyano group, a 4,6-dicyano group, a 5,6-dicyano group, a 3,4-dihydroxy group, a 3,5-dihydroxy group, a 3,6-dihydroxy group, a 4,5-dihydroxy group, a 4,6-dihydroxy group, a 5,6-dihydroxy group, a 3,4-diamino group, a 3,5-diamino group, a 3,6-diamino group, a 4,5-diamino group, a 4,6-diamino group, a 5,6-diamino group, a 3,4-dinitro group, a 3,5-dinitro group, a 3,6-dinitro group, a 4,5-dinitro group, a 4,6-dinitro group, a 5,6-dinitro group, a 3,4-dimethoxy group, a 3,5-dimethoxy group, a 3,6-dimethoxy group, a 4,5-dimethoxy group, a 4,6-dimethoxy group, a 5,6-dimethoxy group, a 3,4-diethoxy group, a 3,5-diethoxy group, a 3,6-diethoxy group, a 4,5-diethoxy group, a 4,6-diethoxy group, a 5,6-diethoxy group, a 3,4-ditrifluoromethyl group, a 3,5-ditrifluoromethyl group, a 3,6-ditrifluoromethyl group, a 4,5-ditrifluoromethyl group, a 4,6-ditrifluoromethyl group, a 5,6-ditrifluoromethyl group, a 3,4,5-trifluoro group, a 3,4,6-trifluoro group, a 4,5,6-trifluoro group, a 3,4,5-trichloro group, a 3,4,6-trichloro group, a 4,5,6-trichloro group, a 3,4,5,6-tetrafluoro group, and a 3,4,5,6-tetrachloro group.

[14] The compound according to any one of [1] to [13] or a pharmaceutically acceptable salt of the compound, wherein the compound is any of compounds represented by the following formulas:

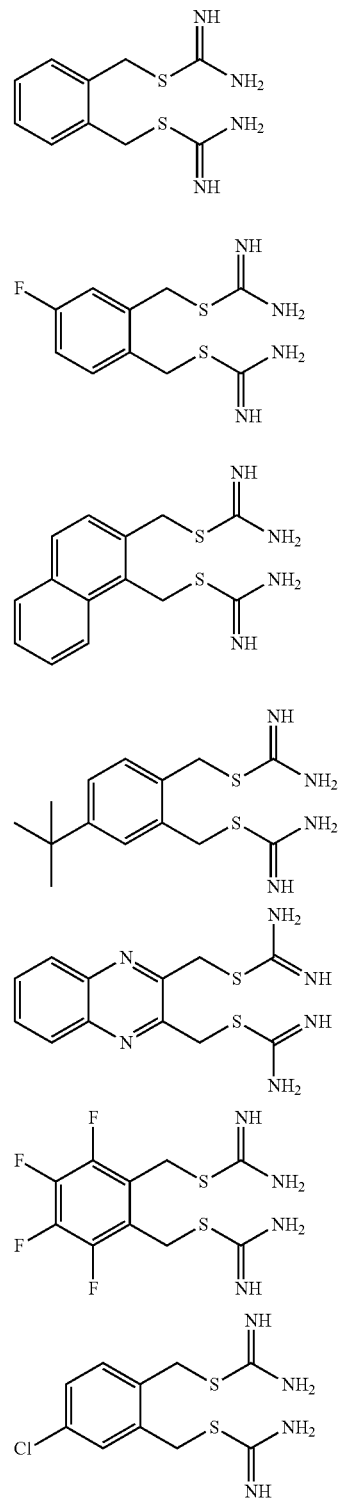

293
-continued
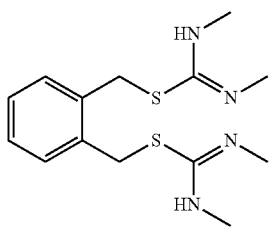
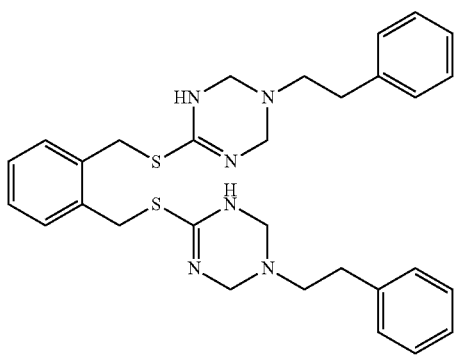
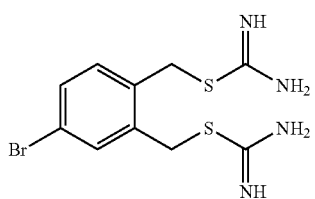
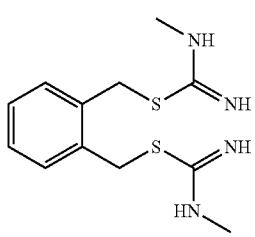
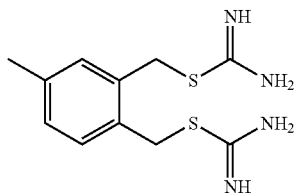
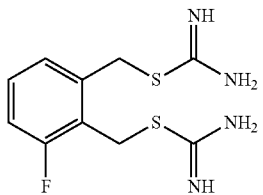
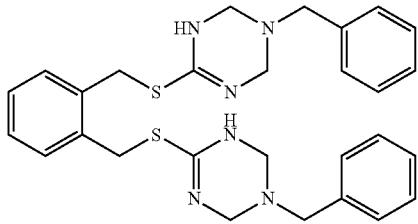
294
-continued
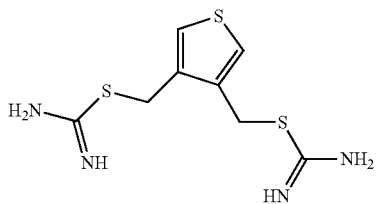
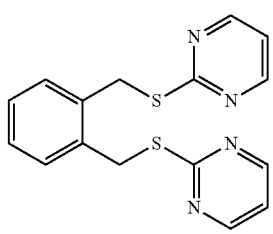
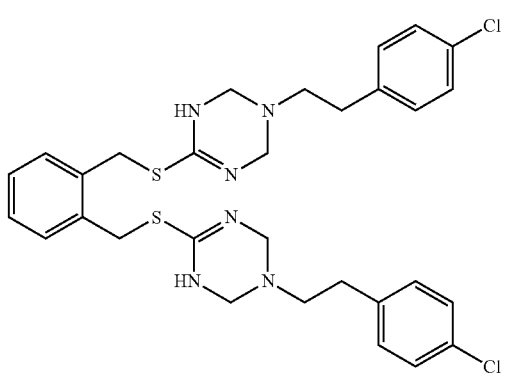
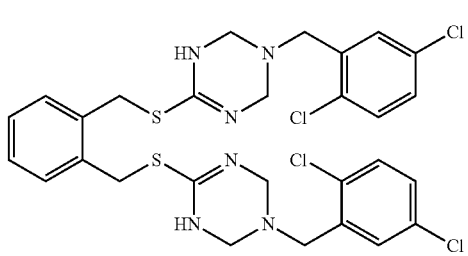
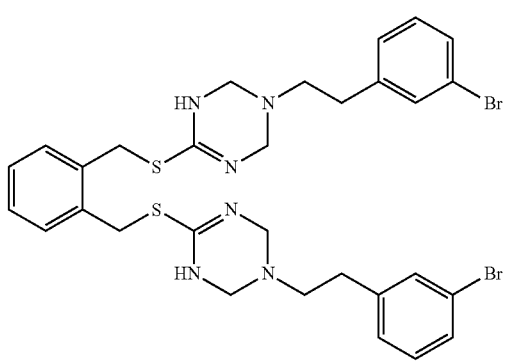

295
-continued
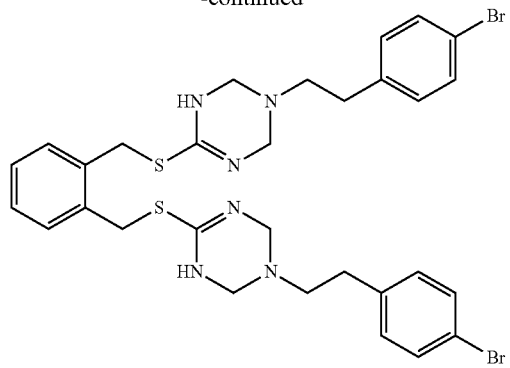
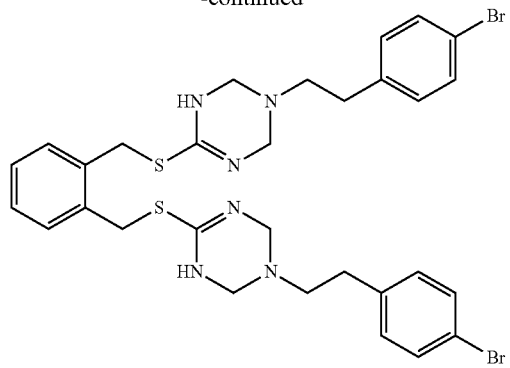
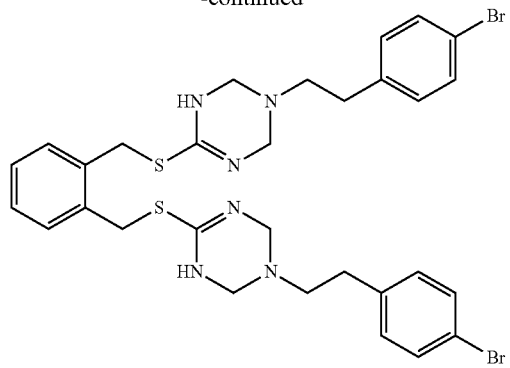
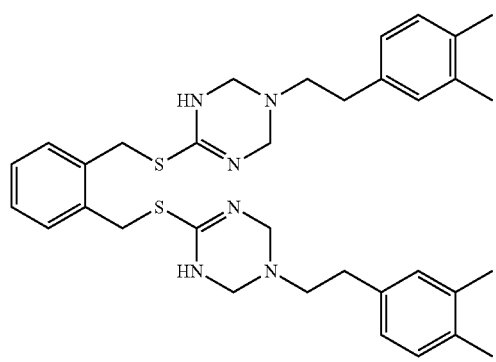
296
-continued
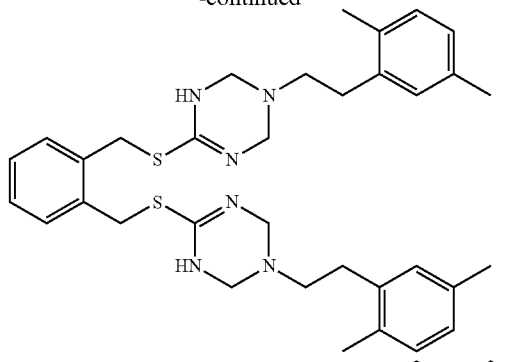
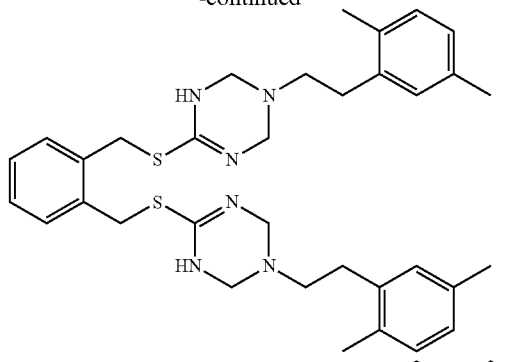
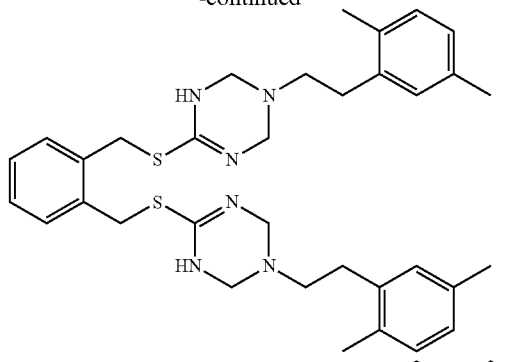
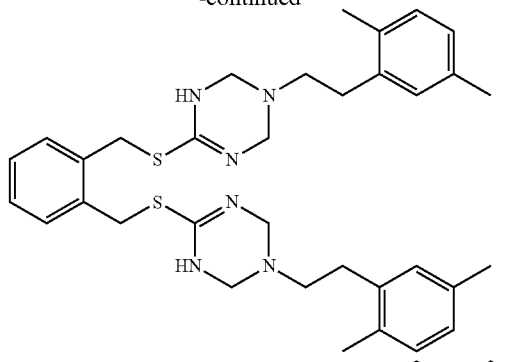
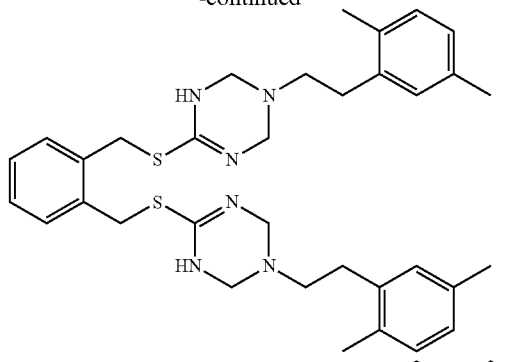

-continued
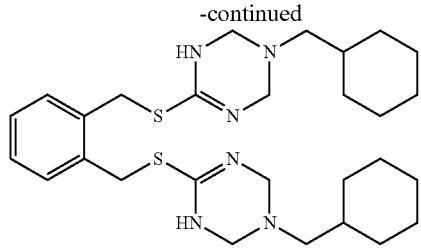
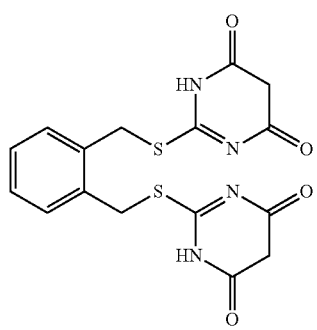
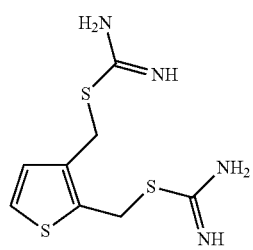
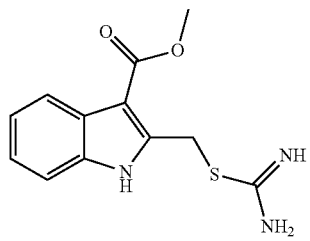
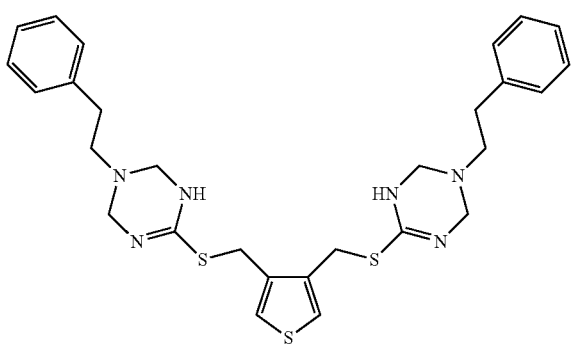
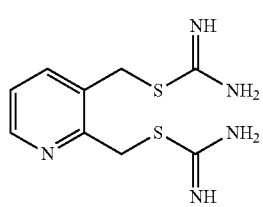
-continued
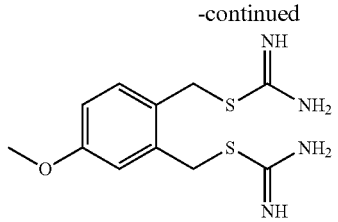
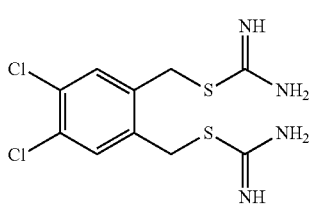
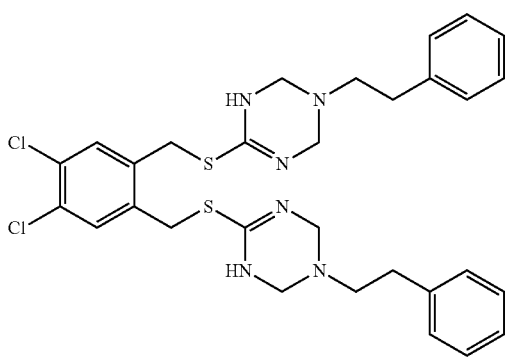
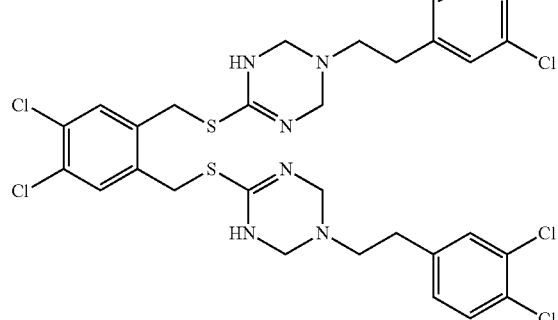
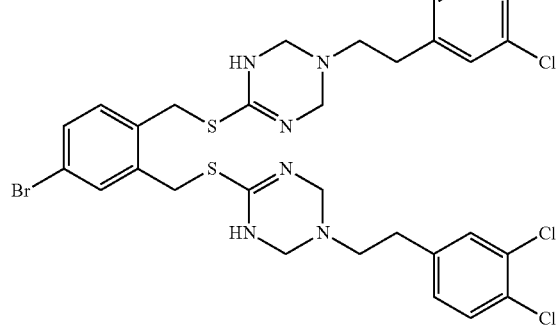

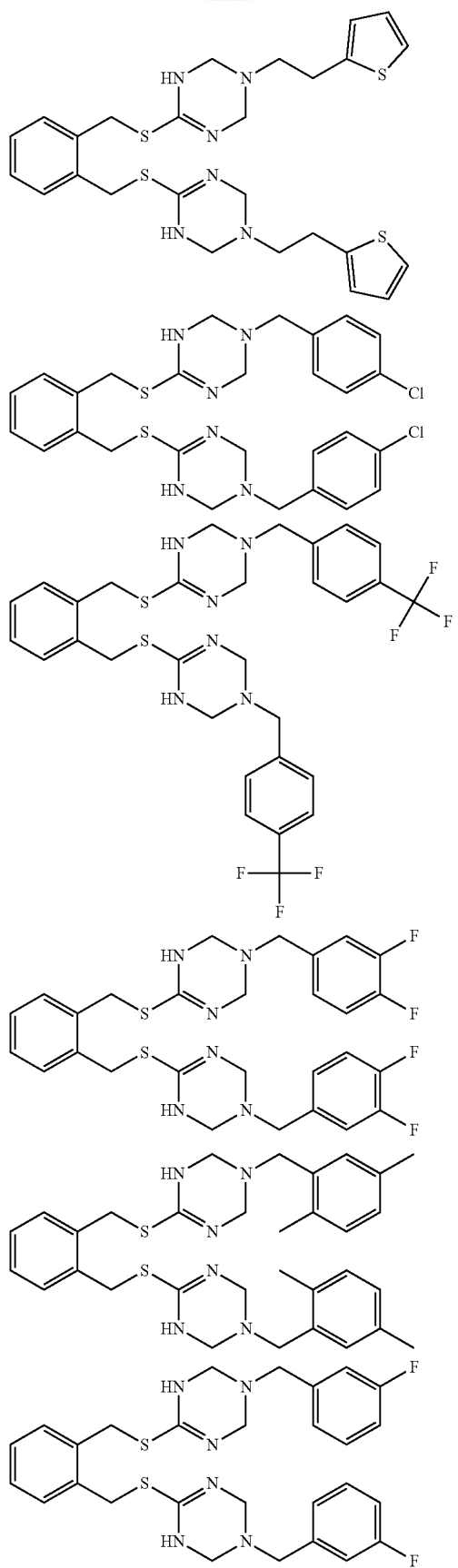
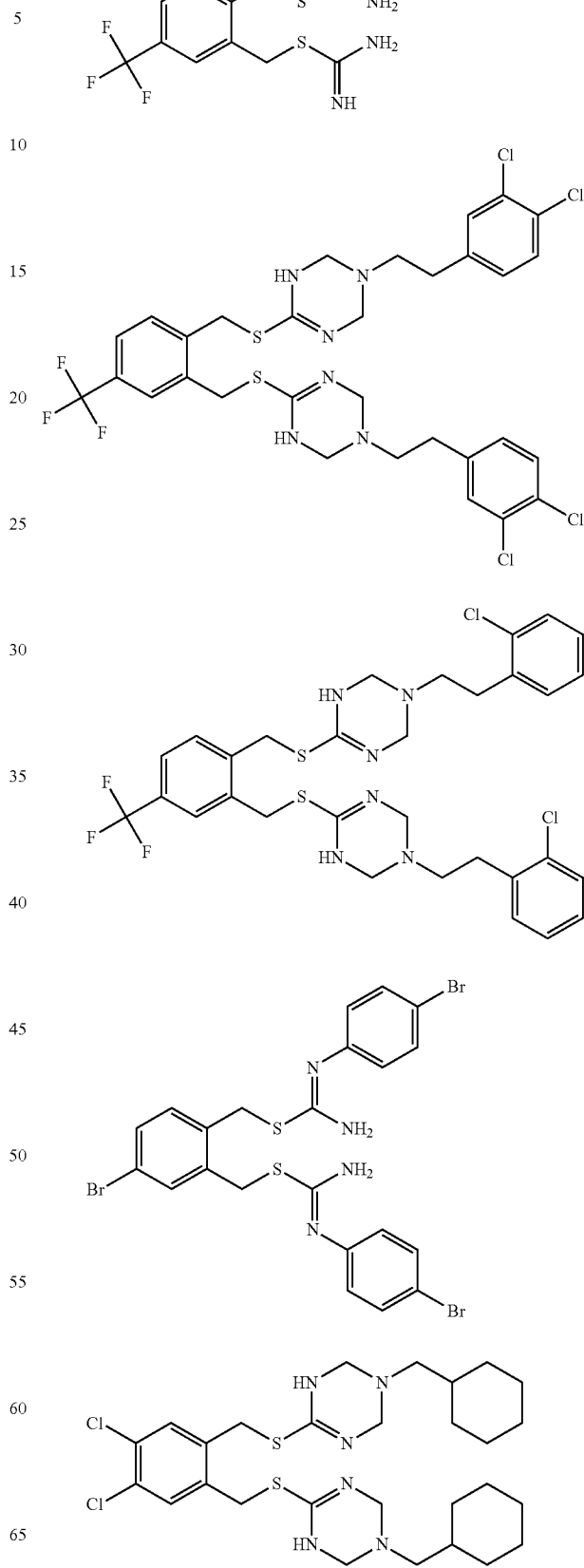

301
-continued
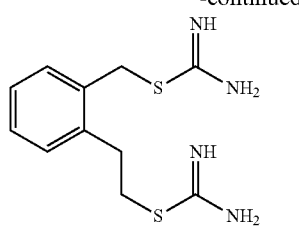
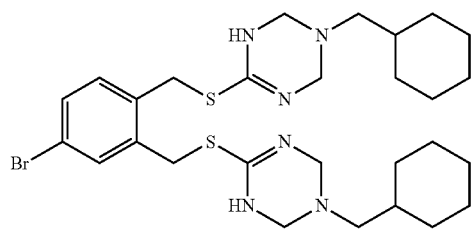
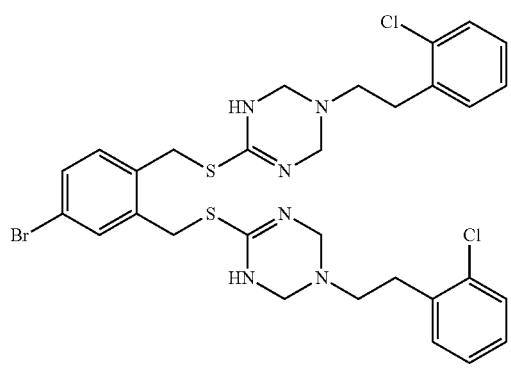
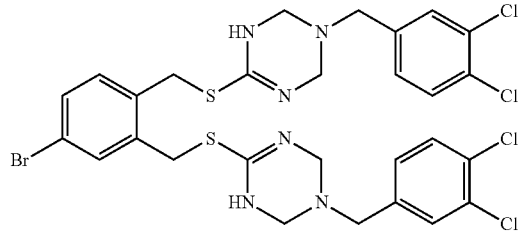
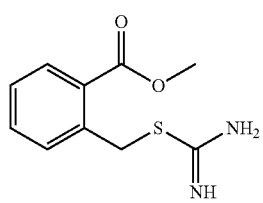
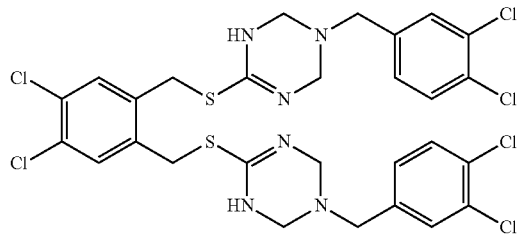
302
-continued
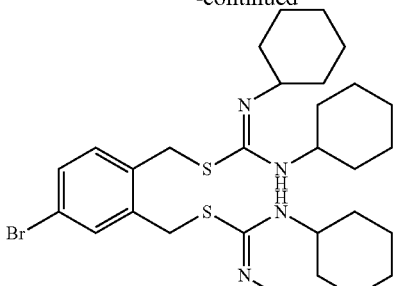
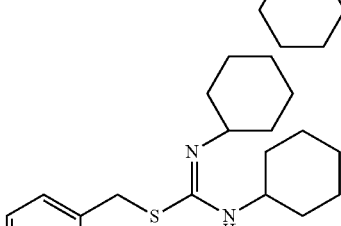
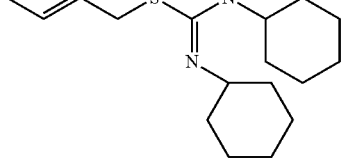
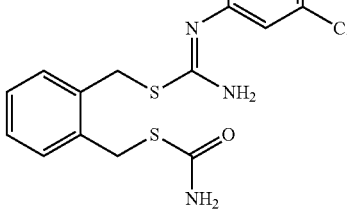
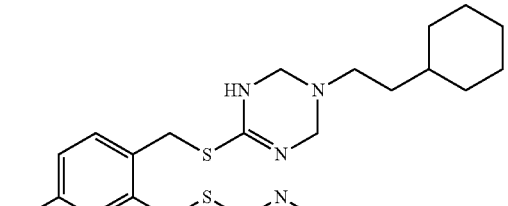
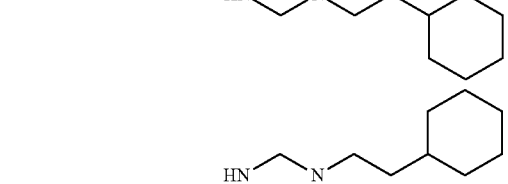
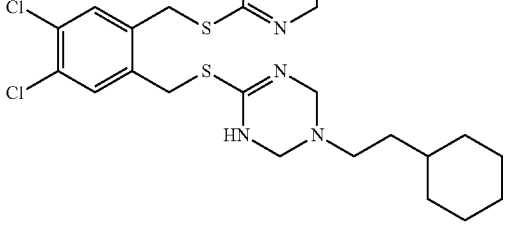

303
-continued
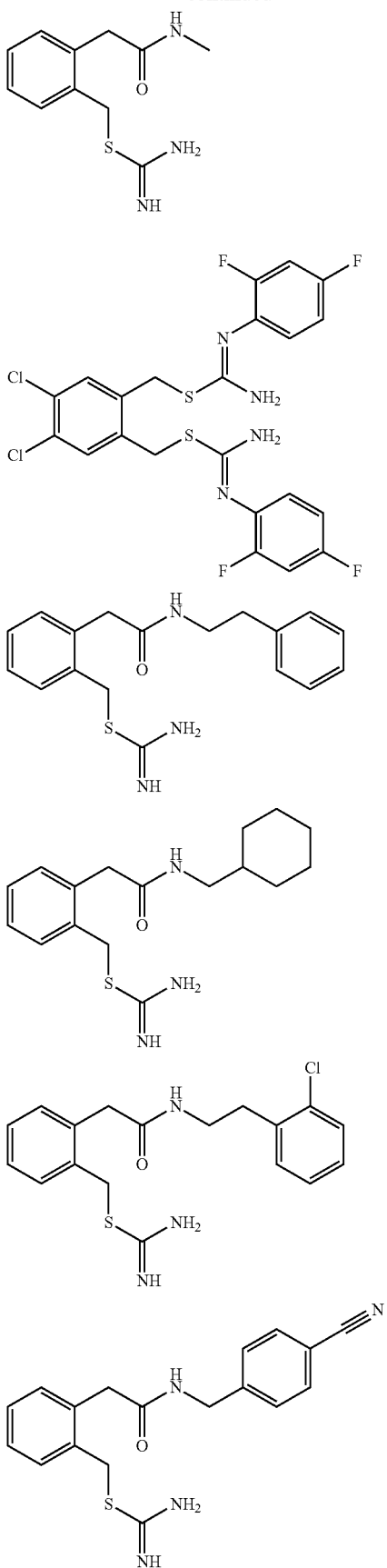
304
-continued
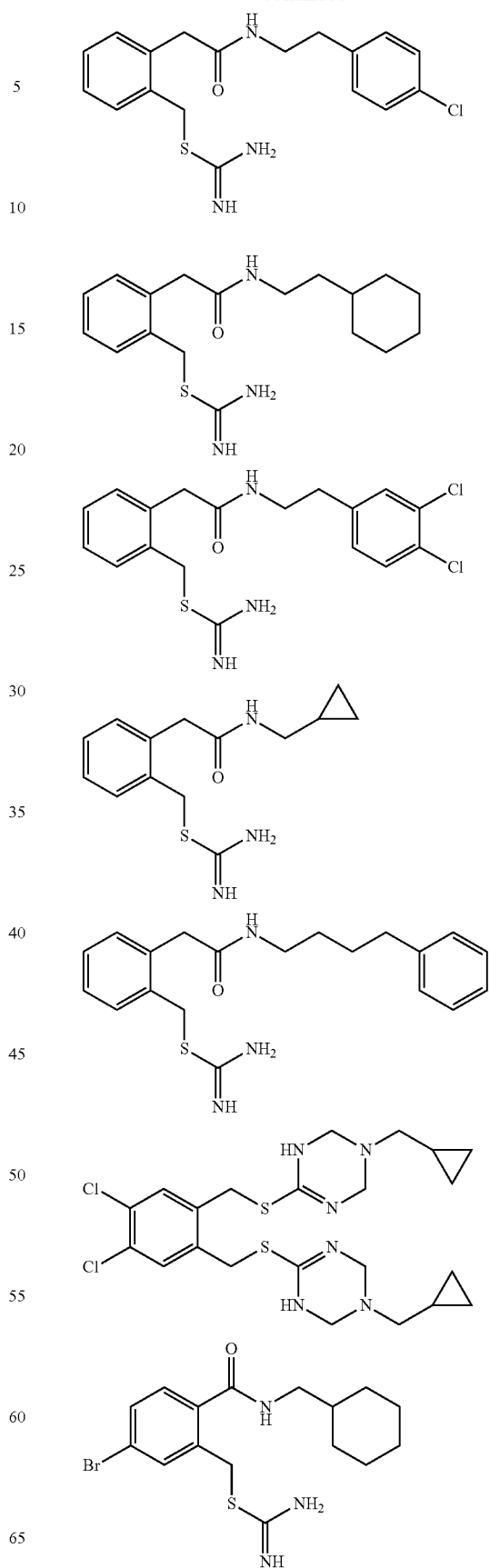

305
-continued
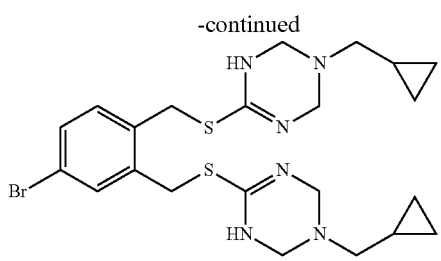
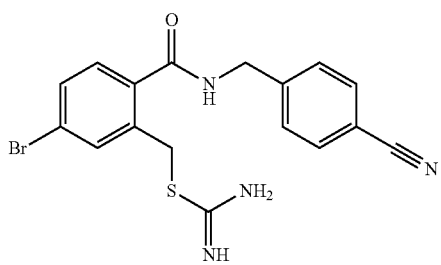
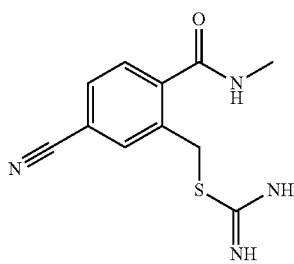
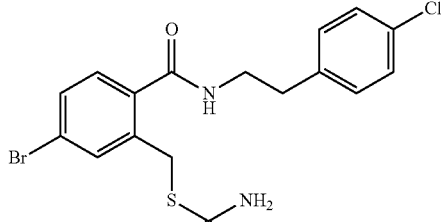
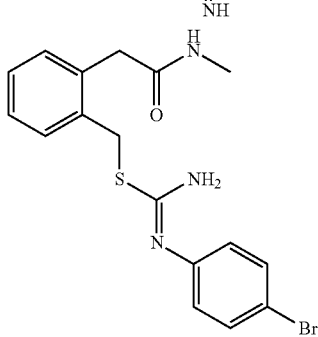
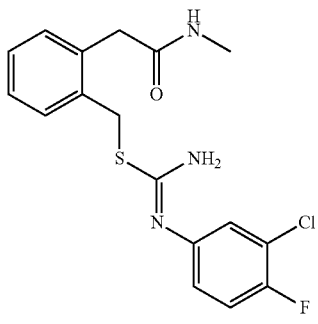
306
-continued
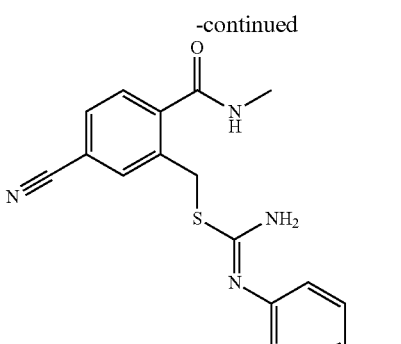
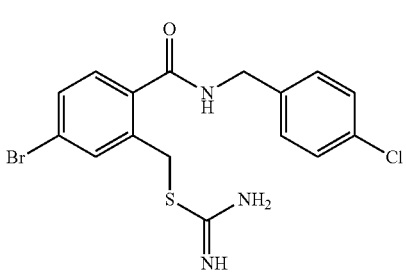
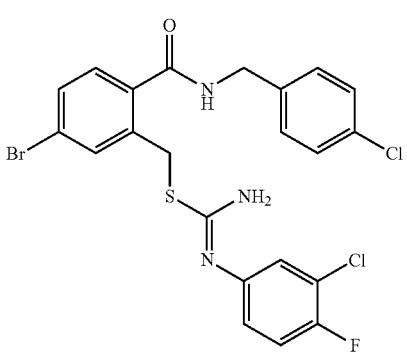
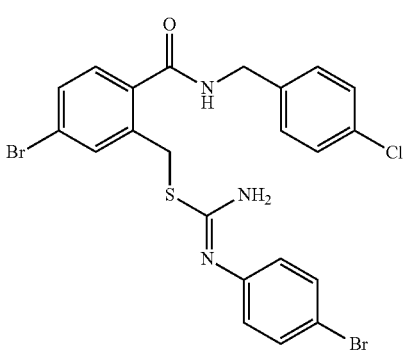
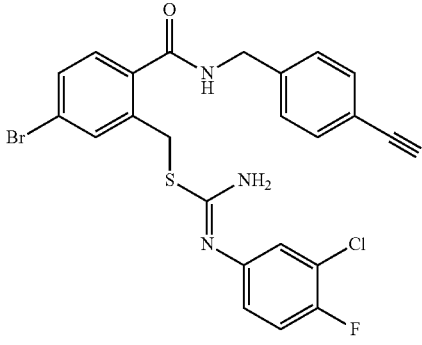

307
-continued
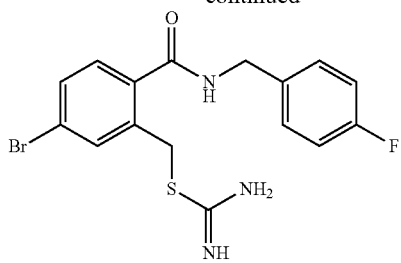
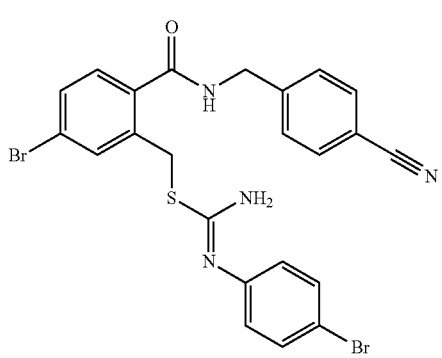
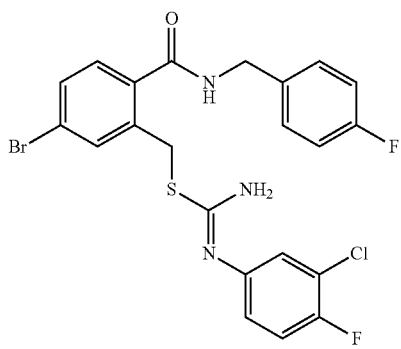
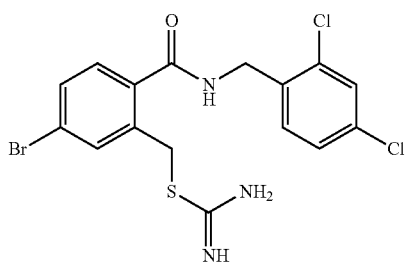
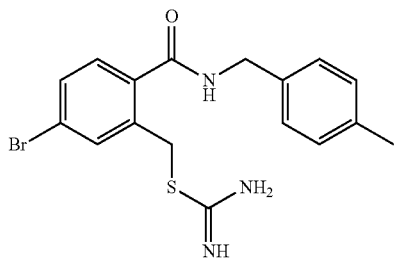
308
-continued
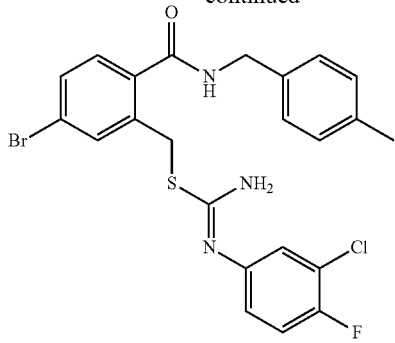
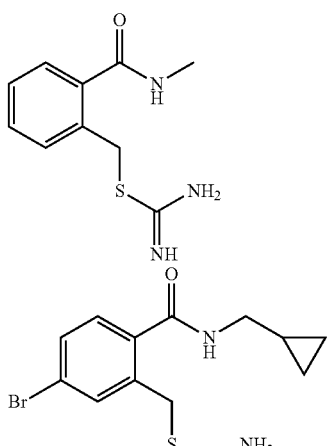
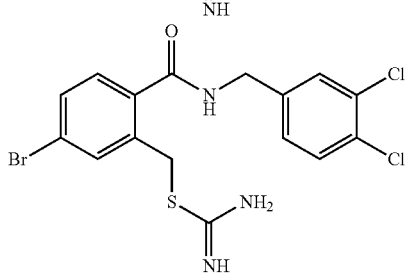
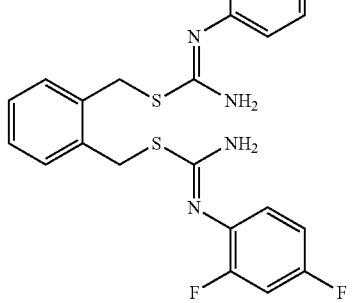
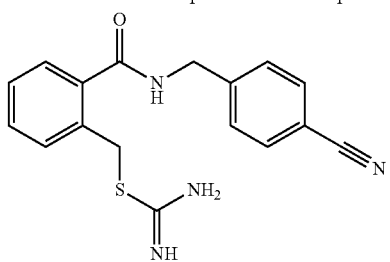

309
-continued
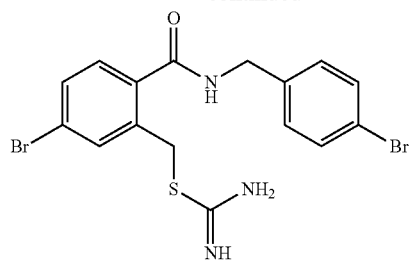
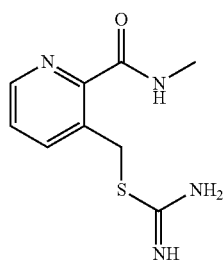
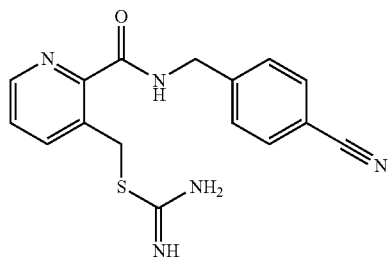
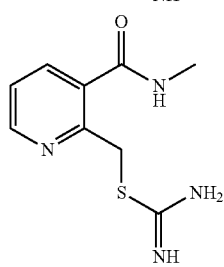
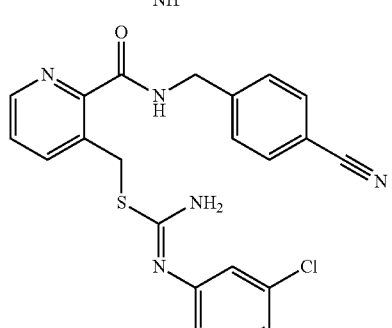
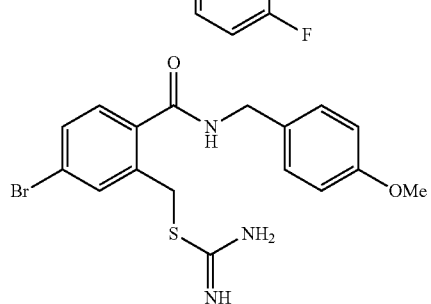
310
-continued
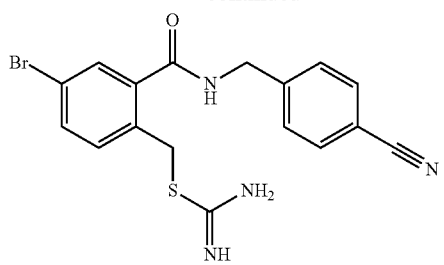
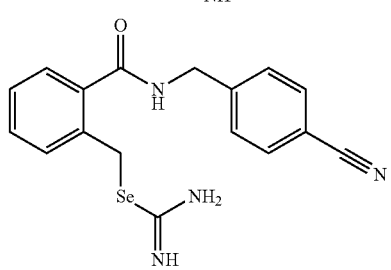
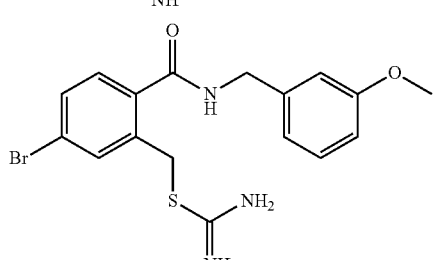
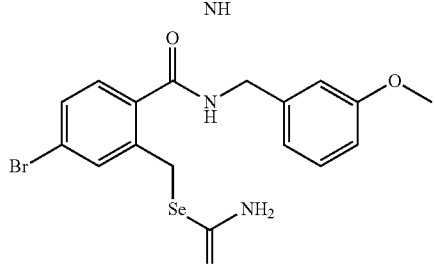
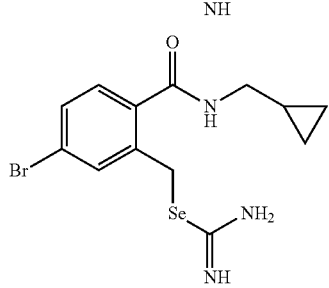
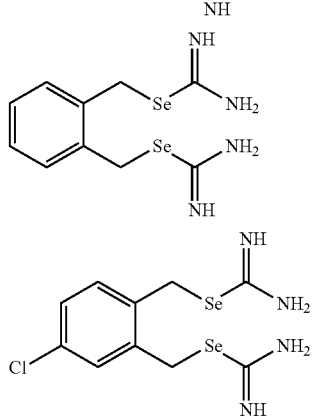

-continued
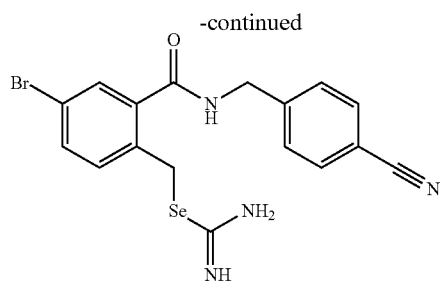
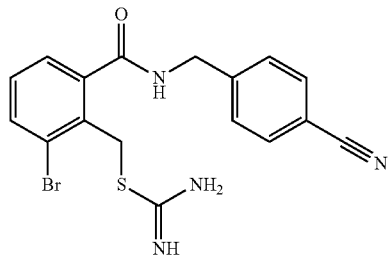
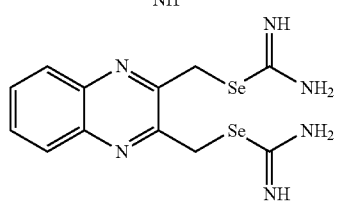
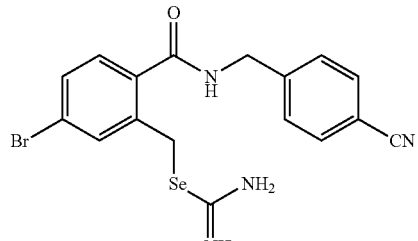
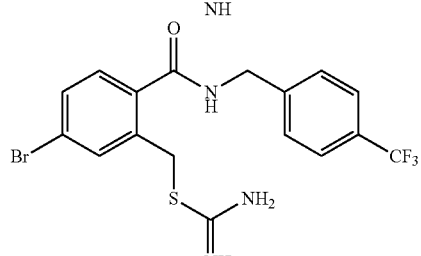
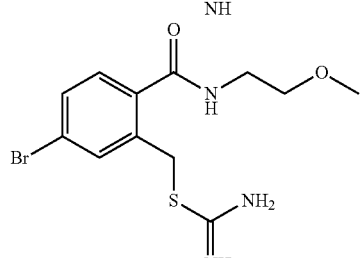
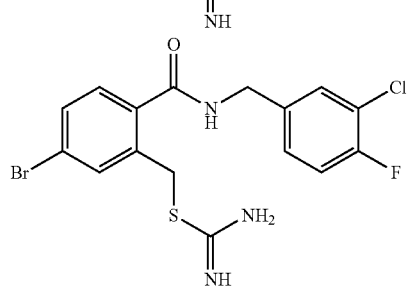
-continued
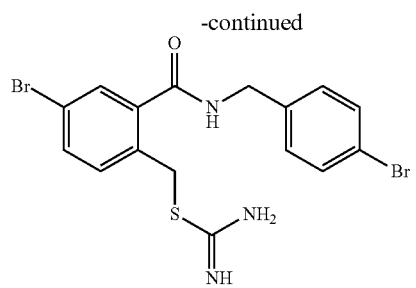
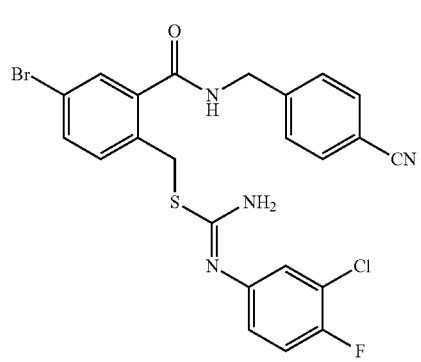
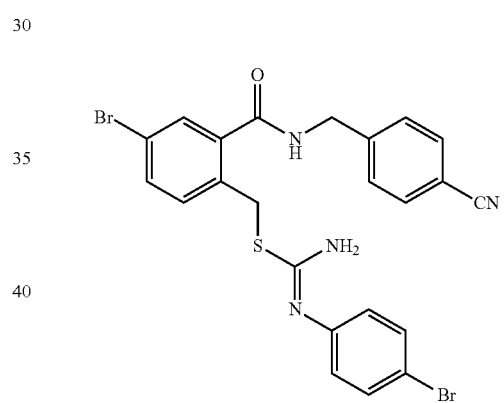
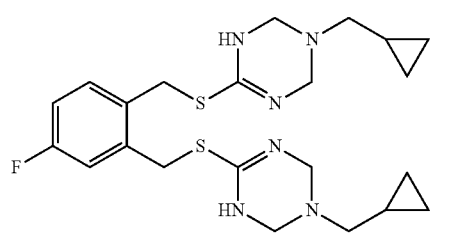
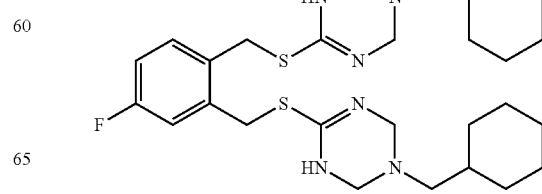

313
-continued
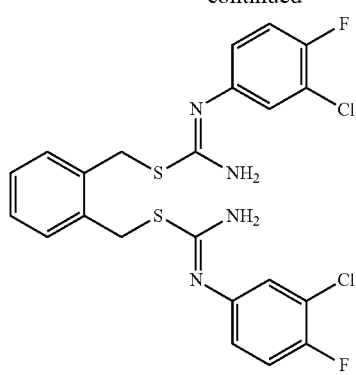
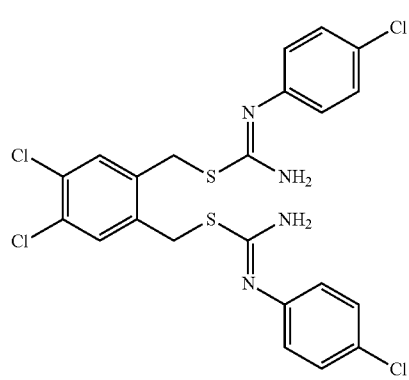
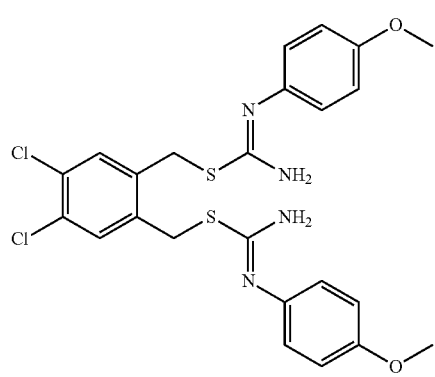
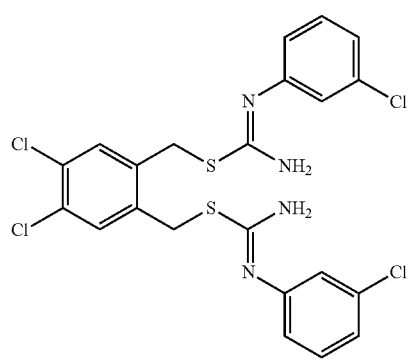
314
-continued
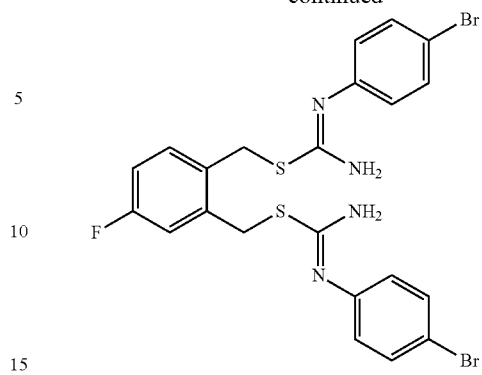
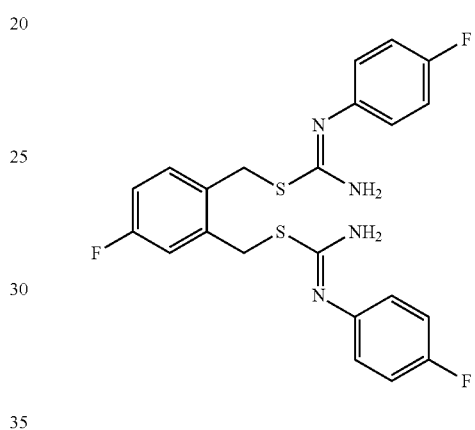
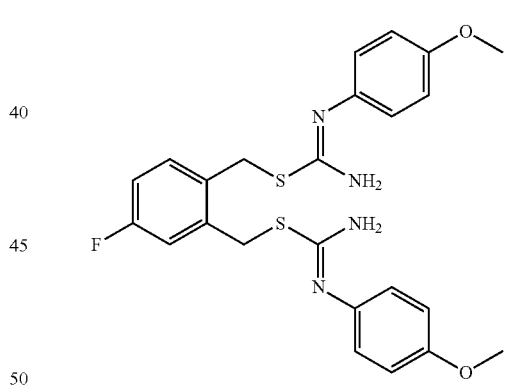
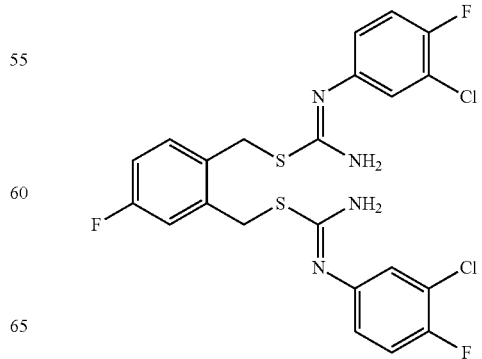

-continued
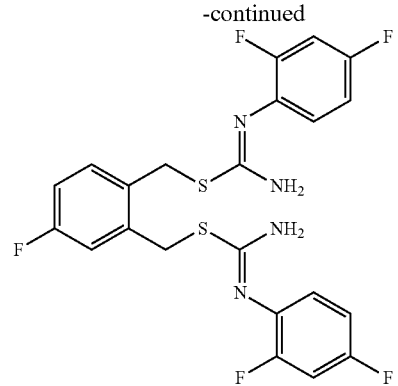
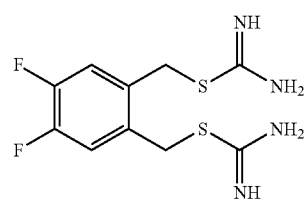
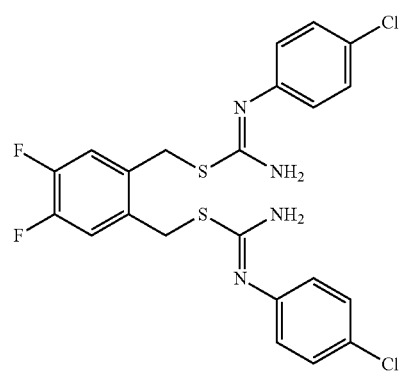
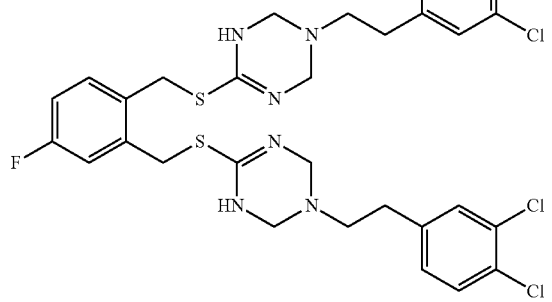
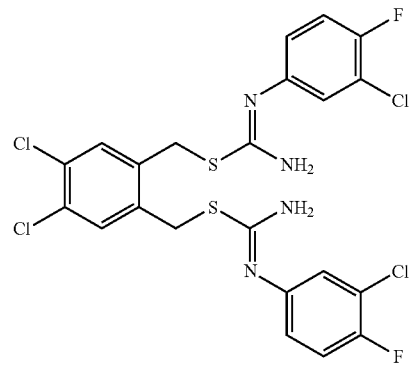
-continued
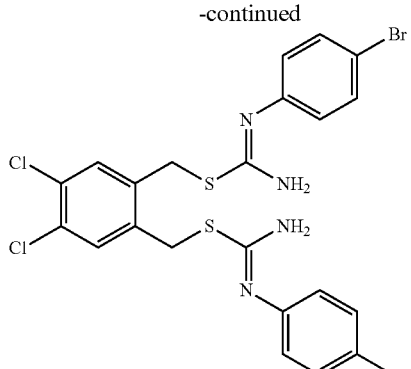
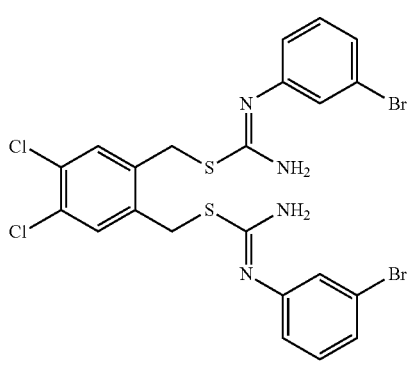
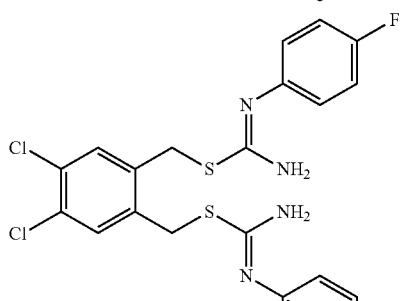
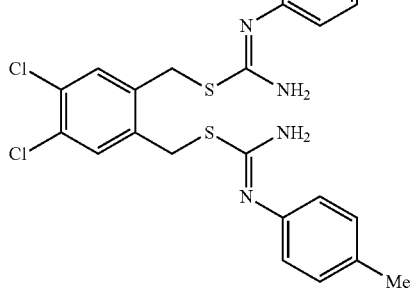
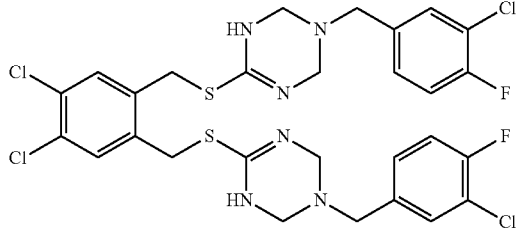

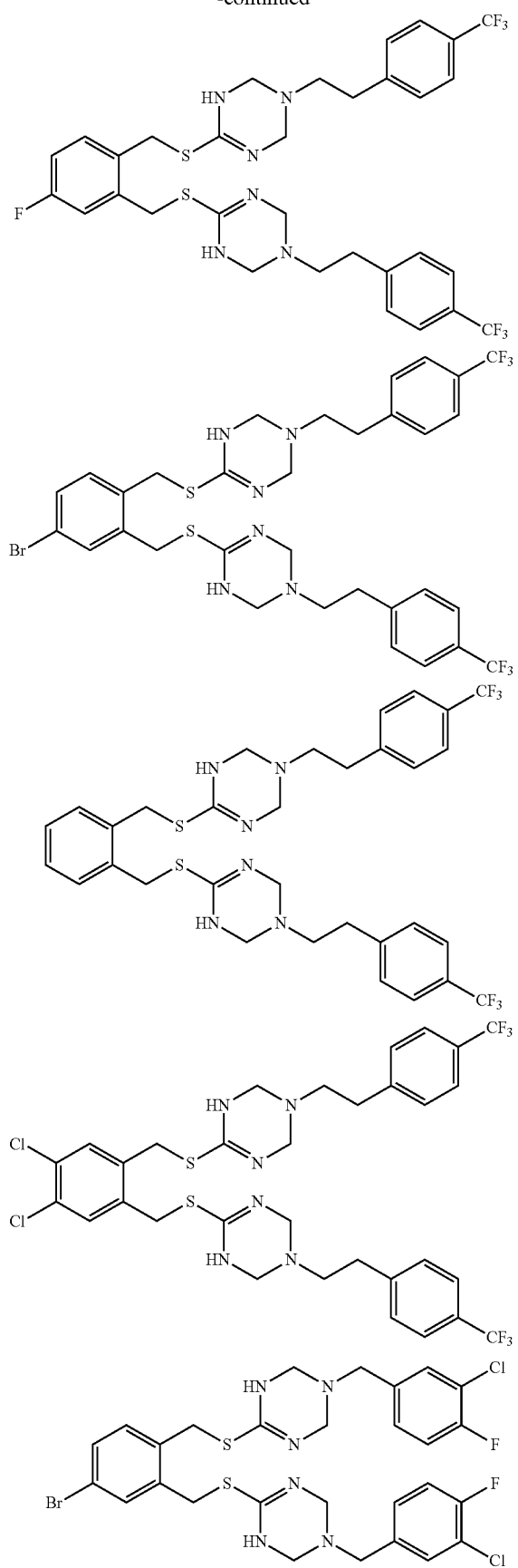
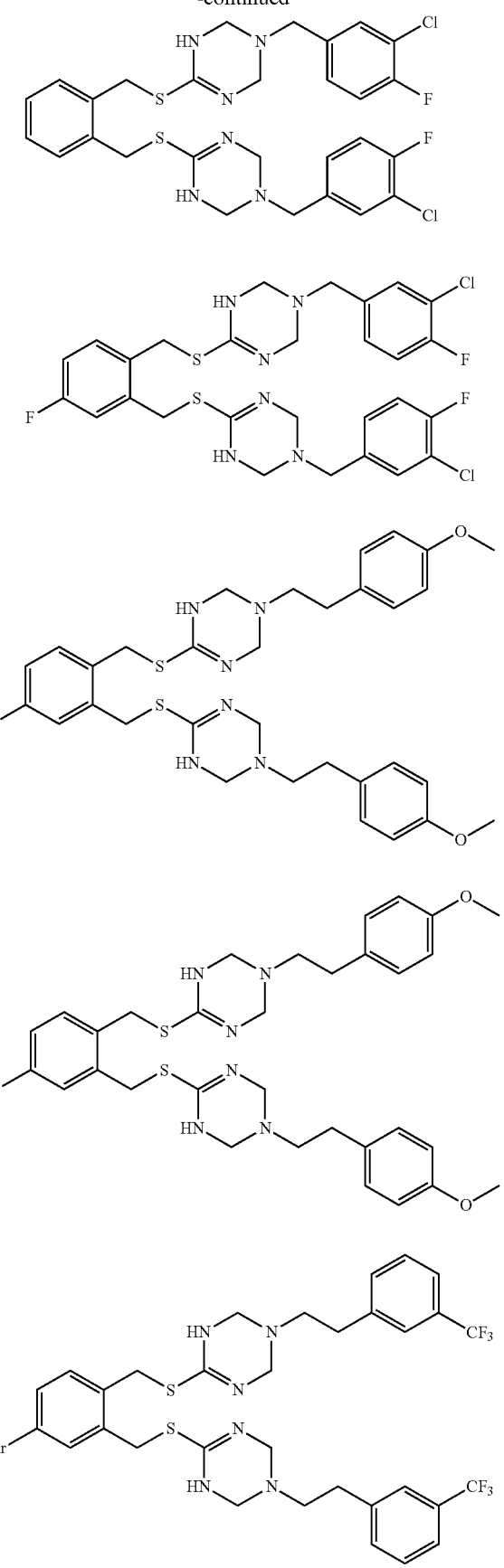

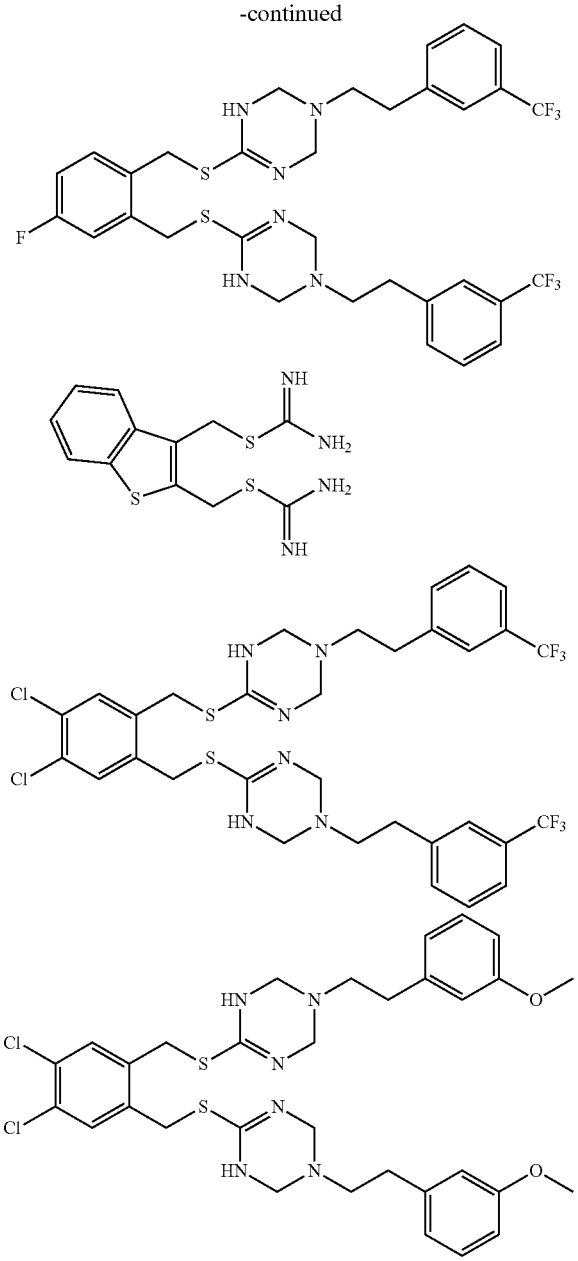

[15] A pharmaceutical composition comprising one or more compounds according to any one of [1] to [14] or pharmaceutically acceptable salts thereof, and a pharmaceutically acceptable carrier.

[16] An inhibitor of IDO and/or TDO, comprising one or more compounds according to any one of [1] to [14] or pharmaceutically acceptable salts thereof as an active ingredient.

[17] A therapeutic agent for a disease or a disorder selected from tumor, infectious disease, neurodegenerative disorder, cataract, organ transplant rejection, autoimmune disease, postoperative cognitive impairment, and disease related to women's reproductive health, comprising one or more compounds according to any one of [1] to [14] or pharmaceutically acceptable salts thereof as an active ingredient.

[18] The therapeutic agent according to [17], wherein the therapeutic agent is an antitumor agent.

[19] The antitumor agent according to [18], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[20] A pharmaceutical kit for treating a disease or a disorder selected from tumor, infectious disease, neurodegenerative disorder, cataract, organ transplant rejection, autoimmune disease, postoperative cognitive impairment, and disease related to women's reproductive health, comprising
    (a) one or more compounds according to any one of [1] to [14] or pharmaceutically acceptable salts thereof, and
    (b) one or more additional therapeutic agents for treating a disease or disorder selected from tumor, infectious disease, neurodegenerative disorder, cataract, organ transplant rejection, autoimmune disease, postoperative cognitive impairment, and disease related to women's reproductive health, wherein
the compounds or the pharmaceutically acceptable salts thereof and the additional agents are suitable for concurrent, sequential or separate administration.

[21] The pharmaceutical kit according to [20] for treating tumor, comprising
    (a) one or more compounds according to any one of [1] to [14] or pharmaceutically acceptable salts thereof, and
    (b) one or more additional antitumor agents, wherein
the compounds or the pharmaceutically acceptable salts thereof and the additional agents are suitable for concurrent, sequential or separate administration.

[22] The kit according to [21], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[23] The compound according to any one of [1] to [14] or the pharmaceutically acceptable salt of the compound for use in the treatment of a disease or a disorder selected from tumor, infectious disease, neurodegenerative disorder, cataract, organ transplant rejection, autoimmune disease, postoperative cognitive impairment, and disease related to women's reproductive health.

[24] The compound according to [23] for use in the treatment of tumor.

[25] The compound according to [24], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[26] Use of a compound according to any one of [1] to [14] or a pharmaceutically acceptable salt thereof for producing a medicament treating a disease or a disorder selected from tumor, infectious disease, neurodegenerative disorder, cataract, organ transplant rejection, autoimmune disease, postoperative cognitive impairment, and disease related to women's reproductive health.

[27] The use according to [26] for producing a medicament for treating a tumor.

[28] The use according to [27], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

[29] A method for treating a disease or a disorder selected from tumor, infectious disease, neurodegenerative disorder, cataract, organ transplant rejection, autoimmune disease, postoperative cognitive impairment, and disease related to women's reproductive health, comprising administering one or more compounds according to any one of [1] to [14] or pharmaceutically acceptable salts thereof, or a pharmaceutical kit according to any one of [20] to [22] to a patient with the disease or the disorder selected from tumor, infectious disease, neurodegenerative disorder, cataract, organ transplant rejection, autoimmune disease, postoperative cognitive impairment, and disease related to women's reproductive health.

[30] The treatment method according to [29], wherein the disease is a tumor.

[31] The treatment method according to [30], wherein the tumor is selected from mesothelioma, tumor of hepatobiliary tract (biliary tract and bile duct), primary or secondary CNS tumor, primary or secondary brain tumor, throat cancer, oral cancer, cancer of nasal cavity, lung cancer, bone cancer, liver cancer, pancreatic cancer, skin cancer, cancer of head or neck, cutaneous or intraocular melanoma, ovary cancer, colon cancer, rectum cancer, cancer of anal region, stomach cancer, duodenum cancer, cancer of colorectum, breast cancer, uterine cancer, cancer of fallopian tube, carcinoma of endometrium, carcinoma of uterine cervix, carcinoma of vagina, carcinoma of vulva, Hodgkin's disease, cancer of esophagus, cancer of small intestine, cancer of endocrine system, cancer of thyroid gland, cancer of parathyroid gland, cancer of adrenal gland, soft tissue sarcoma, cancer of urethra, cancer of penis, prostate cancer, testis cancer, chronic or acute leukemia, acute myeloid leukemia, chronic myeloid leukemia, lymphocytic lymphoma, cancer of urinary bladder, cancer of kidney or ureter, renal cell carcinoma, carcinoma of renal pelvis, neoplasm of central nervous system (CNS), primary CNS lymphoma, non-Hodgkin's lymphoma, spinal axis tumor, brain stem glioma, pituitary adenoma, adrenal cortex cancer, gallbladder cancer, multiple myeloma, bile duct cancer, fibrosarcoma, neuroblastoma, and retinoblastoma.

INDUSTRIAL APPLICABILITY

The compound of the present invention has excellent activity as an IDO/TDO inhibitor and further has excellent antitumor activity. Thus, its application as a therapeutic agent for various diseases including tumors for which an IDO/TDO inhibitor is effective is expected.

The invention claimed is:
1. A compound represented by formula (I-2) or a pharmaceutically acceptable salt of the compound:

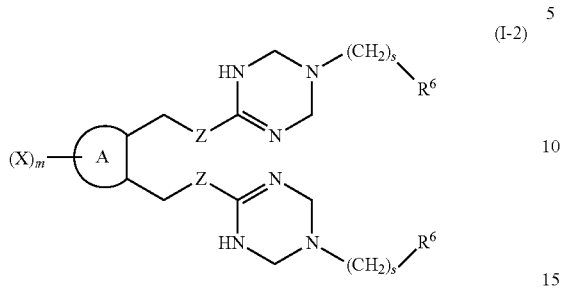

wherein
ring A represents an aromatic ring, a heterocyclic ring, or a condensed ring of two or more rings selected from an aromatic ring, and a heterocyclic ring, wherein ring A is selected from the group consisting of a benzene ring, a naphthalene ring, a quinoxaline ring, a thiophene ring, an indole ring, a benzothiophene ring, an imidazole ring, a quinoline ring, a quinazoline ring, and a pyridine ring;

X is selected from the group consisting of a halogen atom, a substituted or unsubstituted linear or branched alkyl group, a substituted or unsubstituted linear or branched alkoxy group, a substituted or unsubstituted linear or branched alkenyl group, a substituted or unsubstituted linear or branched alkenyloxy group, a substituted or unsubstituted linear or branched alkynyl group, a substituted or unsubstituted linear or branched alkynyloxy group, a substituted or unsubstituted cycloalkyl group, a substituted or unsubstituted cycloalkenyl group, an alkyl halide group, an alkyloxy halide group, a cyano group, and when m is 2 to 6, each X is the same or different;

m represents an integer of 0 to 6;

Z is selected from the group consisting of O, S, SO, $SO_2$, and Se, s represents an integer of 1 to 8, $R^6$ is selected from the group consisting of a substituted or unsubstituted aryl group, a substituted or unsubstituted cycloalkyl group, and a substituted or unsubstituted heterocyclic group.

2. The compound according to claim 1 or a pharmaceutically acceptable salt of the compound, wherein the compound is any of compounds represented by the following formulas:

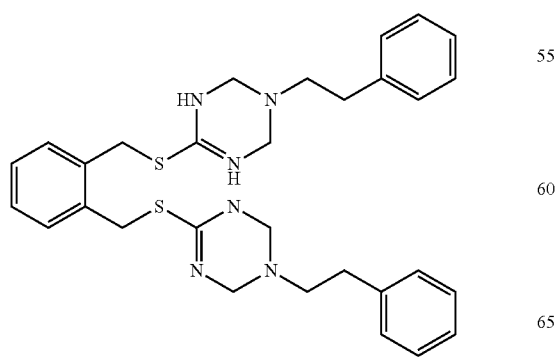

-continued

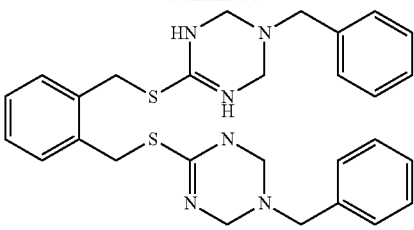

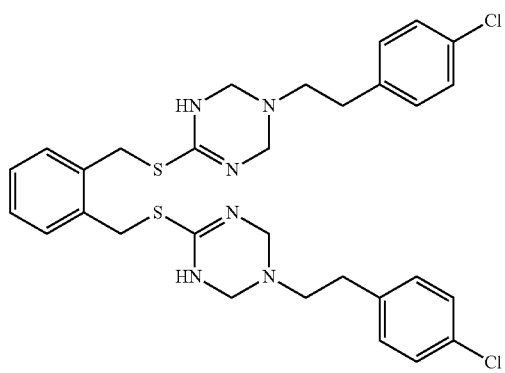

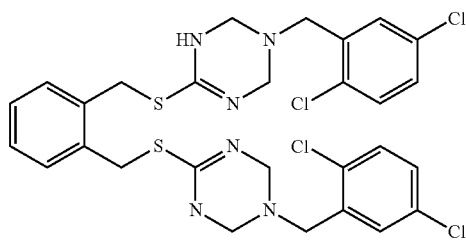

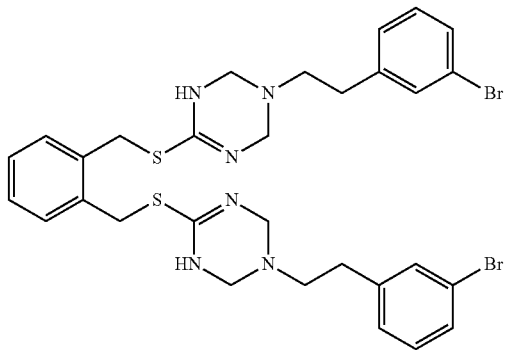

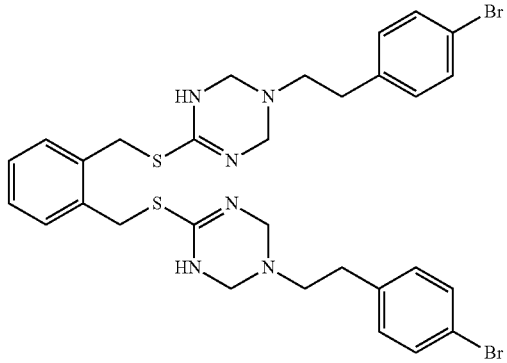

325
-continued
326
-continued
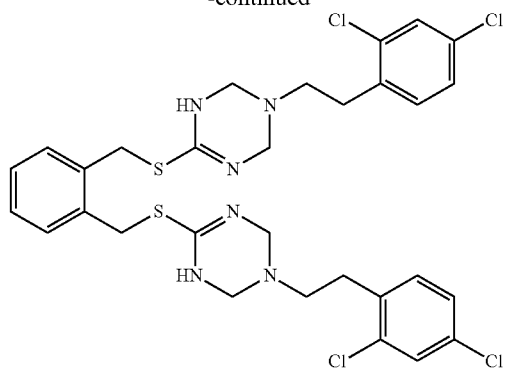
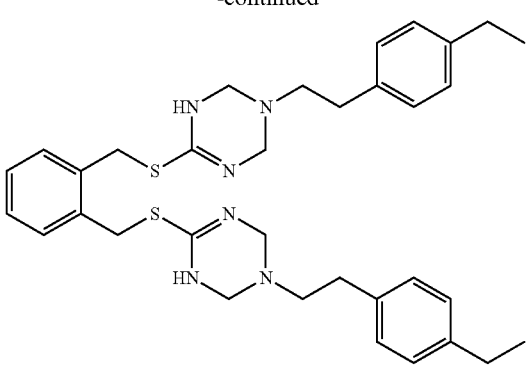

327
-continued
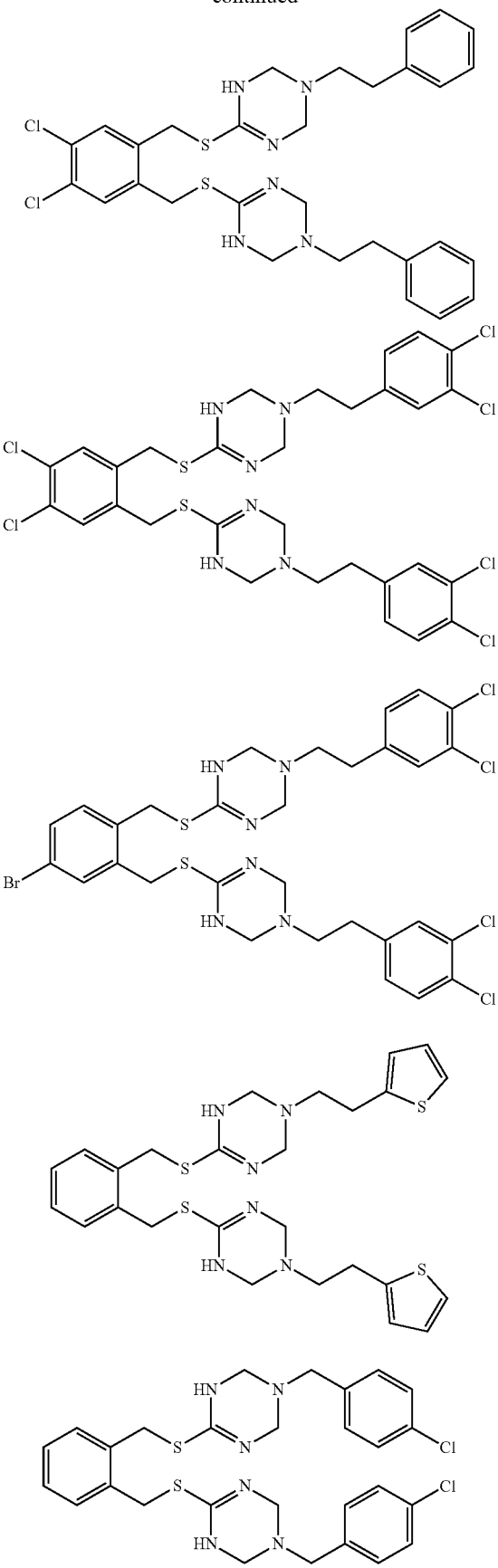
328
-continued
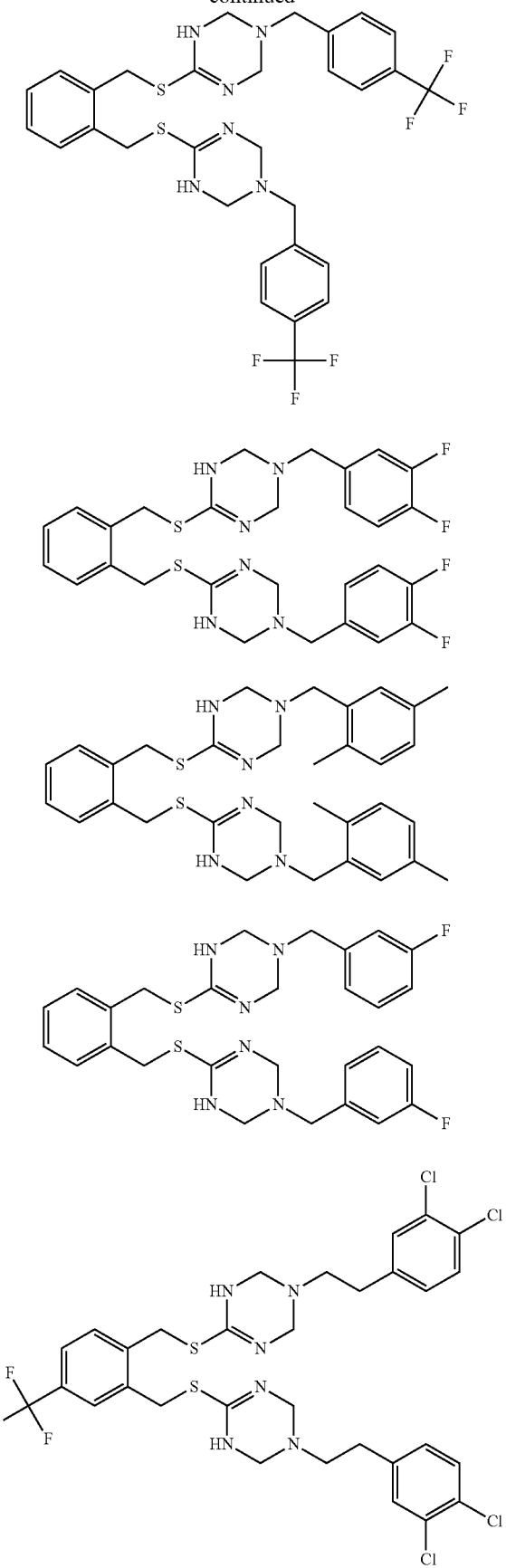

329
-continued
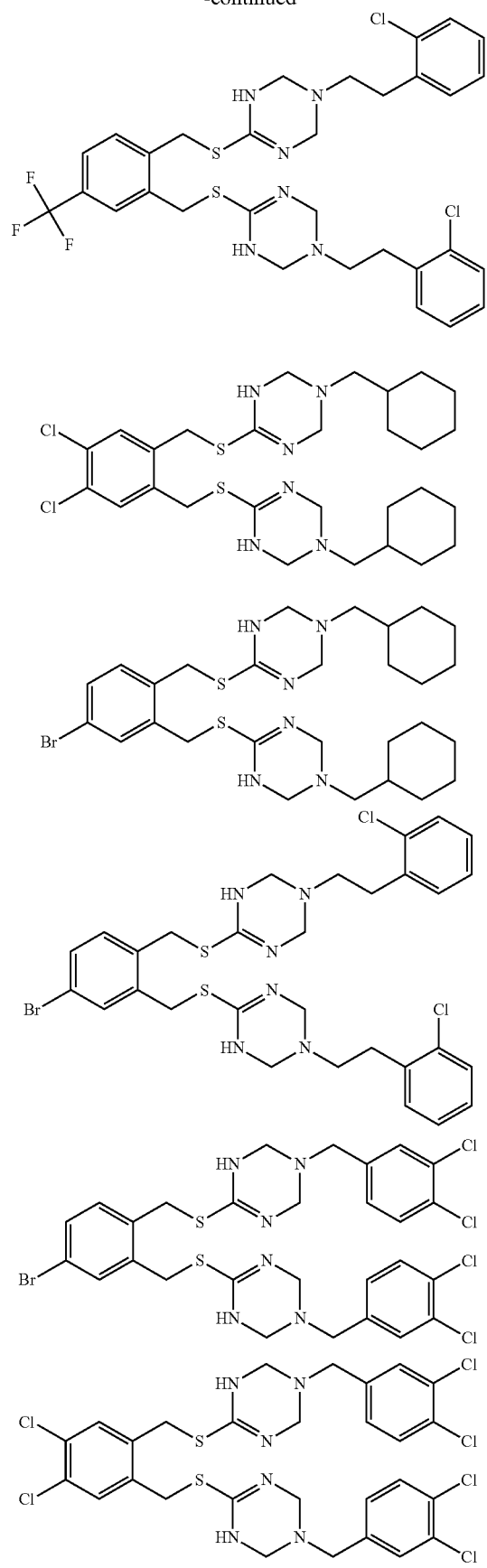
330
-continued
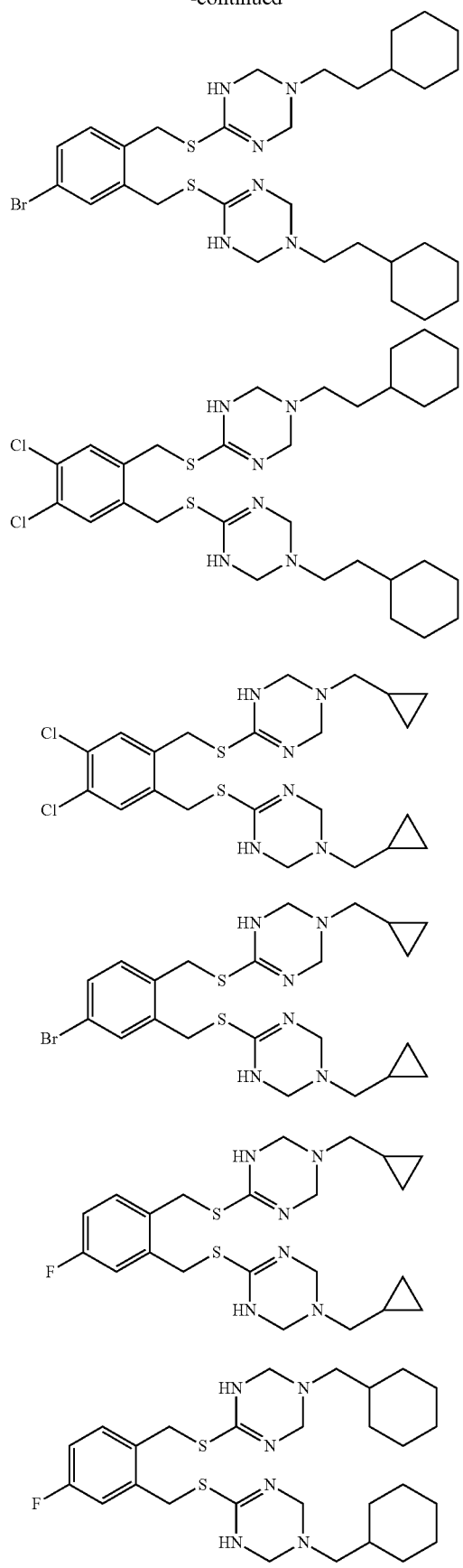

331
-continued
332
-continued
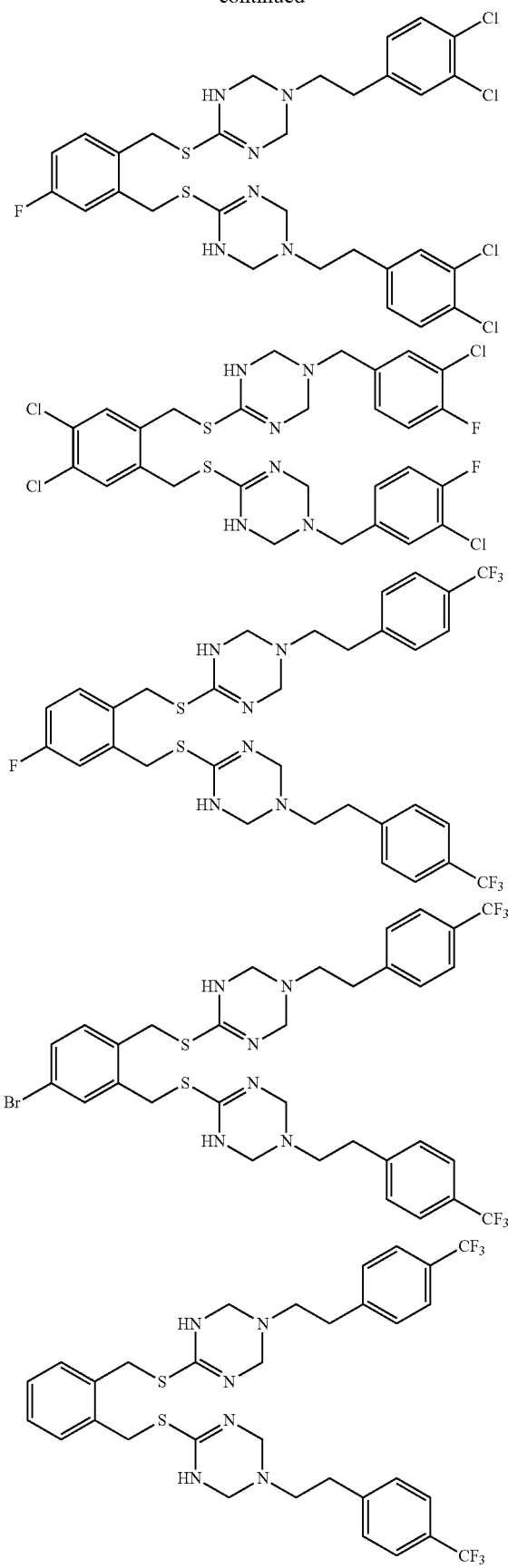
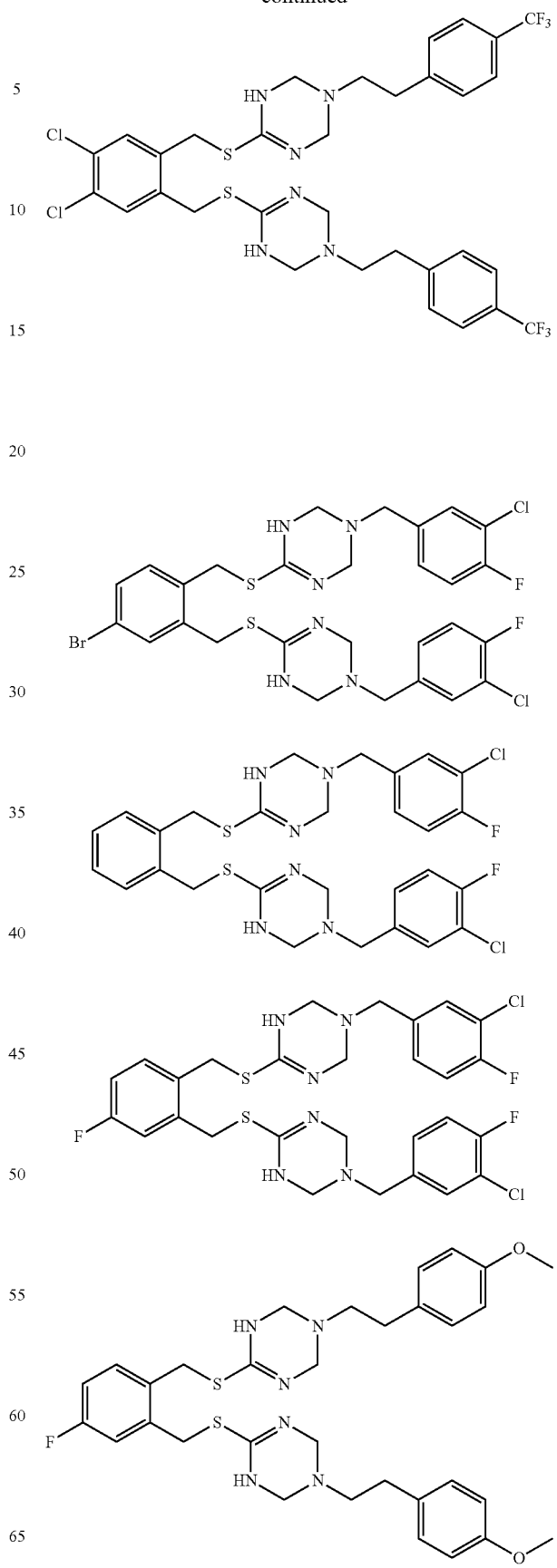

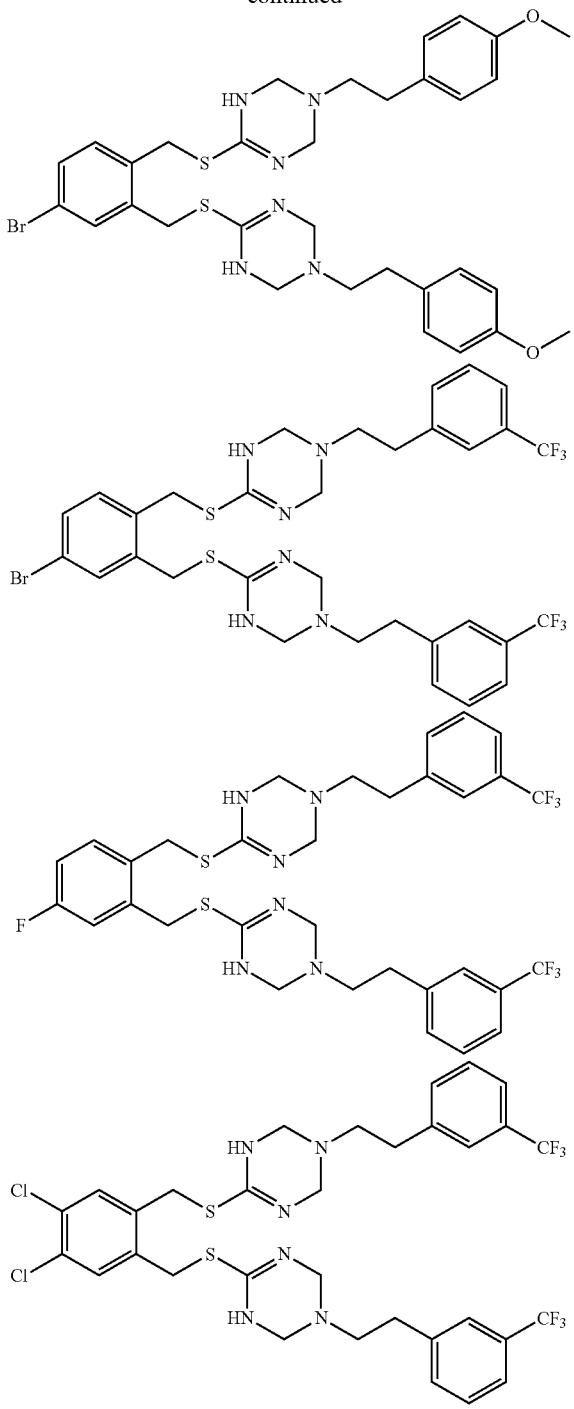

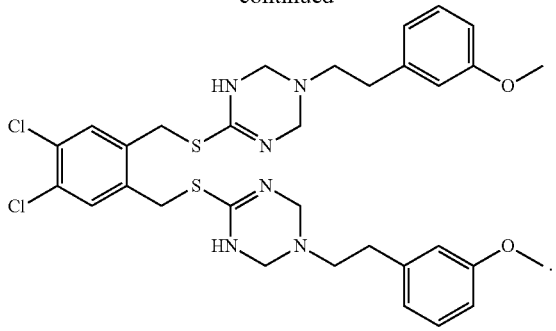

3. A pharmaceutical composition comprising one or more compounds according to claim 1 or pharmaceutically acceptable salts thereof, and a pharmaceutically acceptable carrier.

4. An inhibitor of IDO and/or TDO, comprising one or more compounds according to claim 1 or pharmaceutically acceptable salts thereof as an active ingredient.

5. A therapeutic agent for a disease or a disorder selected from tumor, infectious disease, neurodegenerative disorder, cataract, organ transplant rejection, autoimmune disease, postoperative cognitive impairment, and disease related to women's reproductive health, comprising one or more compounds according to claim 1 or pharmaceutically acceptable salts thereof as an active ingredient.

6. A pharmaceutical kit for treating a tumor, comprising:

(a) one or more compounds according to claim 1, or pharmaceutically acceptable salts thereof for treating the tumor, and (b) one or more additional therapeutic agents for treating the tumor, wherein the compounds or the pharmaceutically acceptable salts thereof and the additional agents are suitable for concurrent, sequential or separate administration, and wherein the tumor to be treated by (a) one or more compounds according to claim 1 or pharmaceutically acceptable salts thereof and the tumor to be treated by the (b) one or more additional therapeutic agents are the same tumor or a different tumor.

* * * * *